US012747224B2

(12) United States Patent
Biancofiore et al.

(10) Patent No.: US 12,747,224 B2
(45) Date of Patent: Sep. 29, 2026

(54) FIBROBLAST ACTIVATION PROTEIN LIGANDS FOR TARGETED DELIVERY APPLICATIONS

(71) Applicant: PHILOCHEM AG, Otelfingen (CH)

(72) Inventors: Ilaria Biancofiore, Otelfingen (CH); Samuele Cazzamalli, Otelfingen (CH); Sheila Plaza Dakhel, Otelfingen (CH); Etienne J. Donckele, Otelfingen (CH); Jacopo Millul, Otelfingen (CH); Florent Samain, Otelfingen (CH); Eleonore Schmidt, Otelfingen (CH)

(73) Assignee: PHILOCHEM AG, Otelfingen (CH)

( * ) Notice: Subject to any disclaimer, the term of this patent is extended or adjusted under 35 U.S.C. 154(b) by 893 days.

(21) Appl. No.: 17/799,611

(22) PCT Filed: Feb. 12, 2021

(86) PCT No.: PCT/EP2021/053494

§ 371 (c)(1),
(2) Date: Aug. 12, 2022

(87) PCT Pub. No.: WO2021/160825

PCT Pub. Date: Aug. 19, 2021

(65) Prior Publication Data

US 2023/0147962 A1 May 11, 2023

(30) Foreign Application Priority Data

| | | |
|---|---|---|
| Feb. 12, 2020 | (EP) | 20157036 |
| May 5, 2020 | (EP) | 20172953 |
| Oct. 20, 2020 | (EP) | 20202856 |

(51) Int. Cl.

| | |
|---|---|
| ***C07D 401/14*** | (2006.01) |
| ***A61P 35/00*** | (2006.01) |
| ***C07D 493/10*** | (2006.01) |
| ***C07D 498/14*** | (2006.01) |
| ***C07D 519/00*** | (2006.01) |
| ***C07F 1/00*** | (2006.01) |
| ***C07F 5/00*** | (2006.01) |
| ***C07F 5/06*** | (2006.01) |
| ***C07F 7/00*** | (2006.01) |
| ***C07F 15/00*** | (2006.01) |

(52) U.S. Cl.

CPC ............ *C07D 401/14* (2013.01); *A61P 35/00* (2018.01); *C07D 493/10* (2013.01); *C07D 498/14* (2013.01); *C07D 519/00* (2013.01); *C07F 1/005* (2013.01); *C07F 5/003* (2013.01); *C07F 5/069* (2013.01); *C07F 7/00* (2013.01); *C07F 15/00* (2013.01)

(58) Field of Classification Search

CPC .. C07D 401/14; C07D 493/10; C07D 498/14; C07D 519/00; A61P 35/00; C07F 1/005; C07F 5/003; C07F 5/069; C07F 7/00; C07F 15/00; A61K 47/55; A61K 49/0032; A61K 49/0052; A61K 51/0455; A61K 51/0497

See application file for complete search history.

(56) References Cited

FOREIGN PATENT DOCUMENTS

| | | | | |
|---|---|---|---|---|
| WO | 2002069905 A2 | 9/2002 | | |
| WO | 2002070511 A1 | 9/2002 | | |
| WO | 2002079146 A2 | 10/2002 | | |
| WO | 2005087235 A1 | 9/2005 | | |
| WO | 2006020060 A2 | 2/2006 | | |
| WO | 2013033396 A2 | 3/2013 | | |
| WO | 2013107820 A1 | 7/2013 | | |
| WO | 2015119998 A1 | 8/2015 | | |
| WO | 2015192123 A1 | 12/2015 | | |
| WO | 2018111989 A1 | 6/2018 | | |
| WO | 2019083990 A2 | 5/2019 | | |
| WO | 2019118932 A1 | 6/2019 | | |
| WO | 2019154859 A1 | 8/2019 | | |
| WO | 2019154886 A1 | 8/2019 | | |
| WO | 2020132661 A2 | 6/2020 | | |
| WO | 2020142742 A1 | 7/2020 | | |
| WO | 2021016392 A1 | 1/2021 | | |
| WO | WO-2021055641 A1 | * | 3/2021 | A61K 49/085 |

OTHER PUBLICATIONS

International Search Report for PCT/EP2021/053494 dated May 19, 2021 (4 pages).
Gilmore, Brendan F. et al. "Dipeptide proline diphenyl phosphonates are potent, irreversible inhibitors of seprase (FAPα)." Biochemical and Biophysical Research Communications vol. 346 (2006): 436-446. doi: 10.1016/j.bbrc.2006.05.175.
Hu, Yi et al. "Synthesis and structure—activity relationship of N—alkyl Gly-boro-Pro inhibitors of DPP4, FAP, and DPP7." Bioorganic & Medicinal Chemistry Letters vol. 15 (2005): 4239-4242. doi: 20.1016/j.bmcl.2005.06.075.
Jansen Koen et al. "Selective inhibitors of fibroblast activation protein (FAP) with a xanthine scaffold." Medicinal Chemistry Communications vol. 5 (2014): 1700-1707. doi: 10.1039/c4md00167b.
Jackson, Kenneth W. et al. "Suppression of Tumor Growth in Mice by Rationally Designed Pseudopeptide Inhibitors of Fibroblast Activation Protein and Prolyl Oligopeptidase." Neoplasia vol. 17,1 (2015): 43-54. doi: 10.1016/j.neo.2014.11.002.

(Continued)

*Primary Examiner* — Clinton A Brooks
*Assistant Examiner* — Kyle Nottingham
(74) *Attorney, Agent, or Firm* — Min Yang

(57) ABSTRACT

The present invention relates to ligands of Fibroblast Activation Protein (FAP) for the active delivery of various payloads (e.g. cytotoxic drugs, radionuclides, fluorophores, proteins and immunomodulators) at the site of disease. In particular, the present invention relates to the development of FAP ligands for targeting applications, in particular diagnostic methods and/or methods for therapy or surgery in relation to a disease or disorder, such as cancer, inflammation or another disease characterized by overexpression of FAP.

6 Claims, 33 Drawing Sheets

Specification includes a Sequence Listing.

(56) References Cited

OTHER PUBLICATIONS

Meletta, Romana et al. "Evaluation of the Radiolabeled Boronic Acid-Based FAP Inhibitor MIP-1232 for Atherosclerotic Plaque Imaging." Molecules vol. 20 (2015): 2081-2099. doi: 10.3390/molecules20022081.

Ryabtsova, Oxana et al. "Acylated Gly-(2-cyano)pyrrolidines as inhibitors of fibroblast activation protein (FAP) and the issue of FAP/prolyl oligopeptidase (PREP)-selectivity." Bioorganic & Medicinal Chemistry Letters vol. 22 (2012):3412-3417. doi: 10.1016/j.bmcl.2012.03.107.

Poplawski, Sarah E. et al. "Identification of Selective and Potent Inhibitors of Fibroblast Activation Protein and Prolyl Oligopeptidase." Journal of Medicinal Chemistry vol. 56 (2013): 3467-3477. doi: 10.1021/jm400351a.

Tsai, Ting-Yueh et al. "Substituted 4-carboxymethylpyroglutamic acid diamides as potent and selective inhibitors of fibroblast activation protein." Journal of Medicinal Chemistry vol. 53,18 (2010): 6572-83. doi: 10.1021/jm1002556.

Tsutsumi, Seiji et al. "Synthesis and structure-activity relationships of peptidyl alpha-keto heterocycles as novel inhibitors of prolyl endopeptidase." Journal of Medicinal Chemistry vol. 37,21 (1994): 3492-3502. doi: 10.1021/jm00047a007.

Coutts,S., et al., "Structure-Activity Relationships of Boronic Acid Inhibitors of Dipeptidyl Peptidase IV. 1. Variation of the P2 Position of Xaa-boroPro Dipeptides" J. Med. Chem., vol. 39, pp. 2087-2094 (1996).

Edosada, C., et al., "Selective Inhibition of Fibroblast Activation Protein Protease Based on Dipeptide Substrate Specificity", J. Bio. Chem., vol. 281, No. 11, pp. 7437-7444, Mar. 17, 2006.

Giesel, F., et al., " 68 Ga-FAPI PET/CT: Biodistribution and PreliminaryDosimetry Estimate of 2 DOTA-Containing FAP-Targeting Agents in Patients with Various Cancers" J. Nuclear Medicine, vol. 60, No. 3, pp. 386-392, Mar. 2019.

Jansen, K., et al., "Selective Inhibitors of Fibroblast Activation Protein (FAP) with a (4-Quinolinoyl)-glycyl-2-cyanopyrrolidine Scaffold", ACS Med. Chem. Lett. 2013, vol. 4, pp. 491-496.

Jansen, K., et al., "Extended Structure-Activity Relationship and Pharmacokinetic Investigation of (4-Quinolinoyl) glycyl-2-cyanopyrrolidine Inhibitors of Fibroblast Activation Protein (FAP)", J. Med. Chem. 2014, vol. 57, pp. 3053-3074.

Kratochwil, C., et al., "68Ga-FAPI PET/CT: Tracer Uptake in 28 Different Kinds of Cancer", J. Nucl. Med., vol. 60, No. 6, pp. 801-805, Jun. 2019.

Lindner, T., et al., "Targeting of activated fibroblasts for Imaging and Therapy", EJNMMI Radiopharmacy and Chemistry, 15 pages, 4:16 (2019).

Lindner, T., et al., "Development of Quinoline-Based Theranostic Ligands for the Targeting of Fibroblast Activation Protein", J. Nucl. Med., vol. 59, No. 9, pp. 1415-1422, Sep. 2018.

Loktev, A., et al., "A Tumor-Imaging Method Targeting Cancer-Associated Fibroblasts", J. Nucl. Med.; vol. 59, pp. 1423-1429 (2018).

Meyer, C., et al., " Radiation Dosimetry and Biodistribution of 68Ga-FAPI-46 PET Imaging in Cancer Patients", J. Nucl. Med., vol. 61, pp. 1171-1177 (2020).

Tran, T., et al., "Synthesis and structure-activity relationship of N-acyl-Gly-, N-acyl-Sar- and N-blocked-boroPro inhibitors of FAP, DPP4, and POP", Bioorganic & Medicinal Chemistry Letters 17, pp. 1438-1442 (2007).

Varasteh, Z., et al., "Molecular Imaging of Fibroblast Activity After Myocardial Infarction Using a 68Ga-Labeled Fibroblast Activation Protein Inhibitor, FAPI-04", J. Nucl. Med., vol. 60, pp. 1743-1749 (2019).

Watabe, T., et al., "Theranostics Targeting Fibroblast Activation Protein in the Tumor Stroma: 64Cu- and 225Ac-Labeled FAPI-04 in Pancreatic Cancer Xenograft Mouse Models", J. Nucl. Med., vol. 61, pp. 563-569 (2020).

Xu, J., et al., "The SAR studies on FAP inhibitors as tumor-targeted agents", Med. Chem. Res, 9 pages (2012).

Simon, P., et al., "Identification of Protein Targets of Bioactive Small Molecules Using Randomly Photomodified Probes", ACS Chem. Biol., vol. 13, pp. 3333-3342 (2018).

De Decker, A., et al., "Novel Small Molecule-Derived, Highly Selective Substrates for Fibroblast Activation Protein (FAP)", ACS Med. Chem. Lett., vol. 10, pp. 1173-1179 (2019).

Dvorakova, P., et al., "Inhibitor-Decorated Polymer Conjugates Targeting Fibroblast Activation Protein", J. Med. Chem., vol. 60, pp. 8385-8393 (2017).

* cited by examiner

A)

B)

ESV6-IRDye750 (18)

"HABERKORN-IRDye750" (17)

QCOOH-IRDye750 (16)

"HABERKORN-ValCit-MMAE" (20)

ESV6-ValCit-MMAE (21)

P4

24

A

B

C

15

25

15

A

B

15

15

9

ESV6-IRDye750 (18)

P4

28

29

ESV6-IRDye750 (18)

ESV6-Alexa Fluor 488 (30)

ESV6-Alexa Fluor 488 (30)

A

B

C

ESV6-ValCit-MMAE (21)

QCOOH-ValCit-MMAE (19)

A

B

ESV6-ValCit-MMAE (21)

ESV6-ValCit-MMAE (21)

27

15

ESV6-ValCit-MMAE (21)

ESV6-DOTAGA (8)

P4

SEQUENCE LISTING

<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: peptide linker

<400> SEQUENCE: 1

Asp Arg Asp Cys
1

<210> SEQ ID NO 2
<211> LENGTH: 741
<212> TYPE: PRT
<213> ORGANISM: Homo sapiens
<220> FEATURE:
<223> OTHER INFORMATION: polyhistidine-tagged human Fibroblast Activating Protein (hFAP)

<400> SEQUENCE: 2

```
Leu Arg Pro Ser Arg Val His Asn Ser Glu Glu Asn Thr Met Arg Ala
1               5                   10                  15

Leu Thr Leu Lys Asp Ile Leu Asn Gly Thr Phe Ser Tyr Lys Thr Phe
            20                  25                  30

Phe Pro Asn Trp Ile Ser Gly Gln Glu Tyr Leu His Gln Ser Ala Asp
        35                  40                  45

Asn Asn Ile Val Leu Tyr Asn Ile Glu Thr Gly Gln Ser Tyr Thr Ile
    50                  55                  60

Leu Ser Asn Arg Thr Met Lys Ser Val Asn Ala Ser Asn Tyr Gly Leu
65                  70                  75                  80

Ser Pro Asp Arg Gln Phe Val Tyr Leu Glu Ser Asp Tyr Ser Lys Leu
                85                  90                  95

Trp Arg Tyr Ser Tyr Thr Ala Thr Tyr Tyr Ile Tyr Asp Leu Ser Asn
            100                 105                 110

Gly Glu Phe Val Arg Gly Asn Glu Leu Pro Arg Pro Ile Gln Tyr Leu
        115                 120                 125

Cys Trp Ser Pro Val Gly Ser Lys Leu Ala Tyr Val Tyr Gln Asn Asn
    130                 135                 140

Ile Tyr Leu Lys Gln Arg Pro Gly Asp Pro Pro Phe Gln Ile Thr Phe
145                 150                 155                 160

Asn Gly Arg Glu Asn Lys Ile Phe Asn Gly Ile Pro Asp Trp Val Tyr
                165                 170                 175

Glu Glu Glu Met Leu Ala Thr Lys Tyr Ala Leu Trp Trp Ser Pro Asn
            180                 185                 190

Gly Lys Phe Leu Ala Tyr Ala Glu Phe Asn Asp Thr Asp Ile Pro Val
        195                 200                 205

Ile Ala Tyr Ser Tyr Tyr Gly Asp Glu Gln Tyr Pro Arg Thr Ile Asn
    210                 215                 220

Ile Pro Tyr Pro Lys Ala Gly Ala Lys Asn Pro Val Val Arg Ile Phe
225                 230                 235                 240

Ile Ile Asp Thr Thr Tyr Pro Ala Tyr Val Gly Pro Gln Glu Val Pro
                245                 250                 255

Val Pro Ala Met Ile Ala Ser Ser Asp Tyr Tyr Phe Ser Trp Leu Thr
            260                 265                 270

Trp Val Thr Asp Glu Arg Val Cys Leu Gln Trp Leu Lys Arg Val Gln
        275                 280                 285
```

```
Asn Val Ser Val Leu Ser Ile Cys Asp Phe Arg Glu Asp Trp Gln Thr
    290                 295                 300

Trp Asp Cys Pro Lys Thr Gln Glu His Ile Glu Glu Ser Arg Thr Gly
305                 310                 315                 320

Trp Ala Gly Gly Phe Phe Val Ser Thr Pro Val Phe Ser Tyr Asp Ala
                325                 330                 335

Ile Ser Tyr Tyr Lys Ile Phe Ser Asp Lys Asp Gly Tyr Lys His Ile
            340                 345                 350

His Tyr Ile Lys Asp Thr Val Glu Asn Ala Ile Gln Ile Thr Ser Gly
        355                 360                 365

Lys Trp Glu Ala Ile Asn Ile Phe Arg Val Thr Gln Asp Ser Leu Phe
    370                 375                 380

Tyr Ser Ser Asn Glu Phe Glu Glu Tyr Pro Gly Arg Arg Asn Ile Tyr
385                 390                 395                 400

Arg Ile Ser Ile Gly Ser Tyr Pro Pro Ser Lys Lys Cys Val Thr Cys
                405                 410                 415

His Leu Arg Lys Glu Arg Cys Gln Tyr Tyr Thr Ala Ser Phe Ser Asp
            420                 425                 430

Tyr Ala Lys Tyr Tyr Ala Leu Val Cys Tyr Gly Pro Gly Ile Pro Ile
        435                 440                 445

Ser Thr Leu His Asp Gly Arg Thr Asp Gln Glu Ile Lys Ile Leu Glu
    450                 455                 460

Glu Asn Lys Glu Leu Glu Asn Ala Leu Lys Asn Ile Gln Leu Pro Lys
465                 470                 475                 480

Glu Glu Ile Lys Lys Leu Glu Val Asp Glu Ile Thr Leu Trp Tyr Lys
                485                 490                 495

Met Ile Leu Pro Pro Gln Phe Asp Arg Ser Lys Lys Tyr Pro Leu Leu
            500                 505                 510

Ile Gln Val Tyr Gly Gly Pro Cys Ser Gln Ser Val Arg Ser Val Phe
        515                 520                 525

Ala Val Asn Trp Ile Ser Tyr Leu Ala Ser Lys Glu Gly Met Val Ile
    530                 535                 540

Ala Leu Val Asp Gly Arg Gly Thr Ala Phe Gln Gly Asp Lys Leu Leu
545                 550                 555                 560

Tyr Ala Val Tyr Arg Lys Leu Gly Val Tyr Glu Val Glu Asp Gln Ile
                565                 570                 575

Thr Ala Val Arg Lys Phe Ile Glu Met Gly Phe Ile Asp Glu Lys Arg
            580                 585                 590

Ile Ala Ile Trp Gly Trp Ser Tyr Gly Gly Tyr Val Ser Ser Leu Ala
        595                 600                 605

Leu Ala Ser Gly Thr Gly Leu Phe Lys Cys Gly Ile Ala Val Ala Pro
    610                 615                 620

Val Ser Ser Trp Glu Tyr Tyr Ala Ser Val Tyr Thr Glu Arg Phe Met
625                 630                 635                 640

Gly Leu Pro Thr Lys Asp Asp Asn Leu Glu His Tyr Lys Asn Ser Thr
                645                 650                 655

Val Met Ala Arg Ala Glu Tyr Phe Arg Asn Val Asp Tyr Leu Leu Ile
            660                 665                 670
```

-continued

His Gly Thr Ala Asp Asp Asn Val His Phe Gln Asn Ser Ala Gln Ile
        675                 680                 685

Ala Lys Ala Leu Val Asn Ala Gln Val Asp Phe Gln Ala Met Trp Tyr
    690                 695                 700

Ser Asp Gln Asn His Gly Leu Ser Gly Leu Ser Thr Asn His Leu Tyr
705                 710                 715                 720

Thr His Met Thr His Phe Leu Lys Gln Cys Phe Ser Leu Ser Asp His
                725                 730                 735

His His His His His
            740

<210> SEQ ID NO 3
<211> LENGTH: 4
<212> TYPE: PRT
<213> ORGANISM: Artificial Sequence
<220> FEATURE:
<223> OTHER INFORMATION: compound in claim 7
<220> FEATURE:
<221> NAME/KEY: BINDING
<222> LOCATION: 1
<223> OTHER INFORMATION: binding moiety A
<220> FEATURE:
<221> NAME/KEY: BINDING
<222> LOCATION: 4
<223> OTHER INFORMATION: Cit-PAB-(moiety C)

<400> SEQUENCE: 3

Gly Gly Gly Val
1

<210> SEQ ID NO 4
<211> LENGTH: 4
<212> TYPE: PRT
<213> ORGANISM: Artificial Sequence
<220> FEATURE:
<223> OTHER INFORMATION: compound in claim 7
<220> FEATURE:
<221> NAME/KEY: BINDING
<222> LOCATION: 1
<223> OTHER INFORMATION: binding moiety A
<220> FEATURE:
<221> NAME/KEY: BINDING
<222> LOCATION: 4
<223> OTHER INFORMATION: Cit-PAB-(N(Me)(CH2)2N(Me)C(O))-(moiety C)

<400> SEQUENCE: 4

Gly Gly Gly Val
1

FIBROBLAST ACTIVATION PROTEIN LIGANDS FOR TARGETED DELIVERY APPLICATIONS

This application is a 35 U.S.C. § 371 national stage filing of International Application No. PCT/EP2021/053494, filed on Feb. 12, 2021, which claims priority to EP 20157036.3, filed on Feb. 12, 2020; EP 20172953.0, filed on May 5, 2020; and EP 20202856.9, filed on Oct. 20, 2020.

INTRODUCTION

Field

The present invention relates to ligands of Fibroblast Activation Protein (FAP) for the active delivery of various payloads (e.g. cytotoxic drugs, radionuclides, fluorophores, proteins and immunomodulators) at the site of disease. In particular, the present invention relates to the development of FAP ligands for targeting applications, in particular diagnostic methods and/or methods for therapy or surgery in relation to a disease or disorder, such as cancer, inflammation or another disease characterized by overexpression of FAP.

BACKGROUND OF THE INVENTION

Chemotherapy is still widely applied for the treatment of cancer patients and of other diseases. Conventional anticancer chemotherapeutic agents act on basic mechanisms of cell survival and cannot distinguish between healthy cells and malignant cells. Moreover, those drugs do not accumulate efficiently to the site of the disease upon systemic administration. Unspecific mechanism of actions and inefficient localization at the tumour site account for unsustainable side-effects and poor therapeutic efficacy of conventional chemotherapy.

The development of targeted drugs, able to selectively localize at the site of the disease after systemic administration, is highly desirable. A strategy to generate such drugs is represented by the chemical conjugation of a therapeutic payload, like cytotoxic drugs or radionuclides, to a ligand specific to a marker of a disease. Disease-specific monoclonal antibodies, peptides and small ligands have been considered as ligands of choice for the development of targeted drug products. The use of small ligands for targeting applications has several advantages compared to bigger molecules like peptides and antibodies: more rapid and efficient tumour penetration, lower immunogenicity and lower manufacturing costs.

Small organic ligands specific to prostate-specific membrane antigen, folate receptor and carbonic anhydrase IX have shown excellent biodistribution profiles in preclinical models of cancer and in patients. These ligands have been conjugated to cytotoxic drugs and to radionuclides to generate small molecule-drug conjugate and small molecule-radio conjugate products (SMDCs and SMRCs) for the treatment of cancer. 177-Lutetium-PSMA-617 represents an example of a late stage SMRC which is now being investigated in a phase III trial for the treatment of metastatic castrate-resistant prostate cancer (mCRPC) patients (VISION trial).

Fibroblast activation protein (FAP) is a membrane-bound gelatinase which promotes tumour growth and progression and is overexpressed in cancer-associated fibroblasts. FAP represents an ideal target for the development of targeted SMDCs and SMRCs due to its low expression in normal organs.

WO2019154886 and WO2019154859 describe heterocyclic compounds as fibroblast activation protein-alpha inhibitors used to treat different cancer types. WO2019118932 describes substituted N-containing cyclic compounds as fibroblast activation protein alpha inhibitors used to treat different pathological conditions. WO2019083990 describes imaging and radiotherapeutic targeting fibroblast-activation protein-alpha (FAP-alpha) compounds as FAP-alpha inhibitors used for imaging disease associated with FAP-alpha and to treat proliferative diseases, and notes that the 4-isoquinolinoyl and 8-quinolinoyl derivatives described therein are characterized by very low FAP-affinity. WO2013107820 describes substituted pyrrolidine derivatives used in the treatment of proliferative disorders such as cancers and diseases indicated by tissue remodelling or chronic inflammation such as osteoarthritis. WO2005087235 describes pyrrolidine derivatives as dipeptidyl peptidase IV inhibitors to treat Type II diabetes. WO2018111989 describes conjugates comprising fibroblast activation protein (FAP) inhibitor, bivalent linker and e.g. near infrared (NIR) dye, useful for removing cancer-associated fibroblasts, imaging population of cells in vitro, and treating cancer.

Tsutsumi et al. (J Med Chem 1994) describe the preparation and in vitro prolyl endopeptidase (PEP) inhibitory activity of a series of a-keto heterocyclic compounds. Hu et al. (Bioorg Med Chem Lett 2005) describe the structure-activity relationship of various N-alkyl Gly-boro-Pro derivatives against FAP and other two dipeptidyl peptidases. Edosada et al. (J Biol Chem 2006) describe the dipeptide substrate specificity of FAP and the development of a Ac-Gly-BoroPro FAP-selective inhibitor. Gilmore et al. (Biochem Biophys Res Commun 2006) describe the design, synthesis, and kinetic testing of a series of dipeptide proline diphenyl phosphonates, against DPP-IV and FAP. Tran et al. (Bioorg Med Chem Lett 2007) describe the structure-activity relationship of various N-acyl-Gly-, N-acyl-Sar-, and N-blocked-boroPro derivatives against FAP. Tsai et al. (J Med Chem 2010) describe structure-activity relationship studies that resulted in a number of FAP inhibitors with excellent selectivity over DPP-IV, DPP-II, DPP8, and DPP9. Ryabtsova et al. (Bioorg Med Chem Lett 2012) describe the synthesis and the evaluation of FAP inhibition properties of a series of N-acylated glycyl-(2-cyano)pyrrolidines. Poplawski et al. (J Med Chem 2013) describe N-(pyridine-4-carbonyl)-D-Ala-boroPro as a potent and selective FAP inhibitor. Jansen et al. (ACS Med Chem Lett 2013) describe FAP inhibitors based on the N-(4-quinolinoyl)-Gly-(2-cyanopyrrolidine) scaffold. Jansen et al. (Med Chem Commun 2014) the structure-activity relationship of FAP inhibitors based on the linagliptin scaffold. Jansen et al. (Med Chem Commun 2014) describe xanthine-based FAP inhibitors with low micromolar potency. Jansen et al. (J Med Chem 2014) describe the structure-activity relationship of FAP inhibitors based on the N-4-quinolinoyl-Gly-(2S)-cyanoPro scaffold. Jackson et al. (Neoplasia 2015) describe the development of a pseudopeptide inhibitor of FAP. Meletta et al. (Molecules 2015) describe the use of a boronic-acid based FAP inhibitor as non-invasive imaging tracers of atherosclerotic plaques. Dvoriakovi et al. (J Med Chem 2017) describe the preparation of a polymer conjugate containing a FAP-specific inhibitor for targeting applications. Loktev et al. (J Nucl Med 2018) describe the development of an iodinated and a DOTA-coupled radiotracer based on a FAP-specific enzyme inhibitor. Lindner et al. (J Nucl Med 2018) describe the modification and optimization of FAP inhibitors for use as theranostic tracers. Giesel et al. (J Nucl Med 2019) describe the clinical imaging performance of quinoline-based PET tracers that act as FAP inhibitors.

Problems to be Solved by the Invention

The present invention aims at the problem of providing improved binders (ligands) of fibroblast activation protein (FAP) suitable for targeting applications. The binders should be suitable for inhibition of FAP and/or targeted delivery of a payload, such as a therapeutic or diagnostic agent, to a site afflicted by or at risk of disease or disorder characterized by overexpression of FAP. Preferably, the binder should form a stable complex with FAP, display an increased affinity, increased inhibitory activity, a slower rate of dissociation from the complex, and/or prolonged residence at a disease site.

SUMMARY OF THE INVENTION

The present inventors have found novel organic ligands of fibroblast activation protein (FAP) suitable for targeting applications. The compounds according to the present invention (also referred to as ligands or binders) comprise a small binding moiety A having the following structure:

A

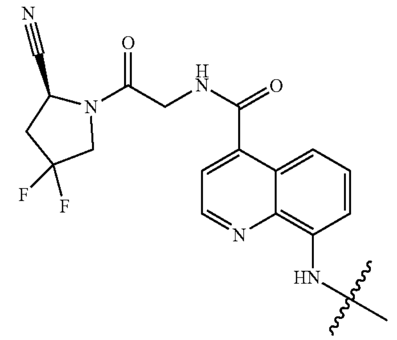

A compound according to the present invention may be represented by following general Formula I, Formula I

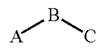

its individual diastereoisomers, its hydrates, its solvates, its crystal forms, its individual tautomers or a pharmaceutically acceptable salt thereof, wherein A is a binding moiety; B is a covalent bond or a moiety comprising a chain of atoms that covalently attaches the moieties A und C; and C is a payload moiety.

The present invention further provides a pharmaceutical composition comprising said compound and a pharmaceutically acceptable excipient.

The present invention further provides said compound or pharmaceutical composition for use in a method for treatment of the human or animal body by surgery or therapy or a diagnostic method practised on the human or animal body; as well as a method for treatment of the human or animal body by surgery or therapy or a diagnostic method practised on the human or animal body comprising administering a therapeutically or diagnostically effective amount of said compound or pharmaceutical composition to a subject in need thereof.

The present invention further provides said compound or pharmaceutical composition for use in a method for therapy or prophylaxis of a subject suffering from or having risk for a disease or disorder; as well as a method for treatment therapy or prophylaxis of a disease or disorder comprising administering a therapeutically or diagnostically effective amount of said compound or pharmaceutical composition to a subject suffering from or having risk for said disease or disorder.

The present invention further provides said compound or pharmaceutical composition for use in a method for guided surgery practised on a subject suffering from or having risk for a disease or disorder; as well as a method for guided surgery comprising administering a therapeutically or diagnostically effective amount of said compound or pharmaceutical composition to a subject suffering from or having risk for a disease or disorder.

The present invention further provides said compound or pharmaceutical composition for use in a method for diagnosis of a disease or disorder, the method being practised on the human or animal body and involving a nuclear medicine imaging technique, such as Positron Emission Tomography (PET); as well as a method for diagnosis of a disease or disorder, the method being practised on the human or animal body and involving a nuclear medicine imaging technique, such as Positron Emission Tomography (PET), and comprising administering a therapeutically or diagnostically effective amount of said compound or pharmaceutical composition to a subject in need thereof.

The present invention further provides said compound or pharmaceutical composition for use in a method for targeted delivery of a therapeutic or diagnostic agent to a subject suffering from or having risk for a disease or disorder; as well as a method for targeted delivery of a therapeutically or diagnostically effective amount of said compound or pharmaceutical composition to a subject suffering from or having risk for a disease or disorder.

Preferably, the aforementioned disease or disorder is characterized by overexpression of FAP and is independently selected from cancer, inflammation, atherosclerosis, fibrosis, tissue remodelling and keloid disorder, preferably wherein the cancer is selected from the group consisting of breast cancer, pancreatic cancer, small intestine cancer, colon cancer, multi-drug resistant colon cancer, rectal cancer, colorectal cancer, metastatic colorectal cancer, lung cancer, non-small cell lung cancer, head and neck cancer, ovarian cancer, hepatocellular cancer, oesophageal cancer, hypopharynx cancer, nasopharynx cancer, larynx cancer, myeloma cells, bladder cancer, cholangiocarcinoma, clear cell renal carcinoma, neuroendocrine tumour, oncogenic osteomalacia, sarcoma, CUP (carcinoma of unknown primary), thymus cancer, desmoid tumours, glioma, astrocytoma, cervix cancer, skin cancer, kidney cancer and prostate cancer. More preferably, the disease or disorder is selected from melanoma and renal cell carcinoma.

25: Structure, chromatographic profile and LC/MS analysis of conjugate 15. MS(ES+) m/z 1348.36 $(M+1H)^+$.

Figure 26:
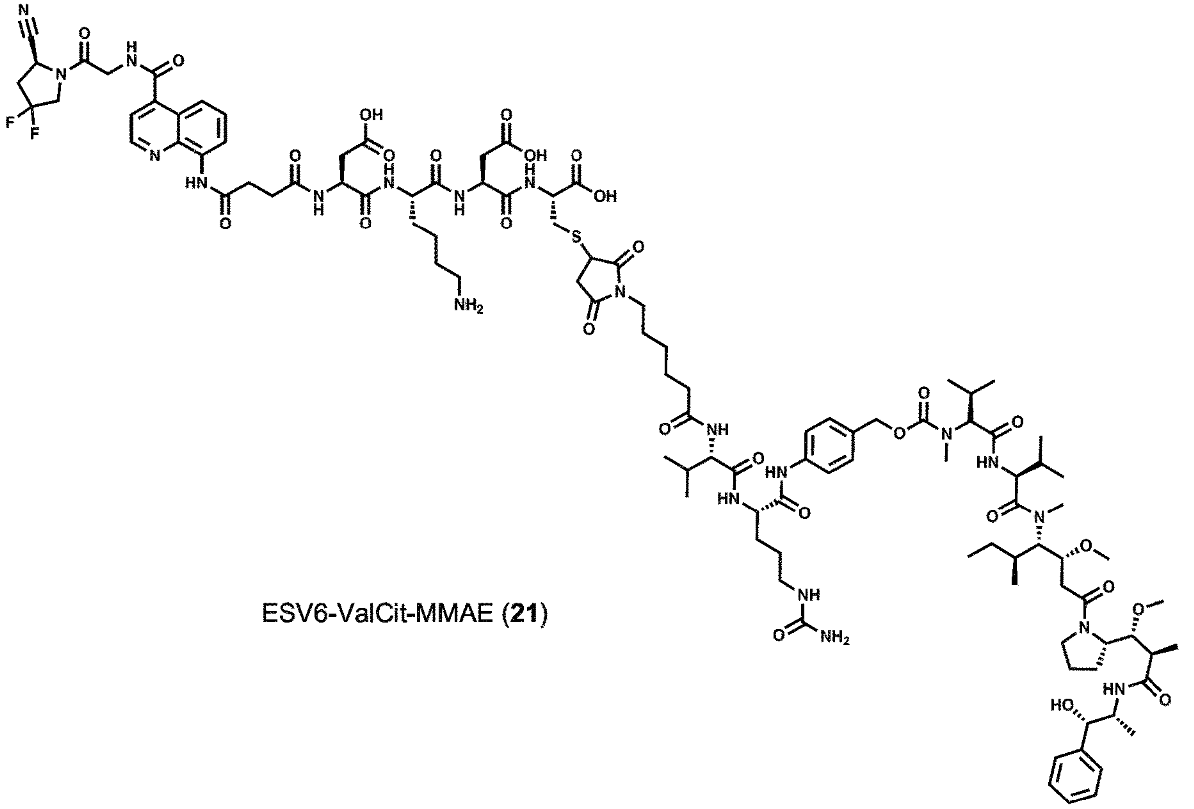
Figure 26:
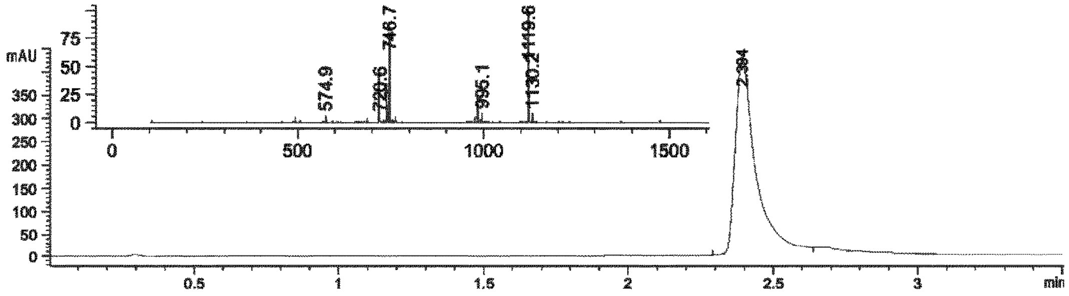

FIG. 26: Structure, chromatographic profile and LC/MS analysis of ESV6-ValCit-MMAE (21). MS(ES+) m/z 1118.05 $(M+2H)^{2+}$.

Figure 27:
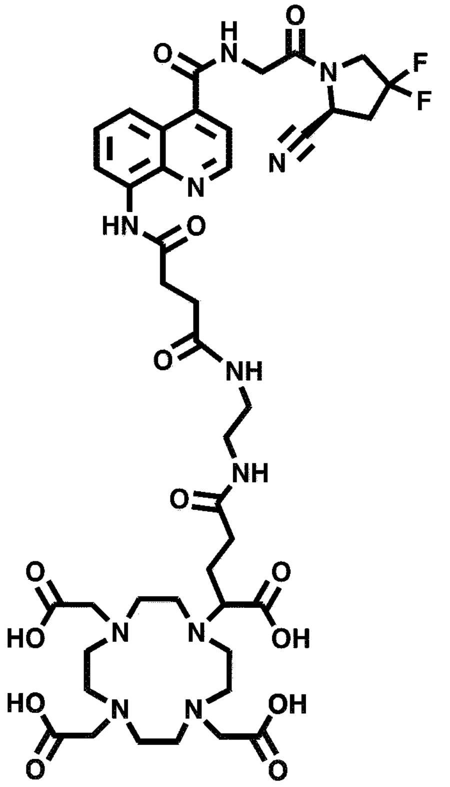
Figure 27:
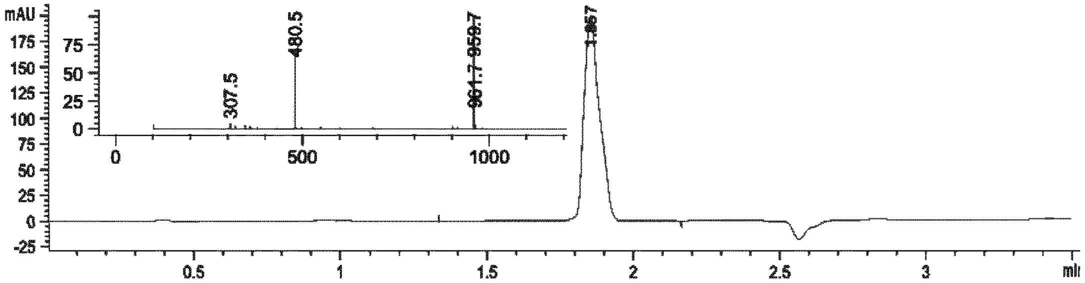

FIG. 27: Structure, chromatographic profile and LC/MS analysis of ESV6-DOTAGA (8). MS(ES+) m/z 960.39 $(M+H)^+$.

Figure 28:
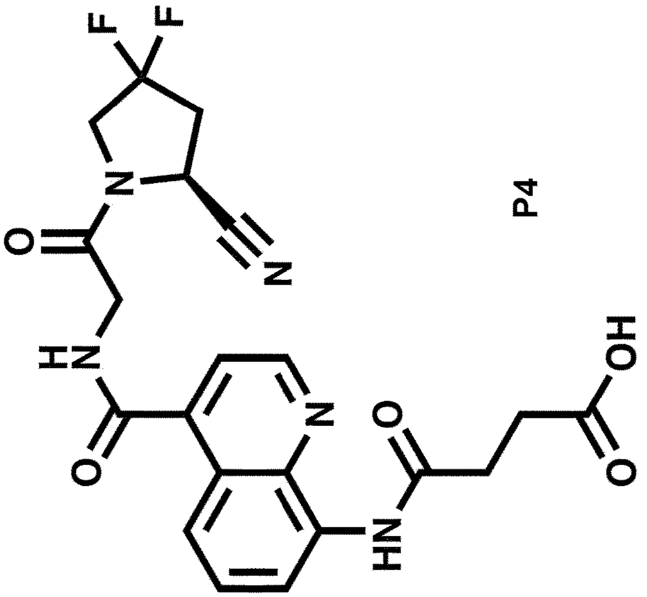
Figure 28:
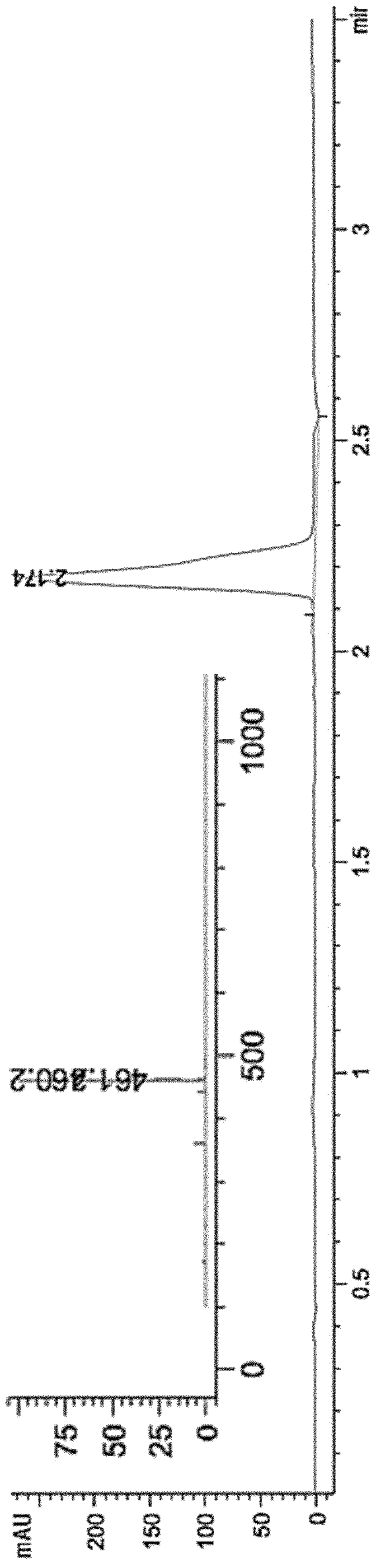

FIG. 28: Structure, chromatographic profile and LC/MS analysis of Example 2, P4. MS(ES+) m/z 460.21 $(M+H)^+$.

DETAILED DESCRIPTION OF THE INVENTION

The present inventors have identified small molecule binders of fibroblast activation protein (FAP) which are suitable for targeting applications. The binders according to the invention provide high inhibition of FAP, high affinity for FAP and/or are suitable for targeted delivery of a payload, such as a therapeutic or diagnostic agent, to a site afflicted by or at risk of disease or disorder characterized by overexpression of FAP. The binders according to the present invention form a stable complex with FAP, display an increased affinity, increased inhibitory activity, a slower rate of dissociation from the complex, and/or prolonged residence at a disease site. The binders according to the invention further can have an increased tumour-to-liver, tumour-to-kidney and/or tumour-to-intestine uptake ratio; a more potent anti-tumour effect (e.g., measured by mean tumour volume increase), and/or lower toxicity (e.g., as assessed by the evaluation of changes (%) in body weight). The binders according to the invention further can have a high or improved affinity for human and murine fibroblast activation protein and/or cross-reactivity to the murine antigen. The binders according to the invention preferably attain FAP-specific cellular binding; FAP-selective accumulation on the cell membrane; FAP-selective accumulation inside the cytosol. The binders according to the invention can further preferably, rapidly and homogeneously localize at the tumour site in vivo with a high tumour-to-organs selectivity, in particular for melanoma and/or renal cell carcinoma. Binders according to the invention comprising a radioactive payload (e.g., $^{177}$Lu) preferably attain dose-dependent response, with target saturation reached between 250 nmol/Kg and 500 nmol/Kg reached and/or maintained at up to 12 h, more preferably 1 to 9 h, further more preferably 3 to 6 h after intravenous administration.

As explained above, the present invention provides a compound, its individual diastereoisomers, its hydrates, its solvates, its crystal forms, its individual tautomers or a pharmaceutically acceptable salt thereof, wherein the compound comprises a moiety A having the following structure:

A

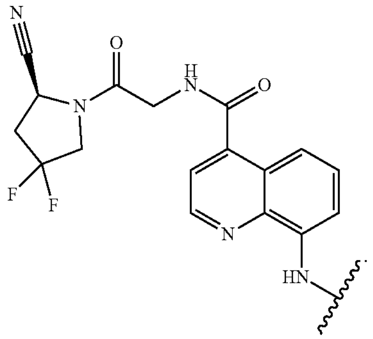

As explained above, a compound according to the present invention may be represented by Formula I:

Formula I

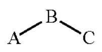

Therein, B is a covalent bond or a moiety comprising a chain of atoms covalently attaching A to C; and C may be an atom, a molecule or a particle, and/or is a therapeutic or diagnostic agent.

Accordingly, a compound according to the present invention may comprise a moiety having the following structure:

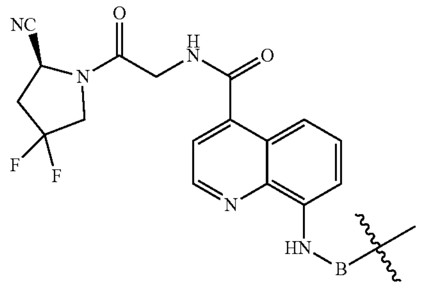

wherein B is a covalent bond or a moiety comprising a chain of atoms covalently bound atoms.

Moiety A

Without wishing to be bound by any theory, it is contemplated that these surprising technical effects are associated with the particular structure of the small binding moiety A wherein the quinoline ring is substituted at the 8-position by a nitrogen-containing group, such as an amino or amido group:

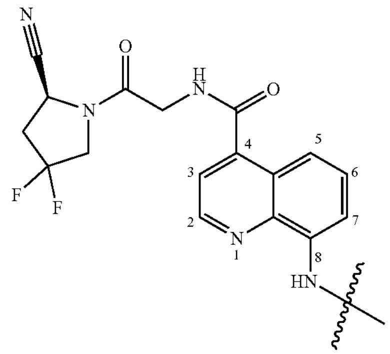

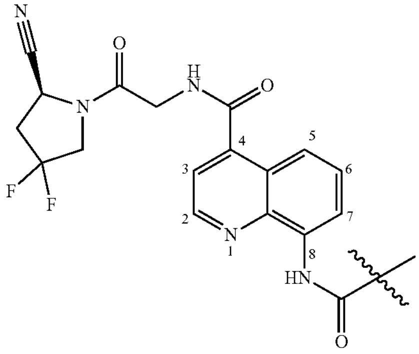

It has been previously shown that the higher target protein affinity of a compound results in longer tumour residence in vivo (Wichert et al., *Nature Chemistry* 7, 241-249 (2015)). The compounds of the present invention have an increased affinity, slower dissociation rate with respect to FAP as compared to prior art compounds, and therefore are also considered to as having a prolonged residence at the disease site at a therapeutically or diagnostically relevant level, preferably beyond 1 h, more preferably beyond 6 h post injection. Preferably, the highest enrichment is achieved after 5 min, 10 min, 20 min, 30 min, 45 min, 1 h, 2 h, 3 h, 4 h, 5 h or 6 h; and/or enrichment in the disease site is maintained at a therapeutically or diagnostically relevant level, over a period of or at least for 5 min, 10 min, 20 min, 30 min, 45 min, 1 h, 2 h, 3 h, 4 h, 5 h or 6 h, more preferably beyond 6 h post injection.

Preferably, the binding moiety A has the following structure $A^1$; more preferably the following structure $A^2$, wherein m is 0, 1, 2, 3, 4 or 5, preferably 1:

$A^1$

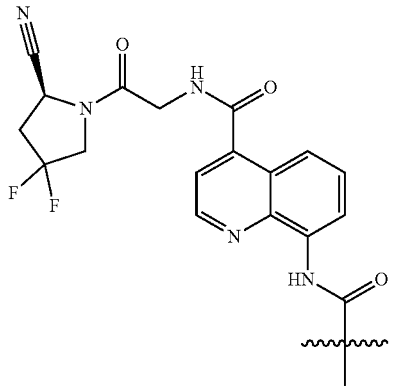

$A^2$

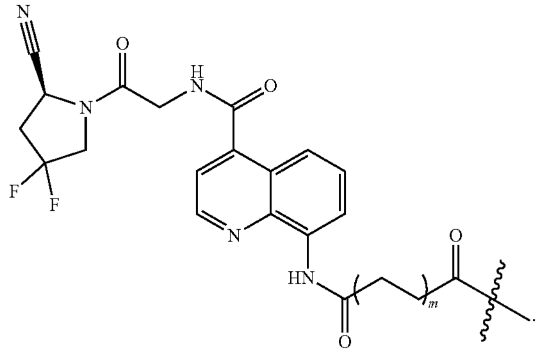

Moiety B

Moiety B is a covalent bond or a moiety comprising a chain of atoms that covalently attaches A to the payload C, e.g., through one or more covalent bond(s). The moiety B may be cleavable or non-cleavable, bifunctional or multi-functional moiety which can be used to link one or more payload and/or binder moieties to form the targeted conjugate of the invention. In some embodiments, the structure of the compound comprises, independently, more than one moieties A, preferably 2, 3, 4, 5, 6, 7, 8, 9 or 10 moieties A; and/or more than one moieties C, preferably 2, 3, 4, 5, 6, 7, 8, 9 or 10 moieties C per molecule. Preferably, the structure of the compound comprises 2 moieties A and 1 moiety C; or 1 moiety A and 2 moieties C per molecule.

When cleavable linker units are present within moiety B, release mechanisms can be identical to those specific to antibodies linked to cytotoxic payloads. Indeed, the nature of the binding moieties is independent in that respect. Therefore, there is envisaged pH-dependent [Leamon, C. P. et al (2006) *Bioconjugate Chem.,* 17, 1226; Casi, G. et al (2012) *J. Am. Chem. Soc.,* 134, 5887], reductive [Bernardes, G. J. et al (2012) *Angew. Chem. Int. Ed Engl.,* 51. 941; Yang, J. et al (2006) *Proc. Natl. Acad Sci. USA,* 103, 13872] and enzymatic release [Doronina S. O. et al (2008) *Bioconjugate Chem,* 19 1960; Sutherland, M. S. K. (2006) *J. Biol. Chem,* 281, 10540]. In a specific setting, when functional groups are present on either the binding moiety or payloads (e.g. thiols, alcohols) a linkerless connection can be established thus releasing intact payloads, which simplifies substantially pharmacokinetic analysis.

Moiety B can comprise or consist of a unit shown in Table 1 below wherein the substituents R and R″ shown in the formulae may suitably be independently selected from H, halogen, substituted or unsubstituted (hetero)alkyl, (hetero) alkenyl, (hetero)alkynyl, (hetero)aryl, (hetero)arylalkyl, (hetero)cycloalkyl, (hetero)cycloalkylaryl, heterocyclylalkyl, a peptide, an oligosaccharide or a steroid group. Preferably, each of R, $R_1$, $R_2$ and $R_3$ is independently selected from H, OH, SH, $NH_2$, halogen, cyano, carboxy, alkyl, cycloalkyl, aryl and heteroaryl, each of which is substituted or unsubstituted. Suitably R and R″ are independently selected from H, or C1-C7 alkyl or heteroalkyl. More suitably, R and R″ are independently selected from H, methyl or ethyl.

TABLE 1

| Linker | Structure | Release mechanism |
|---|---|---|
| Amide | 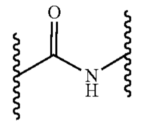 [SMILES: *NC(*)=O] | Proteolysis |
| | 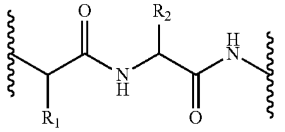 | |
| Ester | 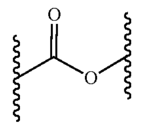 [SMILES: *OC(*)=O] | Hydrolysis |
| Carbamate | 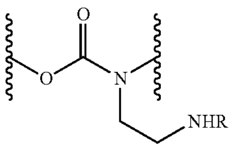 R = H, Me | Hydrolysis |
| Hydrazone | 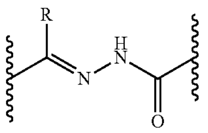 | Hydrolysis |

TABLE 1-continued

| Linker | Structure | Release mechanism |
|---|---|---|
| Thiazolidine | 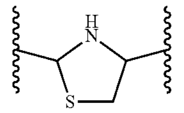 [SMILES: *C1CSC(*)N1] | Hydrolysis |
| Methylene alkoxy carbamate | 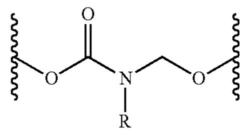 | Hydrolysis |
| Disulfide | 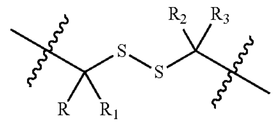 | Reduction |

Moiety B, unit(s) $B_L$ and/or unit(s) $B_S$ may suitably comprise as a cleavable bond a disulfide linkage since these linkages are stable to hydrolysis, while giving suitable drug release kinetics at the target in vivo, and can provide traceless cleavage of drug moieties including a thiol group.

Moiety B, unit(s) $B_L$ and/or unit(s) $B_S$ may be polar or charged in order to improve water solubility of the conjugate. For example, the linker may comprise from about 1 to about 20, suitably from about 2 to about 10, residues of one or more known water-soluble oligomers such as peptides, oligosaccharides, glycosaminoglycans, polyacrylic acid or salts thereof, polyethylene glycol, polyhydroxyethyl (meth) acrylates, polysulfonates, etc. Suitably, the linker may comprise a polar or charged peptide moiety comprising e.g. from 2 to 10 amino acid residues. Amino acids may refer to any natural or non-natural amino acid. The peptide linker suitably includes a free thiol group, preferably a N-terminal cysteine, for forming the said cleavable disulfide linkage with a thiol group on the drug moiety. Any peptide containing L- or D-aminoacids can be suitable; particularly suitable peptide linkers of this type are Asp-Arg-Asp-Cys and/or Asp-Lys-Asp-Cys.

In these and other embodiments, moiety B, unit(s) $B_L$ and/or unit(s) $B_S$ may comprise a cleavable or non-cleavable peptide unit that is specifically tailored so that it will be selectively enzymatically cleaved from the drug moiety by one or more proteases on the cell surface or the extracellular regions of the target tissue. The amino acid residue chain length of the peptide unit suitably ranges from that of a single amino acid to about eight amino acid residues. Numerous specific cleavable peptide sequences suitable for use in the present invention can be designed and optimized in their selectivity for enzymatic cleavage by a particular tumour-associated enzyme e.g. a protease. Cleavable peptides for use in the present invention include those which are optimized toward the proteases MMP-1, 2 or 3, or cathepsin B, C or D. Especially suitable are peptides cleavable by Cathepsin B. Cathepsin B is a ubiquitous cysteine protease.

It is an intracellular enzyme, except in pathological conditions, such as metastatic tumours or rheumatoid arthritis. An example for a peptide cleavable by Cathepsin B is containing the sequence Val-Cit.

In any of the above embodiments, the moiety B and in particular, unit(s) $B_L$ suitably further comprise(s) self-immolative moiety can or cannot be present after the linker. The self-immolative linkers are also known as electronic cascade linkers. These linkers undergo elimination and fragmentation upon enzymatic cleavage of the peptide to release the drug in active, preferably free form. The conjugate is stable extracellularly in the absence of an enzyme capable of cleaving the linker. However, upon exposure to a suitable enzyme, the linker is cleaved initiating a spontaneous self-immolative reaction resulting in the cleavage of the bond covalently linking the self-immolative moiety to the drug, to thereby effect release of the drug in its underivatized or pharmacologically active form. In these embodiments, the self-immolative linker is coupled to the binding moiety through an enzymatically cleavable peptide sequence that provides a substrate for an enzyme to cleave the amide bond to initiate the self-immolative reaction. Suitably, the drug moiety is connected to the self-immolative moiety of the linker via a chemically reactive functional group pending from the drug such as a primary or secondary amine, hydroxyl, sulfhydryl or carboxyl group.

Examples of self-immolative linkers are PABC or PAB (para-aminobenzyloxycarbonyl), attaching the drug moiety to the binding moiety in the conjugate (Carl et al (1981) J. Med. Chem. 24: 479-480; Chakravarty et al (1983) J. Med. Chem. 26: 638-644). The amide bond linking the carboxy terminus of a peptide unit and the para-aminobenzyl of PAB may be a substrate and cleavable by certain proteases. The aromatic amine becomes electron-donating and initiates an electronic cascade that leads to the expulsion of the leaving group, which releases the free drug after elimination of carbon dioxide (de Groot, et al (2001) Journal of Organic Chemistry 66 (26): 8815-8830). Further self-immolating linkers are described in WO2005/082023.

In yet other embodiments, the linker comprises a glucuronyl group that is cleavable by glucoronidase present on the cell surface or the extracellular region of the target tissue. It has been shown that lysosomal beta-glucuronidase is liberated extracellularly in high local concentrations in necrotic areas in human cancers, and that this provides a route to targeted chemotherapy (Bosslet, K. et al. *Cancer Res.* 58, 1195-1201 (1998)).

In any of the above embodiments, the moiety B suitably further comprises a spacer unit. A spacer unit can be the unit $B_S$, which may be linked to the binding moiety A, for example via an amide, amine or thioether bond. The spacer unit is of a length that enables e.g. the cleavable peptide sequence to be contacted by the cleaving enzyme (e.g. cathepsin B) and suitably also the hydrolysis of the amide bond coupling the cleavable peptide to the self-immolative moiety X. Spacer units may for example comprise a divalent radical such as alkylene, arylene, a heteroarylene, repeating units of alkyloxy (e.g. polyethylenoxy, PEG, polymethyleneoxy) and alkylamino (e.g. polyethyleneamino), or diacid ester and amides including succinate, succinamide, diglycolate, malonate, and caproamide.

In any of the embodiments described therein, * represents a point of attachment to moiety A or a point of attachment for which the shortest path to moiety A comprises less atoms than that for •, as the case may be; and • represents a point of attachment a point of attachment to moiety C or a point of attachment to moiety C for which the shortest path to moiety C comprises less atoms than that for *, as the case may be. The same applies also for cases where a reactive moiety L is present rather than payload moiety C. The following notations and all have the meaning of a point of attachment of a certain group or atom (e.g., R) to a further moiety:

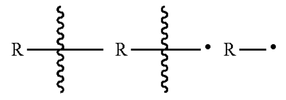

If the structure of relevance is a peptide mono- or oligomer, each * represents a point of attachment for which the shortest path to moiety A comprises less atoms than that for •; and each • represents a point of attachment for which the shortest path to moiety C comprises less atoms than that for *, with the proviso that when n is >1 and a respective point of attachment is indicated on any one of $R^a$, $R^b$ and $R^c$, then it can be independently present in one or more of the peptide monomeric units, preferably in one peptide monomeric unit most distant from the other point of attachment indicated in the respective structure.

In any of the embodiments described herein, the terms "peptide", "dipeptide", "tripeptide", "tetrapeptide" etc. refer to peptide mono- or oligomers having a backbone formed by proteinogenic and/or a non-proteinogenic amino acids. As used herein, the terms "aminoacyl" or "aminoacid" generally refer to any proteinogenic or a non-proteinogenic amino acid. Preferably, in any of the embodiments disclosed therein, the side-chain residues of a proteinogenic or a non-proteinogenic amino acid are represented by any of $R^a$, $R^b$ and $R^c$, each of which is selected from the following list:

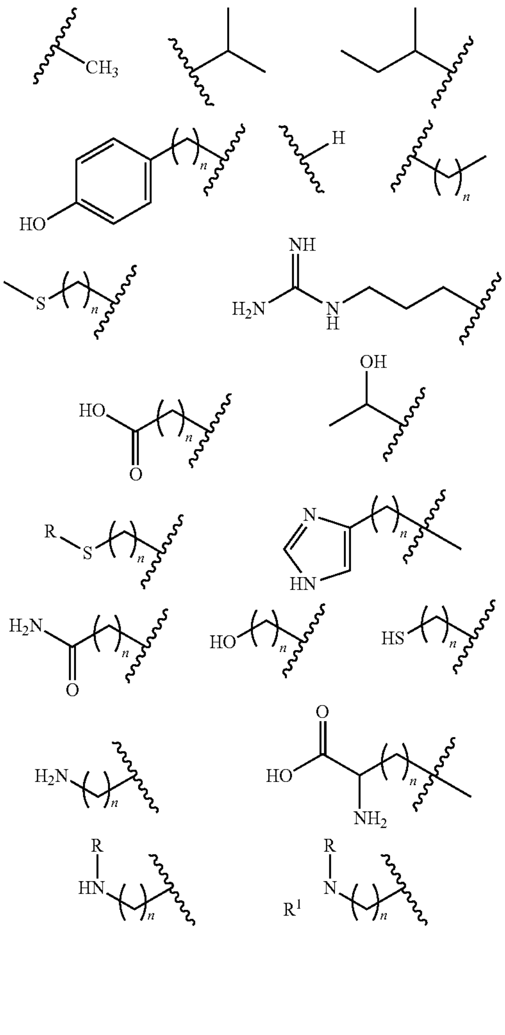

-continued

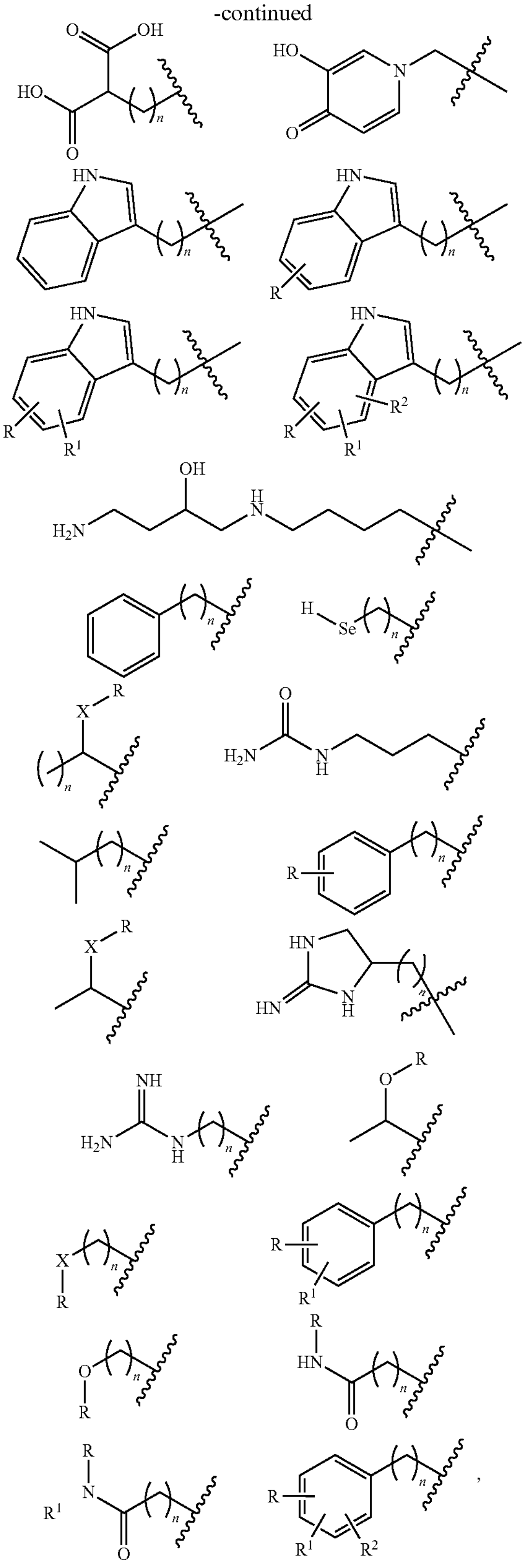

, wherein each of R, $R^1$, $R^2$ and $R^3$ is independently selected from H, OH, SH, $NH_2$, halogen, cyano, carboxy, alkyl, cycloalkyl, aryl and heteroaryl, each of which is substituted or unsubstituted;

each X is independently selected from NH, NR, S, O and $CH_2$, preferably NH; and each n and m is independently an integer preferably selected from 0, 1, 2, 3, 4, 5, 6, 7, 8, 9, 10, 11, 12, 13, 14, 15, 16, 17, 18, 19 and 20.

Preferably, in any of the embodiments disclosed therein, side-chain residues of a proteinogenic or a non-proteinogenic amino acid are represented by any of $R^a$, $R^b$ and $R^c$, each of which may be part of a 3-, 4-, 5-, 6- or 7-membered ring. For instance, the side chain alpha, beta and/or gamma position of said proteinogenic or non-proteinogenic amino acid can be part of a cyclic structure selected from an azetidine ring, pyrrolidine ring and a piperidine ring, such as in the following aminoacids (proline and hydroxyproline):

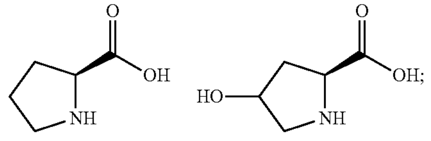 [SMILES: O=C(O)[C@@H]1CCCN1 ; O=C(O)[C@@H]1CC(O)CN1]

or each of which may independently be part of an unsaturated structure (i.e. wherein the H atom geminal to the respective group $R^a$, $R^b$ and $R^c$ is absent), e.g.:

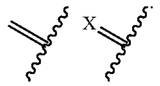

Further preferable non-proteinogenic amino acids can be selected from the following list:

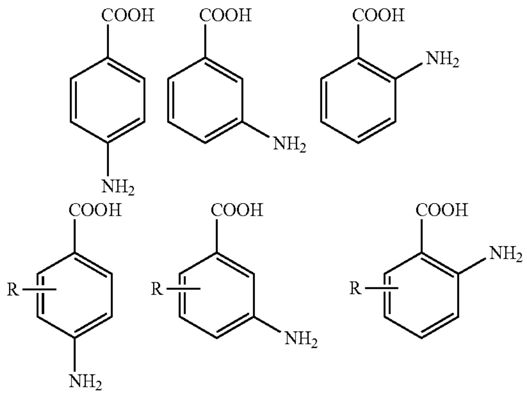

Particularly preferred embodiments for the moiety B as well as the compound according to the present invention are shown in the appended claims.

Preferably, B is represented by any of the following general Formulae II-V, wherein:

Formula II

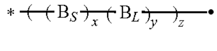

Formula III

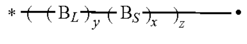

-continued

Formula IV

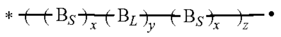

Formula V

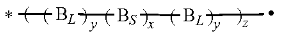

each x is an integer independently selected from the range of 0 to 100, preferably 0 to 50, more preferably 0 to 30, yet more preferably selected from 0, 1, 2, 3, 4, 5, 6, 7, 8, 9, 10, 11, 12, 13, 14, 15, 16, 17, 18, 19 and 20;

each y is an integer independently selected from the range of 0 to 30, preferably selected from 0, 1, 2, 3, 4, 5, 6, 7, 8, 9, 10, 11, 12, 13, 14, 15, 16, 17, 18, 19 and 20;

each z is an integer independently selected from the range of 0 to 5, preferably selected from selected from 0, 1, 2, 3 and 4; and

* represents a point of attachment to moiety A; and

• represents a point of attachment to moiety C, wherein:

(a) $B_S$ and/or $B_L$ is a group comprising or consisting of a structural unit independently selected from the group consisting of alkylene, cycloalkylene, arylalkylene, heteroarylalkylene, heteroalkylene, heterocycloalkylene, alkenylene, cycloalkenylene, arylalkenylene, heteroarylalkenylene, heteroalkenylene, heterocycloalenkylene, alkynylene, heteroalkynylene, arylene, heteroarylene, aminoacyl, oxyalkylene, aminoalkylene, diacid ester, dialkylsiloxane, amide, thioamide, thioether, thioester, ester, carbamate, hydrazone, thiazolidine, methylene alkoxy carbamate, disulfide, vinylene, imine, imidamide, phosphoramide, saccharide, phosphate ester, phosphoramide, carbamate, dipeptide, tripeptide, tetrapeptide, each of which is substituted or unsubstituted; and/or (b) $B_S$ and/or $B_L$ is a group comprising or consisting of a structural unit independently selected from the group consisting of:

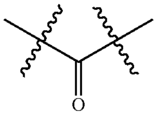
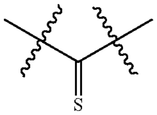
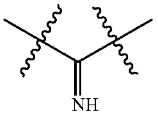
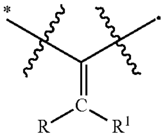
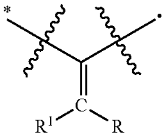
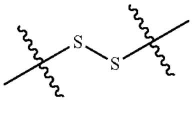
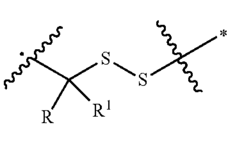
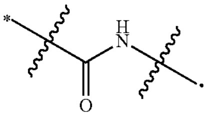
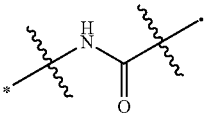
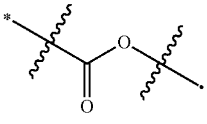
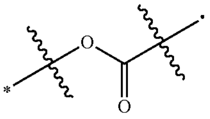
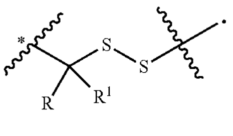
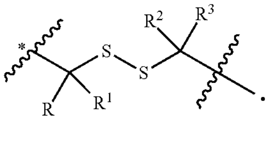

-continued

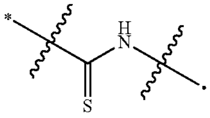
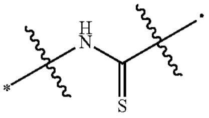
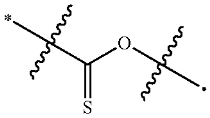
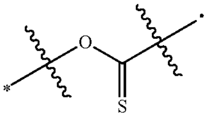
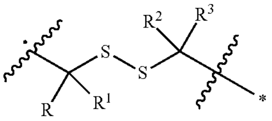
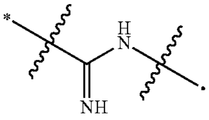
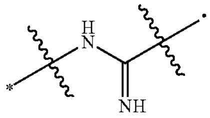
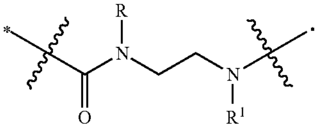
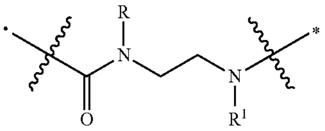
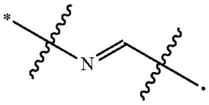
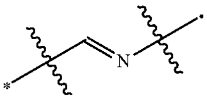
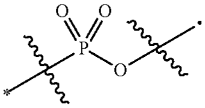
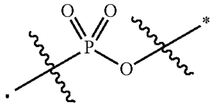
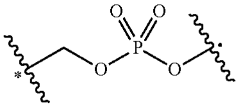
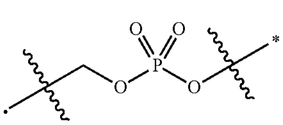
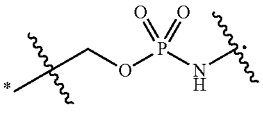
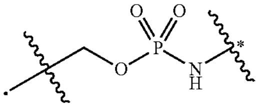
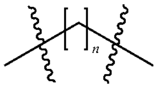
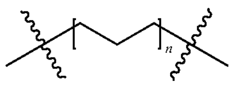
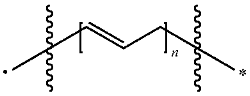
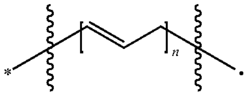
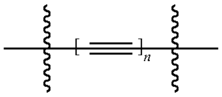
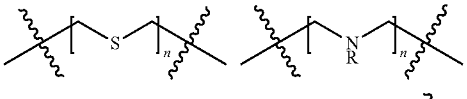
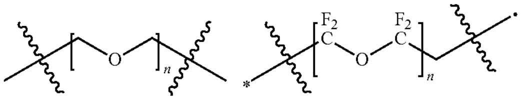
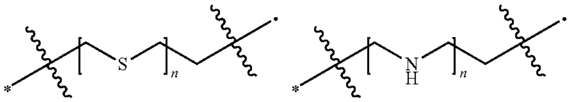

-continued
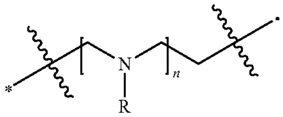
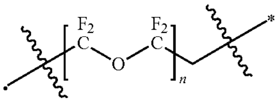
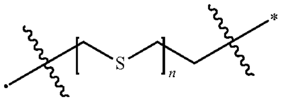
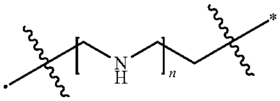
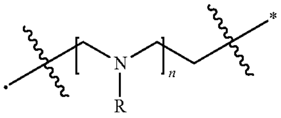
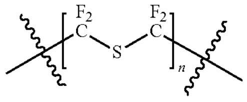
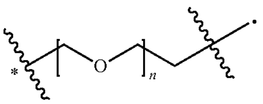
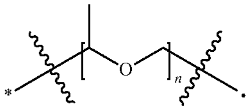
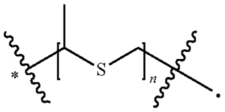
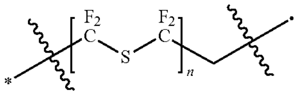
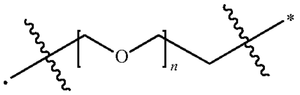
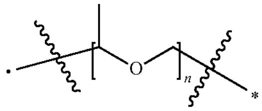
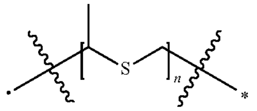
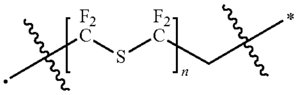
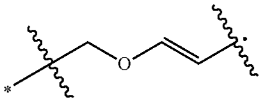
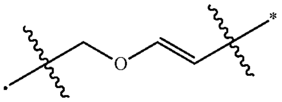
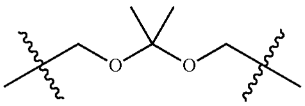
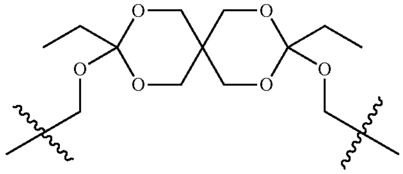
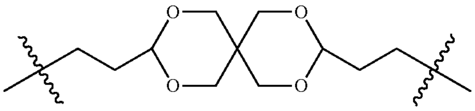
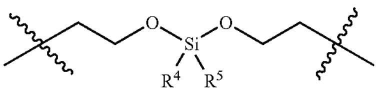
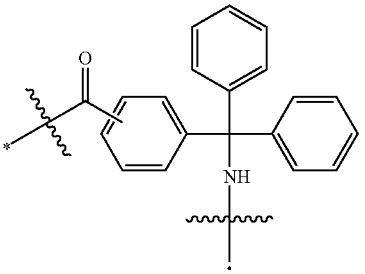
-continued
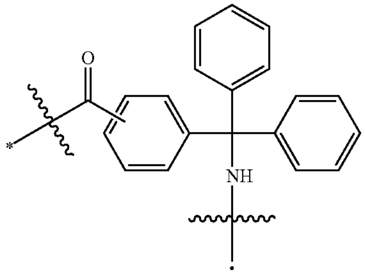
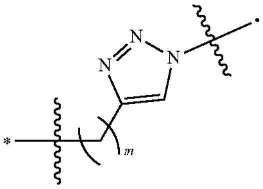
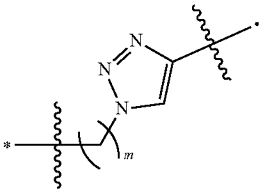
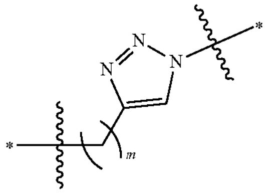
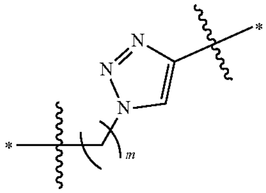
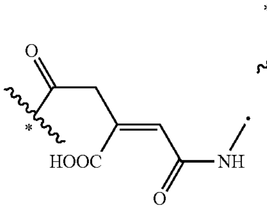
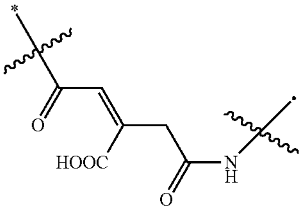
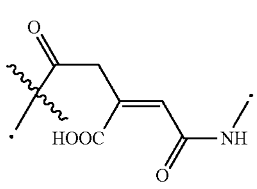
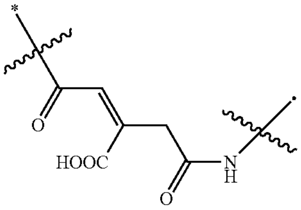
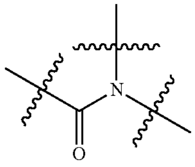
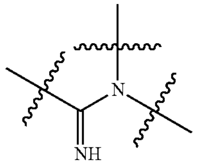
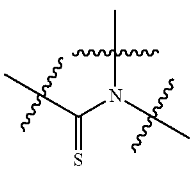
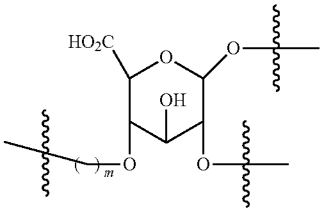
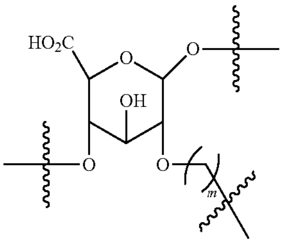

-continued
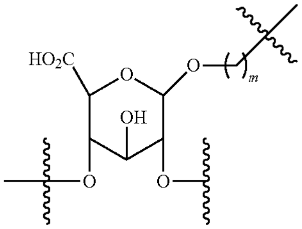
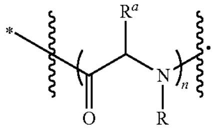
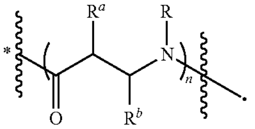
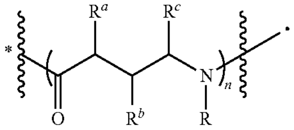
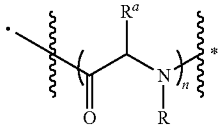
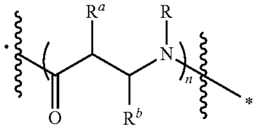
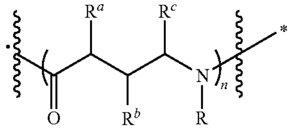
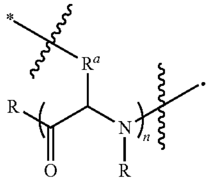
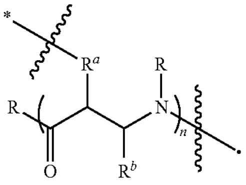
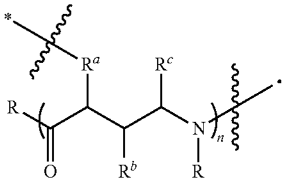
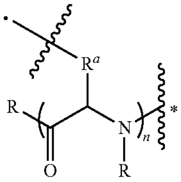
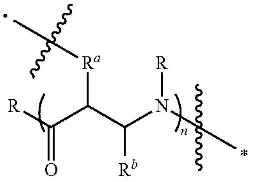
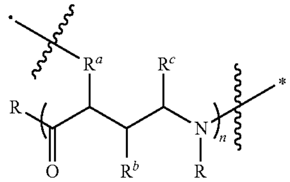
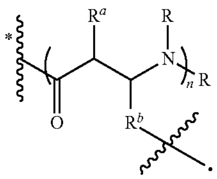
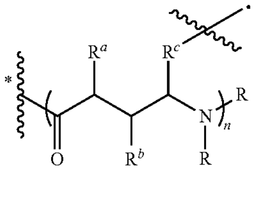
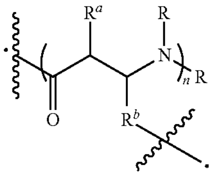
-continued
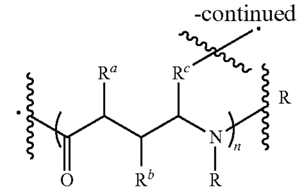
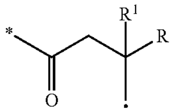
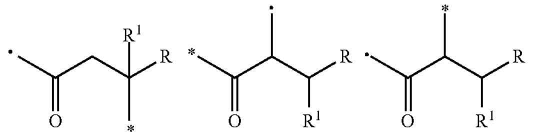
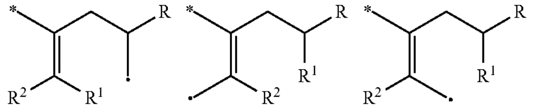
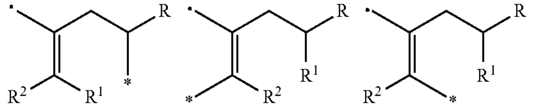
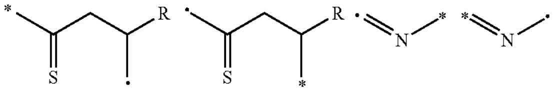
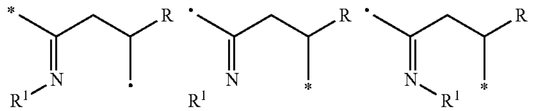
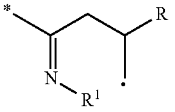
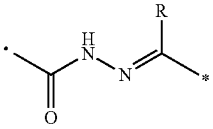
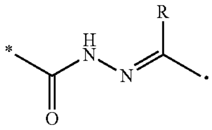
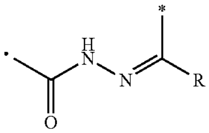
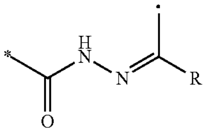
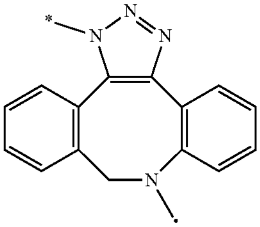
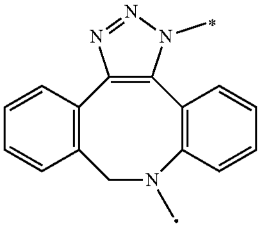
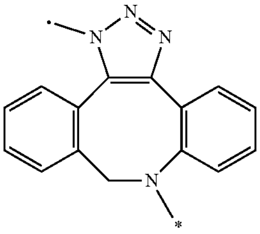
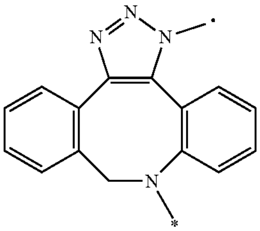
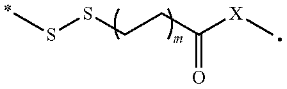

-continued

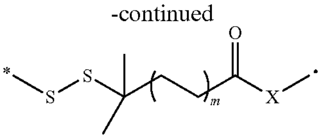

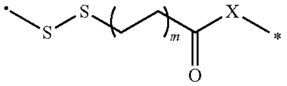

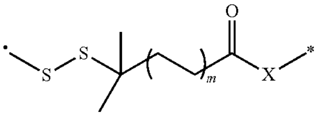

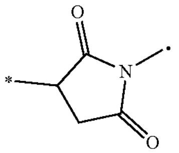

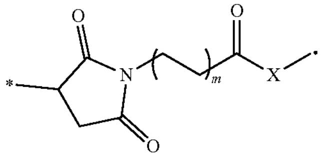

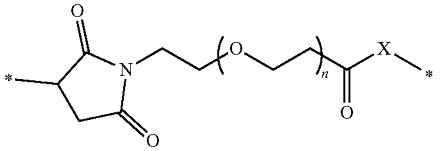

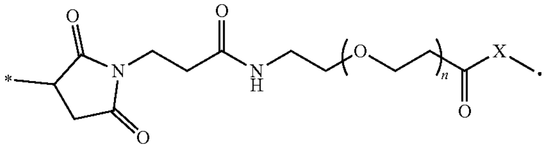

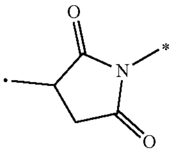

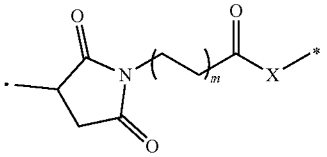

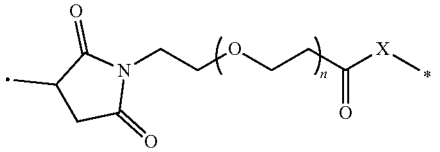

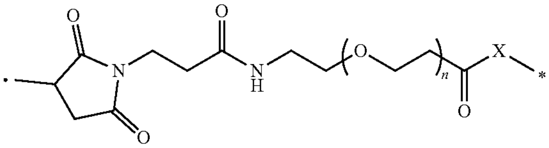

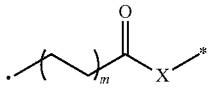

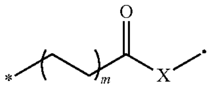

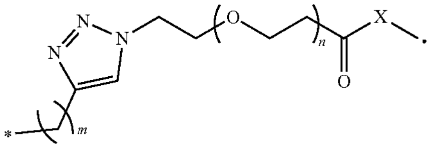

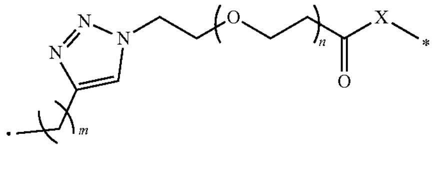

wherein each of R, $R^1$, $R^2$ and $R^3$ is independently selected from H, OH, SH, $NH_2$, halogen, cyano, carboxy, alkyl, cycloalkyl, aryl and heteroaryl, each of which is substituted or unsubstituted;

each of $R^4$ and $R^5$ is independently selected from alkyl, cycloalkyl, aryl and heteroaryl, each of which is substituted or unsubstituted;

each of $R^a$, $R^b$ and $R^c$ is independently selected from side-chain residues of a proteinogenic or a non-proteinogenic amino acid, each of which can be further substituted;

each X is independently selected from NH, NR, S, O and $CH_2$, preferably NH;

each of n and m is independently an integer from 0 to 100, preferably 0 to 50, more preferably 0 to 30, yet more preferably selected from 0, 1, 2, 3, 4, 5, 6, 7, 8, 9, 10, 11, 12, 13, 14, 15, 16, 17, 18, 19 and 20; and wherein each * represents a point of attachment for which the shortest path to moiety A comprises less atoms than that for •; and each • represents a point of attachment for which the shortest path to moiety C comprises less atoms than that for *; and/or (c) one or more $B_L$ independently comprises or consists of one or more of the following structural units:

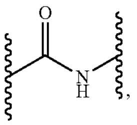

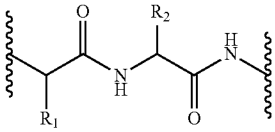

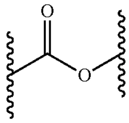

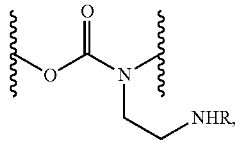

R = H, Me

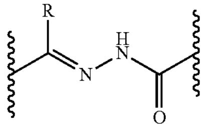

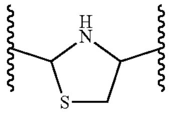

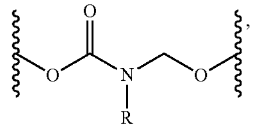

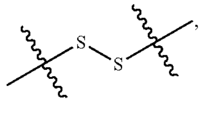

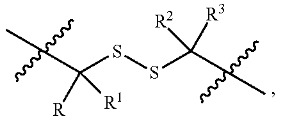

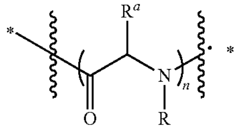

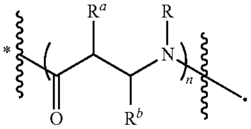

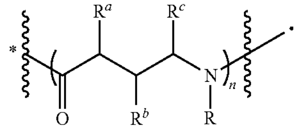

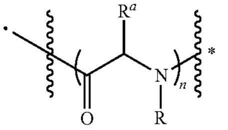

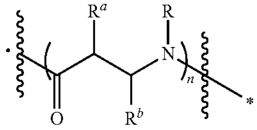

-continued

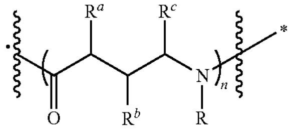
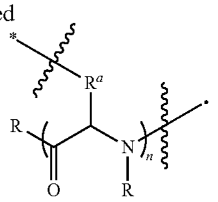
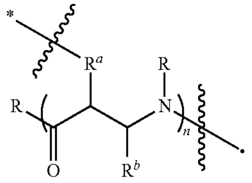
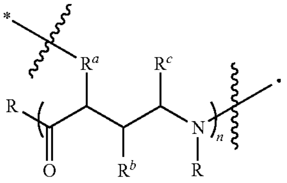
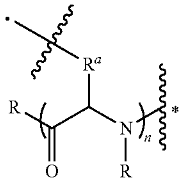
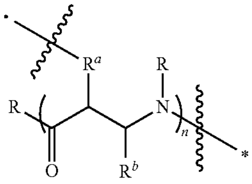
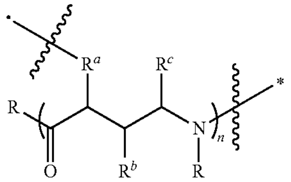
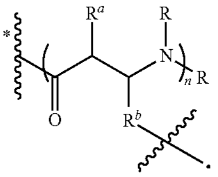
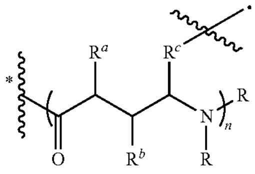
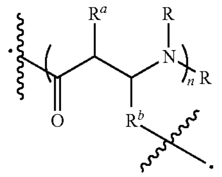
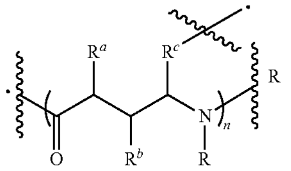

wherein in each of the above structures, n is 1, 2, 3 or 4; and each * represents a point of attachment for which the shortest path to moiety A comprises less atoms than that for •; and each • represents a point of attachment for which the shortest path to moiety C comprises less atoms than that for *, with the proviso that when n is >1 and a respective point of attachment is indicated on any one of $R^a$, $R^b$ and $R^c$, then it can be independently present in one or more of the peptide monomeric units, preferably in one peptide monomeric unit most distant from the other point of attachment indicated in the respective structure; and/or (d) one or more of $B_L$ and $B_S$ is independently selected from the following structures:

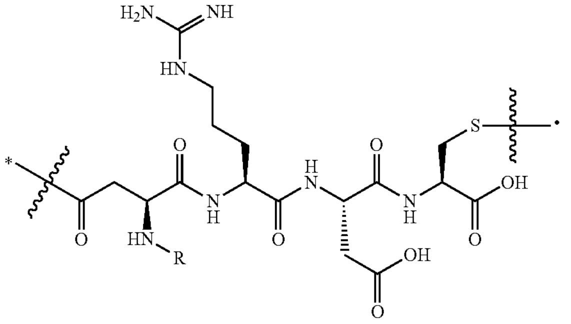
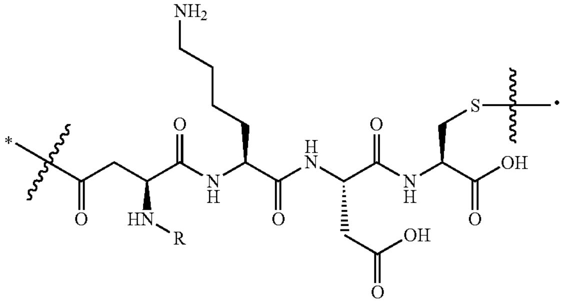
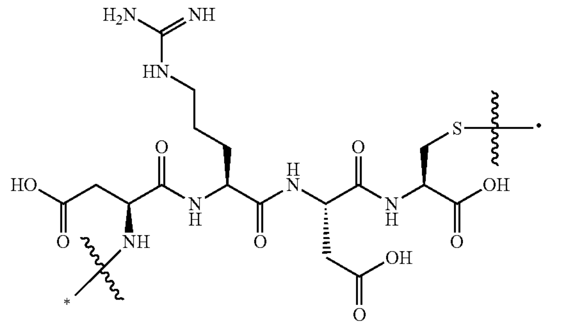
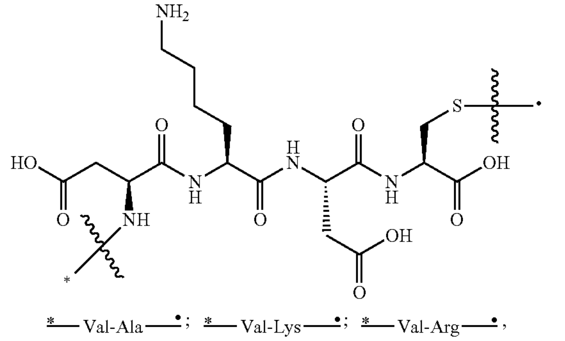

*—Val-Ala—•; *—Val-Lys—•; *—Val-Arg—•, wherein each * represents a point of attachment for which the shortest path to moiety A comprises less atoms than that for •; and each • represents a point of attachment for which the shortest path to moiety C comprises less atoms than that for *; and/or (e) y is 1, 2 or 3; and/or at least one $B_L$ further comprises a cleavable linker group independently selected from the following structures:

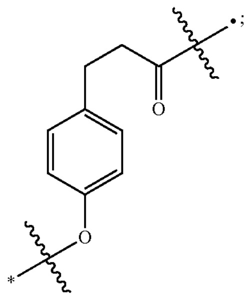
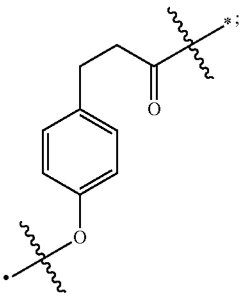
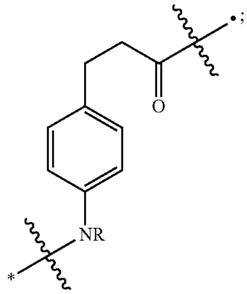
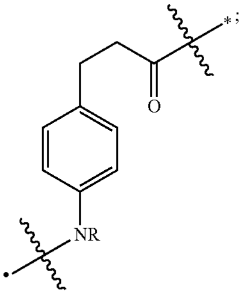
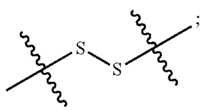
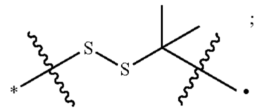
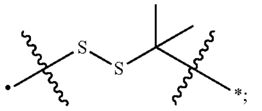
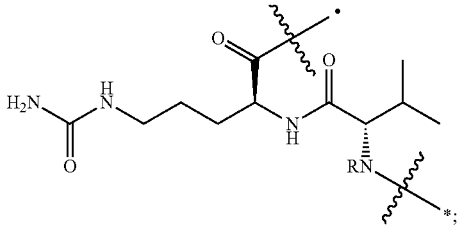
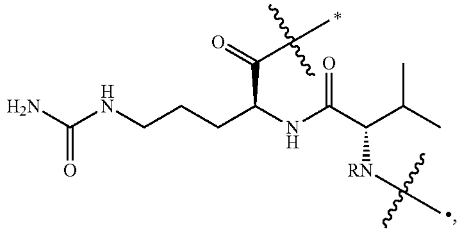

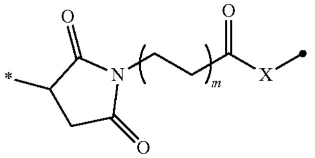
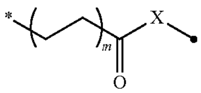
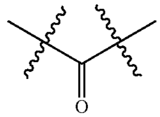
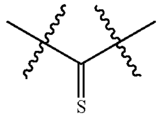
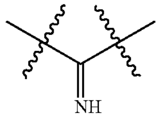
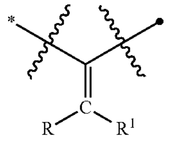
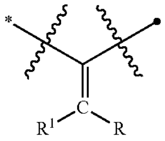
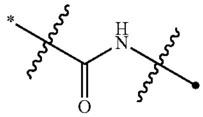
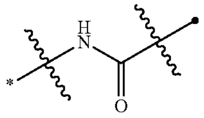
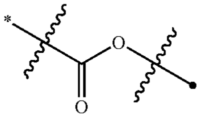
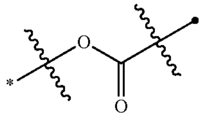
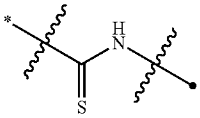
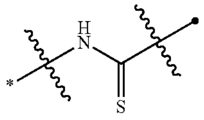
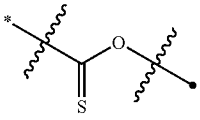
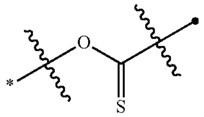
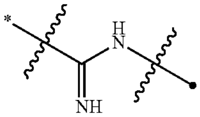
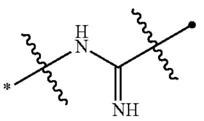
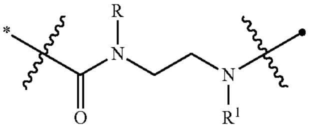
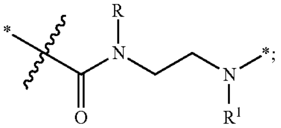

each * represents a point of attachment for which the shortest path to moiety A comprises less atoms than that for •; and each • represents a point of attachment for which the shortest path to moiety C comprises less atoms than that for *.

Preferably, B may be defined as above and/or have the following structure:

$$*\!\left(\left(B'_s\right)_{x'}\left(B_l\right)_y\left(B''_s\right)_{x''}\right)_z\bullet$$

wherein $B'_S$ and $B''_S$ are each independently selected from the group consisting of:

each $B_L$ is independently selected from the group consisting of:

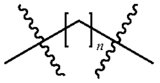
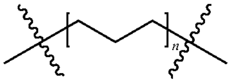
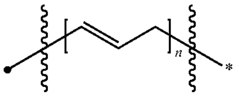
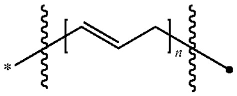
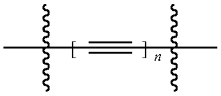
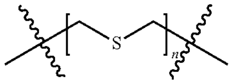
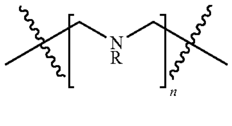
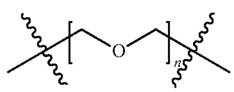

-continued
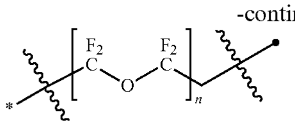
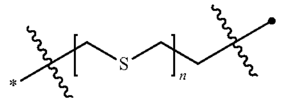
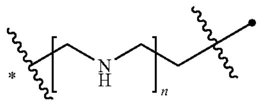
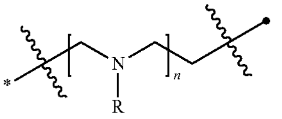
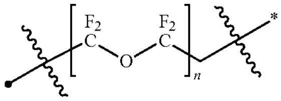
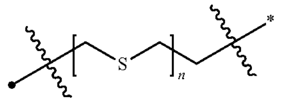
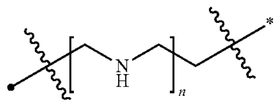
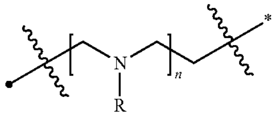
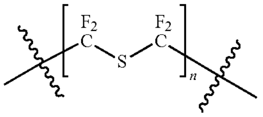
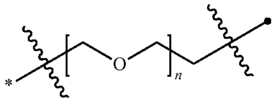
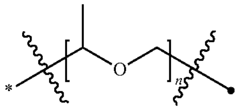
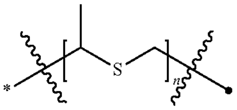
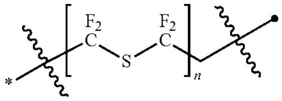
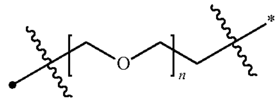
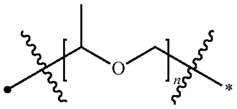
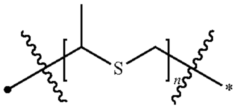
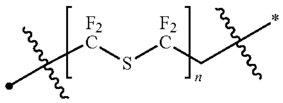
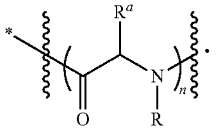
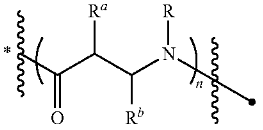
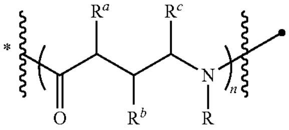
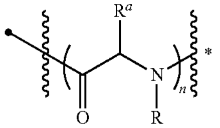
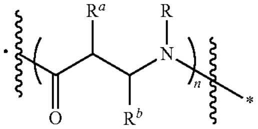
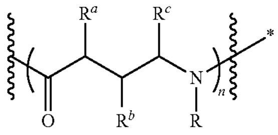
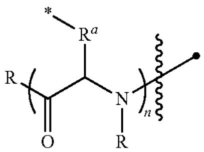
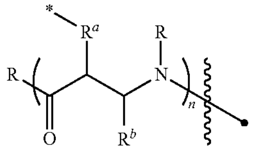
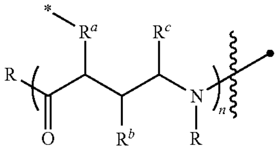
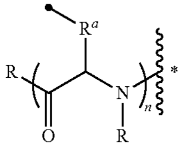
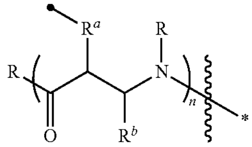
-continued
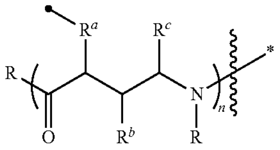
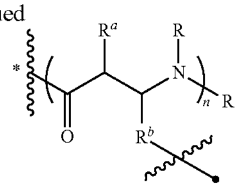
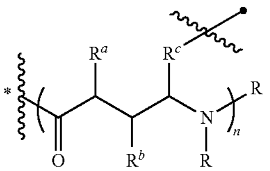
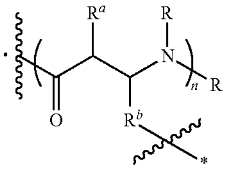
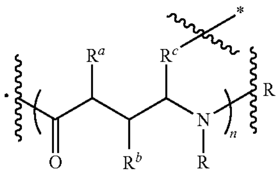
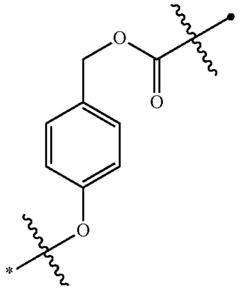
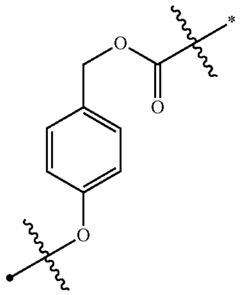
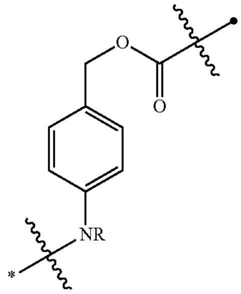
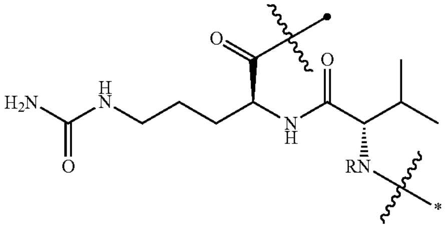
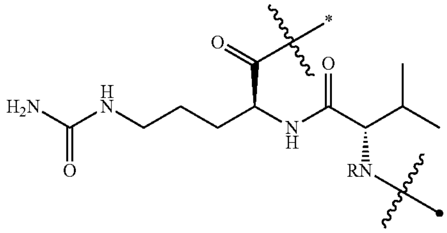,
each n is 0, 1, 2, 3, 4 or 5;
each m is 0, 1, 2, 3, 4 or 5;
each x' is 0, 1 or 2;
each x" is 0, 1 or 2;
each y is 0, 1 or 2; and
z is 1 or 2,
wherein R, $R^1$, $R^2$, $R^3$, $R^a$, $R^b$, R, X, * and • are as defined above.
More preferably, the compound according the invention has a structure represented by one of the following formulae:

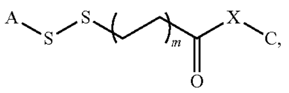
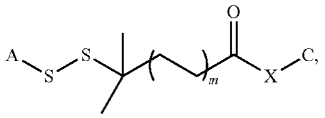
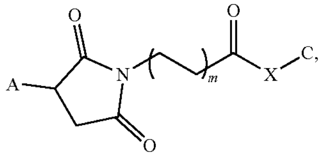
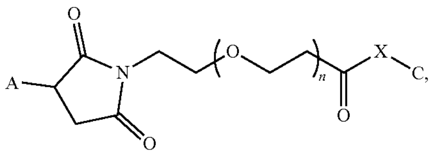
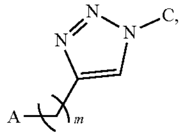
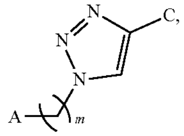
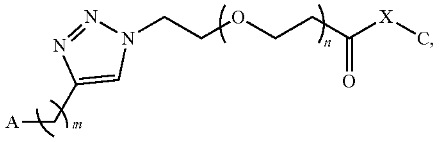
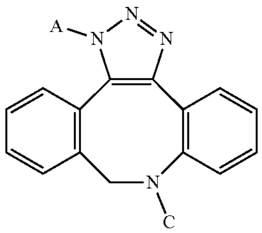
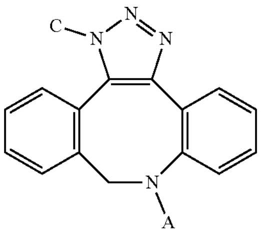
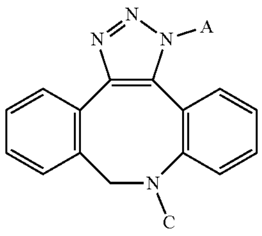
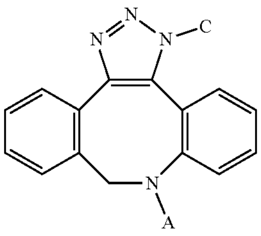
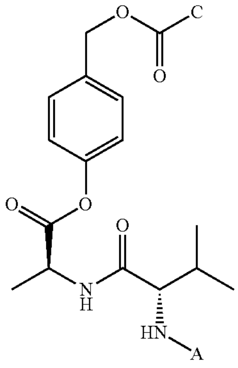
Val-Ala-PAB
-continued
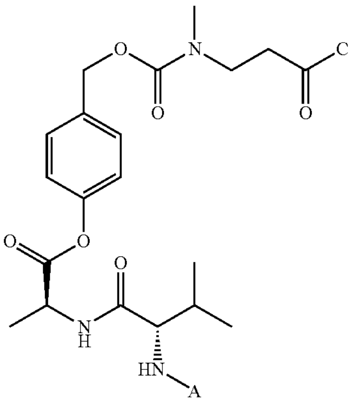
Val-Ala-PAB
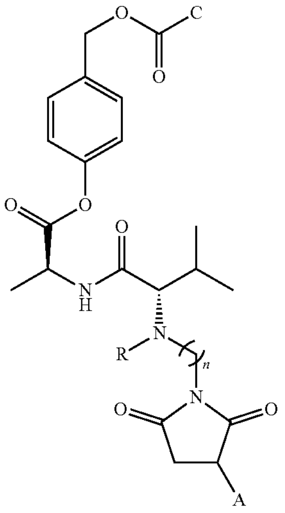
MC-Val-Ala-PAB
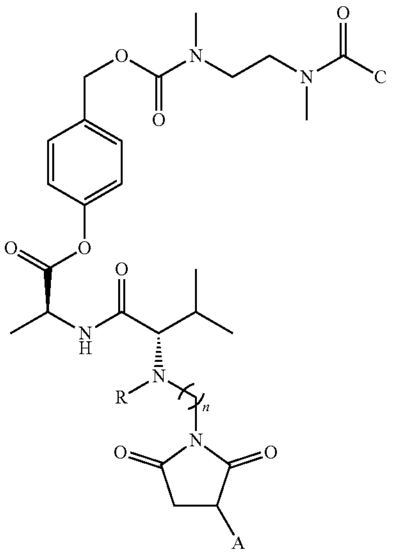
MC-Val-Ala-PAB -continued
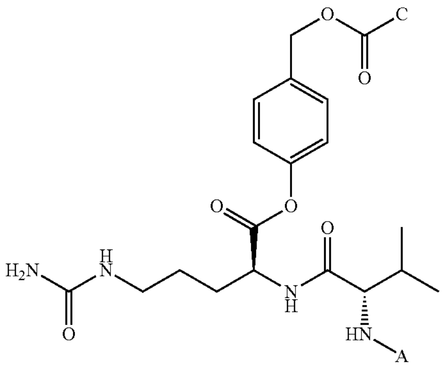
Val-Cit-PAB
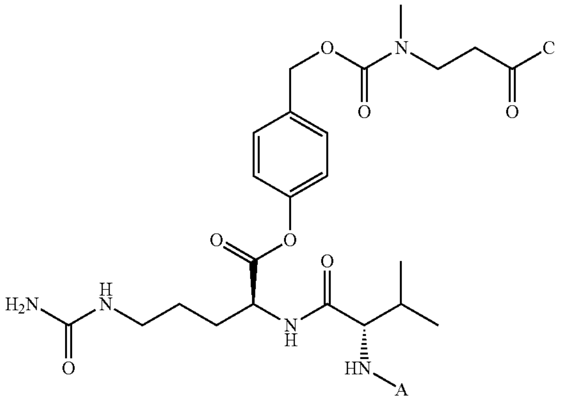
Val-Cit-PAB
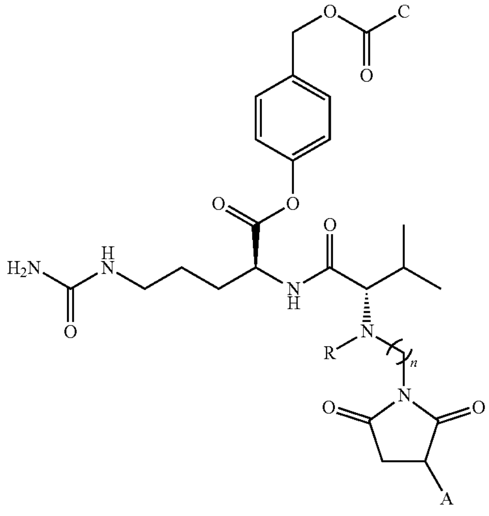
MC-Val-Cit-PAB
-continued
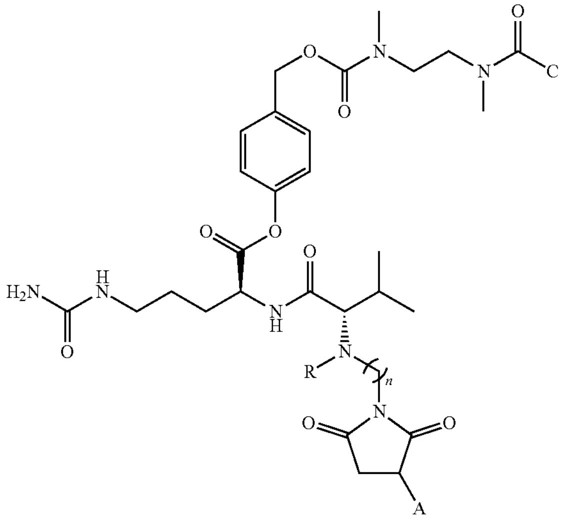
MC-Val-Cit-PAB
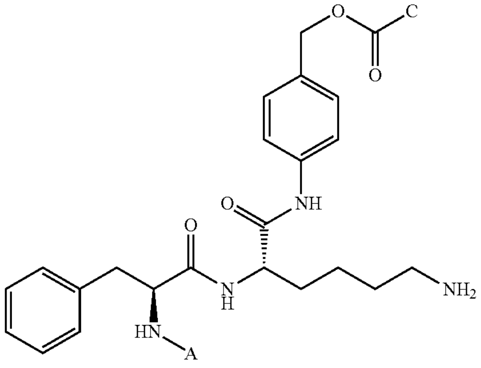
Phe-Lys-PAB
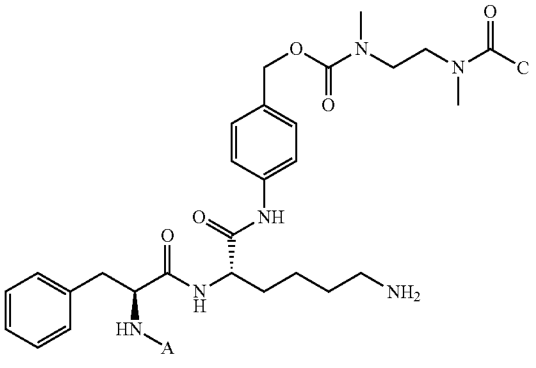
Phe-Lys-PAB
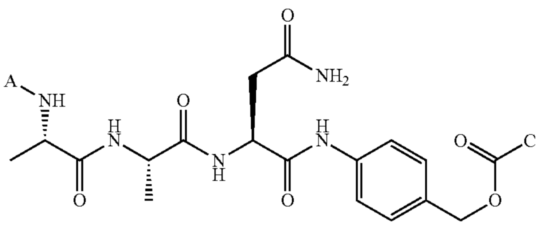
Ala-Ala-Asn-PAB -continued

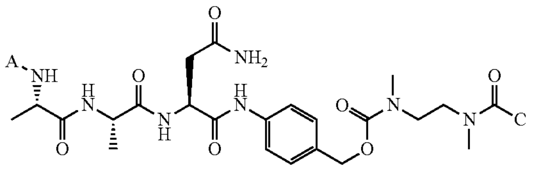

Ala-Ala-Asn-PAB

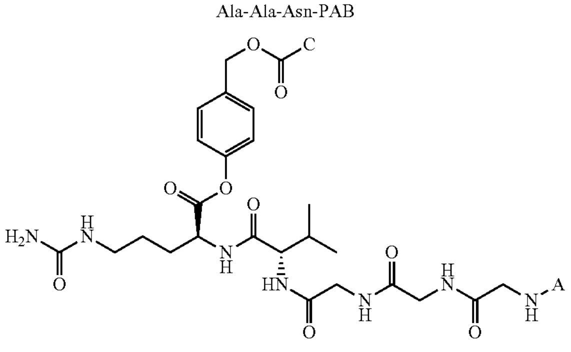

gly-gly-gly-Val-Cit-PAB

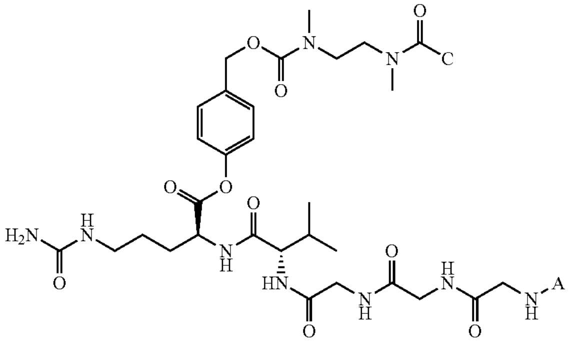

gly-gly-gly-Val-Cit-PAB

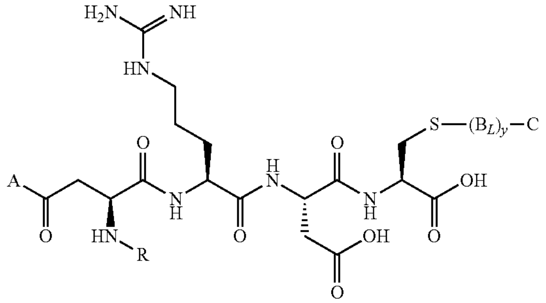

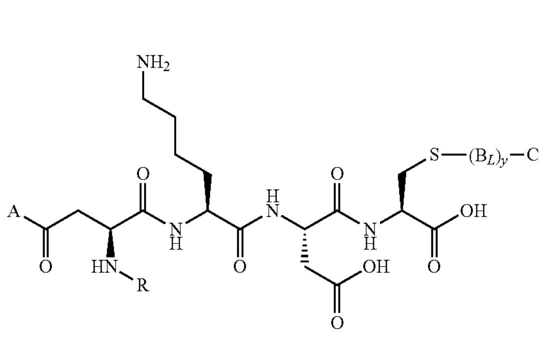

-continued

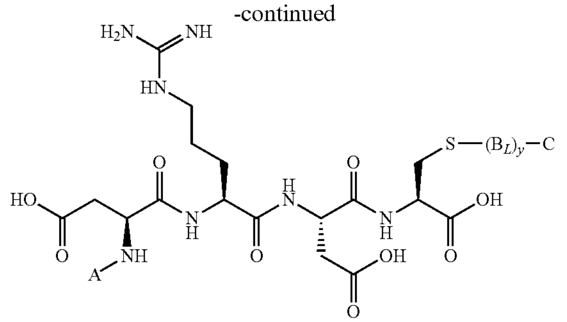

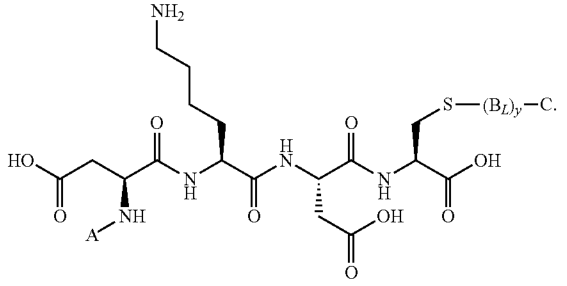

Moiety C

Moiety C in the present invention represents a payload, which can be generally any atom (including H), molecule or particle. Preferably, moiety C is not a hydrogen atom.

The payload may be a chelator for radiolabelling. Suitably the radionuclide is not released. Chelators are well known to those skilled in the art, and for example, include chelators such as sulfur colloid, diethylenetriaminepentaacetic acid (DTPA), ethylenediaminetetraacetic acid (EDTA), 1,4,7,10-tetraazacyclododecane-N,N',N",N'"-tetraacetic acid (DOTA), 1,4,7,10-tetraazacyclodowdecane,N-(glutaric acid)-N',N",N'"-triacetic acid (DOTAGA), 1,4,7-triazacyclononane-N,N',N"-triacetic acid (NOTA), 1,4,8,11-tetraazacyclotetradecane-N,N',N",N'"-tetraacetic acid (TETA), or any of the preferred chelator structures recited in the appended claims.

The payload may be a radioactive group comprising or consisting of radioisotope including isotopes such as $^{223}$Ra, $^{89}$Sr, $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At, $^{225}$Ac, $^{89}$Sr, $^{225}$Ac, $^{117}$Sn and $^{169}$E. Preferably, positron emitters, such as $^{18}$F and $^{124}$I, or gamma emitters, such as $^{99m}$Tc, $^{111}$In and $^{123}$I, are used for diagnostic applications (e.g. for PET), while beta-emitters, such as $^{84}$Sr, $^{131}$I, and $^{177}$Lu, are preferably used for therapeutic applications. Alpha-emitters, such as $^{211}$At, $^{225}$Ac and $^{223}$Ra may also be used for therapy. In one preferred embodiment the radioisotope is $^{89}$Sr or $^{223}$Ra. In a further preferred embodiment the radioisotope is $^{68}$Ga.

The payload may be a chelate of a radioactive isotope, preferably of an isotope listed under above, with a chelating agent, preferably a chelating agent listed above or any of the preferred chelator structures recited in the appended claim 9 (a); or a group selected from the structures listed in claim 9 (c).

The payload may be a fluorophore group, preferably selected from a xanthene dye, acridine dye, oxazine dye, cyanine dye, styryl dye, coumarine dye, porphine dye, fluorescent metal-ligand-complex, fluorescent protein, nanocrystals, perylene dye, boron-dipyrromethene dye and phtalocyanine dye, more preferably selected from the structures listed in claim 9 (d).

The payload may be a cytotoxic and/or cytostatic agent. Such agents can inhibit or prevent the function of cells and/or cause destruction of cells. Examples of cytotoxic agents include radioactive isotopes, chemotherapeutic agents, and toxins such as small molecule toxins or enzymatically active toxins of bacterial, fungal, plant or animal origin, including synthetic analogues and derivatives thereof. The cytotoxic agent may be selected from the group consisting of an auristatin, a DNA minor groove binding agent, a DNA minor groove alkylating agent, an enediyne, a lexitropsin, a duocarmycin, a taxane, a puromycin, a dolastatin, a maytansinoid and a vinca alkaloid or a combination of two or more thereof. Preferred cytotoxic and/or cytostatic payload moieties are listed in claim 9 (e).

In one embodiment the payload is a chemotherapeutic agent selected from the group consisting of a topoisomerase inhibitor, an alkylating agent (e.g., nitrogen mustards; ethylenimes; alkylsulfonates; triazenes; piperazines; and nitrosureas), an antimetabolite (e.g., mercaptopurine, thioguanine, 5-fluorouracil), an antibiotics (e.g., anthracyclines, dactinomycin, bleomycin, adriamycin, mithramycin. dactinomycin) a mitotic disrupter (e.g., plant alkaloids—such as vincristine and/or microtubule antagonists—such as paclitaxel), a DNA methylating agent, a DNA intercalating agent (e.g., carboplatin and/or cisplatin, daunomycin and/or doxorubicin and/or bleomycin and/or thalidomide), a DNA synthesis inhibitor, a DNA-RNA transcription regulator, an enzyme inhibitor, a gene regulator, a hormone response modifier, a hypoxia-selective cytotoxin (e.g., tirapazamine), an epidermal growth factor inhibitor, an anti-vascular agent (e.g., xanthenone 5,6-dimethylxanthenone-4-acetic acid), a radiation-activated prodrug (e.g., nitroarylmethyl quaternary (NMQ) salts) or a bioreductive drug or a combination of two or more thereof. In some embodiments, the payload (i.e., moiety C) is not derived from an anthracycline, preferably not derived from PNU 159682.

The chemotherapeutic agent may selected from the group consisting of Erlotinib (TARCEVA®), Bortezomib (VELCADE®), Fulvestrant (FASLODEX®), Sutent (SU11248), Letrozole (FEMARA®), Imatinib mesylate (GLEEVEC®), PTK787/ZK 222584, Oxaliplatin (Eloxatin®.), 5-FU (5-fluorouracil), Leucovorin, Rapamycin (Sirolimus, RAPAMUNE®.), Lapatinib (GSK572016), Lonafarnib (SCH 66336), Sorafenib (BAY43-9006), and Gefitinib (IRESSA®.), AG1478, AG1571 (SU 5271; Sugen) or a combination of two or more thereof.

The chemotherapeutic agent may be an alkylating agent—such as thiotepa, CYTOXAN® and/or cyclosphosphamide; an alkyl sulfonate—such as busulfan, improsulfan and/or piposulfan; an aziridine—such as benzodopa, carboquone, meturedopa and/or uredopa; ethylenimines and/or methylamelamines—such as altretamine, triethylenemelamine, triethylenepbosphoramide, triethylenethiophosphoramide and/or trimethylomelamine; acetogenin—such as bullatacin and/or bullatacinone; camptothecin; bryostatin; callystatin; cryptophycins; dolastatin; duocarmycin; eleutherobin; pancratistatin; sarcodictyin; spongistatin; nitrogen mustards—such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide and/or uracil mustard; nitrosureas—such as carmustine, chlorozotocin, fotemustine, lomustine, nimustine, and/or ranimnustine; dynemicin; bisphosphonates—such as clodronate; an esperamicin; a neocarzinostatin chromophore; aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®. doxorubicin—such as morpholino-doxorubicin, cyanomorpholino-doxorubicin, 2-pyrrolino-doxorubicin and/or deoxydoxorubicin, epirubicin, esorubicin, idarubicin, marcellomycin, mitomycins—such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites—such as methotrexate and 5-fluorouracil (5-FU); folic acid analogues—such as denopterin, methotrexate, pteropterin, trimetrexate; purine analogues—such as fludarabine, 6-mercaptopurine, thiamiprine, thioguanine; pyrimidine analogues—such as ancitabine, azacitidine, 6-azauridine, carmofur, cytarabine, dideoxyuridine, doxifluridine, enocitabine, floxuridine; androgens—such as calusterone, dromostanolone propionate, epitiostanol, mepitiostane, testolactone; anti-adrenals—such as aminoglutethimide, mitotane, trilostane; folic acid replenisher—such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; macrocyclic depsipeptides such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofiran; spirogermanium; tenuazonic acid; triaziquone; 2,2',2"-trichlorotriethylamine; trichothecenes—such as verracurin A, roridin A and/or anguidine; urethan; vindesine; dacarbazine; mannomustine; mitobronitol; mitolactol; pipobroman; gacytosine; arabinoside; cyclophosphamide; thiotepa; taxoids—such as TAXOL®. paclitaxel, abraxane, and/or TAXOTERE®, doxetaxel; chloranbucil; GEMZAR®. gemcitabine; 6-thioguanine; mercaptopurine; methotrexate; platinum analogues—such as cisplatin and carboplatin; vinblastine; platinum; etoposide; ifosfamide; mitoxantrone; vincristine; NAVELBINE®, vinorelbine; novantrone; teniposide; edatrexate; daunomycin; aminopterin; xeloda; ibandronate; topoisomerase inhibitor RFS 2000; difluoromethylomithine (DMFO); retinoids—such as retinoic acid; capecitabine; and pharmaceutically acceptable salts, acids, derivatives or combinations of two or more of any of the above.

The payload may be a tubulin disruptor including but are not limited to: taxanes—such as paclitaxel and docetaxel, vinca alkaloids, discodermolide, epothilones A and B, desoxyepothilone, cryptophycins, curacin A, combretastatin A-4-phosphate, BMS 247550, BMS 184476, BMS 188791; LEP, RPR 109881A, EPO 906, TXD 258, ZD 6126, vinflunine, LU 103793, dolastatin 10, E7010, T138067 and T900607, colchicine, phenstatin, chalcones, indanocine, T138067, oncocidin, vincristine, vinblastine, vinorelbine, vinflunine, halichondrin B, isohomohalichondrin B, ER-86526, pironetin, spongistatin 1, spiket P, cryptophycin 1, LU103793 (cematodin or cemadotin), rhizoxin, sarcodictyin, eleutherobin, laulilamide, VP-16 and D-24851 and pharmaceutically acceptable salts, acids, derivatives or combinations of two or more of any of the above.

The payload may be a DNA intercalator including but are not limited to: acridines, actinomycins, anthracyclines, benzothiopyranoindazoles, pixantrone, crisnatol, brostallicin, CI-958, doxorubicin (adriamycin), actinomycin D, daunorubicin (daunomycin), bleomycin, idarubicin, mitoxantrone, cyclophosphamide, melphalan, mitomycin C, bizelesin, etoposide, mitoxantrone, SN-38, carboplatin, cis-platin, actinomycin D, amsacrine, DACA, pyrazoloacridine, irinotecan and topotecan and pharmaceutically acceptable salts, acids, derivatives or combinations of two or more of any of the above.

The payload may be an anti-hormonal agent that acts to regulate or inhibit hormone action on tumours—such as anti-estrogens and selective estrogen receptor modulators, including, but not limited to, tamoxifen, raloxifene, droloxifene, 4-hydroxytamoxifen, trioxifene, keoxifene, LY117018, onapristone, and/or fareston toremifene and pharmaceutically acceptable salts, acids, derivatives or combinations of two or more of any of the above. The payload may be an aromatase inhibitor that inhibits the enzyme aromatase, which regulates estrogen production in the adrenal glands—such as, for example, 4(5)-imidazoles, aminoglutethimide, megestrol acetate, AROMASIN®. exemestane, formestanie, fadrozole, RIVISOR®. vorozole, FEMARA®. letrozole, and ARIMIDEX® and/or anastrozole and pharmaceutically acceptable salts, acids, derivatives or combinations of two or more of any of the above.

The payload may be an anti-androgen such as flutamide, nilutamide, bicalutamide, leuprolide, goserelin and/or troxacitabine and pharmaceutically acceptable salts, acids, derivatives or combinations of two or more of any of the above.

The payload may be a protein or an antibody. Preferably, the payload is a cytokine (e.g., an interleukin such as IL2, IL10, IL12, IL15; a member of the TNF superfamily; or an interferon such as interferon gamma.).

Any payload may be used in unmodified or modified form. Combinations of payloads in which some are unmodified and some are modified may be used. For example, the payload may be chemically modified. One form of chemical modification is the derivatisation of a carbonyl group—such as an aldehyde.

In a preferred embodiment, moiety C is an auristatin (i.e., having a structure derived from an auristatin compound family member) or an auristatin derivative. More preferably, moiety C has a structure according to the following formula:

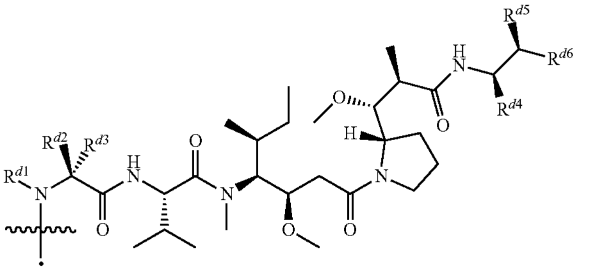

wherein:

$R^{1d}$ is independently H or $C_1$-$C_6$ alkyl; preferably H or $CH_3$;

$R^{2d}$ is independently $C_1$-$C_6$ alkyl; preferably $CH_3$ or iPr;

$R^{3d}$ is independently H or $C_1$-$C_6$ alkyl; preferably H or $CH_3$;

$R^{4d}$ is independently H, $C_1$-$C_6$ alkyl, COO($C_1$-$C_6$ alkyl), CON(H or $C_1$-$C_6$ alkyl), $C_3$-$C_{10}$ aryl or $C_3$-$C_{10}$ heteroaryl; preferably H, $CH_3$, COOH, $COOCH_3$ or thiazolyl;

$R^{5d}$ is independently H, OH, $C_1$-$C_6$ alkyl; preferably H or OH; and $R^{6d}$ is independently $C_3$-$C_10$ aryl or $C_3$-$C_10$ heteroaryl; preferably optionally substituted phenyl or pyridyl.

More preferably, moiety C is derived from MMAE or MMAF.

In a preferred embodiment, moiety C has a structure according to the following formula:

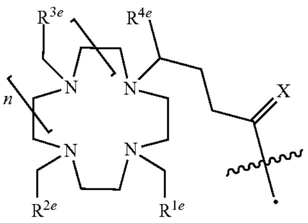

wherein:

n is 0, 1, 2, 3, 4 or 5; preferably 1;

$R^{1e}$ is independently H, COOH, aryl-COOH or heteroaryl-COOH; preferably COOH;

$R^{2e}$ is independently H, COOH, aryl-COOH or heteroaryl-COOH; preferably COOH;

each $R^{3e}$ is independently H, COOH, aryl-COOH or heteroaryl-COOH; preferably COOH;

$R^{4e}$ is independently H, COOH, aryl-COOH or heteroaryl-COOH; preferably COOH; and X is O, NH or S; preferably O.

In a preferred embodiment, moiety C has a structure according to the following formula:

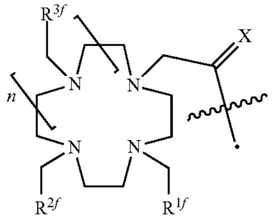

wherein:

n is 0, 1, 2, 3, 4 or 5; preferably 1

$R^{1f}$ is independently H, COOH, aryl-COOH or heteroaryl-COOH; preferably COOH;

$R^{2f}$ is independently H, COOH, aryl-COOH or heteroaryl-COOH; preferably COOH;

$R^{3f}$ is independently H, COOH, aryl-COOH or heteroaryl-COOH; preferably COOH; and X is O, NH or S; preferably O Particularly preferred embodiments for the moiety C as well as the compound according to the present invention are shown in the appended claims.

Preferred compounds are those having a structure according to Table 2 or 3, their individual diastereoisomers, hydrates, solvates, crystal forms, individual tautomers or pharmaceutically acceptable salts thereof.

Further Aspects

In one aspect, herein disclosed a compound of the general Formula I as defined above, its individual diastereoisomers, its hydrates, its solvates, its crystal forms, its individual tautomers or a pharmaceutically acceptable salt thereof, wherein: A is a binding moiety having the structure as defined above; B is a covalent bond or a moiety comprising a chain of atoms that covalently attaches the moieties A und C; and C is a payload moiety.

In one further aspect, B is represented by any of the general Formulae II-V as defined above, wherein each $B_S$ independently represents a spacer group; each $B_L$ independently represents a cleavable or non-cleavable linker group; each x is an integer independently selected from the range of 0 to 100, preferably 0 to 50, more preferably 0 to 30, yet more preferably selected from 0, 1, 2, 3, 4, 5, 6, 7, 8, 9, 10, 11, 12, 13, 14, 15, 16, 17, 18, 19 and 20; each y is an integer independently selected from the range of 0 to 30, preferably selected from 0, 1, 2, 3, 4, 5, 6, 7, 8, 9, 10, 11, 12, 13, 14, 15, 16, 17, 18, 19 and 20; each z is an integer independently selected from the range of 0 to 5, preferably selected from selected from 0, 1, 2, 3 and 4; and * represents a point of attachment to moiety A; and • represents a point of attachment to moiety C.

In one further aspect according to any of the preceding aspects, the binding moiety has the structure $A^1$ as defined above.

In one further aspect according to any of the preceding aspects, $B_S$ and/or $B_L$ is a group comprising or consisting of a structural unit independently selected from the group consisting of alkylene, cycloalkylene, arylalkylene, heteroarylalkylene, heteroalkylene, heterocycloalkylene, alkenylene, cycloalkenylene, arylalkenylene, heteroarylalkenylene, heteroalkenylene, heterocycloalenkylene, alkynylene, heteroalkynylene, arylene, heteroarylene, aminoacyl, oxyalkylene, aminoalkylene, diacid ester, dialkylsiloxane, amide, thioamide, thioether, thioester, ester, carbamate, hydrazone, thiazolidine, methylene alkoxy carbamate, disulfide, vinylene, imine, imidamide, phosphoramide, saccharide, phosphate ester, phosphoramide, carbamate, dipeptide, tripeptide, tetrapeptide, each of which is substituted or unsubstituted.

In one further aspect according to any of the preceding aspects, $B_S$ and/or $B_L$ is a group defined as in appended claim 5 (b). In one preferred aspect according to any of the preceding aspects, one or more $B_L$ are defined as in appended claim 5 (c). In one preferred aspect according to any of the preceding aspects, one or more of $B_L$ and $B_S$ is defined as in appended claim 5 (d). In one preferred aspect according to any of the preceding aspects, y is 1, 2 or 3; and/or at least one $B_L$ defined as in appended claim 5 (e). In one preferred aspect according to any of the preceding aspects, B is defined as in appended claim 6.

In one further aspect according to any of the preceding aspects, compound is defined as in appended claim 7.

In one further aspect according to any of the preceding aspects, the moiety C is as defined in appended claim 8 and/or 9.

In one further aspect according to any of the preceding aspects, the compound having a structure selected from the following: Conjugate 1; Conjugate 2; Conjugate 3; Conjugate 4; Conjugate 5; Conjugate 6; Conjugate 7; Conjugate 8; Conjugate 9; Conjugate 10; Conjugate 11; Conjugate 12; Conjugate 13; Conjugate 14; Conjugate 15; and ESV6-fluo.

Also disclosed is a pharmaceutical composition comprising the compound according to any of the preceding aspects, and a pharmaceutically acceptable excipient. Such pharmaceutical composition is also disclosed for use in: (a) a method for treatment of the human or animal body by surgery or therapy or a diagnostic method practised on the human or animal body; or (b) a method for therapy or prophylaxis of a subject suffering from or having risk for a disease or disorder; or (c) a method for guided surgery practised on a subject suffering from or having risk for a disease or disorder; or (d) a method for diagnosis of a disease or disorder, the method being practised on the human or animal body and involving a nuclear medicine imaging technique, such as Positron Emission Tomography (PET) or Single Photon Emission Computed Tomography (SPECT); or (e) a method for targeted delivery of a therapeutic or diagnostic agent to a subject suffering from or having risk for a disease or disorder, wherein in each of the preceding (b)-(e), said disease or disorder is independently selected from cancer, inflammation, atherosclerosis, fibrosis, tissue remodelling and keloid disorder, preferably wherein the cancer is selected from the group consisting of breast cancer, pancreatic cancer, small intestine cancer, colon cancer, multi-drug resistant colon cancer, rectal cancer, colorectal cancer, metastatic colorectal cancer, lung cancer, non-small cell lung cancer, head and neck cancer, ovarian cancer, hepatocellular cancer, oesophageal cancer, hypopharynx cancer, nasopharynx cancer, larynx cancer, myeloma cells, bladder cancer, cholangiocarcinoma, clear cell renal carcinoma, neuroendocrine tumour, oncogenic osteomalacia, sarcoma, CUP (carcinoma of unknown primary), thymus cancer, desmoid tumours, glioma, astrocytoma, cervix cancer and prostate cancer; preferably wherein the compound has a prolonged residence at the disease site at a therapeutically or diagnostically relevant level, preferably beyond 1 h, more preferably beyond 6 h post injection.

Treatment

The compounds described herein may be used to treat disease. The treatment may be therapeutic and/or prophylactic treatment, with the aim being to prevent, reduce or stop an undesired physiological change or disorder. The treatment may prolong survival as compared to expected survival if not receiving treatment.

The disease that is treated by the compound may be any disease that might benefit from treatment. This includes chronic and acute disorders or diseases including those pathological conditions which predispose to the disorder.

The term "cancer" and "cancerous" is used in its broadest sense as meaning the physiological condition in mammals that is typically characterized by unregulated cell growth. A tumour comprises one or more cancerous cells.

When treating cancer, the therapeutically effect that is observed may be a reduction in the number of cancer cells; a reduction in tumour size; inhibition or retardation of cancer cell infiltration into peripheral organs; inhibition of tumour growth; and/or relief of one or more of the symptoms associated with the cancer.

In animal models, efficacy may be assessed by physical measurements of the tumour during the treatment, and/or by determining partial and complete remission of the cancer. For cancer therapy, efficacy can, for example, be measured by assessing the time to disease progression (TTP) and/or determining the response rate (RR).

Particularly preferred embodiments for the methods of treatment related to the present invention are shown in the appended claims.

Herein disclosed are also methods for treatment of the human or animal body, e.g., by surgery or therapy, or diagnostic method practised on the human or animal body, the methods involving a step of administering a therapeutically or diagnostically effective amount of a compound or a pharmaceutical composition as described herein to a subject in need thereof. More specifically, herein disclosed are methods for treatment, e.g., by therapy or prophylaxis, of a subject suffering from or having risk for a disease or disorder; or by guided surgery practised on a subject suffering from or having risk for a disease or disorder; method for diagnosis of a disease or disorder, e.g., diagnostic method practised on the human or animal body and/or involving a nuclear medicine imaging technique, such as Positron Emission Tomography (PET) or Single Photon Emission Computed Tomography (SPECT); method for targeted delivery of a therapeutic or diagnostic agent to a subject suffering from or having risk for a disease or disorder. In the aforementioned methods, said disease or disorder may be independently selected from cancer, inflammation, atherosclerosis, fibrosis, tissue remodelling and keloid disorder, preferably wherein the cancer is selected from the group consisting of breast cancer, pancreatic cancer, small intestine cancer, colon cancer, multi-drug resistant colon cancer, rectal cancer, colorectal cancer, metastatic colorectal cancer, lung cancer, non-small cell lung cancer, head and neck cancer, ovarian cancer, hepatocellular cancer, oesophageal cancer, hypopharynx cancer, nasopharynx cancer, larynx cancer, myeloma cells, bladder cancer, cholangiocarcinoma, clear cell renal carcinoma, neuroendocrine tumour, oncogenic osteomalacia, sarcoma, CUP (carcinoma of unknown primary), thymus cancer, desmoid tumours, glioma, astrocytoma, cervix cancer, skin cancer, kidney cancer and prostate cancer. When used in the methods disclosed herein, the compound has a prolonged residence at the disease site at a therapeutically or diagnostically relevant level, preferably beyond 1 h, more preferably beyond 6 h post injection.

Pharmaceutical Compositions

The compounds described herein may be in the form of pharmaceutical compositions which may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration, the compositions may be administered in the form of tablets or lozenges which can be formulated in a conventional manner.

The compound of the present invention may be administered in the form of a pharmaceutically acceptable or active salt. Pharmaceutically-acceptable salts are well known to those skilled in the art, and for example, include those mentioned by Berge et al, in J. Pharm. Sci., 66, 1-19 (1977). Salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

The formulations may be packaged in unit-dose or multi-dose containers, for example sealed ampoules and vials, and may be stored in a freeze-dried (lyophilized) condition requiring only the addition of the sterile liquid carrier, for example water, for administration. Extemporaneous injection solutions and suspensions are prepared from sterile powders, granules and tablets of the kind previously described. Exemplary unit dosage formulations contain a daily dose or unit daily sub-dose, or an appropriate fraction thereof, of the active ingredient.

Precursor Compounds

In one aspect of the invention, herein disclosed is a compound, its individual diastereoisomers, its hydrates, its solvates, its crystal forms, its individual tautomers or a salt thereof, wherein the compound (precursor compound) comprises a moiety A and a reactive moiety L capable of reacting and forming a covalent bond with a conjugation partner. Upon conjugation (i.e., reacting and forming a covalent bond), the former precursor compound is bound to the former conjugation partner, which in turn to a payload moiety C. The conjugation partner can be an atom, a molecule, a particle, a therapeutic agent and/or diagnostic agent. Preferably, the conjugation is a therapeutic agent and/or diagnostic agent, and can correspond to the payload moieties already described in detail above with respect to the conjugates according to the invention.

Preferably, the precursor compound comprises a moiety having the structure:

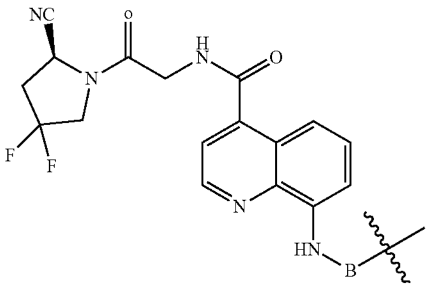

wherein B is a covalent bond or a moiety comprising a chain of atoms covalently bound atoms.

The precursor compound can be represented by the following Formula VI:

Formula VI

wherein B is a covalent bond or a moiety comprising a chain of atoms covalently attaching A to L.

Moiety A preferably has the structure $A^1$ or $A^2$, wherein m is 0, 1, 2, 3, 4 or 5.

Moiety B preferably has the same structure as described in detail above with respect to the conjugates according to the invention.

Moiety L is preferably capable of forming, upon reacting, an amide, ester, carbamate, hydrazone, thiazolidine, methylene alkoxy carbamate, disulphide, alkylene, cycloalkylene, arylalkylene, heteroarylalkylene, heteroalkylene, heterocycloalkylene, alkenylene, cycloalkenylene, arylalkenylene, heteroarylalkenylene, heteroalkenylene, heterocycloalenkylene, alkynylene, heteroalkynylene, arylene, heteroarylene, aminoacyl, oxyalkylene, aminoalkylene, diacid ester, dialkylsiloxane, amide, thioamide, thioether, thioester, ester, carbamate, hydrazone, thiazolidine, methylene alkoxy carbamate, disulfide, vinylene, imine, imidamide, phosphoramide, saccharide, phosphate ester, phosphoramide, carbamate, dipeptide, tripeptide or tetrapeptide linking group. As will be appreciated by a person skilled in the art, multiple possibilities exist how to provide a reactive group capable of reacting with a conjugation partner to form a linking group according to the aforementioned list, and they are all encompassed by the present disclosure.

The moiety B may be cleavable or non-cleavable, bifunctional or multifunctional moiety which can be used to link one or more reactive and/or binder moieties to form the conjugate precursor of the invention. In some embodiments, the structure of the compound comprises, independently, more than one moieties A, preferably 2, 3, 4, 5, 6, 7, 8, 9 or 10 moieties A; and/or more than one moieties L, preferably 2, 3, 4, 5, 6, 7, 8, 9 or 10 moieties L per molecule. Preferably, the structure of the compound comprises 2 moieties A and 1 moiety L; or 1 moiety A and 2 moieties L per molecule.

Moiety L is preferably selected from: H, $NH_2$, $N_3$, COOH, SH, Hal,

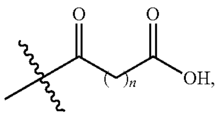 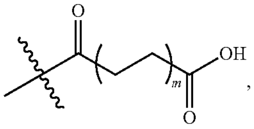,

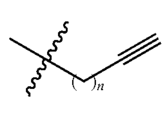, 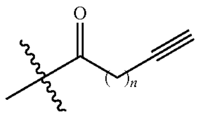,

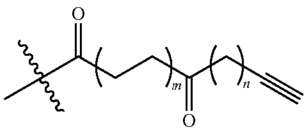, 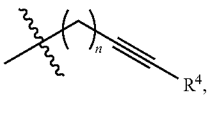

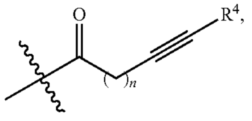

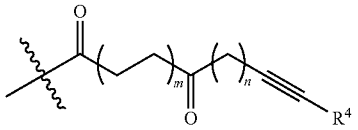 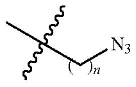

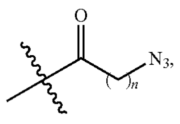 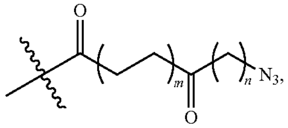

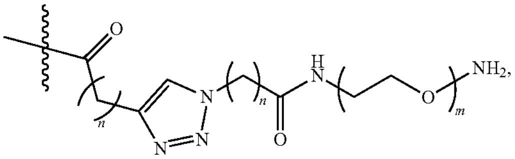

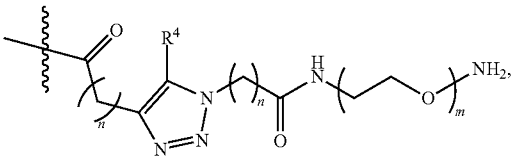

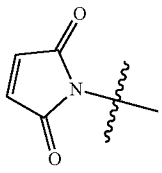, 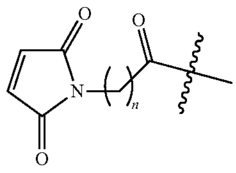,

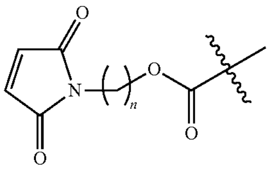, 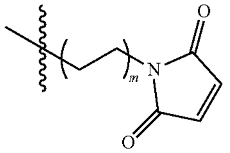,

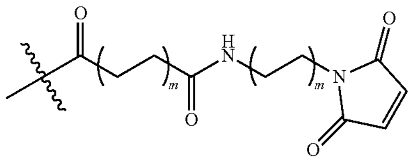,

-continued

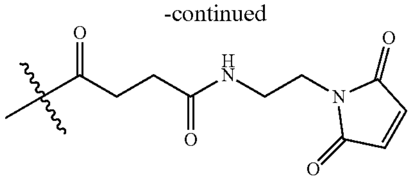

,

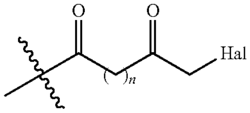

and

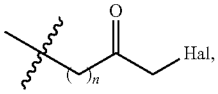

, wherein each n is, independently, 0, 1, 2, 3, 4, 5, 6, 7, 8, 9 or 10; each m is, independently, 0, 1, 2, 3, 4 or 5; each Hal is F, Cl, Br or I; and each $R^4$ is, independently selected from carboxy, alkyl, cycloalkyl, aryl and heteroaryl, wherein each of the foregoing is substituted or unsubstituted, halogen, and cyano.

Preferred compounds are those having a structure according to Table 3, their individual diastereoisomers, hydrates, solvates, crystal forms, individual tautomers or salts thereof.

Methods for Preparing a Conjugate

In one aspect of the invention, herein disclosed is a method for preparing a conjugate comprising the step of conjugating with a precursor compound as described above with a conjugation partner. Preferably, the precursor compound is conjugated to the conjugation partner by reacting therewith to form a covalent bond. Preferably, the thus obtained conjugate is a conjugate compound as described elsewhere in the present specification.

The conjugation partner can be an atom, a molecule, a particle, a therapeutic agent and/or diagnostic agent. Preferably, the conjugation is a therapeutic agent and/or diagnostic agent, and can correspond to the payload moieties already described in detail above with respect to the conjugates according to the invention.

Preferably, the method further comprises formulating the conjugate as a pharmaceutical composition or as a diagnostic composition. The pharmaceutical or diagnostic compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of carrier, excipient or diluent can be selected with regard to the intended route of administration and standard pharmaceutical practice. The pharmaceutical or diagnostic compositions may comprise as—or in addition to—the carrier, excipient or diluent any suitable binder(s), lubricant(s), suspending agent(s), coating agent(s), solubilising agent(s). All formulation details and aspects disclosed above in the section "Pharmaceutical compositions" fully apply here too.

General Techniques

The practice of the present invention employs, unless otherwise indicated, conventional methods of chemistry, biochemistry, molecular biology, cell biology, genetics, immunology and pharmacology, known to those of skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Chemical Synthesis

The compounds described herein may be prepared by chemical synthesis techniques.

It will be apparent to those skilled in the art that sensitive functional groups may need to be protected and deprotected during synthesis of a compound. This may be achieved by conventional techniques, for example as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be epimerised, for example if a base is used in a reaction with a substrate having an optical centre comprising a base-sensitive group. It should be possible to circumvent potential problems such as this by choice of reaction sequence, conditions, reagents, protection/deprotection regimes, etc. as is well-known in the art.

Definitions

Antibody. The term "antibody" is used in its broadest sense and covers monoclonal antibodies, polyclonal antibodies, dimers, multimers, multispecific antibodies (e.g., bispecific antibodies), veneered antibodies, antibody fragments and small immune proteins (SIPs) (see *Int. J. Cancer* (2002) 102, 75-85). An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e. a molecule that contains an antigen binding site that immunospecifically binds an antigen of a target of interest or part thereof. The antibodies may be of any type—such as IgG, IgE, IgM, IgD, and IgA)—any class—such as IgG1, IgG2, IgG3, IgG4, IgA1 and IgA2—or subclass thereof. The antibody may be or may be derived from murine, human, rabbit or from other species.

Antibody fragments. The term "antibody fragment" refers to a portion of a full length antibody, generally the antigen binding or variable region thereof. Examples of antibody fragments include, but are not limited to, Fab, Fab', $F(ab')_2$, and Fv fragments; diabodies; linear antibodies; single domain antibodies, including dAbs, camelid $V_{HH}$ antibodies and the IgNAR antibodies of cartilaginous fish. Antibodies and their fragments may be replaced by binding molecules based on alternative non-immunoglobulin scaffolds, peptide aptamers, nucleic acid aptamers, structured polypeptides comprising polypeptide loops subtended on a non-peptide backbone, natural receptors or domains thereof.

Derivative. A derivative includes the chemical modification of a compound. Examples of such modifications include the replacement of a hydrogen by a halo group, an alkyl group, an acyl group or an amino group and the like. The modification may increase or decrease one or more hydrogen bonding interactions, charge interactions, hydrophobic interactions, van der Waals interactions and/or dipole interactions.

Analog. This term encompasses any enantiomers, racemates and stereoisomers, as well as all pharmaceutically acceptable salts and hydrates of such compounds.

Unless otherwise stated, the following definitions apply to chemical terms used in connection of compounds of the invention and compositions containing such compounds.

Alkyl refers to a branched or unbranched saturated hydrocarbyl radical. Suitably, the alkyl group comprises from 1 to 100, preferably 3 to 30, carbon atoms, more preferably from 5 to 25 carbon atoms. Preferably, alkyl refers to methyl, ethyl, propyl, butyl, pentyl, or hexyl.

Alkenyl refers to a branched or unbranched hydrocarbyl radical containing one or more carbon-carbon double bonds. Suitably, the alkenyl group comprises from 2 to 30 carbon atoms, preferably from 5 to about 25 carbon atoms.

Alkynyl refers to a branched or unbranched hydrocarbyl radical containing one or more carbon-carbon triple bonds. Suitably, the alkynyl group comprises from about 3 to about 30 carbon atoms, for example from about 5 to about 25 carbon atoms.

Halogen refers to fluorine, chlorine, bromine or iodine, preferably fluorine or chlorine.

Cycloalkyl refers to an alicyclic moiety, suitably having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl refers to an aromatic carbocyclic ring system, suitably comprising 6, 7, 8, 9, 10, 11, 12, 13, 14, 15 or 16 ring carbon atoms. Aryl may be a polycyclic ring system, having two or more rings, at least one of which is aromatic. This term includes reference to groups such as phenyl, naphthyl fluorenyl, azulenyl, indenyl, anthryl and the like.

The prefix (hetero) herein signifies that one or more of the carbon atoms of the group may be substituted by nitrogen, oxygen, phosphorus, silicon or sulfur. Heteroalkyl groups include for example, alkyloxy groups and alkythio groups. Heterocycloalkyl or heteroaryl groups herein may have from 3, 4, 5, 6, 7, 8, 9, 10, 11, 12, 13, 14, 15 or 16 ring atoms, at least one of which is selected from nitrogen, oxygen, phosphorus, silicon and sulfur. In particular, a 3- to 10-membered ring or ring system and more particularly a 5- or 6-membered ring, which may be saturated or unsaturated. For example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, 1,3-Dioxo-1,3-dihydro-isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, [beta]-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, 3,4-dihydro-2H-isoquinolin-1-one, 3,4-dihydro-2H-isoquinolinyl, and the like.

"Substituted" signifies that one or more, especially up to 5, more especially 1, 2 or 3, of the hydrogen atoms in said moiety are replaced independently of each other by the corresponding number of substituents. The term "optionally substituted" as used herein includes substituted or unsubstituted. It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Preferably, the term "substituted" signifies one or more, especially up to 5, more especially 1, 2 or 3, of the hydrogen atoms in said moiety are replaced independently of each other by the corresponding number of substituents selected from OH, SH, $NH_2$, halogen, cyano, carboxy, alkyl, cycloalkyl, aryl and heteroaryl. Additionally, the substituents described herein may themselves be substituted by any substituent, subject to the aforementioned restriction to appropriate substitutions as recognised by the skilled person. Preferably, any of the aforementioned substituents may be further substituted by any of the aforementioned substituents, each of which may be further substituted by any of the aforementioned substituents.

Substituents may suitably include halogen atoms and halomethyl groups such as $CF_3$ and $CCl_3$; oxygen containing groups such as oxo, hydroxy, carboxy, carboxyalkyl, alkoxy, alkoyl, alkoyloxy, aryloxy, aryloyl and aryloyloxy; nitrogen containing groups such as amino, alkylamino, dialkylamino, cyano, azide and nitro; sulfur containing groups such as thiol, alkylthiol, sulfonyl and sulfoxide; heterocyclic groups which may themselves be substituted; alkyl groups, which may themselves be substituted; and aryl groups, which may themselves be substituted, such as phenyl and substituted phenyl. Alkyl includes substituted and unsubstituted benzyl.

Where two or more moieties are described as being "each independently" selected from a list of atoms or groups, this means that the moieties may be the same or different. The identity of each moiety is therefore independent of the identities of the one or more other moieties.

For ease of reference, numbers and structures of some compounds disclosed herein are summarised in the following Tables 2, 3 and 4. In case of doubt, the numbers and structures below control.

TABLE 2
| # | Structure |
|---|---|
| 1 | 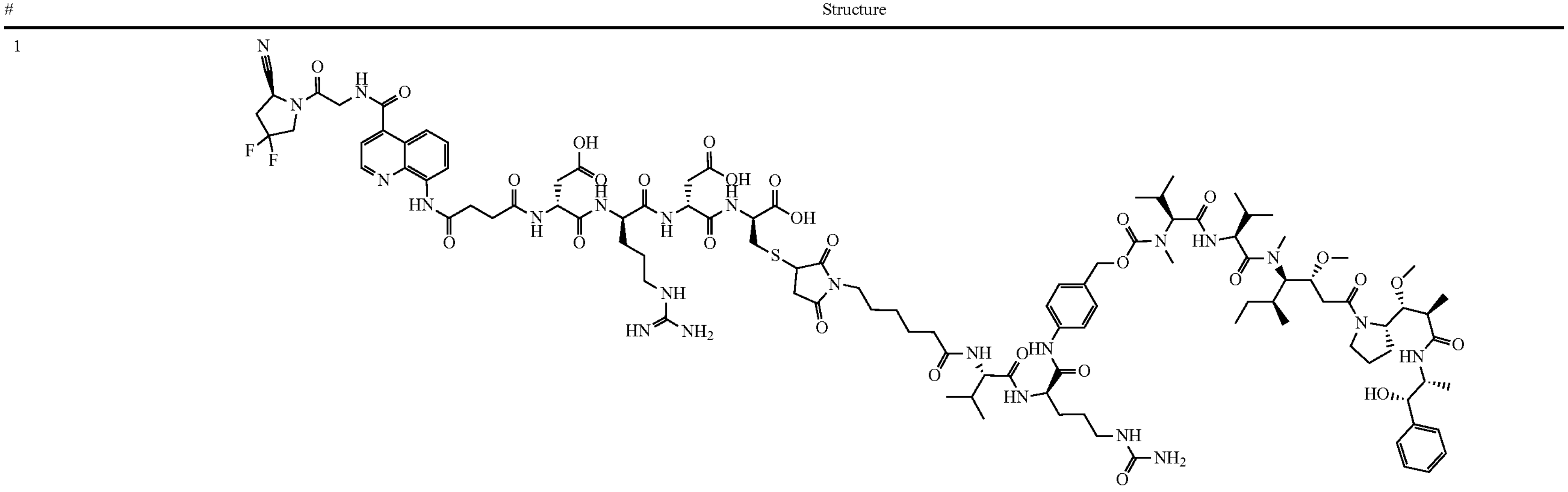 |
| 2 | 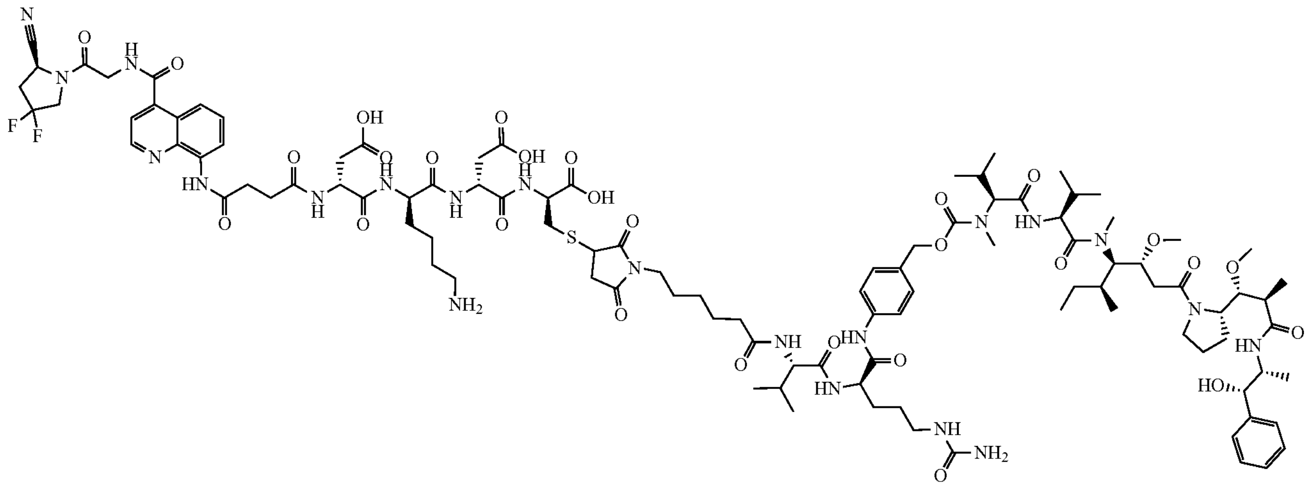 [SMILES: CC[C@H](C)[C@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@@H](CCCNC(N)=O)NC(=O)[C@@H](NC(=O)CCCCCN2C(=O)CC(SC[C@@H](NC(=O)[C@@H](CC(=O)O)NC(=O)[C@@H](CCCCN)NC(=O)[C@@H](CC(=O)O)NC(=O)CCC(=O)Nc3cccc4c(C(=O)NCC(=O)N5CC(F)(F)C[C@H]5C#N)ccnc34)C(=O)O)C2=O)C(C)C)cc1)C(C)C] |

TABLE 2-continued
| # | Structure |
| --- | --- |
| 3 | 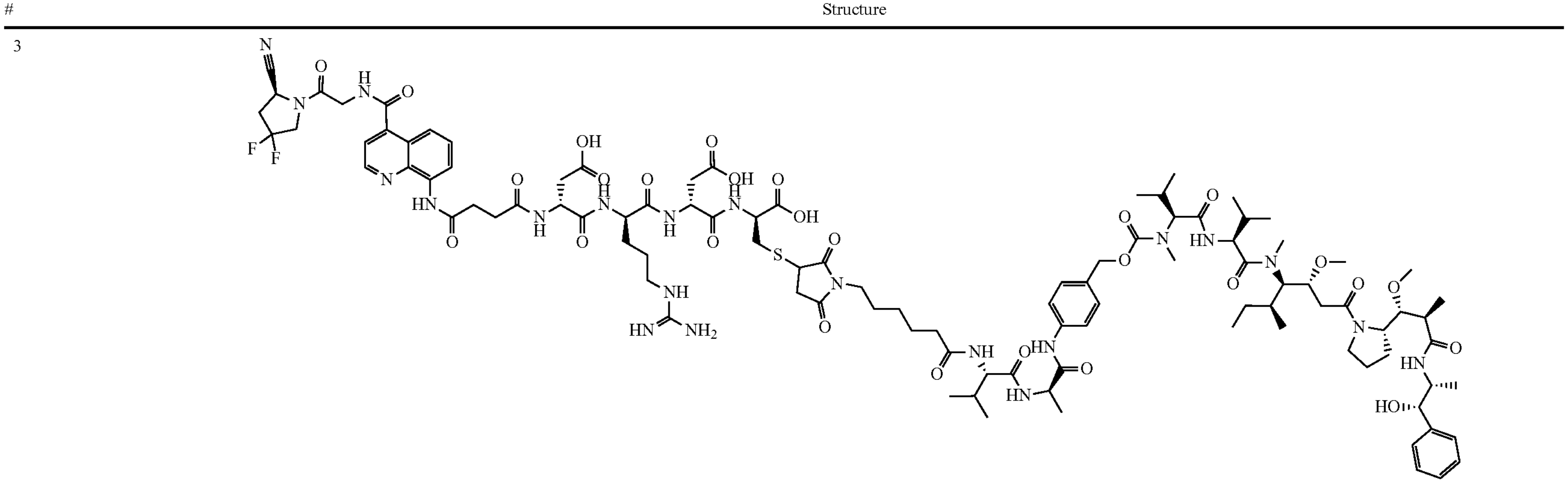 |
| 4 | 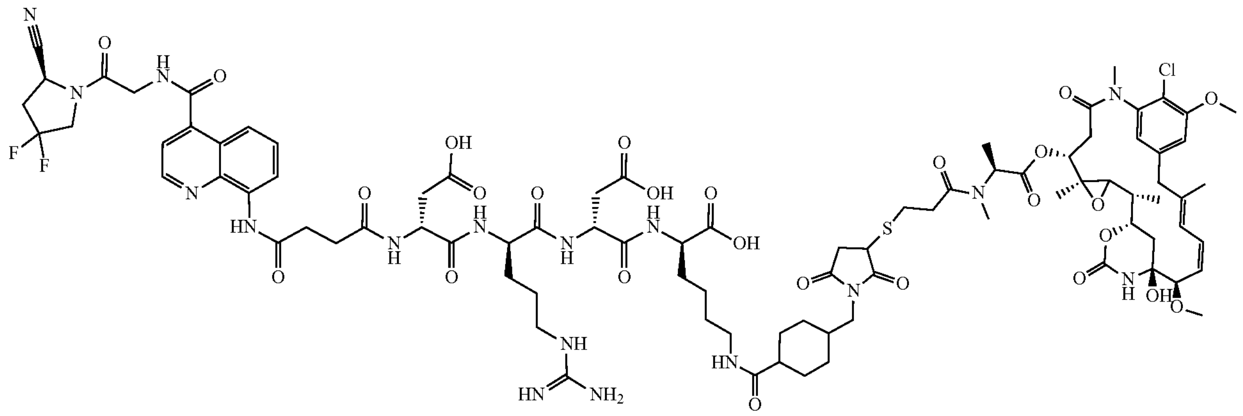 [SMILES: COc1cc2cc(c1Cl)N(C)C(=O)C[C@@H](OC(=O)[C@H](C)N(C)C(=O)CCSC1CC(=O)N(CC3CCC(C(=O)NCCCC[C@@H](NC(=O)[C@@H](CC(=O)O)NC(=O)[C@@H](CCCNC(=N)N)NC(=O)[C@@H](CC(=O)O)NC(=O)CCC(=O)Nc4cccc5c(C(=O)NCC(=O)N6CC(F)(F)C[C@H]6C#N)ccnc45)C(=O)O)CC3)C1=O)[C@]1(C)OC1[C@H](C)[C@@H]1C[C@@](O)(NC(=O)O1)[C@H](OC)/C=C\C=C(/C)C2] |

TABLE 2-continued
| # | Structure |
|---|---|
| 5 | 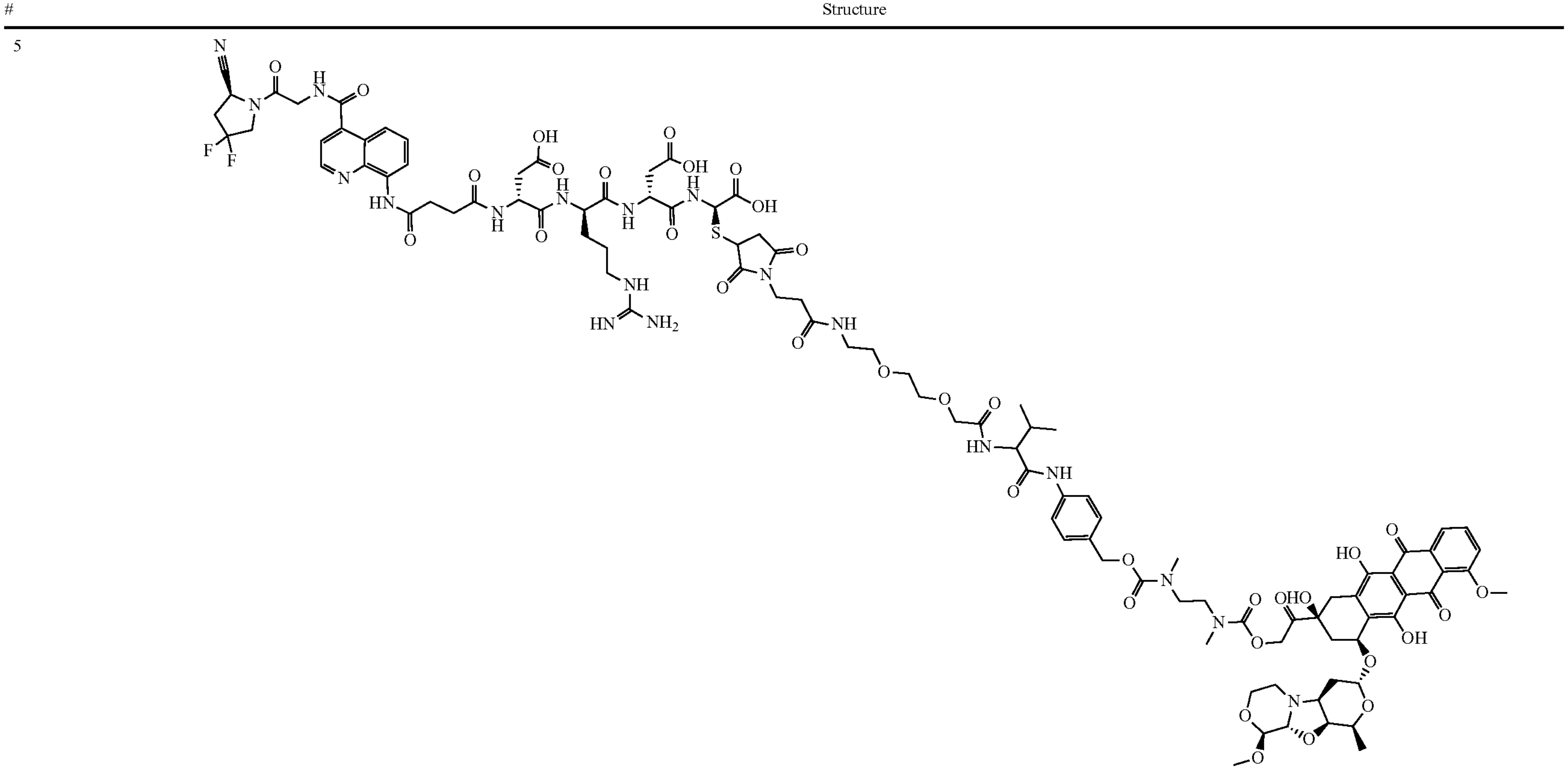 |

TABLE 2-continued
| # | Structure |
| --- | --- |
| 6 | 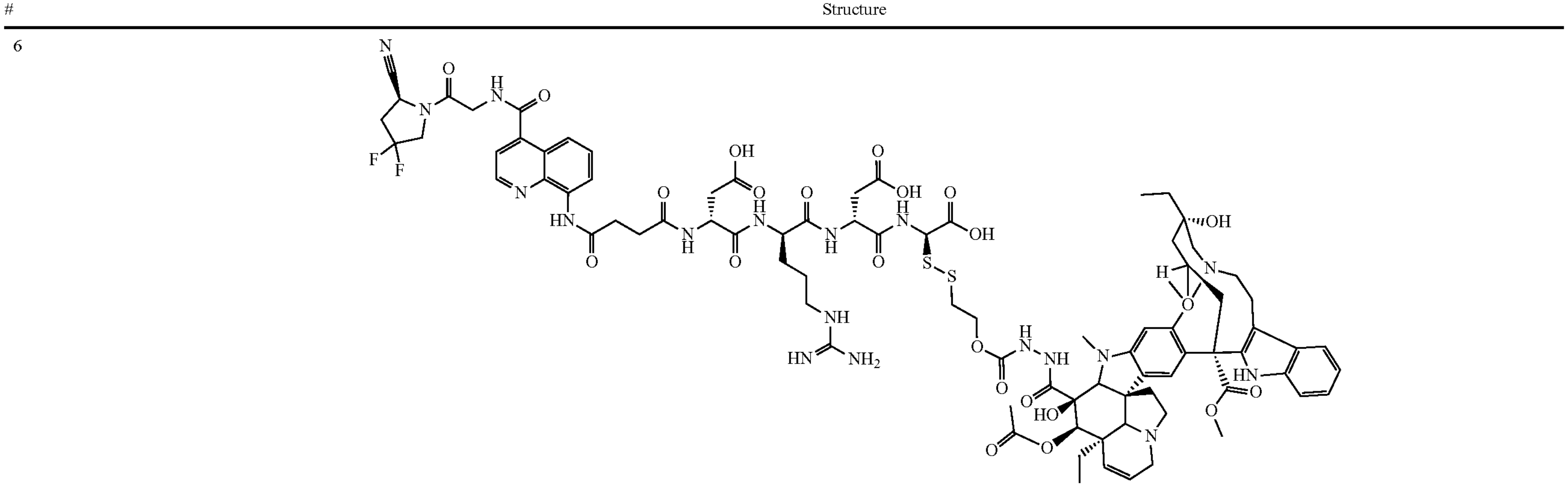 |
| 7 | 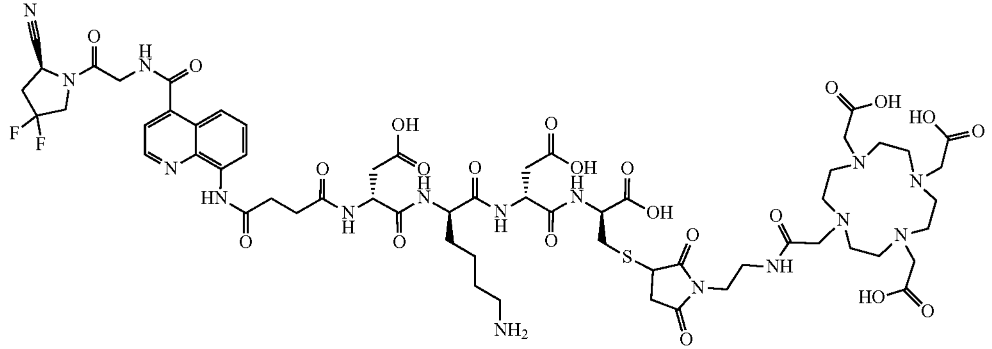 [SMILES: N#C[C@@H]1CC(F)(F)CN1C(=O)CNC(=O)c1ccnc2c(NC(=O)CCC(=O)N[C@H](CC(=O)O)C(=O)N[C@H](CCCCN)C(=O)N[C@H](CC(=O)O)C(=O)N[C@H](CSC3CC(=O)N(CCNC(=O)CN4CCN(CC(=O)O)CCN(CC(=O)O)CCN(CC(=O)O)CC4)C3=O)C(=O)O)cccc12] |

TABLE 2-continued
| # | Structure |
| --- | --- |
| 8 | 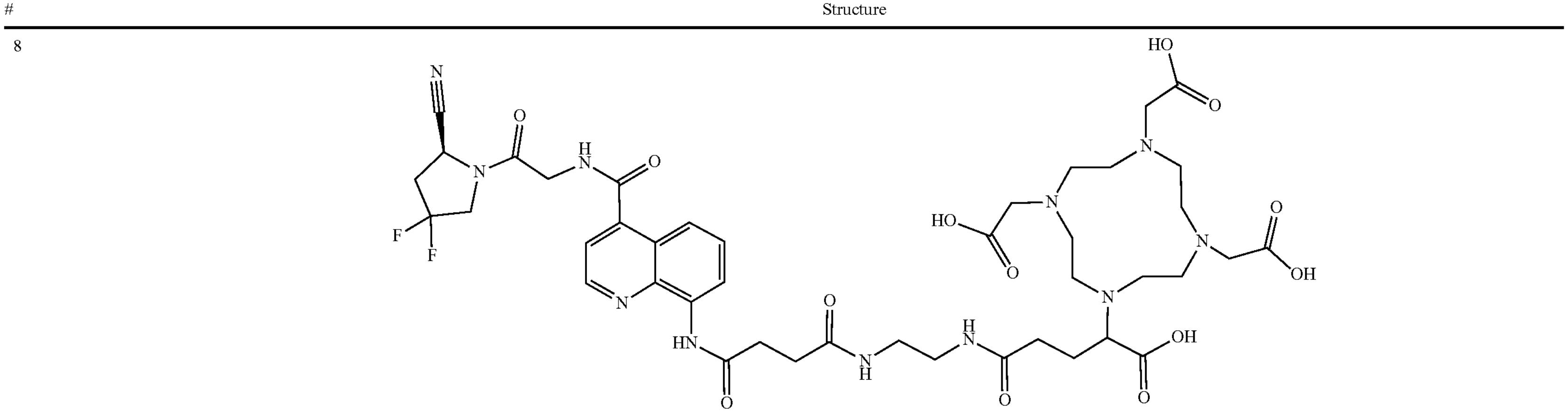 |
| 9 | 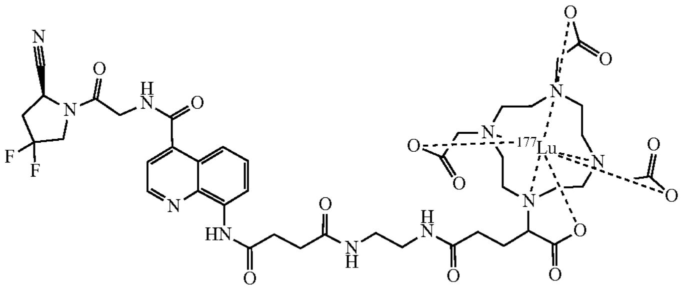 |
| 10 | 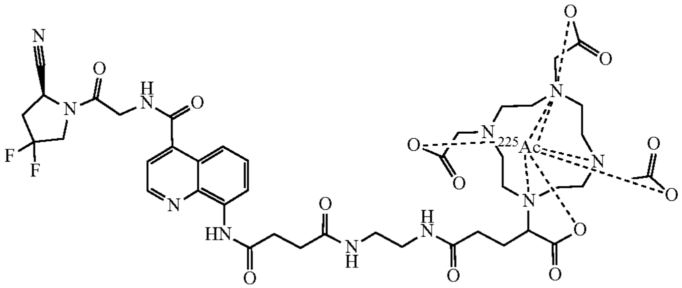 |

TABLE 2-continued
| # | Structure |
|---|---|
| 11 | 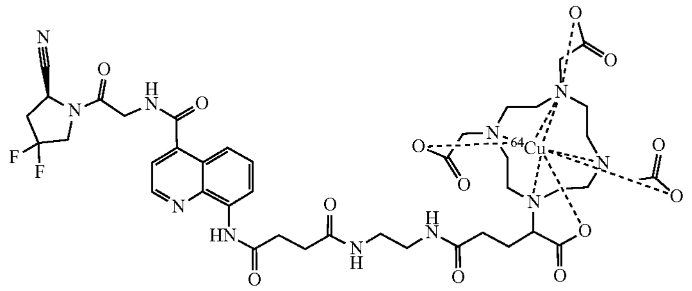 |
| 12 | 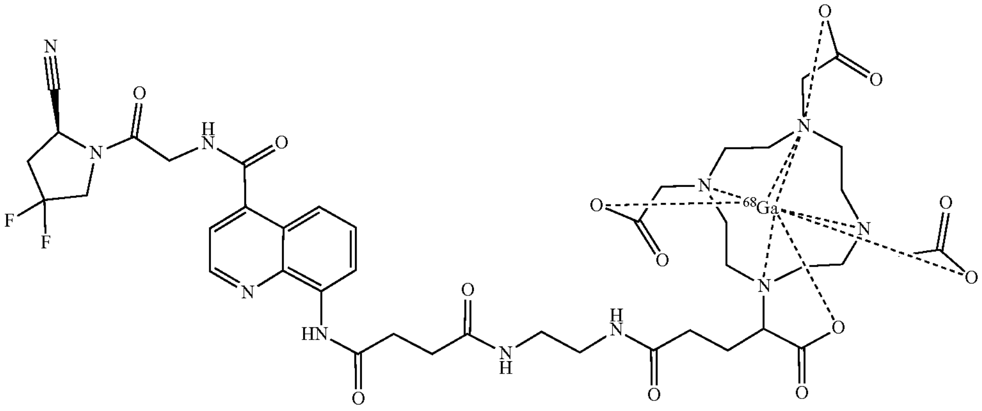 |

TABLE 2-continued
| # | Structure |
| --- | --- |
| 13 | 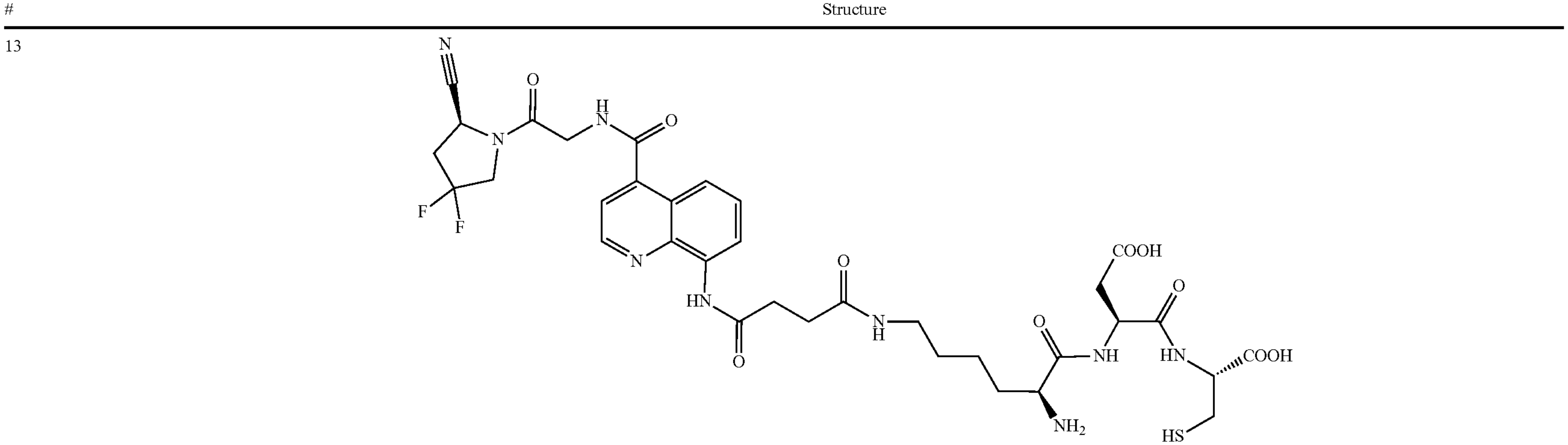 |
| 14 | 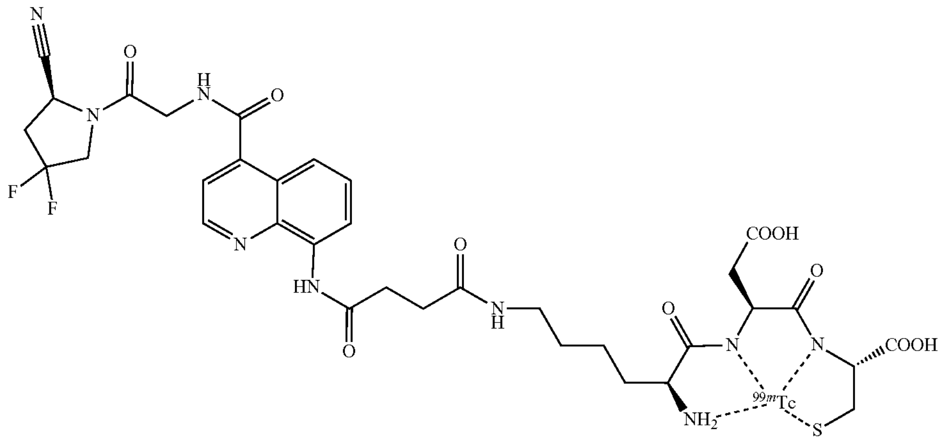 |

TABLE 2-continued
| # | Structure |
|---|---|
| 15 | 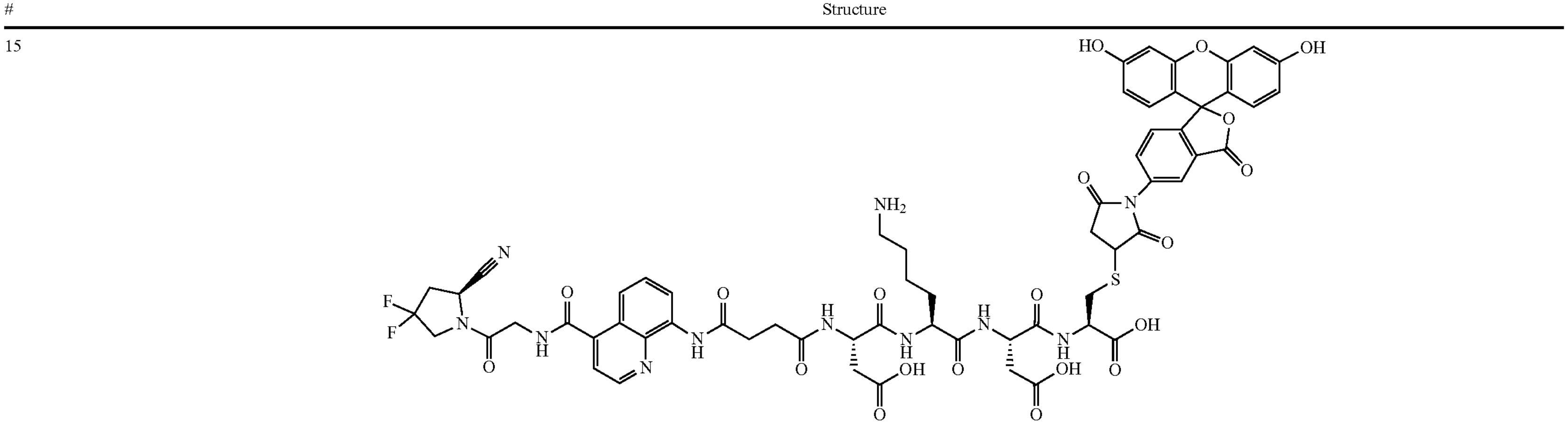 |

TABLE 2-continued
| # | Structure |
|---|---|
| 18 | 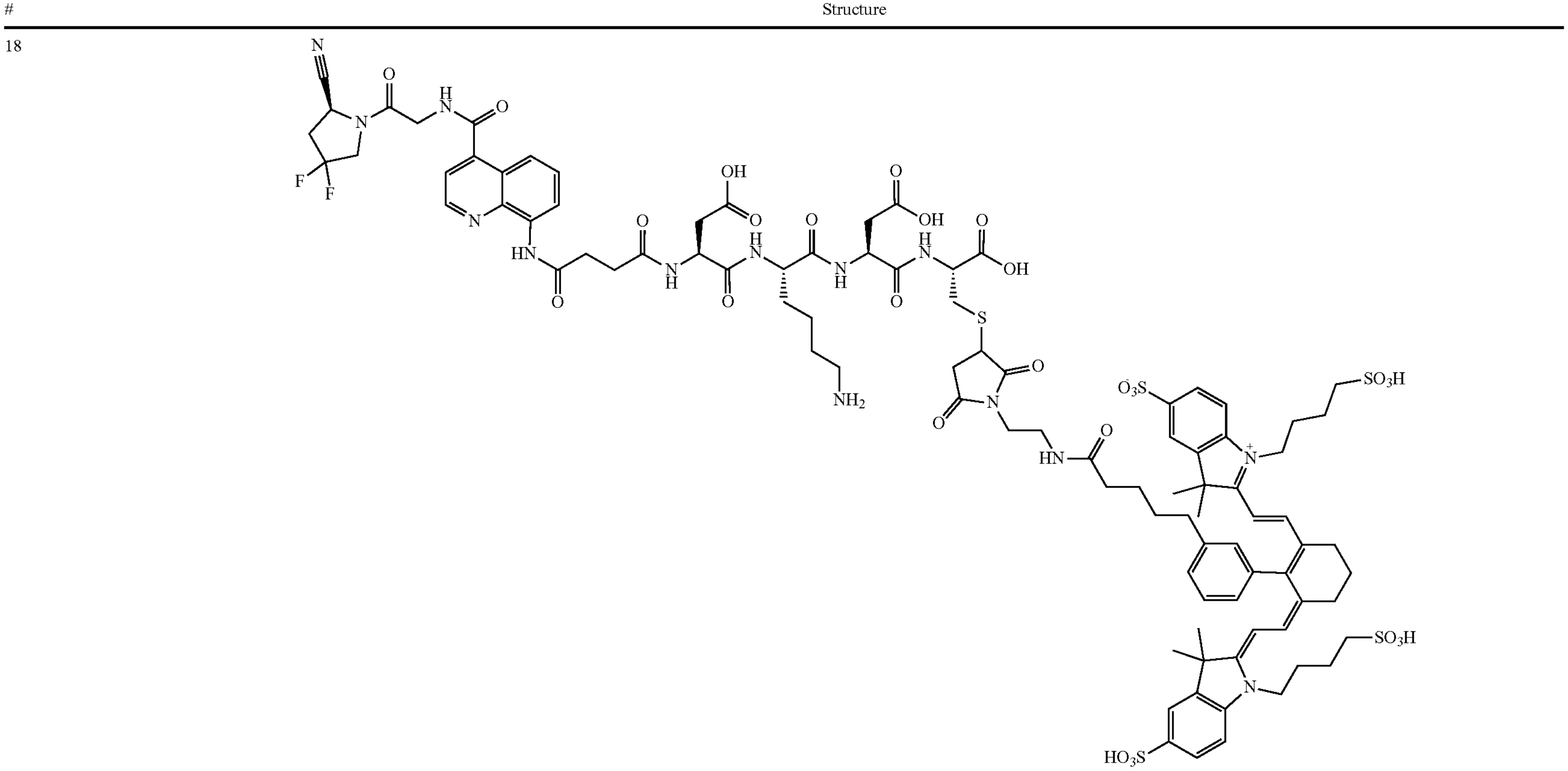 |

TABLE 2-continued
| # | Structure |
|---|---|
| 21 | 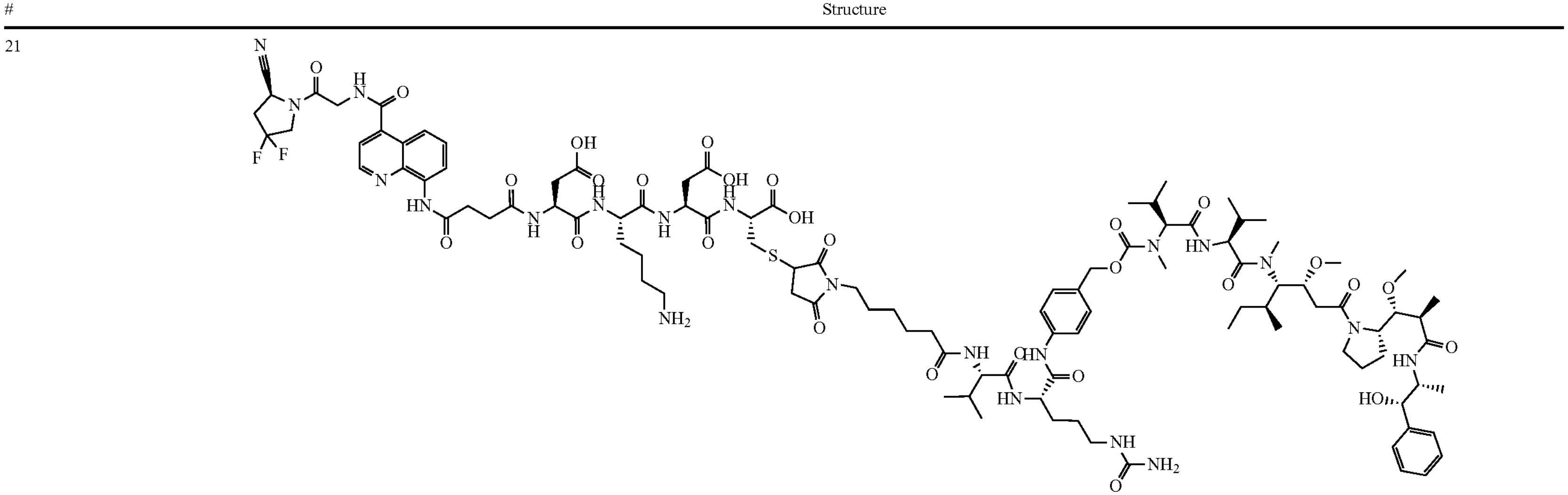 |

TABLE 2-continued
| # | Structure |
|---|---|
| 26 | 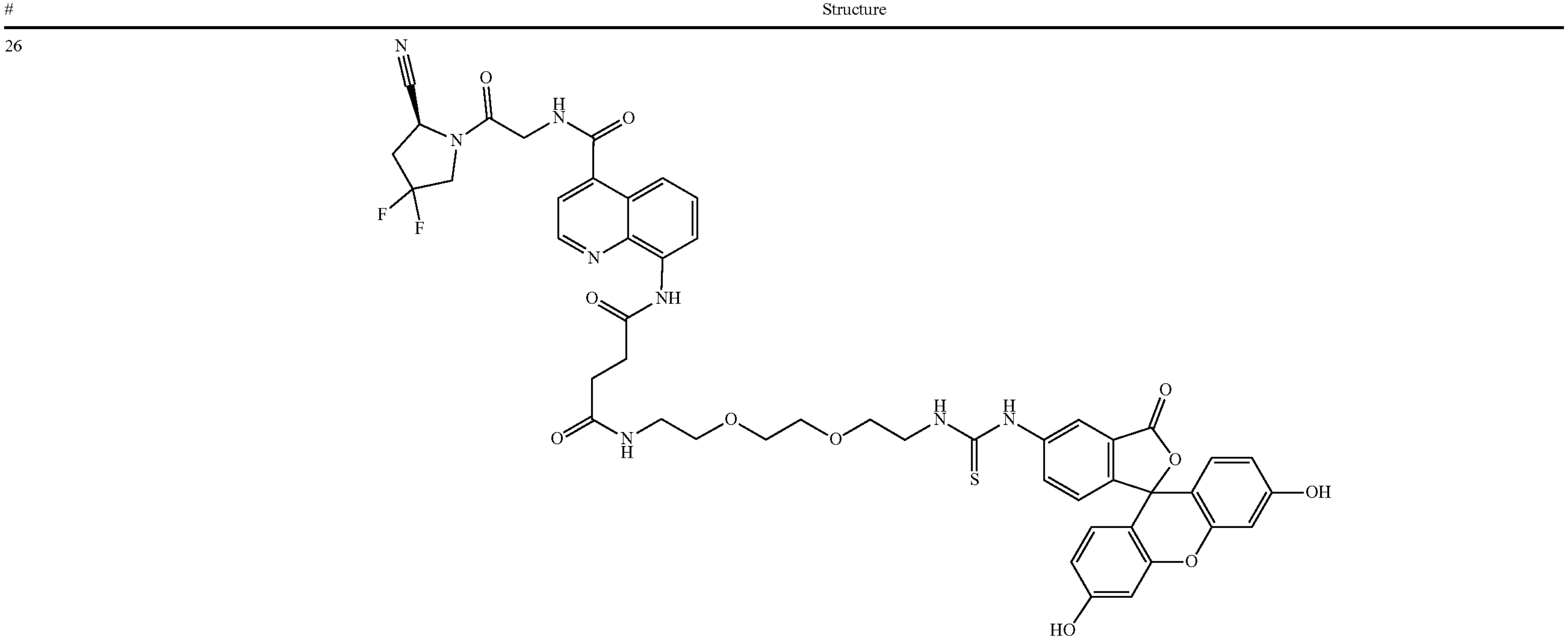 |

TABLE 2-continued
| # | Structure |
|---|---|
| 27 | 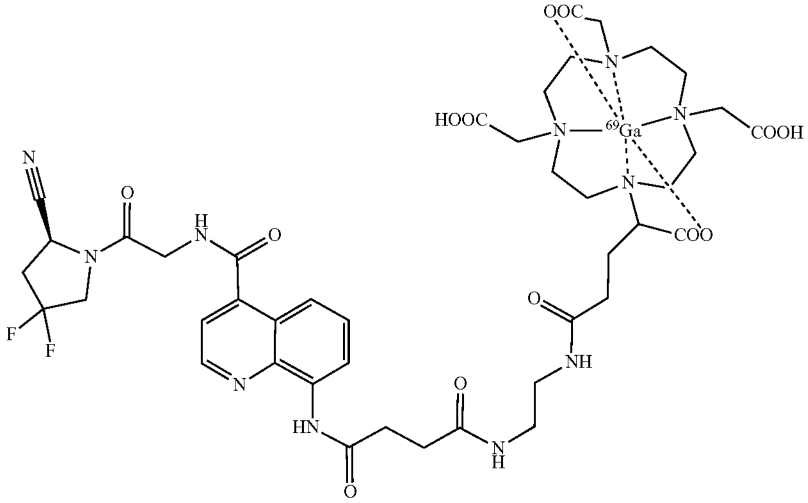 |
| 30 | 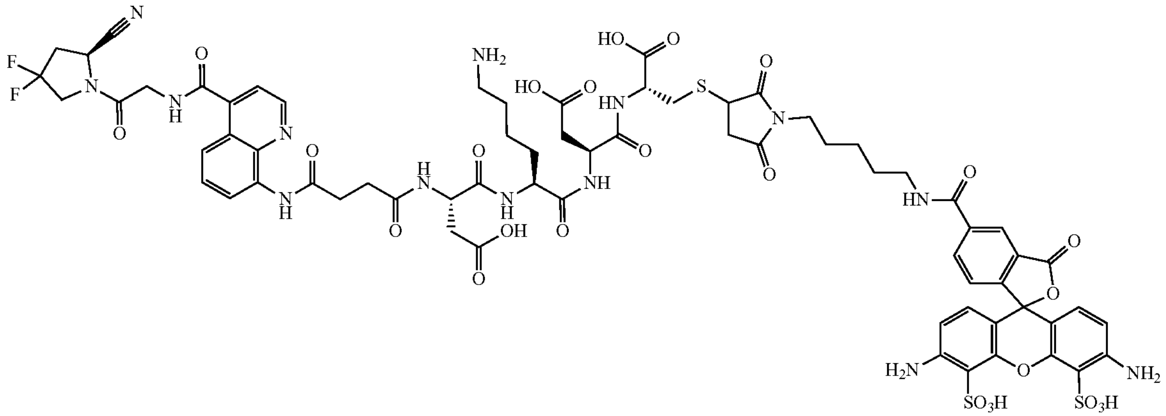 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CSC3CC(=O)N(CCCCCNC(=O)c4ccc5c(c4)C(=O)OC54c5ccc(N)c(S(=O)(=O)O)c5Oc5c4ccc(N)c5S(=O)(=O)O)C3=O)C(=O)O)cccc12] |

TABLE 2-continued
| # | Structure |
|---|---|
| 31 | 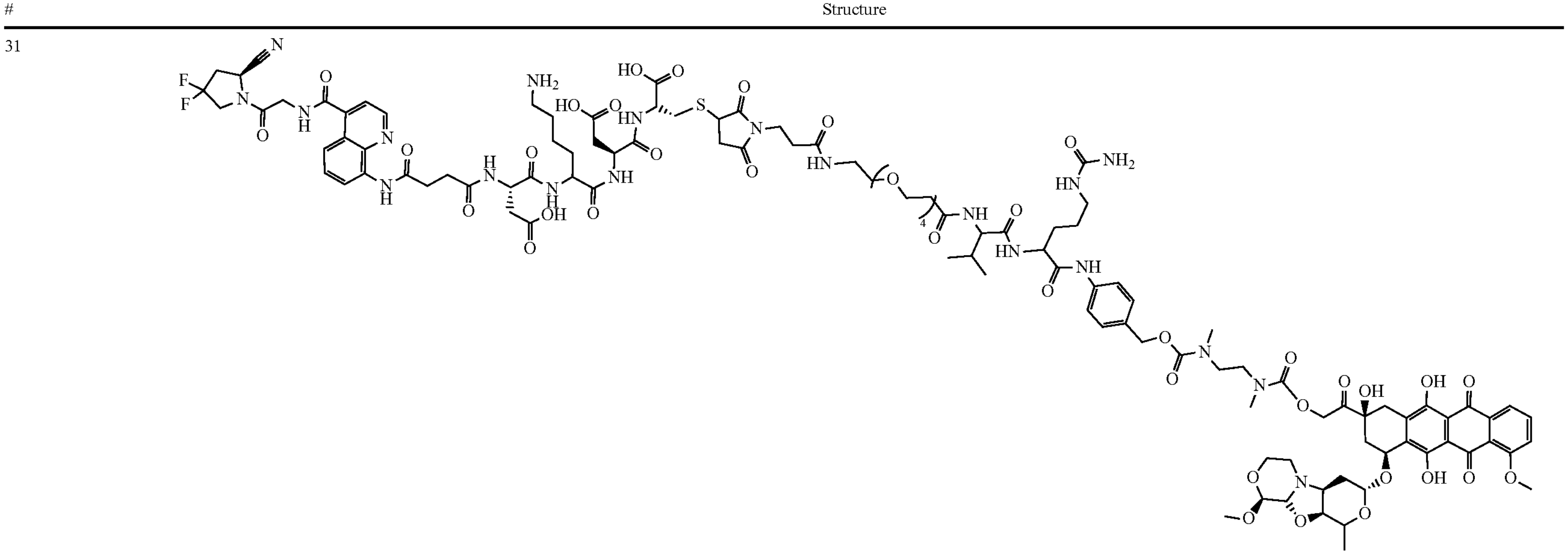 |

TABLE 2-continued
| # | Structure |
|---|---|
| 34 | 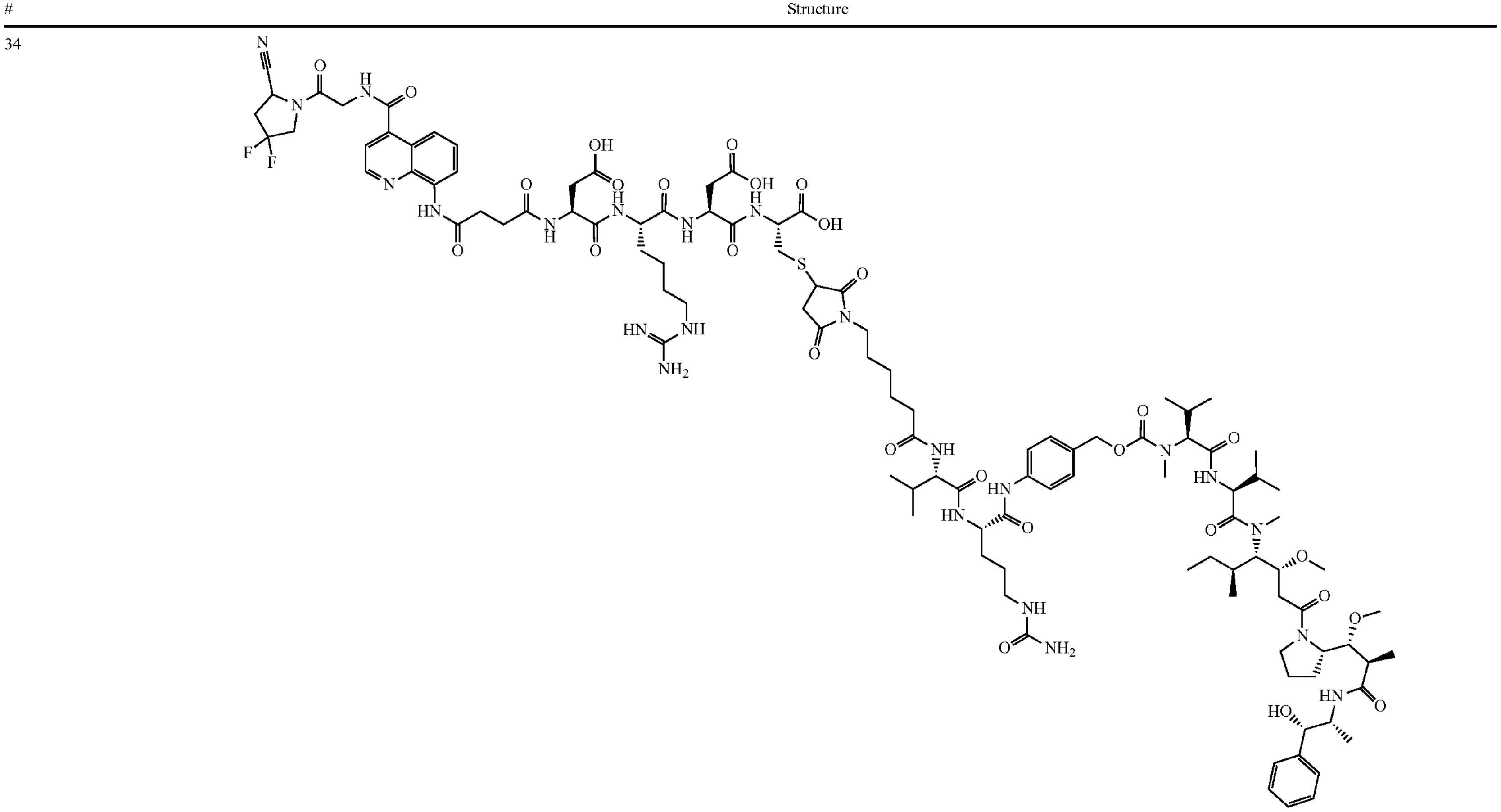 |

TABLE 2-continued
| # | Structure |
|---|---|
| 34a | 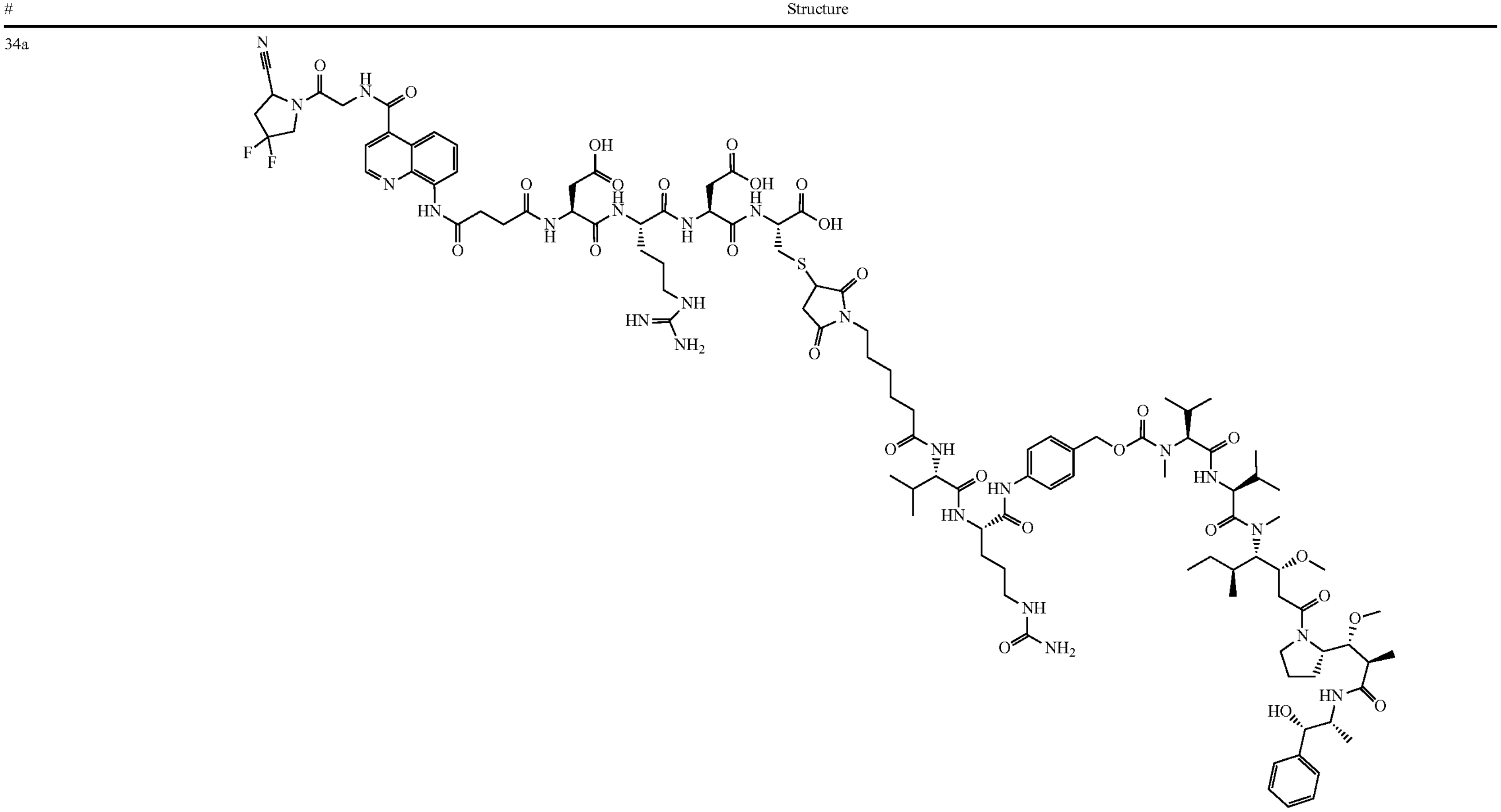 |

TABLE 2-continued
| # | Structure |
|---|---|
| 35 | 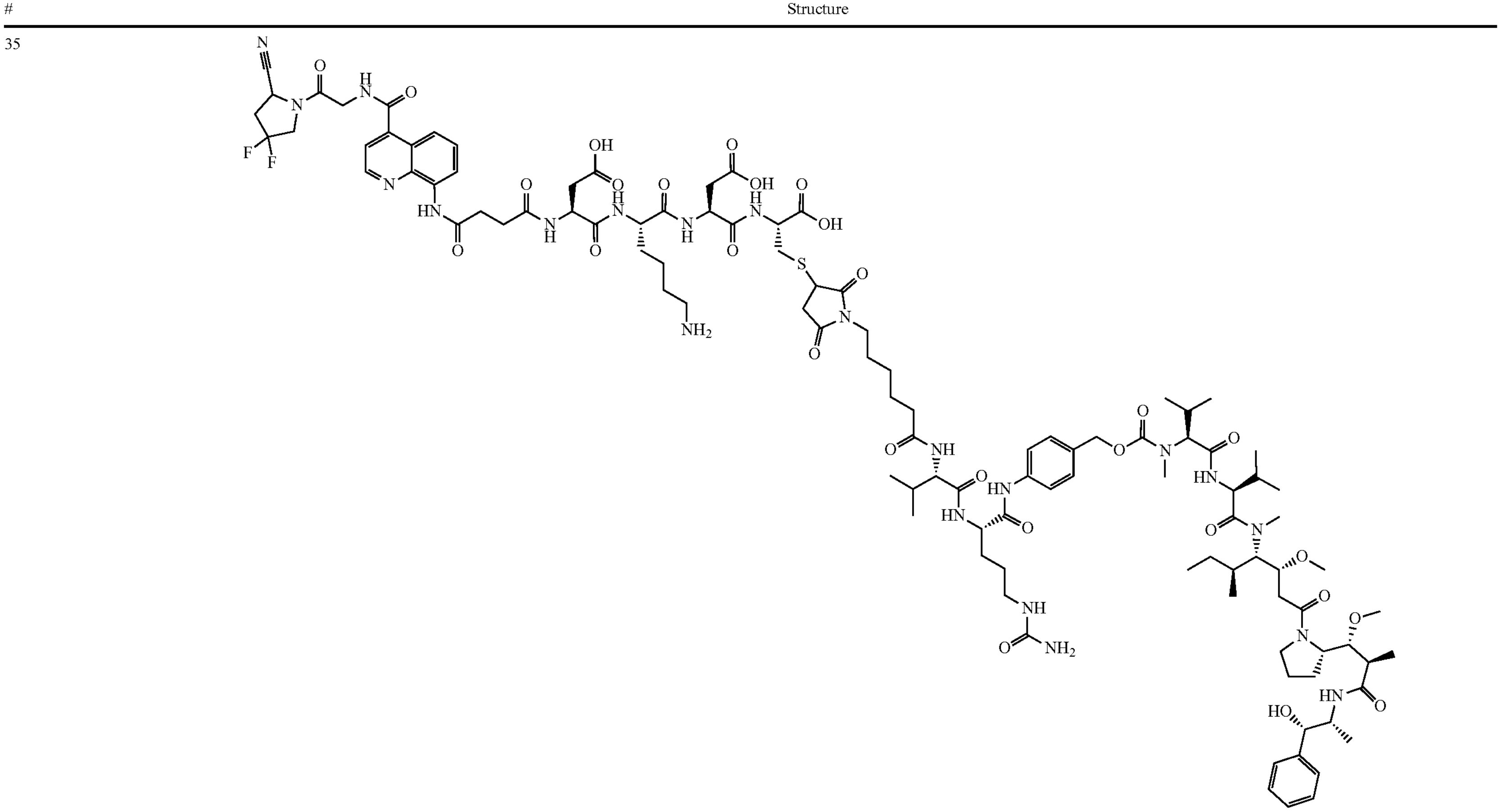 |

TABLE 2-continued
| # | Structure |
| --- | --- |
| 36 | 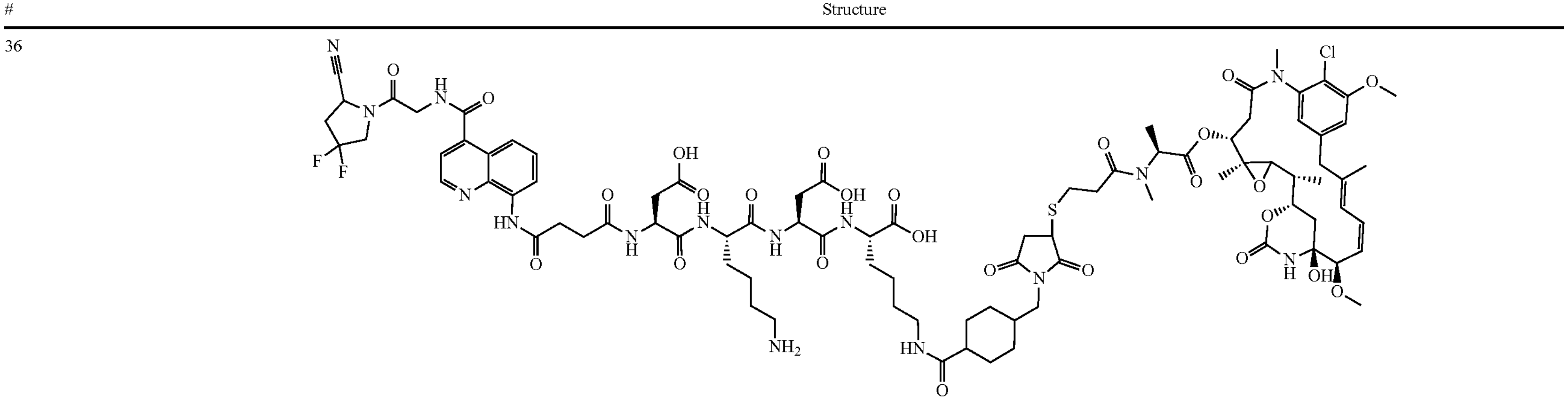 |
| 37 | 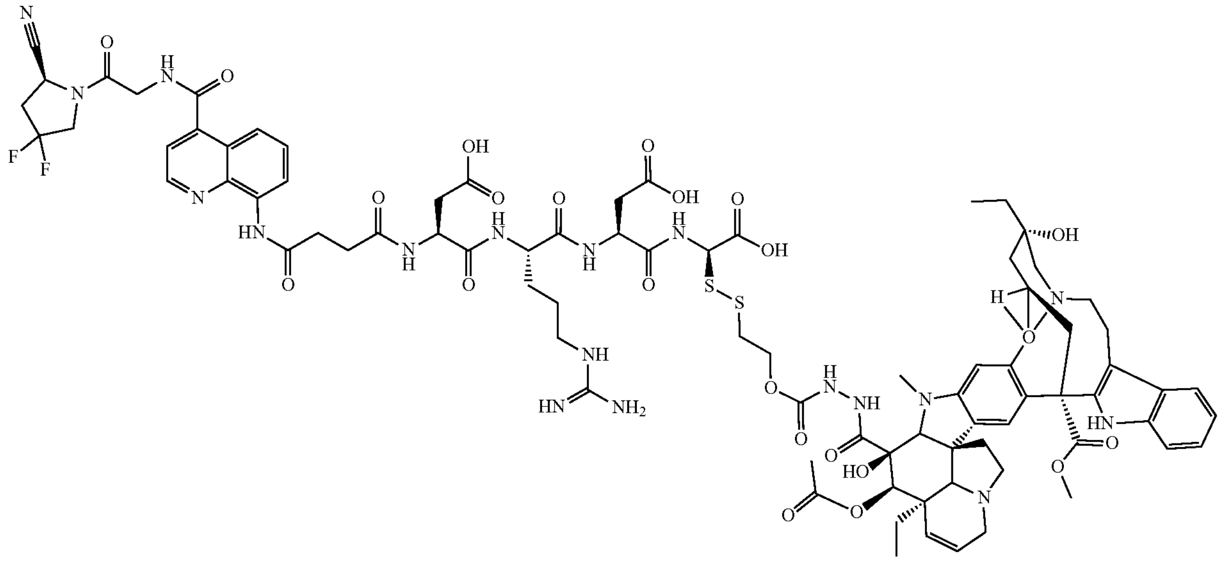 |

TABLE 2-continued
| # | Structure |
|---|---|
| 37a | 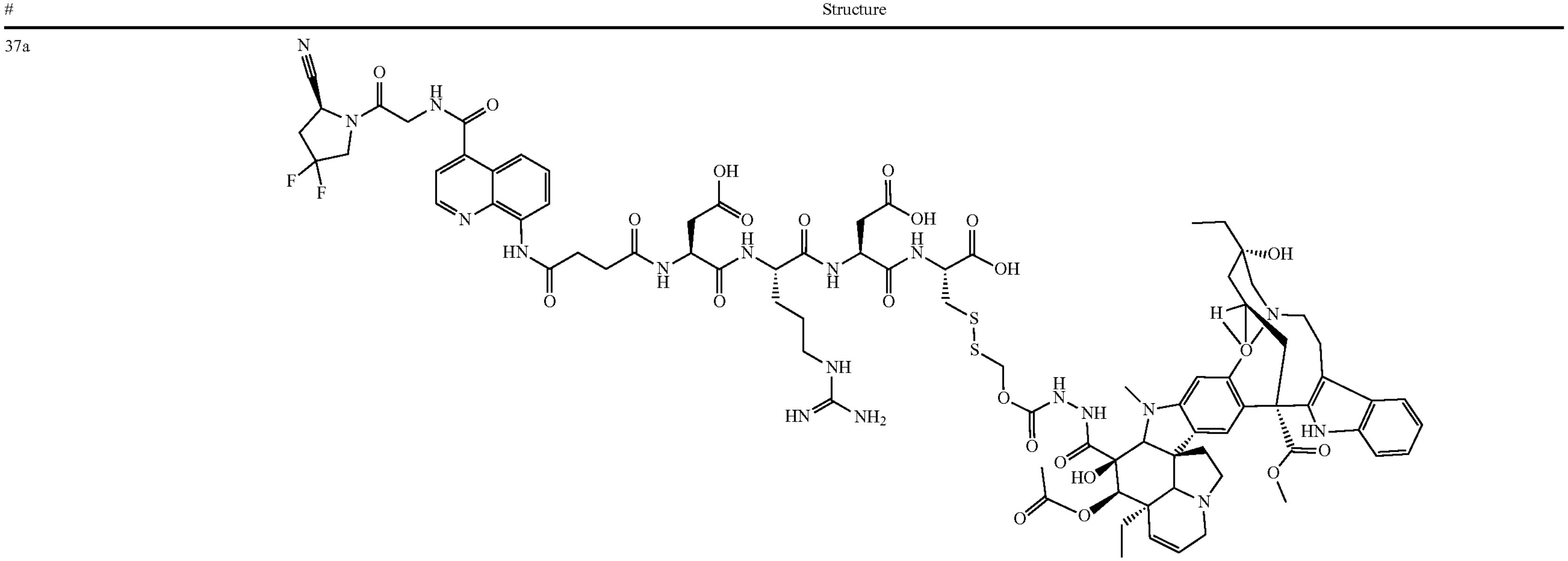 |
| 38 | 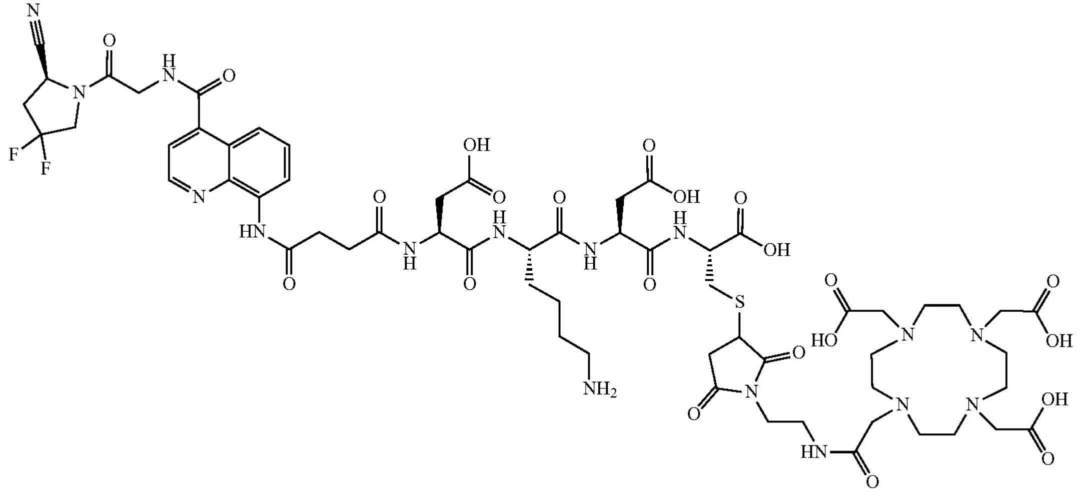 |

TABLE 2-continued
| # | Structure |
| --- | --- |
| 39 | 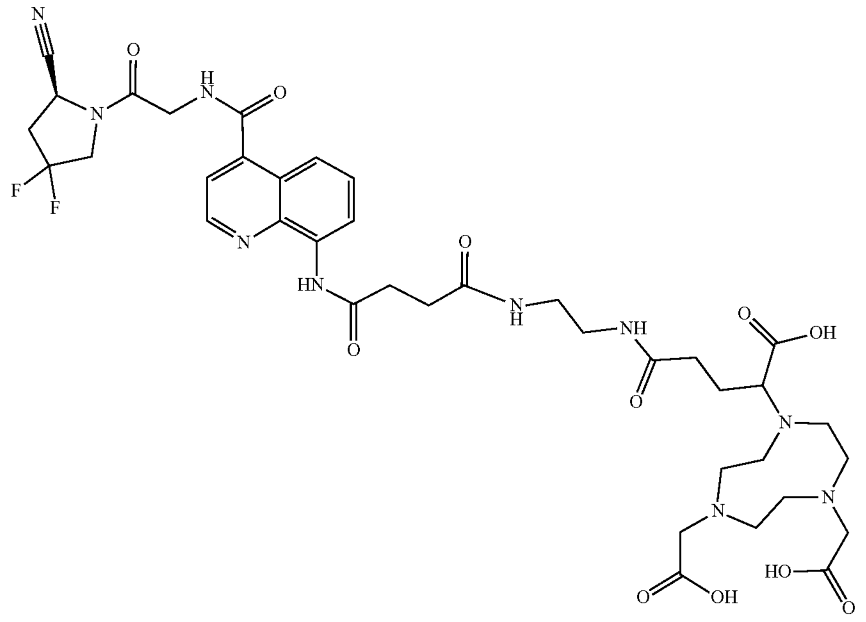 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CC3)cccc12] |

TABLE 2-continued
| # | Structure |
| --- | --- |
| 40 | 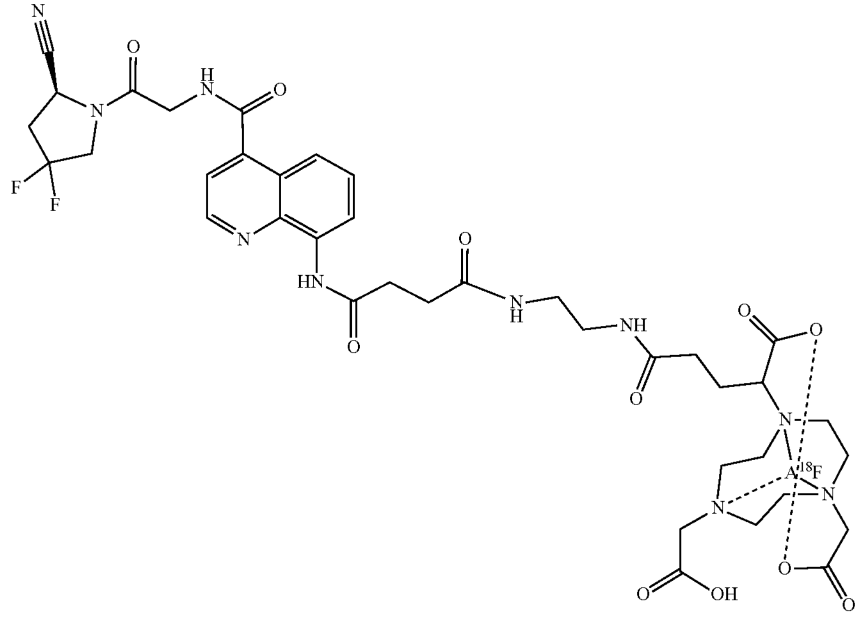 |

TABLE 2-continued
| # | Structure |
|---|---|
| 41 | 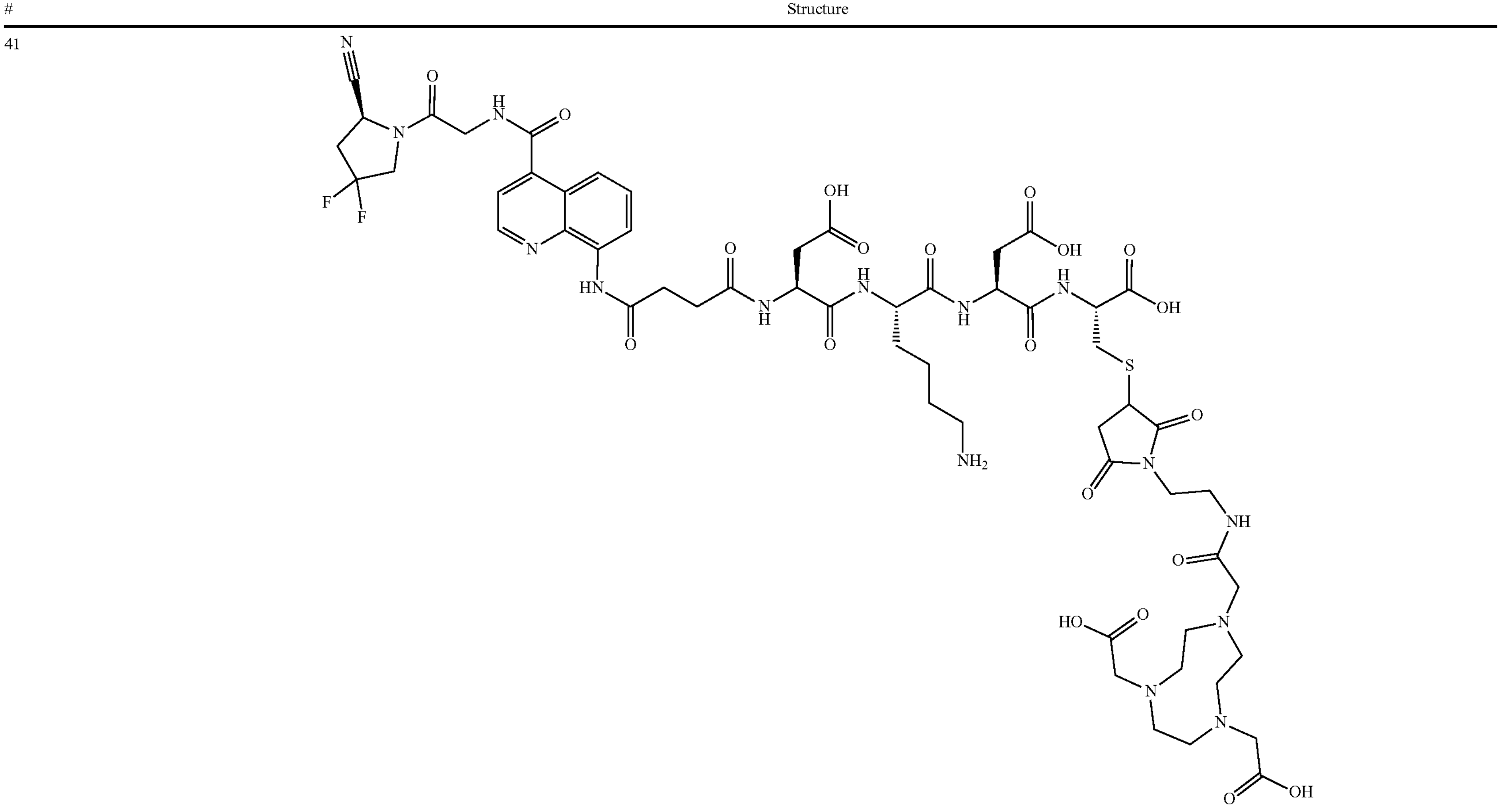 |

TABLE 2-continued
| # | Structure |
| --- | --- |
| 42 | 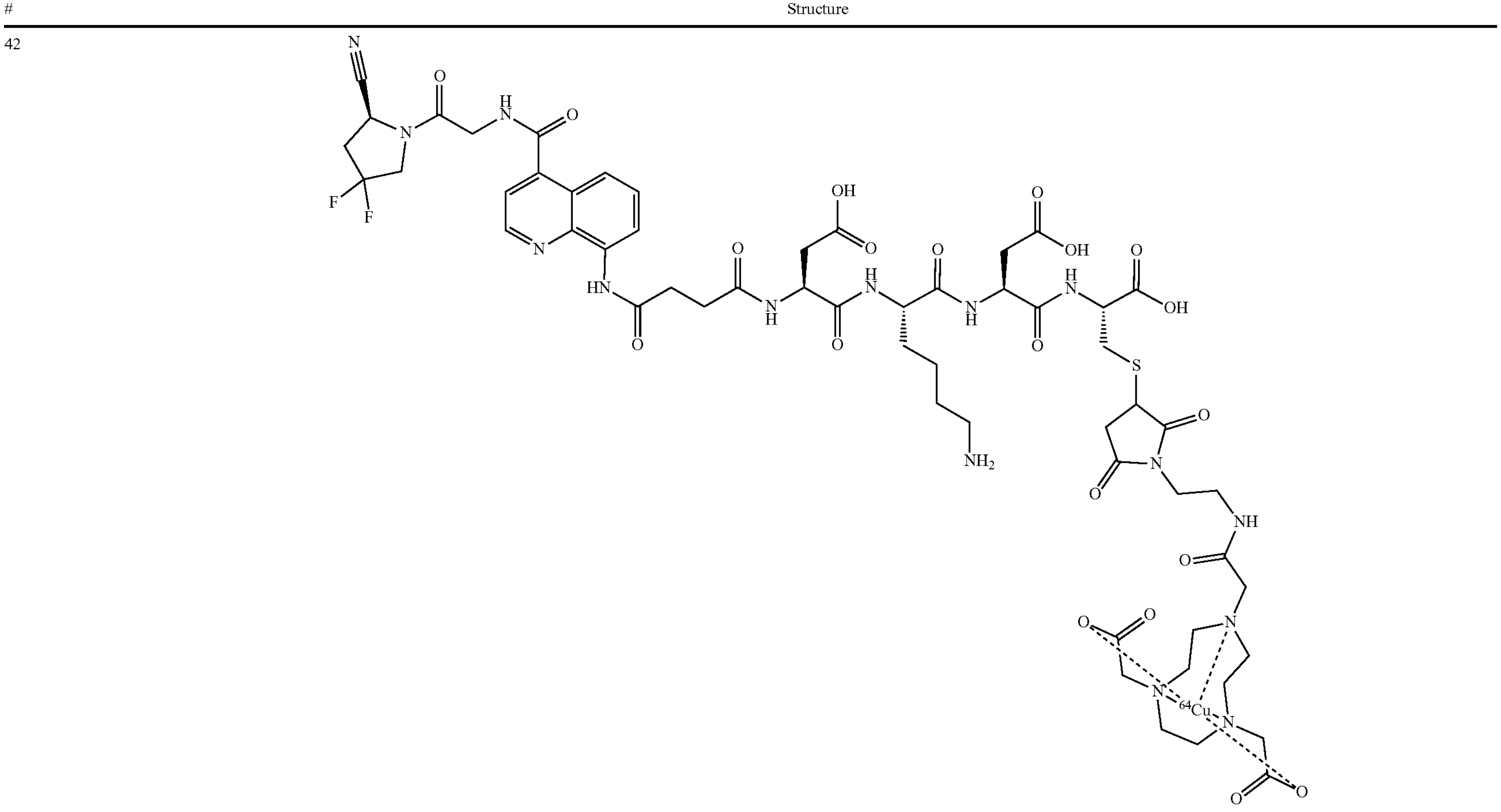 |

TABLE 2-continued
| # | Structure |
| --- | --- |
| 43 | 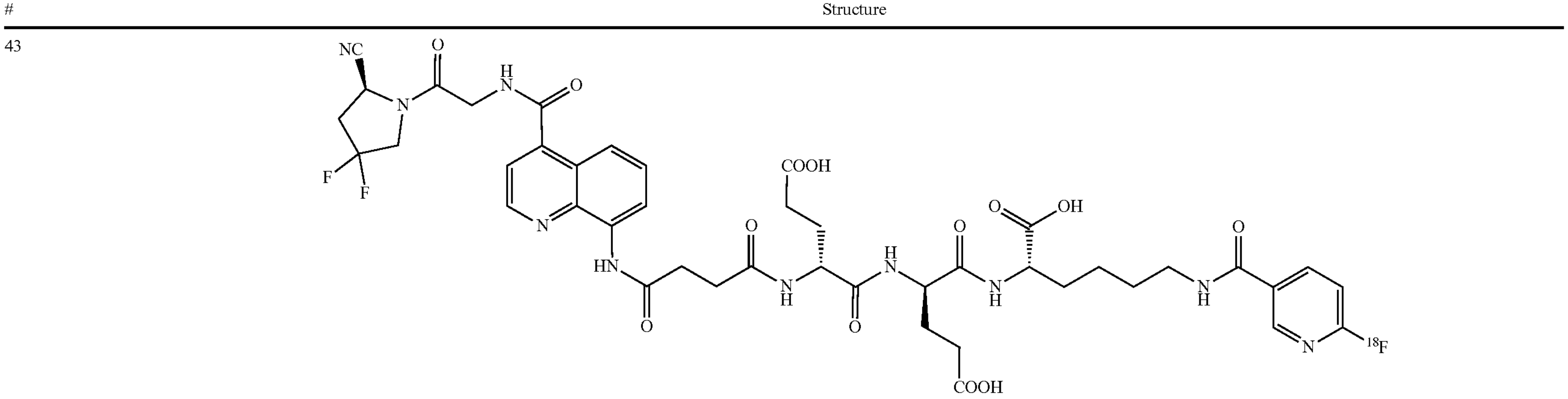 |
| 43a | 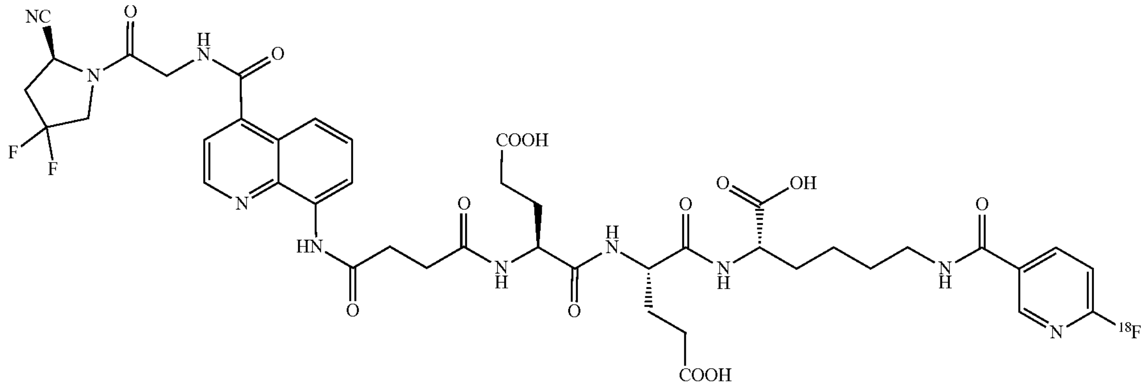 |

TABLE 2-continued
| # | Structure |
| --- | --- |
| 44 | 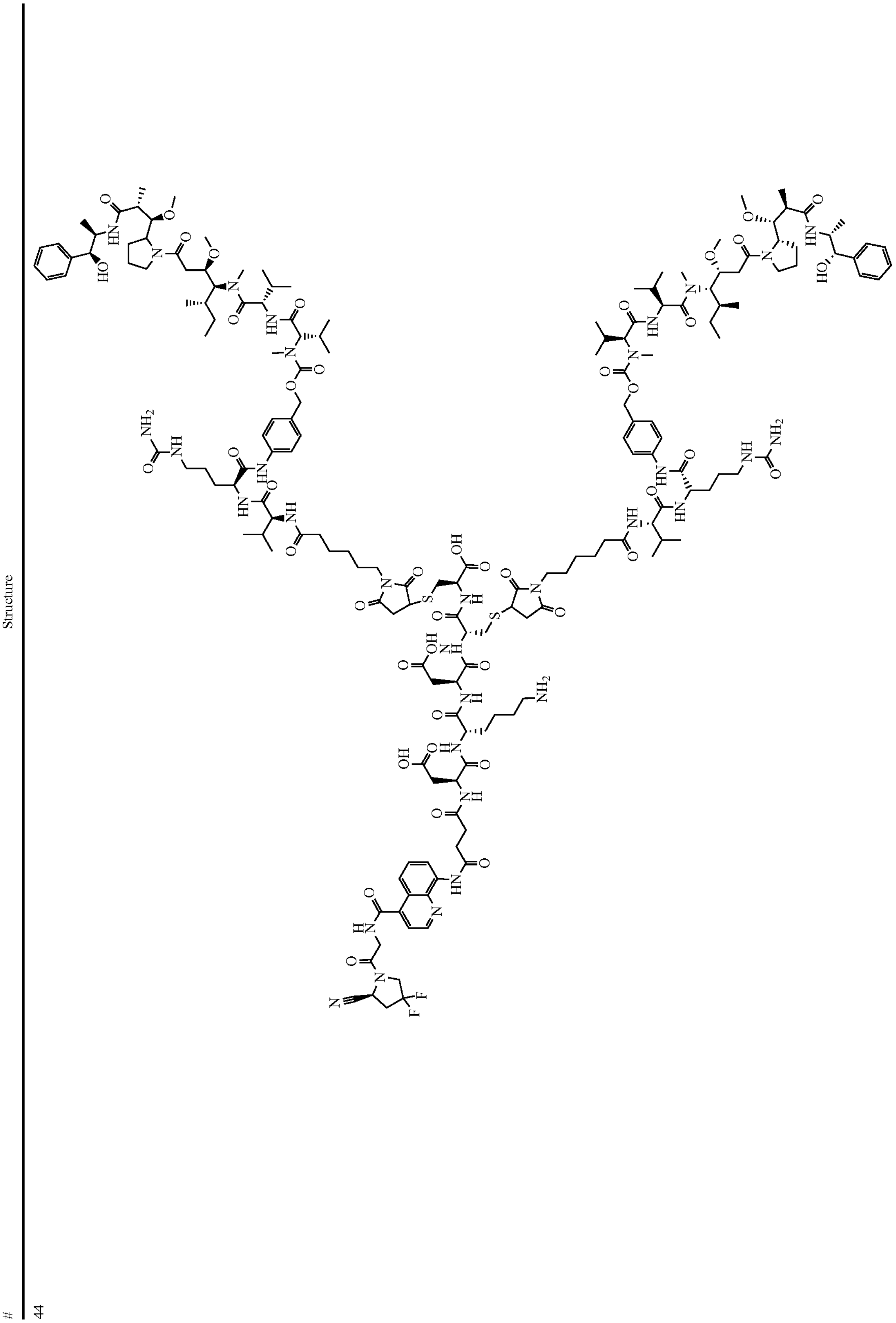 |

TABLE 2-continued
| # | Structure |
|---|---|
| 45 | 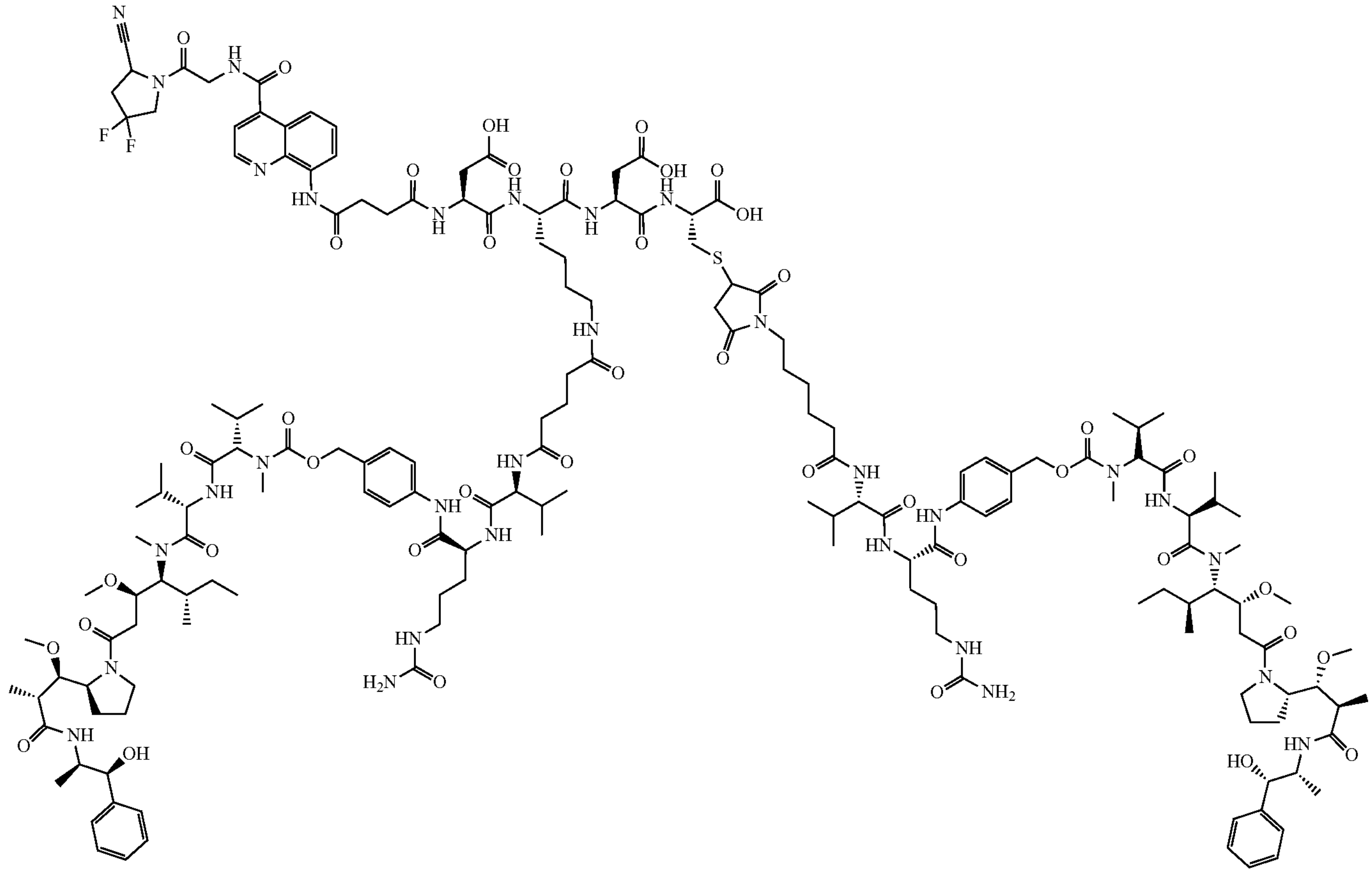 |

TABLE 2-continued
| # | Structure |
| --- | --- |
| 46 | 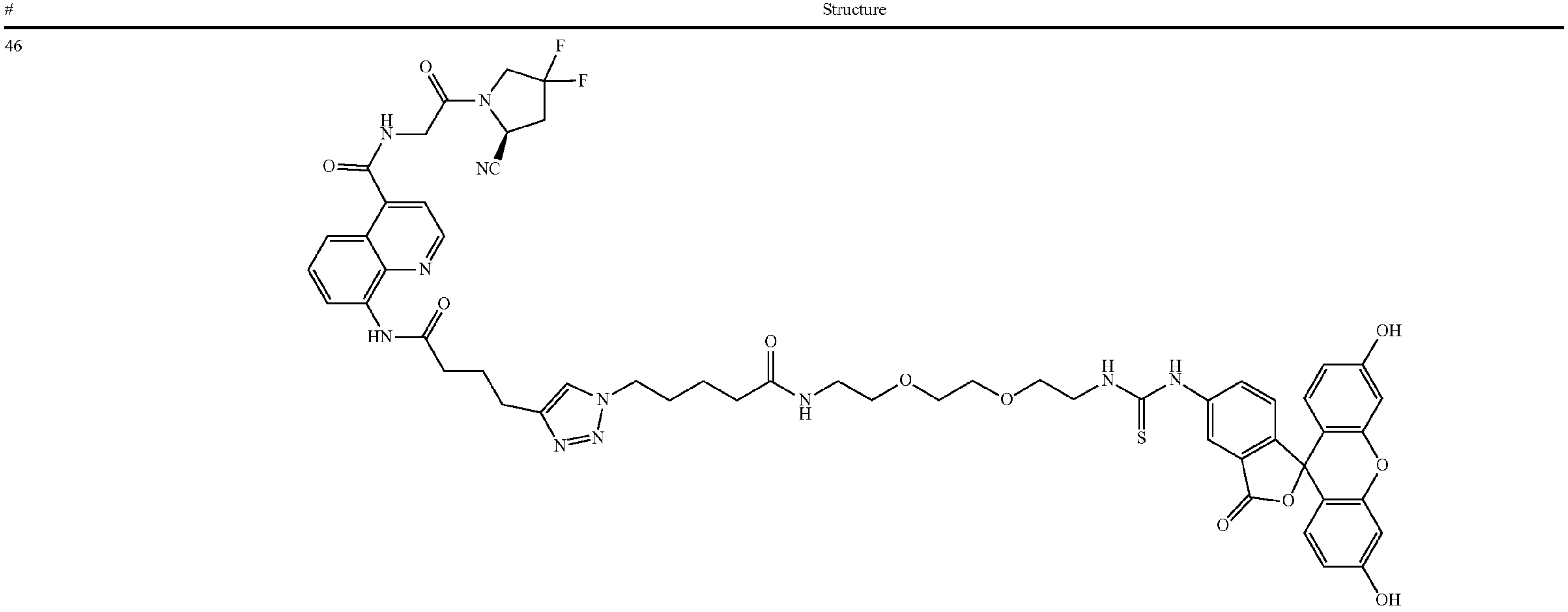 |

TABLE 2-continued
| # | Structure |
| --- | --- |
| 47 | 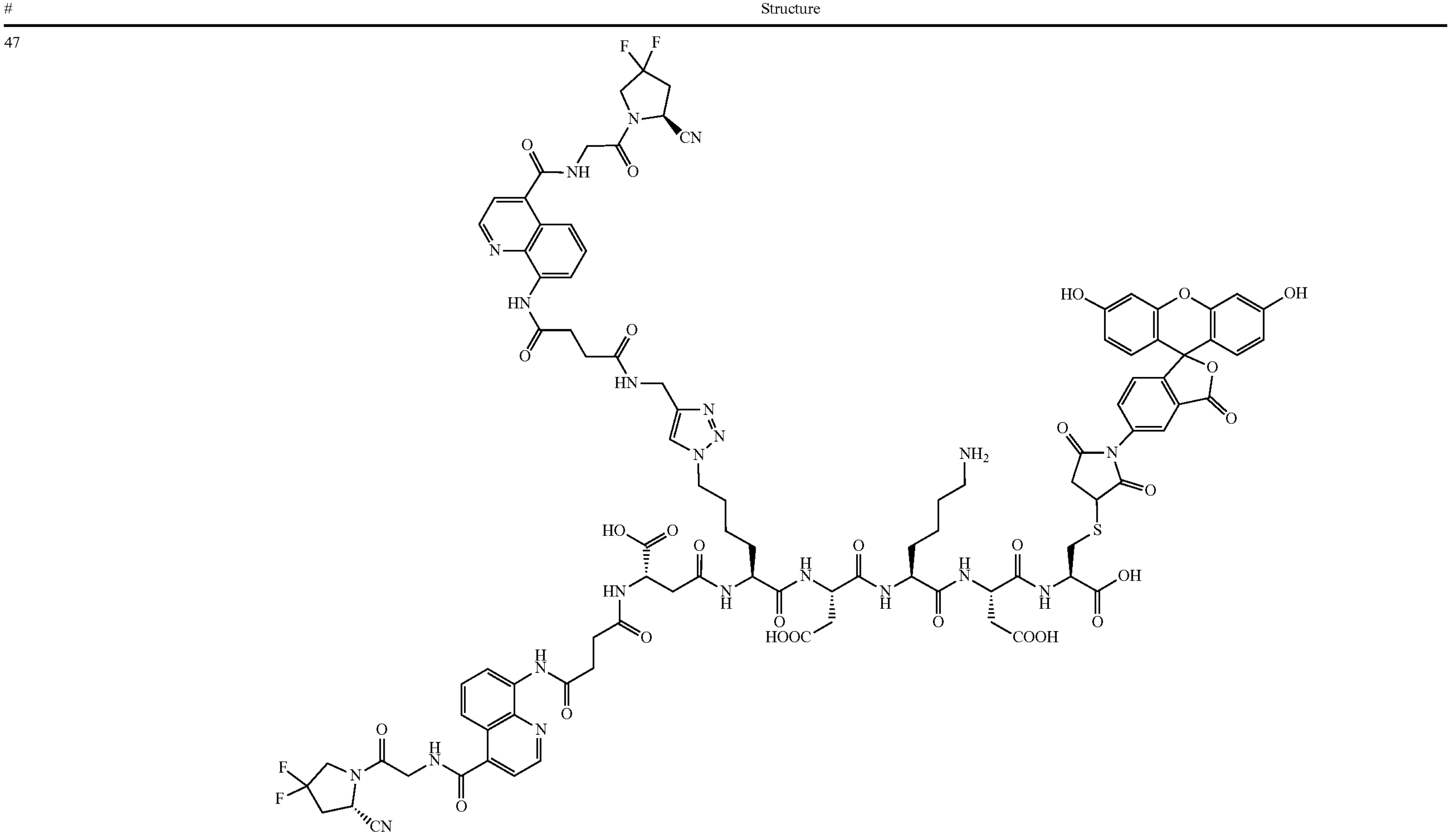 |

TABLE 2-continued
| # | Structure |
|---|---|
| 48 | 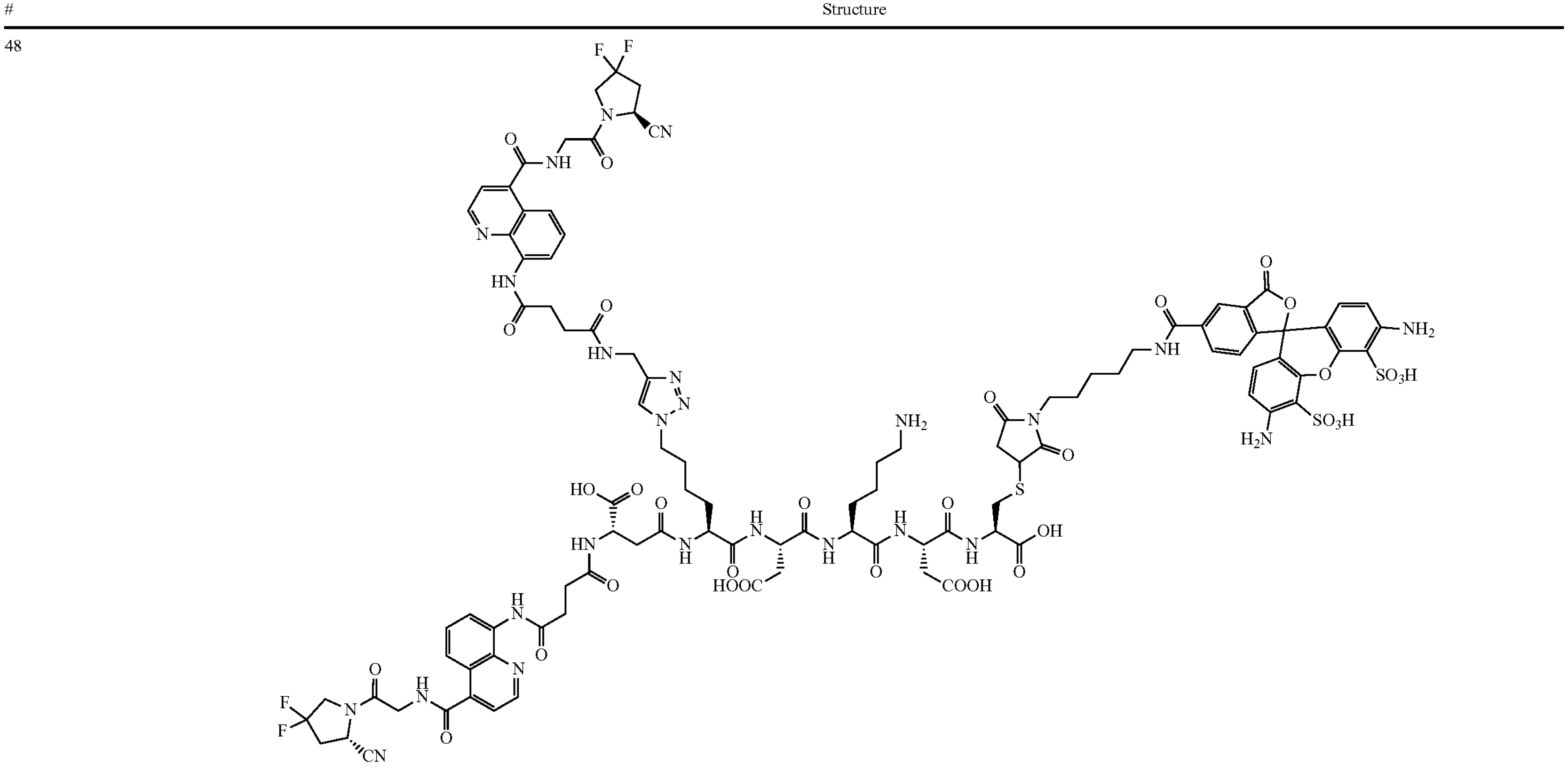 |

TABLE 2-continued
| # | Structure |
| --- | --- |
| 49 | 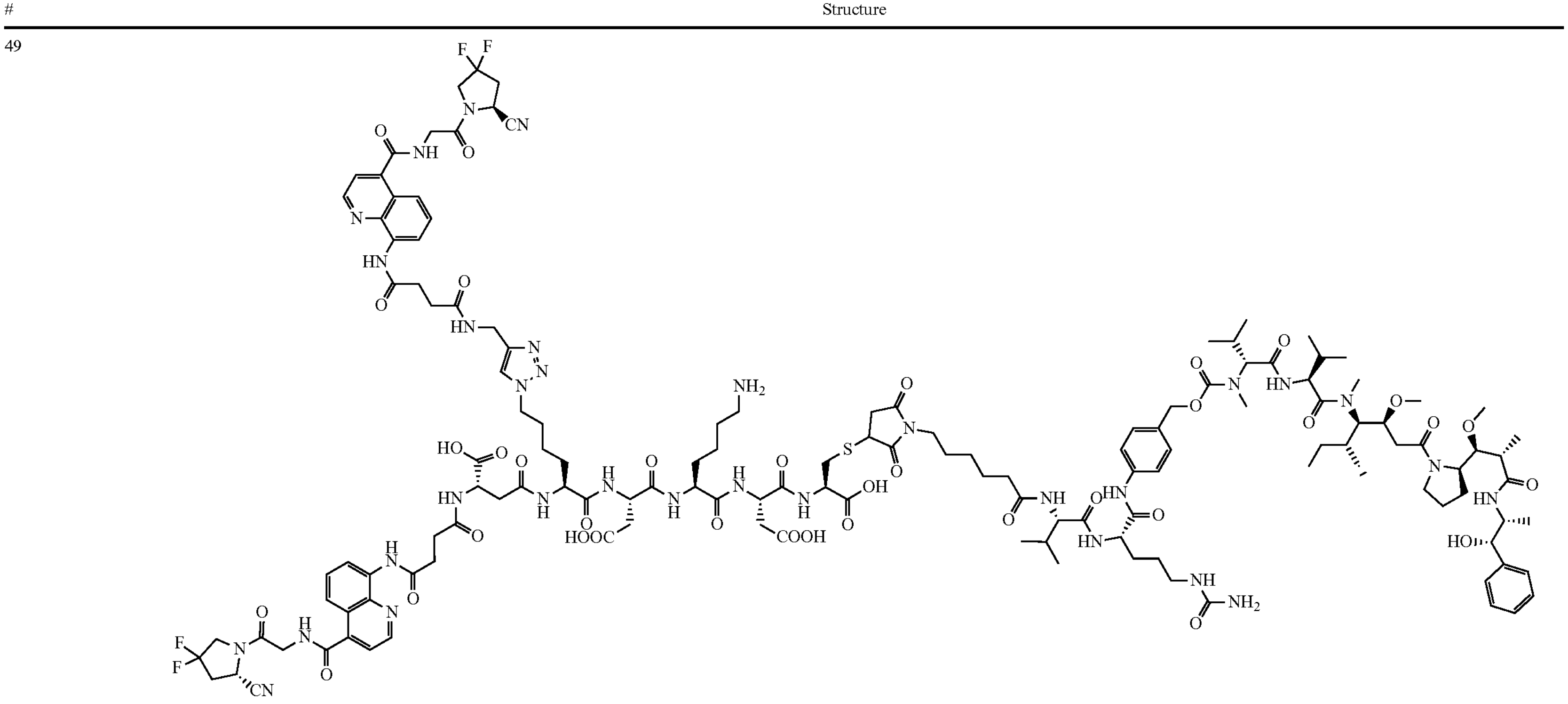 |

TABLE 2-continued
| # | Structure |
| --- | --- |
| 50 | 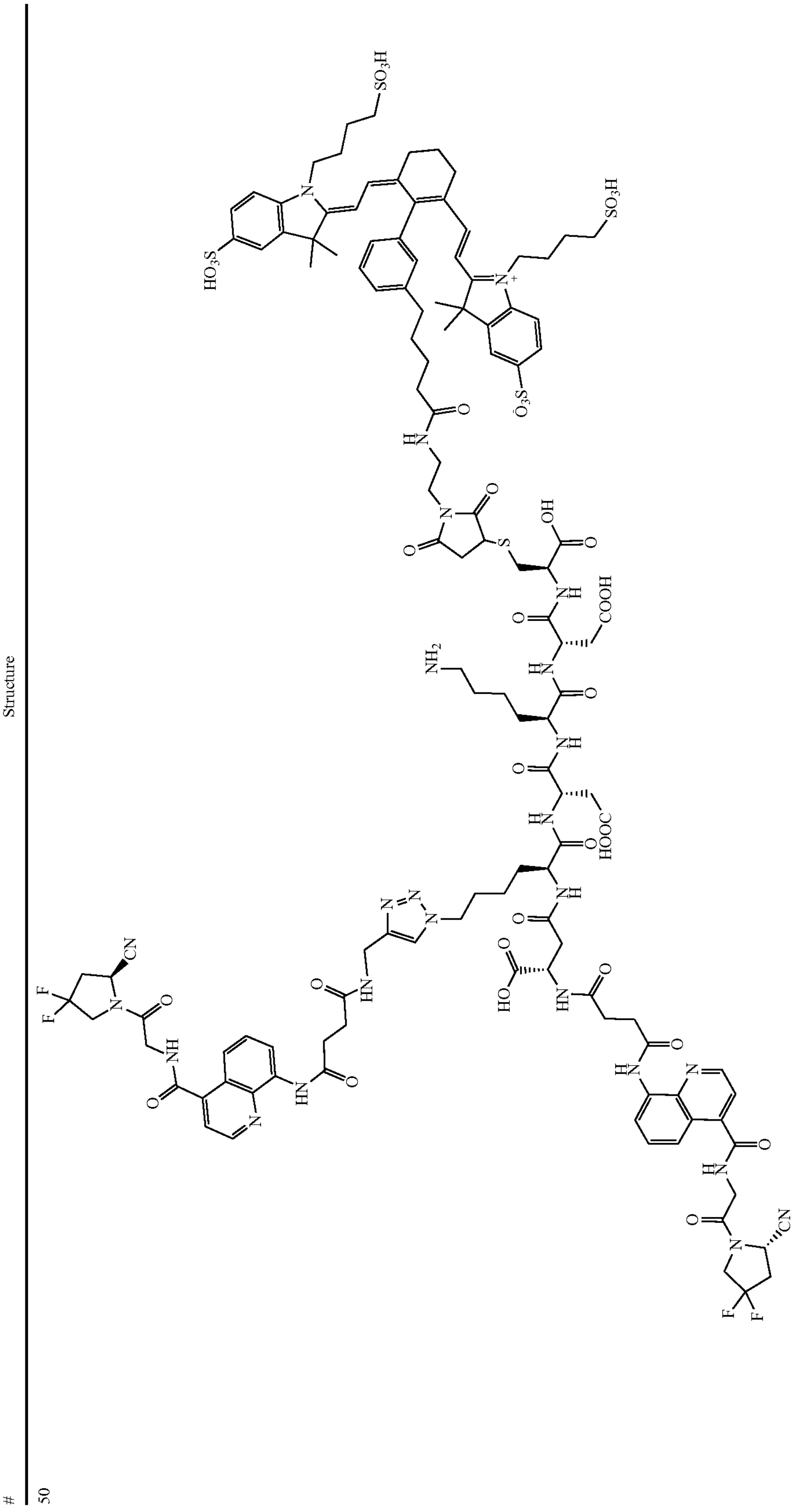 |

TABLE 2-continued
| # | Structure |
|---|---|
| 51 | 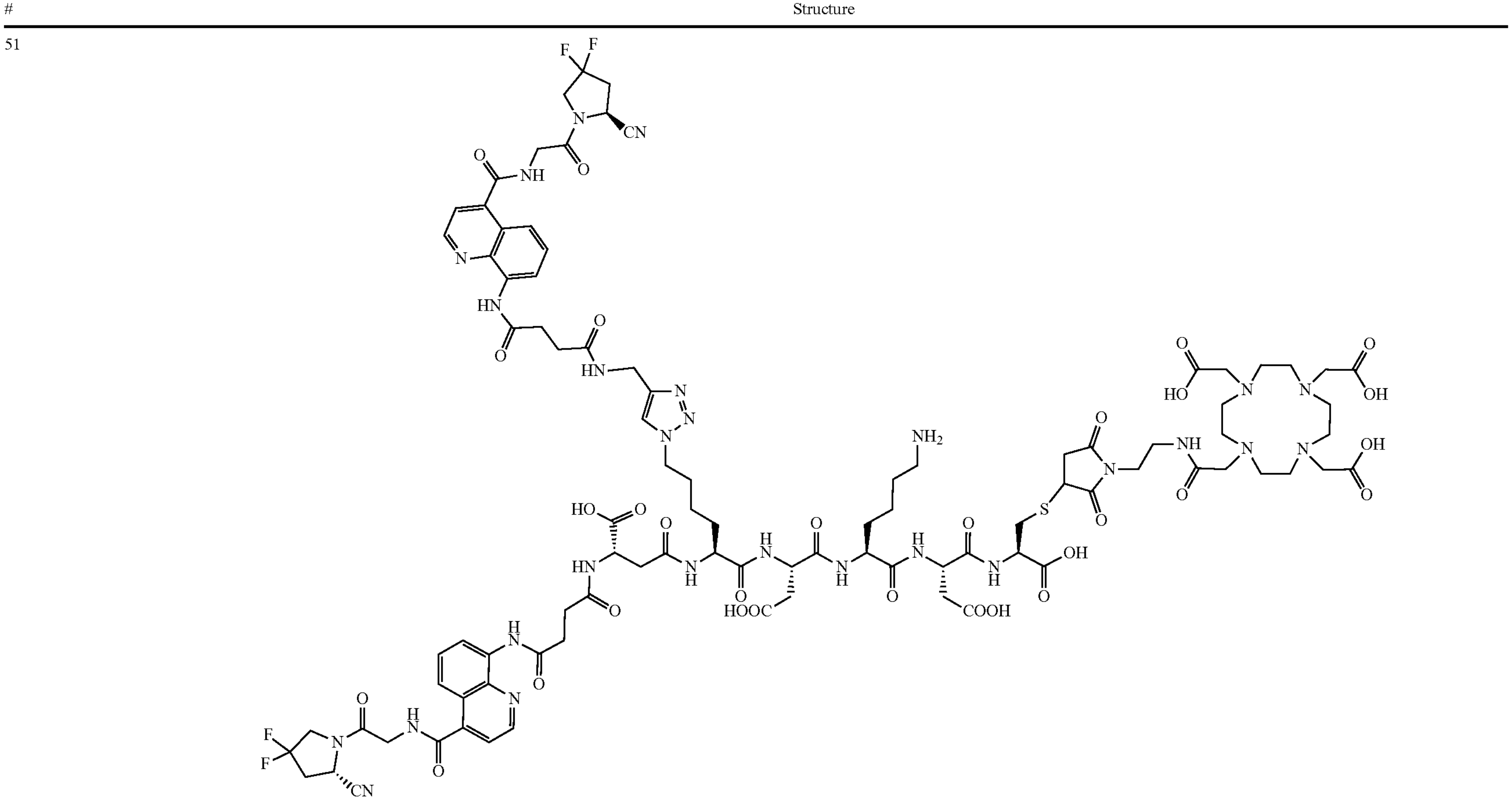 |

TABLE 2-continued
| # | Structure |
|---|---|
| 52 | 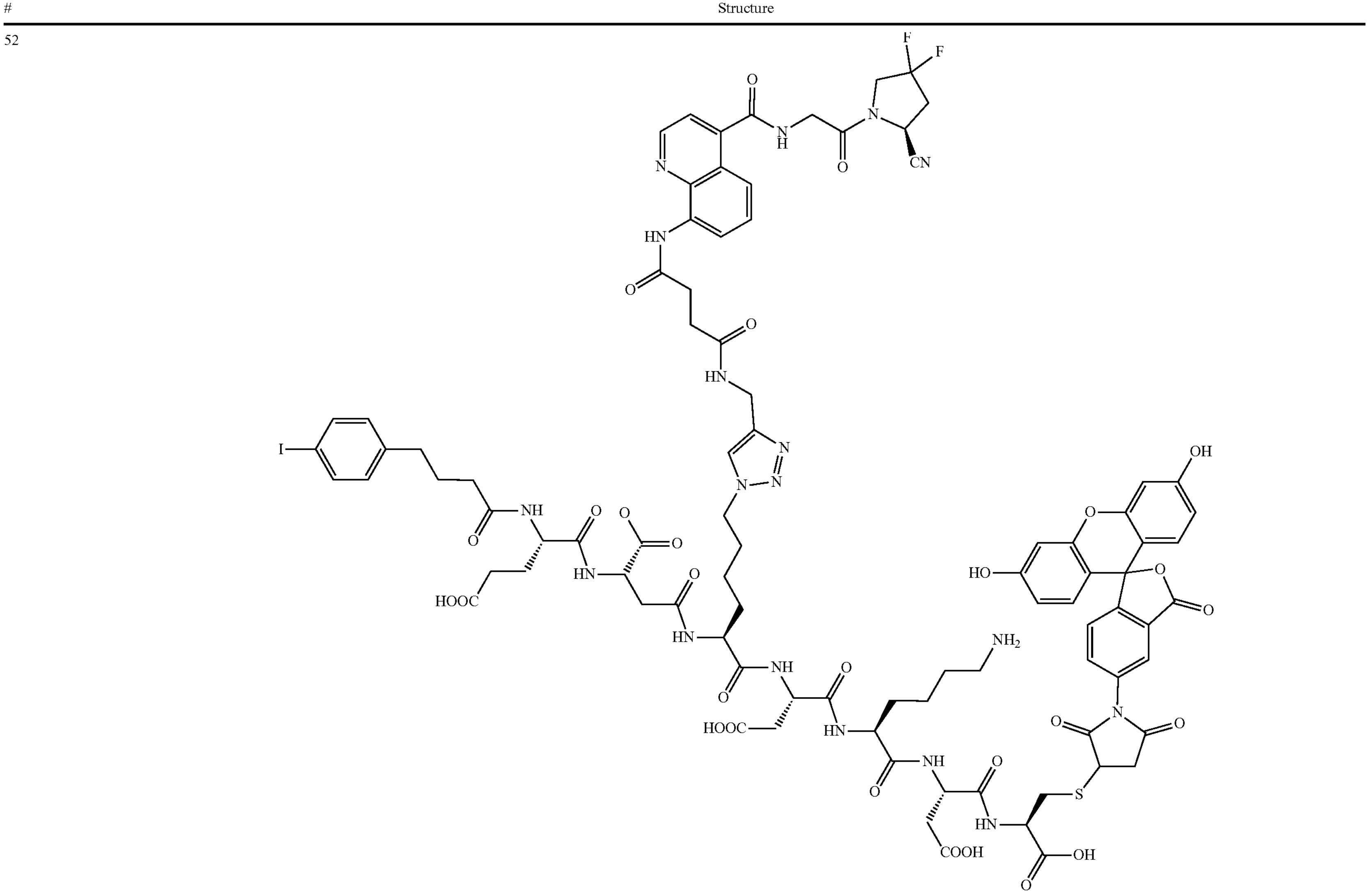 |

TABLE 2-continued
| # | Structure |
| --- | --- |
| 53 | 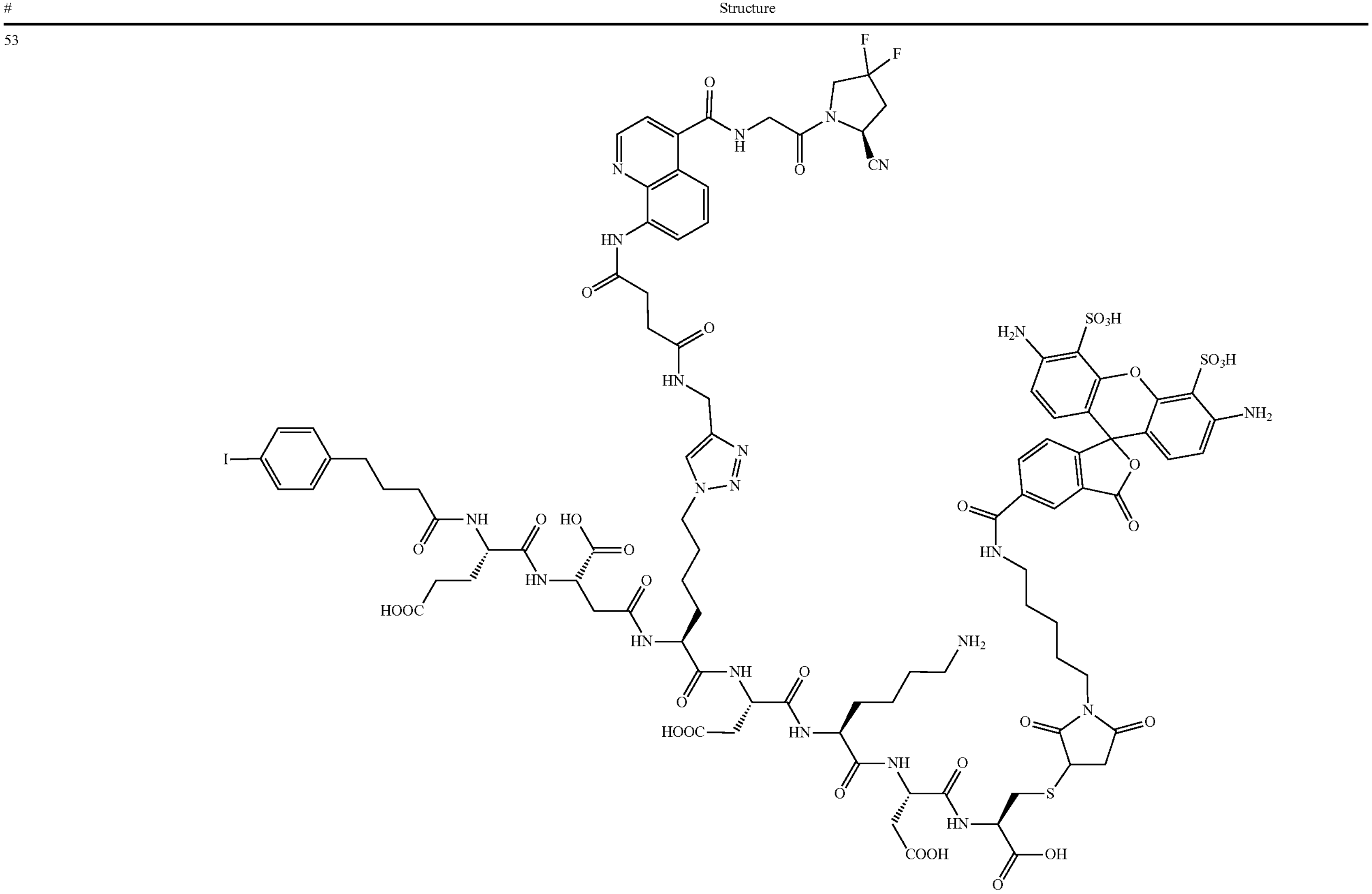 |

TABLE 2-continued
| # | Structure |
|---|---|
| 54 | 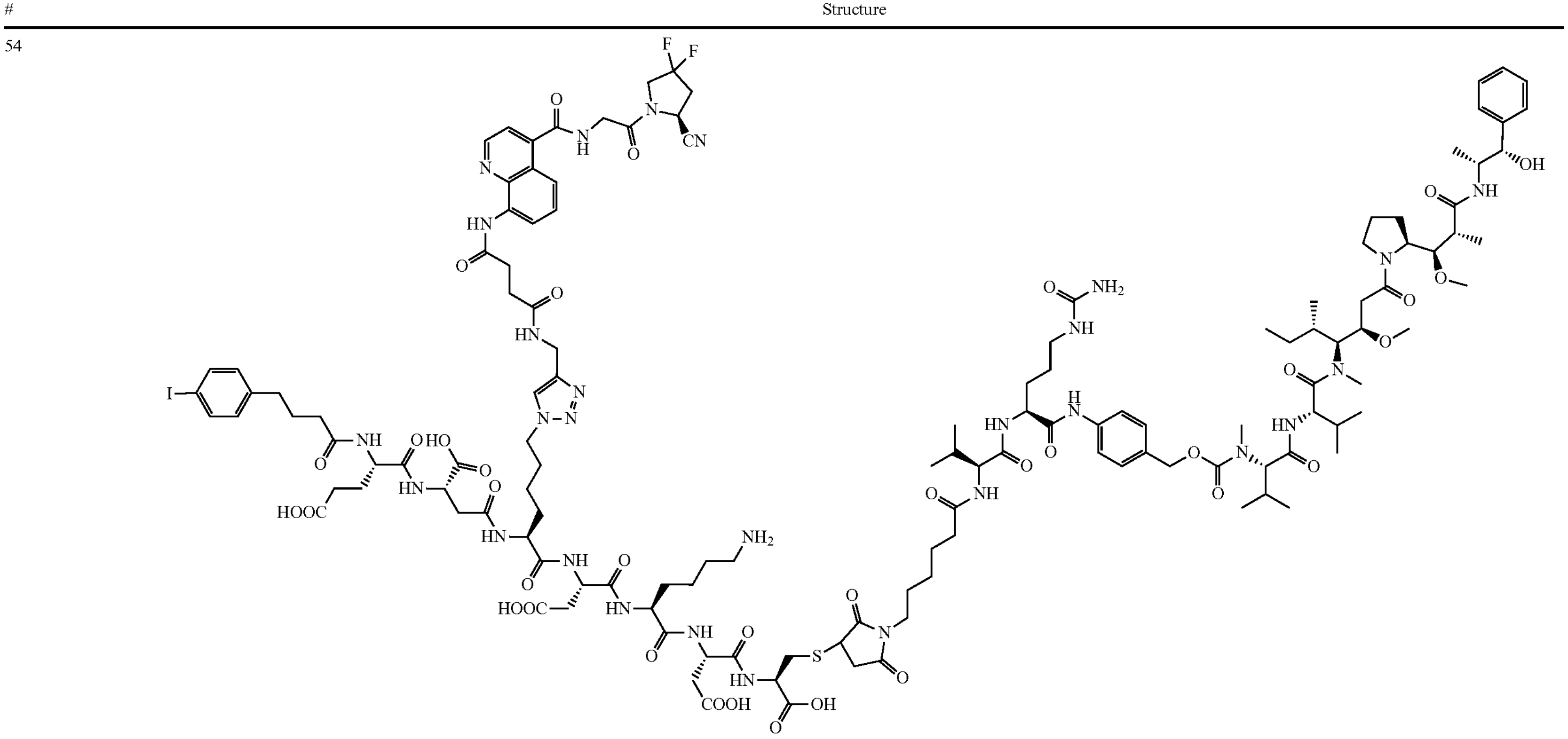 |

TABLE 2-continued
| # | Structure |
| --- | --- |
| 55 | 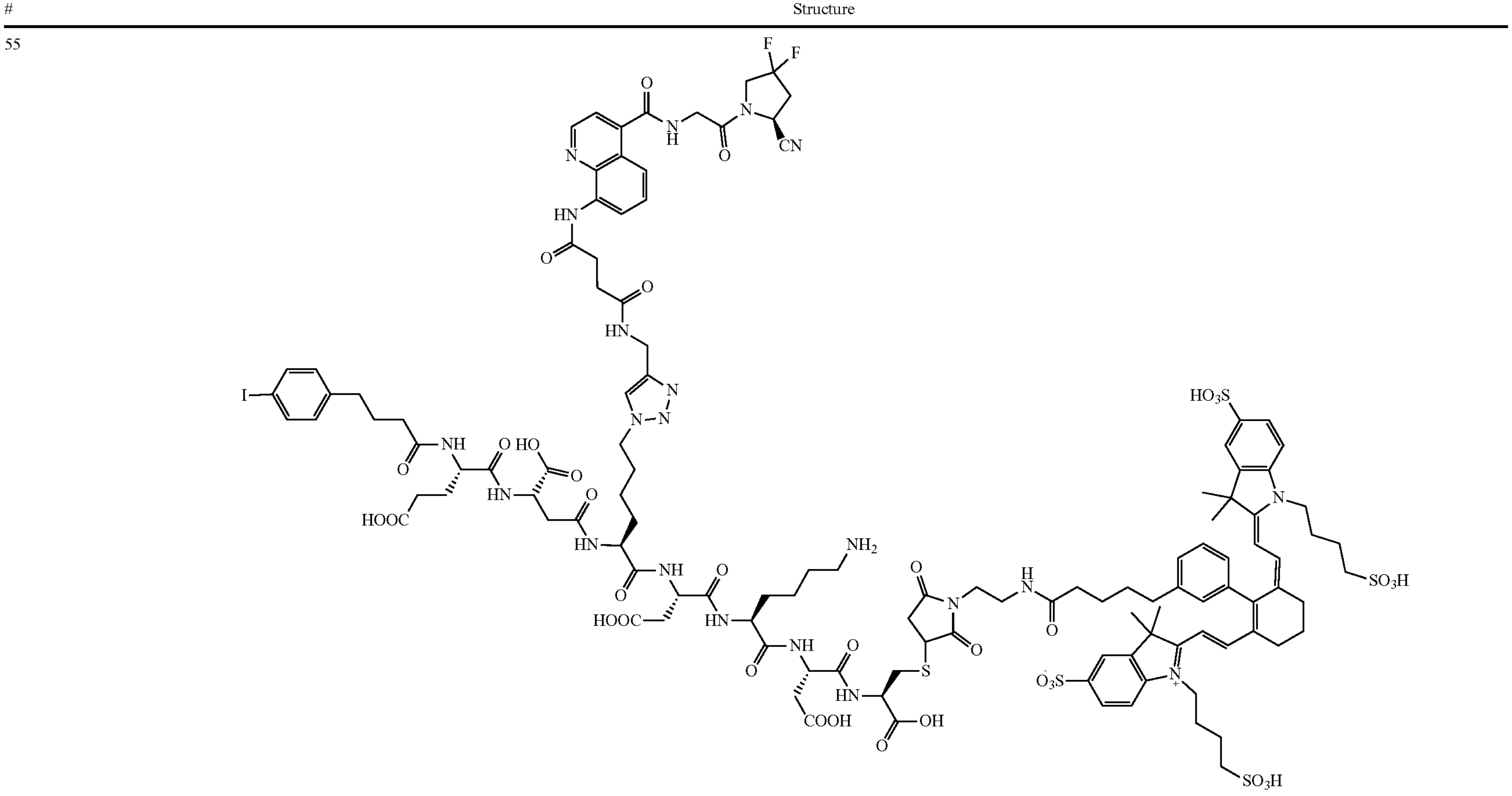 |

TABLE 2-continued
| # | Structure |
| --- | --- |
| 56 | 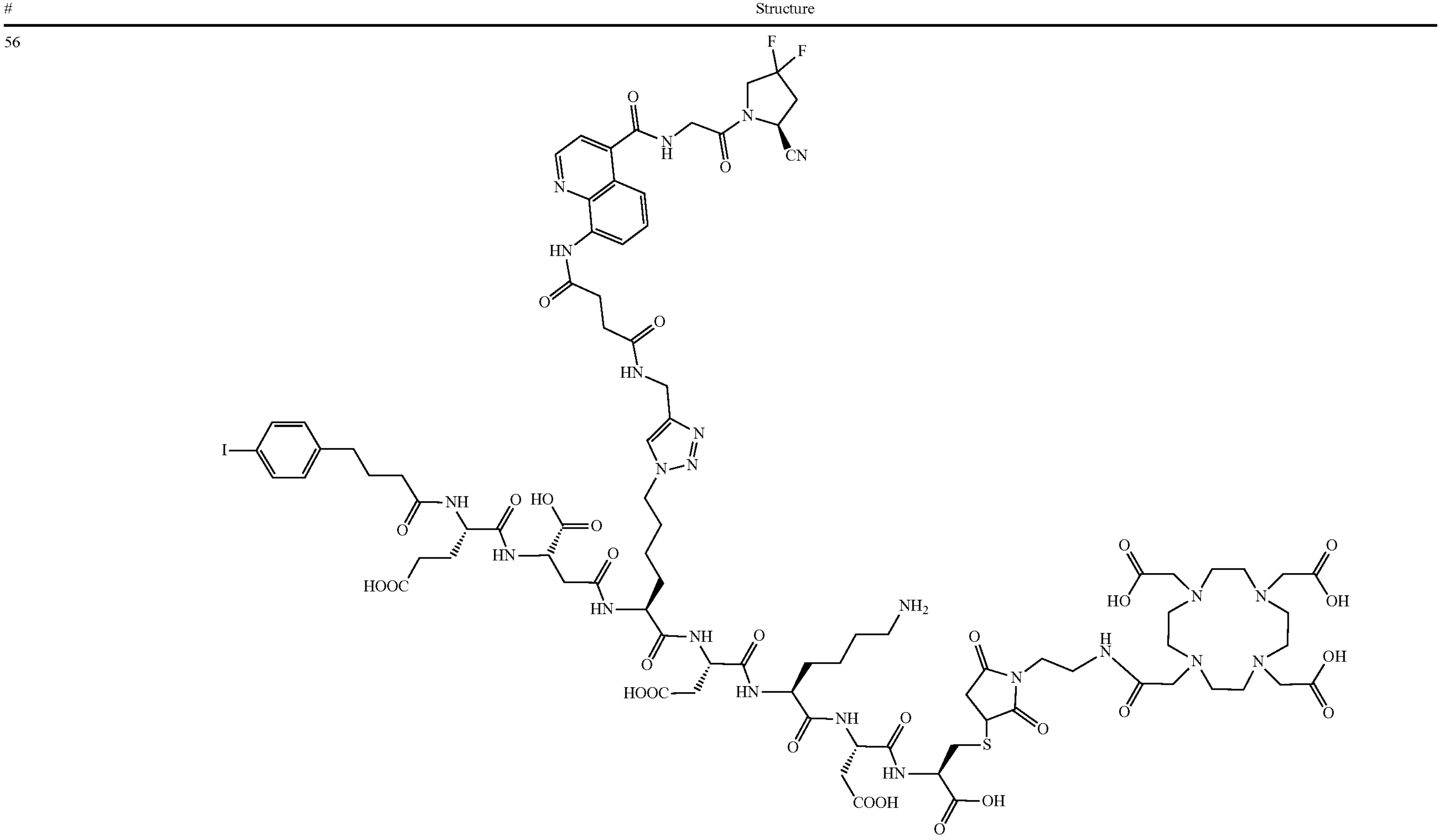 |

TABLE 2-continued
| # | Structure |
|---|---|
| 57 | 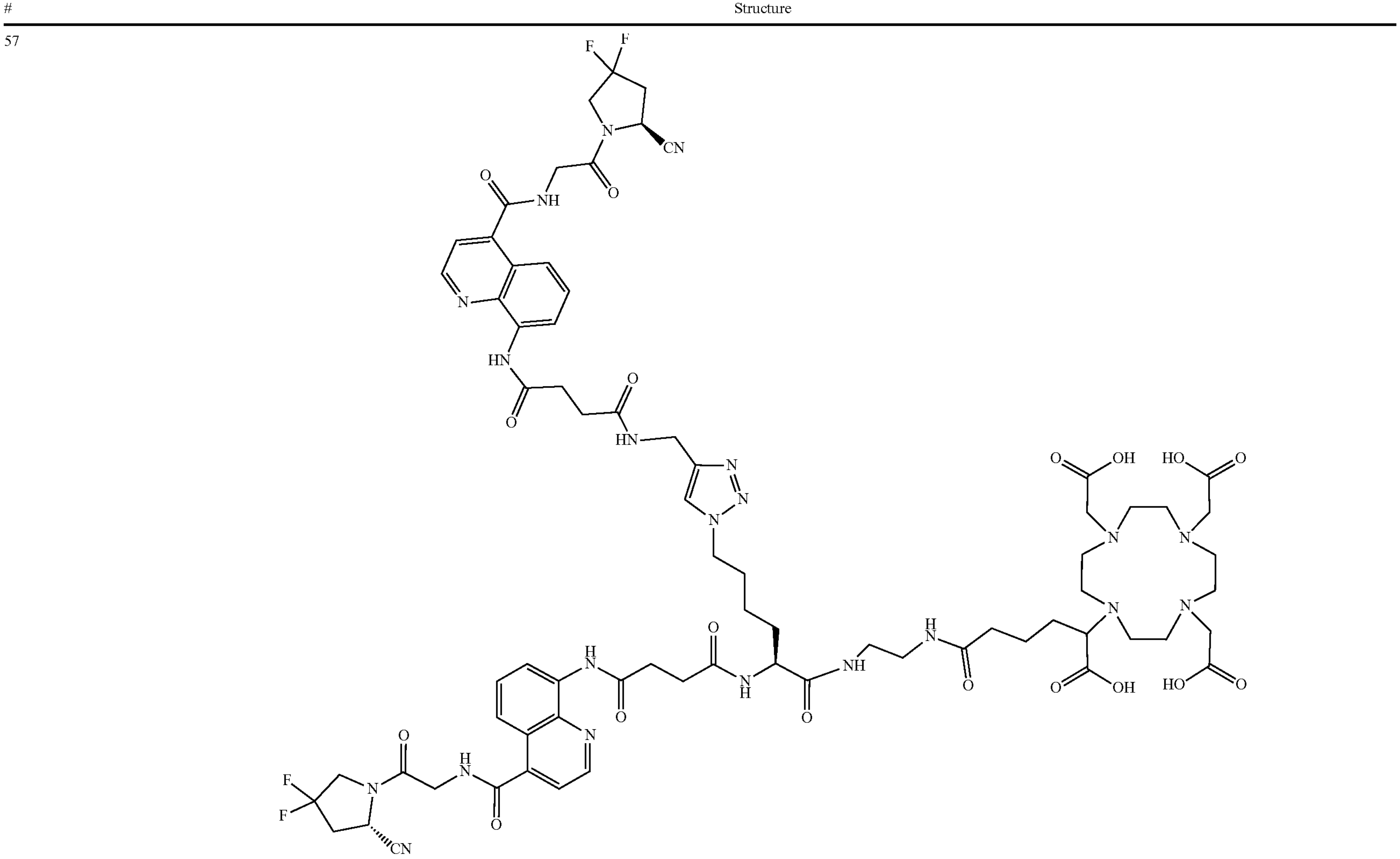 |

TABLE 2-continued
| # | | Structure |
|---|---|---|
| 58 | R derived from AA: | 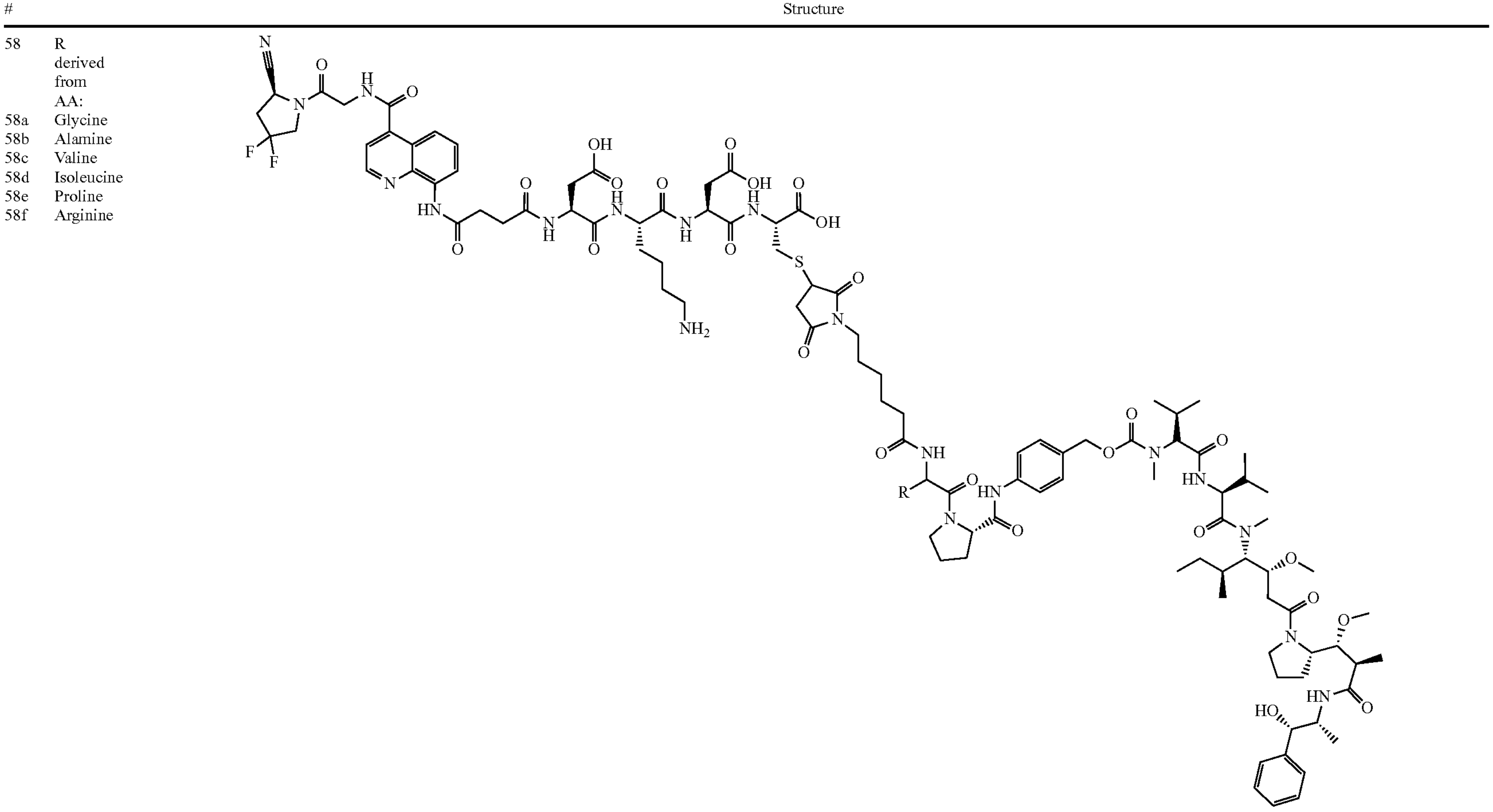 |
| 58a | Glycine | |
| 58b | Alamine | |
| 58c | Valine | |
| 58d | Isoleucine | |
| 58e | Proline | |
| 58f | Arginine | |

TABLE 2-continued
| # | R | R' | Structure |
|---|---|---|---|
| 59 | R | R' | 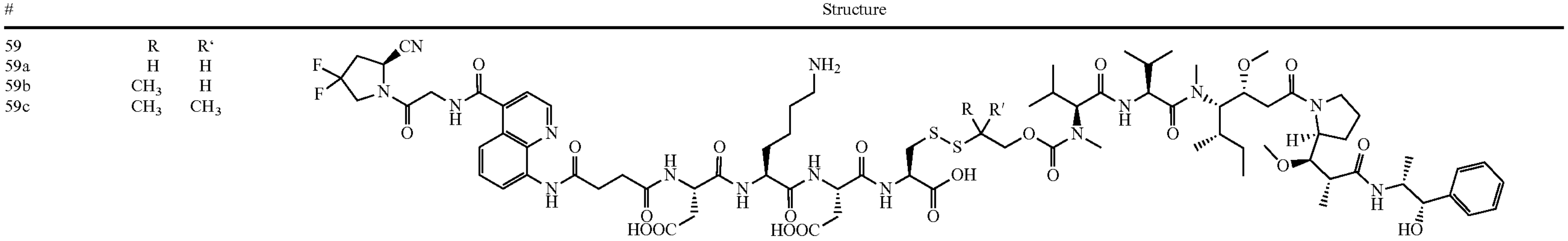 |
| 59a | H | H | |
| 59b | $CH_3$ | H | |
| 59c | $CH_3$ | $CH_3$ | |
| 60 | R | R' | 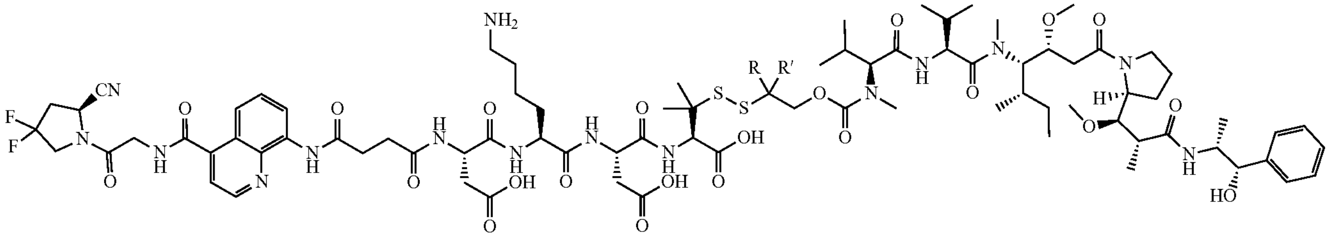 |
| 60a | H | H | |
| 60b | $CH_3$ | H | |
| 60c | $CH_3$ | $CH_3$ | |
| 62 | | | 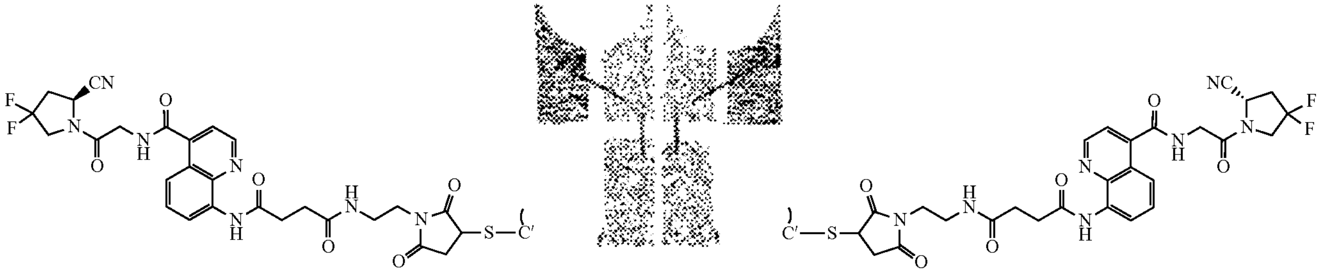 |

TABLE 2-continued
| # | Structure |
| --- | --- |
| 63 | 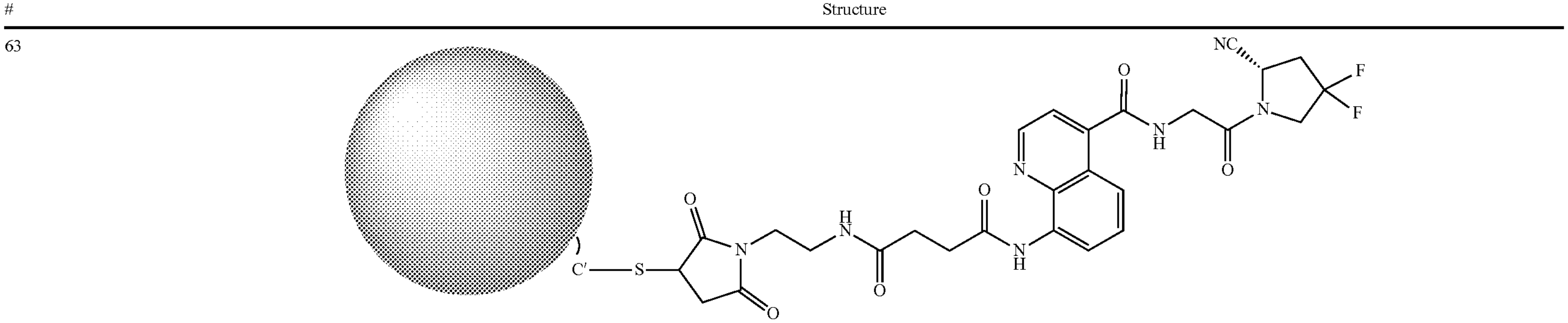 |
| 63a | 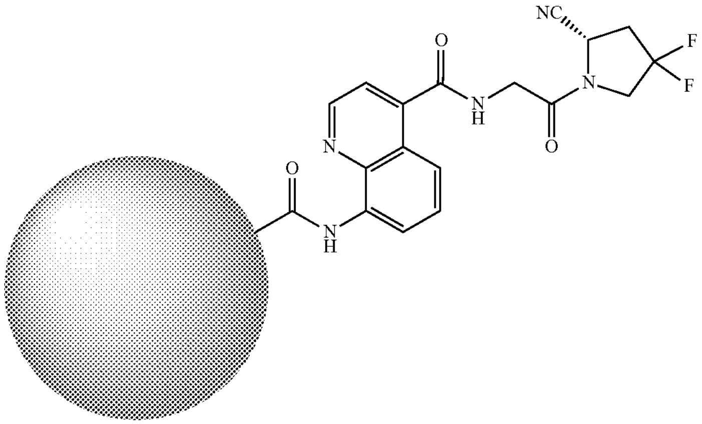 |

TABLE 2-continued
| # | Structure |
|---|---|
| 64 | 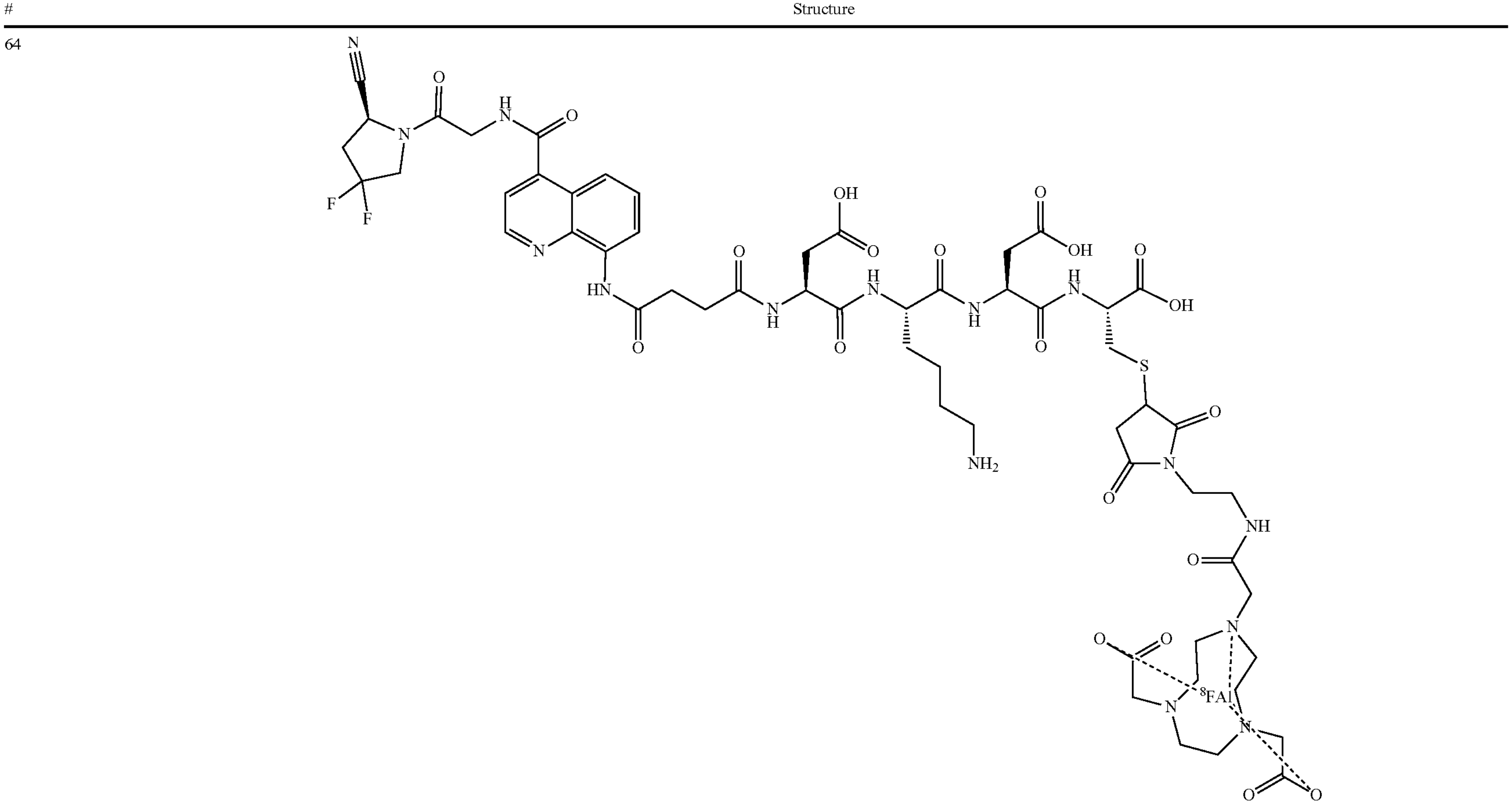 |

TABLE 2-continued
| # | Structure |
|---|---|
| 65 | 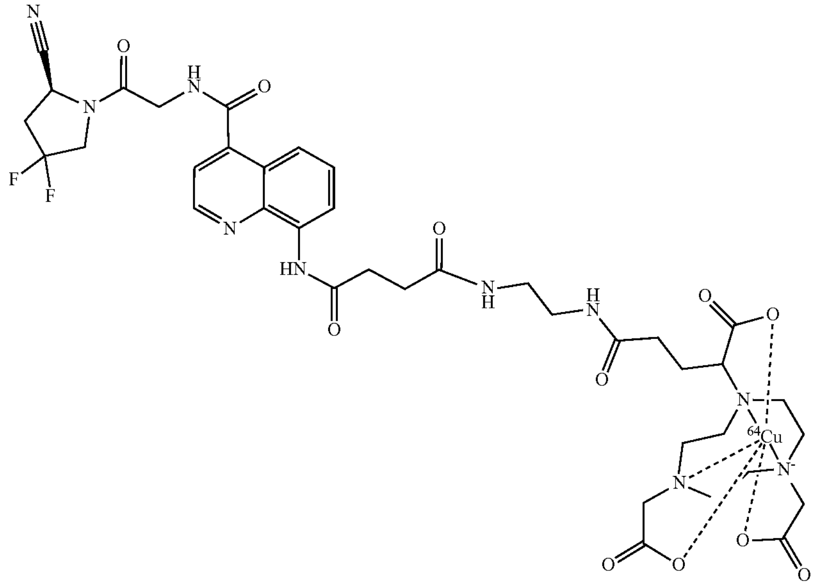 |

TABLE 2-continued
| # | Structure |
|---|---|
| 66 | 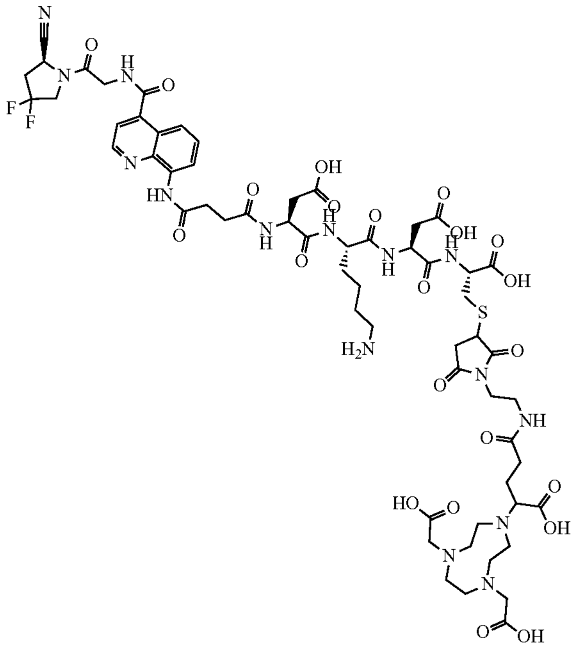 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CSC3CC(=O)N(CCNC(=O)CCC(C(=O)O)N4CCN(CC(=O)O)CCN(CC(=O)O)CC4)C3=O)C(=O)O)cccc12] |

TABLE 2-continued
| # | Structure |
|---|---|
| 67 | 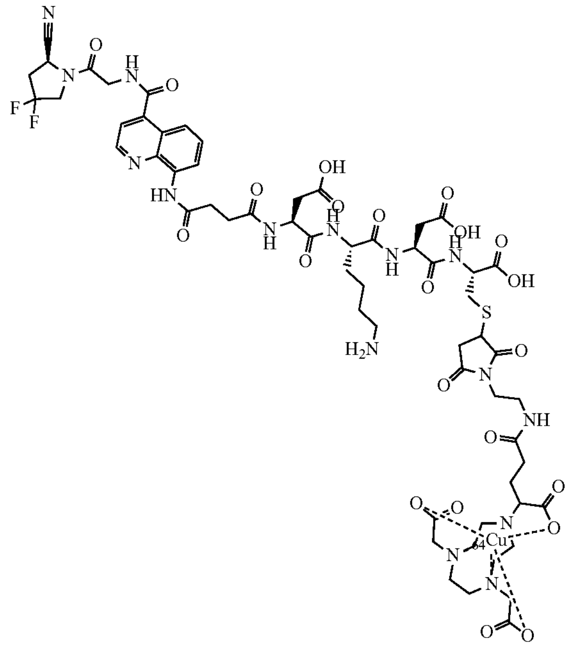 |

TABLE 2-continued
| # | Structure |
| --- | --- |
| 68 | 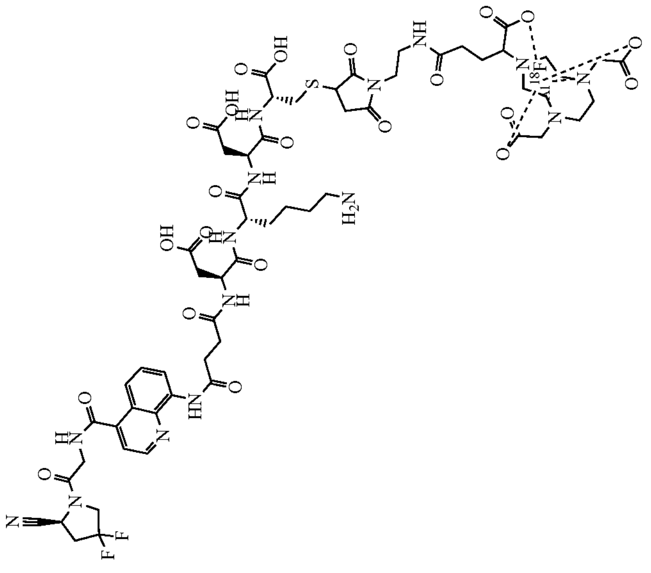 |
| 69 | 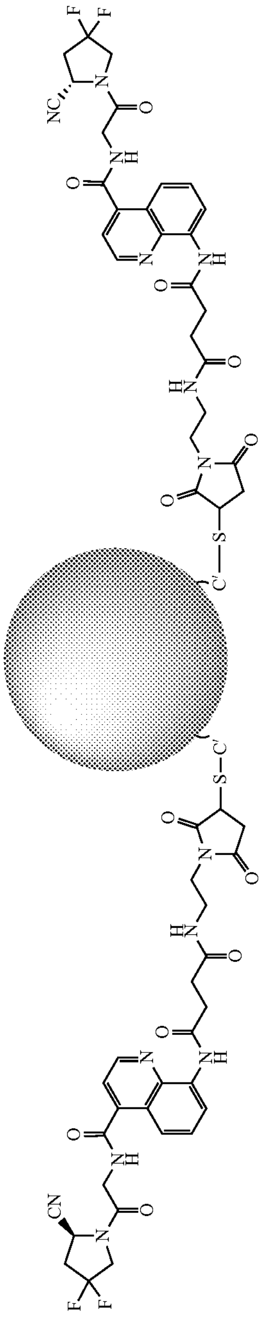 |

TABLE 2-continued
| # | Structure |
|---|---|
| 69a | 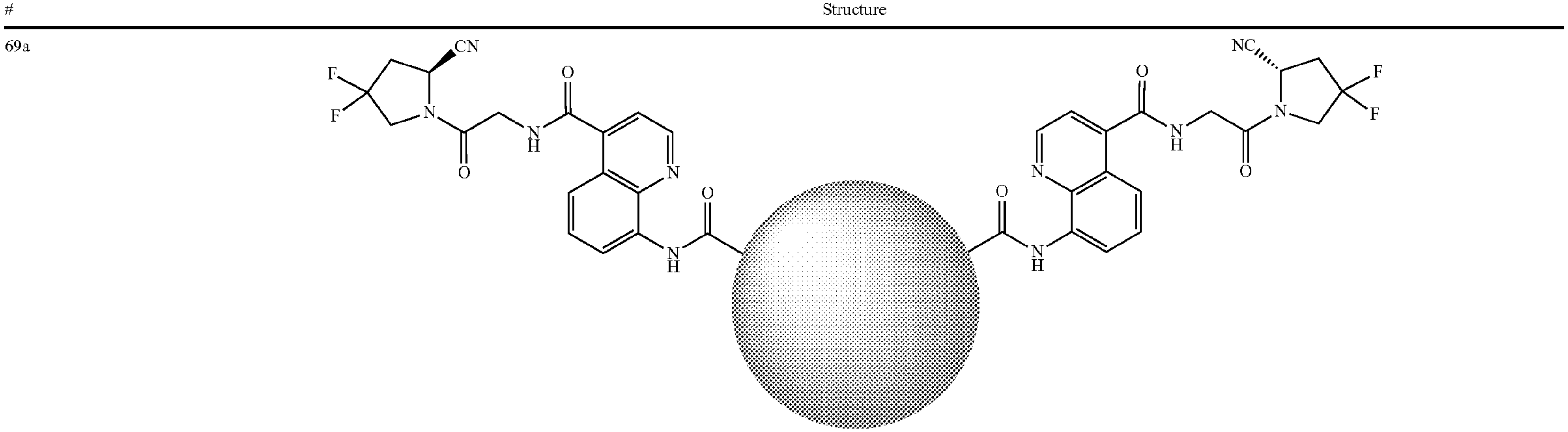 |

TABLE 3
| # | Structure |
|---|---|
| P3 | 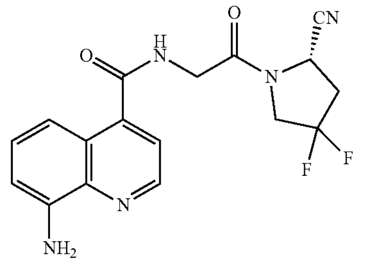 [SMILES: N#C[C@@H]1CC(F)(F)CN1C(=O)CNC(=O)c1ccnc2c(N)cccc12] |
| P4 | 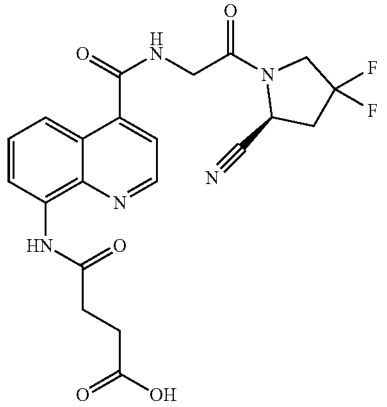 [SMILES: N#C[C@@H]1CC(F)(F)CN1C(=O)CNC(=O)c1ccnc2c(NC(=O)CCC(=O)O)cccc12] |
| P5 | 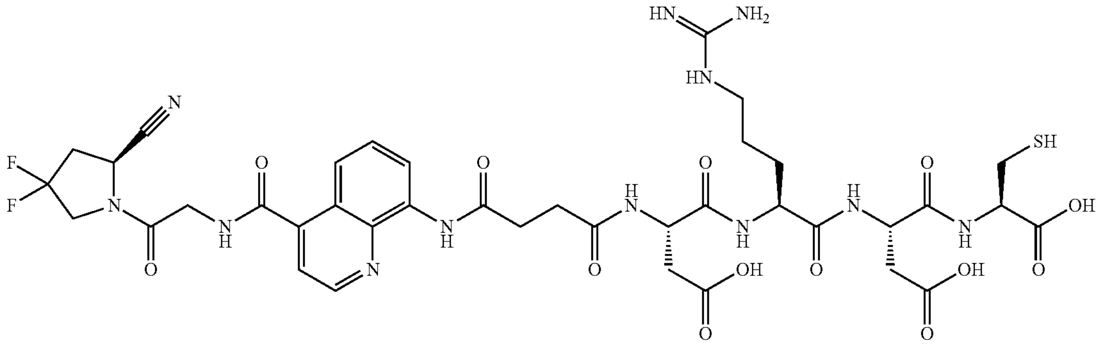 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCNC(=N)N)C(=O)N[C@@H](CC(=O)O)C(=O)N[C@@H](CS)C(=O)O)cccc12] |
| P6 | 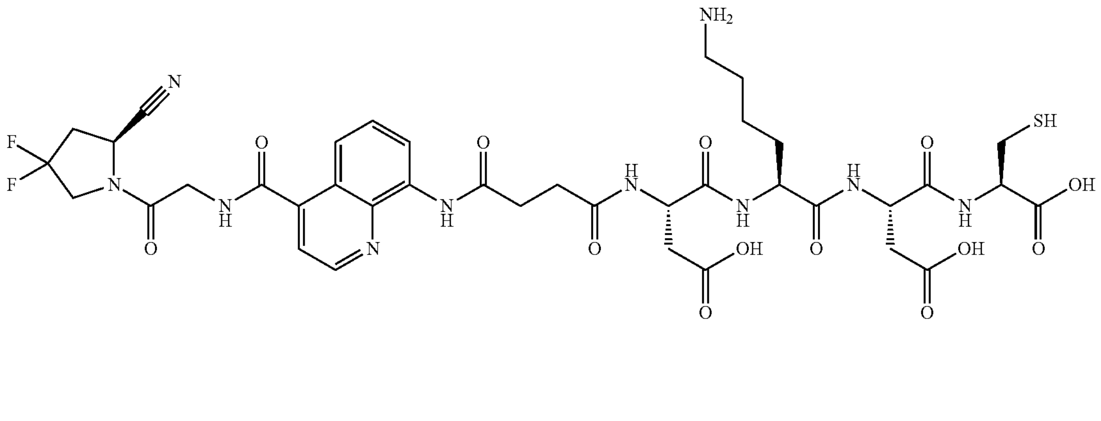 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CS)C(=O)O)cccc12] |

TABLE 3-continued
| # | Structure |
|---|---|
| P7 | 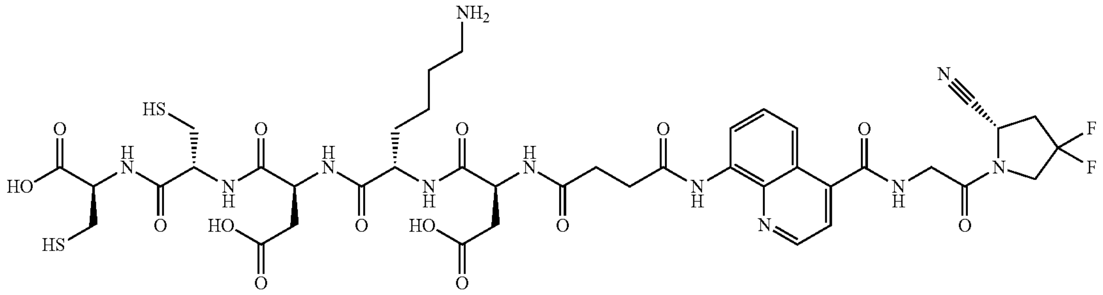 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CS)C(=O)N[C@@H](CS)C(=O)O)cccc12] |
| P8 | 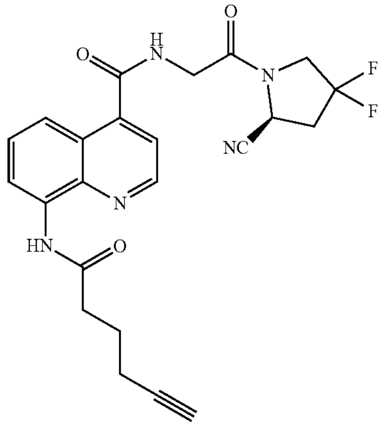 [SMILES: C#CCCCC(=O)Nc1cccc2c(C(=O)NCC(=O)N3CC(F)(F)C[C@H]3C#N)ccnc12] |
| P9 | 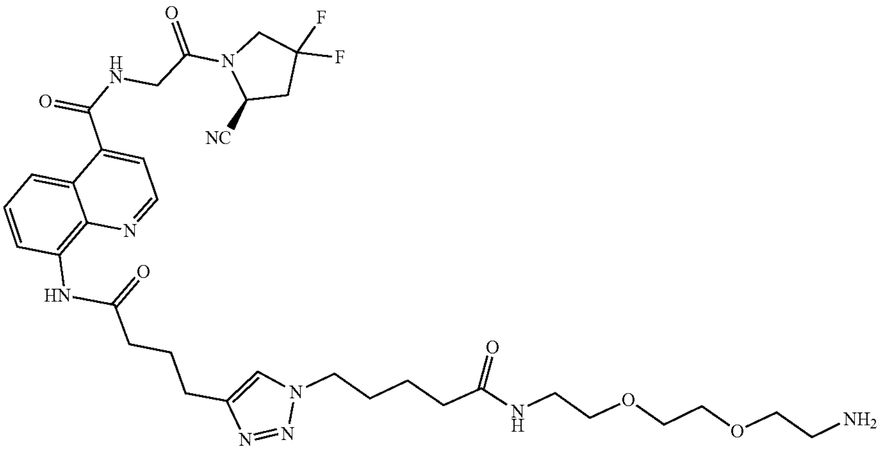 [SMILES: N#C[C@@H]1CC(F)(F)CN1C(=O)CNC(=O)c1ccnc2c(NC(=O)CCCc3cn(CCCCC(=O)NCCOCCOCCN)nn3)cccc12] |

TABLE 3-continued
| # | Structure |
|---|---|
| P10 | 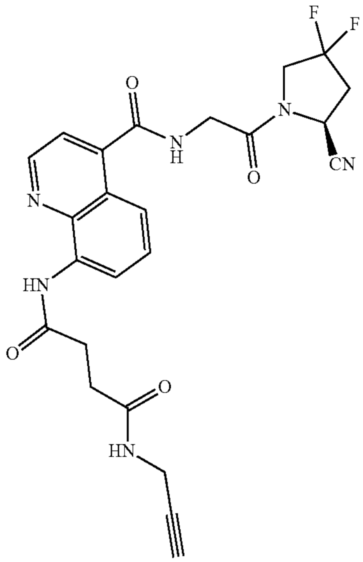 [SMILES: C#CCNC(=O)CCC(=O)Nc1cccc2c(C(=O)NCC(=O)N3CC(F)(F)C[C@H]3C#N)ccnc12] |
| P11 | 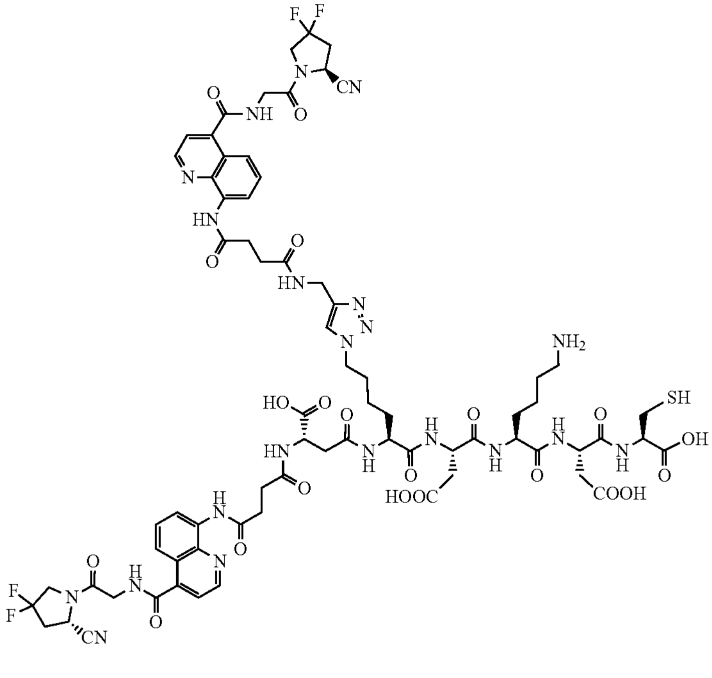 [SMILES: N#C[C@@H]1CC(F)(F)CN1C(=O)CNC(=O)c1ccnc2c(NC(=O)CCC(=O)NCc3cn(CCCC[C@H](NC(=O)C[C@H](NC(=O)CCC(=O)Nc4cccc5c(C(=O)NCC(=O)N6CC(F)(F)C[C@H]6C#N)ccnc45)C(=O)O)C(=O)N[C@@H](CC(=O)O)C(=O)N[C@@H](CCCCN)C(=O)N[C@@H](CC(=O)O)C(=O)N[C@@H](CS)C(=O)O)nn3)cccc12] |

TABLE 3-continued
| # | Structure |
| --- | --- |
| P12 | 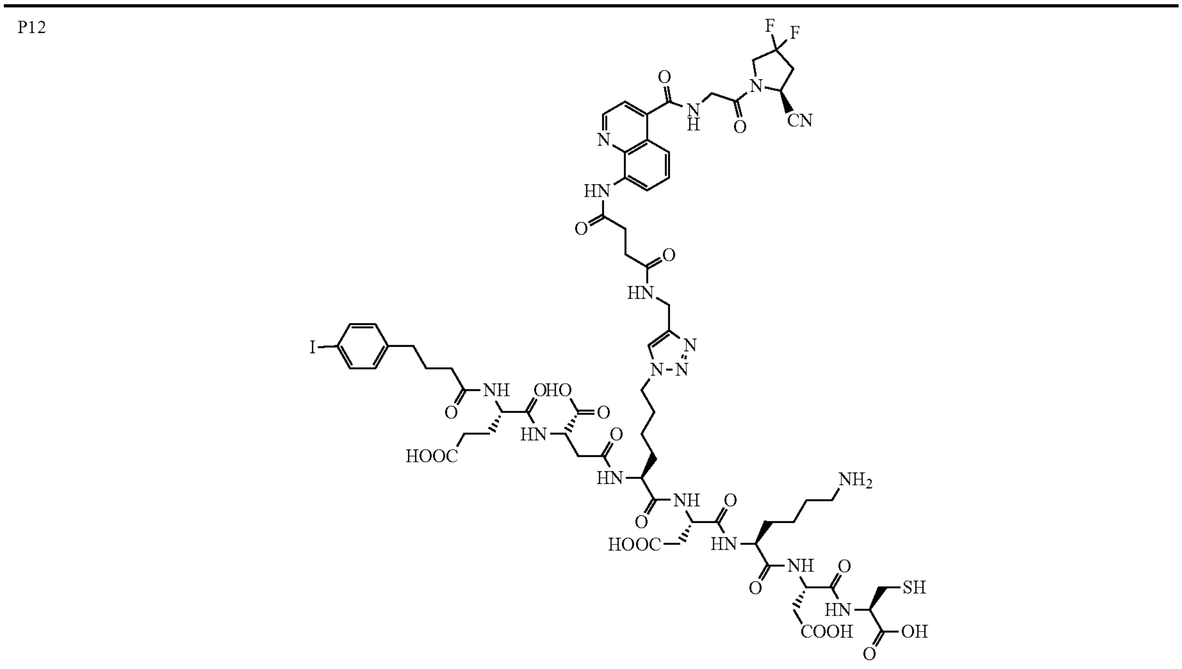 |
| P13 | 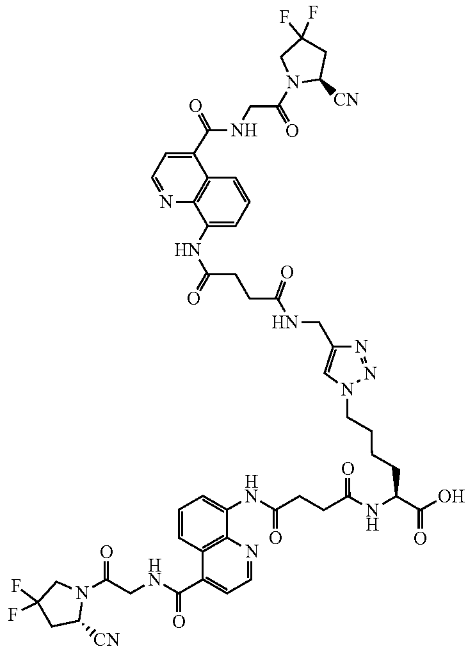 [SMILES: N#C[C@@H]1CC(F)(F)CN1C(=O)CNC(=O)c1ccnc2c(NC(=O)CCC(=O)NCc3cn(CCCC[C@H](NC(=O)CCC(=O)Nc4cccc5c(C(=O)NCC(=O)N6CC(F)(F)C[C@H]6C#N)ccnc45)C(=O)O)nn3)cccc12] |
| P14 | 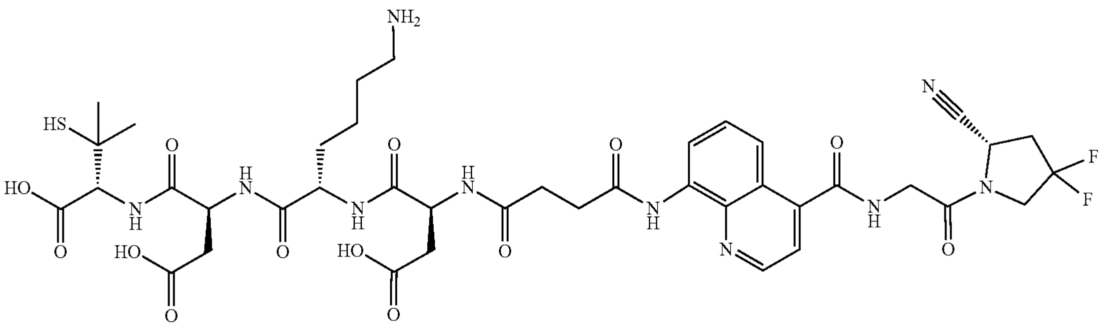 [SMILES: CC(C)(S)[C@H](NC(=O)[C@H](CC(=O)O)NC(=O)[C@H](CCCCN)NC(=O)[C@H](CC(=O)O)NC(=O)CCC(=O)Nc1cccc2c(C(=O)NCC(=O)N3CC(F)(F)C[C@H]3C#N)ccnc12)C(=O)O] |

TABLE 3-continued
| # | Structure |
| --- | --- |
| P15 | 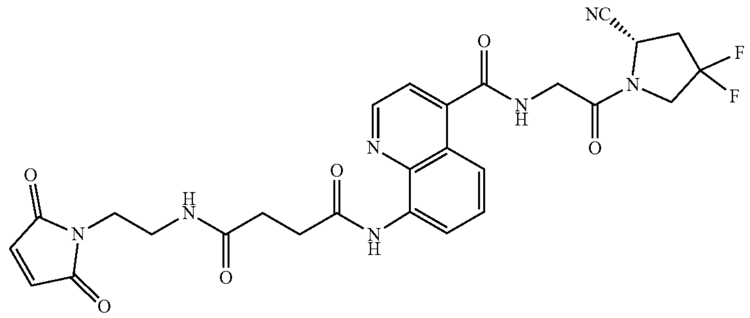 [SMILES: N#C[C@@H]1CC(F)(F)CN1C(=O)CNC(=O)c1ccnc2c(NC(=O)CCC(=O)NCCN3C(=O)C=CC3=O)cccc12] |
TABLE 4
| # | Structure |
| --- | --- |
| H6 | 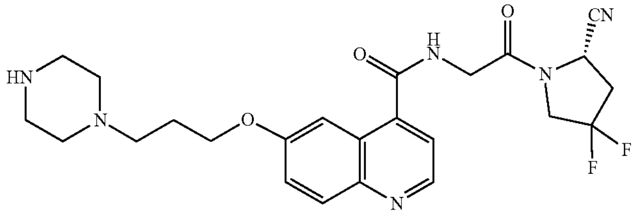 [SMILES: N#C[C@@H]1CC(F)(F)CN1C(=O)CNC(=O)c1ccnc2ccc(OCCCN3CCNCC3)cc12] |
| 16 | 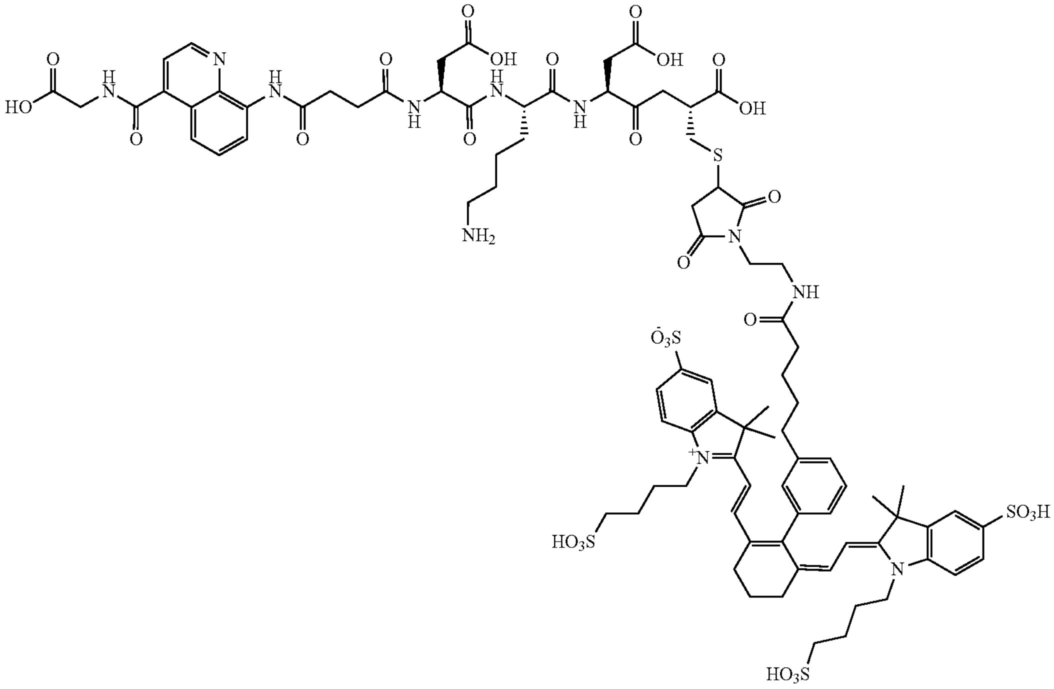 |

TABLE 4-continued
| # | Structure |
|---|---|
| 17 | 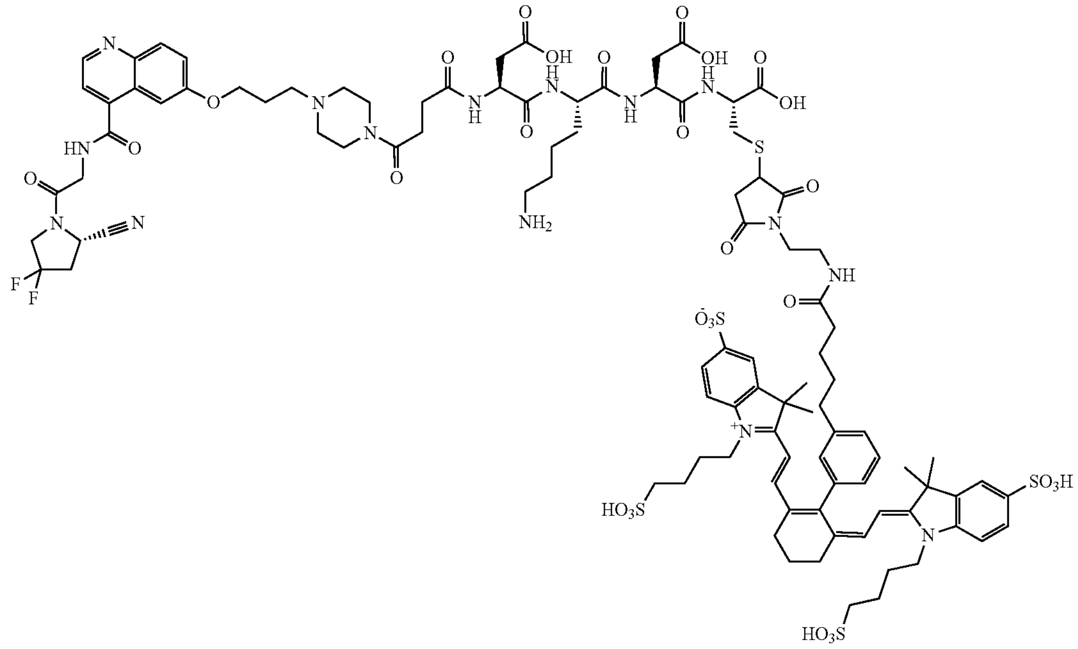 |
| 19 | 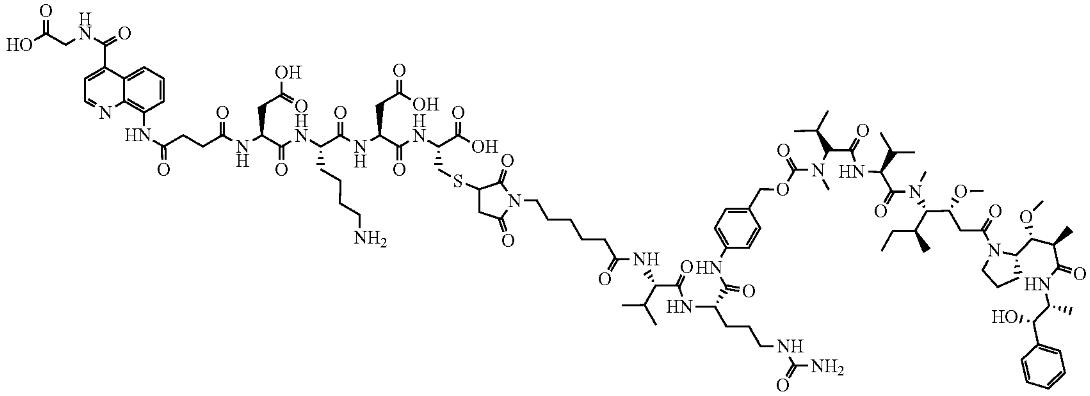 |
| 20 | 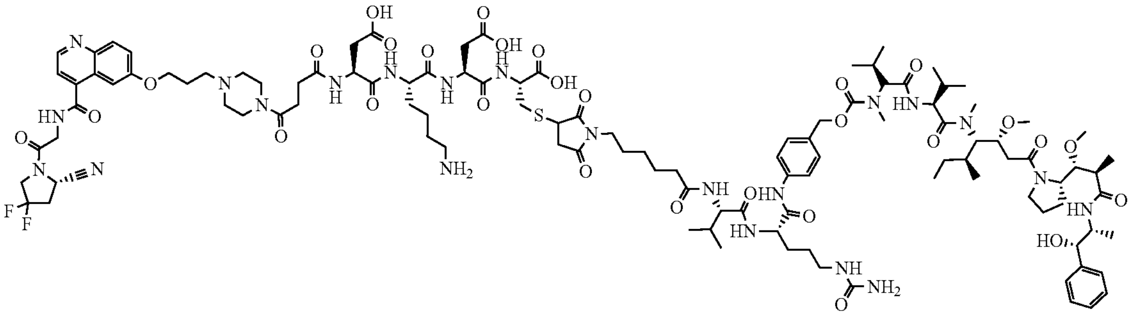 |

TABLE 4-continued
| # | Structure |
|---|---|
| 22 | 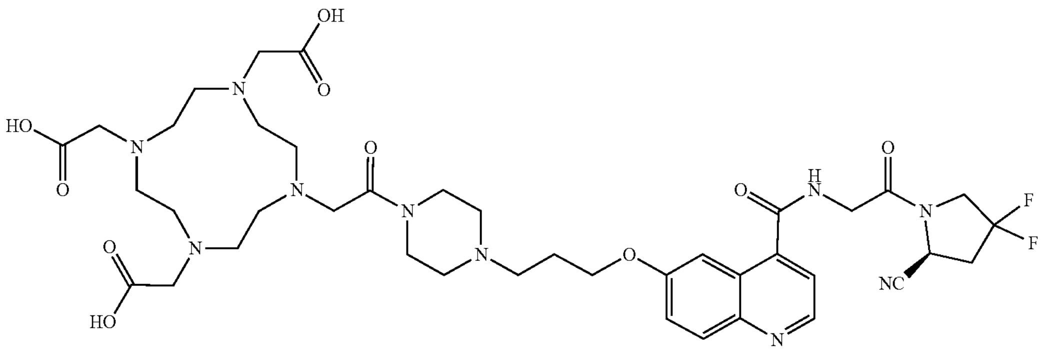 [SMILES: N#C[C@@H]1CC(F)(F)CN1C(=O)CNC(=O)c1ccnc2ccc(OCCCN3CCN(C(=O)CN4CCN(CC(=O)O)CCN(CC(=O)O)CCN(CC(=O)O)CC4)CC3)cc12] |
| 23 | 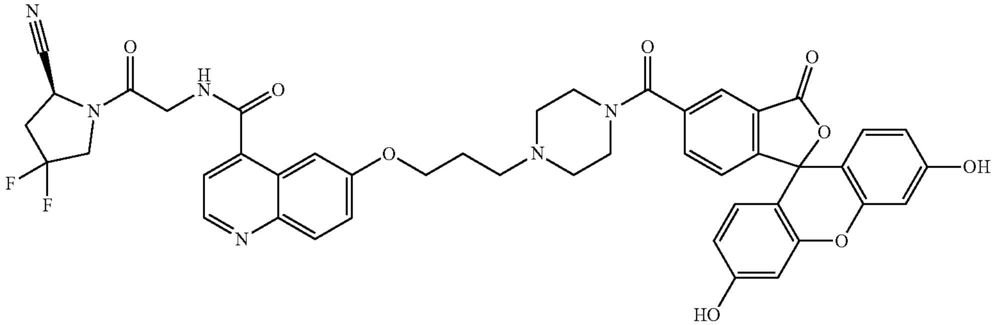 [SMILES: N#C[C@@H]1CC(F)(F)CN1C(=O)CNC(=O)c1ccnc2ccc(OCCCN3CCN(C(=O)c4ccc5c(c4)C(=O)OC54c5ccc(O)cc5Oc5cc(O)ccc54)CC3)cc12] |
| 24 | 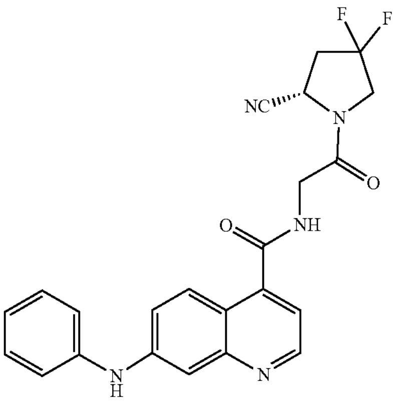 [SMILES: N#C[C@@H]1CC(F)(F)CN1C(=O)CNC(=O)c1ccnc2cc(Nc3ccccc3)ccc12] |
| 25 | 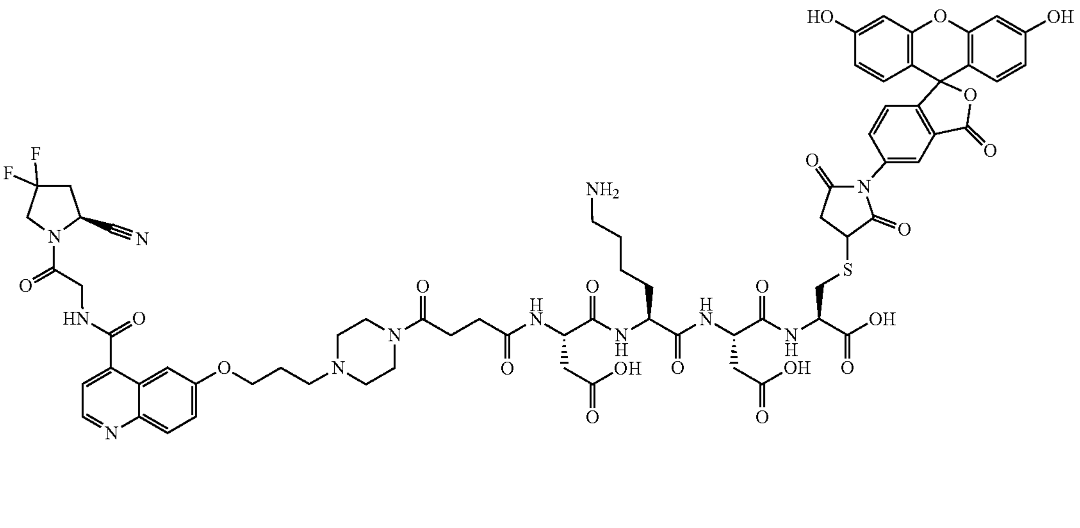 [SMILES: N#C[C@@H]1CC(F)(F)CN1C(=O)CNC(=O)c1ccnc2ccc(OCCCN3CCN(C(=O)CCC(=O)N[C@@H](CC(=O)O)C(=O)N[C@@H](CCCCN)C(=O)N[C@@H](CC(=O)O)C(=O)N[C@@H](CSC4CC(=O)N(c5ccc6c(c5)C(=O)OC65c6ccc(O)cc6Oc6cc(O)ccc65)C4=O)C(=O)O)CC3)cc12] |

TABLE 4-continued
| # | Structure |
|---|---|
| 28 | 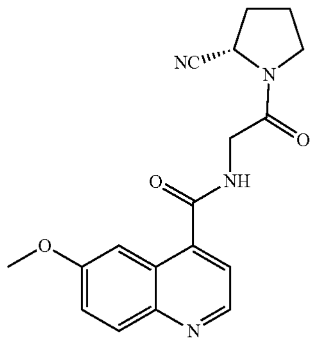 [SMILES: COc1ccc2nccc(C(=O)NCC(=O)N3CCC[C@H]3C#N)c2c1] |
| 29 | 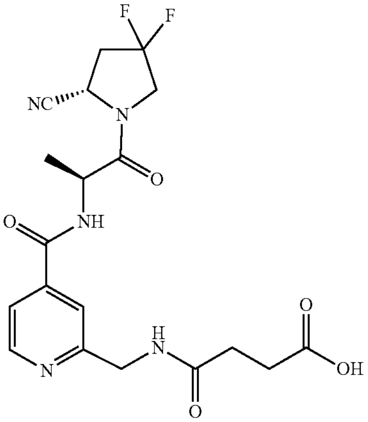 [SMILES: C[C@H](NC(=O)c1ccnc(CNC(=O)CCC(=O)O)c1)C(=O)N1CC(F)(F)C[C@H]1C#N] |
| 32 | 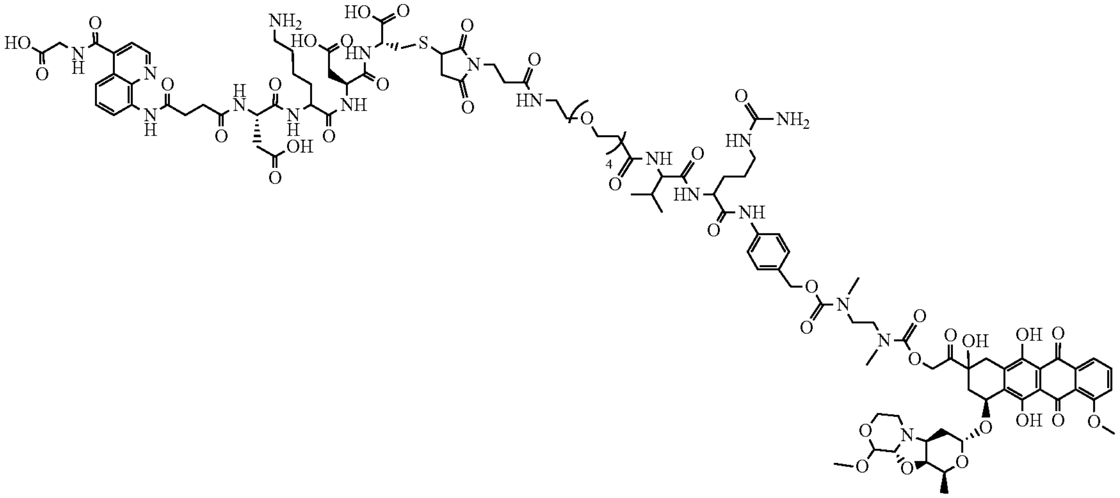 |

TABLE 4-continued

| # | Structure |
|---|---|
| 33 | 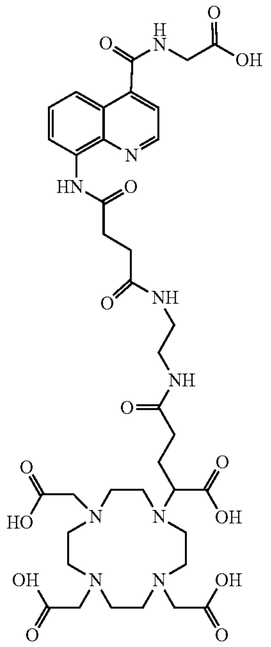 |

MATERIAL & METHODS

General Remarks and Procedures

Yields refer to chromatographically purified compounds.

Proton (1H) nuclear magnetic resonance (NMR) spectra were recorded on a Bruker AV400 (400 MHz) spectrometer. Shifts are given in ppm using residual solvent as the internal standard. Coupling constants (J) are reported in Hz with the following abbreviations used to indicate splitting: s=singlet, d=doublet, t=triplet, q=quartet, m=multiplet.

Mass Spectrometry (LC-ESI-MS) spectra were recorded on an Agilent 6100 Series Single Quadrupole MS System combined with an Agilent 1200 Series LC System, using an InfinityLab Poroshell 120 EC-C18 column, 4.6 min×56 mm at a flow rate of 2 mL $min^{-1}$ with linear gradients of solvents A and B (A=Millipore water with 0.1% formic acid [FA], B=MeCN with 0.1% formic acid [FA]).

High-Resolution Mass Spectrometry (HRMS) spectra and analytical Reversed-Phase Ultra Performance Liquid Chromatography (UPLC) were recorded on a Waters Xevo G2-XS QTOF coupled to a Waters Acquity UPLC H-Class System with PDA UV detector, using a ACQUITY UPLC BEH C18 Column, 130 Å, 1.7 μm, 2.1 min×50 mm at a flow rate of 0.6 mL $min^{-1}$ with linear gradients of solvents A and B (A=Millipore water with 0.1% FA, B=MeCN with 0.1% FA).

Preparative reversed-phase high-pressure liquid chromatography (RP-HPLC) was performed on an Agilent 1200 Series System, using a Phenomenex Gemini® 5 μm NX—C18 semipreparative column, 110 Å, 150 min×10 mm at a flow rate of 5 mL $min^{-1}$ with linear gradients of solvents A and B (A=Millipore water with 0.1% trifluoroacetic acid [TFA], B=MeCN with 0.1% trifluoroacetic acid [TFA]).

Comparative Example 1: Synthesis of (S)—N-(2-(2-cyano-4,4-difluoropyrrolidin-1-yl)-2-oxoethyl)-6-(3-(4-(3,6'-dihydroxy-3-oxo-3H-spiro[isobenzofuran-1,9'-xanthene]-5-carbonyl)piperazin-1-yl)propoxy) quinoline-4-carboxamide ("HABERKORN-FLUO", 23)

Step 1: 6-hydroxy-4-quinolinecarboxylic acid (H1)

A solution of 6-methoxyquinoline-carboxylic acid (250 mg, 1.08 mmol, 1.0 eq) in HBr 48 wt. % in $H_2O$ (5 mL) was heated at 130° C. for 2 h then concentrated under vacuum to obtain product as an orange powder (292 mg, 1.08 mmol, Quant. Yield). MS ($ES^+$) m/z 271 $(M+H)^+$.

Step 2: 1-Boc-4-(3-hydroxypropyl)piperazine (H2)

Anhydrous $K_2CO_3$ (815 mg, 5.91 mmol, 1.1 eq) was added to a solution of 1-Boc-piperazine (1.0 g, 5.37 mmol, 1.0 eq) in dry THF (15 mL) followed by 3-Bromo-1-propanol (530 μL, 5.91 mmol, 1.1 eq) and the reaction mixture was stirred at room temperature for 72 h. Volatiles were removed under reduced pressure, the residue was diluted with water, extracted with EtOAc (twice) and the combined organic layers were dried over $Na_2SO_4$, filtered and concentrated. Crude was purified by flash chromatography (DCM/MeOH from 98:2 to 90:10) to give the title compound as a colourless oil (1.2 g, 4.91 mmol, 91% yield). MS ($ES^+$) m/z 245 $(M+H)^+$.

Step 3: 3-(4-(tert-butoxycarbonyl)piperazin-1-yl) propyl 6-(3-(4-(tert-butoxycarbonyl) piperazin-1-yl) propoxy)quinoline-4-carboxylate (H3)

A stirred solution of H1 (100 mg, 0.37 mmol, 1.0 eq), H2 (180 mg, 0.74 mmol, 2.0 eq) and Triphenylphosphine (193 mg, 0.74 mmol, 2.0 eq) in dry THE (25 mL) was treated with Diisopropyl azodicarboxylate (DIAD; 145 μL, 0.74 mmol, 2.0 eq). The reaction was stirred at room temperature for 1 h then concentrated under vacuum and directly purified by flash chromatography (DCM/MeOH from 95:5 to 90:10) to give the title compound as a white powder (100 mg, 0.156 mmol, 42% yield). MS ($ES^+$) m/z 642 $(M+H)^+$.

Scheme 1. Synthesis route for preparation of the compound of Comparative Example 1 "HABERKORN-FLUO" (23)

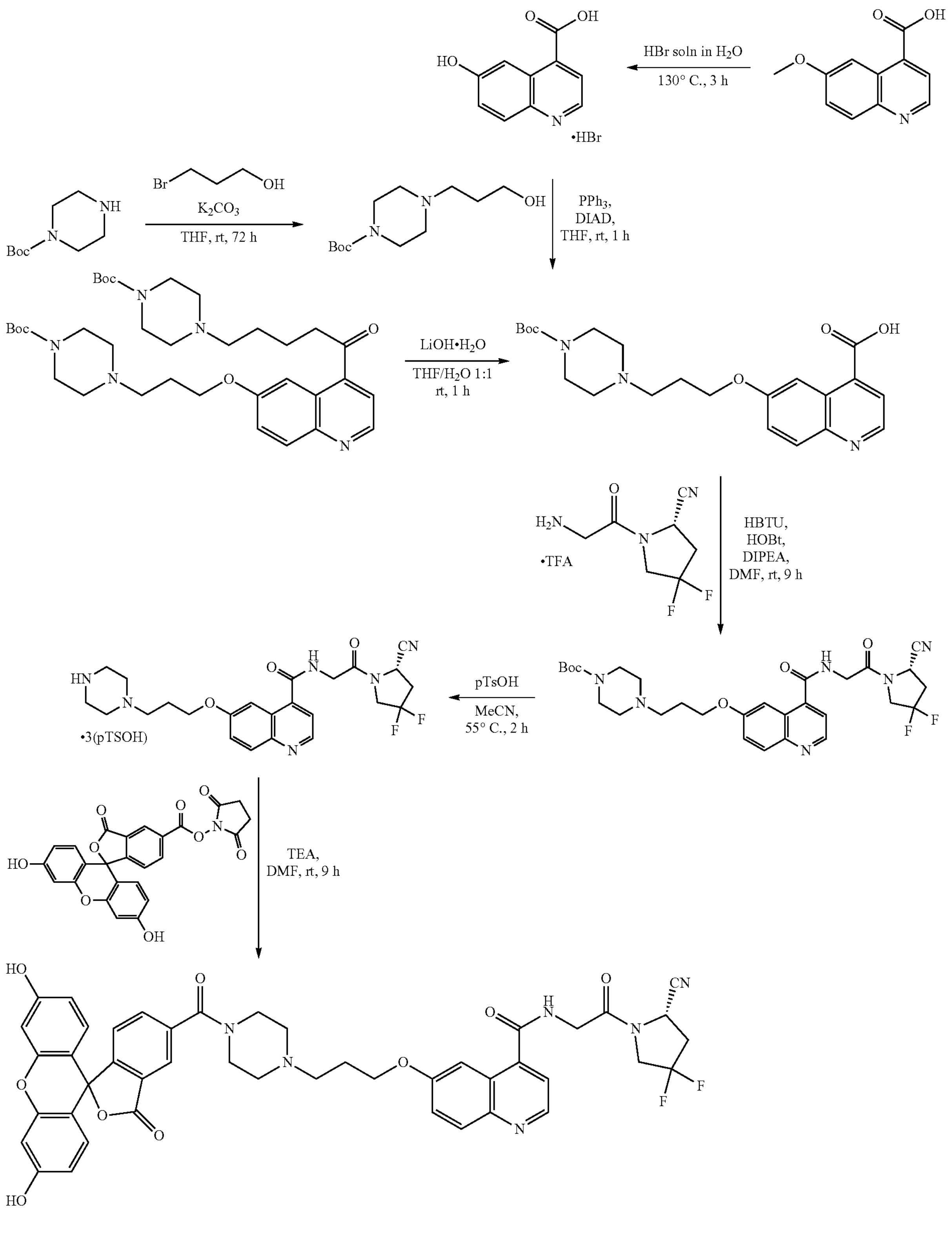

Step 4: 6-(3-(4-tert-butoxycarbonylpiperazin-1-yl) propoxy)quinoline-4-carboxylic acid (H4)

To a stirred solution of H3 (100 mg, 0.156 mmol, 1.0 eq) in THF (5 mL), a solution of LiOH (13 mg, 0.312 mmol, 2.0 eq) in $H_2O$ (2 mL) was added and reaction stirred at room temperature for 2 h. The mixture was diluted with water, extracted with EtOAc, washed with $NH_4Cl$ s.s., dried over $Na_2SO_4$ and filtered to obtain product as a white powder (60 mg, 0.144 mmol, 92% yield). MS ($ES^+$) m/z 416 $(M+H)^+$.

Step 5: 1-Piperazinecarboxylic acid, 4-[3-[[4-[[[2-[(2S)-2-cyano-4,4-difluoro-1-pyrrolidinyl]-2-oxo-ethyl]amino]carbonyl]-6-quinolinyl]oxy]propyl]-, 1,1-dimethylethyl ester (H5)

To a stirred solution of H4 (15 mg, 0.036 mmol, 1.0 eq), HATU (20 mg, 0.054 mmol, 1.5 eq) and HOBt (7.3 mg, 0.054 mmol, 1.5 eq) in DCM (3 mL) a solution of (S)-1-(2-aminoacetyl)-4,4-difluoropyrrolidine-2-carbonitrile (10 mg, 0.054 mmol, 1.5 eq) in DMF (1.0 mL) and DIPEA (25 µL, 0.144 mmol, 4 eq) was added and reaction stirred at room temperature for 9 h. The mixture was evaporated under vacuum, dissolved in DMSO and purified by RP-HPLC to give product as a white solid (6.0 mg, 0.01 mmol, 28% yield). MS ($ES^+$) m/z 587 $(M+H)^+$.

Step 6: (S)—N-(2-(2-cyano-4,4-difluoropyrrolidin-1-yl)-2-oxoethyl)-6-(3-(piperazin-1-yl) propoxy) quinoline-4-carboxamide (H6)

A stirred solution of H5 (5.0 mg, 8.0 µmol, 1.0 eq) and 4-methylbenzenesulfonic acid monohydrate (6.8 mg, 40 µmol, 5.0 eq) in MeCN (3 mL) was heated at 55° C. for 2 h. The mixture was concentrated under vacuum and product used as such in the subsequent step. White powder (8.0 mg, 8.0 µmol, Quant. yield). MS ($ES^+$) m/z 487 $(M+H)^+$.

Step 7: (S)—N-(2-(2-cyano-4,4-difluoropyrrolidin-1-yl)-2-oxoethyl)-6-(3-(4-(3',6'-dihydroxy-3-oxo-3H-spiro[isobenzofuran-1,9'-xanthene]-5-carbonyl) piperazin-1-yl)propoxy)quinoline-4-carboxamide ("HABERKORN-FLUO", 23)

To a stirred solution of H6 (4.5 mg, 4.0 µmol, 1.0 eq.) and TEA (1.1 µL, 8.0 µmol, 2.0 eq) in DMF (1 mL) NHS-Fluorescein (2.8 mg, 6.0 µmol, 1.5 eq) was added and reaction stirred at room temperature for 9 h. The mixture was directly purified by RP-HPLC to give product as an orange powder (0.9 mg, 1.0 mol, 26% yield). MS ($ES^+$) m/z 845 $(M+H)^+$ (Comparative Example 1B; see FIG. 1B).

Example 2: Synthesis of (S)—N1-(4-((2-(2-cyano-4,4-difluoropyrrolidin-1-yl)-2-oxoethyl)carbamoyl) quinolin-8-yl)-N4-(2-(2-(2-(3-(3',6'-dihydroxy-3-oxo-3H-spiro[isobenzofuran-1,9'-xanthen]-5-yl) thioureido)ethoxy)ethoxy)ethyl)succinimide ("ESV6-FLUO", 26)

Step 1: 5,8-Dioxa-2,11-diazadodecanoic acid, 12-[(3',6'-dihydroxy-3-oxospiro [isobenzofuran-1(3H), 9'-[9H]xanthen]-6-yl)amino]-12-thioxo-, 1,1-dimethylethyl ester (P1)

To a stirred solution of tert-butyl N-{2-[2-(2-aminoethoxy)ethoxy]ethyl}carbamate (173 µL, 0.731 mmol, 1.5 eq) in THF (20 mL), Fluorescein-5-Isothiocyanate (190 mg, 0.487 mmol, 1.0 eq) was added and reaction stirred at room temperature for 12 h. The mixture was concentrated under vacuum and crude directly purified by flash chromatography (DCM/EtOAc from 9:1 to 8:2) to give compound as an orange powder (200 mg, 0.314 mmol, 64% yield). MS ($ES^+$) m/z 638 $(M+H)^+$.

Step 2: Thiourea, N-[2-[2-(2-aminoethoxy)ethoxy] ethyl]-N-(3',6'-dihydroxy-3-oxospiro [isobenzo-furan-1(3H),9'-[9H]xanthen]-5-yl)-(P2)

To a stirred solution of P1 (150 mg, 0.235 mmol, 1.0 eq) in DCM (10 mL) cooled to 0° C., HCl 4M in $Et_2O$ (5 mL) was added. The reaction was stirred slowly warmed to room temperature for 2 h, then concentrated under vacuum and co-evaporated with $Et_2O$ several times until an orange powder was obtained (135 mg, 0.235 mmol, Quant. yield). MS ($ES^+$) m/z 538 $(M+H)^+$.

Scheme 2. Synthesisi route for preparation of ESV6-FLUO (26)

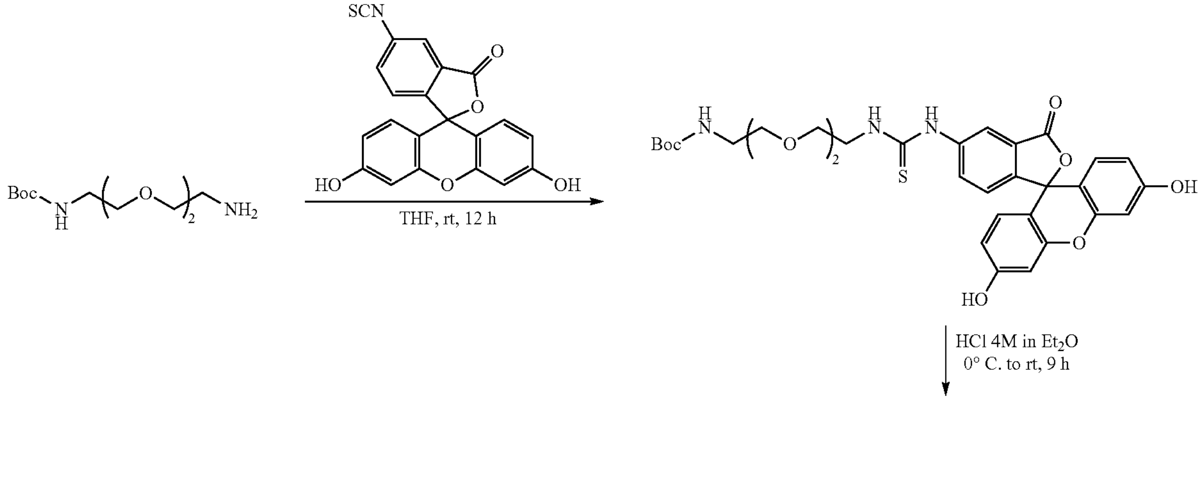

-continued

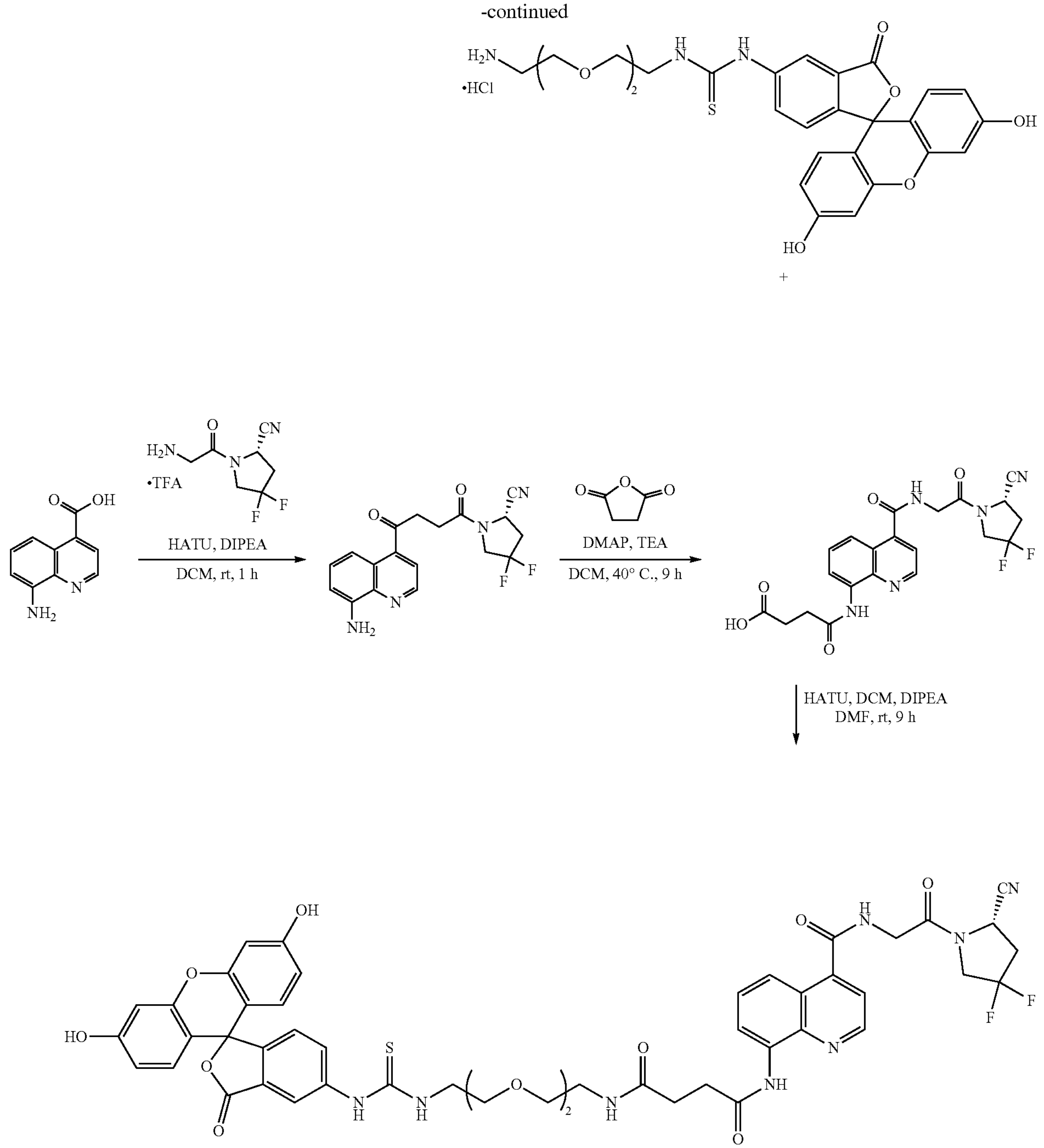

Step 3: (S)-8-amino-N-(2-(2-cyano-4,4-difluoropyrrolidin-1-yl)-2-oxoethyl)quinoline-4-carboxamide (P3)

Commercially available 8-amino-quinoline-4-carboxylic acid (19.0 mg, 100 μmol, 1.0 eq), DIPEA (70.0 μL, 400 μmol, 4.0 eq) and HATU (38.0 mg, 100 μmol, 1.0 eq) were dissolved in a 1:1 DCM/DMF mixture (2 mL). After 15 min a solution of (S)-1-(2-aminoacetyl)-4,4-difluoropyrrolidine-2-carbonitrile trifluoroacetate (30.3 mg, 100 μmol, 1.0 eq) in DCM was added. The reaction mixture was stirred for 1 h at room temperature, washed with water, dried over $Na_2SO_4$, filtered and concentrated to obtain a brown crude as sticky oil. The residue was purified by flash chromatography (DCM/MeOH from 91:1 to 90:10) to yield the pure product as a brownish oil (24.8 mg, 68.9 μmol, 69% yield). MS ($ES^+$) m/z 360 $(M+H)^+$.

Step 4: (S)-4-((4-((2-(2-cyano-4,4-difluoropyrrolidin-1-yl)-2-oxoethyl)carbamoyl)quinolin-8-yl)amino)-4-oxobutanoic acid (P4)

Triethylamine (20.8 μL, 150 μmol, 2.0 eq) and 4-dimethylaminopyridine (0.91 mg, 10.0 μmol, 0.1 eq) were added to a cooled solution (0° C.) of P3 (26.8 mg, 70.0 μmol, 1.0 eq) in DCM, followed by a dropwise addition of succinic anhydride (15.0 mg, 150 μmol, 2.0 eq). The reaction mixture was allowed to warm to room temperature. The reaction mixture was placed in a preheated 40° C. oil bath until full conversion was observed. The solvent was evaporated and the residue was purified by RP-HPLC to yield the pure product as a white powder (9.42 mg, 20.0 μmol, 28% yield). MS ($ES^+$) m/z 460 $(M+H)^+$. FIG. 28 shows structure, chromatographic profile and LC/MS analysis of Example 2, P4. MS($ES^+$) m/z 460.21 $(M+H)^+$.

Step 5: (S)—N1-(4-((2-(2-cyano-4,4-difluoropyrrolidin-1-yl)-2-oxoethyl)carbamoyl)quinolin-8-yl)-N4-(2-(2-(2-(3-(3',6'-dihydroxy-3-oxo-3H-spiro[isobenzofuran-1,9'-xanthen]-5-yl)thioureido)ethoxy)ethoxy)ethyl)succinamide ("ESV6-FLUO", 26)

Figure 1:
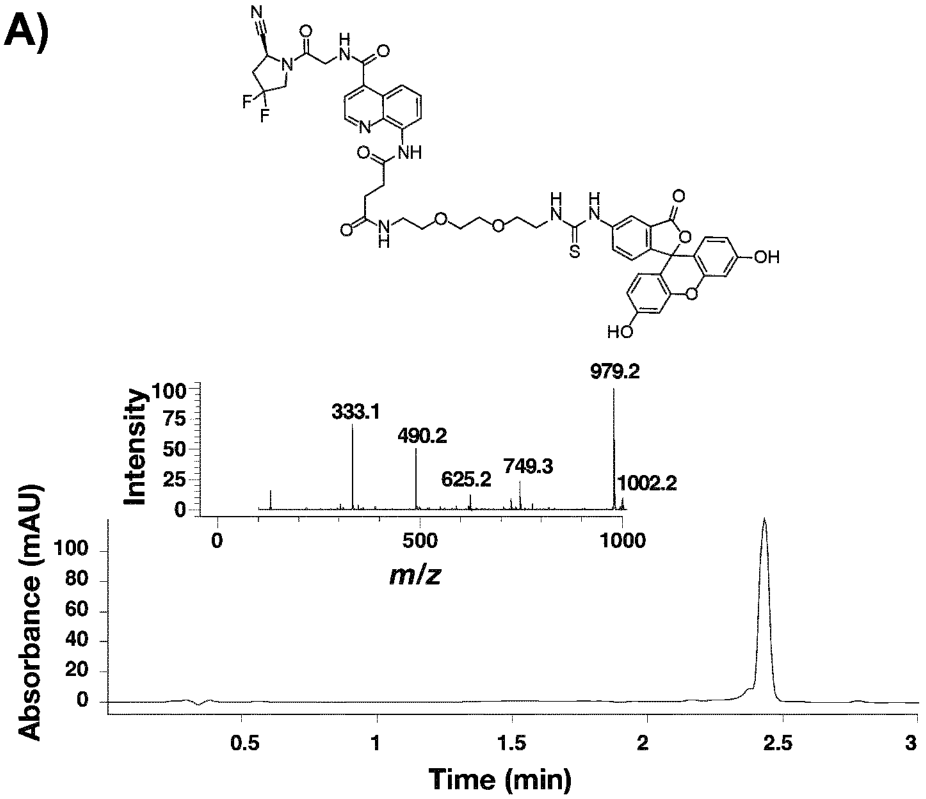
FIG. 1: Chemical structure and LC/MS profiles of compounds (A) ESV6-fluo (26) and (B) Haberkorn-fluo (23).
Figure 1:
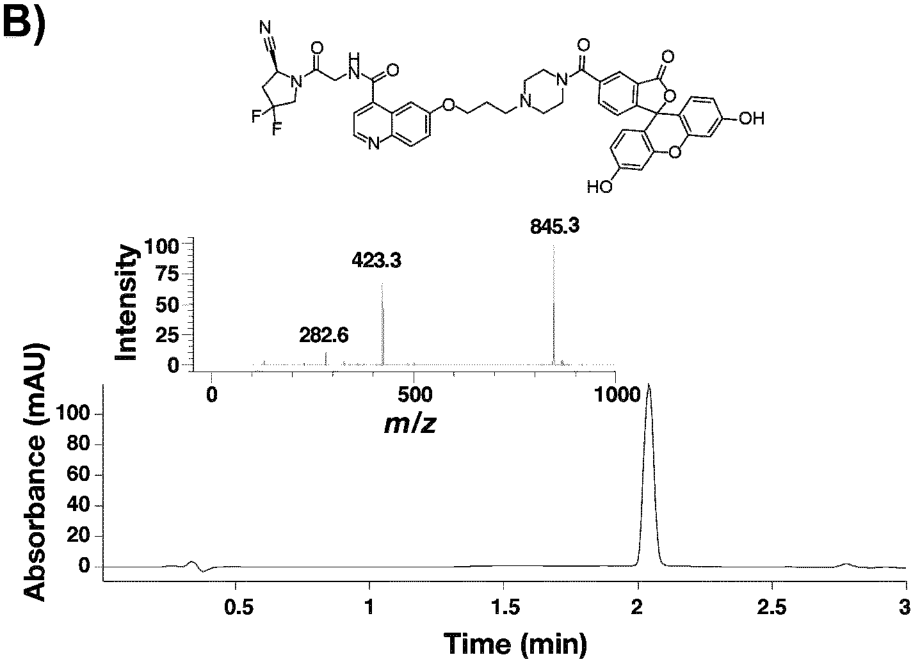

P2 (22.0 mg, 40.0 μmol, 2.0 eq) and HATU (15.6 mg, 40.0 μmol, 2.0 eq) were taken in a 1:1 DCM/DMF mixture (2 mL) and DIPEA (7.20 μl, 40.0 μmol, 2.0 eq). The resulting mixture was stirred for 15 min at room temperature. P4 (9.42 mg, 20.0 μmol, 1.0 eq) in DCM was added and the reaction mixture was stirred at room temperature overnight. The solvent was evaporated and the residue was purified by preparative RP-HPLC to get the pure product as a yellow solid (2.50 mg, 10.0 μmol, 25% yield). MS ($ES^+$) m/z 979 $(M+H)^+$ (FIG. 1A).

Further conjugates according to the present invention are listed below.

Conjugate 1: (2S,5R,8R,11R)-2-(((1-(6-(((S)-1-(((R)-1-((4-((5R,8S,11R,12S)-11-((R)-sec-butyl)-12-(2-((R)-2-((1S,2S)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxo-5-ureidopentan-2-yl)amino)-3-methyl-1-oxobutan-2-yl)amino)-6-oxohexyl)-2,5-dioxopyrrolidin-3-yl)thio)methyl)-5,11-bis(carboxymethyl)-16-((4-((2-((R)-2-cyano-4,4-difluoropyrrolidin-1-yl)-2-oxoethyl)carbamoyl)quinolin-8-yl)amino)-8-(3-guanidinopropyl)-4,7,10,13,16-pentaoxo-3,6,9,12-tetraazahexadecanoic acid

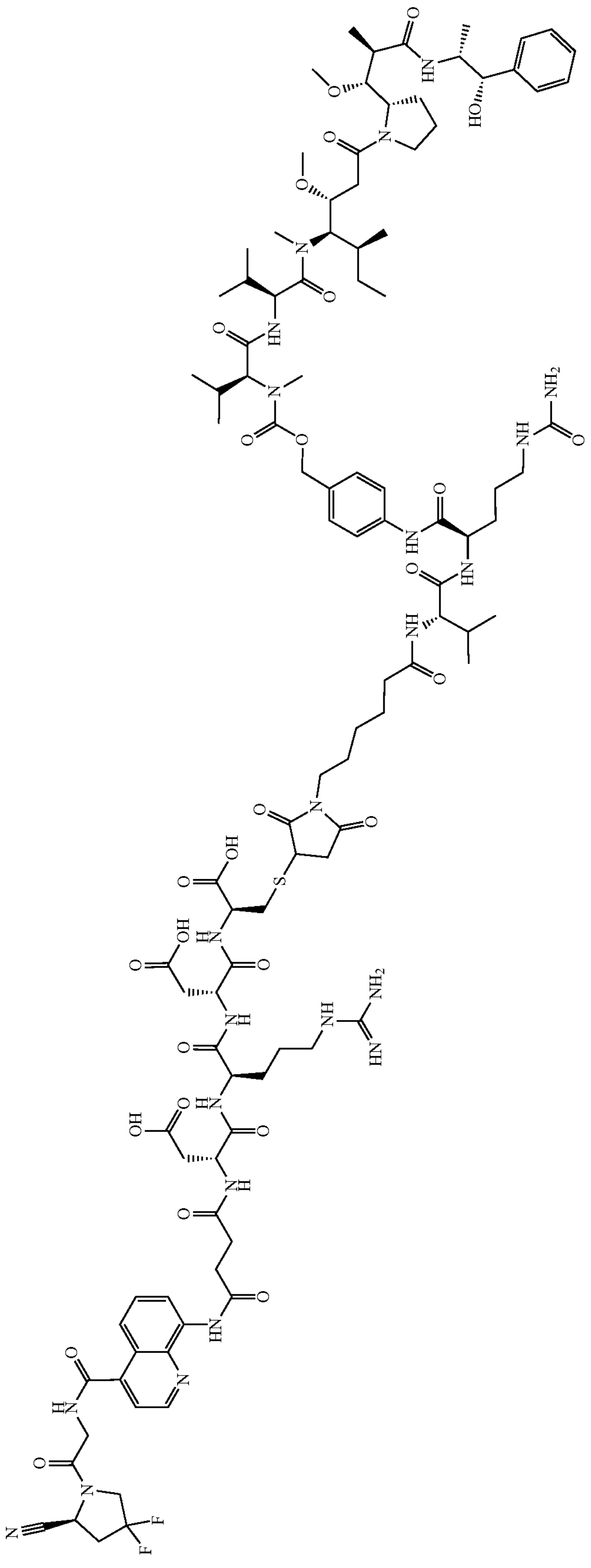

Conjugate 2: (2S,5R,8R,11R)-8-(4-aminobutyl)-2-(((1-(6-(((S)-1-(((R)-1-((4-((5R,8S,11R,12S)-11-((R)-sec-butyl)-12-(2-((R)-2-((1S,2S)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxo-5-ureidopentan-2-yl)amino)-3-methyl-1-oxobutan-2-yl)amino)-6-oxohexyl)-2,5-dioxopyrrolidin-3-yl)thio)methyl)-5,11-bis(carboxymethyl)-16-((4-((2-((R)-2-cyano-4,4-difluoropyrrolidin-1-yl)-2-oxoethyl)carbamoyl)quinolin-8-yl)amino)-4,7,10,13,16-pentaoxo-3,6,9,12-tetraazahexadecanoic acid

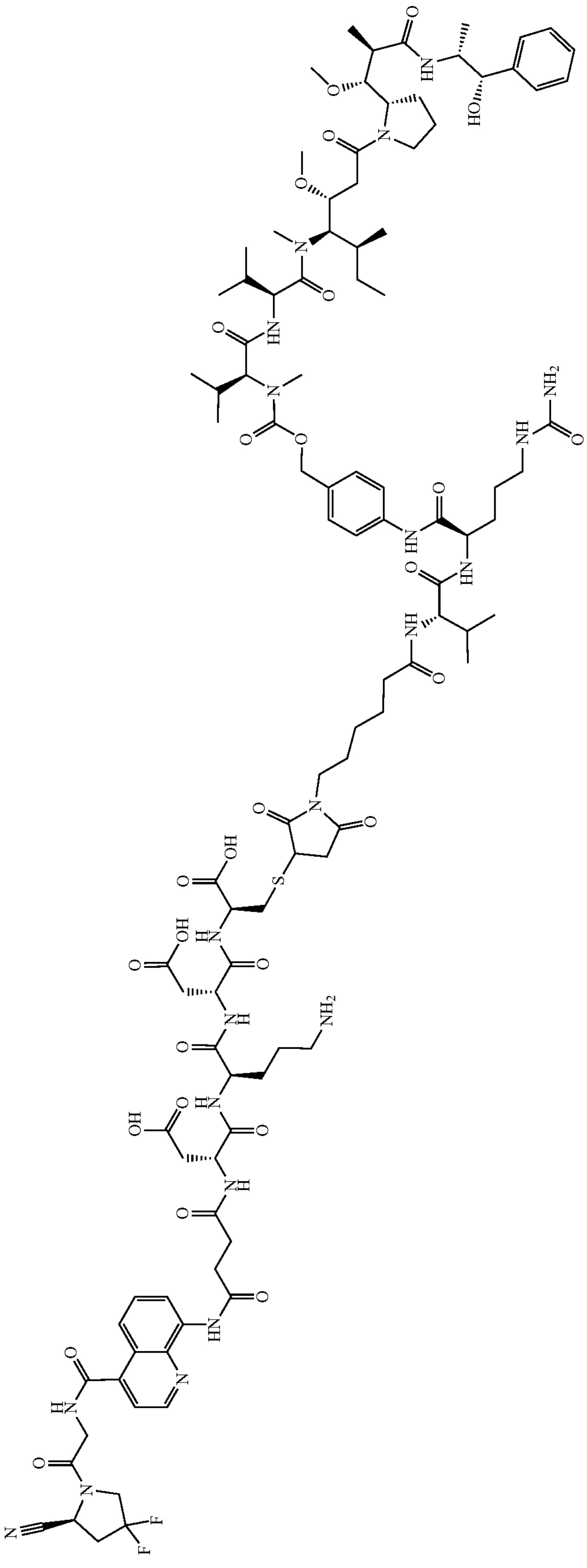

Conjugate 3: (2S,5R,8R,11R)-2-(((1-(6-(((S)-1-(((R)-1-((4-((5R,8S,11R,12S)-11-((R)-sec-butyl)-12-(2-((R)-2-((1S,2S)-3-(((1S,2R)-1-hydroxy-1-phenylpropan-2-yl)amino)-1-methoxy-2-methyl-3-oxopropyl)pyrrolidin-1-yl)-2-oxoethyl)-5,8-diisopropyl-4,10-dimethyl-3,6,9-trioxo-2,13-dioxa-4,7,10-triazatetradecyl)phenyl)amino)-1-oxopropan-2-yl)amino)-3-methyl-1-oxobutan-2-yl)amino)-6-oxohexyl)-2,5-dioxopyrrolidin-3-yl)thio)methyl)-5,11-bis(carboxymethyl)-16-((4-((2-((R)-2-cyano-4,4-difluoropyrrolidin-1-yl)-2-oxoethyl)carbamoyl)quinolin-8-yl)amino)-8-(3-guanidinopropyl)-4,7,10,13,16-pentaoxo-3,6,9,12-tetraazahexadecanoic acid

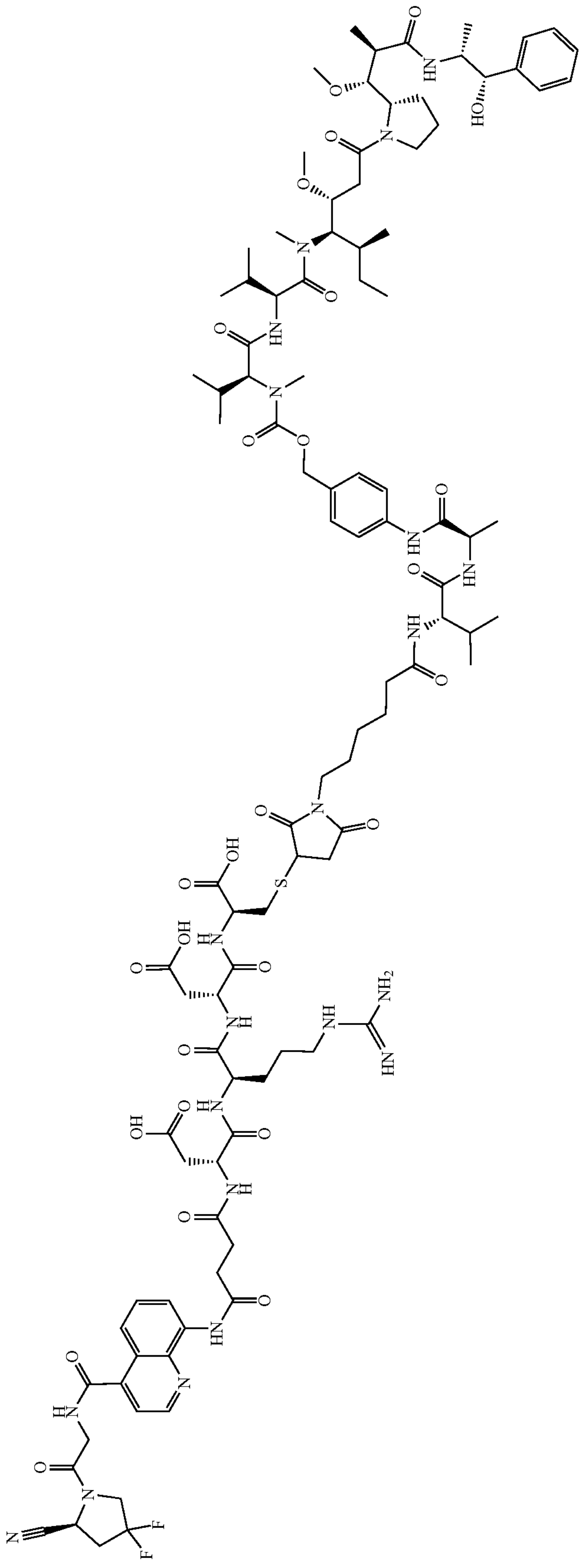

Conjugate 4: $N^6$-(4-((3-((3-(((2R)-1-((($1^4$R,$1^6$R,$3^3$R,2S,4S,10E,12Z,14S)-$8^6$-chloro-$1^4$-hydroxy-$8^5$,14-dimethoxy-$3^3$,2,7,10-tetramethyl-$1^2$,6-dioxo-7-aza-1(6,4)-oxazinana-3(2,3)-oxirana-8(1,3)-benzenacyclotetradecaphane-10,12-dien-4-yl)oxy)-1-oxopropan-2-yl)(methyl)amino)-3-oxopropyl)thio)-2,5-dioxopyrrolidin-1-yl)methyl)cyclohexane-1-carbonyl)-$N^2$-(4-((4-((2-((R)-2-cyano-4,4-difluoropyrrolidin-1-yl)-2-oxoethyl)carbamoyl)quinolin-8-yl)amino)-4-oxobutanoyl)-D-aspartyl-D-arginyl-D-aspartyl-D-lysine

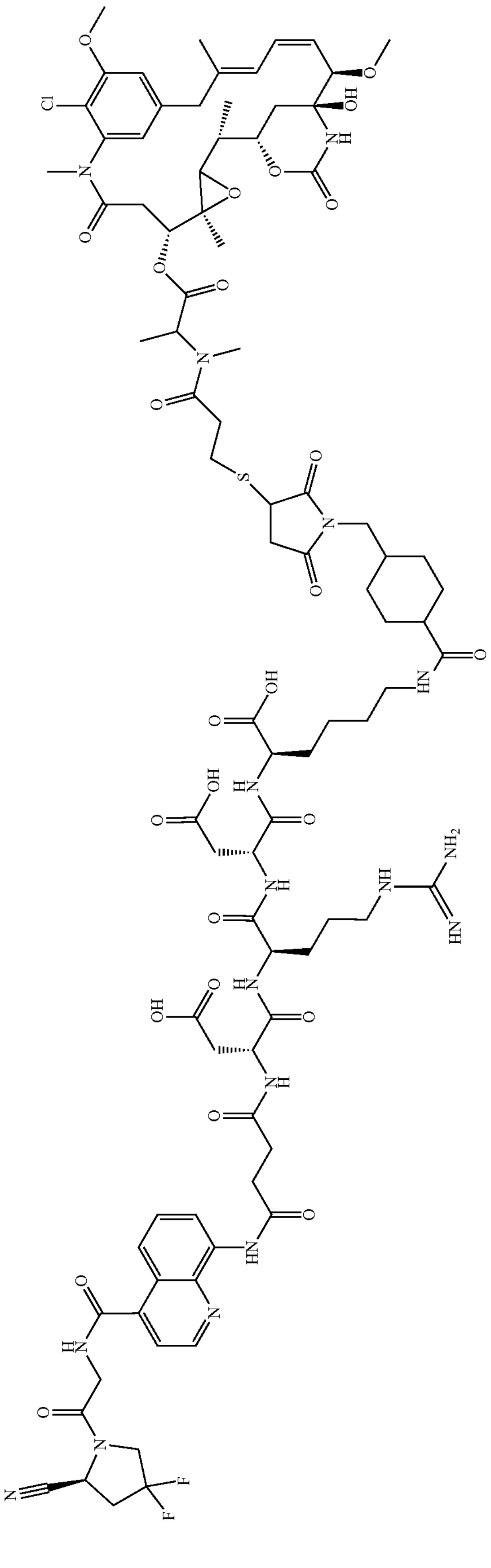

Conjugate 5: (2R,5R,8R,11R)-5,11-bis(carboxymethyl)-16-((4-((2-((R)-2-cyano-4,4-difluoropyrrolidin-1-yl)-2-oxoethyl)carbamoyl)quinolin-8-yl)amino)-2-((1-(14-((4-(4,7-dimethyl-3,8,11-trioxo-11-((2S,4S)-2,5,12-trihydroxy-7-methoxy-4-(((1S,3R,4aS,9S,9aR,10aS)-9-methoxy-1-methyloctahydro-1H-pyrano[4',3':4,5]oxazolo[2,3-c][1,4]oxazin-3-yl)oxy)-6,11-dioxo-1,2,3,4,6,11-hexahydrotetracen-2-yl)-2,9-dioxa-4,7-diazaundecyl)phenyl)carbamoyl)-15-methyl-3,12-dioxo-7,10-dioxa-4,13-diazahexadecyl)-2,5-dioxopyrrolidin-3-yl)thio)-8-(3-guanidinopropyl)-4,7,10,13,16-pentaoxo-3,6,9,12-tetraazahexadecanoic acid

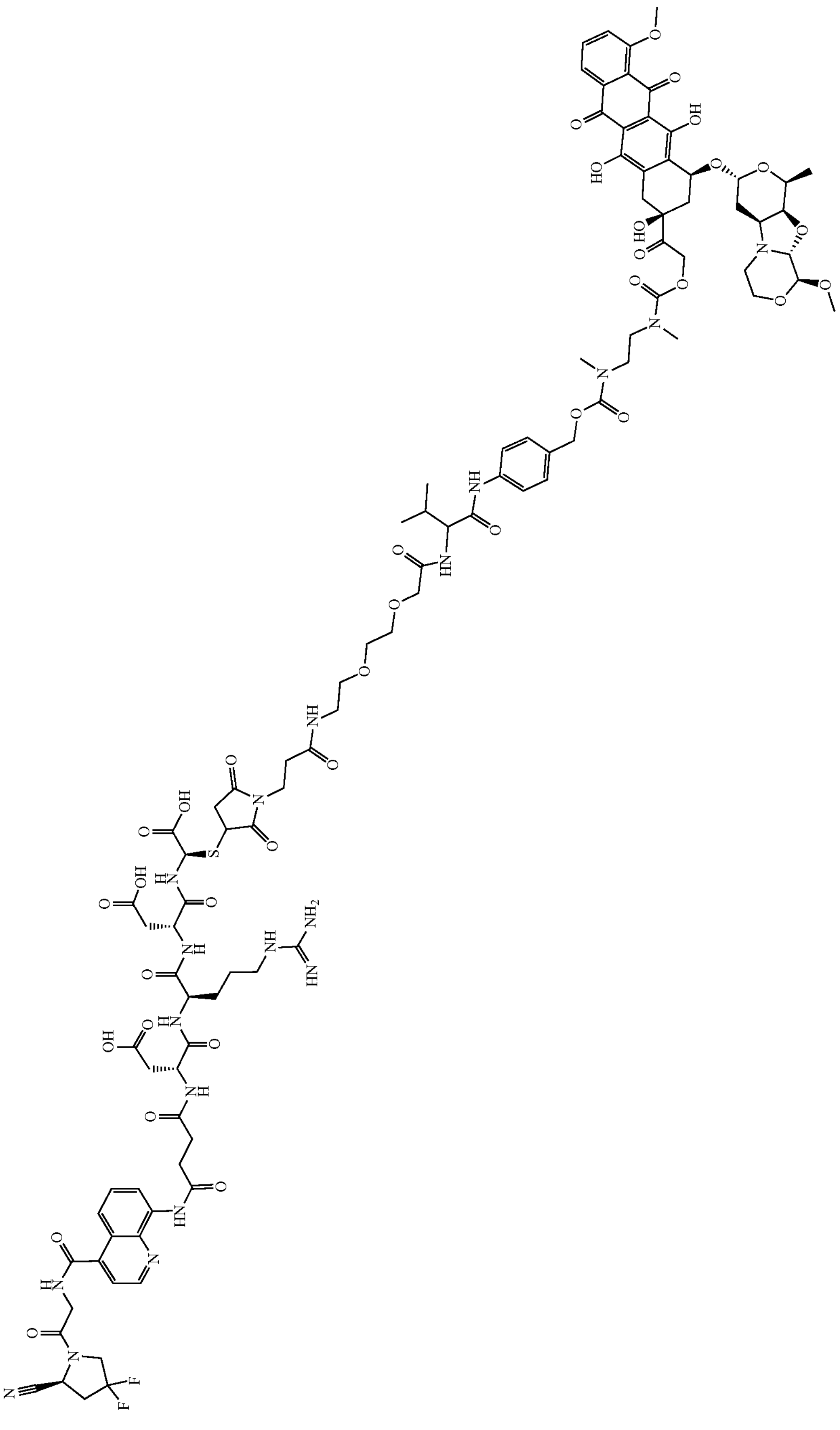

Conjugate 6: (10R,13R,16R,19R)-1-((3aR,4R,5S,10bR)-4-acetoxy-3a-ethyl-9-((3S,5S,7S,9S)-5-ethyl-5-hydroxy-9-(methoxycarbonyl)-1,4,5,6,7,8,9,10-octahydro-2H-3,7-methano[1]azacycloundecino[5,4-b]indol-9-yl)-5-hydroxy-8-methoxy-6-methyl-3a,3a[1],4,5,5a,6,11,12-octahydro-1H-indolizino[8,1-cd]carbazol-5-yl)-10-carboxy-13-(carboxymethyl)-19-(4-((4-((2-((R)-2-cyano-4,4-difluoropyrrolidin-1-yl)-2-oxoethyl)carbamoyl)quinolin-8-yl)amino)-4-oxobutanamido)-16-(3-guanidinopropyl)-1,4,12,15,18-pentaoxo-5-oxa-8,9-dithia-2,3,11,14,17-pentaazahenicosan-21-oic acid

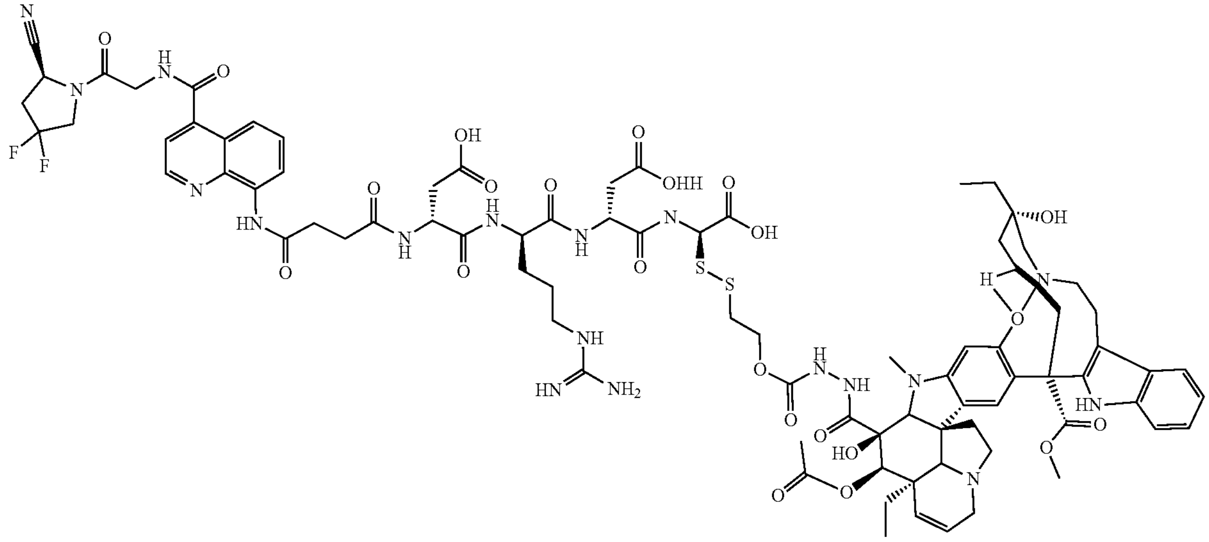

Conjugate 7: 2,2',2"-(10-(2-((2-(3-(((2S,5R,8R,11R)-8-(4-aminobutyl)-2-carboxy-5,11-bis(carboxymethyl)-16-((4-((2-((R)-2-cyano-4,4-difluoropyrrolidin-1-yl)-2-oxoethyl)carbamoyl)quinolin-8-yl)amino)-4,7,10,13,16-pentaoxo-3,6,9,12-tetraazahexadecyl)thio)-2,5-dioxopyrrolidin-1-yl)ethyl)amino)-2-oxoethyl)-1,4,7,10-tetraazacyclododecane-1,4,7-triyl)triacetic acid

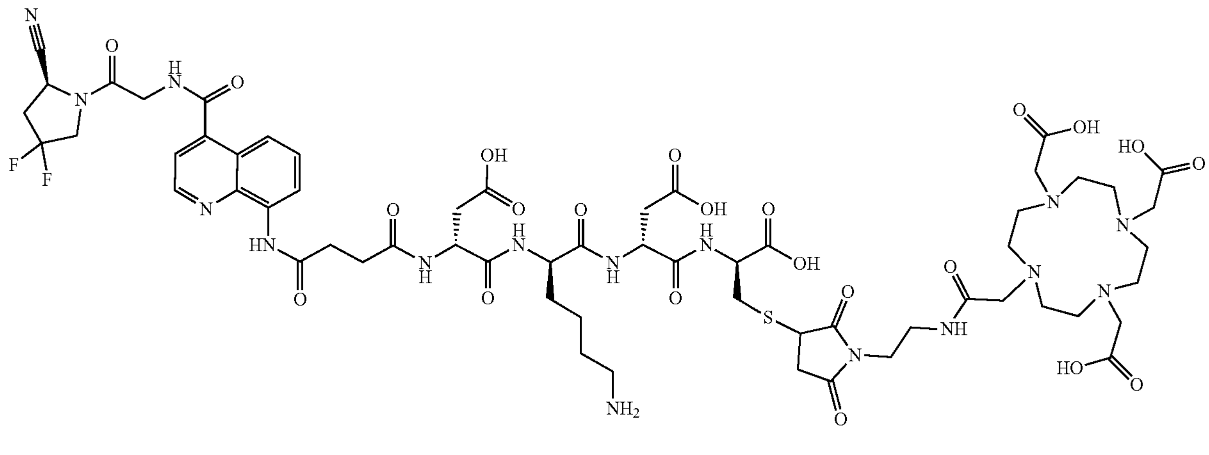 [SMILES: N#C[C@@H]1CC(F)(F)CN1C(=O)CNC(=O)c1ccnc2c(NC(=O)CCC(=O)N[C@H](CC(=O)O)C(=O)N[C@H](CCCCN)C(=O)N[C@H](CC(=O)O)C(=O)N[C@H](CSC3CC(=O)N(CCNC(=O)CN4CCN(CC(=O)O)CCN(CC(=O)O)CCN(CC(=O)O)CC4)C3=O)C(=O)O)cccc12]

Conjugate 8: 2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid

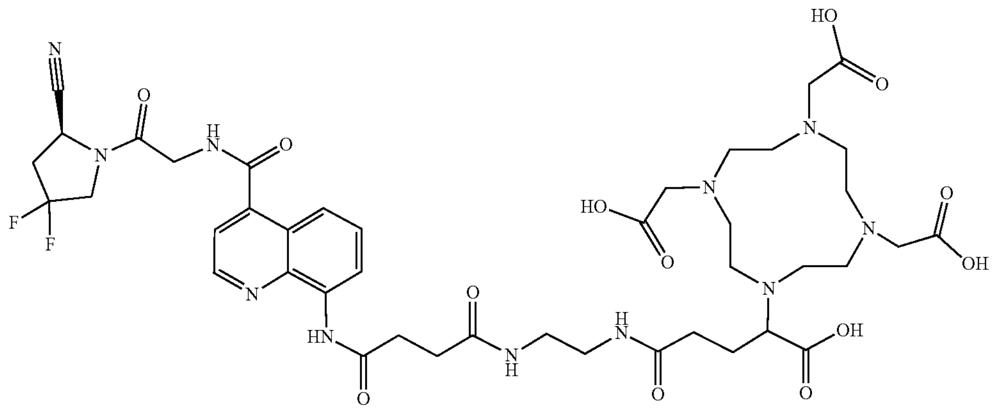 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CCN(CC(=O)O)CC3)cccc12]

Conjugate 9: 2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid labelled with 177-Lutetium

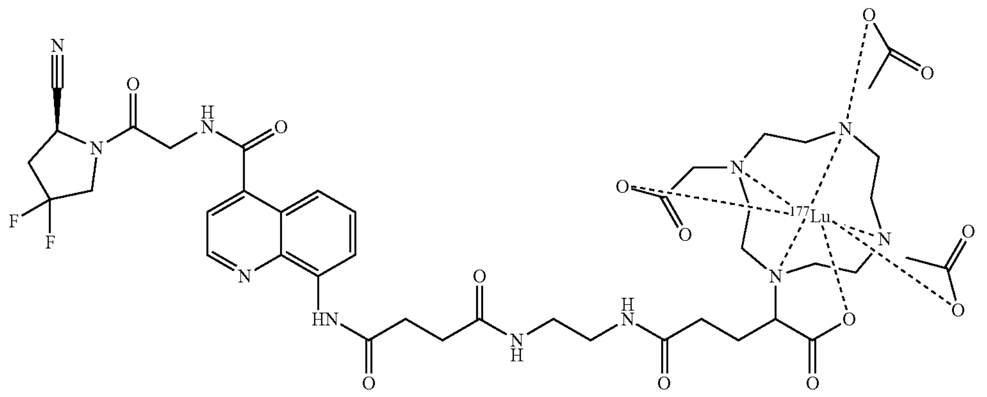

Conjugate 10: 2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid labelled with 225-Actinium

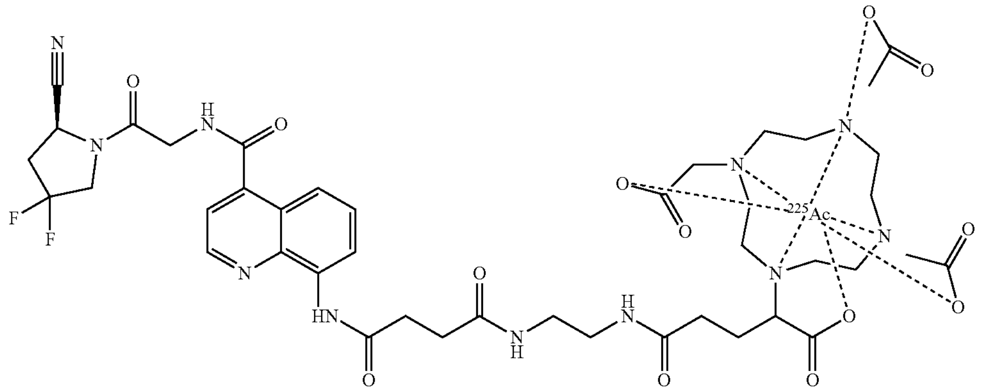

Conjugate 11: 2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid labelled with 64-Cupper

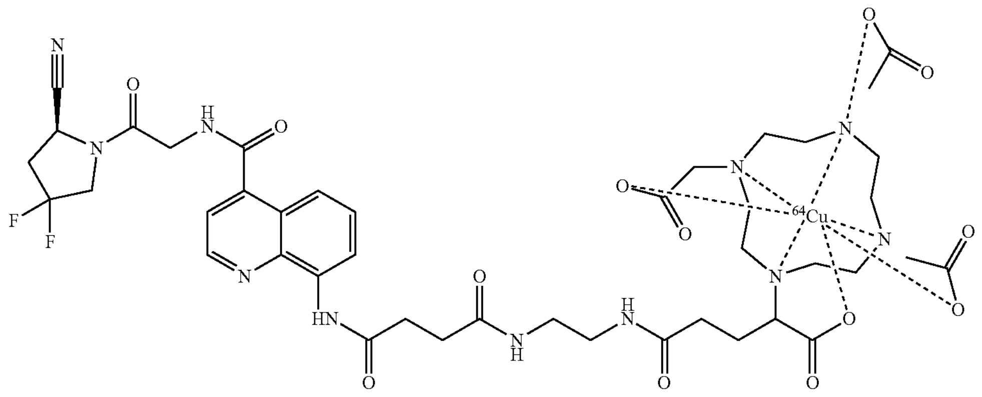

Conjugate 12: (S)-3-((S)-2-amino-6-(4-((4-((2-((R)-2-cyano-4,4-difluoropyrrolidin-1-yl)-2-oxoethyl)carbamoyl)quinolin-8-yl)amino)-4-oxobutanamido)hexanamido)-4-(((R)-1-carboxy-2-mercaptoethyl)amino)-4-oxobutanoic acid labelled with 68-Gallium
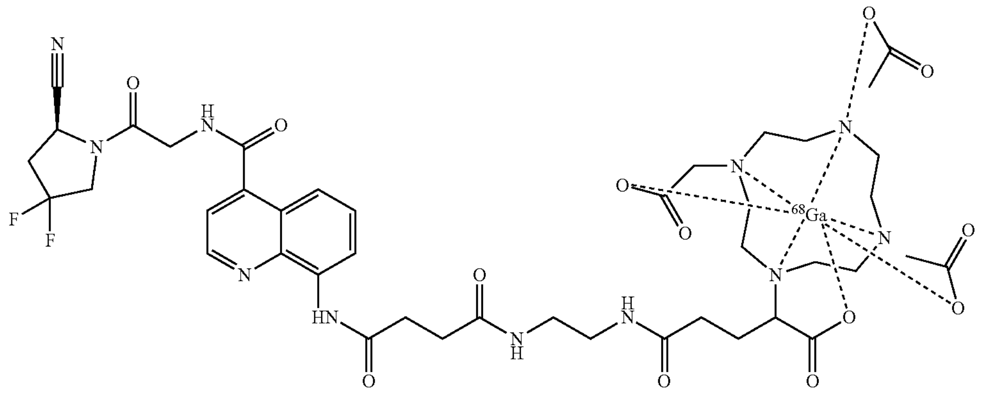
Conjugate 13: (S)-3-((S)-2-amino-6-(4-((4-((2-((R)-2-cyano-4,4-difluoropyrrolidin-1-yl)-2-oxoethyl)carbamoyl)quinolin-8-yl)amino)-4-oxobutanamido)hexanamido)-4-(((R)-1-carboxy-2-mercaptoethyl)amino)-4-oxobutanoic acid
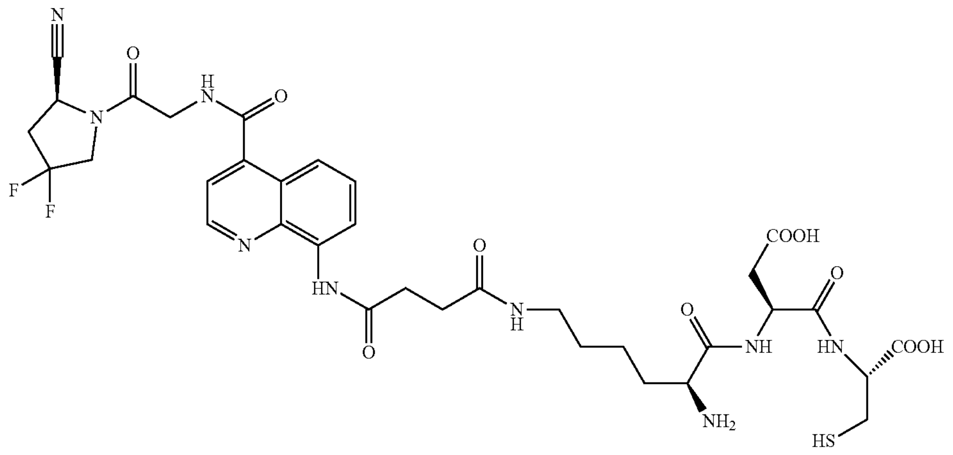 [SMILES: N#C[C@@H]1CC(F)(F)CN1C(=O)CNC(=O)c1ccnc2c(NC(=O)CCC(=O)NCCCC[C@H](N)C(=O)N[C@@H](CC(=O)O)C(=O)N[C@@H](CS)C(=O)O)cccc12]

Conjugate 14: (S)-3-((S)-2-amino-6-(4-((4-((2-((R)-2-cyano-4,4-difluoropyrrolidin-1-yl)-2-oxoethyl)carbamoyl)quinolin-8-yl)amino)-4-oxobutanamido)hexanamido)-4-(((R)-1-carboxy-2-mercaptoethyl)amino)-4-oxobutanoic acid labelled with 99m-Technetium

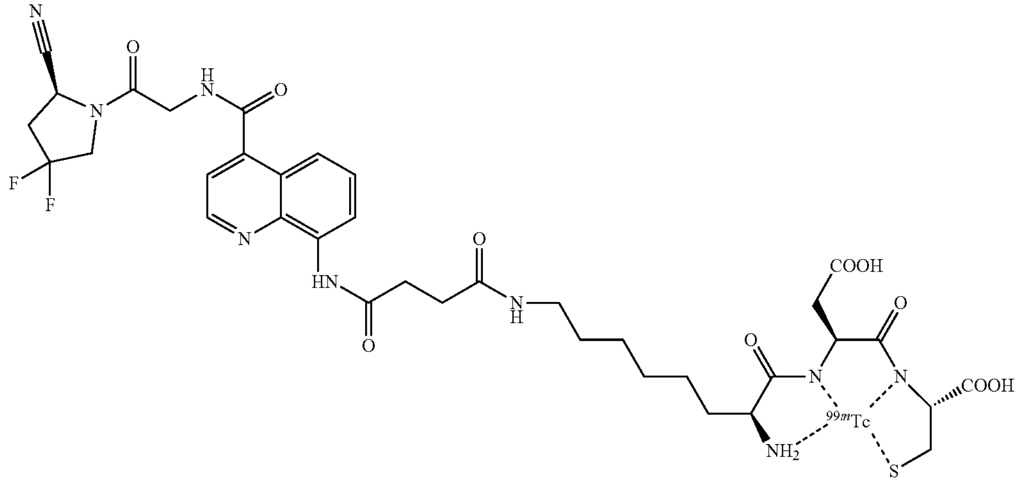

Conjugate 15: (2R,5S,8S,11S)-8-(4-aminobutyl)-5,11-bis(carboxymethyl)-16-((4-((2-((S)-2-cyano-4,4-difluoropyrrolidin-1-yl)-2-oxoethyl)carbamoyl)quinolin-8-yl)amino)-2-(((1-(3',6'-dihydroxy-3-oxo-3H-spiro[isobenzofuran-1,9'-xanthen]-5-yl)-2,5-dioxopyrrolidin-3-yl)thio)methyl)-4,7,10,13,16-pentaoxo-3,6,9,12-tetraazahexadecanoic acid

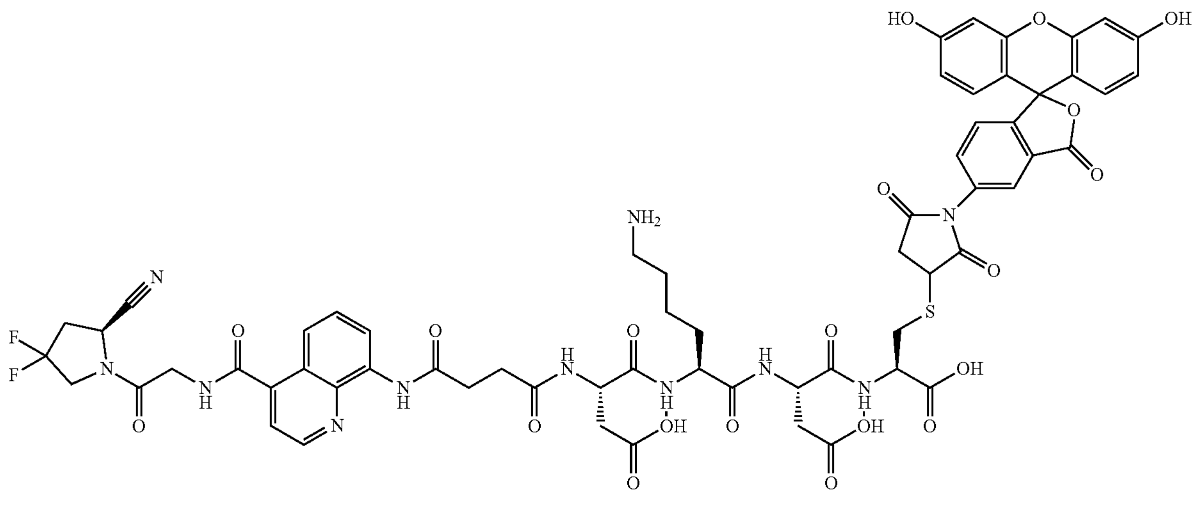 [SMILES: N#C[C@@H]1CC(F)(F)CN1C(=O)CNC(=O)c1ccnc2c(NC(=O)CCC(=O)N[C@H]3CC(=O)ON([C@@H](CCCCN)C(=O)N[C@H]4CC(=O)ON([C@@H](CSC5CC(=O)N(c6ccc7c(c6)C(=O)OC76c7ccc(O)cc7Oc7cc(O)ccc76)C5=O)C(=O)O)C4=O)C3=O)cccc12]

Example 3: Characterization of the Fluorescein-Labelled Binder "ESV6-FLUO" (26)

Expression of Human FAP

Aminoacid sequence of polyhistidine-tagged human Fibroblast Activating Protein (hFAP):

```
LRPSRVHNSEENTMRALTLKDILNGTFSYKTFFPNWISGQEYLHQSADNN

IVLYNIETGQSYTILSNRTMKSVNASNYGLSPDRQFVYLESDYSKLWRYS

YTATYYIYDLSNGEFVRGNELPRPIQYLCWSPVGSKLAYVYQNNIYLKQR

PGDPPFQITFNGRENKIFNGIPDWVYEEEMLATKYALWWSPNGKFLAYAE

FNDTDIPVIAYSYYGDEQYPRTINIPYPKAGAKNPVVRIFIIDTTYPAYV

GPQEVPVPAMIASSDYYFSWLTWVTDERVCLQWLKRVQNVSVLSICDFRE

DWQTWDCPKTQEHIEESRTGWAGGFFVSTPVFSYDAISYYKIFSDKDGYK

HIHYIKDTVENAIQITSGKWEAINIFRVTQDSLFYSSNEFEEYPGRRNIY

RISIGSYPPSKKCVTCHLRKERCQYYTASFSDYAKYYALVCYGPGIPIST

LHDGRTDQEIKILEENKELENALKNIQLPKEEIKKLEVDEITLWYKMILP

PQFDRSKKYPLLIQVYGGPCSQSVRSVFAVNWISYLASKEGMVIALVDGR

GTAFQGDKLLYAVYRKLGVYEVEDQITAVRKFIEMGFIDEKRIAIWGWSY

GGYVSSLALASGTGLFKCGIAVAPVSSWEYYASVYTERFMGLPTKDDNLE

HYKNSTVMARAEYFRNVDYLLIHGTADDNVHFQNSAQIAKALVNAQVDFQ

AMWYSDQNHGLSGLSTNHLYTHMTHFLKQCFSLSDHHHHHH
```

Human Fibroblast Activating Protein (hFAP; UniProtKB-Q12884 (SEPR_HUMAN) Aminoacids 25-760) was cloned in pCDNA3.1(+) with a secretion sequence at its 5'-, and a 6× polyhistidine-tag at its 3'-end and expressed in CHO cells by transient gene expression. The transfection mix was assembled as follow: 0.625 μg of plasmid DNA, 2.5 μg polyethylenimine (PEI) for $10^6$ cells, with a cell density of $4\times10^6$ cells/ml. Cells were incubated for 6 days at 37° C., 5% $CO_2$, 120 rpm. Cells were harvested by centrifugation (4500 rpm 30 min, 4° C.), and 1 mL (dry volume) of complete His-tag purification Resin was added to the filtered supernatant and incubated for 2 hours, 120 rpm at room temperature. Resin was washed with 800 mL of wash-buffer (imidazole 10 mM, PBS/NaCl 250 mM) and hFAP was eluted with 250 mM imidazole PBS/NaCl 250 mM. Elution fractions (1.5 mL) were checked on a spectrophotometer for Absorbance at 280 nm. hFAP-enriched fractions were pooled and dialyzed against HEPES-buffer (50 mM HEPES, 100 mM NaCl, pH=7.4).

Figure 2:
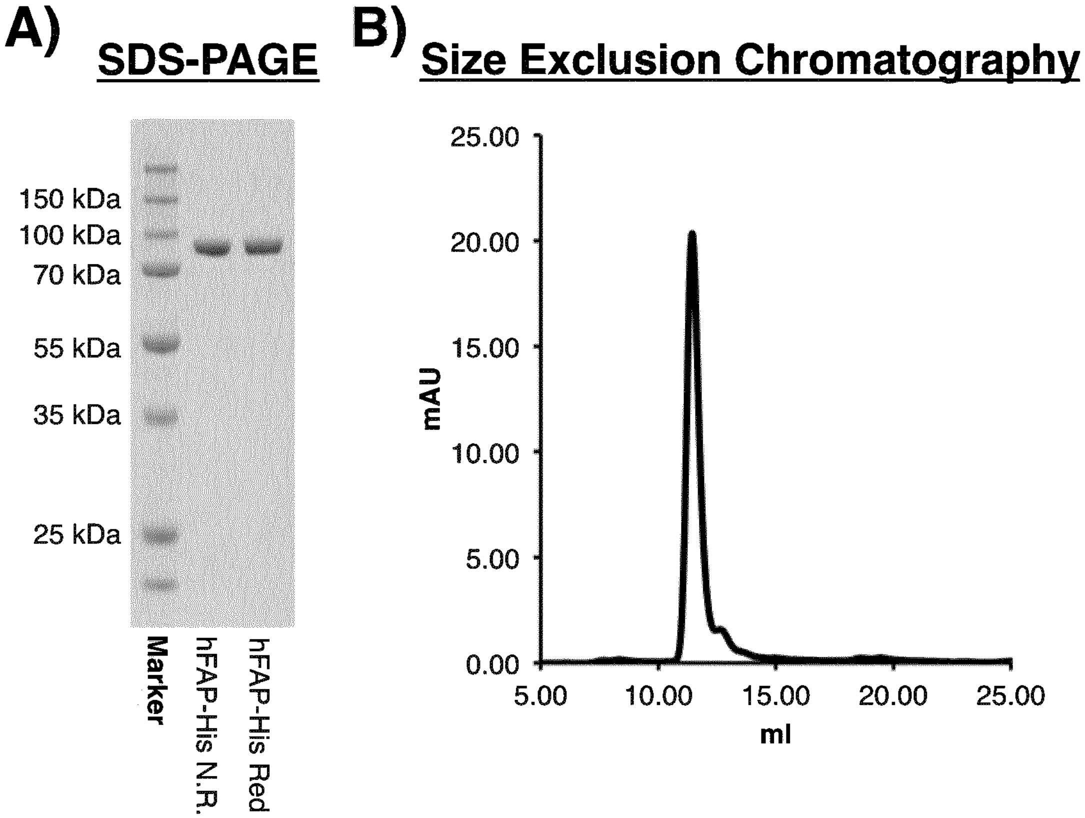
FIG. 2: Quality Control of recombinant hFAP: A) SDS-PAGE; B) Size Exclusion Chromatography (Superdex 200 Increase 10/300 GL).

Samples of recombinant hFAP were analyzed by SDS-PAGE and size exclusion chromatography (see FIG. 2: A) SDS-PAGE; B) Size Exclusion Chromatography (Superdex 200 Increase 10/300 GL)), and activity of the Enzyme was confirmed in Inhibition-assays (see section "In Vitro human FAP enzyme $IC_{50}$ assay").

Figure 4:
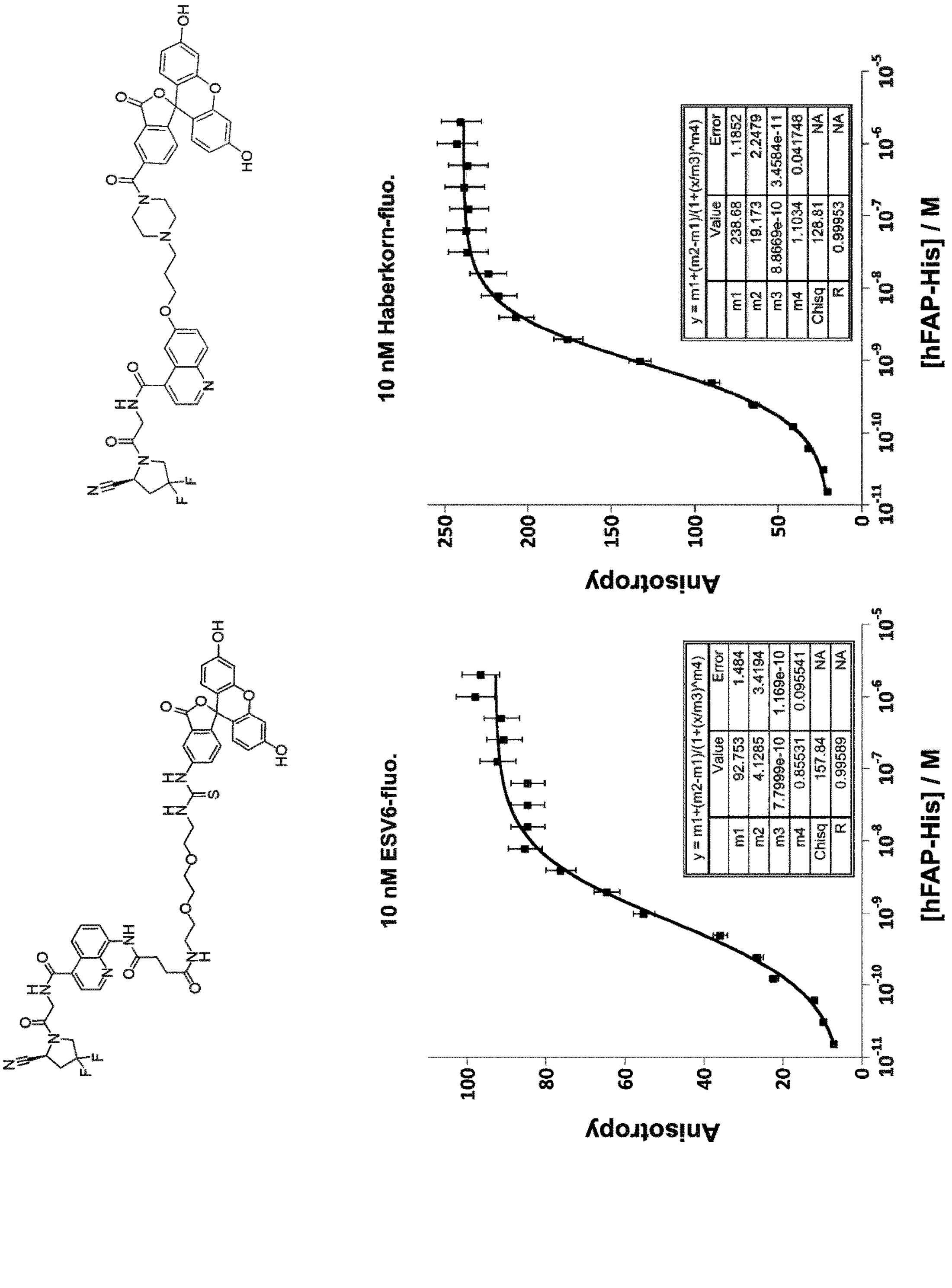
FIG. 4: Affinity determination of small organic ligands for human fibroblast activation protein (hFAP) by fluorescent polarization. ESV6-fluo (26) displays a higher affinity to hFAP ($K_D$ of 0.78 nM) compared to the previously described ligand, Haberkorn-fluo (23) ($K_D$ of 0.89 nM).

Affinity Measurement to Human FAP by Fluorescence Polarization (FIG. 4)

Fluorescence polarization measurements were performed in 384-well plates (non-binding, ps, f-bottom, black, high volume, 30 μL final volume). A stock solution of human FAP (4 μM) was serially diluted with buffer (50 mM Tris, 100 mM NaCl, 1 mM EDTA, pH=7.4), while the final concentration of the binders was kept constant at 10 nM. The measurements were carried out after incubating for 30 min at 37° C. in the dark by fluorescent polarization (FIG. 4).

ESV6-fluo displays a higher affinity to hFAP ($K_D$ of 0.78 nM) compared to the previously described ligand, Haberkorn-fluo ($K_D$ of 0.89 nM).

Figure 5:
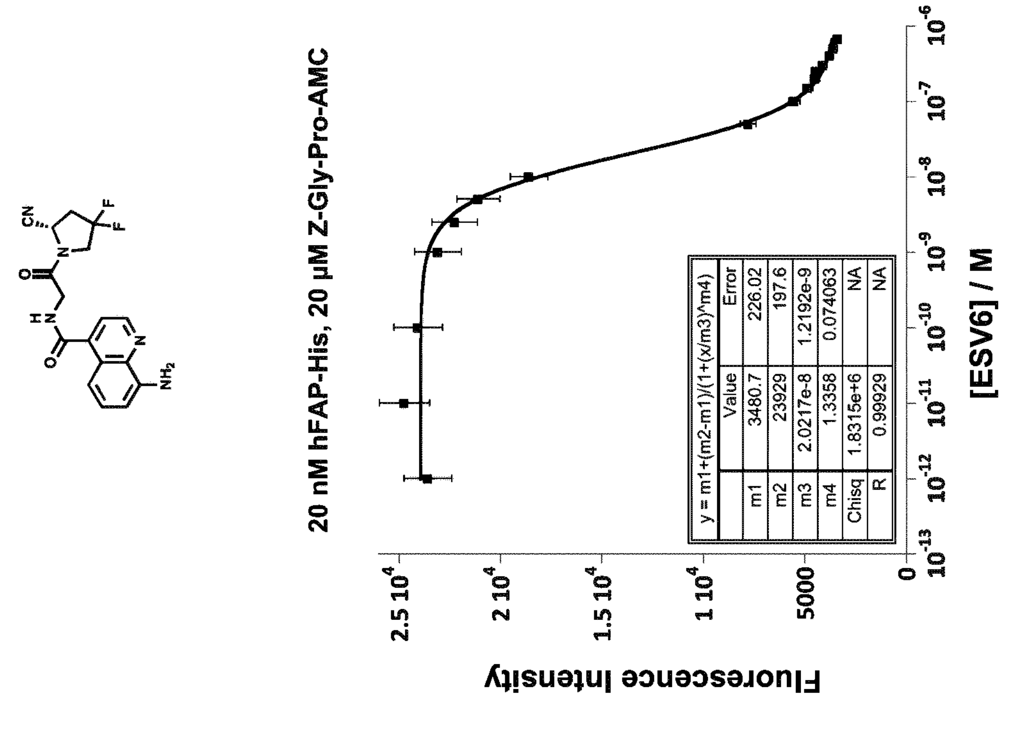
FIG. 5: hFAP inhibition experiment in the presence of small organic ligands. ESV6 ligand (P3) displays a lower IC50 (20.2 nM) compared to the previously described ligand, Haberkorn ligand (H6) (24.6 nM).
Figure 5:
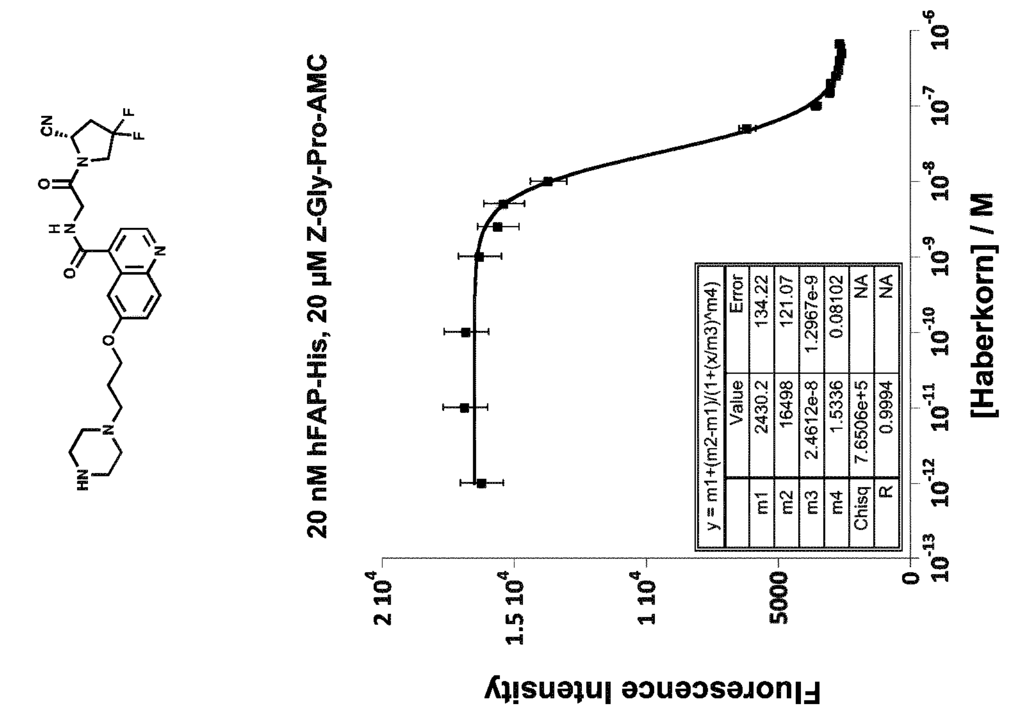

In Vitro Human FAP Enzyme IC50 Assay (FIG. 5)

Enzymatic activity of human FAP on the Z-Gly-Pro-AMC substrate was measured at room temperature on a microtiter plate reader, monitoring the fluorescence at an excitation wavelength of 360 nm and an emission wavelength of 465 nm. The reaction mixture contained 20 μM substrate, 20 nM human FAP, assay buffer (50 mM Tris, 100 mM NaCl, 1 mM EDTA, pH=7.4) and inhibitor (ranging between $10^{-6}$ and $10^{-11}$ M) in a total volume of 30 μL. The $IC_{50}$ value is defined as the concentration of inhibitor required to reduce the enzyme activity by 50% after a 30 min preincubation with the enzyme at 37° C. prior to addition of the substrate.

Inhibitor stock solutions (200 mM) were prepared in DMSO. Immediately prior to the commencement of the experiment, the stocks were further diluted to $10^{-6}$ M in the assay buffer, from which 1:2 serial dilutions were prepared. All measurements were done in triplicate.

FIG. 5 shows results from the hFAP inhibition experiment in the presence of small organic ligands. ESV6 ligand displays a lower IC50 (20.2 nM) compared to the previously described ligand, Haberkorn ligand (24.6 nM).

Figure 3:
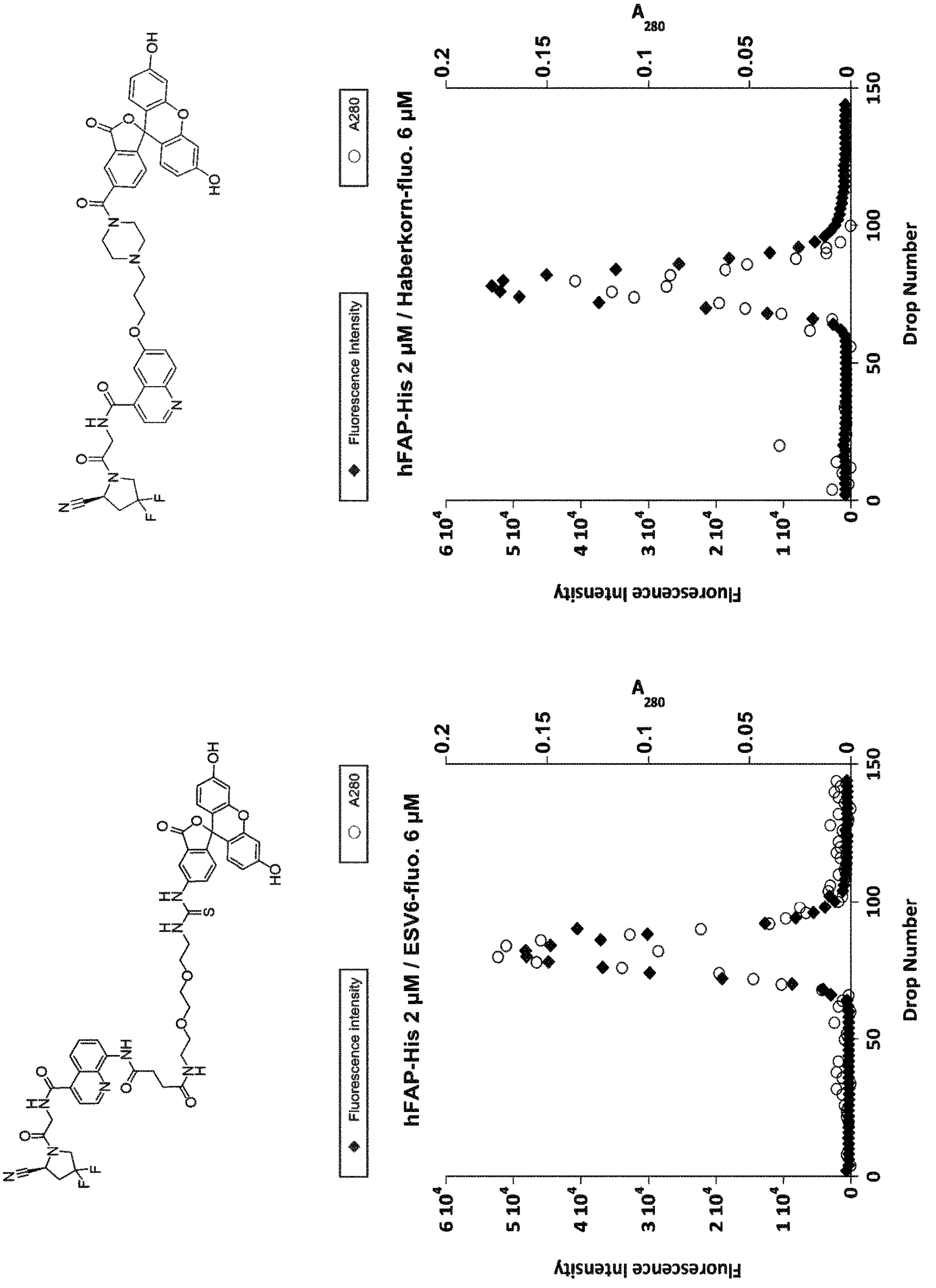
FIG. 3: Co-elution PD-10 experiment of compounds ESV6-fluo (26) and Haberkorn-fluo (23) and hFAP. A stable complex is formed between hFAP and small ligands ESV6-fluo and Haberkorn-fluo.

Chromatographic Co-Elution Experiments of Ligand-Protein Complexes (FIG. 3)

A PD-10 column was pre-equilibrated with assay buffer (50 mM Tris, 100 mM NaCl, 1 mM EDTA, pH=7.4) prior to the loading of the complex. Human FAP (2 μM) and fluorescein-labeled binders (6 μM) were incubated for 30 min at 37° C. in the dark. The mixture was loaded and the column was flushed using the assay buffer. The flow through was collected in 96-well plates and the fluorescence was measured immediately on a TECAN microtiter plate reader, monitoring the fluorescence at an excitation wavelength of 485 nm and an emission wavelength of 535 nm. The protein quantities were estimated by measuring the absorbance at 280 nM using a Nanodrop 2000/2000c spectrophotometer.

FIG. 3 shows results of the co-elution PD-10 experiment of small molecule ligands ESV6-fluo and Haberkorn-fluo and hFAP. A stable complex is formed between hFAP and small ligands ESV6-fluo and Haberkorn-fluo.

Figure 6:
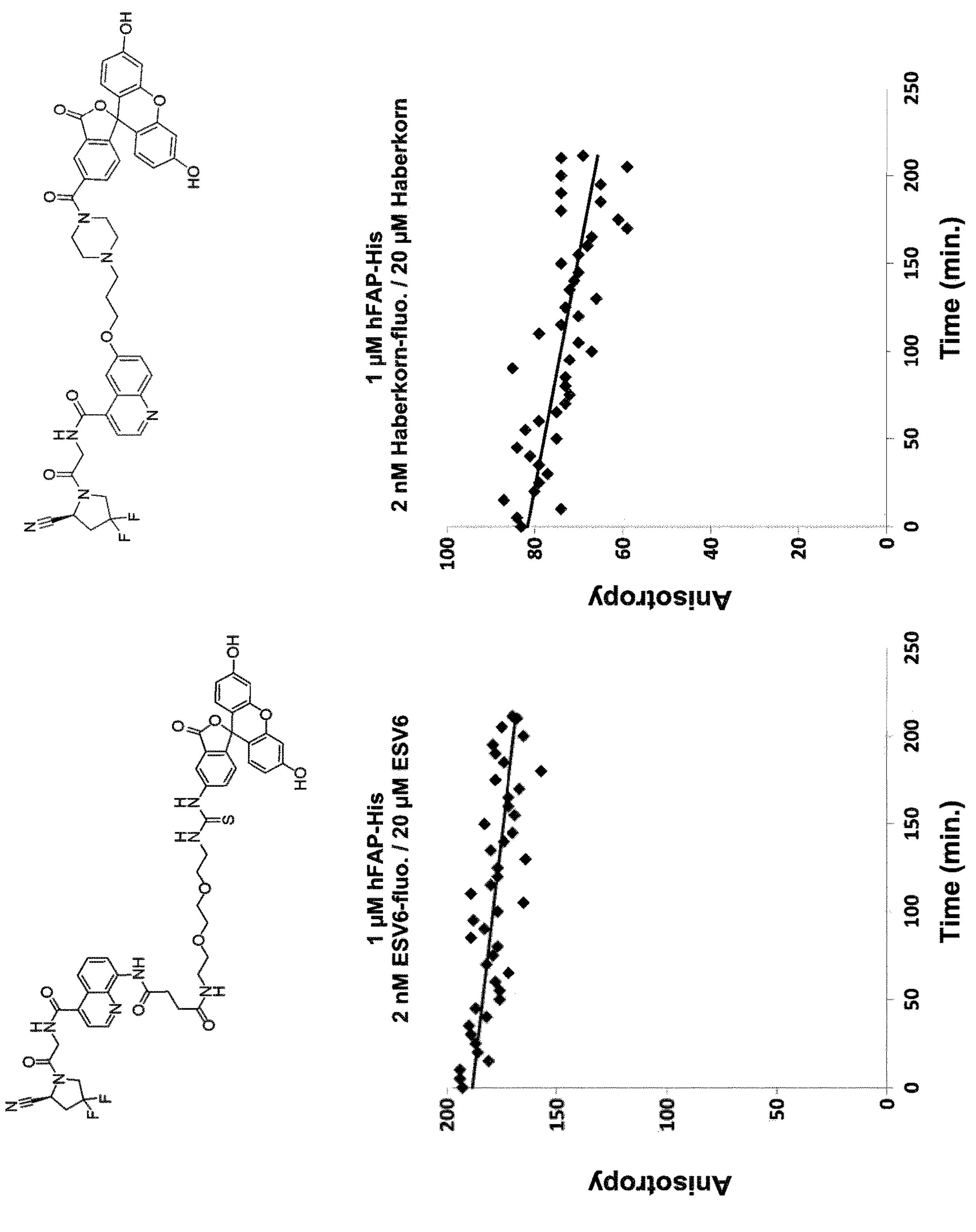
FIG. 6: Dissociation rate measurements of ESV6-fluo (26) and Haberkorn-fluo (23) from hFAP. ESV6-fluo dissociates (regression coefficient=−0.093564) with a slower pace compared to Haberkorn-fluo (regression coefficient=−0.075112).

Dissociation Rate Measurement (FIG. 6)

Fluorescence polarization measurements to determine the $k_{off}$ values were performed in 384-well plates (non-binding, ps, f-bottom, black, high volume, 30 μL final volume). The measurements were carried out after pre-incubation of 2.0 nM fluorescein-labelled binders with human FAP at a constant concentration of 1.0 μM at 37° C. in the dark. The dissociation of the fluorescein-labeled compound was induced by adding a large excess of the corresponding fluorescein-free binders (compound P3 obtained in Step 3 of Example 2 and compound H6 obtained in Step 6 of Comparative Example 1, respectively, each at 20 μM final concentration).

FIG. 6 shows results from the dissociation rate measurements of ESV6-fluo and Haberkorn-fluo from hFAP. ESV6-fluo dissociates (regression coefficient=−0.093564) with a slower pace compared to Haberkorn-fluo (regression coefficient=−0.075112).

The compound of Comparative Example 1 in the present application ("HABERKORN-FLUO") can be considered representative for the disclosure of the prior art, and in particular for the structure of the ligand FAPI-04 described in the prior art (WO 2019/154886 and WO 2019/154859). The above results show that the compounds according to the present invention not only form a stable complex with hFAP, but also surprisingly show a significantly increased affinity (lower $K_D$), increased inhibitory activity (lower $IC_{50}$), and a slower rate of dissociation as compared to the prior art.

Example 4: Comparative experiments in tumour models

PART 1—Preparation of Conjugates

Synthesis of tert-butyl (8-aminoquinoline-4-carbonyl)glycinate

Scheme 3. Synthesis route for preparation Synthesis of tert-butyl (8-aminoquinoline-4-carbonyl)glycinate

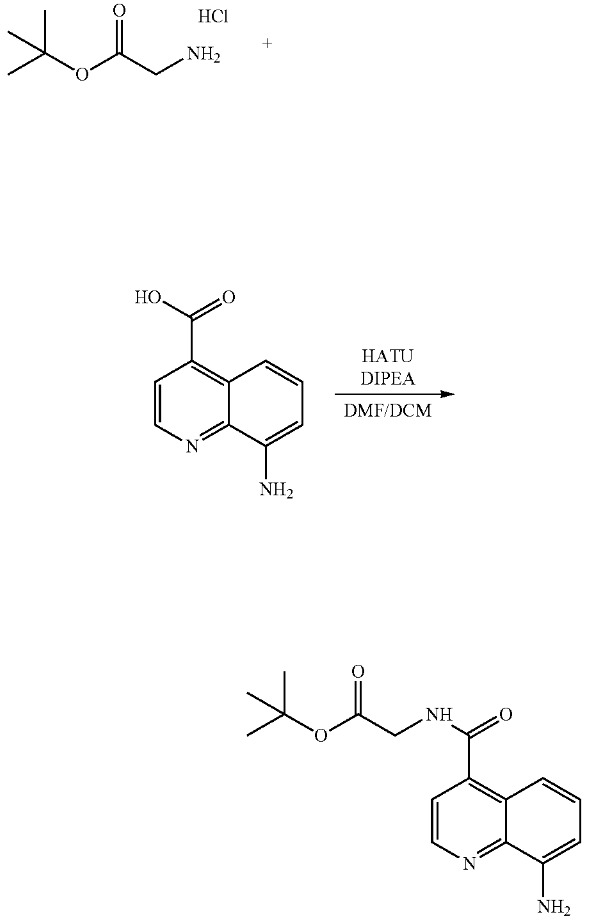

DIPEA (185 μL, 1.063 mmol, 4 eq) was added dropwise to a stirred solution of tert-butyl glycinate hydrochloride (89 mg, 0.532 mmol, 2.0 eq), 8-aminoquinoline-4-carboxylic acid (50 mg, 0.266 mmol, 0.1 eq) and HATU (111 mg, 0.292 mmol, 1.1 eq) in 300 μL of DMF and 3 mL of DCM. The reaction mixture was stirred at room temperature for 1 h. The mixture was concentrated under vacuum and the crude material was directly purified by flash chromatography (DMC/MeOH from 100% to 9.5:0.5) to yield tert-butyl (8-aminoquinoline-4-carbonyl)glycinate as brown oil (70 mg, 0.232 mmol, 87.5%). MS($ES^+$) m/z 302.14 $(M+H)^+$

Synthesis of 4-((4-((2-(tert-butoxy)-2-oxoethyl)carbamoyl)quinolin-8-yl)amino)-4-oxobutanoic acid Scheme 4. Synthesis route for preparation of 4-((4-((2-(tert-butoxy)-2-oxoethyl)carbamoyl)quinolin-8-yl)amino)-4-oxobutanoic acid

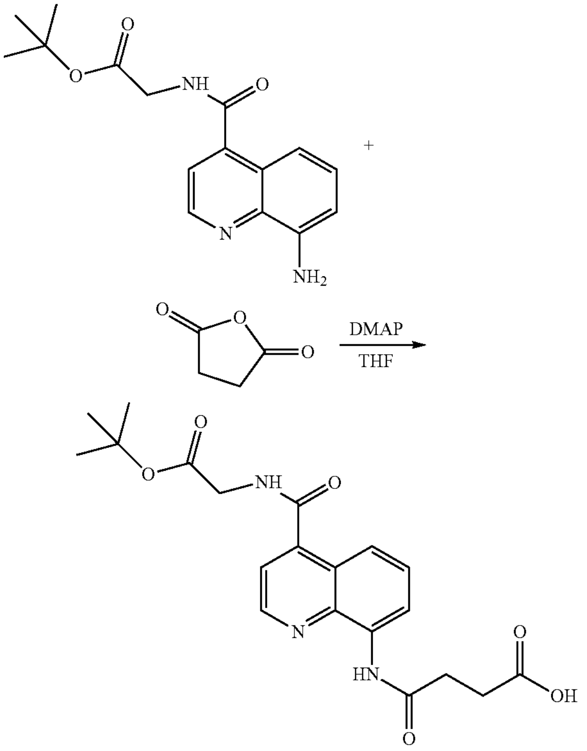

4-dimethylaminopyridine (14 mg, 0.116 mmol, 0.5 eq) was added to a stirred solution of tert-butyl (8-aminoquinoline-4-carbonyl)glycinate (70 mg, 0.232 mmol, 1.0 eq) and dihydrofuran-2,5-dione (232 mg, 2.324 mmol, 10.0 eq) in THF (3 mL). The reaction was heated at 50° C. for 6 h. The mixture was concentrated under vacuum, diluted in DCM and washed with water. The organic phase was concentrated under vacuum and purified by flash chromatography (DMC/MeOH from 9:1 to 7:3) to give compound as brown oil (50 mg, 0.125 mmol, 83.3%). MS($ES^+$) m/z 402.16 $(M+H)^+$

Synthesis of on-resin Cys(STrt)-Asp(OtBu)-Lys(NHBoc)-Asp(OtBu)-NHFmoc

Scheme 5. Synthesis route for preparation of on-resin Cys(STrt)-Asp(OtBu)-Lys(NHBoc)-Asp(OtBu)-NHFmoc

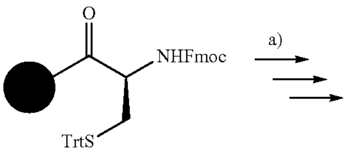

-continued

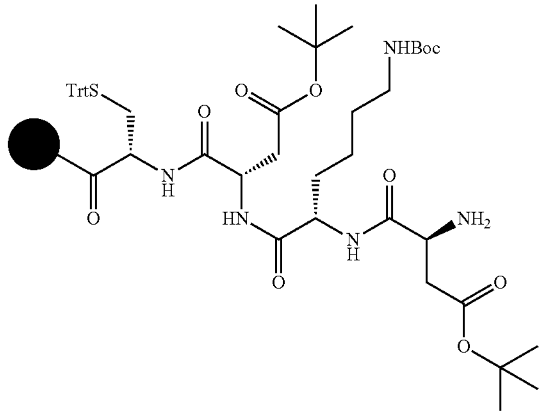

Commercially available pre-loaded Fmoc-Cys(Trt) on Tentagel resin (500 mg, 0.415 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide was extended with Fmoc-Asp(tBu)-OH, Fmoc-Lys(NHBoc)-OH and Fmoc-Asp(tBu)-OH in the indicated order. For this purpose, the Fmoc protected amino acid (2.0 eq), HBTU (2.0 eq), HOBt (2.0 eq) and DIPEA (4.0 eq) were dissolved in DMF (5 mL). The mixture was allowed to stand for 10 min at 0° C. and then reacted with the resin for 1 h under gentle agitation. After washing with DMF (6×1 min×5 mL) the Fmoc group was removed with 20% piperidine in DMF (1×1 min×5 min and 2×10 min×5 mL). Deprotection steps were followed by wash steps with DMF (6×1 min×5 mL) prior to coupling with the next aminoacid.

Synthesis of (2R,5S,8S,11R)-8-(4-aminobutyl)-5,11-bis(carboxymethyl)-16-((4-((carboxymethyl)carbamoyl)quinolin-8-yl)amino)-2-(mercaptomethyl)-4,7,10,13,16-pentaoxo-3,6,9,12-tetraazahexadecanoic acid Scheme 6. Synthesis route for preparation of (2R,5S,8S,11R)-8-(4-aminobutyl)-5,11-bis(carboxymethyl)-16-((4-((carboxymethyl)carbamoyl) quinolin-8-yl)amino)-2-(mercaptomethyl)-4,7,10,13,16-pentaoxo-3,6,9,12-tetraazahexadecanoic acid (SH-Cys-Asp-Lys-Asp-QCOOH)

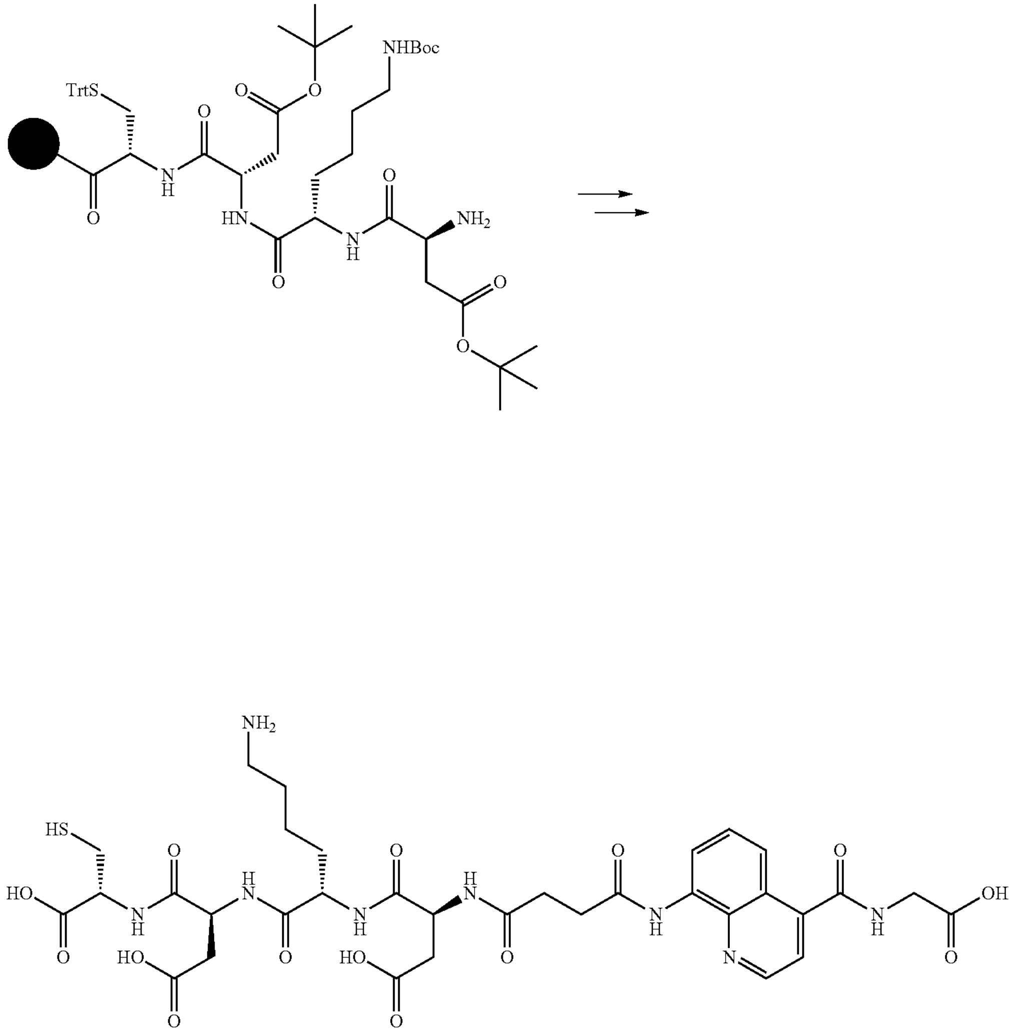

On-resin Cys(STrt)-Asp(OtBu)-Lys(NHTBoc)-Asp (OtBu)-NHFmoc (50 mg, 0.025 mmol) was swollen in DMF (3×5 min×5 mL). The peptide was extended with 4-((4-((2-(tert-butoxy)-2-oxoethyl)carbamoyl)quinolin-8-yl)amino)-4-oxobutanoic acid (20 mg, 0.05 mmol, 2.0 eq), HATU (19 mg, 0.05 mmol, 2.0 eq), and DIPEA (17 µL, 0.1 mmol, 4.0 eq) and let react for 1 h under gentle agitation. After washing with DMF (6×1 min×5 mL), the compound was cleaved by agitating the resin with a mixture of TFA (15%), TIS (2.5%) and H2O (2.5%) in DCM for 4 h at room temperature. The resin was washed with methanol (2×5 mL) and the combined cleavage and washing solutions concentrated under vacuum. The crude product was purified by reversed-phase HPLC (Water 0.1% TFA/Acetonitrile 0.1% TFA 9.5:0.5 to 2:8 in 20 min) and lyophilized, to obtain a white solid (2.4 mg, 0.003 mmol, 12%). MS($ES^+$) m/z 807.45 $(M+H)^+$

Synthesis of (2R,5S,8S,11S)-8-(4-aminobutyl)-5,11-bis(carboxymethyl)-16-(4-(3-((4-((2-((S)-2-cyano-4,4-difluoropyrrolidin-1-yl)-2-oxoethyl)carbamoyl)quinolin-6-yl)oxy)propyl)piperazin-1-yl)-2-(mercaptomethyl)-4,7,10,13,16-pentaoxo-3,6,9,12-tetraazahexadecanoic acid Scheme 7. Synthesis route for preparation of (2R,5S,8S,11R)-8-(4-aminobutyl)-5,11-bis(carboxymethyl)-16-(4-(3-((4-((2-((S)-2-cyano-4,4-difluoropyrrolidin-1-yl)-2-oxoethyl)carbamoyl)quinolin-6-yl)oxy)propyl)piperazin-1-yl)-2-(mercaptomethyl)-4,7,10,13,16-pentaoxo-3,6,9,12-tetraazahexadecanoic acid (SH-Cys-Asp-Lys-Asp-HK)

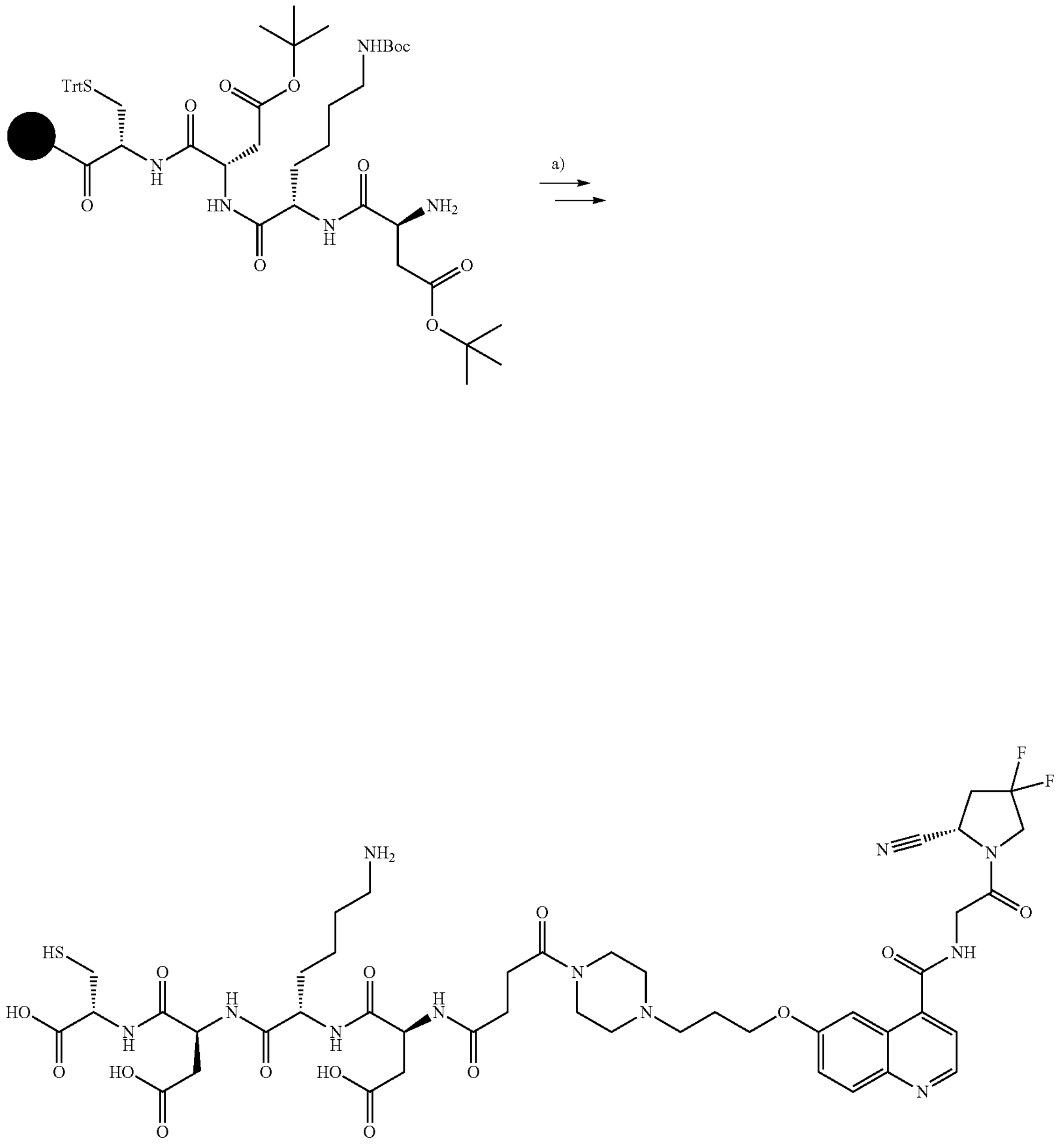

On-resin Cys(STrt)-Asp(OtBu)-Lys(NHBoc)-Asp (OtBu)-NHFmoc (60 mg, 0.03 mmol) was swollen in DMF (3×5 min×5 mL). The peptide was extended with (S)-4-(4-(3-((4-((2-(2-cyano-4,4-difluoropyrrolidin-1-yl)-2-oxo-ethyl)carbamoyl)quinolin-6-yl)oxy)propyl)piperazin-1-yl)-4-oxobutanoic acid (17.5 mg, 0.03 mmol, 1.0 eq), HATU (22 mg, 0.06 mmol, 2.0 eq), and DIPEA (200 μL, 1.2 mmol, 40 eq) and let react for 1 h under gentle agitation. After washing with DMF (6×1 min×5 mL), the compound was cleaved by agitating the resin with a mixture of TFA (15%), TIS (2.5%) and H2O (2.5%) in DCM for 4 h at room temperature. The resin was washed with methanol (2×5 mL) and the combined cleavage and washing solutions concentrated under vacuum. The crude product was purified by reversed-phase HPLC (Water 0.1% TFA/Acetonitrile 0.1% TFA 9.5:0.5 to 2:8 in 20 min) and lyophilized, to obtain a white solid (1 mg, 0.95 μmol, 0.3%). MS(ES$^+$) m/z 1048.39 (M+H)$^+$ Synthesis of (2R,5S,8S,11S)-8-(4-aminobutyl)-5,11-bis(carboxymethyl)-16-((4-((2-((S)-2-cyano-4,4-difluoropyrrolidin-1-yl)-2-oxoethyl)carbamoyl)quinolin-8-yl)amino)-2-(mercaptomethyl)-4,7,10,13,16-pentaoxo-3,6,9,12-tetraazahexadecanoic acid Scheme 8. Synthesis route for preparation of (2R,5S,8S,11R)-8-(4-aminobutyl)-5,11-bis(carboxymethyl)-16-((4-((2-((S)-2-cyano-4,4-difluoropyrrolidin-1-yl)-2-oxoethyl)carbamoyl)quinolin-8-yl)amino)-2-(mercaptomethyl)-4,7,10,13,16-pentaoxo-3,6,9,12-tetaazahexadecanoic acid (SH-Cys-Asp-Lys-Asp-ESV6)

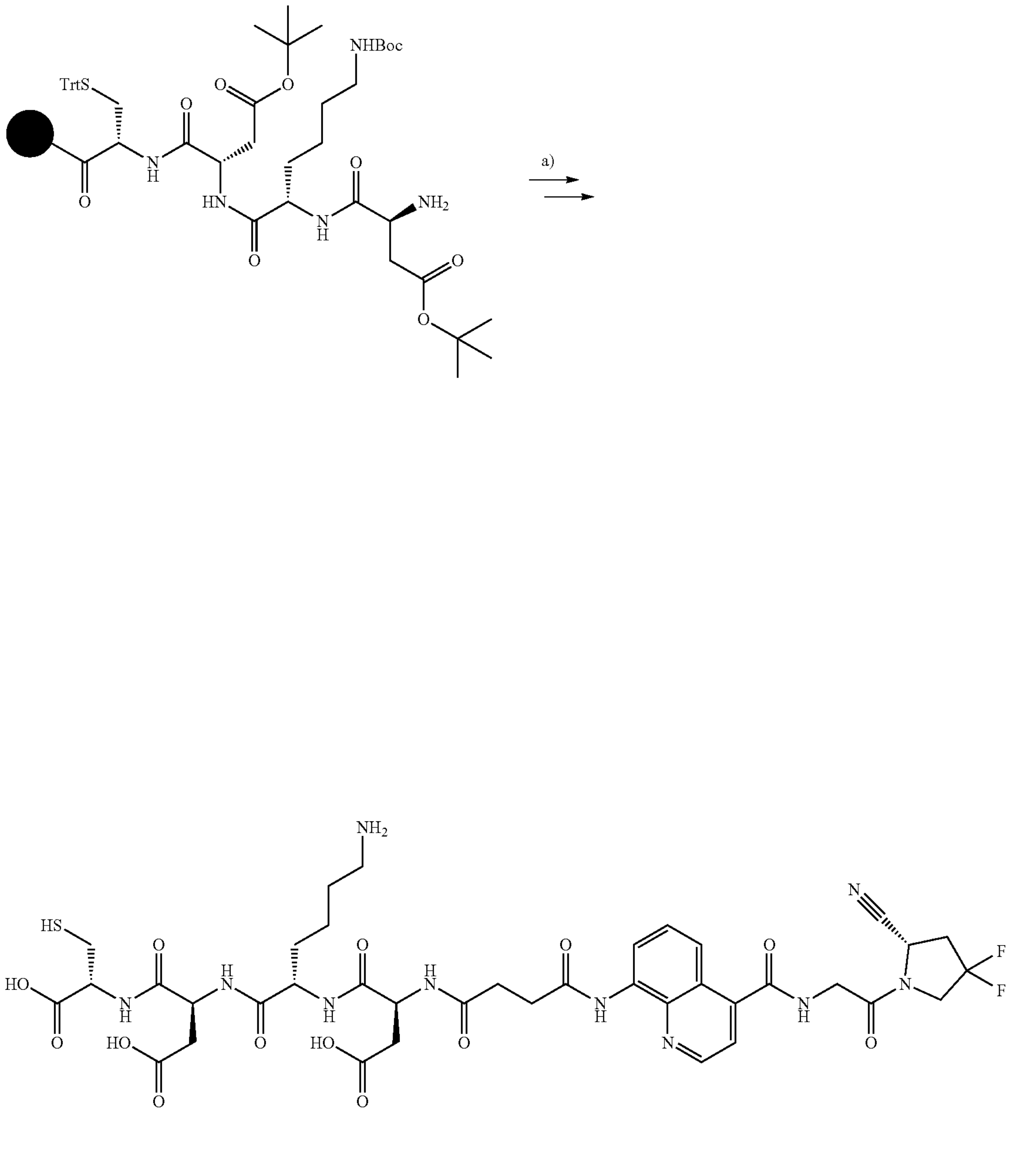

On-resin Cys(STrt)-Asp(OtBu)-Lys(NHBoc)-Asp(OtBu)-NHFmoc (80 mg, 0.04 mmol) was swollen in DMF (3×5 min×5 mL). The peptide was extended with (S)-4-((4-((2-(2-cyano-4,4-difluoropyrrolidin-1-yl)-2-oxoethyl)carbamoyl)quinolin-8-yl)amino)-4-oxobutanoic acid (37 mg, 0.08 mmol, 2 eq), HATU (30 mg, 0.08 mmol, 2.0 eq), and DIPEA (28 μL, 0.16 mmol, 4.0 eq) and let react for 1 h under gentle agitation. After washing with DMF (6×1 min×5 mL), the compound was cleaved by agitating the resin with a mixture of TFA (15%), TIS (2.5%) and H2O (2.5%) in DCM for 4 h at room temperature. The resin was washed with methanol (2×5 mL) and the combined cleavage and washing solutions concentrated under vacuum. The crude product was purified by reversed-phase HPLC (Water 0.1% TFA/Acetonitrile 0.1% TFA 9.5:0.5 to 2:8 in 20 min) and lyophilized, to obtain a white solid (1 mg, 0.95 μmol, 0.3%). MS(ES$^+$) m/z 921.29 $(M+H)^+$ Synthesis of "QCOOH-IRDye750"

SH-Cys-Asp-Lys-Asp-QCOOH (140 μg, 0.174 μmol, 1.0 eq) was dissolved in PBS pH 7.4 (800 μL). IRDye750 maleimide (200 μg, 0.174 μmol, 1.0 eq) was added as dry DMF solution (200 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a green solid (0.06 μmol, 40%). MS(ES$^+$) m/z 978 $(M+2H)^{2+}$

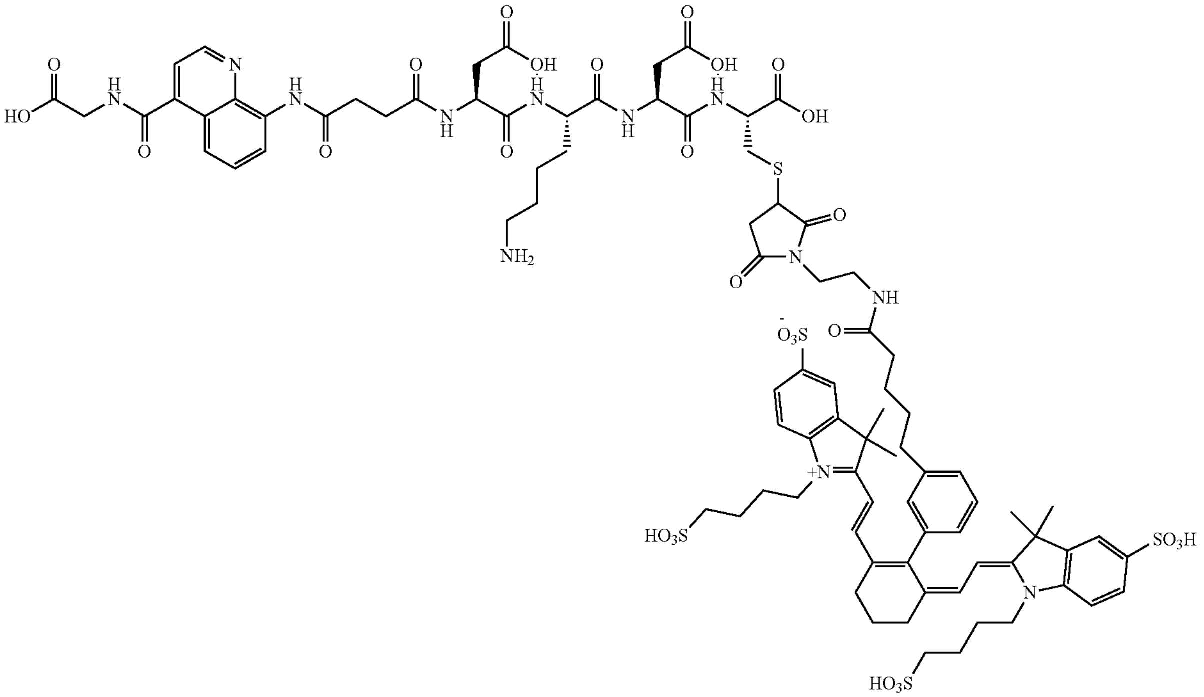

Conjugate 16: Structure of "QCOOH-IRDye750"

Synthesis of "HABERKORN-IRDye750"

SH-Cys-Asp-Lys-Asp-HK (181 μg, 0.174 μmol, 1.0 eq) was dissolved in PBS pH 7.4 (800 μL). IRDye750 maleimide (200 g, 0.174 μmol, 1.0 eq) was added as dry DMF solution (200 μL). The reaction was stirred for 3 h. The crude material was purified by reversed-phase HPLC (Water 0.11% TFA/Acetonitrile 0.1% TFA 9.5:0.5 to 2:8 in 20 min) and lyophilized, to obtain a green solid (0.06 μmol, 40%). MS($ES^+$) m/z 1099.8 $(M+2H)^{2+}$

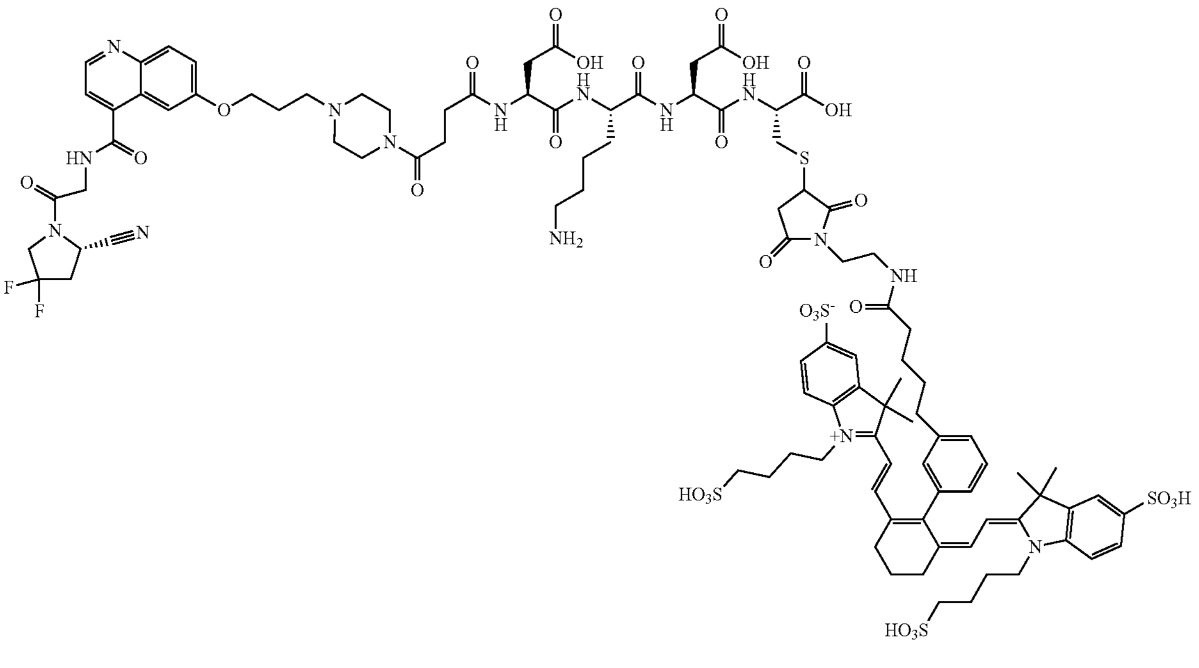

Conjugate 17: Structure of "HABERKORN-IRDye750"

Synthesis of ESV6-IRDye750

SH-Cys-Asp-Lys-Asp-ESV6 (160 μg, 0.174 μmol, 1.0 eq) was dissolved in PBS pH 7.4 (800 μL). IRDye750 maleimide (200 μg, 0.174 μmol, 1.0 eq) was added as dry DMF solution (200 μL). The reaction was stirred for 3 h. The crude material was purified by reversed-phase HPLC (Water 0.10% TFA/Acetonitrile 0.1% TFA 9.5:0.5 to 2:8 in 20 min) and lyophilized, to obtain a green solid (0.08 μmol, 50%). MS($ES^+$) m/z 1036.3 $(M+2H)^{2+}$

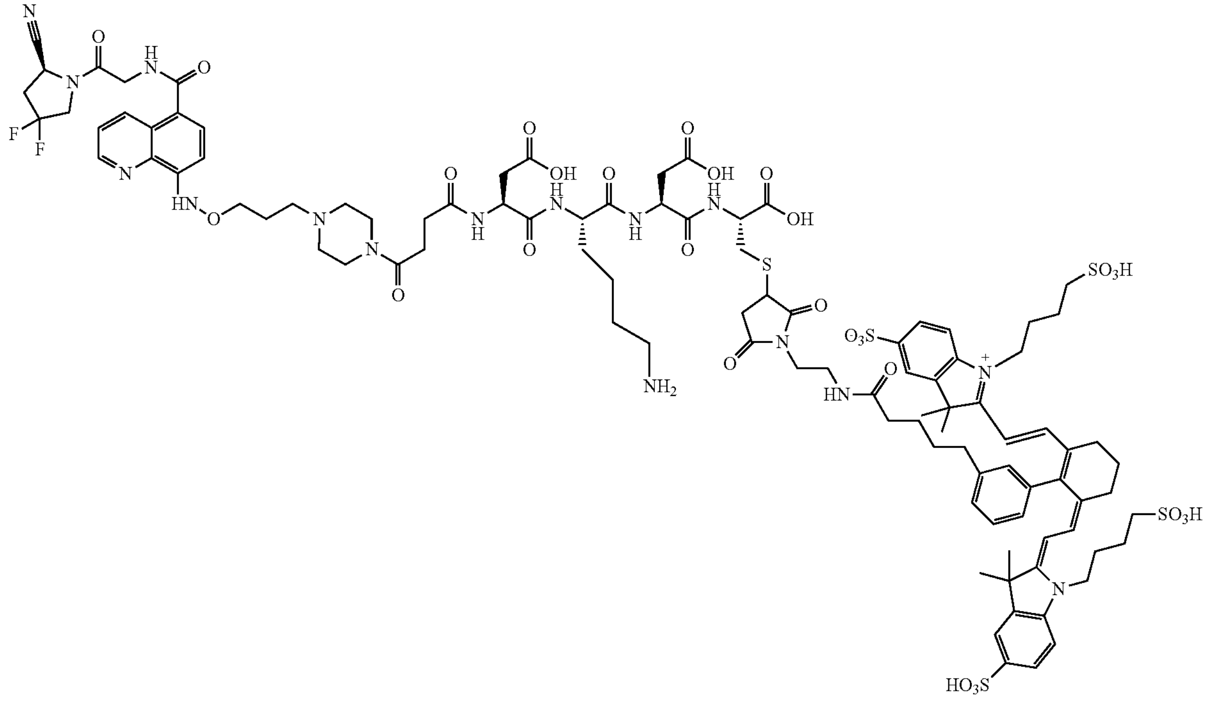

Conjugate 18: Structure of ESV6-IRDye750

Synthesis of "QCOOH-ValCit-MMAE"

SH-Cys-Asp-Lys-Asp-QCOOH (612 μg, 0.760 μmol, 1.0 eq) was dissolved in PBS pH 7.4 (840 μL). MC-ValCit-PAB-MMAE (1000 μg, 0.760 μmol, 1.0 eq) was added as dry DMF solution (160 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a white solid (322 μg, 20%). MS(ES$^+$) m/z 2124.03 $(M+H)^+$

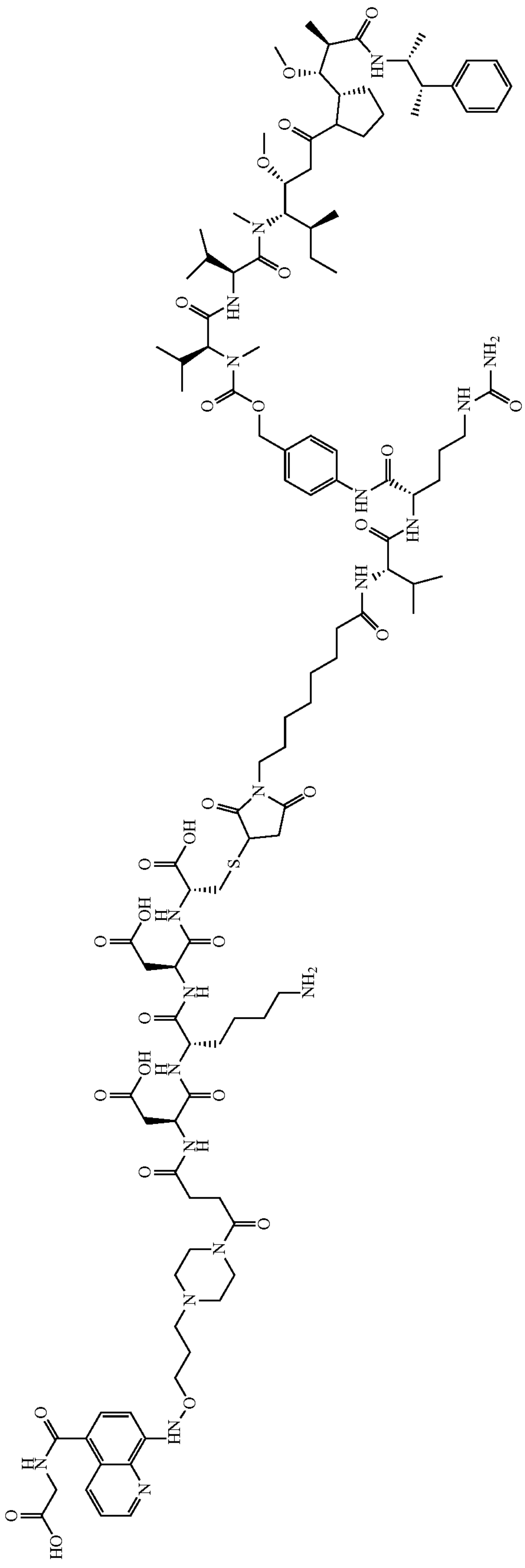

Conjugate 19: Structure of "QCOOH-ValCit-MMAE"

Synthesis of "HABERKORN-ValCit-MMAE"

SH-Cys-Asp-Lys-Asp-HK (795 μg, 0.760 μmol, 1.0 eq) was dissolved in PBS pH 7.4 (840 μL). MC-ValCit-PAB-MMAE (1000 μg, 0.760 μmol, 1.0 eq) was added as dry DMF solution (160 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a white solid (322 μg, 20%). MS($ES^+$) m/z 2364.18 $(M+H)^+$

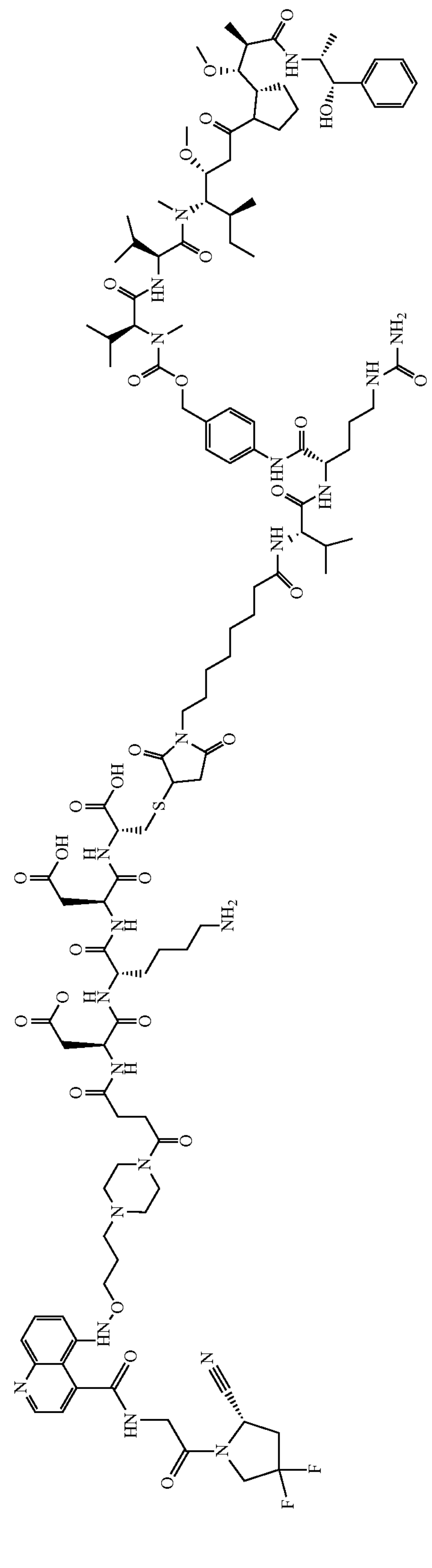

Conjugate 20: Structure of "HABERKORN-ValCit-MMAE"

Synthesis of "ESV6-ValCit-MMAE"

SH-Cys-Asp-Lys-Asp-ESV6 (700 μg, 0.760 μmol, 1.0 eq) was dissolved in PBS pH 7.4 (840 μL). MC-ValCit-PAB-MMAE (1000 g, 0.760 μmol, 1.0 eq) was added as dry DMF solution (160 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a white solid (322 μg, 20%). MS($ES^+$) m/z 2236.07 $(M+H)^+$

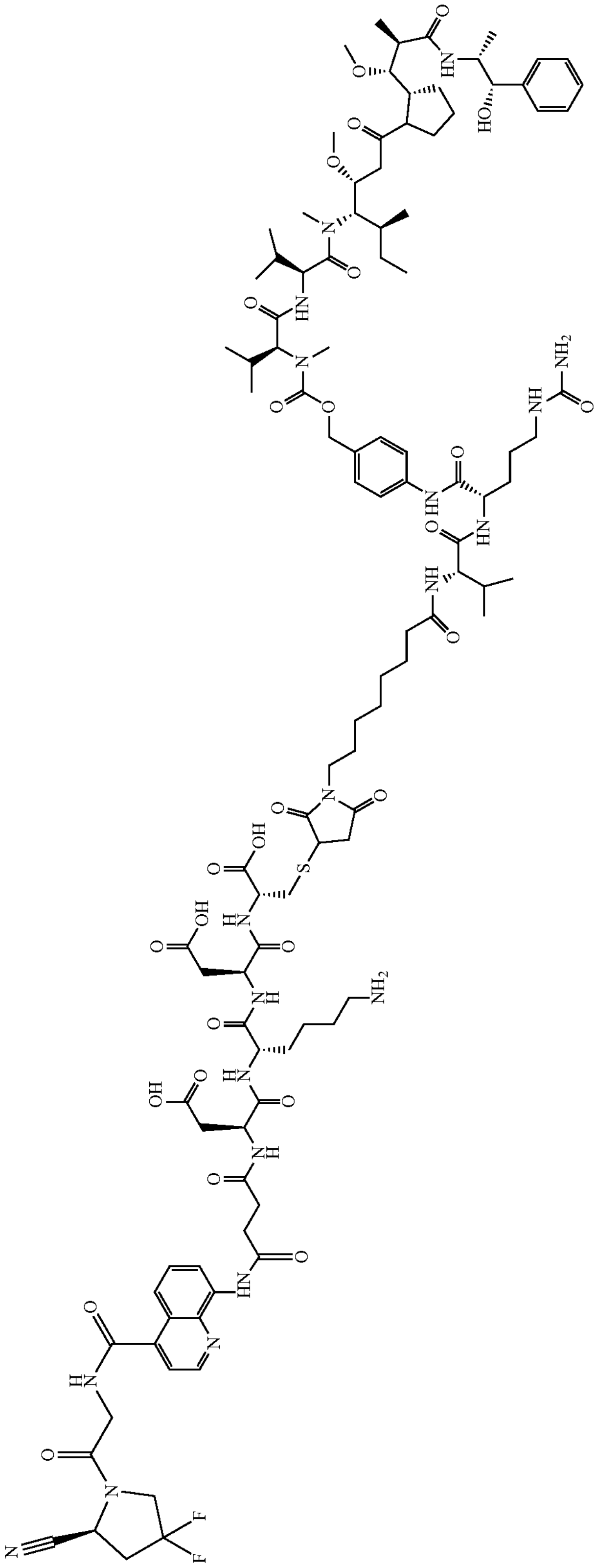

Conjugate 21: Structure of "ESV6-ValCit-MMAE"

FIG. 26 shows structure, chromatographic profile and LC/MS analysis of ESV6-ValCit-MMAE (21). MS($ES^+$) m/z 1118.05 $(M+2H)^{2+}$.

PART 2—Animal Experiments

Tumour Cells Preparation

Upon thawing, SK-MEL-187 tumour cells were kept in culture in RPMI medium supplemented with fetal bovine serum (10%, FBS) and Antibiotic-Antimycotic (1%, AA) at 37° C. and 5% $CO_2$. For passaging, cells were detached using Trypsin-EDTA 0.05% when reaching 90% confluence and re-seeded at a dilution of 1:4.

IVIS Experiments

SK-MEL-187 xenografted tumours were implanted into female athymic BALB/C nu/nu mice (6-8 weeks of age) as described above, and allowed to grow to an average volume of 0.1 mL. Mice bearing subcutaneous SK-MEL-187 tumours were injected intravenously with ESV6-IRDye750, HABERKORN-IRDye750 or QCOOH-IRDye750 (150 nmol/Kg, as 30 μM solutions prepared in sterile PBS, pH 7.4). Mice were anesthetized with isoflurane and fluorescence images acquired on an IVIS Spectrum imaging system (Xenogen, exposure Is, binning factor 8, excitation at 745 nm, emission filter at 800 nm, f number 2, field of view 13.1). Images were taken 5 min, 20 min and 1 h after the injection. Food and water were given ad libitum during that period. Mice were subsequently sacrificed by $CO_2$ asphyxiation (2 h time point). Blood, heart, lung, kidneys, liver, spleen, stomach, a section of the intestine and the SK-MEL-187 tumour were collected and imaged individually using the abovementioned parameters (FIG. 7).

Figure 7:
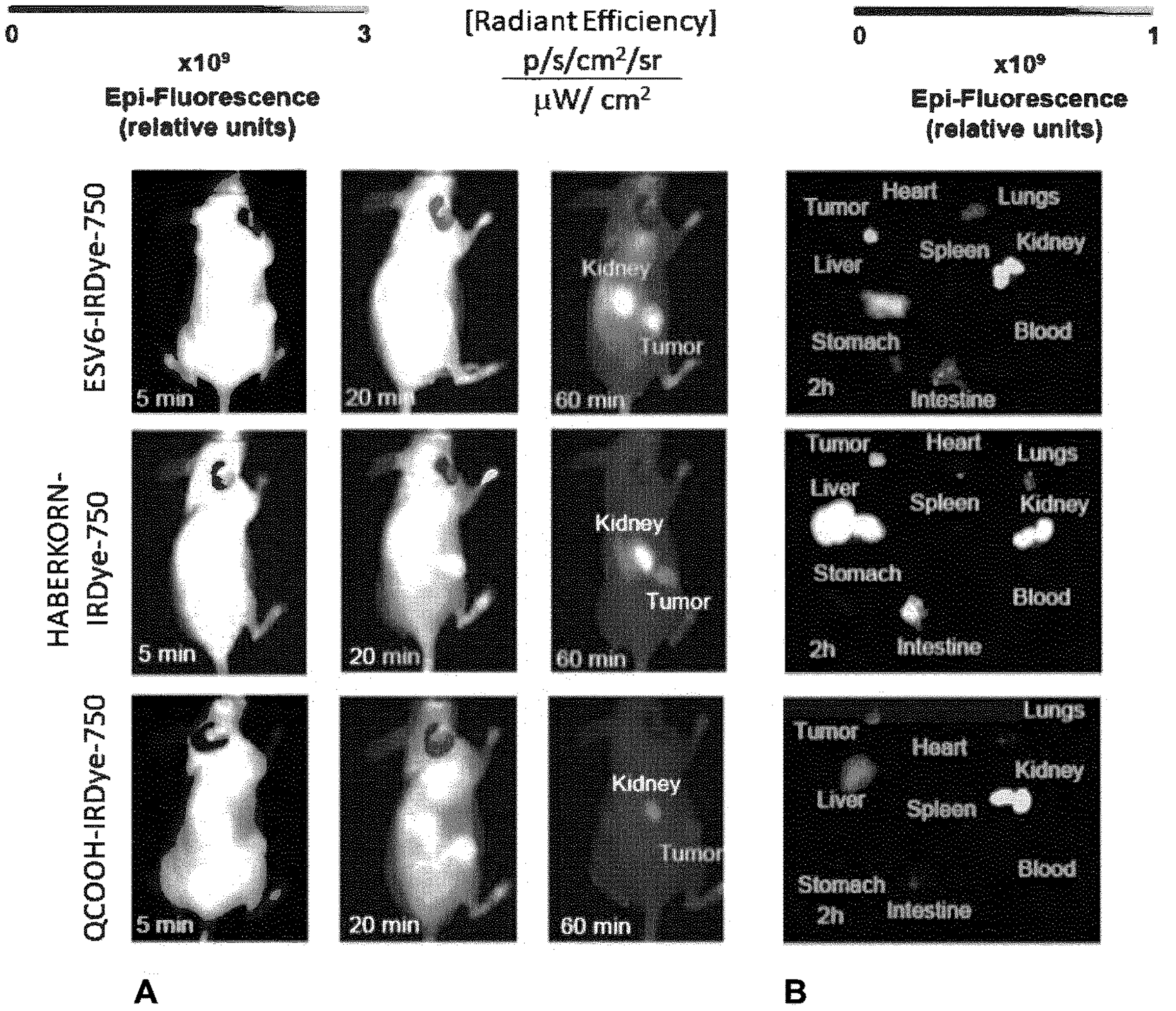
FIG. 7: Evaluation of targeting performance of IRDye 750 conjugates in near-infrared fluorescence imaging of BALB/C nu/nu mice bearing SK-MEL-187 melanoma xenografts after intravenous administration (dose of 150 nmol/Kg). (A) Images of live animals at various time points (5 min, 20 min and 1 h after injection). (B) Ex vivo organ images at 2 h are presented. Compound ESV6-IRDye750 (18), a derivative of the high-affinity FAP ligand "ESV6", displays a higher tumour-to-liver, tumour-to-kidney and tumour-to-intestine uptake ratio as compared to HABERKORN-IRDye750 (17). QCOOH-IRDye750 (16) (untargeted control) does not localize to SK-MEL-187 lesions in vivo.
Figure 7:
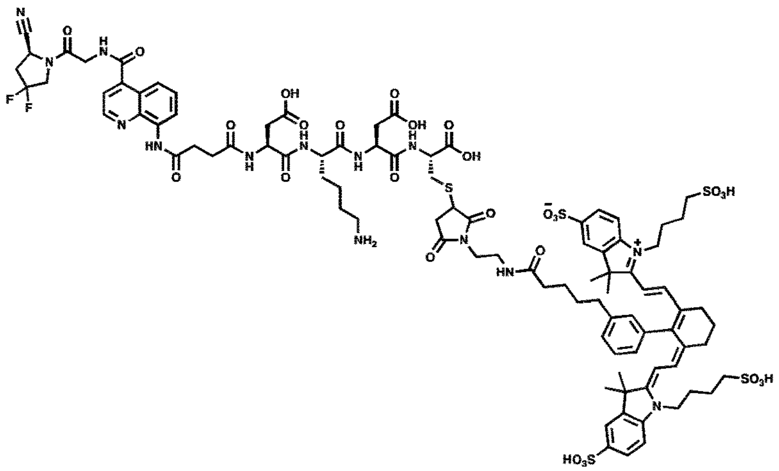
Figure 7:
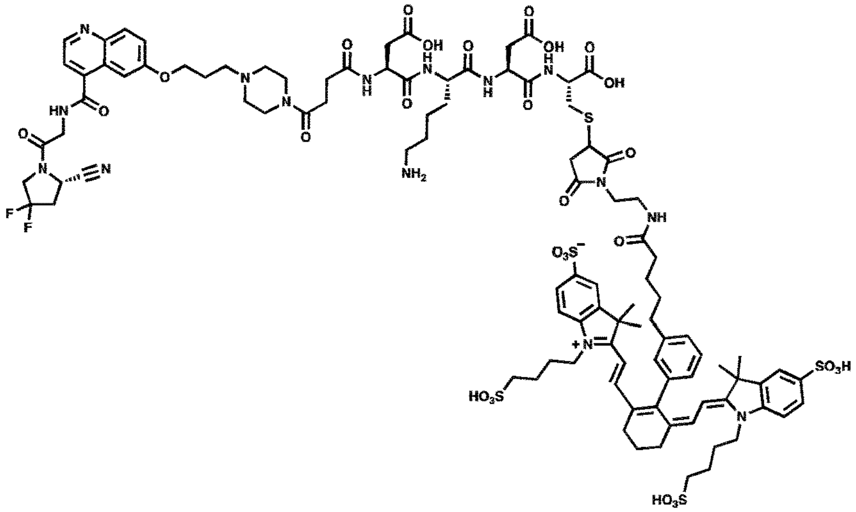
Figure 7:
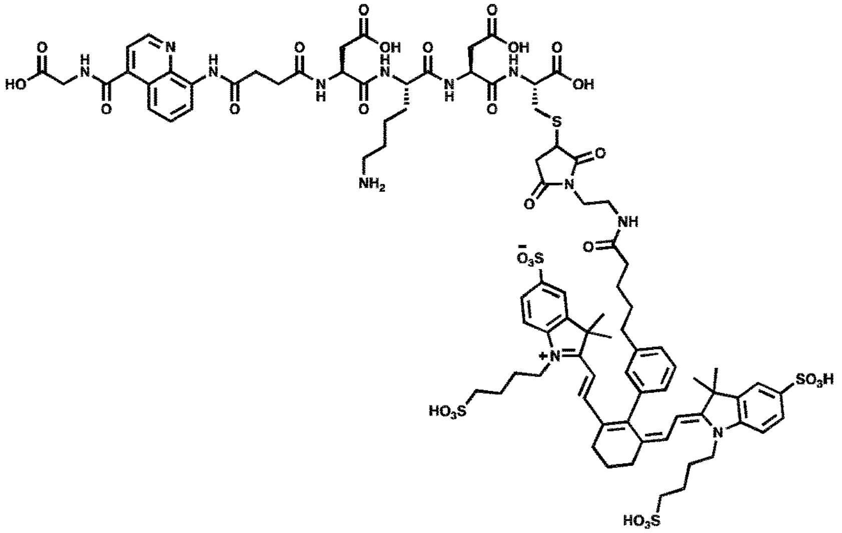

Specifically, FIG. 7 shows evaluation of targeting performance of IRDye 750 conjugates in near-infrared fluorescence imaging of BALB/C nu/nu mice bearing SK-MEL-187 melanoma xenografts after intravenous administration (dose of 150 nmol/Kg): (A) images of live animals at various time points (5 min, 20 min and 1 h after injection); (B) ex vivo organ images at 2 h are presented. Compound ESV6-IRDye750, a derivative of the high-affinity FAP ligand "ESV6", displays a higher tumour-to-liver, tumour-to-kidney and tumour-to-intestine uptake ratio as compared to HABERKORN-IRDye750. QCOOH-IRDye750 (untargeted control) does not localize to SK-MEL-187 lesions in vivo.

Therapy Experiments

Figure 8:
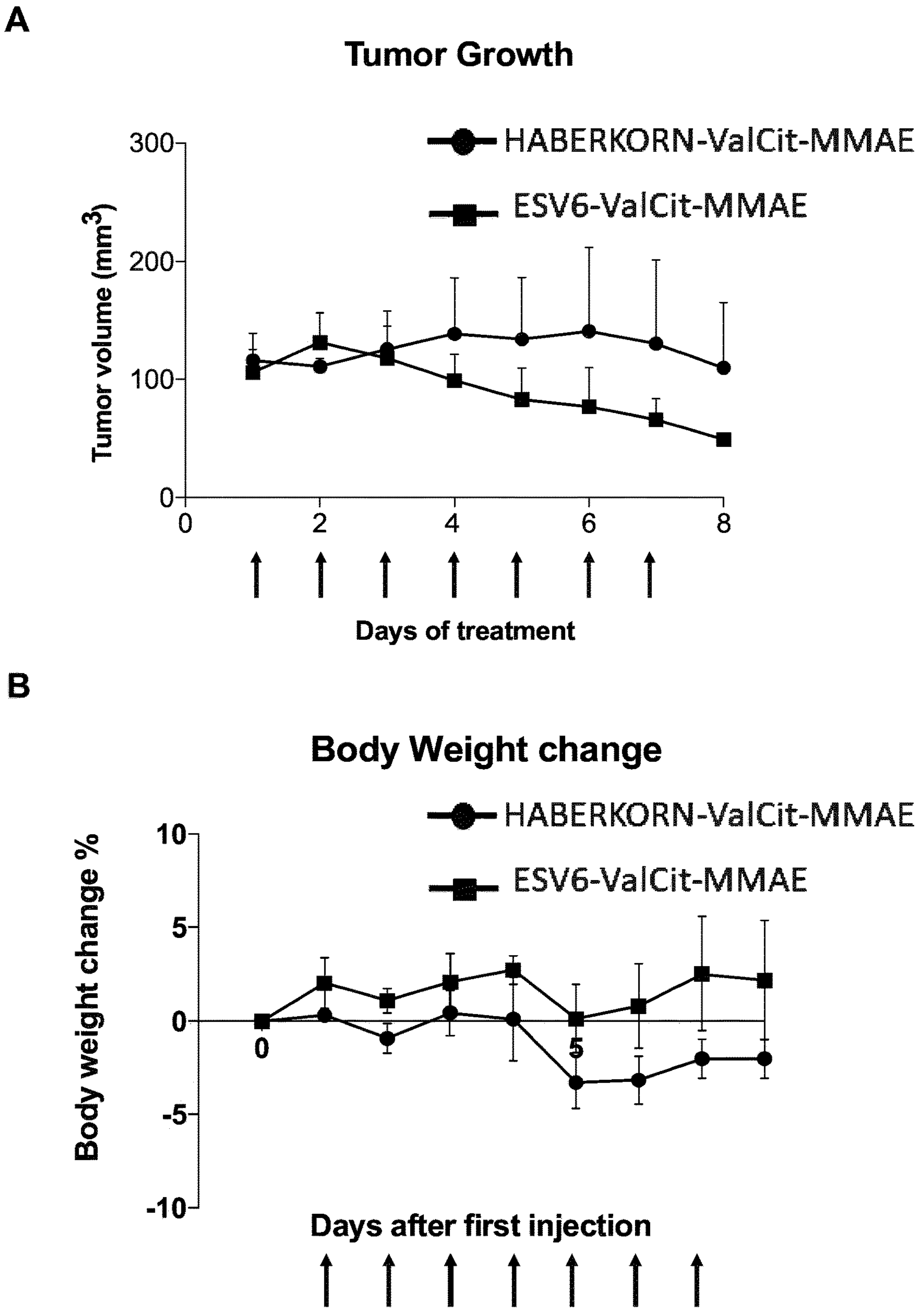
FIG. 8: (A) Assessment of therapeutic activity of ESV6-ValCit-MMAE (21) and HABERKORN-ValCit-MMAE (20) in SK-MEL-187 tumour bearing mice. Data points represent mean tumour volume f SEM (n=3 per group). Arrows indicate IV infection of the different treatments. ESV6-ValCit-MMAE, a drug conjugate derivative of the high-affinity FAP ligand "ESV6", displays a more potent anti-tumour effect as compared with HABERKORN-ValCit-MMAE. (B) Tolerability of the different treatments as assessed by the evaluation of changes (%) in body weight of the animals during the experiment. ESV6-ValCit-MMAE displays a lower acute toxicity as compared to HABERKORN-ValCit-MMAE.
Figure 8:
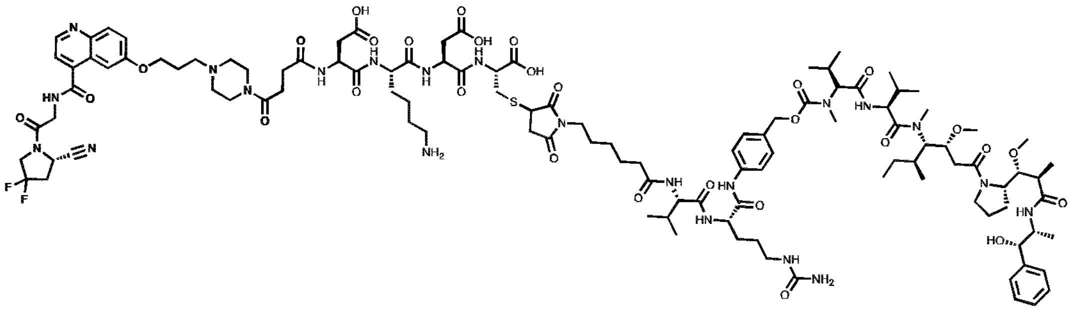
Figure 8:
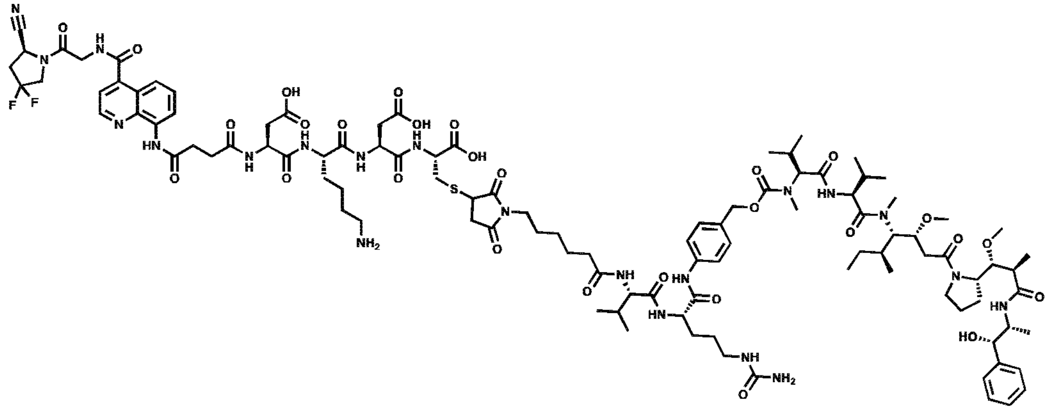

SK-MEL-187 xenografted tumours were implanted into female athymic BALB/C nu/nu mice (6-8 weeks of age) as described above, and allowed to grow to an average volume of 0.1 mL. Mice were randomly assigned into therapy groups of 3 animals. HABERKORN-ValCit-MMAE (250 nmol/kg) and ESV6-ValCit-MMAE (250 nmol/kg) were injected daily as sterile PBS solution with 1% of DMSO for 7 consecutive days. Tumours were measured with an electronic caliper and animals were weighted daily. Tumour volume ($mm^3$) was calculated with the formula (long side, mm)×(short side, mm)×(short side, mm)×0.5 (FIG. 8). Prism 6 software (GraphPad Software) was used for data analysis (regular two-way ANOVA followed by Bonferroni test).

Specifically, FIG. 8 shows assessment of therapeutic activity of ESV6-ValCit-MMAE and HABERKORN-ValCit-MMAE in SK-MEL-187 tumour bearing mice. Data points represent mean tumour volume±SEM (n=3 per group). (A) Arrows indicate IV infection of the different treatments. ESV6-ValCit-MMAE, a drug conjugate derivative of the high-affinity FAP ligand "ESV6", displays a more potent anti-tumour effect as compared with HABERKORN-ValCit-MMAE. (B) Tolerability of the different treatments is shown, as assessed by the evaluation of changes (%) in body weight of the animals during the experiment. ESV6-ValCit-MMAE displays a lower acute toxicity as compared to HABERKORN-ValCit-MMAE.

Example 5: Preparation of Conjugates for Radio-Labeling

Synthesis of "HABERKORN-DOTA"

(S)—N-(2-(2-cyano-4,4-difluoropyrrolidin-1-yl)-2-oxoethyl)-6-(3-(piperazin-1-yl) propoxy)quinoline-4-carboxamide (15 mg, 0.030 mol, 1.0 eq), HATU (13 mg, 0.039 mmol, 1.1 eq) and Tri-tert-butyl 1,4,7,10-Tetraazacyclododecane-1,4,7,10-tetraacetate (19 mg, 0.039 mmol, 1.1 eq) were dissolved in DCM/MDF (800 μL/50 μL). DIPEA (18 μL, 0.101 mmol, 3 eq) was added dropwise and the reaction was stirred at room temperature for 1 h. The crude product was treated with TFA (40%) overnight and purified by reversed-phase HPLC (Water 0.1% TFA/Acetonitrile 0.1% TFA 9.5:0.5 to 2:8 in 20 min) and lyophilized, to obtain a white solid (4 mg, 15%). MS($ES^+$) m/z 873.4 $(M+H)^+$

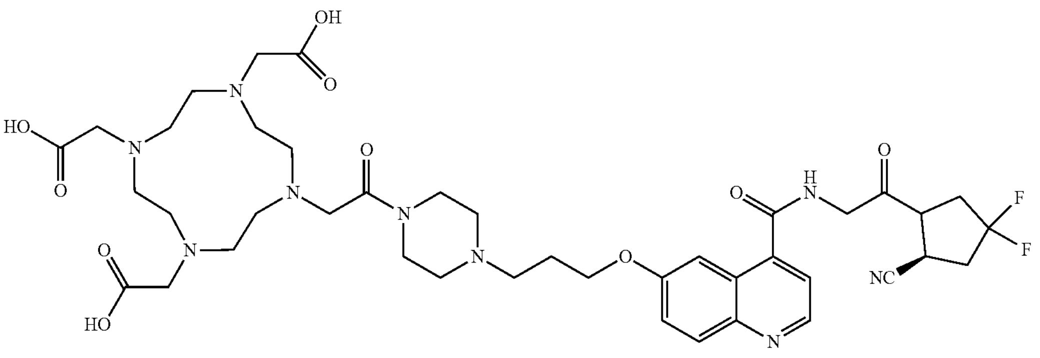 [SMILES: N#C[C@@H]1CC(F)(F)CC1C(=O)CNC(=O)c1ccnc2ccc(OCCCN3CCN(C(=O)CN4CCN(CC(=O)O)CCN(CC(=O)O)CCN(CC(=O)O)CC4)CC3)cc12]

Conjugate 22: Structure of "HABERKORN-DOTA"

Synthesis of "ESV6-DOTA" (8)

(S)-4-((4-((2-(2-cyano-4,4-difluoropyrrolidin-1-yl)-2-oxoethyl)carbamoyl)quinolin-8-yl)amino)-4-oxobutanoic acid (15 mg, 0.032 mmol, 1.0 eq) was dissolved in dry DMSO (400 μL). Dicyclohexylcarbodiimide (9 mg, 0.042 mmol, 1.3 eq) and N-hydroxysuccinimide (4.5 mg, 0.039 mmol, 1.3 eq) were added and the reaction was stirred overnight at room temperature, protected from light. 100 μL of PBS solution containing 2,2',2"-(10-(4-((2-aminoethyl)amino)-1-carboxy-4-oxobutyl)-1,4,7,10-tetraazacyclododecane-1,4,7-triyl)triacetic acid (20 mg, 0.039 mmol, 1.2 eq) were added and the reaction was stirred for 2h. The crude product was purified by reversed-phase HPLC (Water 0.1% TFA/Acetonitrile 0.1% TFA 9.5:0.5 to 2:8 in 20 min) and lyophilized, to obtain a white solid (2.4 mg, 8%). MS($ES^+$) m/z 960.39 $(M+H)^+$

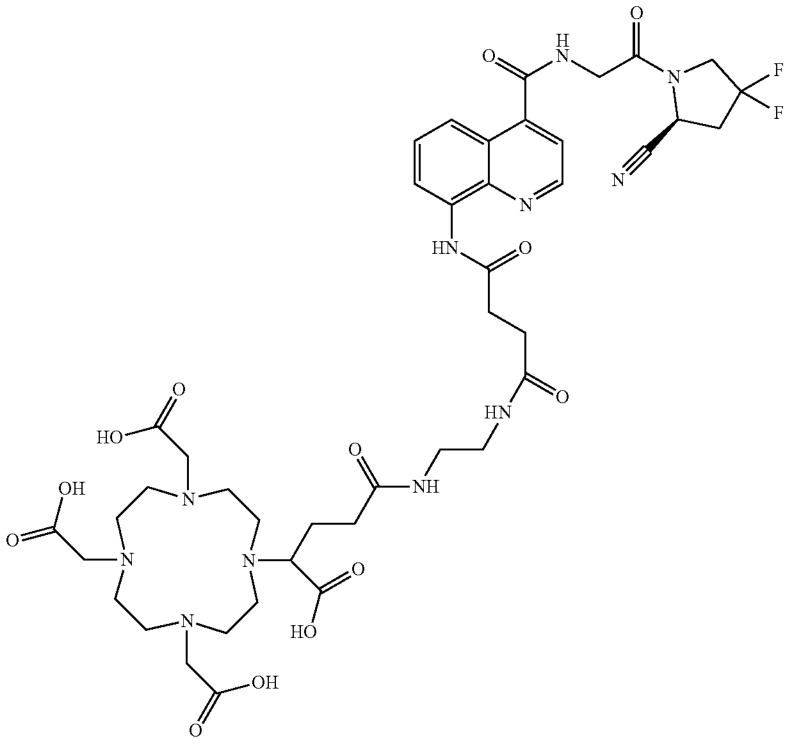 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CCN(CC(=O)O)CC3)cccc12]

Conjugate 8: Structure of "ESV6-DOTA"

FIG. 27 shows structure, chromatographic profile and LC/MS analysis of ESV6-DOTAGA (8). MS(ES$^+$) m/z 960.39 $(M+H)^+$.

Example 6: Comparative Experiment Between Compound P4 and Compound 24

PART 1—Preparation of Compound 24

Synthesis of 7-(phenylamino)quinoline-4-carboxylic acid

Scheme 9. Synthesis route for preparation of 7-(phenylamino)quinoline-4-carboxylic acid

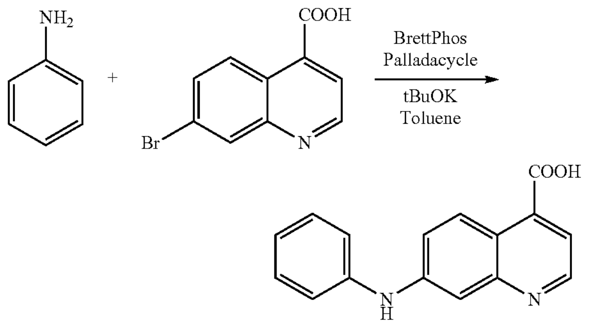

7-Bromoquinoline-4-carboxylic acid (30 mg, 0.119 mmol, 1.0 eq) was added to a stirred solution of aniline (111 mg, 1.19 mmol, 198 μL, 10.0 eq) in toluene (1 mL) and dioxane (500 μL) in a pressure-vial. The solution was degassed for 5 minutes (Argon-vacuum cycles) and then BrettPhos Palladacycle (10 mg, 0.0119 mmol, 0.1 eq) and potassium tert-butoxide (53 mg, 0.476 mmol, 4.0 eq) were added and the reaction was warmed up at 110° C. for 4h and checked via LC/MS. The crude was absorbed on silica and purified by flash chromatography (DMC/MeOH from 9:1 to 2:8) to give compound as orange oil (31 mg, 0.119 mmol, 100%). MS(ES$^+$) m/z 265.09 $(M+H)^+$

Synthesis of (S)—N-(2-(2-cyano-4,4-difluoropyrrolidin-1-yl)-2-oxoethyl)-7-(phenylamino)quinoline-4-carboxamide (compound 24)

Scheme 10. Synthesis route for preparation of (S)-N-(2-(2-cyano-4,4-difluoropyrrolidin-1-yl)-2-oxoethyl)-7-(phenylamino)quinoline-4-carboxamide (compound 24)

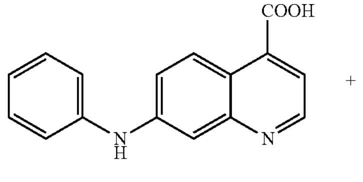

-continued

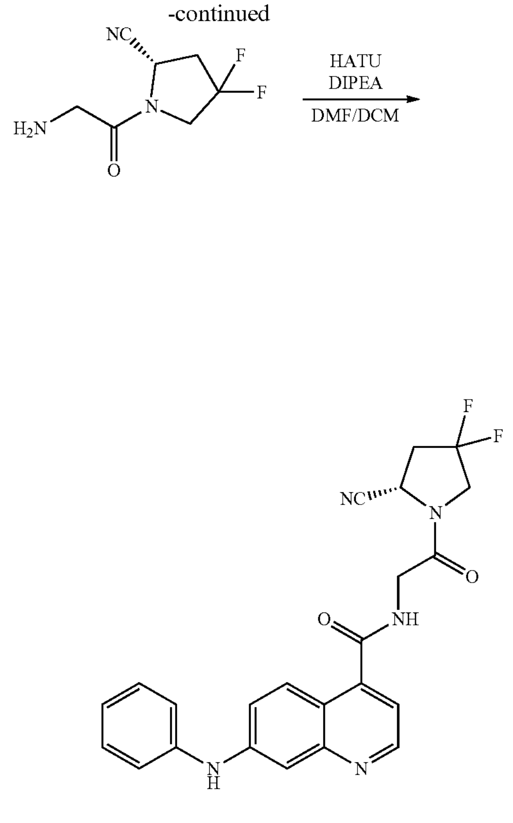

7-(phenylamino)quinoline-4-carboxylic acid (31 mg, 0.119 mmol, 1.0 eq), (S)-4,4-difluoro-1-glycylpyrrolidine-2-carbonitrile (24 mg, 0.129 mmol, 1.1 eq) and HATU (89 mg, 0.234 mmol, 2 eq) were added in a solution DMF (200 μL) and dichloromethane (1 mL). DIPEA (45 mg, 0.352 mmol, 61 μL, 3 eq) was added dropwise and the reaction was stirred for 15 minutes at room temperature. The DCM was evaporated and the crude material was purified by reversed-phase HPLC (Water 0.1% TFA/Acetonitrile 0.1% TFA 9.5:0.5 to 2:8 in 20 min) and lyophilized, to obtain a yellow solid (3.5 mg, 0.008 mmol, 6.9%). MS(ES$^+$) m/z 436.15 $(M+1H)^{1+}$ PART 2—In Vitro Experiments In Vitro inhibition assay on hFAP Enzymatic activity of human FAP on the Z-Gly-Pro-AMC substrate in the presence of different small organic ligands (compound P4 from Example 2; compound 24) was measured at room temperature on a microtiter plate reader, monitoring the fluorescence at an excitation wavelength of 360 nm and an emission wavelength of 465 nm. The reaction mixture contained 20 μM substrate, 20 nM human FAP (constant), assay buffer (50 mM Tris, 100 mM NaCl, 1 mM EDTA, pH=7.4) and inhibitor (serial dilution from $10^{-6}$ to $10^{-11}$ M, 1:2) in a total volume of 20 μL. The $IC_{50}$ value is defined as the concentration of inhibitor required to reduce the enzyme activity by 50% after addition of the substrate).

Figure 9:
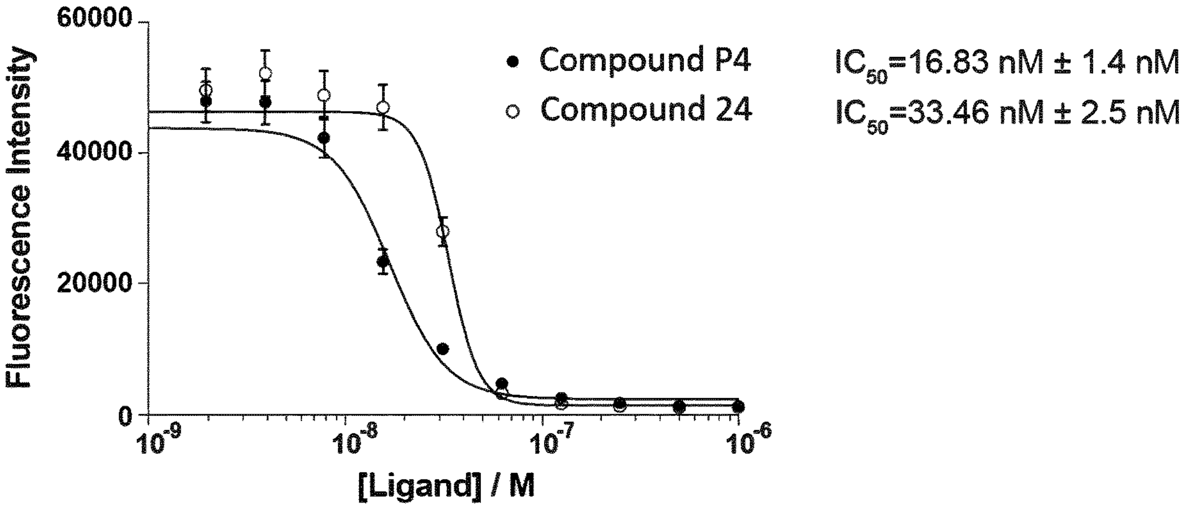
FIG. 9: hFAP inhibition experiment in the presence of different small organic ligands. The compound P4 from Example 2 displays a lower $IC_{50}$ (16.83 nM, higher inhibition) compared to the compound 24 (33.46 nM, lower inhibition).
Figure 9:
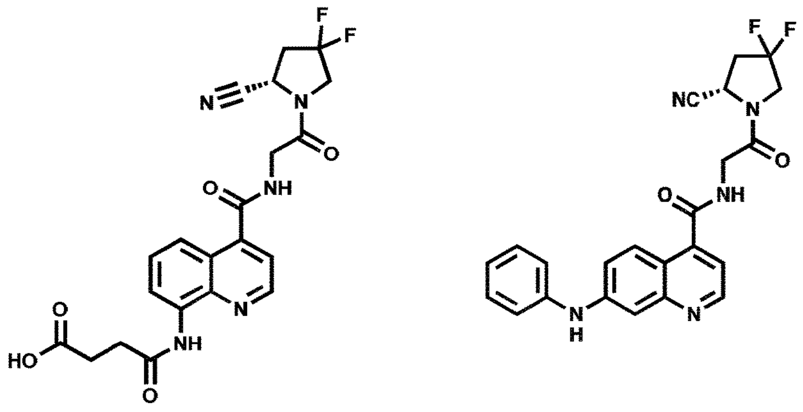

FIG. 9 shows that the compound P4 from Example 2 displays a lower $IC_{50}$ (16.83 nM, higher inhibition) compared to the compound 24 (33.46 nM, lower inhibition).

Example 7: Synthesis of conjugates 15 and 25 and their characterization

PART 1—Preparation of Conjugates

Synthesis of Conjugate 15

Scheme 11. Structure of conjugate 15

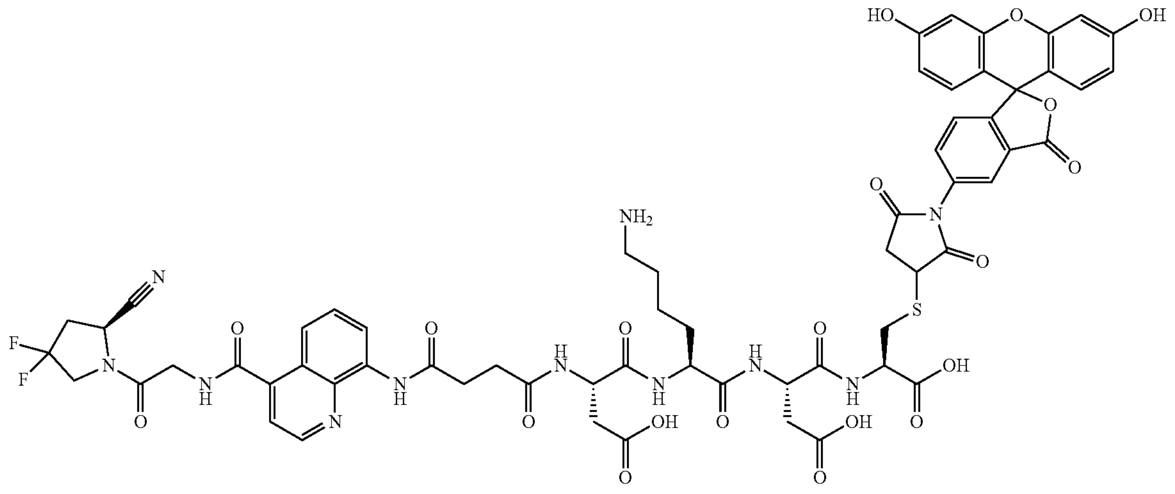

Figure 25:
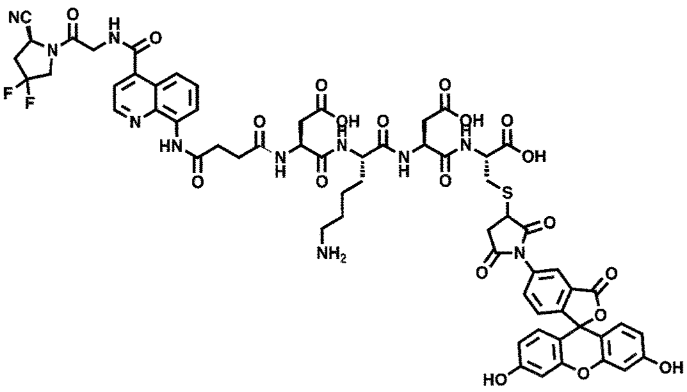
Figure 25:
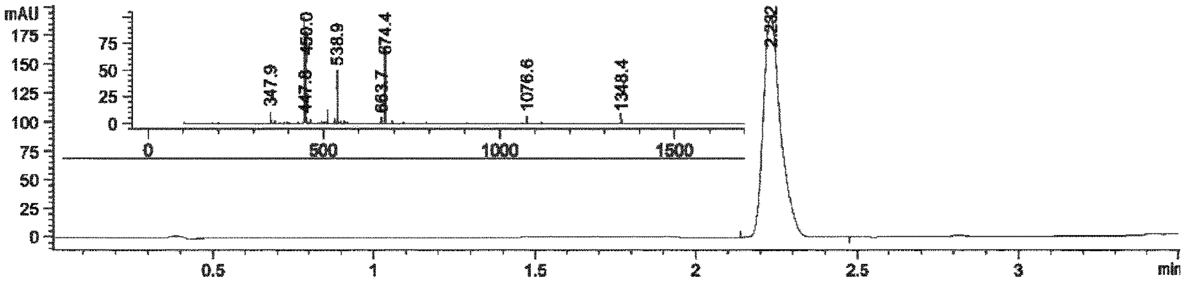

SH-Cys-Asp-Lys-Asp-ESV6 (2 mg, 2.171 μmol, 1.0 eq) was dissolved in PBS pH 7.4 (800 μL). Fluorescein-5-maleimide (1.8 mg, 4.343 μmol, 2.0 eq) was added as dry DMSO solution (200 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a yellow solid (420 nmol, 19.3%). MS($ES^+$) m/z 1348.36 $(M+1H)^{1+}$ FIG. 25 shows structure, chromatographic profile and LC/MS analysis of conjugate 15. MS($ES^+$) m/z 1348.36 $(M+1H)^+$.

Synthesis of Conjugate 25

Scheme 12. Structure of conjugate 25.

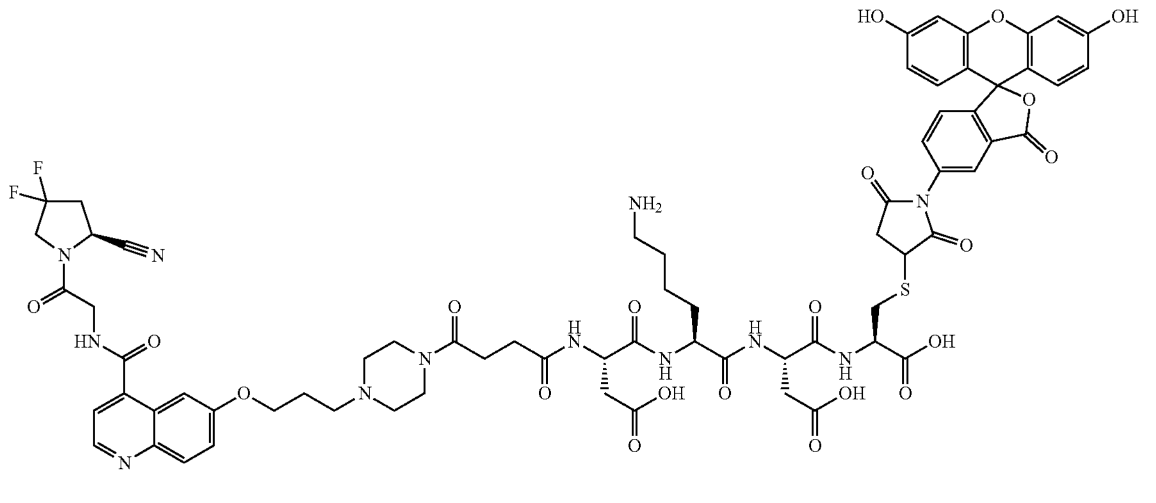

SH-Cys-Asp-Lys-Asp-HK (1 mg, 0.954 μmol, 1.0 eq) was dissolved in PBS pH 7.4 (800 μL). Fluorescein-5-maleimide (817 μg, 1.909 μmol, 2.0 eq) was added as dry DMSO solution (200 μL). The reaction was stirred for 3 h. The crude material was purified by reversed-phase HPLC (Water 0.1% TFA/Acetonitrile 0.1% TFA 9.5:0.5 to 2:8 in 20 min) and lyophilized, to obtain a yellow solid (373 nmol, 39.1%). MS($ES^+$) m/z 1476.47 $(M+1H)^+$ PART 2—In Vitro Experiments Affinity Measurement to Human and Murine FAP by Fluorescence Polarization (FP)

Fluorescence polarization experiments were performed in 384-well plates (non-binding, ps, f-bottom, black, high volume, 30 μL final volume). Stock solutions of human FAP (4 μM) and murine FAP (5 μM) were serially diluted with buffer (50 mM Tris, 100 mM NaCl, 1 mM EDTA, pH=7.4), while the final concentration of the binders was kept constant at 10 nM. The fluorescence anisotropy was measured on a TECAN microtiter plate reader. Experiments were performed in triplicate and the mean anisotropy values fitted using Prism 7.

Figure 10:
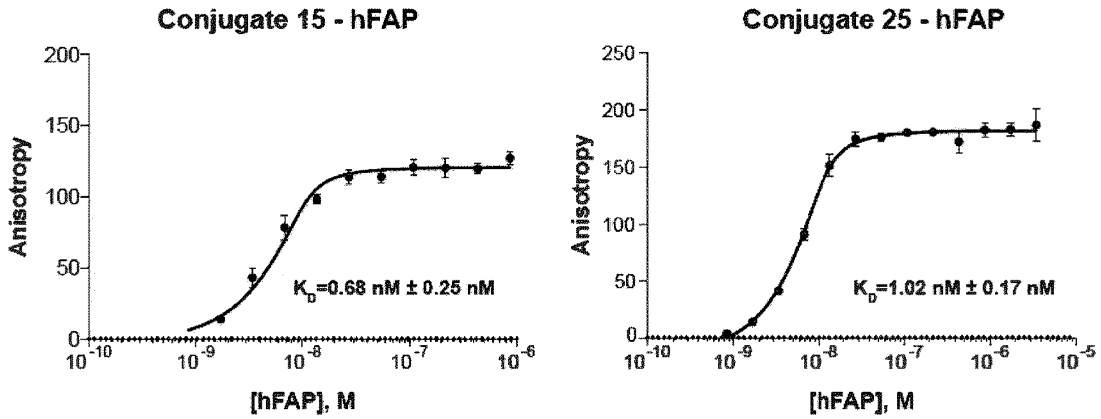
FIG. 10: Affinity determination of small organic ligands for human and murine fibroblast activation protein by fluorescent polarization (FP). (A) Conjugate 15 shows a higher affinity to hFAP ($K_D$=0.68 nM) compared to the conjugate 25 ($K_D$=1.02 nM). (B) Conjugate 15 shows a higher affinity to mFAP ($K_D$=11.61 nM) compared to the conjugate 25 ($K_D$=30.94 nM). Conjugate 15 presents superior binding properties to hFAP and a better cross-reactivity to the murine antigen compared to the conjugate 25. (C) Structures of conjugates 15 and 25.
Figure 10:
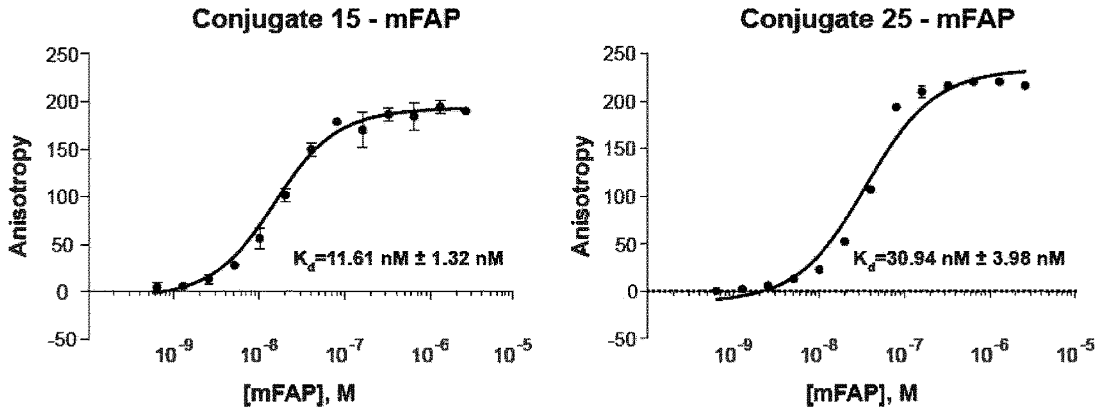
Figure 10:
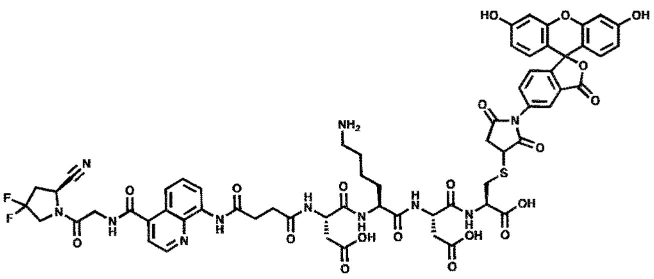
Figure 10:
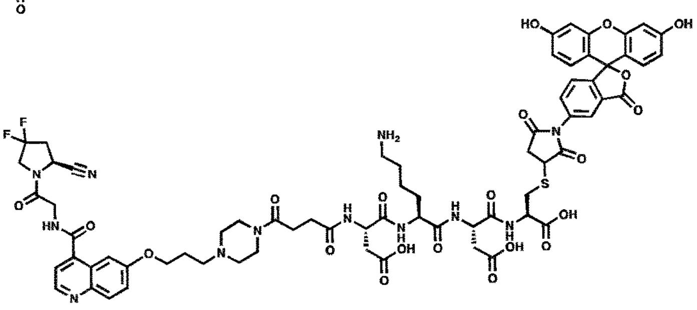

FIG. 10A shows that conjugate 15 has a higher affinity to hFAP ($K_D$=0.68 nM) compared to the conjugate 25 ($K_D$=1.02 nM). FIG. 10B shows that conjugate 15 has a higher affinity to mFAP ($K_D$-11.61 nM) compared to the conjugate 25 ($K_D$=30.94 nM). Conjugate 15 presents superior binding properties to hFAP and a better cross-reactivity to the murine antigen compared to the conjugate 25.

Chromatographic Co-Elution Experiments of Ligand-Protein Complexes

A PD-10 column was pre-equilibrated with assay buffer (50 mM Tris, 100 mM NaCl, 1 mM EDTA, pH=7.4) prior to the loading of the complex. A mixture of different proteins (hFAP=2 μM, mFAP=5 μM) and conjugate 15 (100 nM) were incubated and loaded on the column. The mixture was flushed using the assay buffer. The flow through was collected in 96-well plates and the fluorescence intensity was measured immediately on a TECAN microtiter plate reader, monitoring the fluorescence at an excitation wavelength of 485 nm and an emission wavelength of 535 nm. The concentration of the proteins was estimated by measuring the absorbance at 280 nM using a Nanodrop 2000/2000c spectrophotometer.

Figure 11:
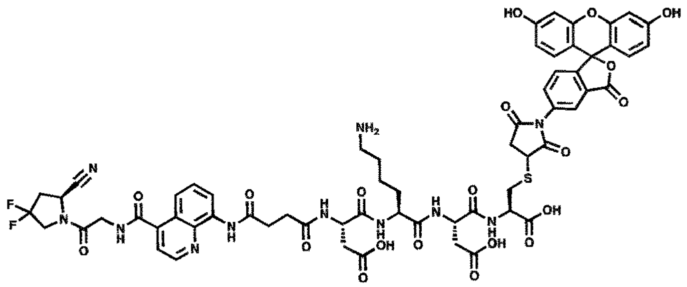
FIG. 11: Co-elution PD-10 experiment of small molecule ligand conjugate 15 with hFAP (A) and mFAP (B). A stable complex is formed between both proteins and the small ligand conjugate 15, allowing a co-elution of the two molecules together.
Figure 11:
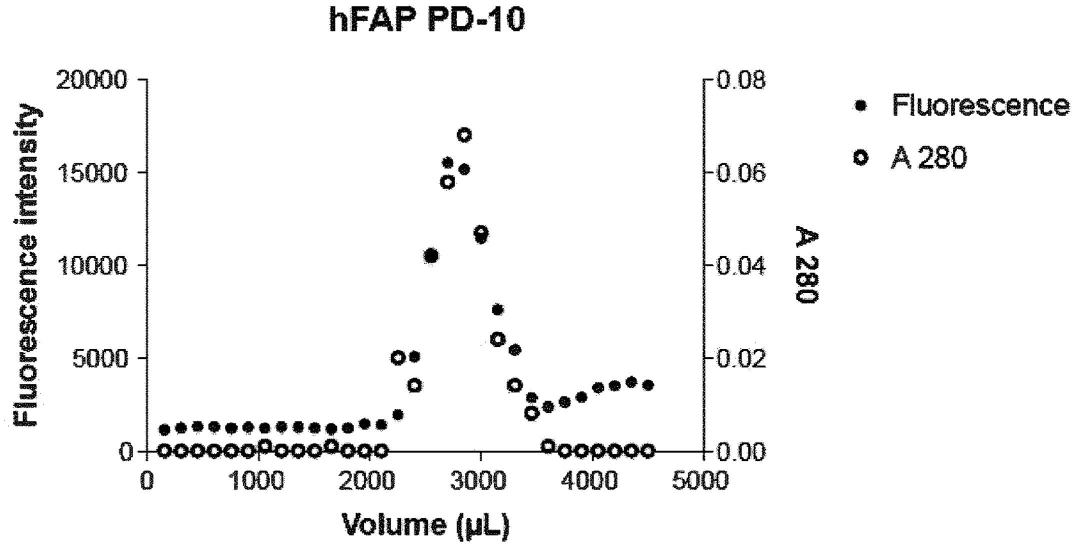
Figure 11:
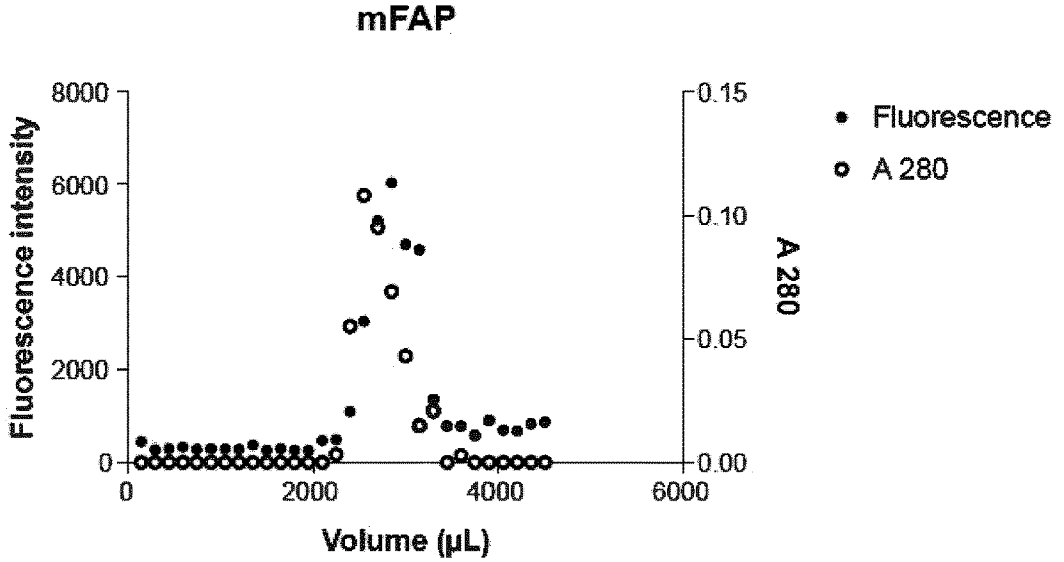

FIG. 11 shows results of the co-elution PD-10 experiment of small molecule ligand conjugate 15 with hFAP (A) and mFAP (B). A stable complex is formed between both proteins and the small ligand conjugate 15, allowing a co-elution of the two molecules together.

PART 3—Animal Experiments

Cell Cultures

Upon thawing, SK-RC-52.hFAP and SK-RC-52 cells were kept in culture in RPMI medium supplemented with fetal bovine serum (10%, FBS) and Antibiotic-Antimycotic (1%, AA) at 37° C. and 5% $CO_2$. For passaging, cells were detached using Trypsin-EDTA 0.05% when reaching 90% confluence and re-seeded at a dilution of 1:4.

Upon thawing, HT-1080.hFAP and HT-1080 cells were kept in culture in DMEM medium supplemented with fetal bovine serum (10%, FBS) and Antibiotic-Antimycotic (1%, AA) at 37° C. and 5% $CO_2$. For passaging, cells were detached using Trypsin-EDTA 0.05% when reaching 90% confluence and re-seeded at a dilution of 1:4.

Confocal Microscopy Analysis on SK-RC-52.hFAP, SK-RC-52, HT-1080.hFAP and HT-1080

SK-RC-52.hFAP and SK-RC-52 cells were seeded into 4-well cover slip chamber plates at a density of $10^4$ cells per well in RPMI medium (1 mL) supplemented with 10% FCS, AA and HEPES (10 mM) and allowed to grow for 24 hours under standard culture conditions. Hoechst 33342 nuclear dye was used to stain nuclear structures.

The culture medium was replaced with fresh medium containing conjugate 15 (100 nM). Randomly selected colonies imaged on a SP8 confocal microscope equipped with an AOBS device (Leica Microsystems).

HT-1080.hFAP and HT-1080 cells were seeded into 4-well cover slip chamber plates at a density of $10^4$ cells per well in DMEM medium (1 mL) supplemented with 10% FCS, AA and HEPES (10 mM) and allowed to grow for 24 hours under standard culture conditions. Hoechst 33342 nuclear dye was used to stain nuclear structures.

The culture medium was replaced with fresh medium containing conjugate 15 (100 nM). Randomly selected colonies imaged on a SP8 confocal microscope equipped with an AOBS device (Leica Microsystems).

Figure 12:
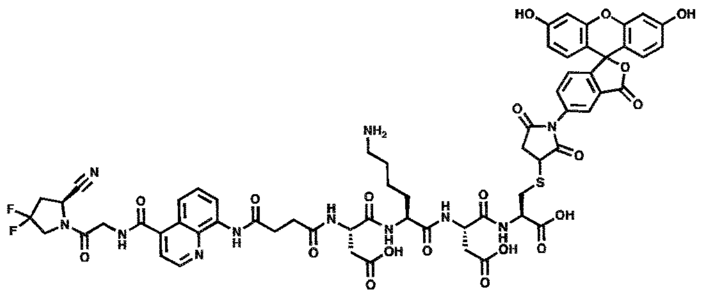
FIG. 12: Evaluation of selective accumulation of conjugate 15 (10 nM) on SK-RC-52.hFAP, HT-1080.hFAP and wild type tumour cells trough confocal microscopy and FACS analysis. (A) Images of SK-RC-52.hFAP incubated with the compound at different time points (t=0 and 1 h) show accumulation of conjugate 15 on the cell membrane. (B) Images of SK-RC-52 Wild type after incubation with the compound show no accumulation on the cell membrane (negative control). (C) FACS analysis on SK-RC-52 Wild type (dark gray peak) and SK-RC-52.hFAP (light gray peak) shows FAP-specific cellular binding of conjugate 15 (10 nM). (D) Images of HT-1080.hFAP incubated with the compound at different timepoints (t=0 and 1 h) show accumulation of conjugate 15 on the cell membrane and inside the cytosol. (E) Images of HT-1080 Wild type after incubation with the compound show no accumulation on the cell membrane and in the cytosol (negative control). (F) FACS analysis on HT-1080 Wild type (dark gray peak) and HT-1080.hFAP (light gray peak) shows FAP-specific cellular binding of conjugate 15 (10 nM).
Figure 12:
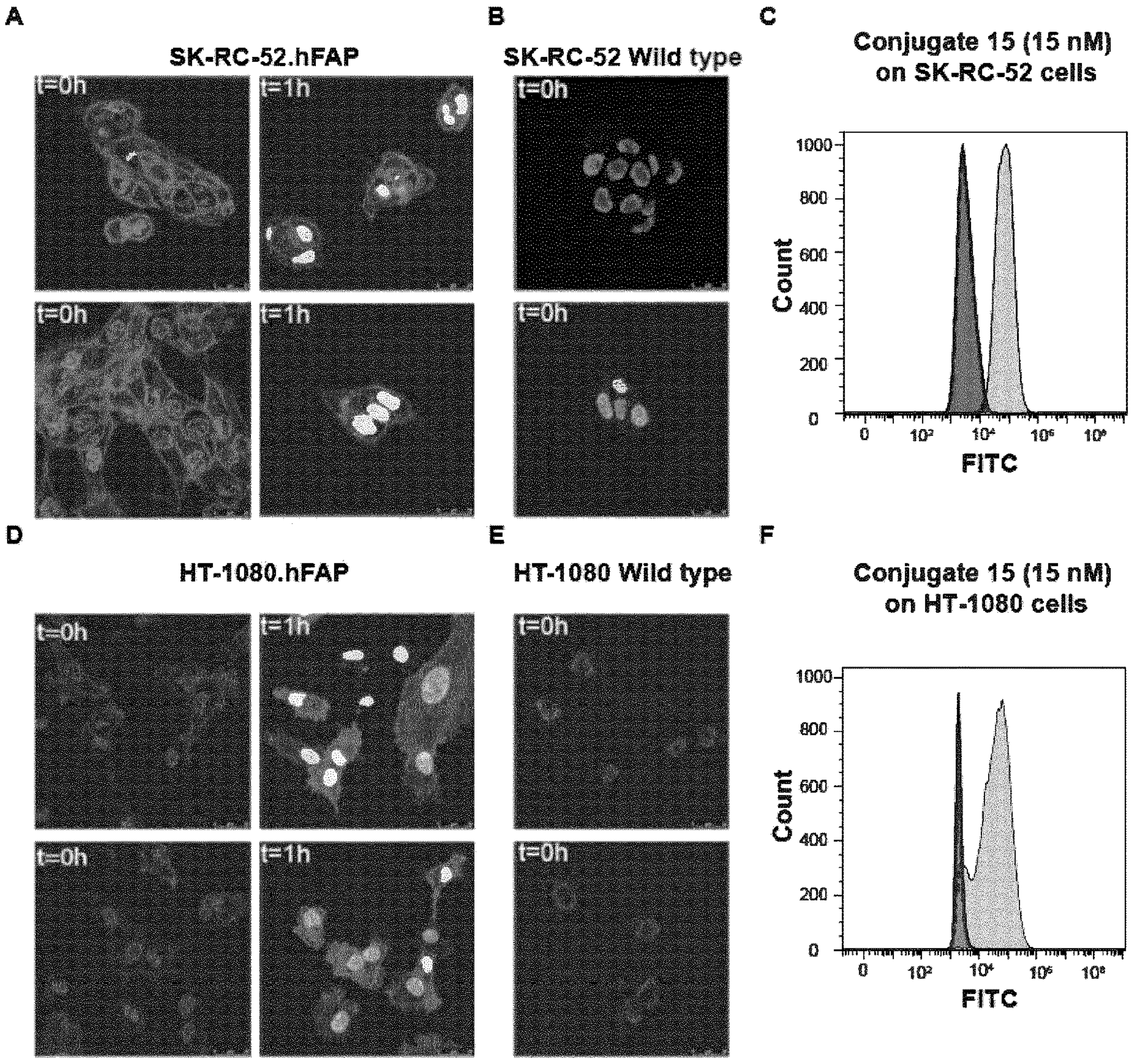

FIG. 12 shows evaluation of selective accumulation of conjugate 15 (10 nM) on SK-RC-52.hFAP, HT-1080.hFAP and wild type tumour cells trough confocal microscopy and FACS analysis. (A) Images of SK-RC-52.hFAP incubated with the compound at different time points (t=0 and 1 h) show accumulation of conjugate 15 on the cell membrane. (B) Images of SK-RC-52 Wild type after incubation with the compound show no accumulation on the cell membrane (negative control). (C) FACS analysis on SK-RC-52 Wild type (dark gray peak) and SK-RC-52.hFAP (light gray peak) shows FAP-specific cellular binding of conjugate 15 (10 nM). (D) Images of HT-1080.hFAP incubated with the compound at different timepoints (t=0 and 1 h) show accumulation of conjugate 15 on the cell membrane and inside the cytosol. (E) Images of HT-1080 Wild type after incubation with the compound show no accumulation on the cell membrane and in the cytosol (negative control).

FACS Analysis

SK-RC-52.hFAP, SK-RC-52.wt, HT-1080.wt and HT-1080.hFAP were detached from culture plates using Accutase, counted and suspended to a final concentration of $1.5\times10^6$ cells/mL in a 1% v/v solution of FCS in PBS pH 7.4. Aliquots of $3\times10^5$ cells (200 μL) were spun down and resuspended in solutions of conjugate 15 (15 nM) in a 1% v/v solution of FCS in PBS pH 7.4 (200 μL) and incubated on ice for 1 h. Cells were washed once with 200 μL 1% v/v solution of FCS in PBS pH 7.4 (200 μL), spun down, resuspended in a 1% v/v solution of FCS in PBS pH 7.4 (300 μL) and analyzed on a CytoFLEX cytometer (Beckman Coulter). The raw data were processed with the FlowJo 10.4 software.

Results are shown in FIG. 12F: FACS analysis on HT-1080 Wild type (dark gray peak) and HT-1080.hFAP (light gray peak) shows FAP-specific cellular binding of conjugate 15 (10 nM).

Animal Studies

All animal experiments were conducted in accordance with Swiss animal welfare laws and regulations under the license number ZH04/2018 granted by the Veterinäramt des Kantons Zürich.

Implantation of Subcutaneous SK-RC-52.hFAP Tumours

SK-RC-52.hFAP cells were grown to 80% confluence and detached with Trypsin-EDTA 0.05%. Cells were re-suspended in HBSS medium to a final concentration of $5\times10^7$ cells/mL. Aliquots of $5\times10^6$ cells (100 μL of suspension) were injected subcutaneously in the right flank of female athymic BALB/C nu/nu mice (6-8 weeks of age).

Ex Vivo Experiment

Mice bearing subcutaneous SK-RC-52.hFAP tumour was injected intravenously with conjugate 15 (40 nmol in sterile PBS, pH 7.4). Animals were sacrificed by $CO_2$ asphyxiation 1h after the intravenous injection and the organs and the tumour were excised, snap-frozen in OCT medium and stored at −80° C. Cryostat sections (7 m) were cut and nuclei were stained with Fluorescence Mounting Medium (Dako Omnis, Agilent). Images were obtained using an Axioskop2 mot plus microscope (Zeiss) and analyzed by ImageJ 1.53 software.

Figure 13:
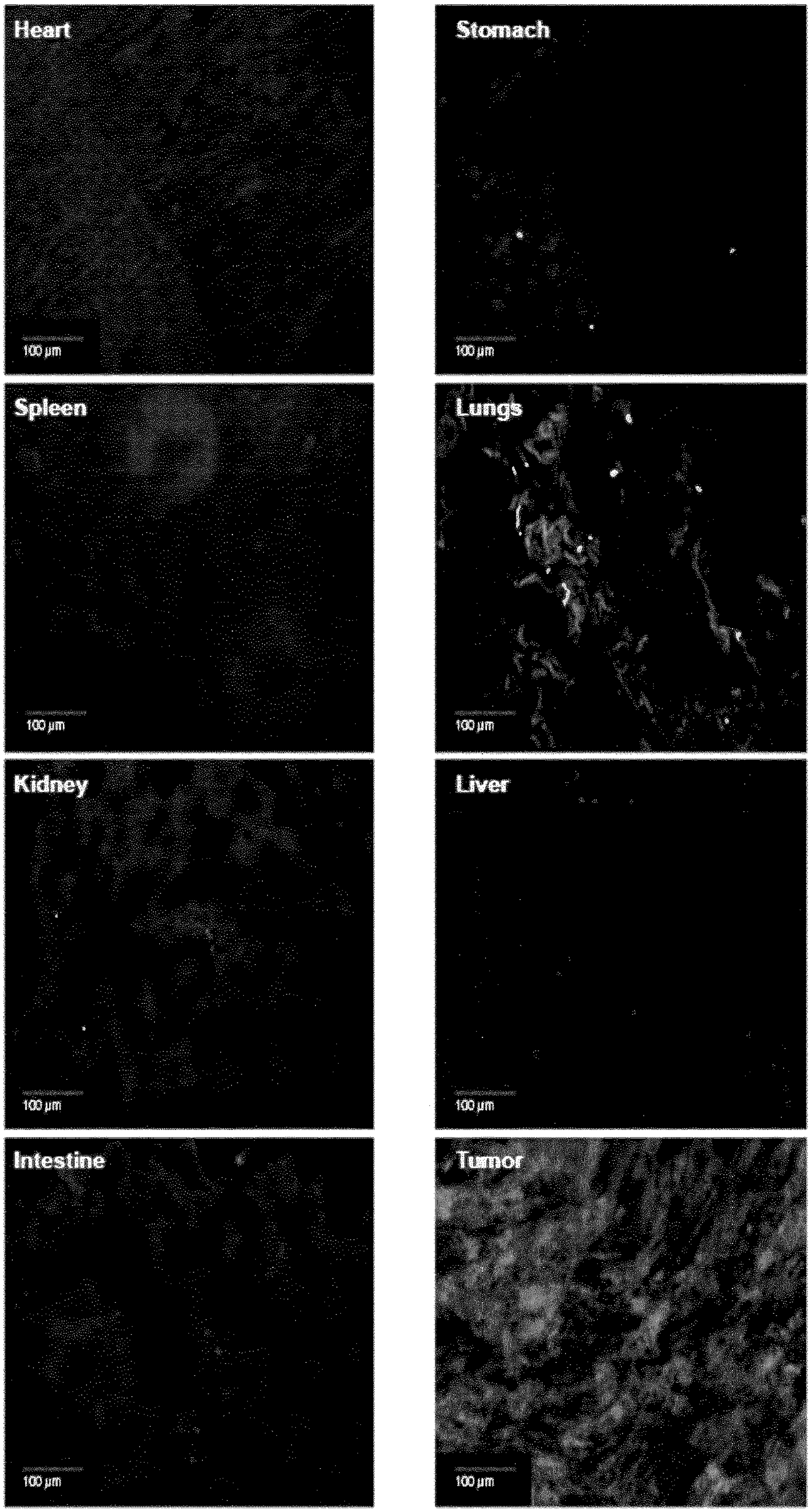
FIG. 13: Evaluation of targeting performance of conjugate 15 in BALB/C nu/nu mice bearing SK-RC-52.hFAP renal cell carcinoma xenografts after intravenous administration (40 nmol). Ex vivo organ images 1 h after administration are presented. The compound rapidly and homogeneously localizes at the tumour site in vivo 1 hour after the intravenous injection, with a high tumour-to-organs selectivity.
Figure 13:
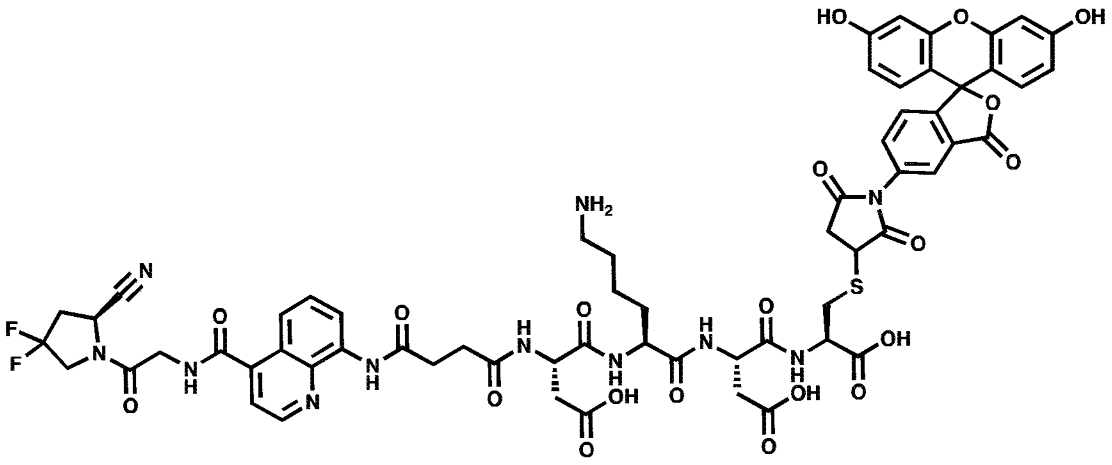

FIG. 13 shows results of the evaluation of targeting performance of conjugate 15 in BALB/C nu/nu mice bearing SK-RC-52.hFAP renal cell carcinoma xenografts after intravenous administration (40 nmol). Ex vivo organ images 1 h after administration are presented. The compound rapidly and homogeneously localizes at the tumour site in vivo 1 hour after the intravenous injection, with a high tumour-to-organs selectivity.

Example 8: Synthesis and Characterization of Conjugate 9

PART 1—Preparation of Conjugate

Figure 14:
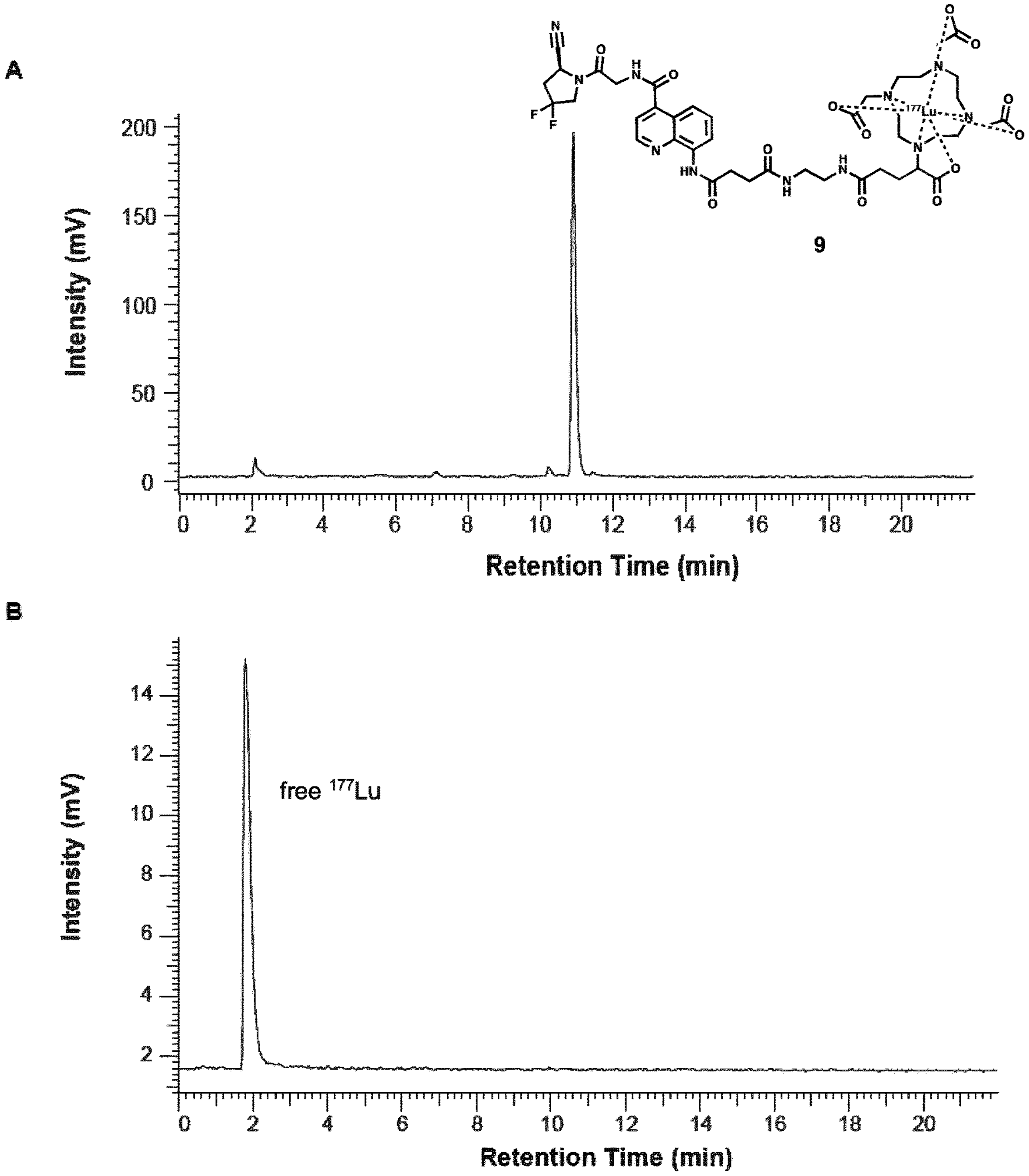
FIG. 14: RadioHPLC profile of radioactive compounds. (A) RadioHPLC profile of conjugate 9 after labelling with $^{177}$Lu (r.t. 11 min). (B) radioHPLC profile of free $^{177}$Lu (2 min). After the radiolabeling, conjugate 9 appear as single peak with a >99% of conversion.

Synthesis of Conjugate 9 (2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid labelled with 177-Lutetium)

flow rate 1 ml/min). Quantitative conversion to conjugate 9 was achieved (radiolabeling efficiency >99%, FIG. 14).

FIG. 14A shows a radioHPLC profile of conjugate 9 after labelling with $^{77}$Lu (r.t. 11 min). FIG. 14B shows a radioHPLC profile of free $^{17}$Lu (2 min). After the radiolabeling, conjugate 9 appears as single peak with a >99% of conversion.

PART 2—Animal Experiments

Radiolabelling and Biodistribution Experiment in SK-RC-52.hFAP

Figure 15:
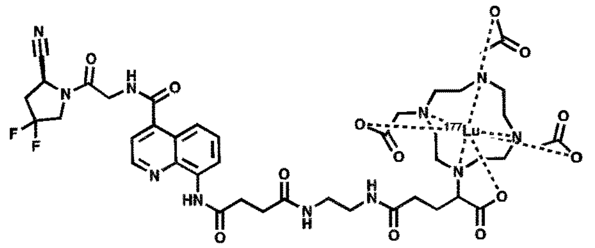
FIG. 15: Biodistribution experiment of conjugate 9 (which includes a $^{177}$Lu radioactive payload) in BALB/C nu/nu bearing SK-RC-52.hFAP renal cell carcinoma xenografts. (A) % ID/g in tumours and healthy organs and tumour-to-organ ratio analysis at different time points (10 min, 1 h, 3 h and 6 h) after intravenous administration of conjugate 9 (dose=50 nmol/Kg; 0.5-2 MBq). (B) % ID/g in tumours and healthy organs and tumour-to-organ ratio analysis 3 h after intravenous administration of $^{177}$Lu conjugate 9 at different doses (125 nmol/Kg, 250 nmol/Kg, 500 nmol/Kg and 1000 nmol/Kg; 0.5-2 MBq). A dose-dependent response can be observed, and target saturation can be reached between 250 nmol/Kg and 500 nmol/Kg. (C) % ID/g in tumours and healthy organs 3 h after intravenous administration of $^{177}$Lu solution (negative control; 1 MBq) and tumour-to-organs ratio analysis.
Figure 15:
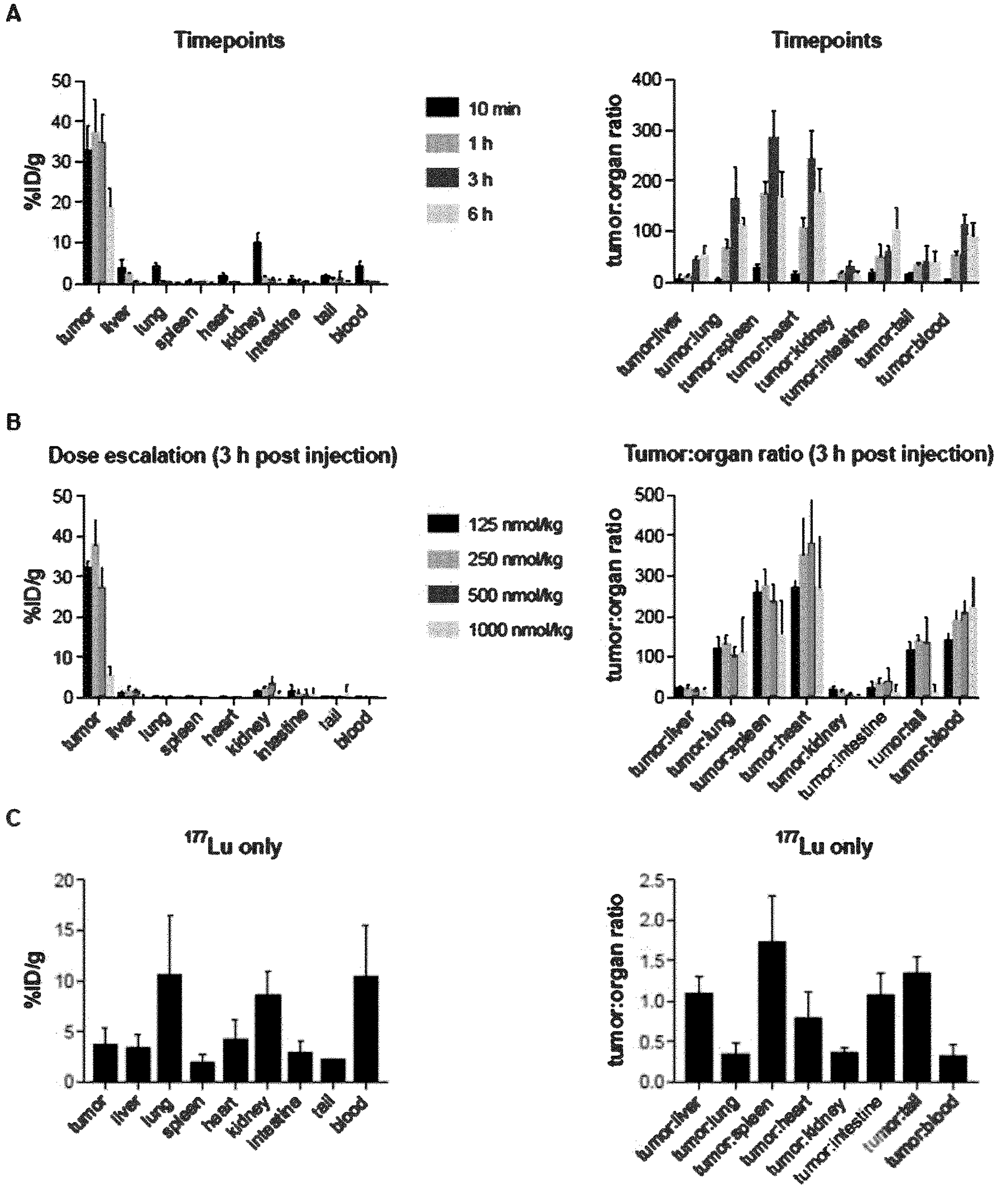

SK-RC-52.hFAP tumour cells were implanted into female BALB/c nu/nu mice as described in Example 7, and allowed to grow for three weeks to an average volume of 250 $mm^3$. Mice were randomized (n=4 per group) and injected intravenously with radiolabeled preparations of conjugate 9 (50, 125, 250, 500 or 1000 nmol/Kg; 0.5-2 MBq). Mice were sacrificed 10 minutes, 1 h, 3 h and 6 h after the injection by $CO_2$ asphyxiation and organs extracted, weighted and radioactivity measured with a Packard Cobra γ-counter. Values are expressed as % ID/g±SD (FIG. 15). Food and water were given ad libitum during that period.

FIG. 15 shows results of the biodistribution experiment of conjugate 9 (which includes a $^{17}$Lu radioactive payload) in BALB/C nu/nu bearing SK-RC-52.hFAP renal cell carcinoma xenografts. (A) % ID/g in tumours and healthy organs and tumour-to-organ ratio analysis at different time points Scheme 13. Structure of conjugate 9

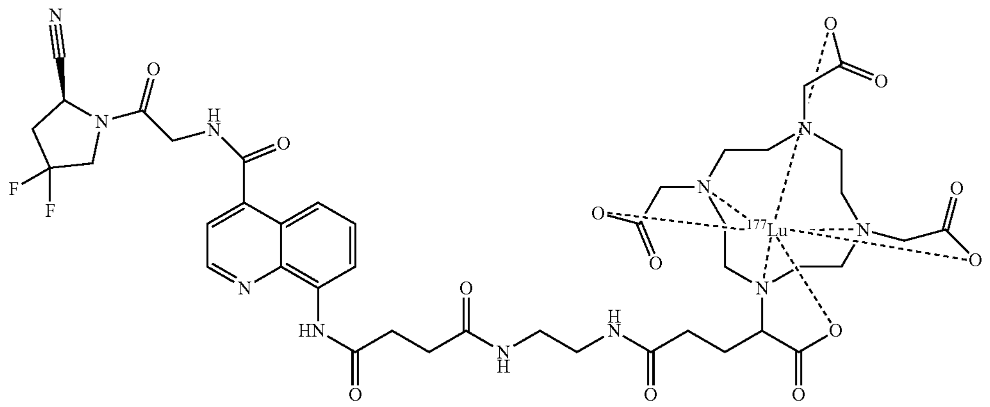

The conjugate 8 was dissolved in acetate buffer (1M, pH=4) to a final concentration of 1 μg/μL. Stock solution of conjugate 8 (25 μg in 25 μL) was diluted with 250 μL of acetate buffer (1M, pH=4). $^{177}LuCl_3$ solution (250 μL, 25 MBq) was added and the mixture was heated at 95° C. for 15 minutes. The labelling mixture was diluted by the addition of sterile PBS (1975 μL, pH=7.4) and labelling efficiency was monitored via radio-HPLC (5-10 μL, 0.5-1 MBq, 0.1% TFA in water as solvent A and 0.1% TFA in acetonitrile as solvent B. program: 0-8 min, 20%-65% solvent B and (10 min, 1 h, 3 h and 6 h) after intravenous administration of conjugate 9 (dose=50 nmol/Kg; 0.5-2 MBq). (B) % ID/g in tumours and healthy organs and tumour-to-organ ratio analysis 3h after intravenous administration of $^{17}$Lu conjugate 9 at different doses (125 nmol/Kg, 250 nmol/Kg, 500 nmol/Kg and 1000 nmol/Kg; 0.5-2 MBq). A dose-dependent response can be observed, and target saturation can be reached between 250 nmol/Kg and 500 nmol/Kg. (C) % ID/g in tumours and healthy organs 3 h after intravenous administration of $^{17}$Lu solution (negative control; 1 MBq) and tumour-to-organs ratio analysis.

Example 9: Synthesis of Compounds 27-32

Synthesis of 2,2',2"-(10-(1-carboxy-4-((2-(4-((4-((2-((R)-2-cyano-4,4-difluoropyrrolidin-1-yl)-2-oxoethyl)carbamoyl)quinolin-8-yl)amino)-4-oxobutanamido)ethyl)amino)-4-oxobutyl)-1,4,7,10-tetraazacyclododecane-1,4,7-triyl)triacetic acid Labelled with 69-Gallium, Conjugate 27

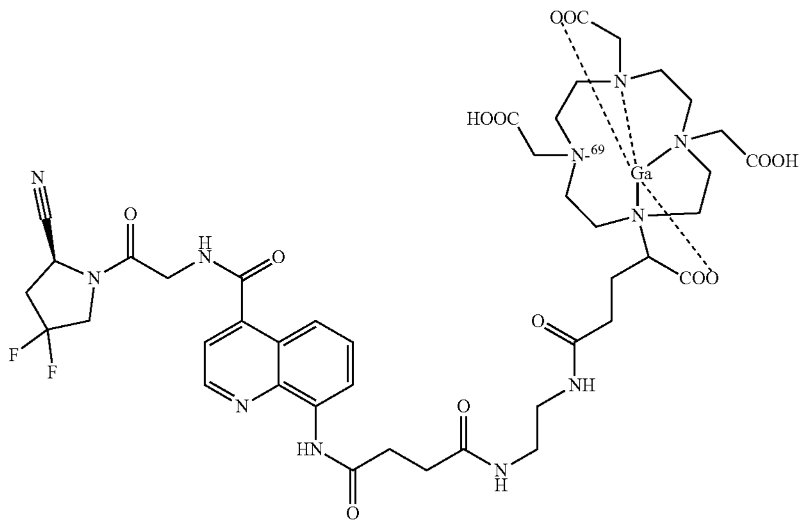

Conjugate 8 was dissolved in acetate buffer (1M, pH=4) to a final concentration of 1 μg/μL.

Stock solution of conjugate 8 (100 μg in 100 μL) was diluted with 250 μL of acetate buffer (1M, pH=4). $GaCl_3$ solution (183 μg in 183 μL of HCl) was added and the mixture was heated at 90° C. for 15 minutes. The reaction was checked via LC/MS. MS($ES^+$) m/z 1027.30 $(M+H)^+$ Synthesis of methyl (6-methoxyquinoline-4-carbonyl) glycinate Scheme 14. Synthesis route for preparation of methyl (6-methoxyquinoline-4-carbonyl) glycinate

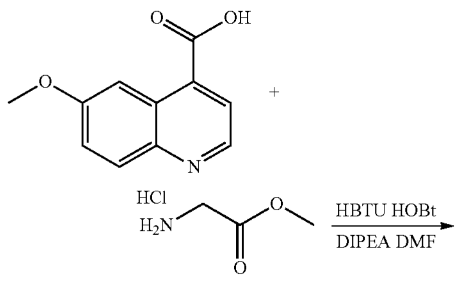

-continued

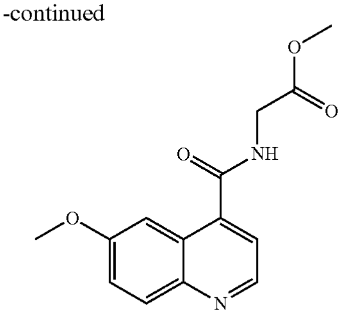

6-methoxyquinoline-4-carboxylic acid (200 mg, 0.985 mmol, 1.0 eq), HBTU (400 mg, 1.03 mmol, 1.05 eq), HOBt (167 mg, 1.05 mmol, 1.15 eq) and methyl glycinate hydrochloride (107 mg, 1.08 mmol, 1.1 eq) were dissolved in 5 mL of DMF and stirred at room temperature. DIPEA (613 μL, 4.42 mmol, 4.5 eq) was added dropwise and the reaction was checked via LC/MS until competition. The crude was directly purified via chromatography (DCM:MeOH 100:0 to 80:20 in 10 min) to afford a pale yellow solid (40 mg, 0.145 mmol, 14.7%). MS($ES^+$) m/z 275.1 (M+1H).

Synthesis of (6-methoxyquinoline-4-carbonyl) glycinate

Scheme 15. Synthesis route for preparation of (6-methoxyquinoline-4-carbonyl) glycinate

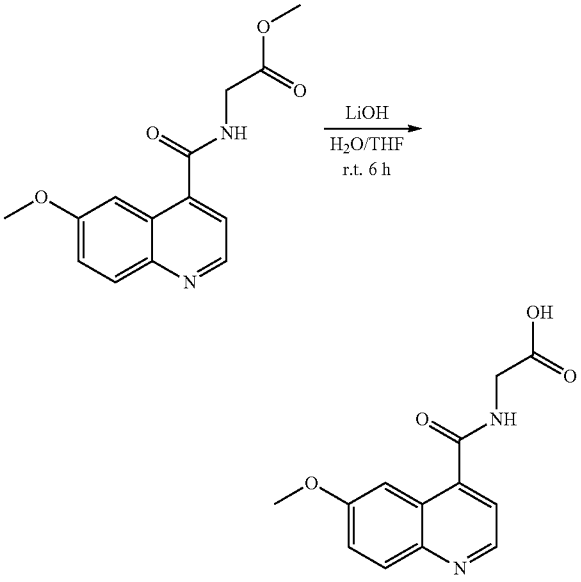

Methyl (6-methoxyquinoline-4-carbonyl) glycinate (30 mg, 0.109 mmol, 1.0 eq), was dissolved in 2 mL THF/$H_2O$ (1:1) of a 1M LiOH solution and stirred at room temperature for 6 hours. When completed, the base was quenched with HCl 1M until a slightly acidic pH was reached and the crude was lyophilized, to obtain a white solid (quantitative yield). MS($ES^+$) m/z 261.08 $(M+1H)^{1+}$

Synthesis of (S)—N-(2-(2-cyanopyrrolidin-1-yl)-2-oxoethyl)-6-methoxyquinoline-4-carboxamide, conjugate 28

Scheme 16. Synthesis route for preparation of (S)-N-(2-(2-cyanopyrrolidin-1-yl)-2-oxoethyl)-6-methoxyquinoline-4-carboxamide

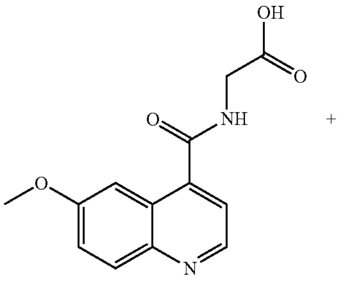

-continued

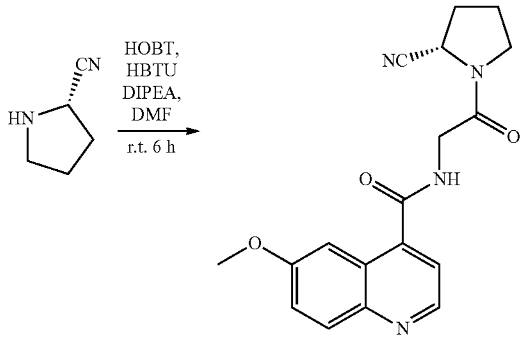

(6-methoxyquinoline-4-carbonyl) glycinate (28 mg, 0.109 mmol, 1.0 eq), (S)-pyrrolidine-2-Carbonitrile (16 mg, 0,120 mmol, 1.1 eq) and HATU (62 mg, 0.164 mmol, 1.5 eq) were dissolved in 2 mL of DMF and the suspension was stirred at room temperature. DIPEA (47 μL, 2.62 mmol, 24 eq) was added dropwise and the reaction was checked via LC/MS until competition. The crude was directly purified via reverse phase HPLC (Water 0.1% TFA/Acetonitrile 0.1% TFA 9.5:0.5 to 2:8 in 20 min) and lyophilized, to obtain a yellow solid (2 mg, 5.91 μmol, 5.4%). MS($ES^+$) m/z 339.14 $(M+1H)^{1+}$

Synthesis of tert-butyl ((S)-1-((S)-2-cyano-4,4-difluoropyrrolidin-1-yl)-1-oxopropan-2-yl)carbamate Scheme 17. Synthesis route for preparation of tert-butyl ((S)-1-((S)-2-cyano-4,4-difluoropyrrolidin-1-yl)-1-oxopropan-2-yl)carbamate

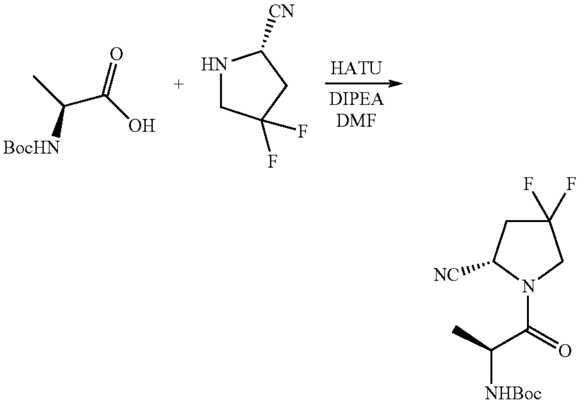

(S)-4,4-difluoro-pyrrolidine-2-Carbonitrile (50 mg, 0,379 mmol, 1 eq), (tert-butoxycarbonyl-L-alanine (154 mg, 0.75 mmol, 2.0 eq), and HATU (288 mg, 0.75 mmol, 2 eq) were dissolved in 4 mL of DMF and the suspension was stirred at room temperature. DIPEA (335 μL, 1.893 mmol, 5 eq) was added dropwise and the reaction was checked via LC/MS until competition. The DMF was removed under vacuum and the crude was diluted in DCM. The organic phase was washed with water and 1M HCl and then dried, to obtain a white foam (115 mg, 0.379 mmol, quantitative yield). MS($ES^+$) m/z 304.14 $(M+1H)^{1+}$

Synthesis of (S)-1-(L-alanyl)-4,4-difluoropyrrolidine-2-carbonitrile

Scheme 18. Synthesis route for preparation of (S)-1-(L-alanyl)-4,4-difluropyrrolidine-2-carbonitrile

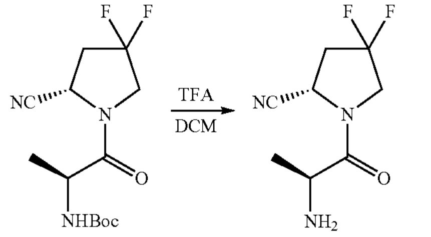

tert-butyl ((5)-1-((S)-2-cyano-4,4-difluoropyrrolidin-1-yl)-1-oxopropan-2-yl)carbamate (115 mg, 0,379 mmol, 1 eq), was dissolved in 2 mL of DCM and TFA (203 μL, 7 eq) was added dropwise and the reaction was stirred at room temperature and checked via LC/MS until competition. The crude was diluted in DCM and the product was extracted with HCl 1M. The acidic water phase was then quenched with NaOH 1M and the product was extracted with DCM and dried, to afford a pale yellow oil (30 mg, 0.147 mmol, 38.7%). MS($ES^+$) m/z 204.07 $(M+1H)^{1+}$

Synthesis of tert-butyl ((4-(((S)-1-((S)-2-cyano-4,4-difluoropyrrolidin-1-yl)-1-oxopropan-2-yl)carbamoyl)pyridin-2-yl)methyl)carbamate Scheme 19. Synthesis route for preparation of tert-butyl ((4-(((S)-1-((S)-2-cyano-4,4-difluoropyrrolidin-1-yl)-1-oxopropan-2-yl)carbamoyl)pyridin-2-yl)methyl)carbamate

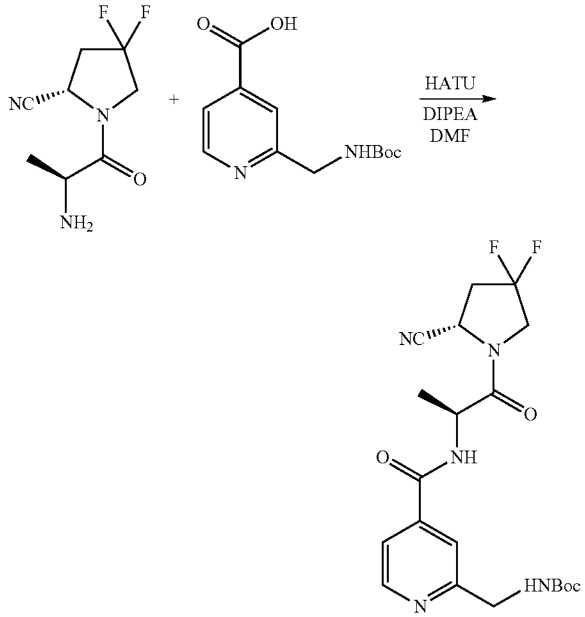

(S)-1-(L-alanyl)-4,4-difluoropyrrolidine-2-carbonitrile (30 mg, 0,147 mmol, 1 eq), 2-(((tert-butoxycarbonyl)amino)methyl)isonicotinic acid (74 mg, 0.295 mmol, 2.0 eq), and HATU (112 mg, 0.295 mmol, 2 eq) were dissolved in 1 mL of DMF and the suspension was stirred at room temperature. DIPEA (102 μL, 0.590 mmol, 4 eq) was added dropwise and the reaction was checked via LC/MS until competition. The DMF was removed under vacuum and the crude was diluted in DCM and purified via chromatography (DCM:MeOH 99:1 to 70:30 in 15 min) to afford a yellow solid (15 mg. 0.034 mmol, 19.7%). MS($ES^+$) m/z 438.19 $(M+1H)^{1+}$

Synthesis of 2-(aminomethyl)-N—((S)-1-((S)-2-cyano-4,4-difluoropyrrolidin-1-yl)-1-oxopropan-2-yl)isonicotinamide Scheme 20. Synthesis route for preparation of 2-(aminomethyl)-N-((S)-1-((S)-2-cyano-4,4-difluoropyrrolidin-1-yl)-1-oxopropan-2-yl)isonicotinamide

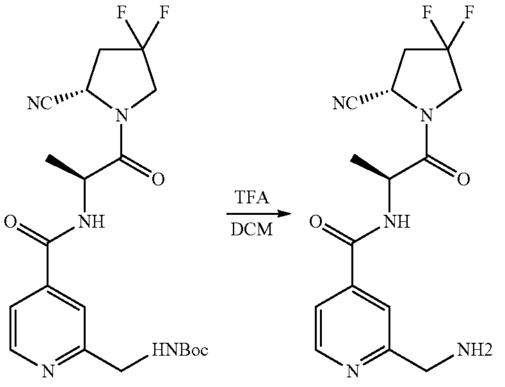

tert-butyl ((4-(((S)-1-((S)-2-cyano-4,4-difluoropyrrolidin-1-yl)-1-oxopropan-2-yl)carbamoyl)pyridin-2-yl)methyl)carbamate (15 mg, 0.034 mmol, 1.0 eq), was dissolved in 400 μL of DCM and TFA (200 μL, 20% of volume) was added dropwise. the reaction was stirred at room temperature and checked via LC/MS until competition. The crude was dried and lyophilized in 500 μL of a 1:1 solution of water:Acetonitrile, to obtain a yellow powder (4 mg, 11.86 μmol, 34.8%). MS($ES^+$) m/z 338.14 $(M+1H)^{1+}$ Synthesis of 4-(((4-(((S)-1-((S)-2-cyano-4,4-difluoropyrrolidin-1-yl)-1-oxopropan-2-yl)carbamoyl) pyridin-2-yl)methyl)amino)-4-oxobutanoic acid, Conjugate 29

Scheme 21. Synthesis route for preparation of 4-(((4-(((S)-1-((S)-2-cyano-4,4-difluoropyrrolidin-1-yl)-1-oxopropan-2-yl)carbamoyl) pyridin-2-yl)methyl)amino)-4-oxobutanoic acid

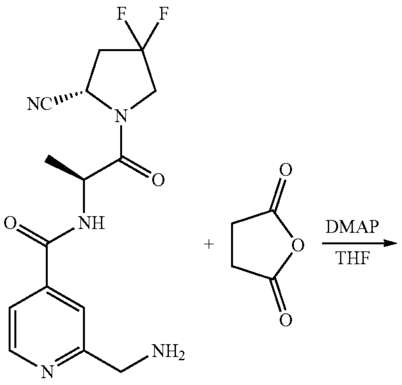

-continued

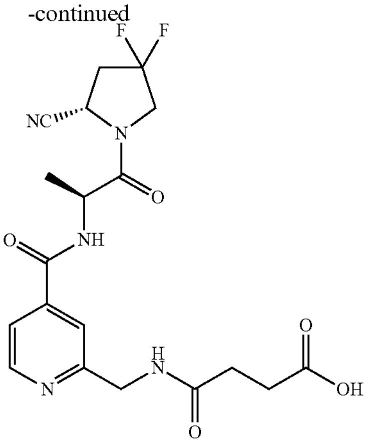

2-(aminomethyl)-N—((S)-1-((S)-2-cyano-4,4-difluoropyrrolidin-1-yl)-1-oxopropan-2-yl)isonicotinamide (4 mg, 11.86 μmol, 1.0 eq), was dissolved in 500 μL of THF. DMAP (6 mg, 48 μmol, 4.0 eq) and succinic anhydride (3.5 mg, 35.6 μmol, 3.0 eq) were added and the reaction was stirred at room temperature and checked via LC/MS until competition. The crude was directly purified via reverse phase HPLC (Water 0.1% TFA/Acetonitrile 0.1% TFA 9.5:0.5 to 2:8 in 20 min) and lyophilized, to obtain a yellow solid (1.3 mg, 2.97 μmol, 25%). MS($ES^+$) m/z 438.15 $(M+1H)^{1+}$ Synthesis of ESV6-Alexa Fluor 488, Conjugate 30

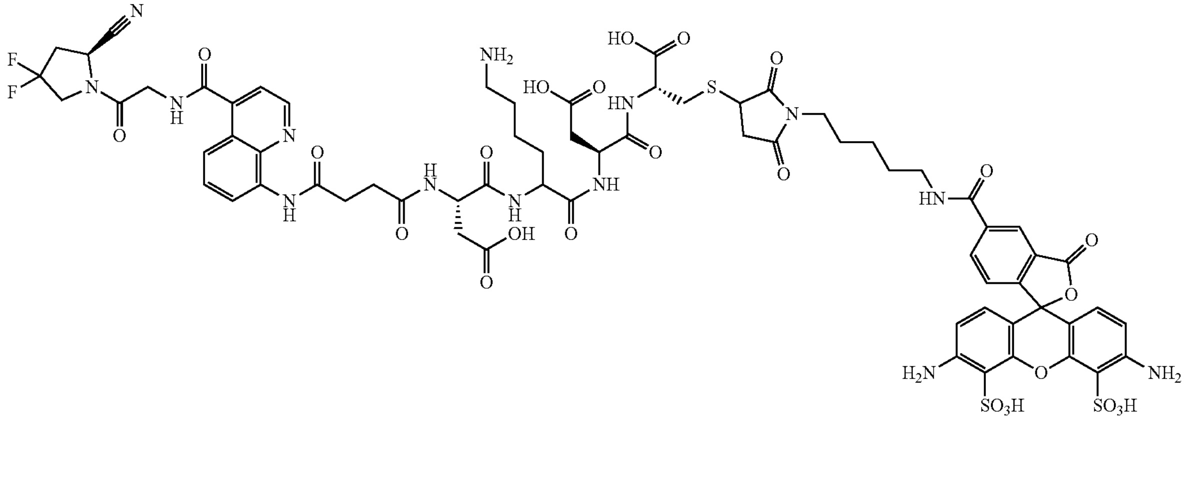 [SMILES: N#C[C@@H]1CC(F)(F)CN1C(=O)CNC(=O)c1ccnc2c(NC(=O)CCC(=O)N[C@@H](CC(=O)O)C(=O)NC(CCCCN)C(=O)N[C@@H](CC(=O)O)C(=O)N[C@@H](CSC3CC(=O)N(CCCCCNC(=O)c4ccc5c(c4)C(=O)OC54c5ccc(N)c(S(=O)(=O)O)c5Oc5c4ccc(N)c5S(=O)(=O)O)C3=O)C(=O)O)cccc12]

SH-Cys-Asp-Lys-Asp-ESV6 (293 μg, 0.32 μmol, 1.0 eq) was dissolved in PBS pH 7.4 (300 μL). Alexa Fluor™ 488 C5 Maleimide (200 μg, 0.29 μmol, 0.9 eq) was added as dry DMSO solution (200 μL). The reaction was stirred for 3 h.

The crude material was purified by reversed-phase HPLC (Water 0.1% TFA/Acetonitrile 0.10% TFA 9.5:0.5 to 2:8 in 20 min) and lyophilized, to obtain an orange solid (70 nmol, 21.9%). MS($ES^+$) m/z 1619.39 $(M+1H)^{1+}$ Synthesis of ESV6-ValCit-PNU 159682 Conjugate 31

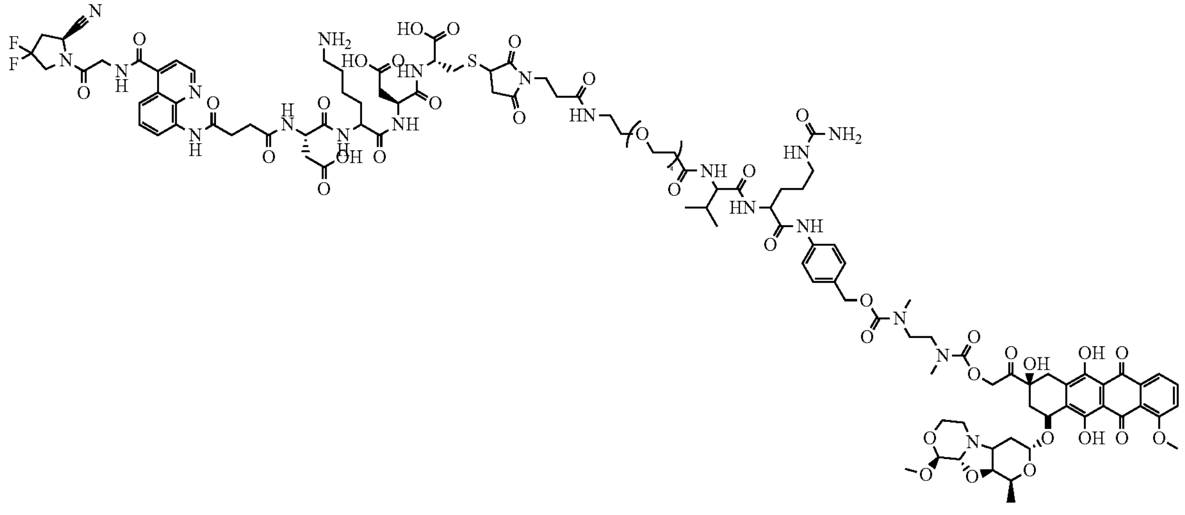

SH-Cys-Asp-Lys-Asp-ESV-6 (2 mg, 2.17 μmol, 1.2 eq) was dissolved in PBS pH 7.4 (750 μL). MA-PEG4-VC-PAB-DMAE-PNU 159682 (2.5 mg, 1.75 μmol, 1.0 eq) was added as dry DMF solution (250 μL). The reaction was stirred for 3 h.

The crude material was purified by reversed-phase HPLC (Water 0.1% TFA/Acetonitrile 0.10% TFA 9.5:0.5 to 2:8 in 20 min) and lyophilized, to obtain a white solid (3 mg, 73%). MS($ES^+$) m/z 2348.88 $(M+H)^+$ Synthesis of QCOOH-ValCit-PNU 159682 Conjugate 32

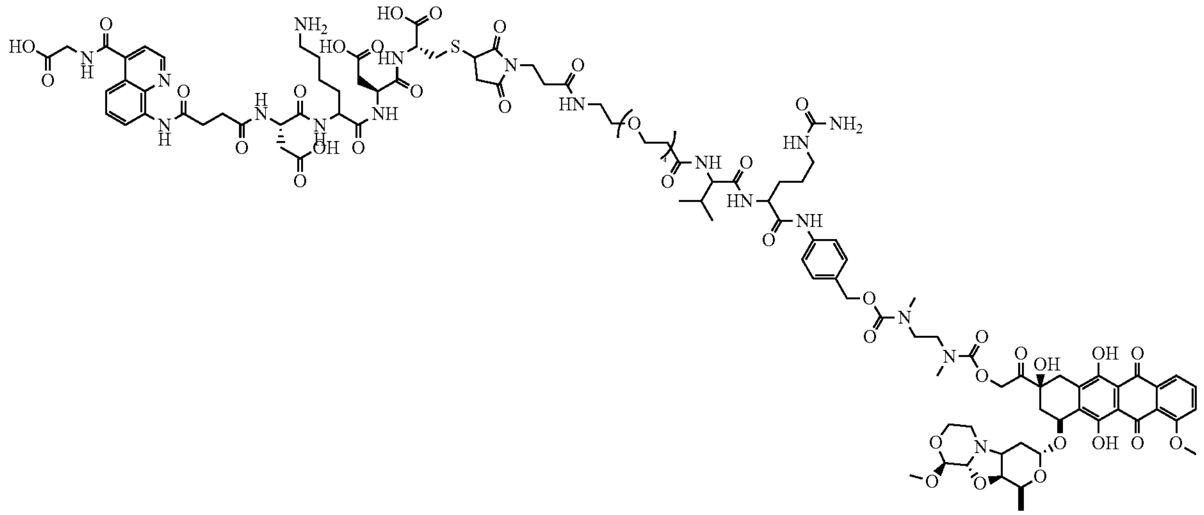

SH-Cys-Asp-Lys-Asp-QCOOH (1.6 mg, 2.17 μmol, 1.2 eq) was dissolved in PBS pH 7.4 (750 μL). MA-PEG4-VC-PAB-DMAE-PNU 159682 (2.5 mg, 1.75 μmol, 1.0 eq) was added as dry DMF solution (250 μL). The reaction was stirred for 3 h.

The crude material was purified by reversed-phase HPLC (Water 0.1% TFA/Acetonitrile 0.10% TFA 9.5:0.5 to 2:8 in 20 min) and lyophilized, to obtain a white solid (2.8 mg, 73%).

Example 10: Characterization and Biological Testing of Compounds 18, 19, 21, P4, 27, 28, 29, 30

Materials and Methods

In Vitro Inhibition Assay on hFAP

Enzymatic activity of human FAP on the Z-Gly-Pro-AMC substrate was measured at room temperature on a microtiter plate reader, monitoring the fluorescence at an excitation wavelength of 360 nm and an emission wavelength of 465 nm. The reaction mixture contained 20 μM substrate, 20 nM human FAP (constant), assay buffer (50 mM Tris, 100 mM NaCl, 1 mM EDTA, pH=7.4) and tested compound (serial dilution from $10^{-6}$ to $10^{-11}$ M, 1:2) in a total volume of 20 μL. The $IC_{50}$ value is defined as the concentration of inhibitor required to reduce the enzyme activity by 50% after addition of the substrate.

Cell Cultures

Upon thawing, SK-MEL-187, SK-RC-52.hFAP and SK-RC-52.wt cells were kept in culture in RPMI medium supplemented with fetal bovine serum (10%, FBS) and Antibiotic-Antimycotic (1%, AA) at 37° C. and 5% $CO_2$. For passaging, cells were detached using Trypsin-EDTA 0.05% when reaching 90% confluence and re-seeded at a dilution of 1:4.

Upon thawing, HT-1080.hFAP and HT-1080.wt cells were kept in culture in DMEM medium supplemented with fetal bovine serum (10%, FBS) and Antibiotic-Antimycotic (1%, AA) at 37° C. and 5% $CO_2$. For passaging, cells were detached using Trypsin-EDTA 0.05% when reaching 90% confluence and re-seeded at a dilution of 1:4.

Animal Studies

All animal experiments were conducted in accordance with Swiss animal welfare laws and regulations under the license number ZH04/2018 granted by the Veterinäramt des Kantons Zürich.

Implantation of Subcutaneous SK-RC-52.hFAP and HT-1080.hFAP Tumors

SK-RC-52.hFAP, HT-1080.hFAP, SK-RC-52.wt cells were grown to 80% confluence and detached with Trypsin-EDTA 0.05%. Cells were re-suspended in HBSS medium to a final concentration of $5\times10^7$ cells/mL. Aliquots of $5\times10^6$ cells (100 μL of suspension) were injected subcutaneously in the flank of female athymic BALB/C nu/nu mice (6-8 weeks of age). SK-MEL-187 cells were grown to 80% confluence and detached with Trypsin-EDTA 0.05%. Cells were re-suspended in a 1:1 mixture of HBSS:Matrigel to a final concentration of $10\times10^7$ cells/mL. Aliquots of $5\times10^6$ cells (200 μL of suspension) were injected subcutaneously in the flank of female athymic BALB/C nu/nu mice (6-8 weeks of age).

IVIS Experiments

In a first experiment, HT-1080.hFAP xenografted tumors were implanted into the right flank of female athymic BALB/C nu/nu mice (6-8 weeks of age) as described above, and allowed to grow to an average volume of 0.1 mL. SK-RC-52.wt xenografted tumors were implanted into the right flank of female athymic BALB/C nu/nu mice (6-8 weeks of age) as described above, and allowed to grow to an average volume of 0.1 mL.

Mice were injected intravenously with ESV6-IRDye750 (18, 150 nmol/Kg, as 30 μM solutions prepared in sterile PBS, pH 7.4). Mice were sacrificed by $CO_2$ asphyxiation (1 h time point) and fluorescence images of all collected organs (blood, heart, muscle, lung, kidneys, liver, spleen, stomach, a section of the intestine, SK-RC-52.wt tumor and HT-1080.hFAP) were acquired on an IVIS Spectrum imaging system (Xenogen, exposure Is, binning factor 8, excitation at 745 nm, emission filter at 800 nm, f number 2, field of view 13.1).

In a different experiment, SK-MEL-187 xenografted tumors were implanted into the right flank of female athymic BALB/C nu/nu mice (6-8 weeks of age) as described above, and allowed to grow to an average volume of 0.1 mL. SK-RC-52.hFAP xenografted tumors were implanted into the left flank of female athymic BALB/C nu/nu mice (6-8 weeks of age) as described above, and allowed to grow to an average volume of 0.1 mL. Mice were injected intravenously with ESV6-IRDye750 (18, 150 nmol/Kg, as 30 μM solutions prepared in sterile PBS, pH 7.4). Mice were sacrificed by $CO_2$ asphyxiation (1 h time point) and fluorescence images of all collected organs (blood, heart, muscle, lung, kidneys, liver, spleen, stomach, a section of the intestine, SK-MEL-187 tumor and SK-RC-52.hFAP) were acquired on an IVIS Spectrum imaging system (Xenogen, exposure Is, binning factor 8, excitation at 745 nm, emission filter at 800 nm, f number 2, field of view 13.1).

Ex Vivo Experiments

Mice bearing subcutaneous SK-RC-52.hFAP or HT-1080.hFAP tumors on the right flank and SK-RC-52.wt tumor on the left flank were injected intravenously with conjugate 30 (40 nmol in sterile PBS, pH 7.4). Animals were sacrificed by $CO_2$ asphyxiation 1 h after the intravenous injection and the organs and the tumors were excised, snap-frozen in OCT medium (Thermo Scientific) and stored at −80° C. Cryostat sections (7 m) were cut and nuclei were stained with Fluorescence Mounting Medium (Dako Omnis, Agilent). Images were obtained using an Axioskop2 mot plus microscope (Zeiss) and analyzed by ImageJ 1.53 software.

Therapy Experiments

SK-RC-52.hFAP xenografted tumors were implanted into female athymic BALB/C nu/nu mice (6-8 weeks of age) as described above, and allowed to grow to an average volume of 0.1 mL.

Mice were randomly assigned into 8 therapy groups of 4 animals each (5 single-agent groups, 2 combination groups and vehicle group). ESV6-ValCit-MMAE (21, 500 nmol/kg), QCOOH-ValCit-MMAE (19, 500 nmol/kg) were injected as sterile PBS solution with 2% of DMSO. L19-IL2 was diluted at 330 μg/mL in the appropriate formulation buffer and intravenously administered at the dose of 2.5 mg/kg.

Mice in single-agent groups received daily injections of ESV6-ValCit-MMAE, QCOOH-ValCit-MMAE or L 19-IL2.

Mice in combination groups received daily injections of ESV6-ValCit-MMAE on day 8,10 and 12 after tumor implantation, and of L 19-IL2 on day 9,11 and 13 after tumor implantation.

Tumors were measured with an electronic caliper and animals were weighted daily. Tumor volume ($mm^3$) was calculated with the formula (long side, mm)×(short side, mm)×(short side, mm)×0.5.

Prism 6 software (GraphPad Software) was used for data analysis (regular two-way ANOVA followed by Bonferroni test).

Biodistribution Experiment

SK-RC-52.hFAP (right flank) and SK-RC-52.wt (left flank) xenografted tumors were implanted into female athymic BALB/C nu/nu mice (6-8 weeks of age) as described above, and allowed to grow to an average volume of 0.1 mL.

Mice were injected with ESV6-ValCit-MMAE (21, 250 nmol/kg) and sacrificed by $CO_2$ asphyxiation 6 h after the intravenous injection and the organs and the tumors were excised and conserved at −80° C. Frozen organs were cutted with a scalpel (50 mg), and suspended in 600 μL of 95:5 Acetonitrile/water (0.1% TFA). A solution of D8-MMAE in 3:97 Acetonitrile/water (0.1% FA; internal standard, 50 μL, 50 nM) was added. The samples were mechanically lysed with a Tissue Lyser II (Qiagen, 30 Hz shaking, 15 minutes). Plasma samples (50 μL) were added with a solution of D8-MMAE in 3:97 Acetonitrile/water (0.1% FA; internal standard, 50 μL, 50 nM) and proteins were precipitated by addition of 600 μL of 95:5 Acetonitrile/water (0.1% TFA). Proteins from both organs and plasma samples were pelleted by centrifugation and supernatants were dried with a vacuum centrifuge. Solid remanences were resuspended in 1 mL of 3:97 Acetonitrile/water (0.1% TFA) and solutions were cleaned up through a first purification step on HBL Oasis columns and a second purification on C18 Macro Spin Columns. Purified dried eluates were resuspended in 150 μL of 3:97 Acetonitrile/water (0.1% FA) and analyzed by MS. All samples were analysed by liquid chromatography-tandem mass spectrometry (LC-MS/MS) using a Q Exactive Mass Spectrometer fitted with an EASY-nLC 1000 (both Thermo Fisher Scientific). Analytes were resolved with an Acclaim PepMap RSLC C18, 50 m×150 mm, 2 m analytical column (Thermo Fisher Scientific) at a flow rate of 0.3 It/min by running a linear gradient from 3% to 50% ACN over 60 min. All buffers contained 0.1% formic acid. MS spectra were recorded in SIM scan mode with a resolution of 70000 and a maximum injection time of 100 ms. MS/MS were recorded at a resolution of 35000 and a maximum injection time of 250 ms. The 4 SIM windows were centred on the doubly and triply charged ions of ESV6-ValCit-MMAE, 1119.0435 m/z and 746.3648 m/z respectively.

Raw files were then analysed with the Skyline software. MS1 areas of the two ions were used for quantification.

Mouse Serum Stability

Labelling solution of Conjugate 27 (100 μL, 200 μM) was spiked into 100 μL of mouse serum and incubated at room temperature. Right after the addition and after 10 min, 1 h, 3 h and 6 h, the proteins were precipitated by adding 100 μL of methanol and the samples were centrifuged at 16300 rpm for 10 minutes. The supernatant was collected and checked with analytical HPLC (Water 0.1% TFA/Acetonitrile 0.1% TFA 9.5:0.5 to 2:8 in 20 min) and the identity of the peak was assessed via LC/MS.

Results

Figure 16:
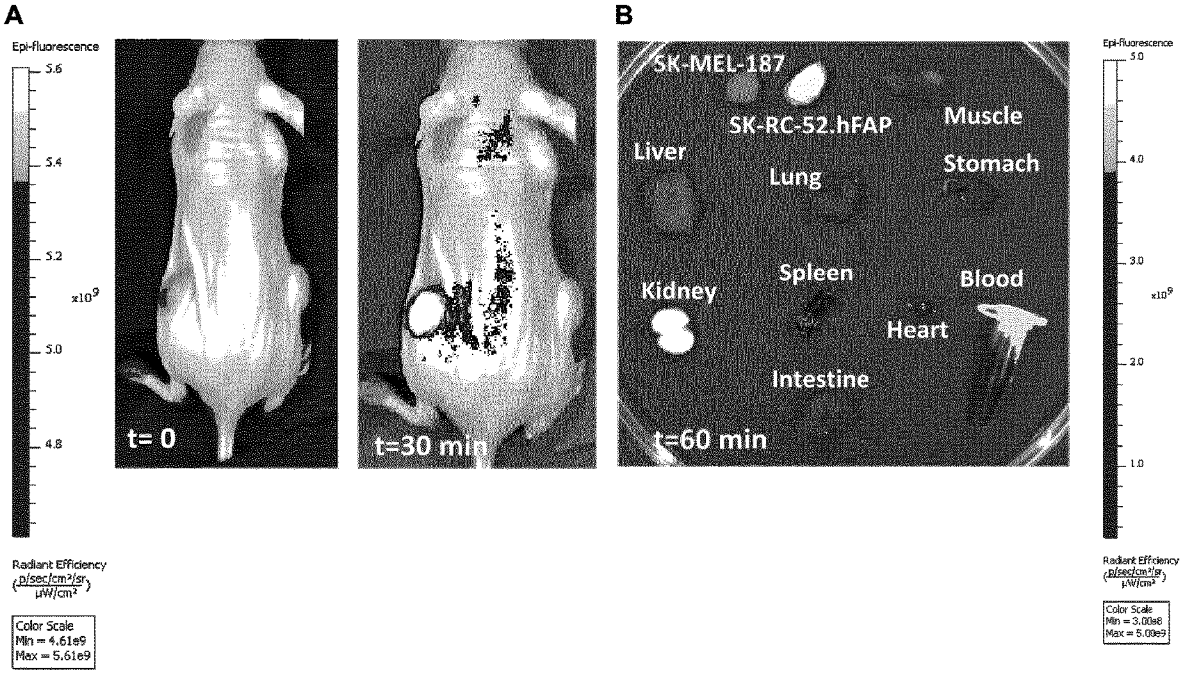
FIG. 16: Evaluation of targeting performance of IRDye 750 conjugate 18 in near-infrared fluorescence imaging of BALB/C nu/nu mice bearing SK-MEL-187 (right flank) and SK-RC-52.hFAP (left flank) xenografts after intravenous administration (dose of 150 nmol/Kg). (A) Images of live animals before the injection (t=0) and 30 minutes after the intravenous injection. (B) Ex vivo organ images at 60 minutes are presented. Compound ESV6-IRDye750 (18) accumulates both to SK-RC-52.hFAP and to SK-MEL-187 tumours, presenting a higher accumulation in SK-RC-52.hFAP tumours due to higher FAP expression compared to SK-MEL-187.
Figure 16:
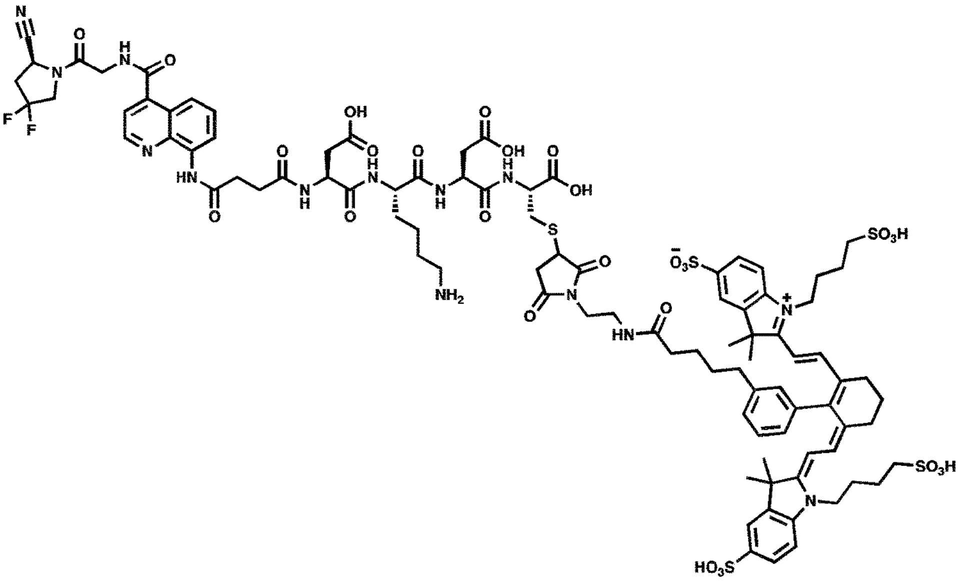

FIG. 16 shows results of evaluation of targeting performance of IRDye 750 conjugate 18 in near-infrared fluorescence imaging of BALB/C nu/nu mice bearing SK-MEL-187 (right flank) and SK-RC-52.hFAP (left flank) xenografts after intravenous administration (dose of 150 nmol/Kg): (A) Images of live animals before the injection and 30 minutes after the intravenous injection; (B) Ex vivo organ images at 1 h are presented. Compound ESV6-IRDye750 (18) accumulates both to SK-RC-52.hFAP and to SK-MEL-187 tumours, presenting a higher accumulation in SK-RC-52.hFAP tumours due to higher FAP expression compared to SK-MEL-187.

Figure 17:
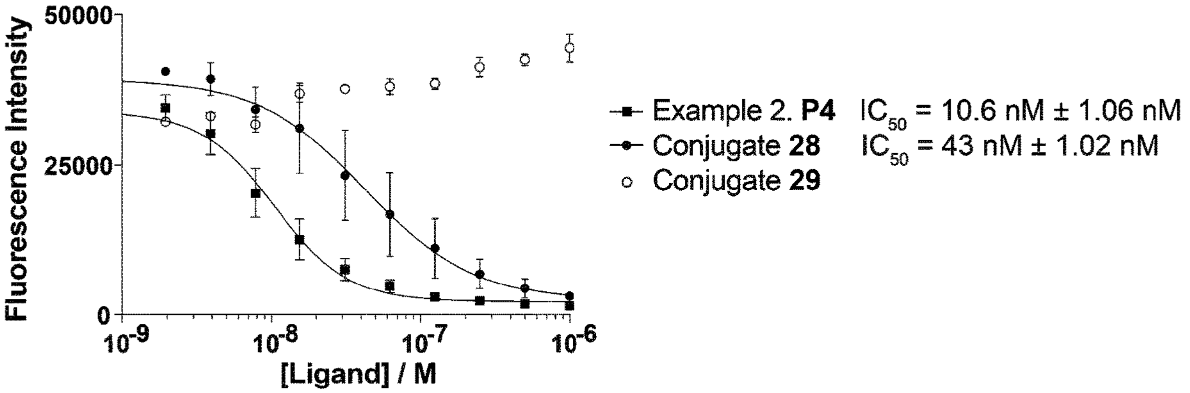
FIG. 17: hFAP inhibition experiment in the presence of different small organic ligands. Conjugate 28 displays a lower FAP inhibition property compared with Example 2, P4. Conjugate 29, including a L-alanine building block between the cyanopyrrolidine headpiece and the pyridine ring, does not inhibit FAP proteolytic activity at the concentrations tested in the assay.
Figure 17:
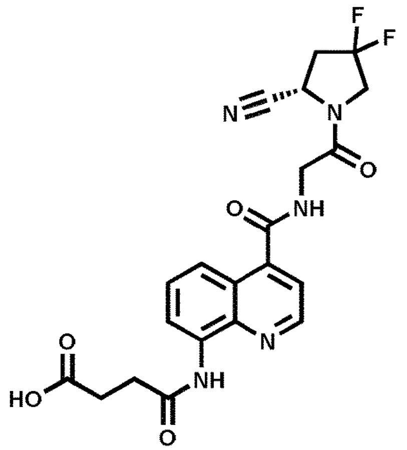
Figure 17:
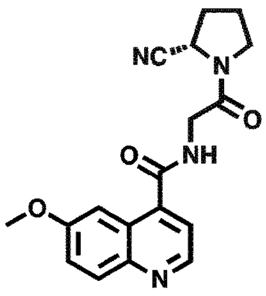
Figure 17:
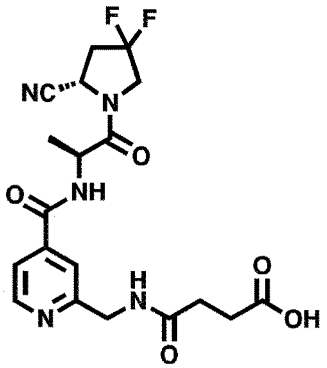

FIG. 17 shows hFAP inhibition experiment in the presence of different small organic ligands. Conjugate 28 displays a lower FAP inhibition property compared with Example 2, P4. Conjugate 29, including a L-alanine building block between the cyanopyrrolidine headpiece and the pyridine ring, does not inhibit FAP proteolytic activity at the concentrations tested in the assay.

Figure 18:
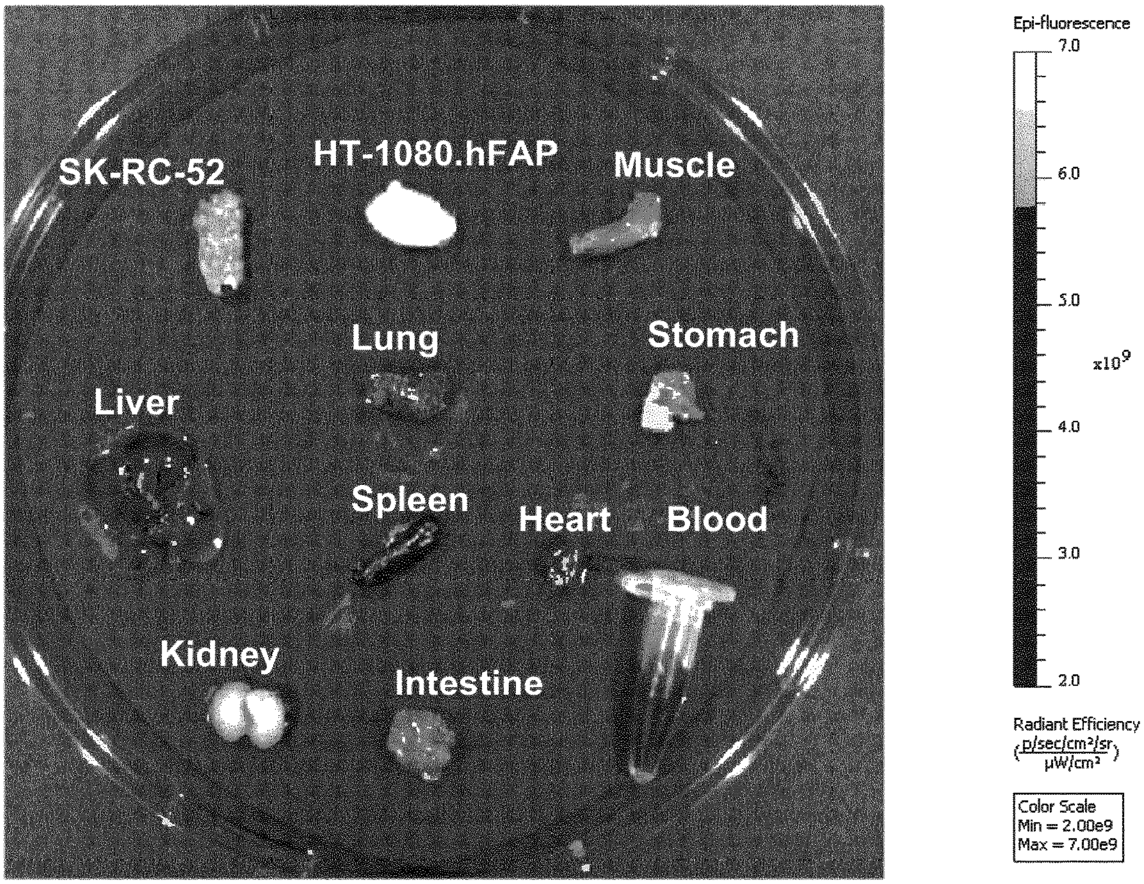
FIG. 18: Evaluation of targeting performance of IRDye 750 conjugate 18 in near-infrared fluorescence imaging of BALB/C nu/nu mice bearing HT-1080.hFAP and SK-RC-52.wt xenografts after intravenous administration (dose of 150 nmol/Kg). Ex vivo organ images at 1 h are presented. Compound ESV6-IRDye750 (18) selectively accumulates to HT-1080.hFAP tumour which presents FAP expression and does not accumulate in SK-RC-52.wt.
Figure 18:
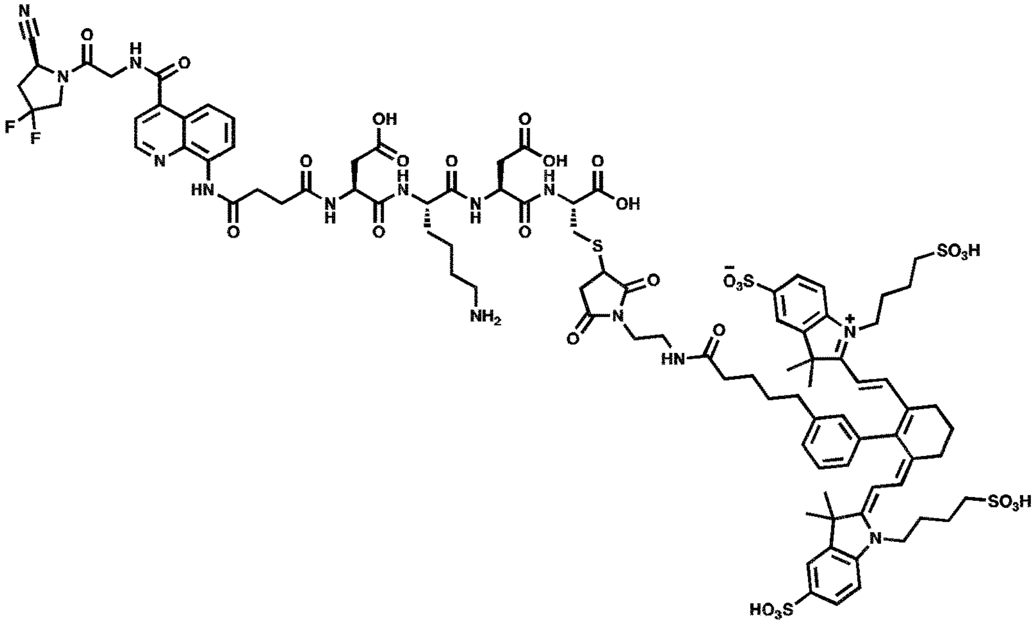

FIG. 18 shows results of evaluation of targeting performance of IRDye 750 conjugate 18 in near-infrared fluorescence imaging of BALB/C nu/nu mice bearing HT-1080.hFAP and SK-RC-52.wt xenografts after intravenous administration (dose of 150 nmol/Kg). Ex vivo organ images at 1 h are presented. Compound ESV6-IRDye750 (18) selectively accumulates to HT-1080.hFAP tumour which presents FAP expression and does not accumulate in SK-RC-52.wt.

Figure 19A:
FIG. 19: (A) Evaluation of targeting performance of conjugate 30 in BALB/C nu/nu mice bearing SK-RC-52.hFAP (right flank) and SK-RC-52.wt (left flank) xenografts after intravenous administration (40 nmol). Ex vivo organ images 1 h after administration are presented. The compound localises rapidly, homogeneously and selectively in vivo at the tumour which presents FAP expression 1 hour after the intravenous injection, with an excellent tumour-to-organs selectivity. (B) Structure of ESV6-Alexa Fluor 488 (30).
Figure 19B:
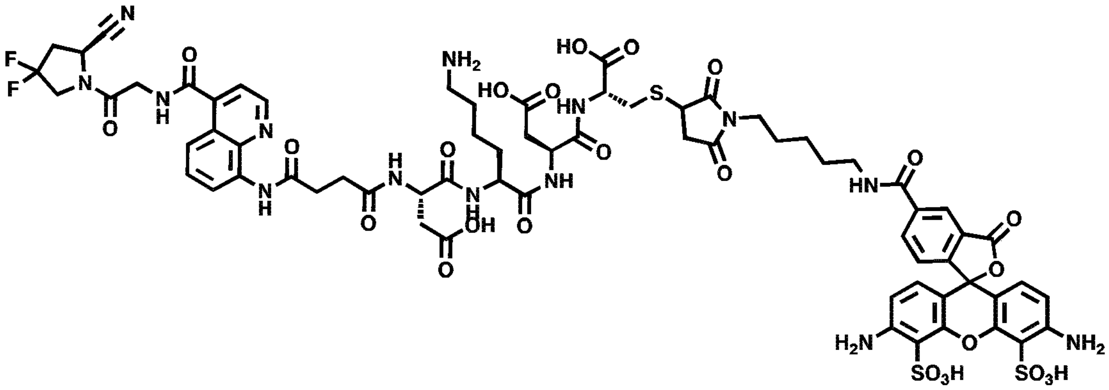

FIG. 19 shows results of evaluation of targeting performance of conjugate 30 in BALB/C nu/nu mice bearing SK-RC-52.hFAP (right flank) and SK-RC-52.wt (left flank) xenografts after intravenous administration (40 nmol). Ex vivo organ images 1 h after administration are presented. The compound localises rapidly, homogeneously and selectively in vivo at the tumour which presents FAP expression 1 hour after the intravenous injection, with an excellent tumour-to-organs selectivity. (B) shows the structure of ESV6-Alexa Fluor 488 (30).

Figure 20A:
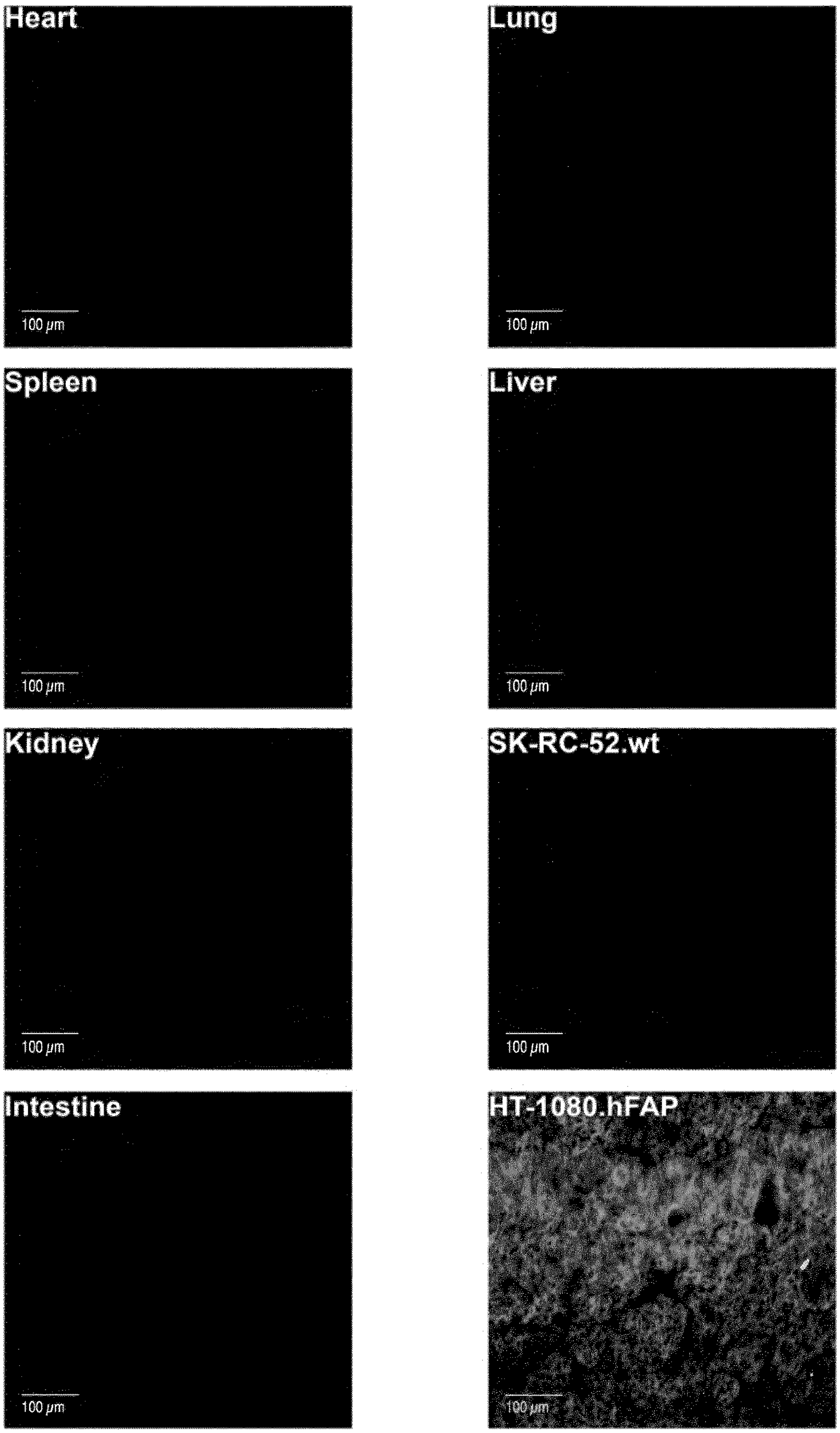
FIG. 20: (A) Evaluation of targeting performance of conjugate 30 in BALB/C nu/nu mice bearing HT-1080.hFAP (right flank) and SK-RC-52.wt (left flank) xenografts after intravenous administration (40 nmol). Ex vivo organ images 1 h after administration are presented. The compound rapidly, homogeneously and selectively localizes in vivo at the tumour which presents FAP expression 1 hour after the intravenous injection, with an excellent tumour-to-organs selectivity. (B) Structure of ESV6-Alexa Fluor 488 (30).
Figure 20B:
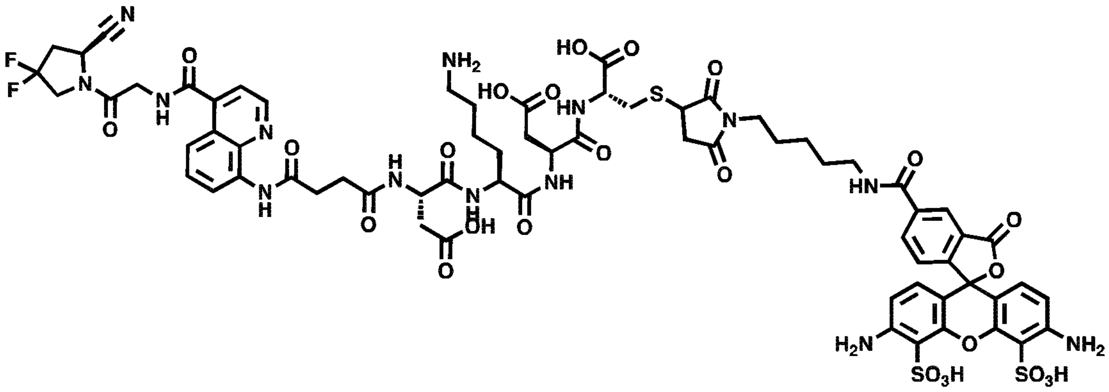

FIG. 20 shows results of Evaluation of targeting performance of conjugate 30 in BALB/C nu/nu mice bearing HT-1080.hFAP (right flank) and SK-RC-52.wt (left flank) xenografts after intravenous administration (40 nmol). Ex vivo organ images 1 h after administration are presented (A). The compound rapidly, homogeneously and selectively localizes in vivo at the tumour which presents FAP expression 1 hour after the intravenous injection, with an excellent tumour-to-organs selectivity. (B) shows the structure of ESV6-Alexa Fluor 488 (30).

Figure 21:
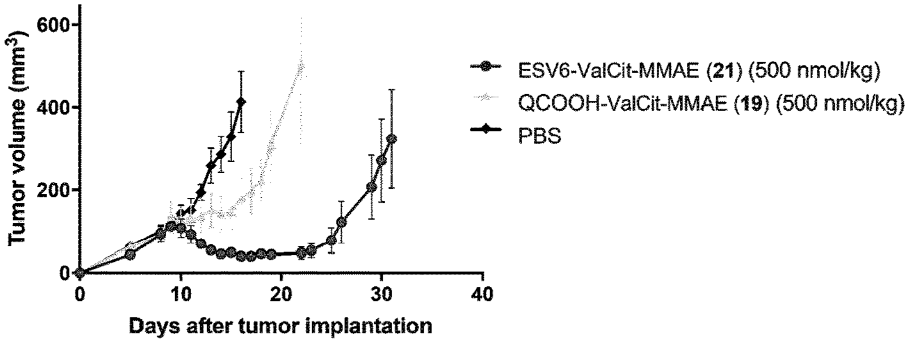
FIG. 21: (A) Assessment of therapeutic activity of ESV6-ValCit-MMAE (21) and QCOH-ValCit-MMAE (19) in SK-RC-52.hFAP tumour bearing mice. Data points represent mean tumour volume±SEM (n=4 per group). The compounds were administered intravenously (tail vein injection) starting from day 8, for 6 consecutive days. ESV6-ValCit-MMAE (21), a drug conjugate derivative of the high-affinity FAP ligand "ESV6", displays a more potent anti-tumour effect as compared with QCOOH-ValCit-MMAE (19), an untargeted version of the molecule. (B) Tolerability of the different treatments as assessed by the evaluation of changes (%) in body weight of the animals during the experiment. (C) Structures of ESV6-ValCit-MMAE (21) and QCOOH-ValCit-MMAE (19).
Figure 21:
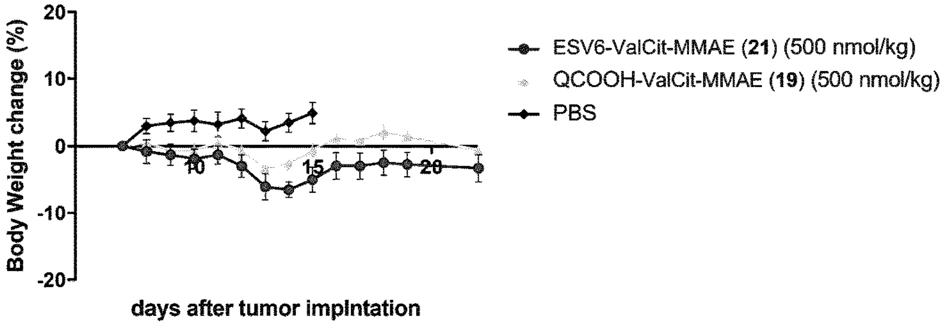
Figure 21:
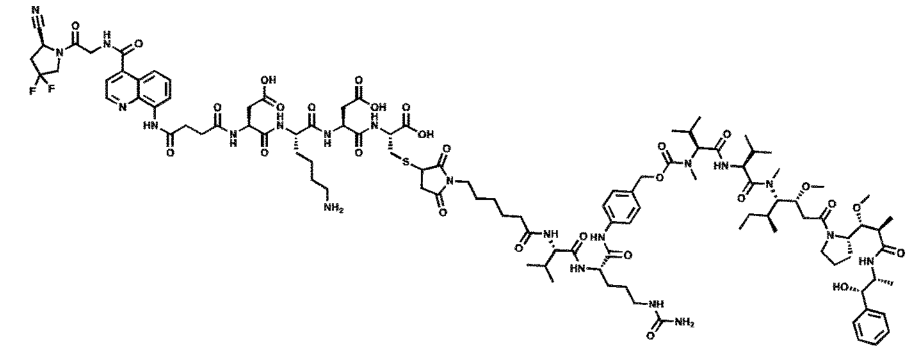
Figure 21:
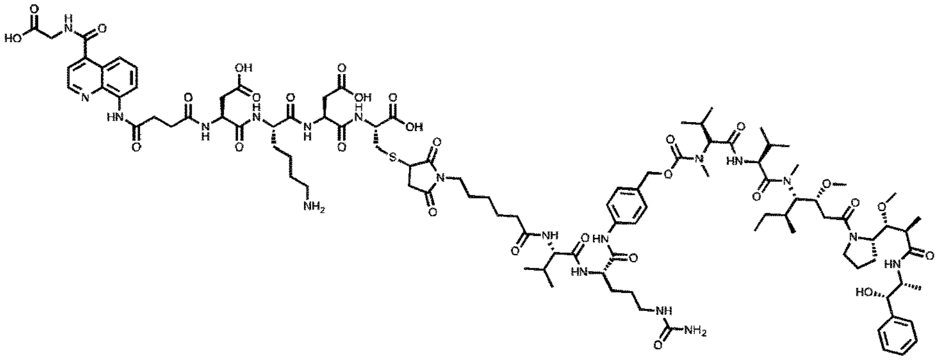

FIG. 21 shows results of assessment of therapeutic activity of ESV6-ValCit-MMAE (21) and QCOH-ValCit-MMAE (19) in SK-RC-52.hFAP tumour bearing mice (A). Data points represent mean tumour volume±SEM (n=4 per group). The compounds were administered intravenously (tail vein injection) starting from day 8, for 6 consecutive days. ESV6-ValCit-MMAE (21), a drug conjugate derivative of the high-affinity FAP ligand "ESV6", displays a more potent anti-tumour effect as compared with QCOOH-ValCit-MMAE (19), an untargeted version of the molecule. (B) shows tolerability of the different treatments as assessed by the evaluation of changes (%) in body weight of the animals during the experiment. (C) Structures of ESV6-ValCit-MMAE (21) and QCOOH-ValCit-MMAE (19).

Figure 22:
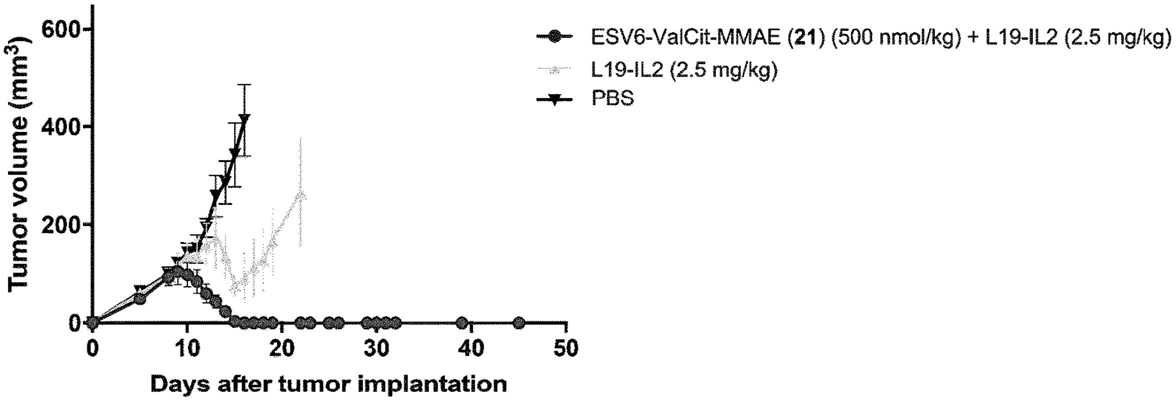
FIG. 22: (A) Assessment of therapeutic activity of ESV6-ValCit-MMAE (21), L19-IL2 and their combination in SK-RC-52.hFAP tumour bearing mice. Data points represent mean tumour volume±SEM (n=4 per group). ESV6-ValCit-MMAE was administered intravenously (tail vein injection) on days 8, 10, 12. L19-IL2 was administered intravenously (tail vein injection) on days 9, 11, 13. ESV6-ValCit-MMAE combined with L19-IL2 displays a very potent anti-tumour effect (4/4 complete tumour regression) as compared with L19-2 alone. (B) Tolerability of the different treatments as assessed by the evaluation of changes (%) in body weight of the animals during the experiment.
Figure 22:
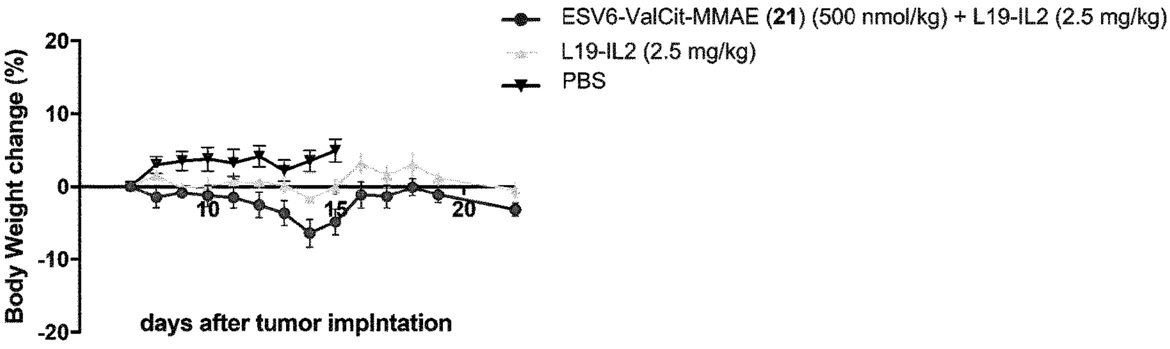
Figure 22:
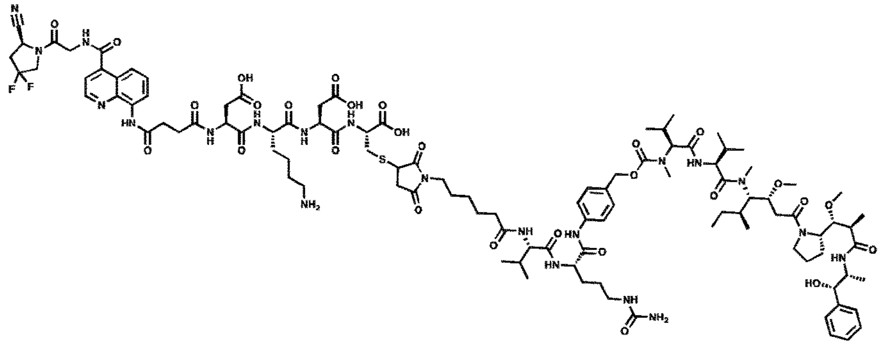

FIG. 22 shows results of assessment of therapeutic activity of ESV6-ValCit-MMAE (21), L19-IL2 and their combination in SK-RC-52.hFAP tumour bearing mice (A). Data points represent mean tumour volume±SEM (n=4 per group). ESV6-ValCit-MMAE was administered intravenously (tail vein injection) on days 8, 10, 12. L19-IL2 was administered intravenously (tail vein injection) on days 9, 11, 13. ESV6-ValCit-MMAE combined with L19-IL2 displays a very potent anti-tumour effect (4/4 complete tumour regression) as compared with L19-2 alone. (B) shows the tolerability of the different treatments as assessed by the evaluation of changes (%) in body weight of the animals during the experiment.

Figure 23:
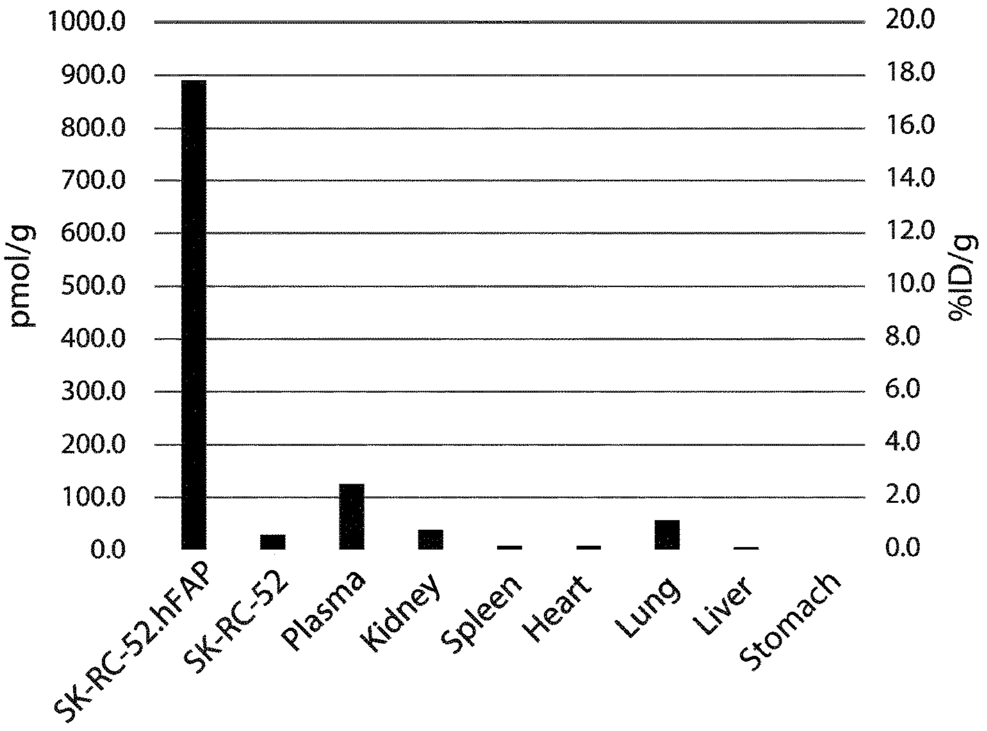
FIG. 23: Quantitative biodistribution experiment of small molecule-drug conjugate ESV6-ValCit-MMAE (21) in BALB/C nu/nu mice bearing SK-RC-52.hFAP on the right flank and SK-RC-52.wt on the left flank. The compound selectively accumulates in FAP-positive SK-RC-52 tumours, (i.e., 18% ID/g at the tumour site, 6 hours after intravenous administration). In contrast, the ESV6-ValCit-MMAE does not accumulate in FAP-negative SK-RC-52 wild type tumours. Uptake of the conjugate in healthy organs is negligible (lower than 1% ID/g).
Figure 23:
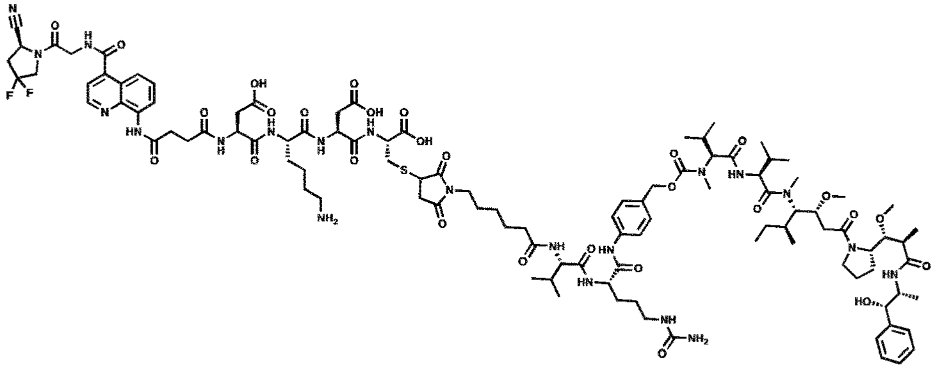

FIG. 23 shows results of quantitative biodistribution experiment of small molecule-drug conjugate ESV6-ValCit-MMAE (21) in BALB/C/nu-/nu mice bearing SK-RC-52.hFAP on the right flank and SK-RC-52.wt on the left flank. The compound selectively accumulates in FAP-positive SK-RC-52 tumours, (i.e., 18% ID/g at the tumour site, 6 hours after intravenous administration). In contrast, the ESV6-ValCit-MMAE does not accumulate in FAP-negative SK-RC-52 wild type tumours. Uptake of the conjugate in healthy organs is negligible (lower than 1% ID/g).

Figure 24:
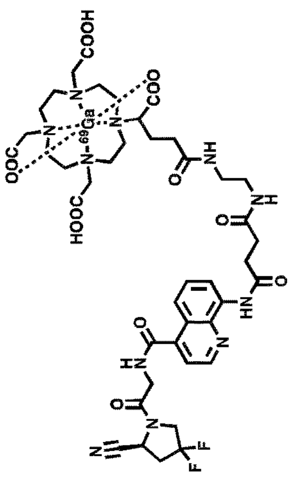
FIG. 24: Stability study of conjugate 27 (which includes a $^{69}$Ga payload) in mouse serum. HPLC and LC/MS profiles of the processed sample at time 0 and 6 hours after the incubation show a single peak with the correct mass (expected mass: 1028.30. MS(ES+) m/z 514.3 (M+2H)) FIG.
Figure 24:
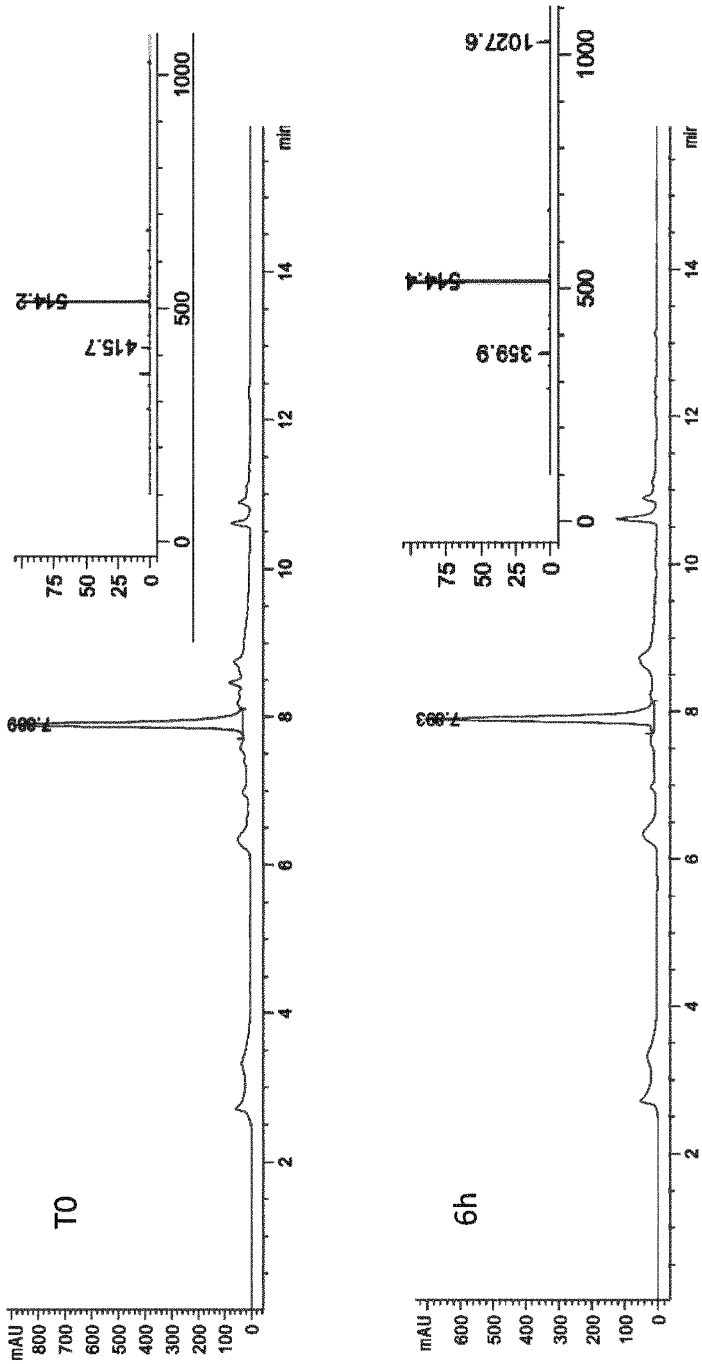

FIG. 24 shows results of stability study of conjugate 27 (which includes a $^{69}$Ga payload) in mouse serum. HPLC and LC/MS profiles of the processed sample at time 0 and 6 hours after the incubation show a single peak with the correct mass (expected mass: 1028.30. MS(ES$^+$) m/z 514.3 (M+2H)).

Example 11: Synthesis of Further Conjugates

Synthesis of Conjugate 39

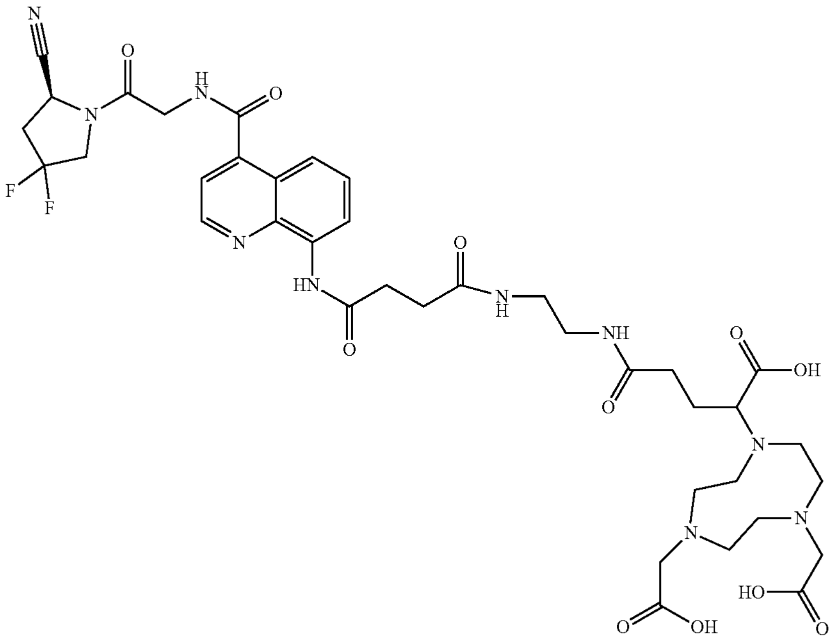 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CC3)cccc12]

(S)-4-((4-((2-(2-cyano-4,4-difluoropyrrolidin-1-yl)-2-oxoethyl)carbamoyl)quinolin-8-yl)amino)-4-oxobutanoic acid (15 mg, 0.032 mmol, 1.0 eq) is dissolved in dry DMSO (400 μL). Dicyclohexylcarbodiimide (9 mg, 0.042 mmol, 1.3 eq) and N-hydroxysuccinimide (4.5 mg, 0.039 mmol, 1.3 eq) are added and the reaction is stirred overnight at room temperature, protected from light. 100 μL of PBS solution containing 2,2'-(7-(4-((2-aminoethyl)amino)-1-carboxy-4-oxobutyl)-1,4,7-triazonane-1,4-diyl)diacetic acid (16.2 mg, 0.039 mmol, 1.2 eq) are added and the reaction is stirred for 2h. The crude product is purified by reversed-phase HPLC (Water 0.1% TFA/Acetonitrile 0.1% TFA 9.5:0.5 to 2:8 in 20 min) and lyophilized, to obtain a white solid. MS(ES$^+$) m/z 858.35 (M+H)$^+$ Synthesis of Conjugate 40

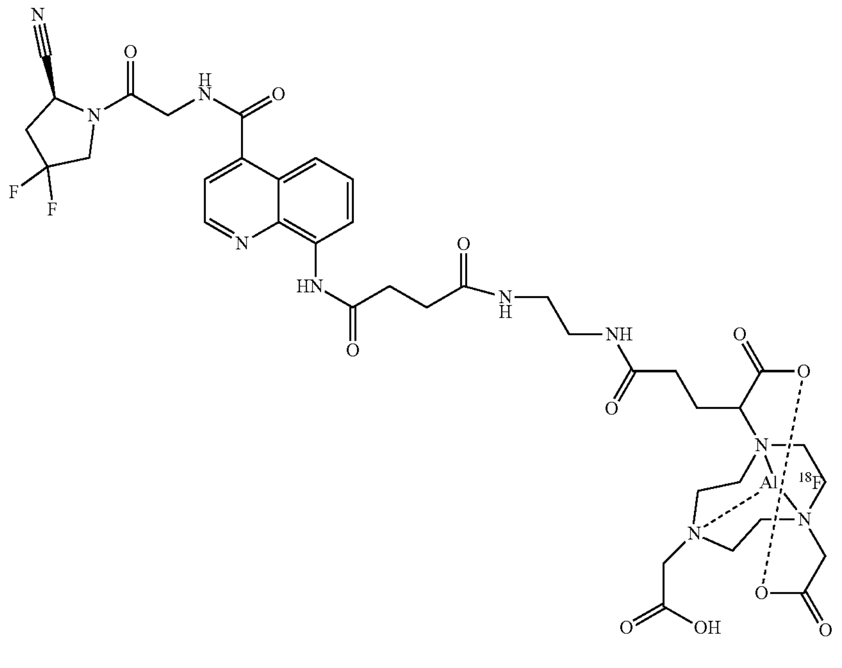

A solution of Conjugate 39 (1 mL, 150 μM) in sodium acetate buffer (0.1 M, pH 4) is added to a separate vial which contain a freshly prepared $(Al^{18}F)^{2+}$ solution (obtained as previously described in the literature, Cleeren et al., *Bioconjugate. Chem.* 2016). The closed vial is heated at 95° C. temperatures for 12 min. the formation of the complex is confirmed by Radio-HPLC and radio-TLC analysis.

Synthesis of Conjugate 41
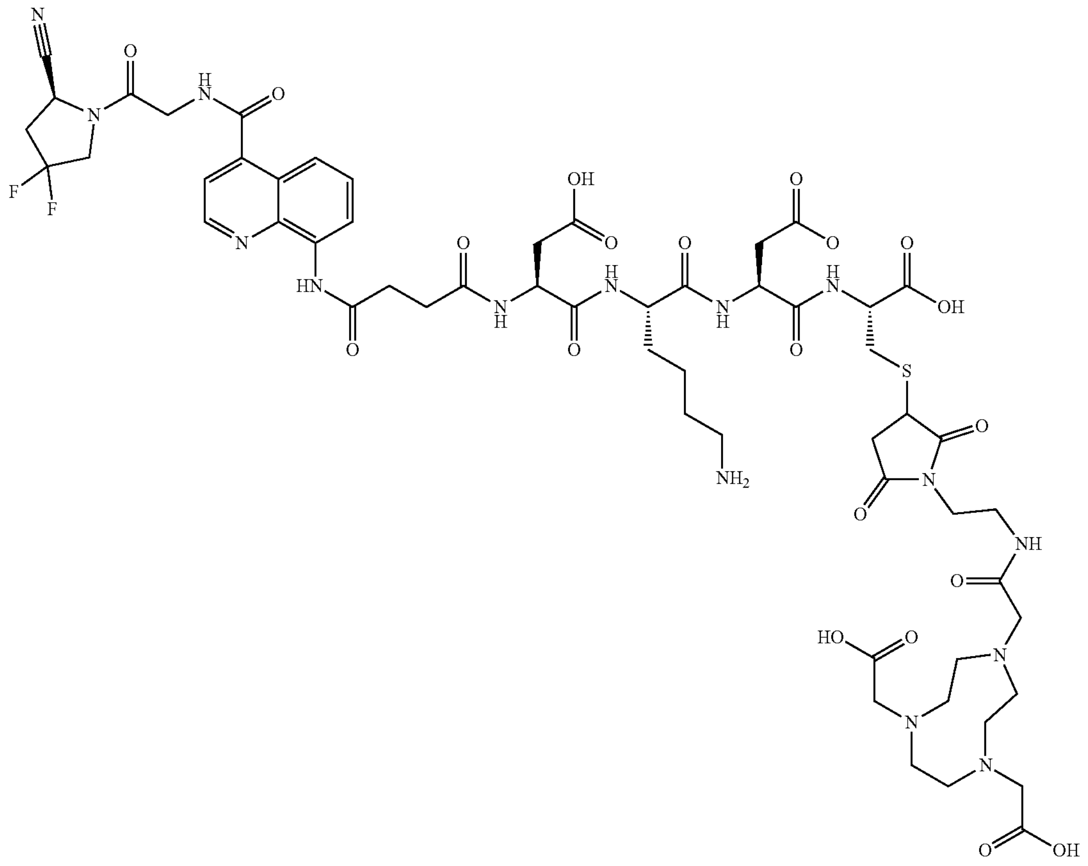 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CSC3CC(=O)N(CCNC(=O)CN4CCN(CC(=O)O)CCN(CC(=O)O)CC4)C3=O)C(=O)O)cccc12]
SH-Cys-Asp-Lys-Asp-ESV6 (2 mg, 2.171 μmol, 1.0 eq) is dissolved in PBS pH 7.4 (800 μL). Maleimido-NOTA (3.0 mg, 4.343 μmol, 2.0 eq) is added as dry DMSO solution (200 μL). The reaction is stirred for 3 h. The crude material is purified by reversed-phase HPLC (Water 0.1% TFA/Acetonitrile 0.1% TFA 9.5:0.5 to 2:8 in 20 min) and lyophilized, to obtain a yellow solid. MS($ES^+$) m/z 1345.48 $(M+1H)^{1+}$.
Synthesis of Conjugate 43a
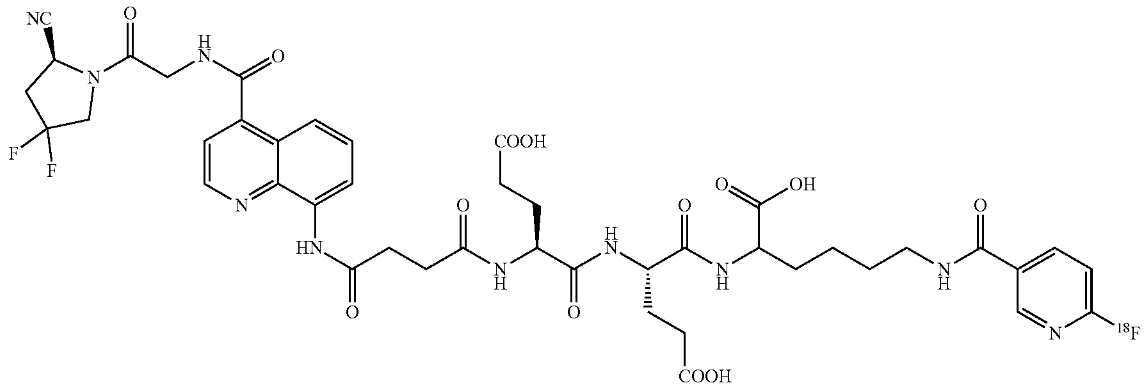 [SMILES: N#C[C@@H]1CC(F)(F)CN1C(=O)CNC(=O)c1ccnc2c(NC(=O)CCC(=O)N[C@@H](CCC(=O)O)C(=O)N[C@@H](CCC(=O)O)C(=O)NC(CCCCNC(=O)c3ccc([18F])nc3)C(=O)O)cccc12]

Commercially available pre-loaded Fmoc-Lys(NeBoc) on Tentagel resin (300 mg, 0.18 mmol, RAPP Polymere) is swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide is extended with Fmoc-Glu(tBu)-OH, Fmoc-Glu(tBu)-OH and (S)-4-((4-((2-(2-cyano-4,4-difluoropyrrolidin-1-yl)-2-oxoethyl)carbamoyl)quinolin-8-yl)amino)-4-oxobutanoic acid in the indicated order. For this purpose, the Fmoc protected amino acid (2.0 eq), HBTU (2.0 eq), HOBt (2.0 eq) and DIPEA (4.0 eq) are dissolved in DMF (5 mL). The mixture is allowed to stand for 10 min at 0° C. and then reacted with the resin for 1 h under gentle agitation. After washing with DMF (6×1 min×5 mL) the Fmoc group is removed with 20% piperidine in DMF (1×1 min×5 min and 2×10 min×5 mL). Deprotection steps are followed by wash steps with DMF (6×1 min×5 mL) prior to coupling with the next aminoacid. The peptide is cleaved from the resin with a mixture of 20% TFA in DCM at room temperature for 1 h. The solvent is removed under reduced pressure and the crude precipitated in cold diethyl ether, centrifuged, dissolved in water/ACN and purify via HPLC (Water 0.10 TFA/Acetonitrile 0.1% TFA 9.5:0.5 to 5:5 in 15 min) and lyophilized, to obtain a white solid. The compound is reacted with 2,3,5,6-tetrafluorophenyl 6-(trimethyl-$\lambda^4$-azaneyl)nicotinate (2.0 eq) in dry acetonitrile (2 mL) overnight. The crude compound is reacted with [$^{18}$F]TBAF (2.0 eq), $TBAHCO_3$ (2.0 eq) in a mixture of tBuOH:MeOH (5:2) at 50° C. for 10 minutes to afford the final compound. MS($ES^+$) m/z 967.33 $(M+1H)^{1+}$

Synthesis of on-resin Cys(STrt)-Cys(STrt)-Asp(OtBu)-Lys(NHBoc)-Asp(OtBu)-NHFmoc Scheme 22. Synthesis route for preparation of on-resin Cys(STrt)-Cys(STrt)-Asp(OtBu)-Lys(NHBoc)-Asp(OtBu)-NHFmoc

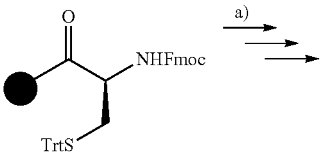

-continued

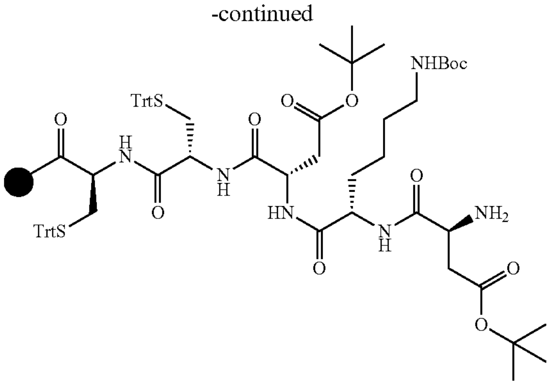

Commercially available pre-loaded Fmoc-Cys(Trt) on Tentagel resin (500 mg, 0.415 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide was extended with Fmoc-Cys(Trt), Fmoc-Asp(tBu)-OH, Fmoc-Lys(NHBoc)-OH and Fmoc-Asp(tBu)-OH in the indicated order. For this purpose, the Fmoc protected amino acid (2.0 eq), HBTU (2.0 eq), HOBt (2.0 eq) and DIPEA (4.0 eq) were dissolved in DMF (5 mL). The mixture was allowed to stand for 10 min at 0° C. and then reacted with the resin for 1 h under gentle agitation. After washing with DMF (6×1 min×5 mL) the Fmoc group was removed with 20% piperidine in DMF (1×1 min×5 min and 2×10 min×5 mL). Deprotection steps were followed by wash steps with DMF (6×1 min×5 mL) prior to coupling with the next amino acid.

Synthesis of (2R,5R,8S,11S,14S)-11-(4-aminobutyl)-8-(carboxymethyl)-14-(4-((4-((2-((S)-2-cyano-4,4-difluoropyrrolidin-1-yl)-2-oxoethyl)carbamoyl)quinolin-8-yl-amino)-4-oxobutanamido)-2,5-bis(mercaptomethyl)-4,7,10,13-tetraoxo-3,6,9,12-tetraazahexadecanedioic acid (SH-Cys-SH-Cys-Asp-Lys-Asp-ESV6, P7)

Scheme 23. Synthesis route for preparation of (2R,5R,8S,11S,14S)-11-(4-aminobutyl)-8-carboxymethyl)-14-((4-((2-((S)-2-cyano-4,4-difluoropyrrolidin-1-yl)-2-oxoethyl)carbamoyl)quinolin-8-yl)amino)-4-oxobutanamido)-2,5-bis(mercaptomethyl)-4,7,10,13-tetraoxo-3,6,9,12-tetraazahexadecanedioic acid (SH-Cys-SH-Cys-Asp-Lys-Asp-ESV6, P7)

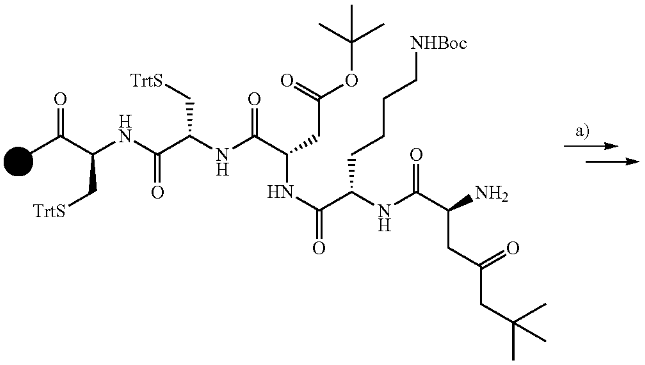

-continued

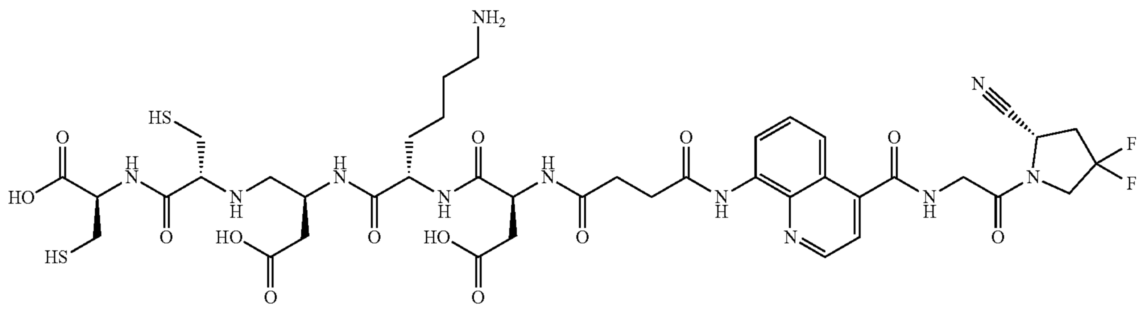

On-resin Cys(STrt)-Cys(STrt)-Asp(OtBu)-Lys(NHBoc)-Asp(OtBu)-NHFmoc (80 mg, 0.04 mmol) was swollen in DMF (3×5 min×5 mL). The peptide was extended with (S)-4-((4-((2-(2-cyano-4,4-difluoropyrrolidin-1-yl)-2-oxoethyl)carbamoyl)quinolin-8-yl)amino)-4-oxobutanoic acid (37 mg, 0.08 mmol, 2 eq), HATU (30 mg, 0.08 mmol, 2.0 eq), and DIPEA (28 μL, 0.16 mmol, 4.0 eq) and let react for 1 h under gentle agitation. After washing with DMF (6×1 min×5 mL), the compound was cleaved by agitating the resin with a mixture of TFA (150), TIS (2.5%) and H2O (2.5 h) in DCM for 4 h at room temperature. The resin was washed with methanol (2×5 mL) and the combined cleavage and washing solutions concentrated under vacuum. The crude product was purified by reversed-phase HPLC (Water 0.1% TFA/Acetonitrile 0.1% TFA 9.5:0.5 to 2:8 in 20 min) and lyophilized, to obtain a white solid (8 mg, 0.95 μmol, 2.4%). MS($ES^+$) m/z 1024.28 $(M+H)^+$ Synthesis of ESV6-ValCit-MMAE-bis (44)
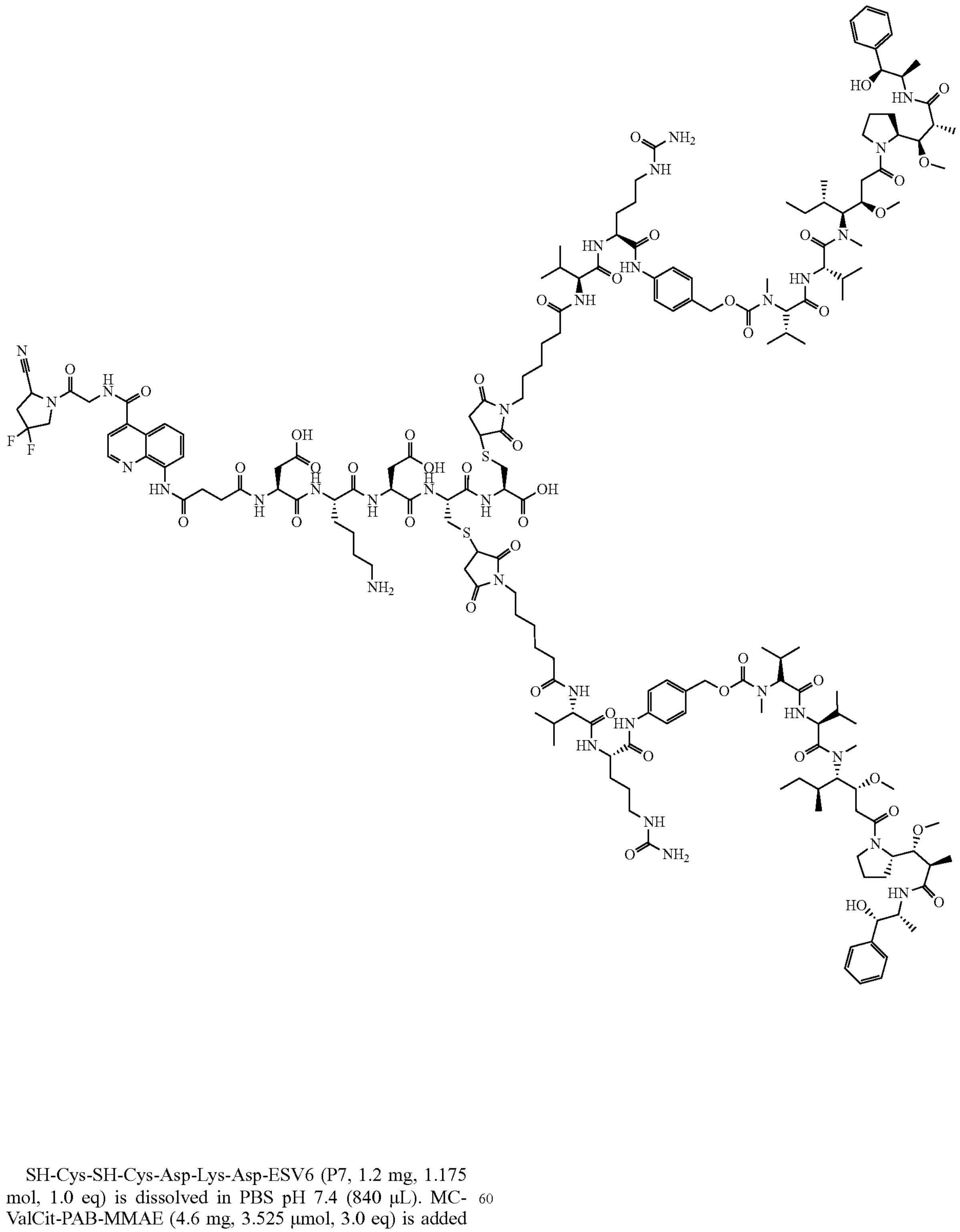
SH-Cys-SH-Cys-Asp-Lys-Asp-ESV6 (P7, 1.2 mg, 1.175 mol, 1.0 eq) is dissolved in PBS pH 7.4 (840 μL). MC-ValCit-PAB-MMAE (4.6 mg, 3.525 μmol, 3.0 eq) is added as dry DMF solution (160 μL). The reaction is stirred for 3 h.
The crude material is purified by reversed-phase HPLC (Water 0.1% TFA/Acetonitrile 0.1% TFA 9.5:0.5 to 2:8 in 20 mi) and lyophilized, to obtain a white solid.
MS($ES^+$) m/z 3656.9 $(M+H)^+$ Synthesis of ESV6_2-ValCit-MMAE-bis (45)

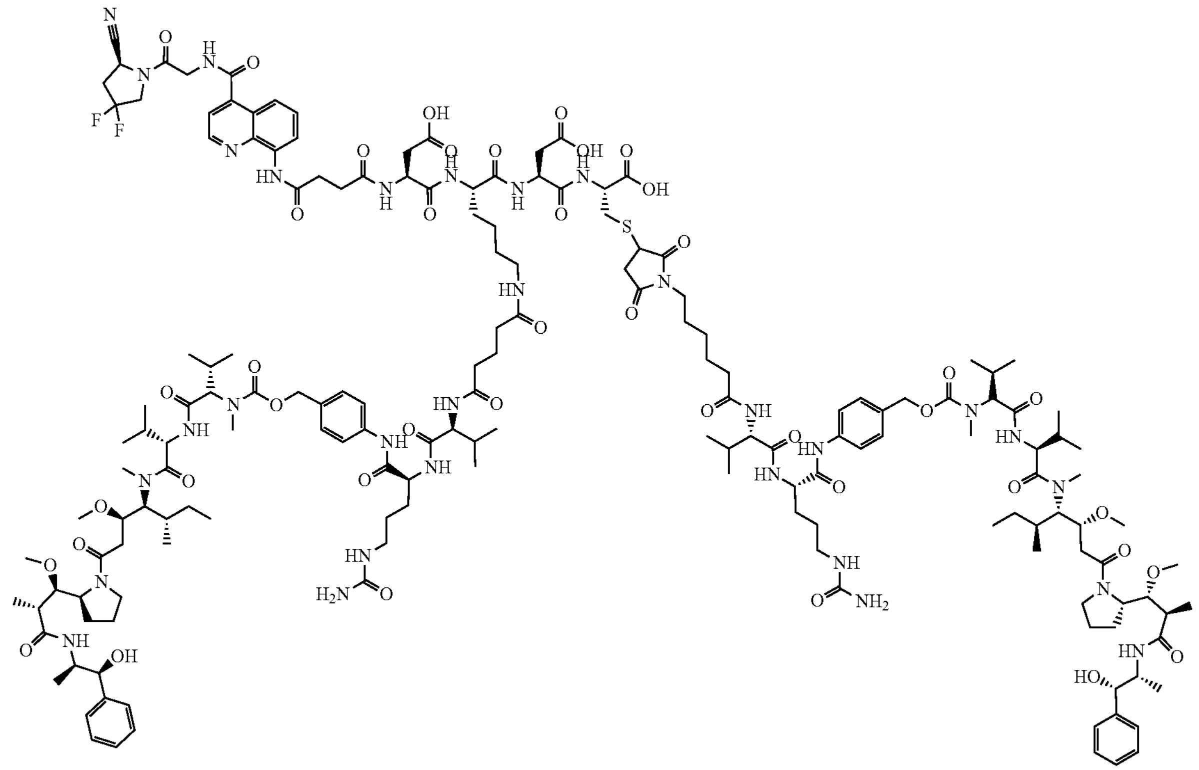

SH-Cys-Asp-Lys-Asp-ESV6 (P7, 1 mg, 1.09 μmol, 1.0 eq) is dissolved in PBS pH 7.4 (840 μL). MC-ValCit-PAB-MMAE (1.4 mg, 1.09 μmol, 1.0 eq) and OSu-Glu-ValCit-PAB-MMAE (1.4 mg, 1.09 μmol, 1.0 eq) are added as dry DMF solution (160 μL). The reaction is stirred for 3 h. The crude material is purified by reversed-phase HPLC (Water 0.1% TFA/Acetonitrile 0.1% TFA 9.5:0.5 to 2:8 in 20 min) and lyophilized, to obtain a white solid.

MS($ES^+$) m/z 3456.8 $(M+H)^+$

Synthesis of (S)—N-(2-(2-cyano-4,4-difluoropyrrolidin-1-yl)-2-oxoethyl)-8-(hex-5-ynamido)quinoline-4-carboxamide (P8)

Scheme 24. Synthesis route for preparation of (S)-N-(2-(2-cyano-4,4-difluoropyrrolidin-1-yl)-2-oxoethyl)-8-(hex-5-ynamido)quinoline-4-carboxamide (P8)

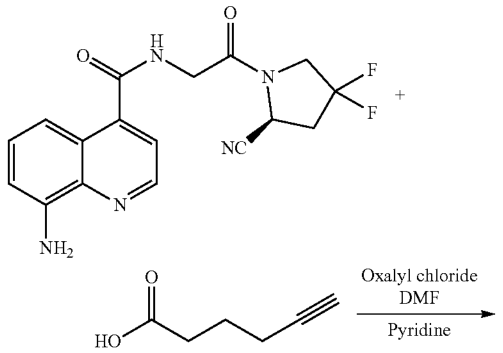

-continued

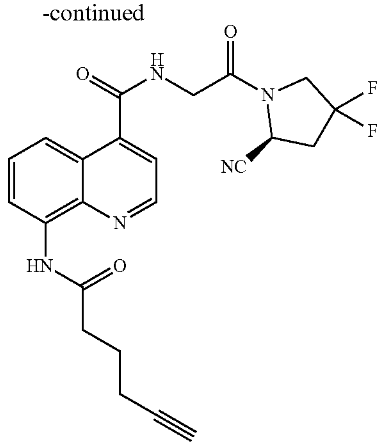

5-hexynoic acid (94 mg, 0.84 mmol, 1.5 eq) was dissolved in 1.5 mL of DCM and 20 μL of DMF in a 25 mL round bottom flask. The mixture was cooled down at 0° C. and oxalyl chloride (107 mg, 0.84 mmol, 1.5 eq) was added dropwise. The ice bath was removed and the reaction stirred for 15 minutes. The mixture was then added to a cooled solution of Example 2-P4 in DMF. After 30 minutes, the crude was diluted with aqueous $NaHCO_3$, extract with DCM, dried over $Na_2SO_4$ anhydrous, filter and concentrated. The crude was purified via chromatography (DCM/MeOH 100:0 to 90:10 in 10 min) to afford a yellow oil (78 mg. 0.267 mmol, 34%). MS($ES^+$) m/z 454.16 $(M+1H)^{1+}$ Synthesis of (S)-8-(4-(1-(5-((2-(2-(2-aminoethoxy)ethoxy)ethyl)amino)-5-oxopentyl)-1H-1,2,3-triazol-4-yl)butanamido)-N-(2-(2-cyano-4,4-difluoropyrrolidin-1-yl)-2-oxoethyl)quinoline-4-carboxamide (P9)

Scheme 25. Synthesis of route for preparation of (S)-8-(4-(1-(5-((2-(2-aminoethoxy)ethoxy)ethyl)amino)-5-oxopentyl)-1H-1,2,3-triazol-4-yl)butanamido)-N-(2-(2-cyano-4,4-difluoropyrrolidin-1-yl)-2-oxoethyl)quinoline-4-carboxamide (P9)

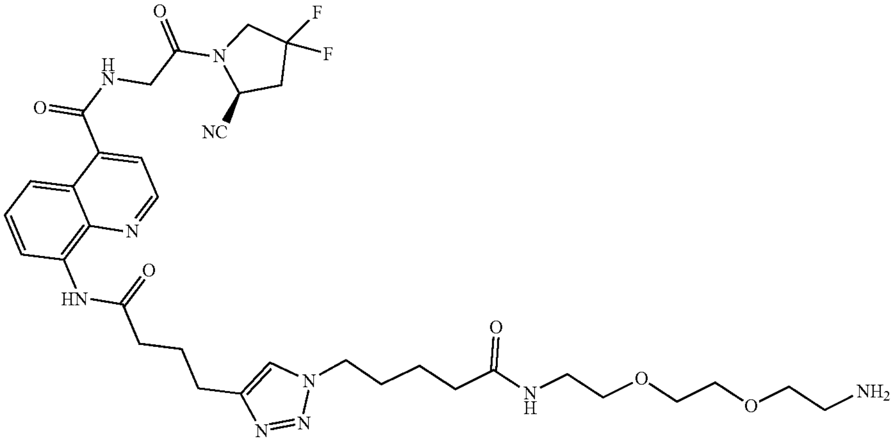

Commercially available pre-loaded Amino-PEG2 on Tentagel resin (300 mg, 0.2 mmol, Novabiochem) was swollen in DMF (3×5 min×5 mL). The resin was extended with 5 azidovalerianic acid (2.0 eq), HBTU (2.0 eq), HOBt (2.0 eq) and DIPEA (4.0 eq) in DMF (5 mL). The mixture was allowed to stand for 10 min at 0° C. and then reacted with the resin for 1 h under gentle agitation. (S)—N-(2-(2-cyano-4,4-difluoropyrrolidin-1-yl)-2-oxoethyl)-8-(hex-5-ynamido)quinoline-4-carboxamide (78 mg, 0.17 mmol, 0.86 eq), CuI (4 mg, 0.02 mmol, 0.1 eq) and TBTA (34 mg, 0.06 mmol, 0.3 eq) were dissolved in 5 mL of a mixture 1:1 DMF/THF.

The peptide was cleaved from the resin with a mixture of 20% TFA in DCM at room temperature for 1 h. The solvent was removed under reduced pressure and the crude precipitated in cold diethyl ether, centrifuged, dissolved in water/ACN and purify via HPLC (Water 0.1% TFA/Acetonitrile 0.1% TFA 9.5:0.5 to 5:5 in 15 min) and lyophilized, to obtain a white solid (30 mg, 21%). MS(ES$^+$) m/z 727.8 $(M+H)^+$ Synthesis of Conjugate 46

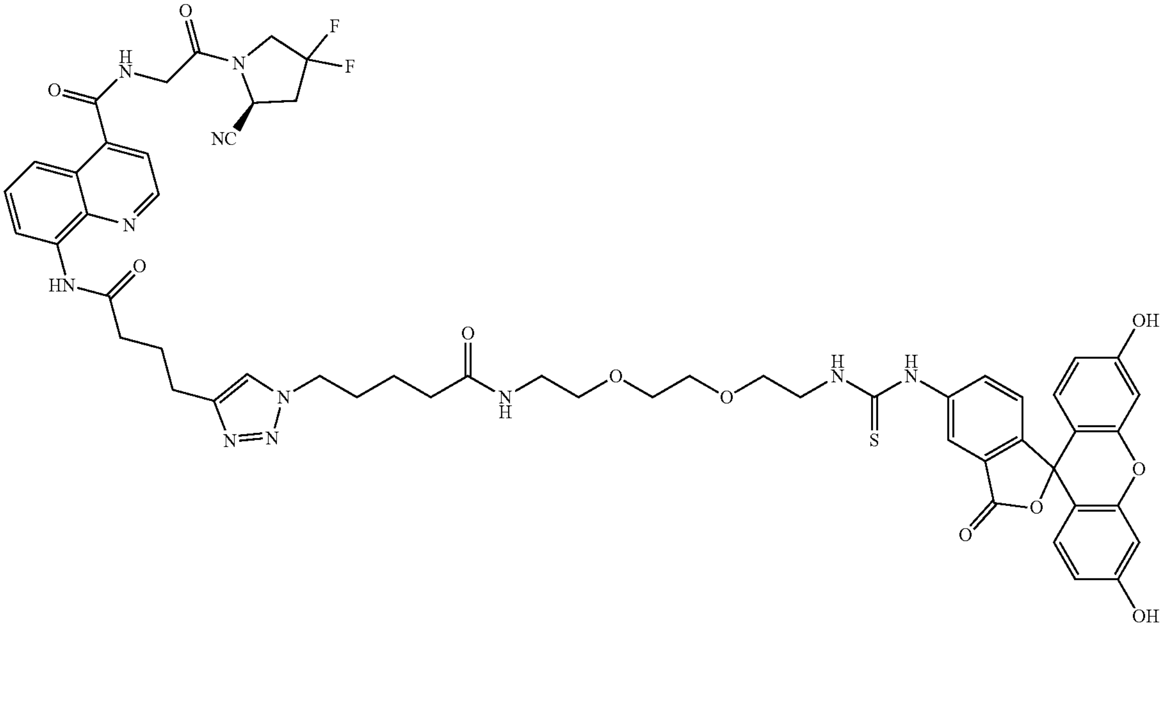 [SMILES: N#C[C@@H]1CC(F)(F)CN1C(=O)CNC(=O)c1ccnc2c(NC(=O)CCCc3cn(CCCCC(=O)NCCOCCOCCNC(=S)Nc4ccc5c(c4)C(=O)OC54c5ccc(O)cc5Oc5cc(O)ccc54)nn3)cccc12]

(S)-8-(4-(1-(5-((2-(2-(2-aminoethoxy)ethoxy)ethyl)amino)-5-oxopentyl)-1H-1,2,3-triazol-4-yl)butanamido)-N-(2-(2-cyano-4,4-difluoropyrrolidin-1-yl)-2-oxoethyl)quinoline-4-carboxamide (1 mg, 1.4 μmol, 1.0 eq) was dissolved in THF (200 μL) and dry DIPEA (400 μg, 3.3 μmol, 2.4 eq) was added dropwise. FITC isomer I (0.8 mg, 2.1 μmol, 1.5 eq) was added as DMSO solution at the concentration of 1 mg in 20 μL, The reaction was stirred for 3 h, protected from light and the crude material was directly purified by reversed-phase HPLC (Water 0.1% TFA/Acetonitrile 0.1% TFA 9.5:0.5 to 2:8 in 20 min) and lyophilized, to obtain a yellow powder (1.1 mg, 70.4%). MS($ES^+$) m/z 1116.4 $(M+H)^+$ Synthesis of (S)—N-(2-(2-cyano-4,4-difluoropyrrolidin-1-yl)-2-oxoethyl)-8-(hex-5-ynamido)quinoline-4-carboxamide (P10)

Scheme 26. Synthesis route for preparation of (S)-N-(2-(2-cyano-4,4-difluoropyrrolidin-1-yl)-2-oxoethyl)-8-(hex-5-ynamido)quinoline-4-carboxamide (P10)

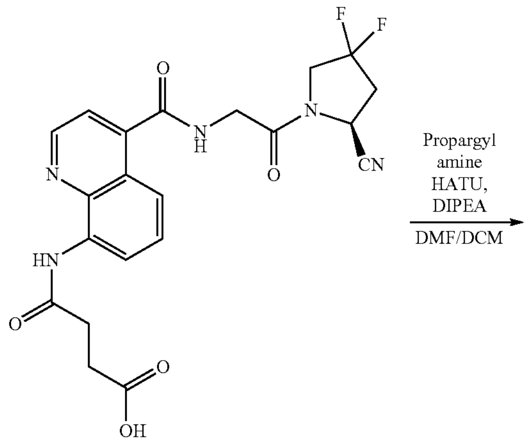

-continued

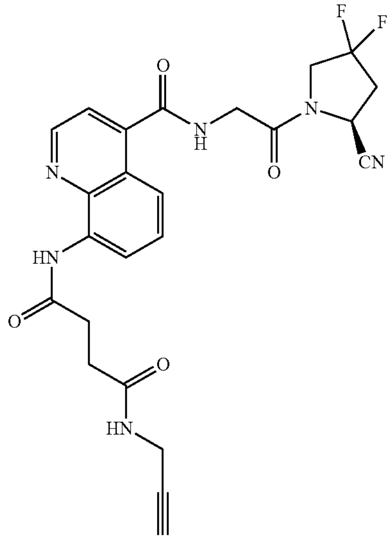

(S)-4-((4-((2-(2-cyano-4,4-difluoropyrrolidin-1-yl)-2-oxoethyl)carbamoyl)quinolin-8-yl)amino)-4-oxobutanoic acid (50 mg, 0.11 mmol, 1 eq), propargylamine (7 mg, 0.13 mmol, 1.2 eq) and HATU (49 mg, 0.13 mmol, 1.2 eq) were dissolved in 2 mL of DCM and 100 μL of DMF. DIPEA (56 mg, 0.44 mmol, 4 eq) was added dropwise and the reaction was stirred for 30 minutes at room temperature. Water was added, separated from organic layer and then extracted three times with DCM. The crude was dried over sodium sulfate, filtered and evaporated. The crude was purified via chromatography (DCM/MeOH 100:0 to 95:5 in 10 min) to afford a dark oil (32 mg. 0.0638 mmol, 58%). MS($ES^+$) m/z 495.47 $(M+1H)^+$ Synthesis of Bi-ESV6-peptide (P11)

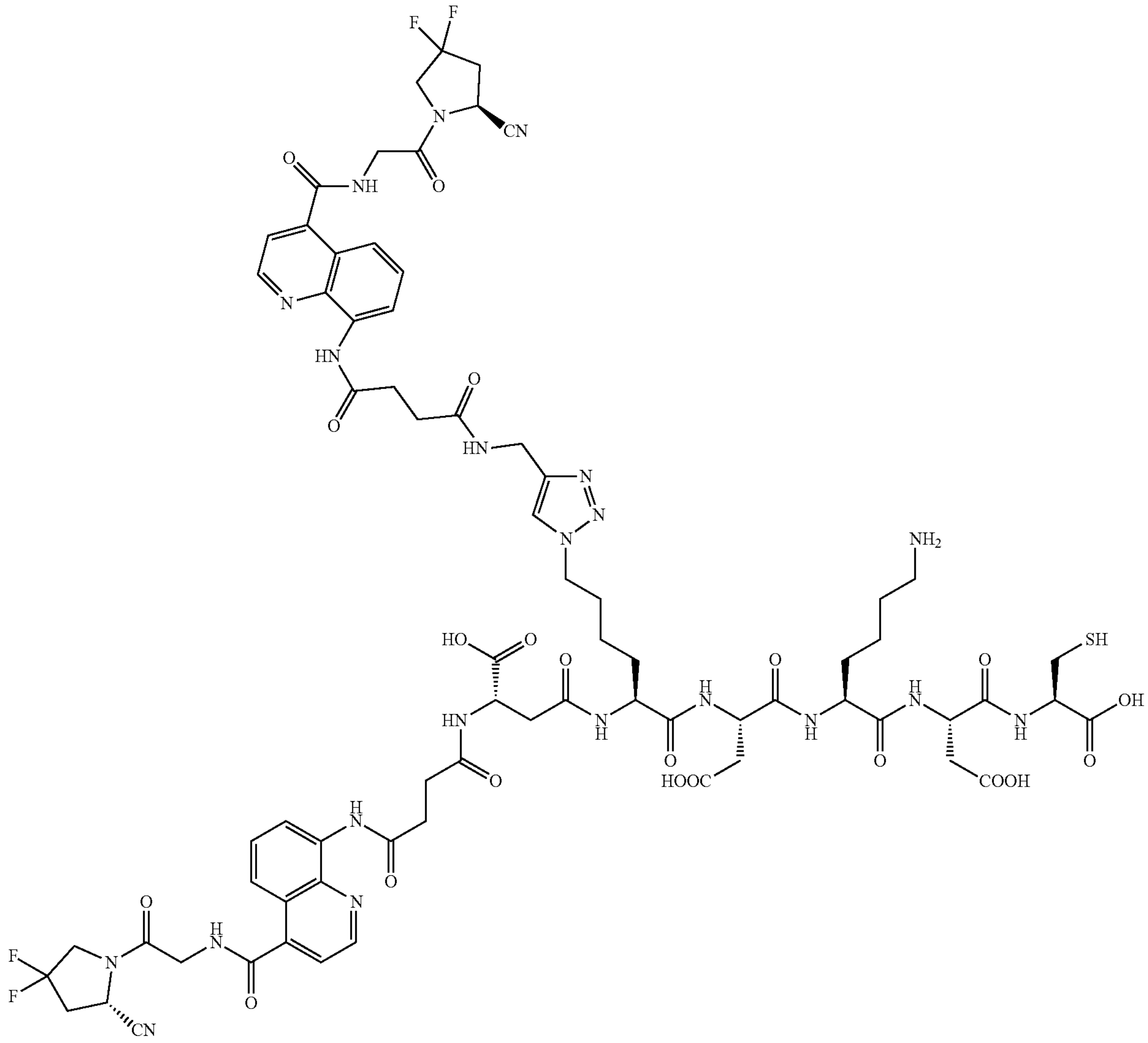 [SMILES: N#C[C@@H]1CC(F)(F)CN1C(=O)CNC(=O)c1ccnc2c(NC(=O)CCC(=O)NCc3cn(CCCC[C@H](NC(=O)C[C@H](NC(=O)CCC(=O)Nc4cccc5c(C(=O)NCC(=O)N6CC(F)(F)C[C@H]6C#N)ccnc45)C(=O)O)C(=O)N[C@@H](CC(=O)O)C(=O)N[C@@H](CCCCN)C(=O)N[C@@H](CC(=O)O)C(=O)N[C@@H](CS)C(=O)O)nn3)cccc12]

Commercially available pre-loaded Fmoc-Cys(Trt) on Tentagel resin (300 mg, 0.18 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide was extended with Fmoc-Asp(tBu)-OH, Fmoc-Lys(NHBoc)-OH, Fmoc-Asp(tBu)-OH, Fmoc-N3-Lys, Fmoc-Asp(tBu)-OH and (S)-4-((4-((2-(2-cyano-4,4-difluoropyrrolidin-1-yl)-2-oxoethyl)carbamoyl)quinolin-8-yl)amino)-4-oxobutanoic acid in the indicated order. For this purpose, the Fmoc protected amino acid (2.0 eq), HBTU (2.0 eq), HOBt (2.0 eq) and DIPEA (4.0 eq) were dissolved in DMF (5 mL). The mixture was allowed to stand for 10 min at 0° C. and then reacted with the resin for 1 h under gentle agitation. After washing with DMF (6×1 min×5 mL) the Fmoc group was removed with 20% piperidine in DMF (1×1 min×5 min and 2×10 min×5 mL). Deprotection steps were followed by wash steps with DMF (6×1 min×5 mL) prior to coupling with the next aminoacid. (S)—N-(2-(2-cyano-4,4-difluoropyrrolidin-1-yl)-2-oxoethyl)-8-(hex-5-ynamido)quinoline-4-carboxamide (174 mg, 0.35 mmol, 2 eq), CuI (4 mg, 0.02 mmol, 0.1 eq) and TBTA (28 mg, 0.05 mmol, 0.3 eq) were dissolved in 5 mL of a mixture 1:1 DMF/THF. The peptide was cleaved from the resin with a mixture of 20% TFA in DCM at room temperature for 1 h. The solvent was removed under reduced pressure and the crude precipitated in cold diethyl ether, centrifuged, dissolved in water/ACN and purify via HPLC (Water 0.1% TFA/Acetonitrile 0.1% TFA 9.5:0.5 to 5:5 in 15 min) and lyophilized, to obtain a white solid (18 mg, 6%). MS($ES^+$) m/z 1687.7 $(M+H)^+$ Synthesis of Conjugate 47
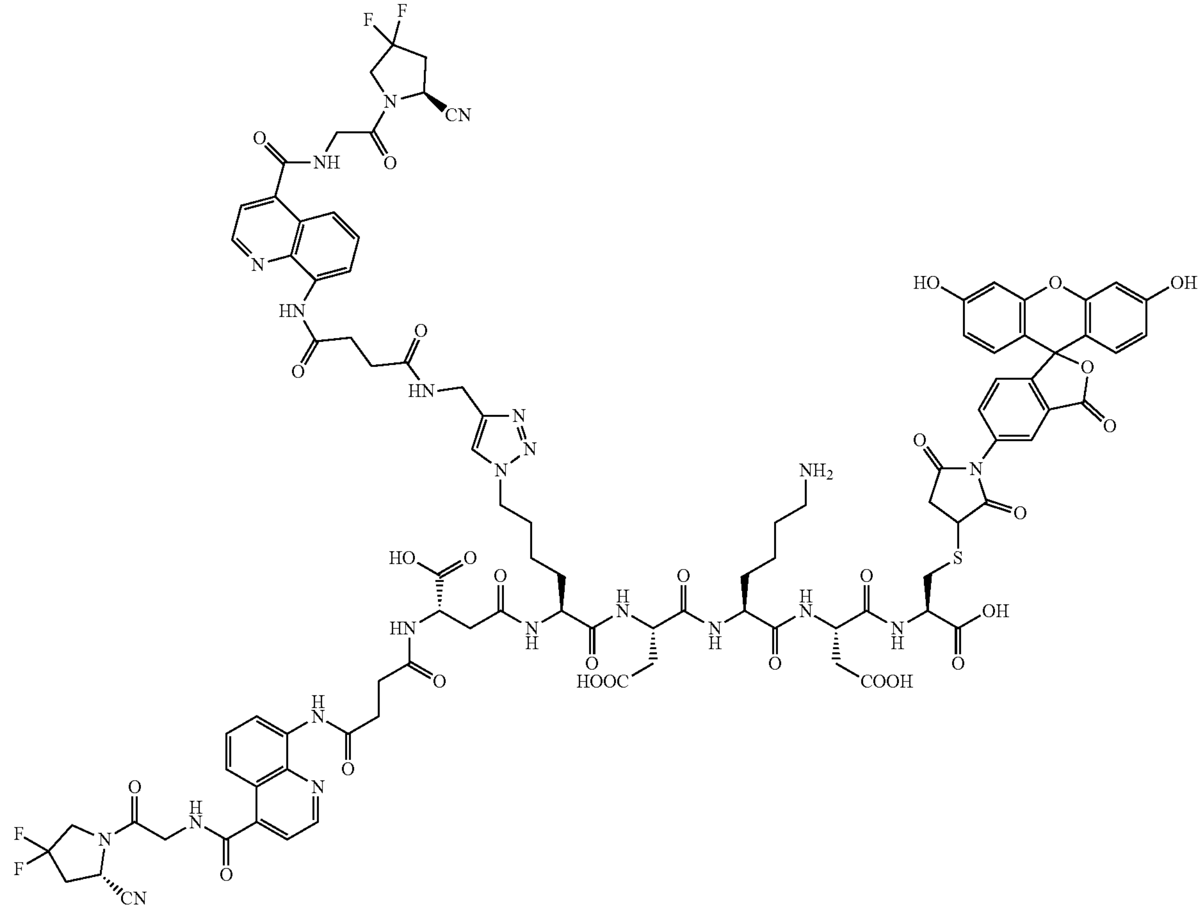 [SMILES: N#C[C@@H]1CC(F)(F)CN1C(=O)CNC(=O)c1ccnc2c(NC(=O)CCC(=O)NCc3cn(CCCC[C@H](NC(=O)C[C@H](NC(=O)CCC(=O)Nc4cccc5c(C(=O)NCC(=O)N6CC(F)(F)C[C@H]6C#N)ccnc45)C(=O)O)C(=O)N[C@@H](CC(=O)O)C(=O)N[C@@H](CCCCN)C(=O)N[C@@H](CC(=O)O)C(=O)N[C@@H](CSC4CC(=O)N(c5ccc6c(c5)C(=O)OC65c6ccc(O)cc6Oc6cc(O)ccc65)C4=O)C(=O)O)nn3)cccc12]
Bi-ESV6-Peptide (P11, 1 mg, 0.59 μmol, 1.0 eq) is dissolved in PBS pH 7.4 (840 μL). Maleimido-Fluorescein (0.76 mg, 1.77 μmol, 3.0 eq) is added as dry DMF solution (160 μL). The reaction is stirred for 3 h.
The crude material is purified by reversed-phase HPLC (Water 0.1% TFA/Acetonitrile 0.1% TFA 9.5:0.5 to 2:8 in 20 min) and lyophilized, to obtain a yellow solid.
MS($ES^+$) m/z 2114.7 $(M+H)^+$ Synthesis of Conjugate 48
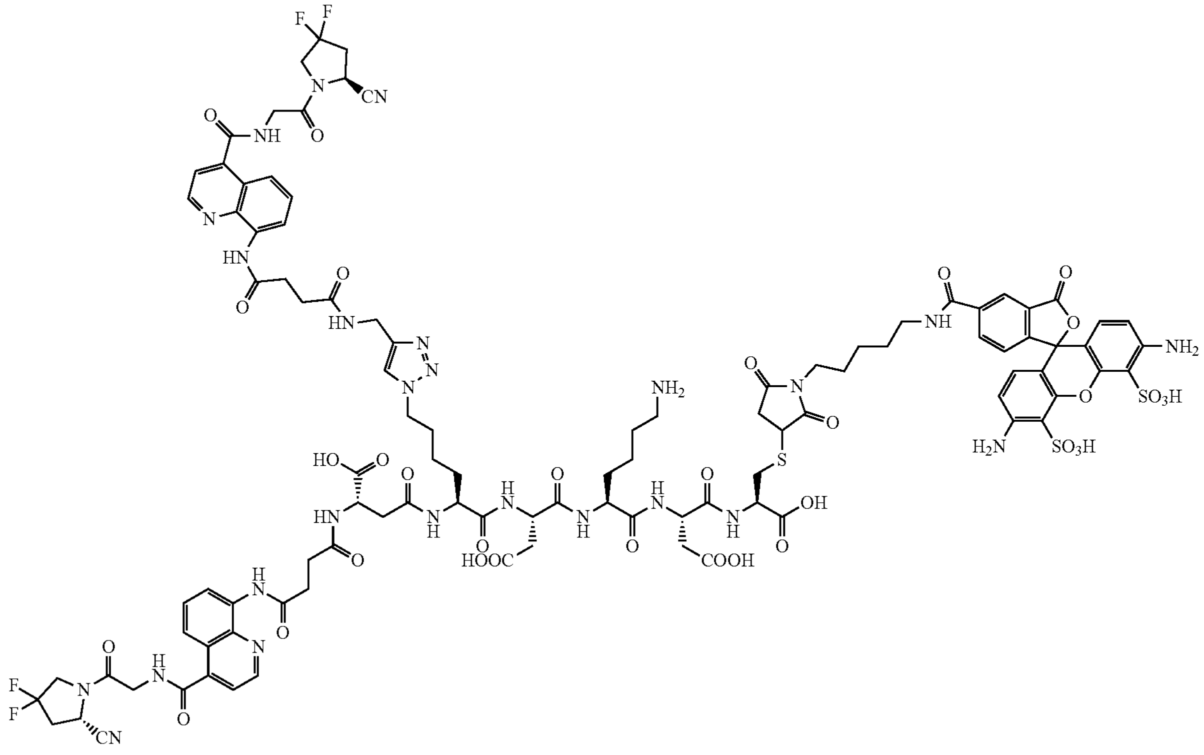 [SMILES: N#C[C@@H]1CC(F)(F)CN1C(=O)CNC(=O)c1ccnc2c(NC(=O)CCC(=O)NCc3cn(CCCC[C@H](NC(=O)C[C@H](NC(=O)CCC(=O)Nc4cccc5c(C(=O)NCC(=O)N6CC(F)(F)C[C@H]6C#N)ccnc45)C(=O)O)C(=O)N[C@@H](CC(=O)O)C(=O)N[C@@H](CCCCN)C(=O)N[C@@H](CC(=O)O)C(=O)N[C@@H](CSC4CC(=O)N(CCCCCNC(=O)c5ccc6c(c5)C(=O)OC65c6ccc(N)c(S(=O)(=O)O)c6Oc6c5ccc(N)c6S(=O)(=O)O)C4=O)C(=O)O)nn3)cccc12]
Bi-ESV6-Peptide (P11, 1 mg, 0.59 μmol, 1.0 eq) is dissolved in PBS pH 7.4 (300 μL). Alexa Fluor™ 488 C5 Maleimide (200 μg, 0.29 μmol, 0.5 eq) is added as dry DMSO solution (200 μL). The reaction is stirred for 3 h.
The crude material is purified by reversed-phase HPLC (Water 0.1% TFA/Acetonitrile 0.1% TFA 9.5:0.5 to 2:8 in 20 min) and lyophilized, to obtain an orange solid.
MS($ES^+$) m/z 2385. 8 $(M+1H)^{1+}$
Synthesis of Conjugate 49
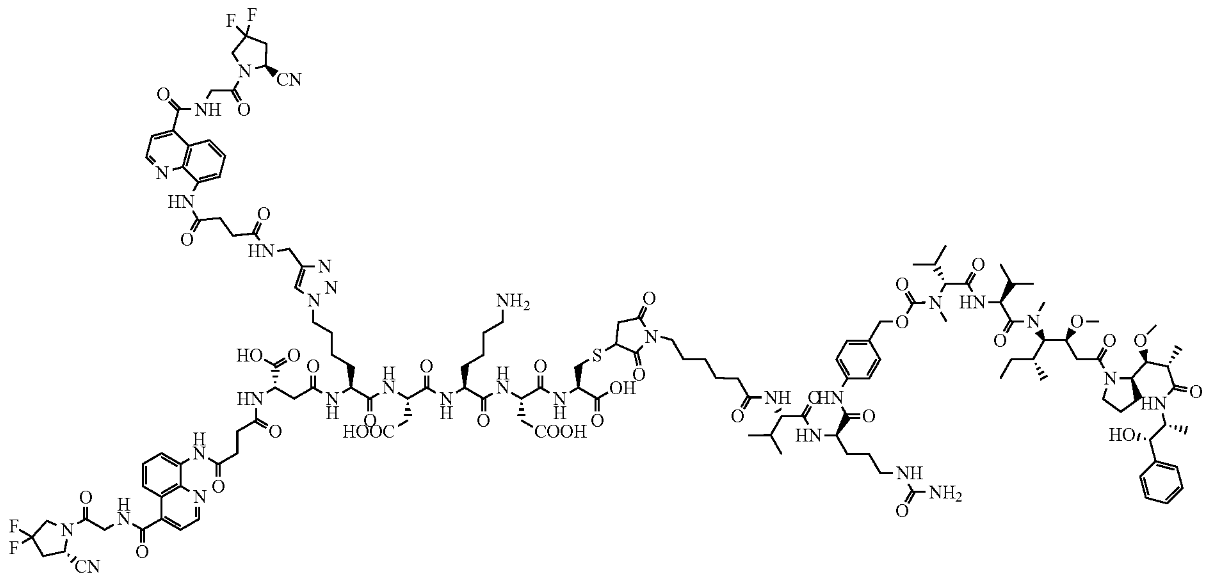 [SMILES: CC[C@@H](C)[C@H]([C@H](CC(=O)N1CCC[C@@H]1[C@@H](OC)[C@H](C)C(=O)N[C@H](C)[C@@H](O)c1ccccc1)OC)N(C)C(=O)[C@@H](NC(=O)[C@@H](C(C)C)N(C)C(=O)OCc1ccc(NC(=O)[C@@H](CCCNC(N)=O)NC(=O)[C@@H](NC(=O)CCCCCN2C(=O)CC(SC[C@H](NC(=O)[C@H](CC(=O)O)NC(=O)[C@H](CCCCN)NC(=O)[C@H](CC(=O)O)NC(=O)[C@H](CCCCn3cc(CNC(=O)CCC(=O)Nc4cccc5c(C(=O)NCC(=O)N6CC(F)(F)C[C@H]6C#N)ccnc45)nn3)NC(=O)C[C@H](NC(=O)CCC(=O)Nc3cccc4c(C(=O)NCC(=O)N5CC(F)(F)C[C@H]5C#N)ccnc34)C(=O)O)C(=O)O)C2=O)C(C)C)cc1)C(C)C]

Bi-ESV6-Peptide (P11, 1 mg, 0.59 μmol, 1.0 eq) is dissolved in PBS pH 7.4 (840 μL). MC-ValCit-PAB-MMAE (1 mg, 0.76 μmol, 1.3 eq) is added as dry DMF solution (160 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain a white solid.

MS($ES^+$) m/z 3003.5 $(M+H)^+$

Synthesis of Conjugate 50

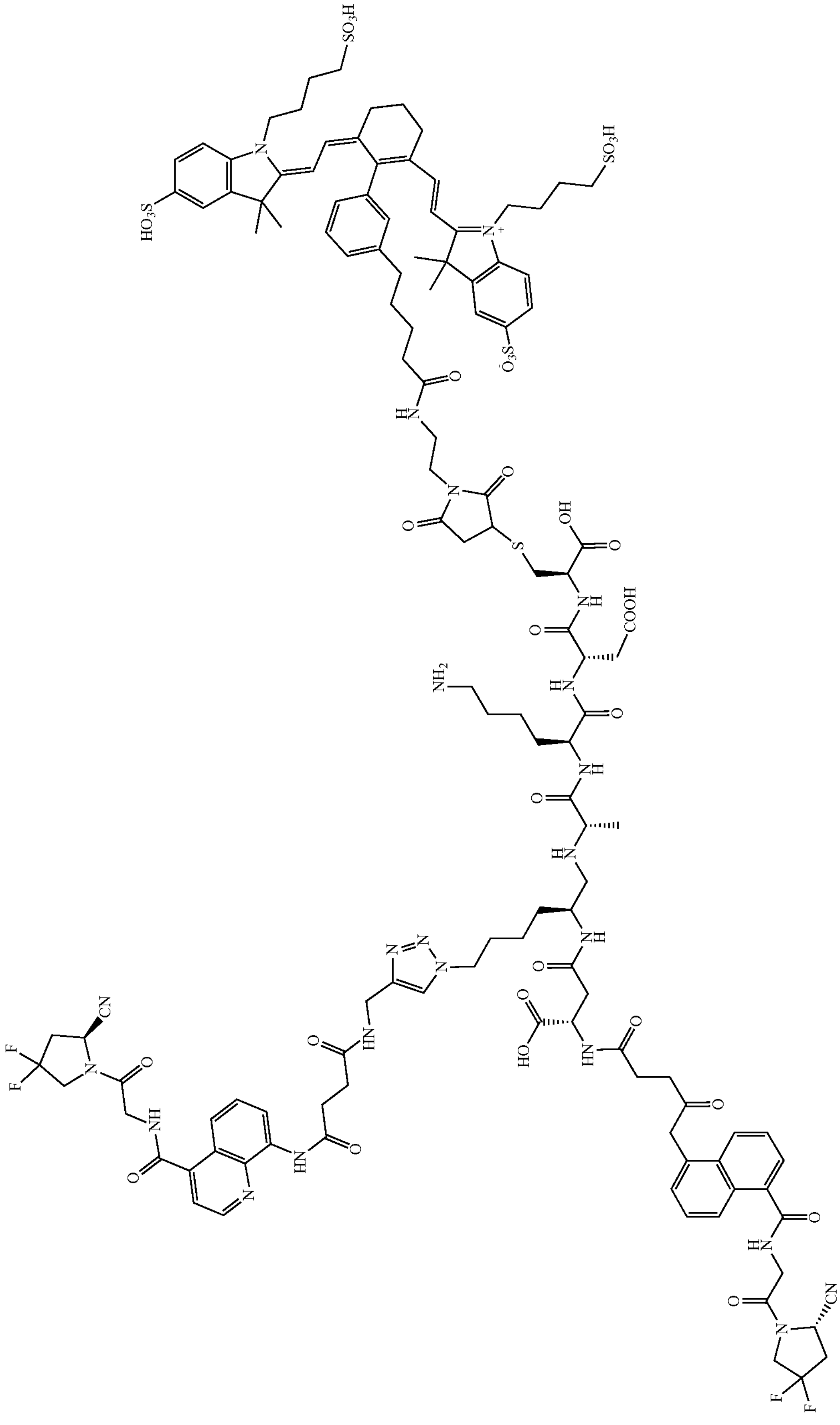

Bi-ESV6-Peptide (P11, 1 mg, 0.59 μmol, 3.3 eq) is dissolved in PBS pH 7.4 (300 μL). IRDye750 (200 μg, 0.174 μmol, 1.0 eq) is added as dry DMSO solution (200 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain an orange solid.

MS($ES^+$) m/z 2838.0 $(M+1H)^{1+}$

Synthesis of Conjugate 51

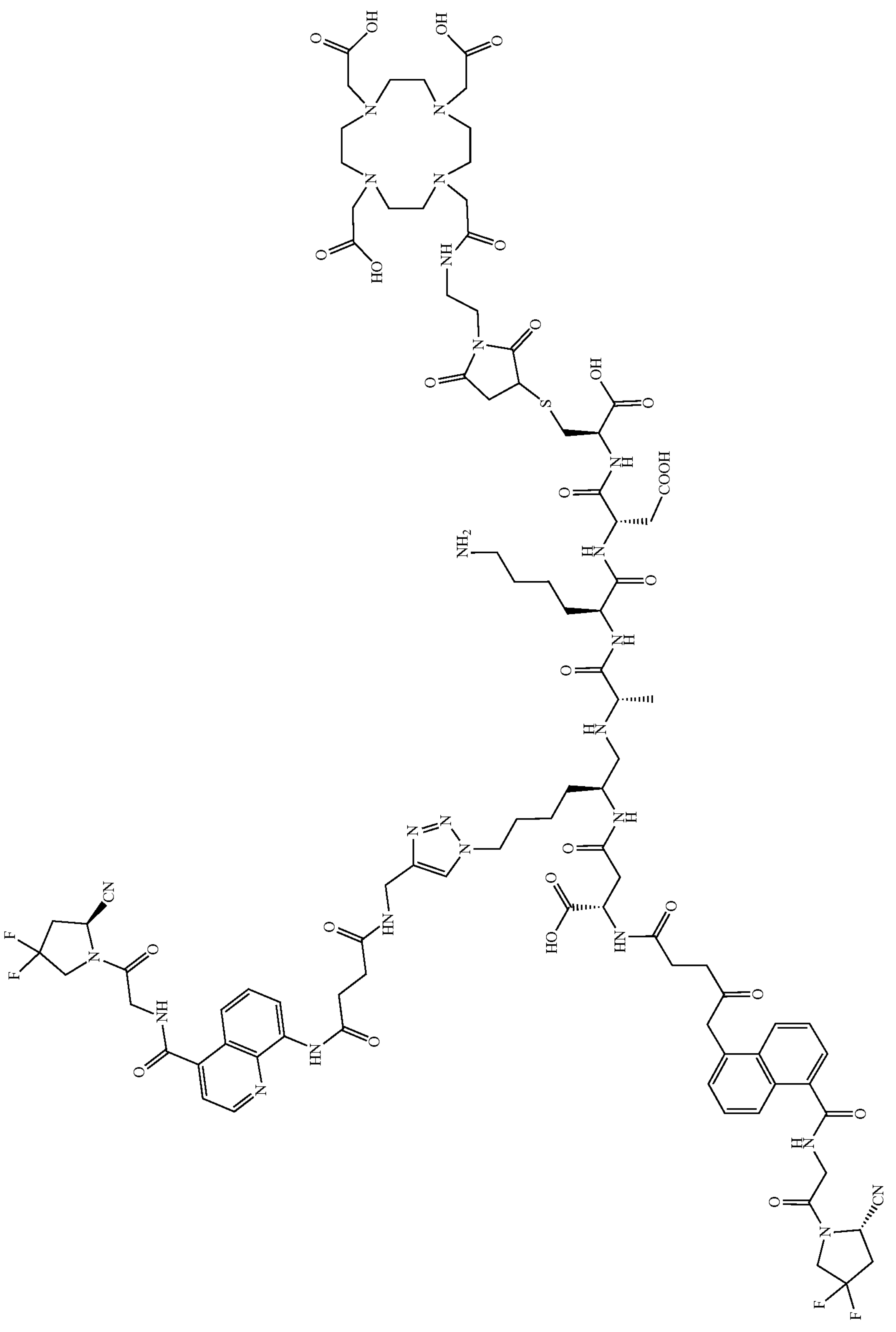

Bi-ESV6-Peptide (P11, 1 mg, 0.59 μmol, 1 eq) is dissolved in PBS pH 7.4 (300 μL). Maleimide-DOTA (465 μg, 0.59 μmol, 1.0 eq) is added as dry DMSO solution (200 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain an orange solid.

MS($ES^+$) m/z 2213.9 $(M+1H)^{1+}$

Synthesis of AlbuTag-ESV6-Peptide (P12)

(2.0 eq), HOBt (2.0 eq) and DIPEA (4.0 eq) were dissolved in DMF (5 mL). The mixture was allowed to stand for 10 min at 0° C. and then reacted with the resin for 1 h under gentle agitation. After washing with DMF (6×1 min×5 mL) the Fmoc group was removed with 20% piperidine in DMF (1×1 min×5 min and 2×10 min×5 mL). Deprotection steps were followed by wash steps with DMF (6×1 min×5 mL) prior to coupling with the next aminoacid. (S)—N-(2-(2-cyano-4,4-difluoropyrrolidin-1-yl)-2-oxoethyl)-8-(hex-5-ynamido)quinoline-4-carboxamide

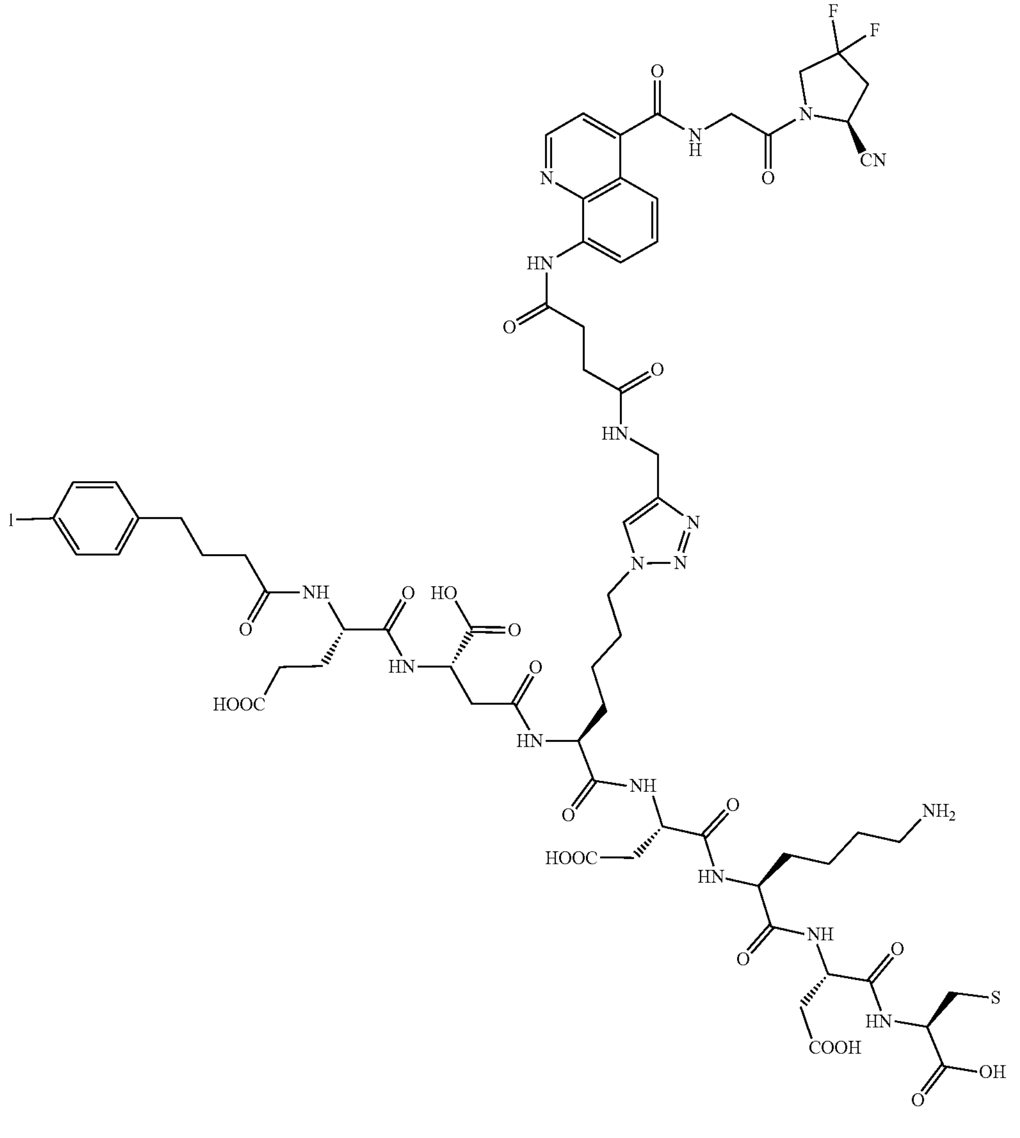

Commercially available pre-loaded Fmoc-Cys(Trt) on Tentagel resin (300 mg, 0.18 mmol, RAPP Polymere) was swollen in DMF (3×5 min×5 mL), the Fmoc group removed with 20% piperidine in DMF (1×1 min×5 mL and 2×10 min×5 mL) and the resin washed with DMF (6×1 min×5 mL). The peptide was extended with Fmoc-Asp(tBu)-OH, Fmoc-Lys(NHBoc)-OH, Fmoc-Asp(tBu)-OH, Fmoc-N3-Lys, Fmoc-α(tBu)-Asp-OH, Fmoc-Glu(tBu)-OH and 4-(4-Iodophenyl) butanoic acid in the indicated order. For this purpose, the Fmoc protected amino acid (2.0 eq), HBTU (174 mg, 0.35 mmol, 2 eq), CuI (4 mg, 0.02 mmol, 0.1 eq) and TBTA (28 mg, 0.05 mmol, 0.3 eq) were dissolved in 5 mL of a mixture 1:1 DMF/THF. The peptide was cleaved from the resin with a mixture of 20% TFA in DCM at room temperature for 1 h. The solvent was removed under reduced pressure and the crude precipitated in cold diethyl ether, centrifuged, dissolved in water/ACN and purify via HPLC (Water 0.1% TFA/Acetonitrile 0.1% TFA 9.5:0.5 to 5:5 in 15 min) and lyophilized, to obtain a white solid (6 mg, 2%). MS($ES^+$) m/z 1646.6 $(M+H)^+$ Synthesis of Conjugate 52
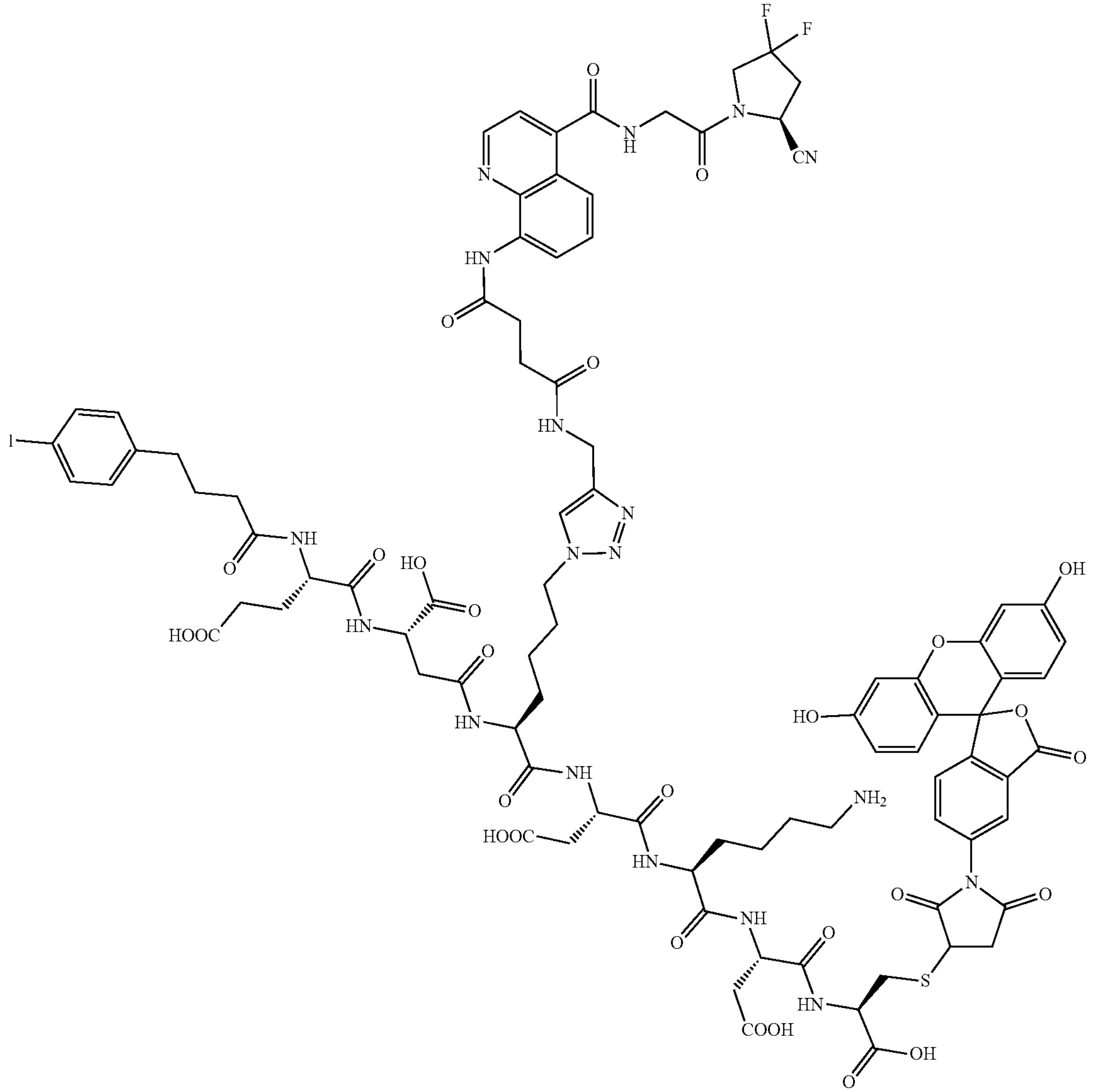
AlbuTag-ESV6-Peptide (P12, 1 mg, 0.61 μmol, 1.0 eq) is dissolved in PBS pH 7.4 (840 μL). Maleimido-Fluorescein (0.78 mg, 1.82 μmol, 3.0 eq) is added as dry DMF solution (160 μL). The reaction is stirred for 3h.
The crude material is purified by reversed-phase HPLC (Water 0.1% TFA/Acetonitrile 0.1% TFA 9.5:0.5 to 2:8 in 20 min) and lyophilized, to obtain a yellow solid.
MS($ES^+$) m/z 2073.6 $(M+H)^+$ Synthesis of Conjugate 53

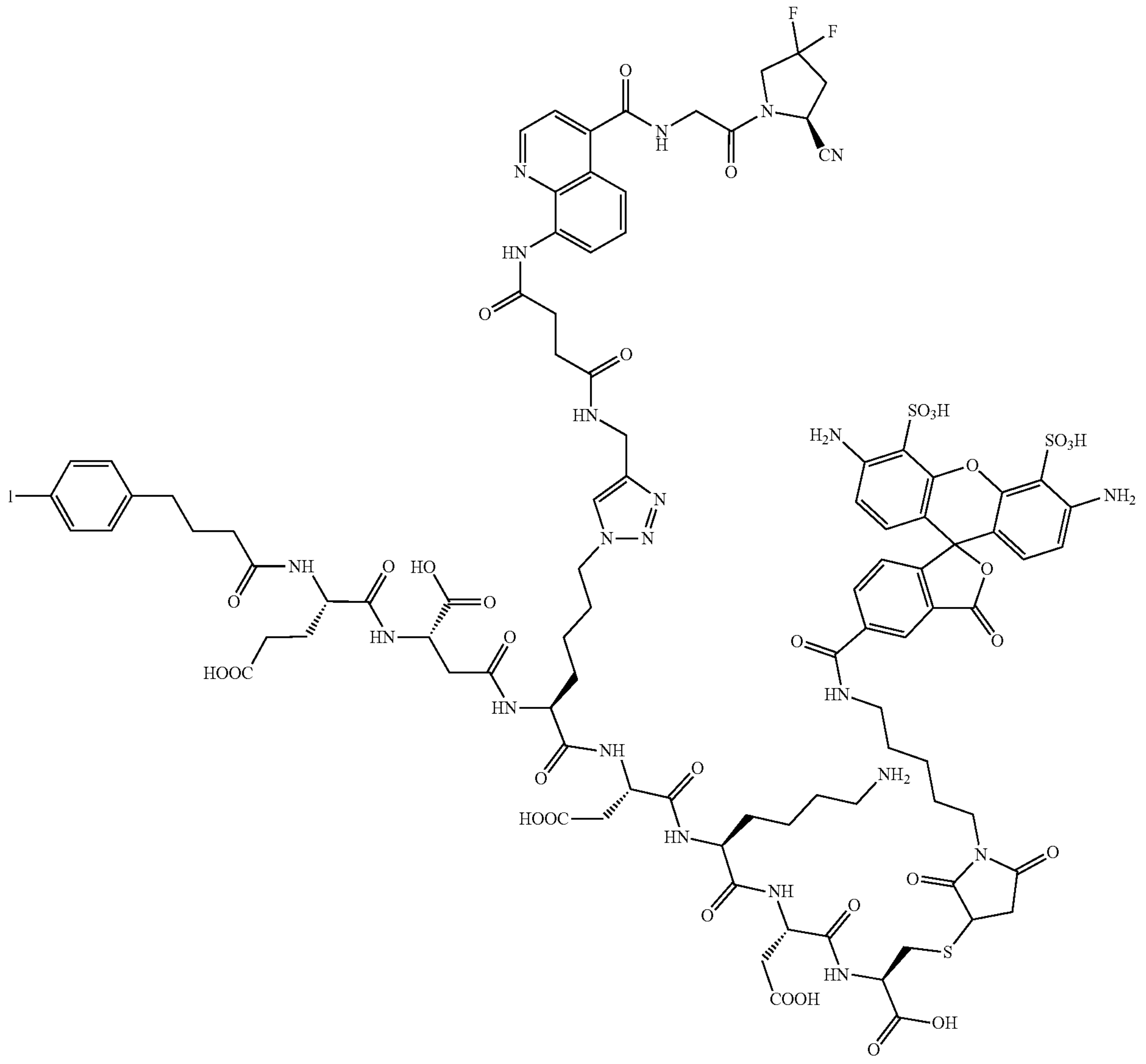

AlbuTag-ESV6-Peptide (P12, 1 mg, 0.61 μmol, 1.0 eq) was dissolved in PBS pH 7.4 (300 μL). Alexa Fluor™ 488 C5 Maleimide (400 μg, 0.58 μmol, 0.95 eq) was added as dry DMSO solution (200 μL). The reaction was stirred for 3 h. The crude material was purified by reversed-phase HPLC (Water 0.1% TFA/Acetonitrile 0.10% TFA 9.5:0.5 to 2:8 in 20 min) and lyophilized, to obtain an orange solid (180 nmol, 30%). MS(ES+) m/z 2345. 7 $(M+1H)^{1+}$ Synthesis of Conjugate 54

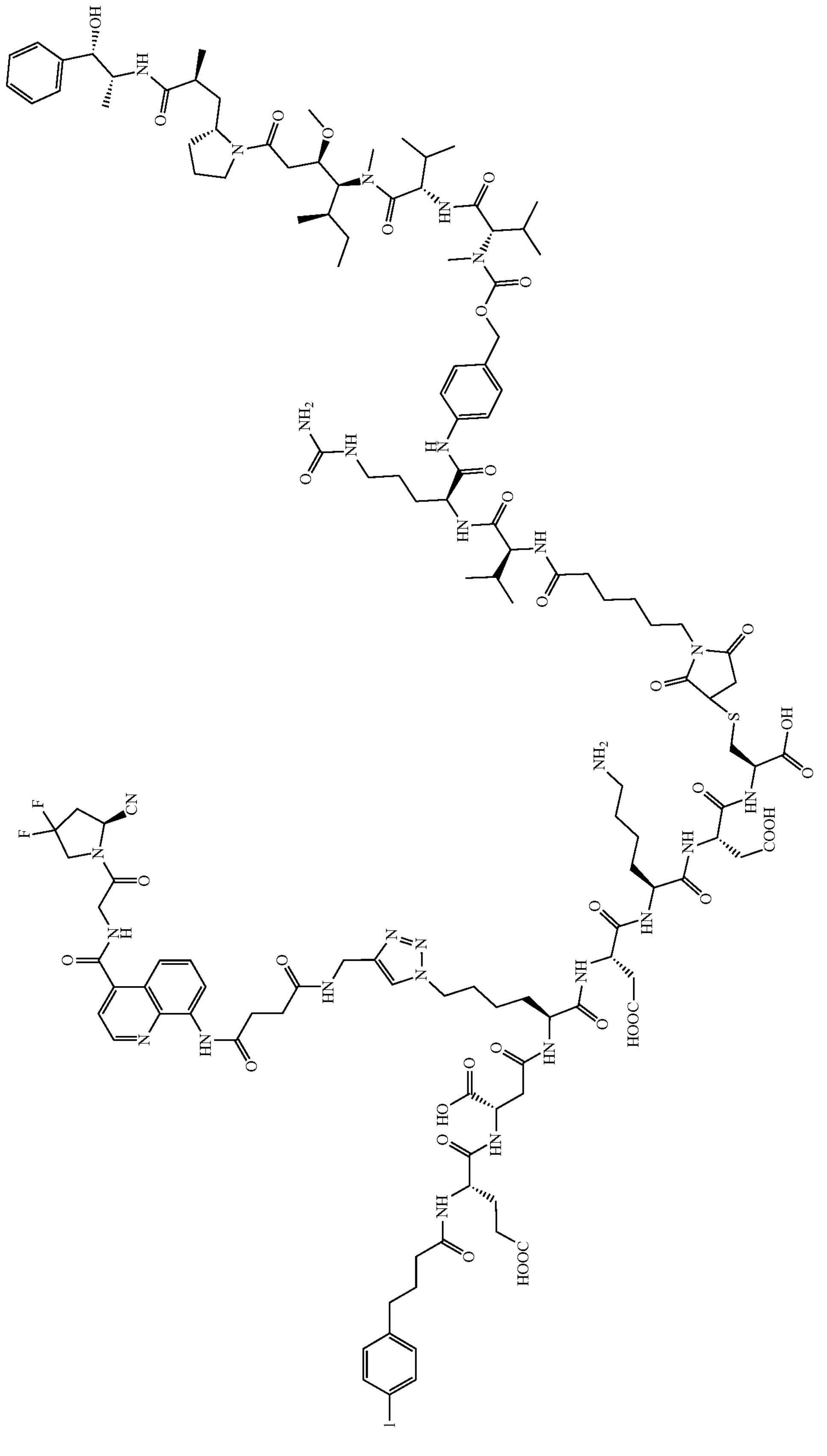

AlbuTag-ESV6-Peptide (P12, 1 mg, 0.61 μmol, 1.0 eq) is dissolved in PBS pH 7.4 (840 μL). MC-ValCit-PAB-MMAE (1 mg, 0.76 μmol, 1.25 eq) is added as dry DMF solution (160 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain a white solid.

MS($ES^+$) m/z 2963.8 $(M+H)^+$

Synthesis of Conjugate 55

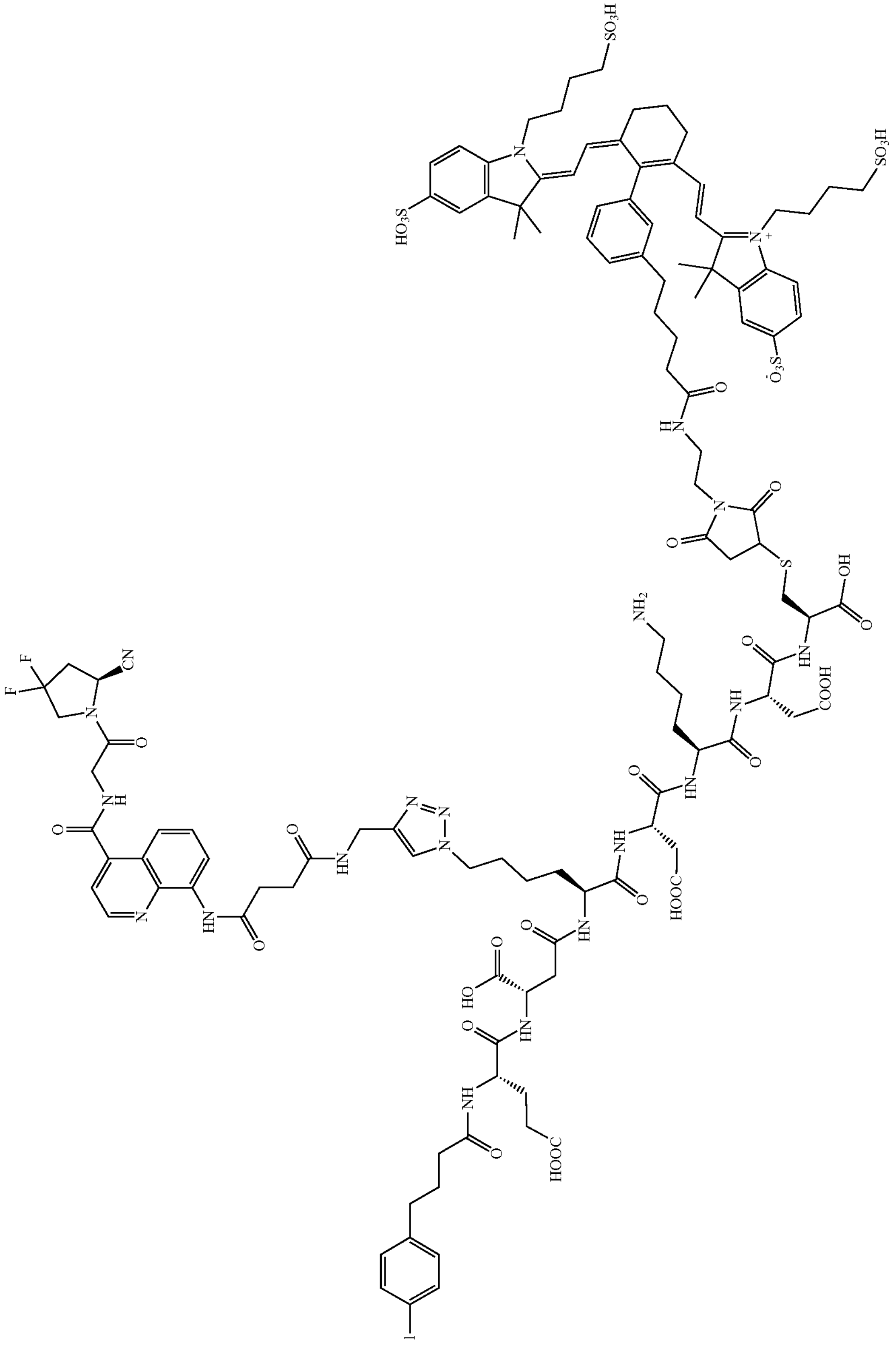

AlbuTag-ESV6-Peptide (P12, 1 mg, 0.61 μmol, 1.0 eq) was dissolved in PBS pH 7.4 (300 μL). IRDye750 (400 μg, 0.384 μmol, 0.58 eq) was added as dry DMSO solution (200 μL). The reaction was stirred for 3 h.

The crude material was purified by reversed-phase HPLC (Water 0.1% TFA/Acetonitrile 0.10% TFA 9.5:0.5 to 2:8 in 20 min) and lyophilized, to obtain an orange solid (55 nmol, 9%). MS($ES^+$) m/z 2797.9 $(M+1H)^{1+}$ Synthesis of Conjugate 56

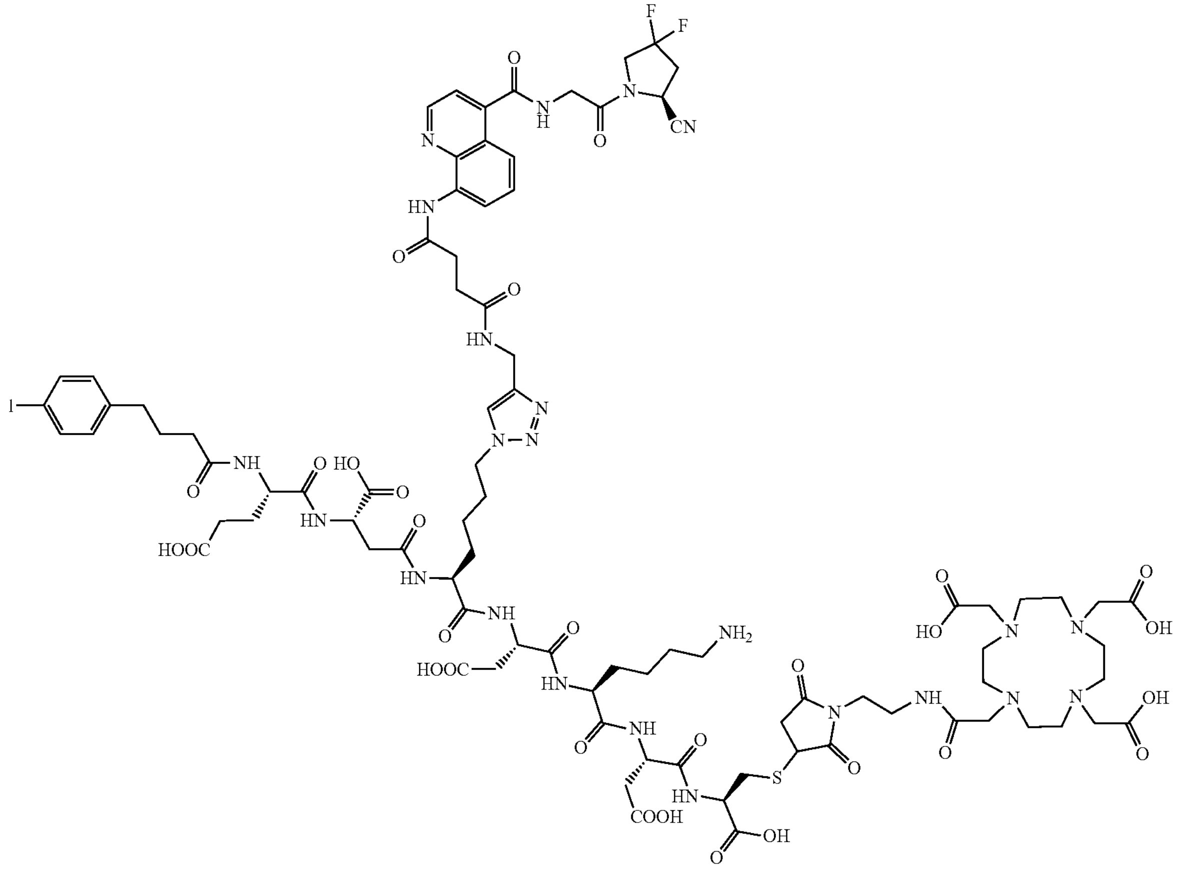

AlbuTag-ESV6-Peptide (P12, 1 mg, 0.61 μmol, 1.0 eq) is dissolved in PBS pH 7.4 (300 μL). Maleimide-DOTA (480 μg, 0.61 μmol, 1.0 eq) is added as dry DMSO solution (200 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain an orange solid.

MS($ES^+$) m/z 2172.7 $(M+1H)^{1+}$

Synthesis of Bi-ESV6 (P13)

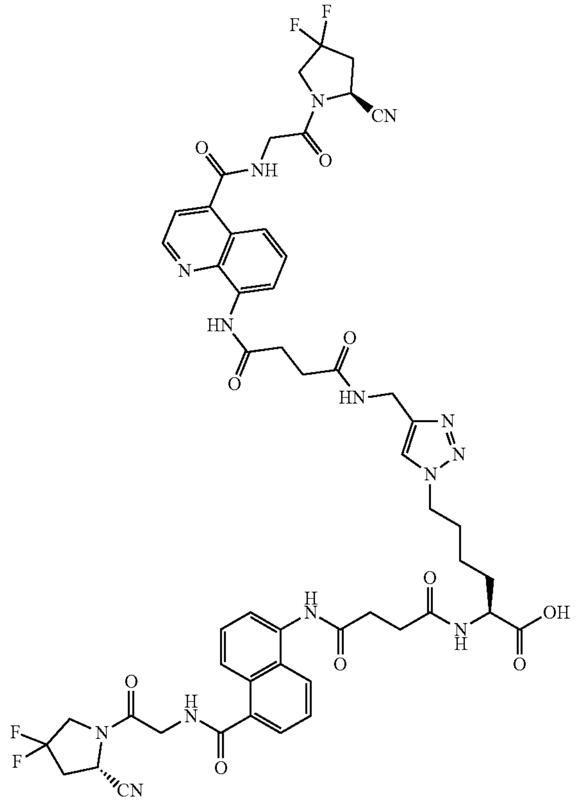 [SMILES: N#C[C@@H]1CC(F)(F)CN1C(=O)CNC(=O)c1cccc2c(NC(=O)CCC(=O)N[C@@H](CCCCn3cc(CNC(=O)CCC(=O)Nc4cccc5c(C(=O)NCC(=O)N6CC(F)(F)C[C@H]6C#N)ccnc45)nn3)C(=O)O)cccc12]

Commercially available 2-Chloro-trityl chloride resin (300 mg) is swollen in DMF (3×5 min×5 mL). The resin is extended with NHFmoc-Azido-Lysine (1 mmol), HBTU (1.0 eq), HOBt (1.0 eq) and DIPEA (2.0 eq) in DMF (5 mL). The mixture is allowed to stand for 10 min at 0° C. and then react with the resin for 1 h under gentle agitation. The resin is then washed with methanol. The resin is extended with (S)-4-((4-((2-(2-cyano-4,4-difluoropyrrolidin-1-yl)-2-oxoethyl)carbamoyl)quinolin-8-yl)amino)-4-oxobutanoic acid (1 mmol), HOBt (1.0 eq) and DIPEA (2.0 eq) in DMF (5 mL). (S)—N-(2-(2-cyano-4,4-difluoropyrrolidin-1-yl)-2-oxoethyl)-8-(hex-5-ynamido)quinoline-4-carboxamide (78 mg, 0.17 mmol, 0.86 eq), CuI (4 mg, 0.02 mmol, 0.1 eq) and TBTA (34 mg, 0.06 mmol, 0.3 eq) is dissolved in 5 mL of a mixture 1:1 DMF/THF. The peptide is cleaved from the resin with a mixture of 50% HFIP in DCM at room temperature for 1 h. The solvent is removed under reduced pressure and the crude precipitated in cold diethyl ether, centrifuged, dissolved in water/ACN and purify via HPLC (Water 0.1% TFA/Acetonitrile 0.1% TFA 9.5:0.5 to 5:5 in 15 min) and lyophilized, to obtain a white solid. MS($ES^+$) m/z 1111.1 $(M+H)^+$ Synthesis of DOTA-GA-Bi-ESV6 (57)

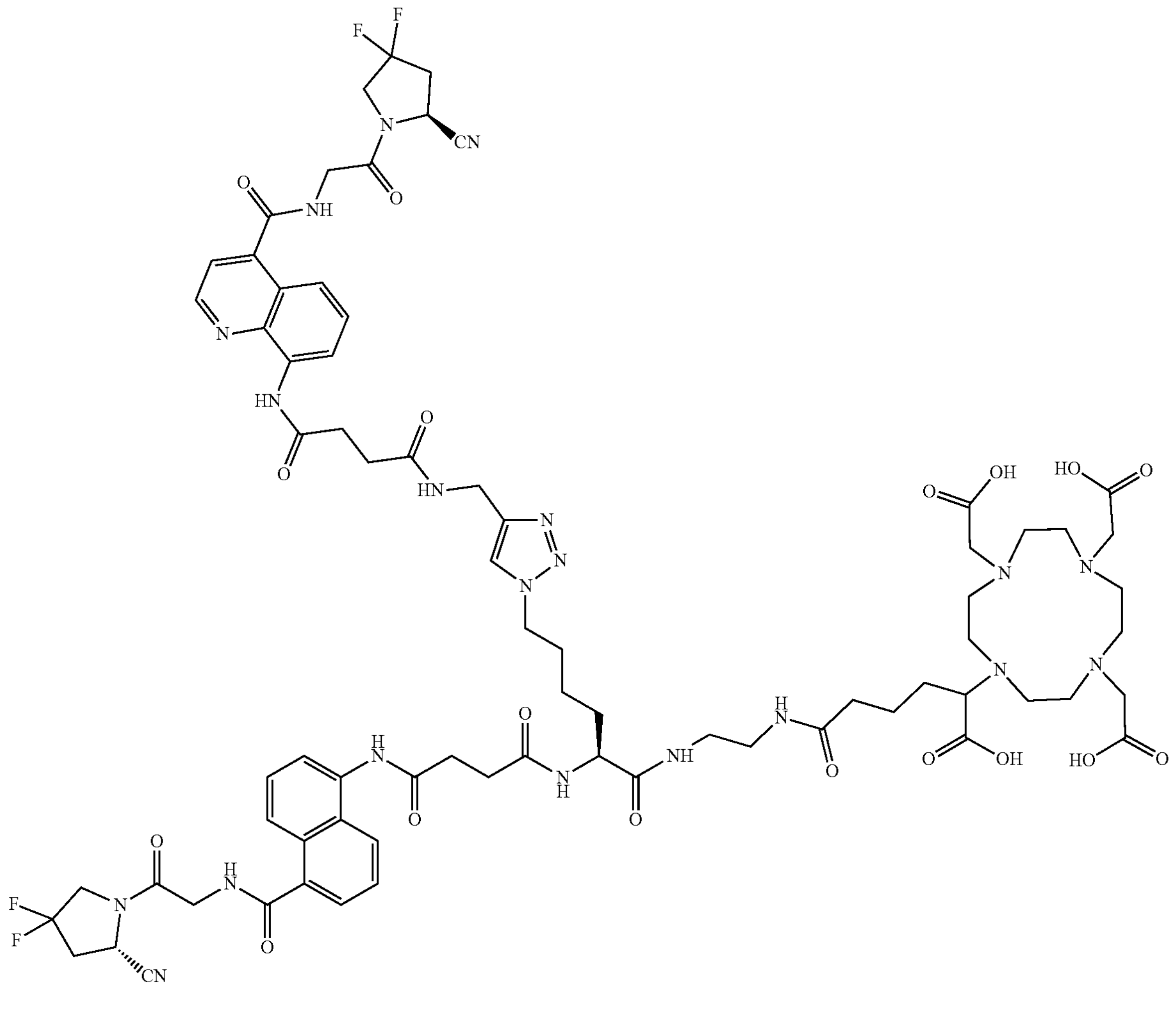 [SMILES: N#C[C@@H]1CC(F)(F)CN1C(=O)CNC(=O)c1cccc2c(NC(=O)CCC(=O)N[C@@H](CCCCn3cc(CNC(=O)CCC(=O)Nc4cccc5c(C(=O)NCC(=O)N6CC(F)(F)C[C@H]6C#N)ccnc45)nn3)C(=O)NCCNC(=O)CCCC(C(=O)O)N3CCN(CC(=O)O)CCN(CC(=O)O)CCN(CC(=O)O)CC3)cccc12]

Bi-ESV6 (P13, 45 mg, 40.5 μmol, 1.0 eq) is dissolved in dry DMSO (400 μL). Dicyclohexylcarbodiimide (10.9 mg, 52.7 μmol, 1.3 eq) and N-hydroxysuccinimide (14 mg, 122 μmol, 3 eq) are added and the reaction was stirred overnight at room temperature, protected from light.

100 μL of PBS solution containing 2,2',2"-(10-(4-((2-aminoethyl)amino)-1-carboxy-4-oxobutyl)-1,4,7,10-tetraazacyclododecane-1,4,7-triyl)triacetic acid (25 mg, 48.6 μmol, 1.2 eq) is added and the reaction was stirred for 2h.

The crude product is purified by reversed-phase HPLC (Water 0.1% TFA/Acetonitrile 0.1% TFA 9.5:0.5 to 2:8 in 20 min) and lyophilized, to obtain a white solid.

MS(ES$^+$) m/z 1624.8 (M+H)$^+$

General Procedure for Synthesis of MC-Aminoacids(OtBu)

Scheme 27. General synthesis route for preparation of MC-Aminoacids(OtBu)

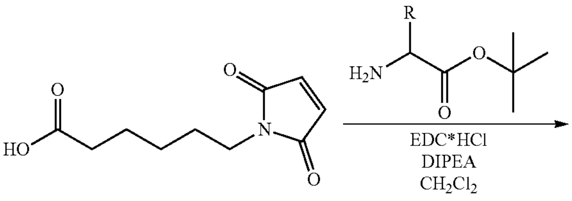

-continued

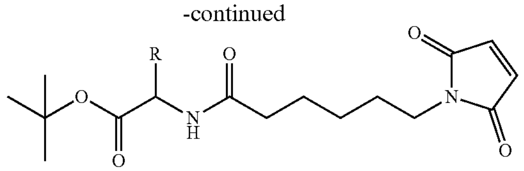

The above general procedure can be performed as described below, e.g., for AA=glycine.

6-maleimidohexanoic acid (1.0 eq) is dissolved in dry CH2Cl2 (1 mL/mmol) under argon atmosphere and the solution was cooled to 0° C. EDC HCl (1.1 eq), DIPEA (2.3 eq) and the desired H-AA-OtBu·HCl (1.1 eq) are added subsequently. The reaction is stirred at room temperature until completion. The mixture is diluted with AcOEt, washed with aqueous $KHSO_4$ 1M, saturated $NaHCO_3$ solution and brine. The organic phase is dried and concentrated to afford the desired product as white powder.

General Procedure for Synthesis of MC-Aminoacids

Scheme 28. General synthesis route for preparation of MC-Aminoacids

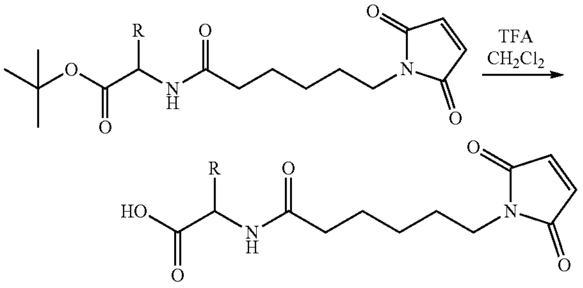

The above general procedure can be performed as described below, e.g., for R corresponding to AA=glycine.

Desired MC-Aminoacid-OtBu (1.0 eq) is dissolved in dry CH2C12 (0.3 mL/mmol) under argon atmosphere. TFA (22.0 eq) is added and the mixture is stirred at room temperature for 2 hours. The solution is concentrated and precipitated with hexane, affording the product as white powder.

Synthesis of (9H-fluoren-9-yl)methyl (2S)-2-((4-(hydroxymethyl)phenyl)carbamoyl)-1λ$^4$-pyrrolidine-1-carboxylate Scheme 29. Synthesis route for preparation of (9H-fluoren-9-yl) methyl (2S)-2-((4-(hydroxymethyl)phenyl)carbamoyl)-1λ$^4$-pyrrolidine-1-carboxylate

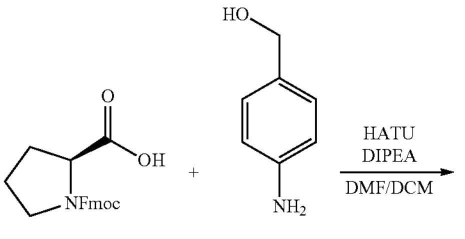

-continued

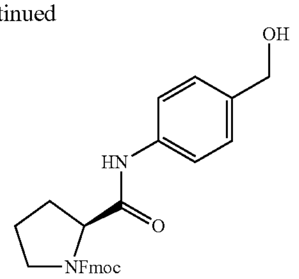

Fmoc-Pro-OH (312 mg; 0.92 mmol; 1.0 eq) and HATU (393 mg; 1.01 mmol; 1.1 eq) were dissolved in dry DMF (4 mL) under argon atmosphere and the solution was cooled to 0° C. DIPEA (505 μL; 2.76 mmol; 3.0 eq) was added dropwise and the mixture was stirred at the same temperature for 15 minutes. 4-aminobenzyl alcohol (226 mg, 1.84 mmol, 2 eq.) was added as a solution in dry DMF. The mixture was stirred overnight at room temperature. The reaction mixture was diluted with AcOEt and washed with aqueous 1M $KHSO_4$, saturated $NaHCO_3$ and brine. The pooled organic phases were dried and concentrated under vacuum. The crude was purified via chromatography (DCM/MeOH 99:1 to 95:5 in 10 min) to afford the product as a white powder (274 mg; 0.66 mmol; 66% yield). MS($ES^+$) m/z 443.19 $(M+1H)^{1+}$

Synthesis of (S)—N-(4-(hydroxymethyl)phenyl) pyrrolidine-2-carboxamide

Scheme 30. Synthesis route for preparation of (S)-N-(4-(hydroxymethyl)phenyl)pyrrolidine-2-carboxamide

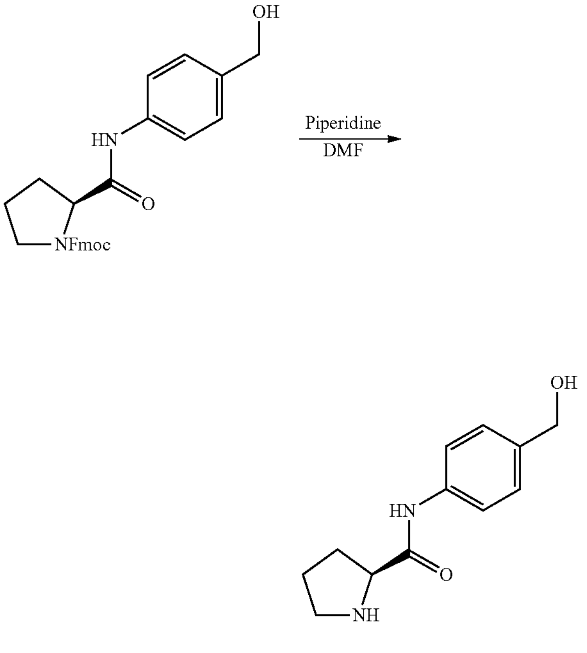

(9H-fluoren-9-yl)methyl (2S)-2-((4-(hydroxymethyl)phenyl)carbamoyl)-1λ$^4$-pyrrolidine-1-carboxylate (274 mg; 0.66 mmol) is dissolved in dry DMF (30 mL) under argon atmosphere and cooled to 0° C. Piperidine (325 μL; 3.29 mmol) is added and the mixture is stirred at room temperature for 1 hour. The solution is concentrated under high vacuum, dissolved in AcOEt (100 mL), washed with aqueous $NaHCO_3$ and brine. The organic phase is dried and concentrated under vacuum. The crude material is purified via chromatography (DCM/MeOH 99:1 to 90:10 with 0.5% TEA), to afford the product as a brown oil.

MS($ES^+$) m/z 221.12 $(M+1H)^{1+}$

General Procedure for Synthesis of MC-AA-Pro-PAB

Scheme 31. General synthesis route for preparation of MC-AA-Pro-PAB

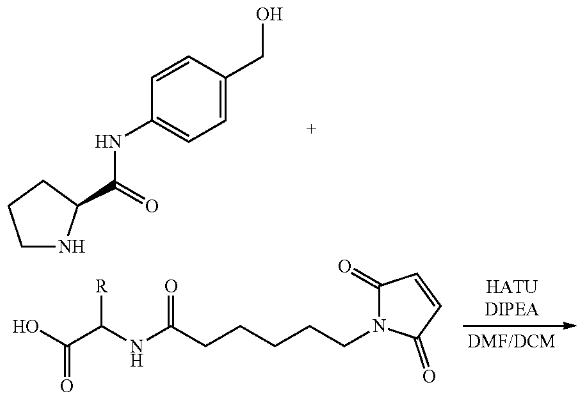

-continued

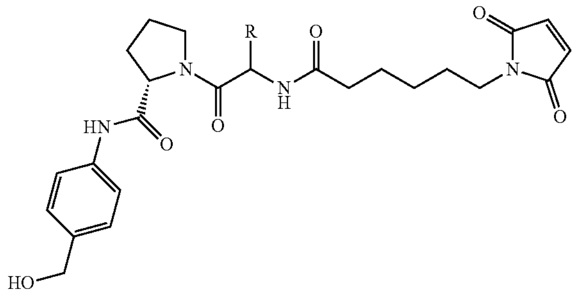

Desired MC-Aminoacid (1.1 eq) is dissolved in dry DMF (0.5 mL/mmol) under argon atmosphere and the solution is cooled to 0° C. HATU (1.1 eq), (S)—N-(4-(hydroxymethyl) phenyl)pyrrolidine-2-carboxamide (1.0 eq) and DIPEA (1.5 eq) are added subsequently. The reaction is allowed to slowly reach room temperature and stirred overnight. The mixture is diluted with AcOEt and washed with 1M $KHSO_4$ and brine. The organic phase is dried and concentrated under vacuum and the crude is purified via chromatography (DCM/MeOH 93:7) to afford the desired MC-AA-Pro-PAB

General Procedure for Synthesis of MC-AA-Pro-PAB-PNP

Scheme 32. General Synthesis route for preparation of MC-AA-Pro-PAB-PNP

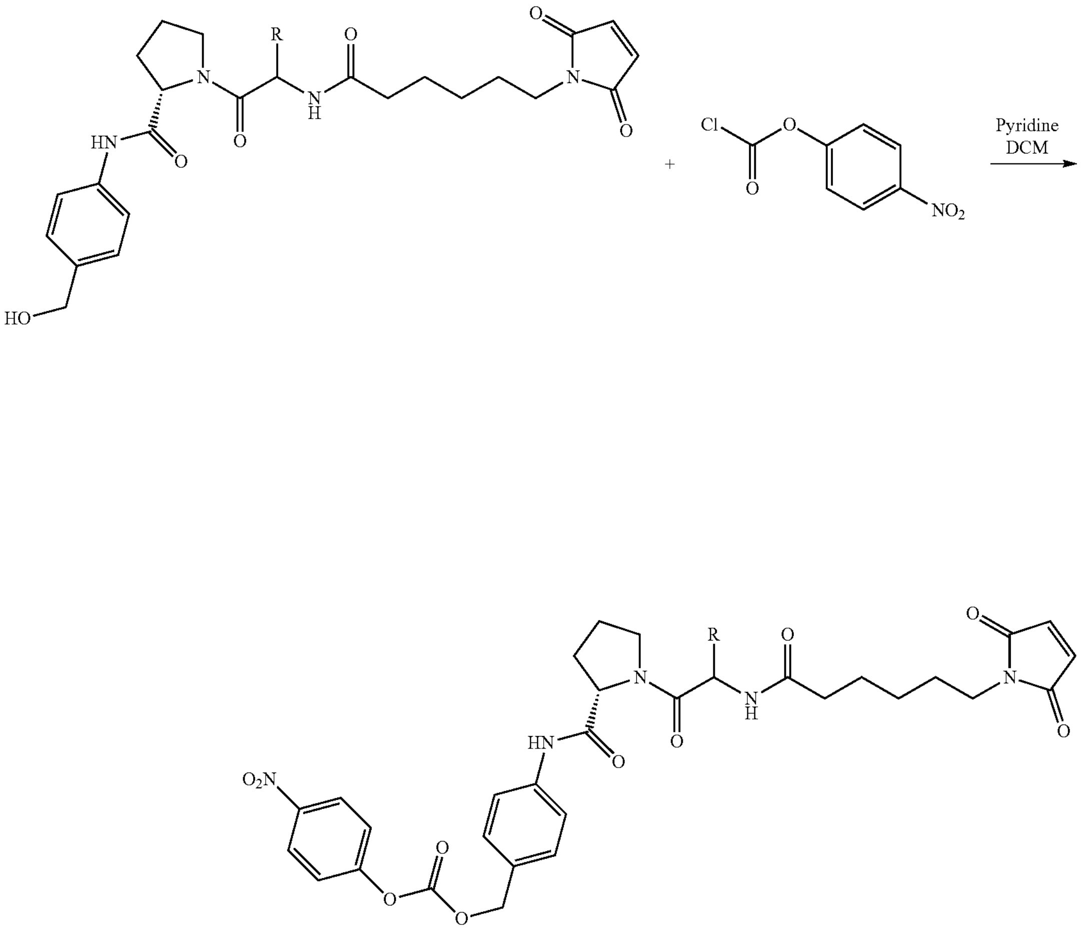

A solution of 4-Nitrophenyl chloroformate (2.2 eq) in dry $CH_2Cl_2$ (1 mL/mmol) is added under argon atmosphere to a suspension of the desired MC-AA-Pro-PAB (1.0 eq) in dry $CH_2Cl_2$ (1 mL/mmol) and pyridine (1.5 eq). After completion the solvent is removed under vacuum and the crude mixture is filtered over a pad of silica eluting with AcOEt to give MC-AA-Pro-PAB-PNP.

General Procedure for Synthesis of MC-AA-Pro-PAB-MMAE

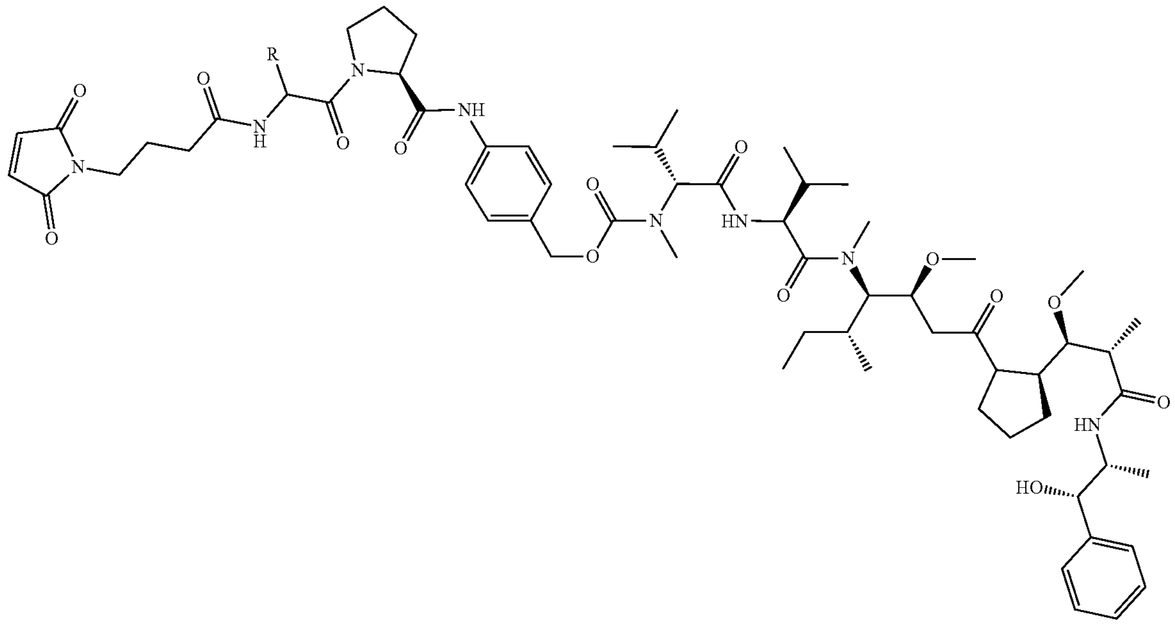

Monomethyl auristatin E (MMAE-TFA 1.1 eq) is dissolved in dry DMF (200 μL) under nitrogen atmosphere. MC-AA-Pro-PAB-PNP (1.0 eq), HOAt (0.5 eq) and DIPEA (5.0 eq) are added subsequently. The mixture is stirred at room temperature for 48 hours and concentrated under vacuum. The crude is diluted with a 200 μl of a mixture 1:1 water/methanol, and purified over reversed-phase HPLC (Water 0.1% TFA/Acetonitrile 0.1% TFA 9.5:0.5 to 2:8 in 20 min) to obtain the desired w products as white solids.

General Procedure for Synthesis of ESV6-AA-Pro-MMAE (58)

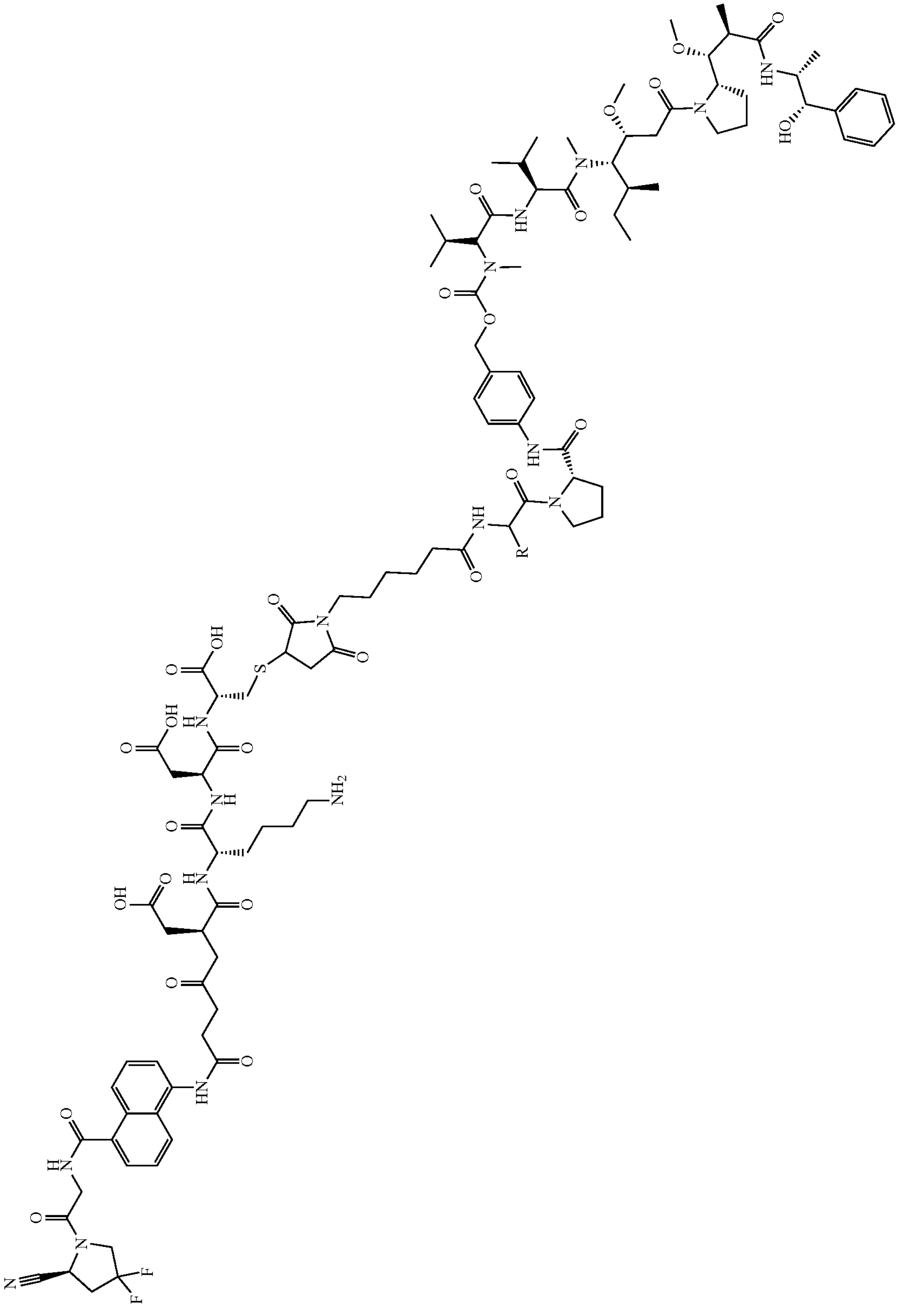

SH-Cys-Asp-Lys-Asp-ESV6 (P7, 700 μg, 0.760 μmol, 1.0 eq) is dissolved in PBS pH 7.4 (840 μL). MC-AA-Pro-PAB-MMAE (1.0 eq) is added as dry DMF solution (160 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain a white solid.

The AA used, the m/z and the yield of the derivatives are listed in the table below

| Compound | AA | MS(ES+) m/z (M + 1H)[1+] |
|---|---|---|
| 58a | Glycine | 2136.0 |
| 58b | Alanine | 2150.0 |
| 58c | Valine | 2178.1 |
| 58d | Isoleucine | 2192.1 |
| 58e | Proline | 2176.1 |
| 58f | Arginine | 2235.1 |

General Procedure for Synthesis of Py-S—S-MMAE

Scheme 33. General synthesis route for preparation of Py-S-S-MMAE

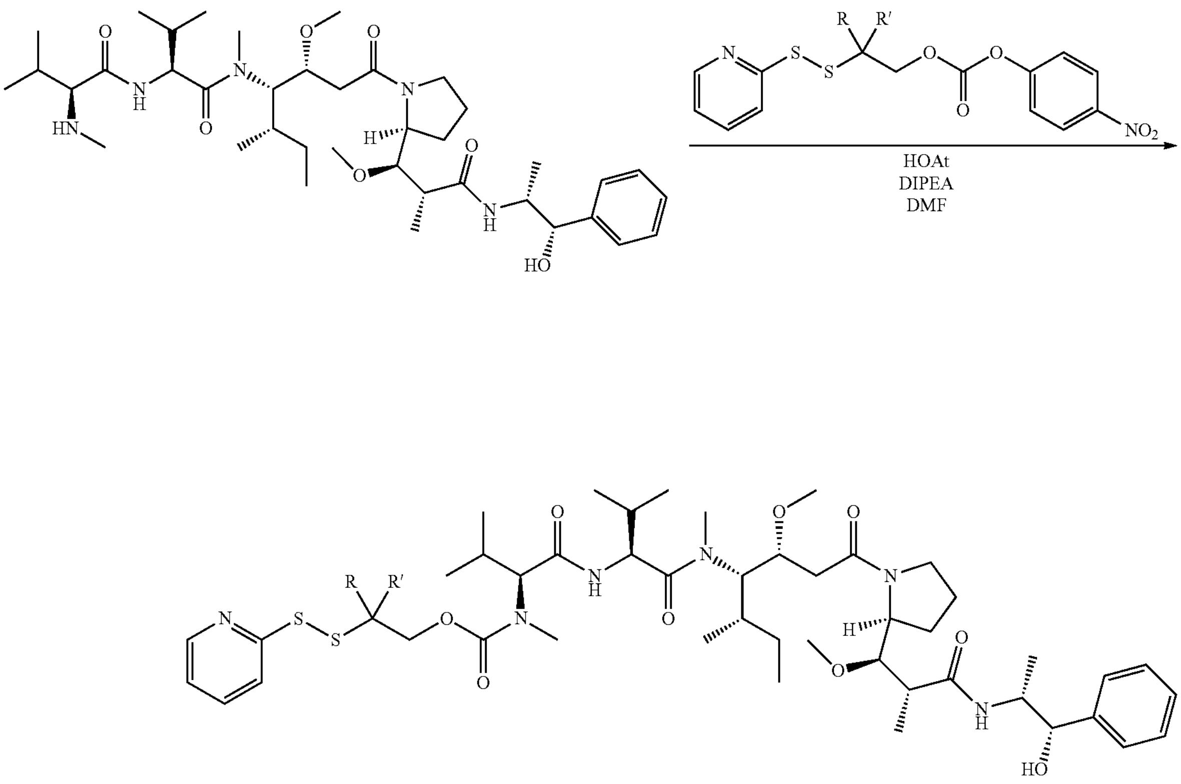

Monomethyl auristatin E (MMAE-TFA 1.1 eq) is dissolved in dry DMF (200 μL) under nitrogen atmosphere. Variously substituted 4-nitrophenyl (2-(pyridin-2-yldisulfaneyl)ethyl) carbonate (1.0 eq), HOAt (0.5 eq) and DIPEA (5.0 eq) are added subsequently. The mixture is stirred at room temperature for 48 hours and concentrated under vacuum. The crude is diluted with a 200 μl of a mixture 1:1 water/methanol, and purified over reversed-phase HPLC (Water 0.1% TFA/Acetonitrile 0.1% TFA 9.5:0.5 to 2:8 in 20 min). to obtain the desired products as white solids.

General Procedure for Synthesis of ESV6-S—S-MMAE (59)

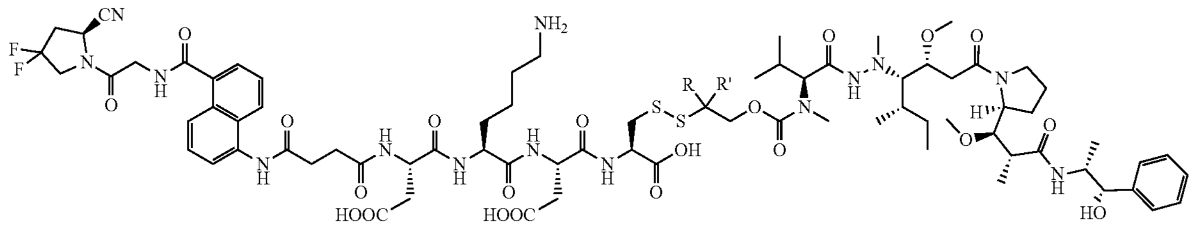

SH-Cys-Asp-Lys-Asp-ESV6 (P7, 700 μg, 0.760 μmol, 1.0 eq) is dissolved in PBS pH 7.4 (840 μL). Desired Py-S—S-MMAE (1.0 eq) is added as dry DMF solution (160 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain a white solid.

The R group used, the m/z and the yield of the derivatives are listed in the table below

| Compound | R | R' | MS(ES+) m/z $(M + 1H)^{1+}$ |
|---|---|---|---|
| 59a | —H | —H | 1740.6 |
| 59b | $—CH_3$ | —H | 1755.6 |
| 59c | $—CH_3$ | $—CH_3$ | 1770.6 |

Synthesis of PenCys-Asp-Lys-Asp-ESV6 peptide (P14)

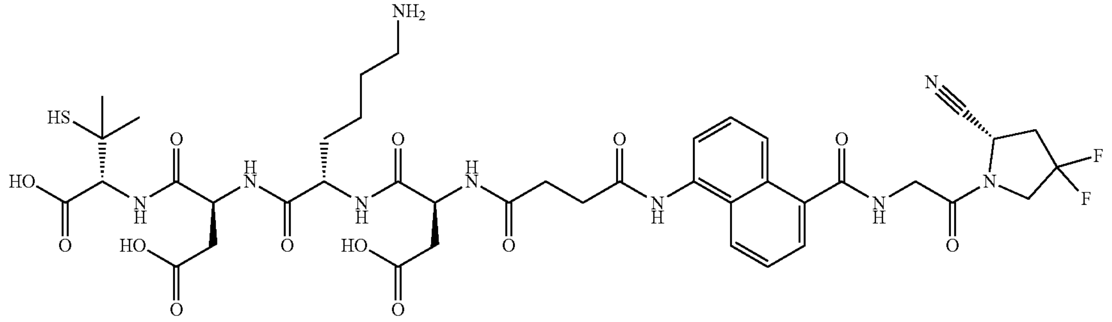 [SMILES: CC(C)(S)[C@H](NC(=O)[C@H](CC(=O)O)NC(=O)[C@H](CCCCN)NC(=O)[C@H](CC(=O)O)NC(=O)CCC(=O)Nc1cccc2c(C(=O)NCC(=O)N3CC(F)(F)C[C@H]3C#N)cccc12)C(=O)O]

Commercially available 2-Chloro-trityl chloride resin (300 mg) is swollen in DMF (3×5 min×5 mL). The resin is extended with Fmoc-PenCys(Trt), Fmoc-Asp(tBu)-OH, Fmoc-Lys(NHBoc)-OH and Fmoc-Asp(tBu)-OH in the indicated order. For this purpose, the Fmoc protected amino acid (2.0 eq), HBTU (2.0 eq), HOBt (2.0 eq) and DIPEA (4.0 eq) are dissolved in DMF (5 mL). The resin is extended with (S)-4-((4-((2-(2-cyano-4,4-difluoropyrrolidin-1-yl)-2-oxoethyl)carbamoyl)quinolin-8-yl)amino)-4-oxobutanoic acid (1 mmol), HBTU (2.0 eq) and DIPEA (2.0 eq) in DMF (5 mL). The peptide is cleaved from the resin with a mixture of 50% HFIP in DCM at room temperature for 1 h. The solvent is removed under reduced pressure and the crude precipitated in cold diethyl ether, centrifuged, dissolved in water/ACN and purify via HPLC (Water 0.1% TFA/Acetonitrile 0.1% TFA 9.5:0.5 to 5:5 in 15 min) and lyophilized, to obtain a white solid. MS($ES^+$) m/z 949.3 $(M+H)^+$ General Procedure for Synthesis Synthesis of PenESV6-S—S-MMAE (60)

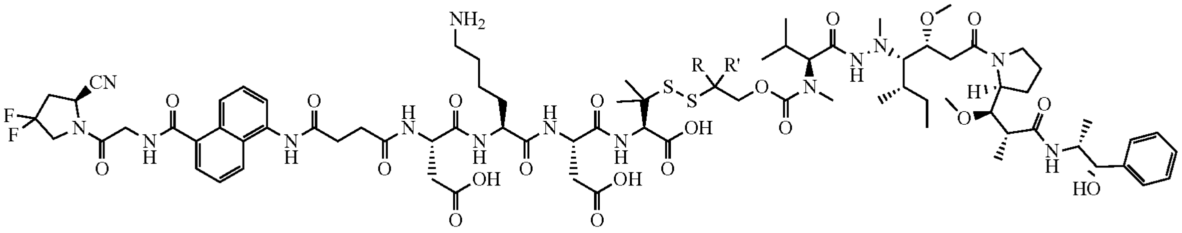

PenCys-Asp-Lys-Asp-ESV6 (700 μg, 0.760 μmol, 1.0 eq) is dissolved in PBS pH 7.4 (840 μL). Desired Py-S—S-MMAE (1.0 eq) was added as dry DMF solution (160 μL). The reaction is stirred for 3 h.

The crude material is purified by reversed-phase HPLC (Water 0.1% TFA/Acetonitrile 0.1% TFA 9.5:0.5 to 2:8 in 20 min) and lyophilized, to obtain a white solid.

The R group used and the m/z of the derivatives are listed in the table below

| Compound | R | R' | MS(ES+) m/z $(M + 1H)^{1+}$ |
|---|---|---|---|
| 60a | —H | —H | 1770.6 |
| 60b | $—CH_3$ | —H | 1785.6 |
| 60c | $—CH_3$ | $—CH_3$ | 1800.6 |

Synthesis of (S)—$N^1$-(4-((2-(2-cyano-4,4-difluoro-pyrrolidin-1-yl)-2-oxoethyl)carbamoyl)quinolin-8-yl)-$N^4$-(2-(2,5-dioxo-2,5-dihydro-1H-pyrrol-1-yl)ethyl)succinimide (P15)

Scheme 34. Synthesis route for preparation of (S)-$N^1$-(4-((2-(2-cyano-4,4-difluoropyrrolidin-1-yl)-2-oxethyl)carbamoyl) quinolin-8-yl)$N^4$-(2-(2,5-dioxo-2,5-dihydro-1H-pyrrol-1-yl) ethyl(succinimide (P15)

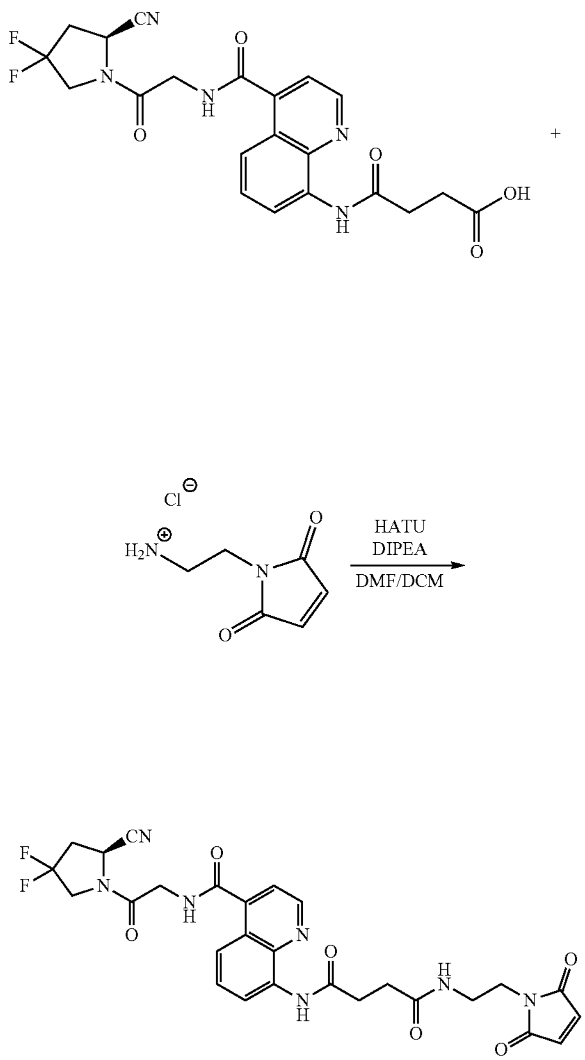

(S)-4-((4-((2-(2-cyano-4,4-difluoropyrrolidin-1-yl)-2-oxoethyl)carbamoyl)quinolin-8-yl)amino)-4-oxobutanoic acid (65 mg, 0.14 mmol, 1 eq), HATU (54 mg, 0.14 mmol, 1 eq) and 1-(2-Aminoethyl)maleimide HCl (25 mg, 0.14 mmol, 1 eq) were dissolved in 1.5 mL of DCM and 500 μL of DMF. DIPEA (54 mg, 0.43 mmol, 3 eq) was added dropwise and the reaction was stirred for 30 minutes at room temperature. Water was added, separated from organic layer and then extracted three times with DCM. The crude was dried over sodium sulfate, filtered and evaporated. The crude was purified via chromatography (DCM/MeOH 100:0 to 95:5 in 10 min) to afford a yellow oil (50 mg. 0.0868 mmol, 62%). MS($ES^+$) m/z 582.6 $(M+1H)^{1+}$ Synthesis of Conjugate 66

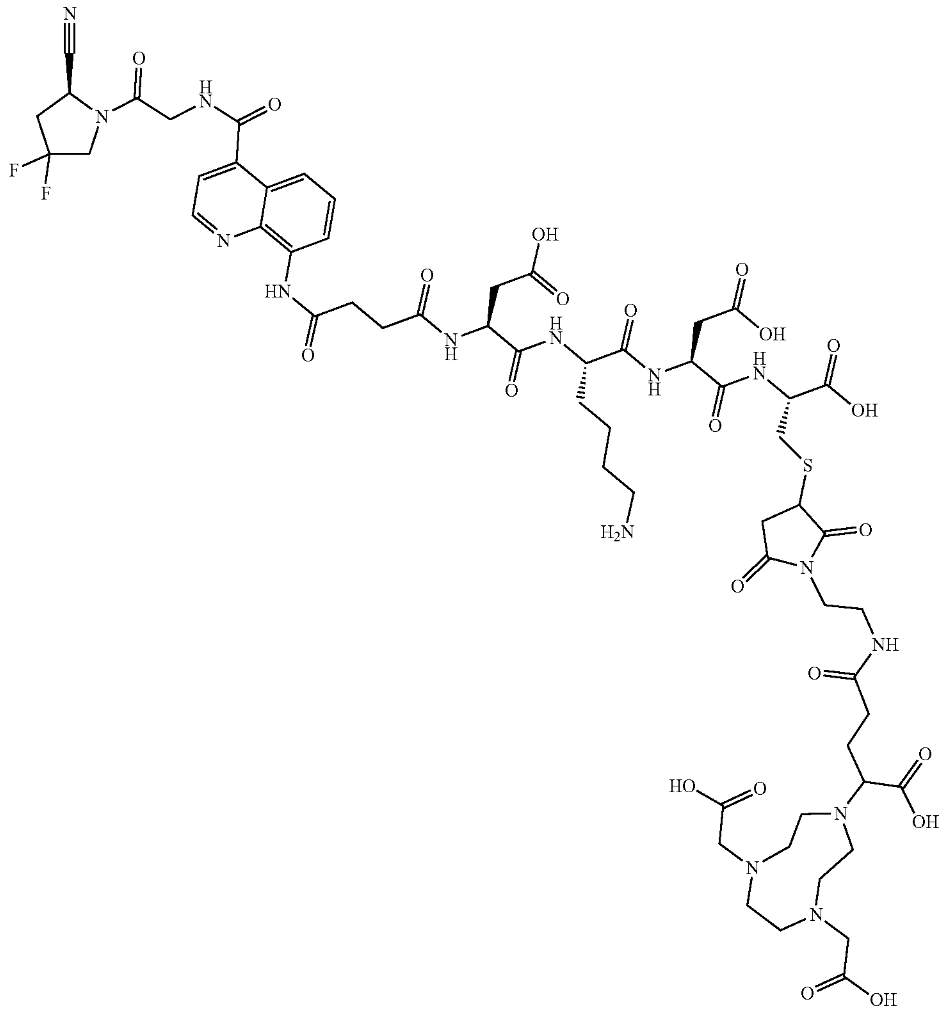 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CSC3CC(=O)N(CCNC(=O)CCC(C(=O)O)N4CCN(CC(=O)O)CCN(CC(=O)O)CC4)C3=O)C(=O)O)cccc12]

SH-Cys-Asp-Lys-Asp-ESV6 (2 mg, 2.171 μmol, 1.0 eq) is dissolved in PBS pH 7.4 (800 μL). Maleimido-NODAGA (3.3 mg, 4.343 μmol, 2.0 eq) is added as dry DMSO solution (200 μL). The reaction is stirred for 3 h. The crude material is purified by reversed-phase HPLC (Water 0.1% TFA/Acetonitrile 0.1% TFA 9.5:0.5 to 2:8 in 20 min) and lyophilized, to obtain a yellow solid. MS($ES^+$) m/z 1346.36 $(M+1H)^{1+}$ General synthesis of Protein-OncoFAP

62

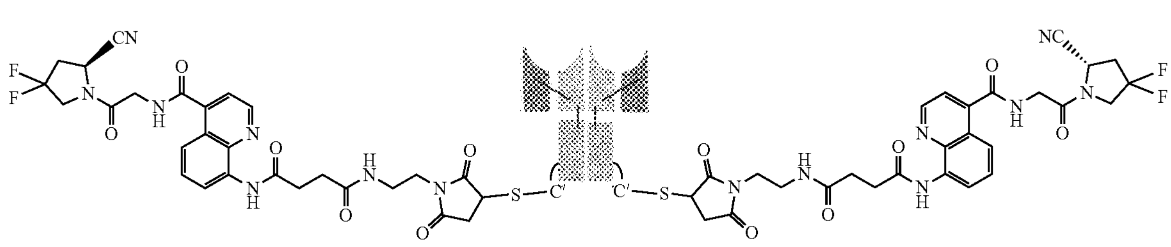

The protein is reduced overnight at 4° C. using 30 equivalents of TCEP-HCl per cysteine residue. The product is purified via FPLC and the fractions containing the products are merged.

The reduced protein is then reacted with 20 equivalents per cysteine residue with (S)—N-(4-((2-(2-cyano-4,4-difluoropyrrolidin-1-yl)-2-oxoethyl)carbamoyl)quinolin-8-yl)-$N^4$-(2-(2,5-dioxo-2,5-dihydro-1H-pyrrol-1-yl)ethyl)succinamide for 1 hour at room temperature, under gentle shaking.

The product is then purified via FPLC and analyzed with LC/MS to confirm the identity.

The described protocol can be used to functionalize proteins, enzymes, targets, antibodies, immunocytokines, pro-inflammatory proteins and peptides containing one or more cysteine residues.

Further examples of protein conjugates according to the present invention are: protein coupled to FAP targeting agent (e.g., conjugate 63, 63a), and protein coupled to multiple FAP targeting agents (e.g., 69, 69a), as exemplified below. The ball represents a generic protein structure.

63

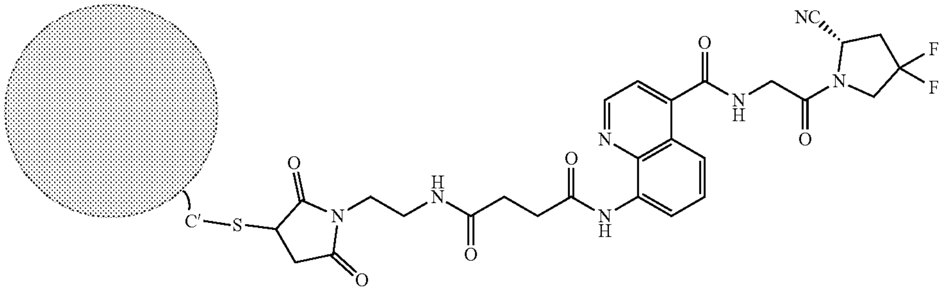

63a

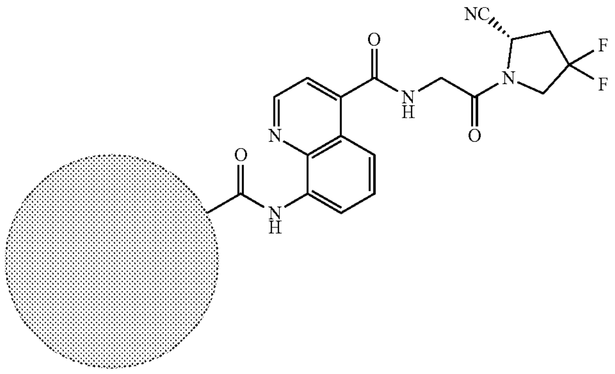

69

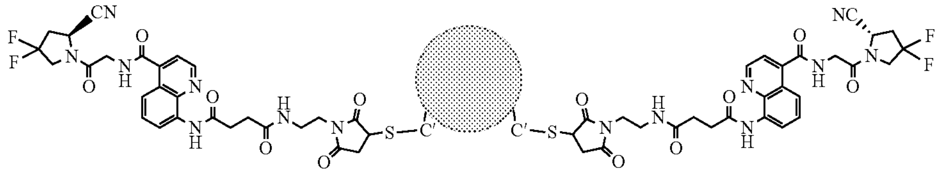

69a

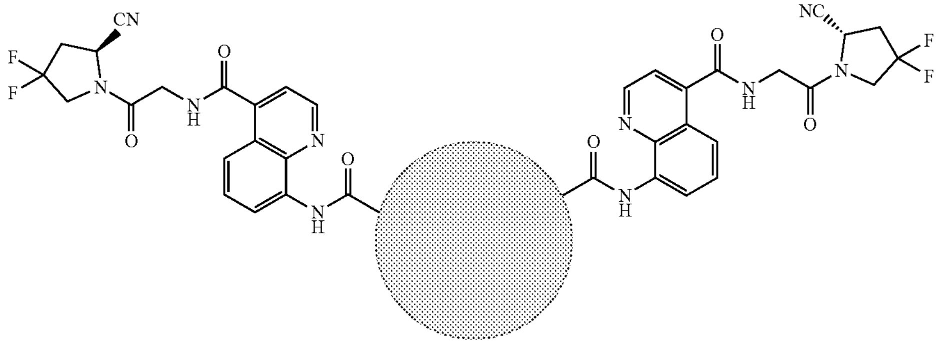

The invention claimed is:

1. A compound having one the following structures, its individual diastereoisomers, its hydrates, its solvates, its crystal forms, its individual tautomers or a pharmaceutically acceptable salt thereof:

| # | Structure |
| --- | --- |
| 1 | 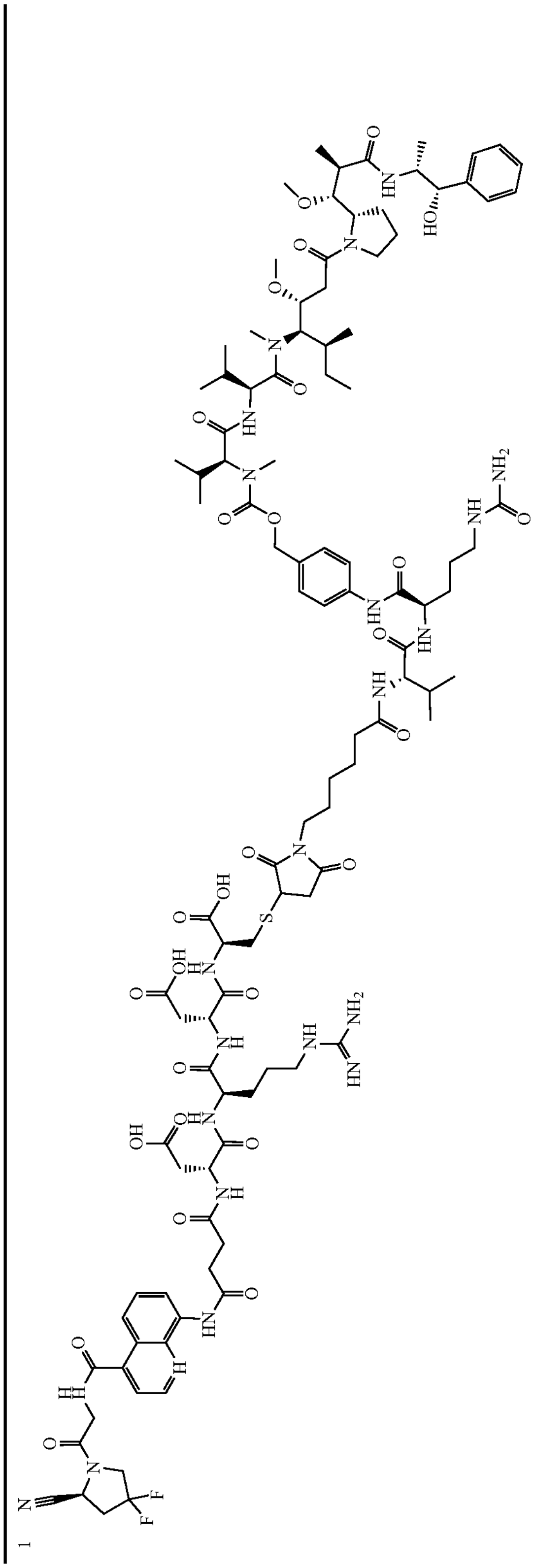 |

-continued
| # | Structure |
|---|---|
| 2 | 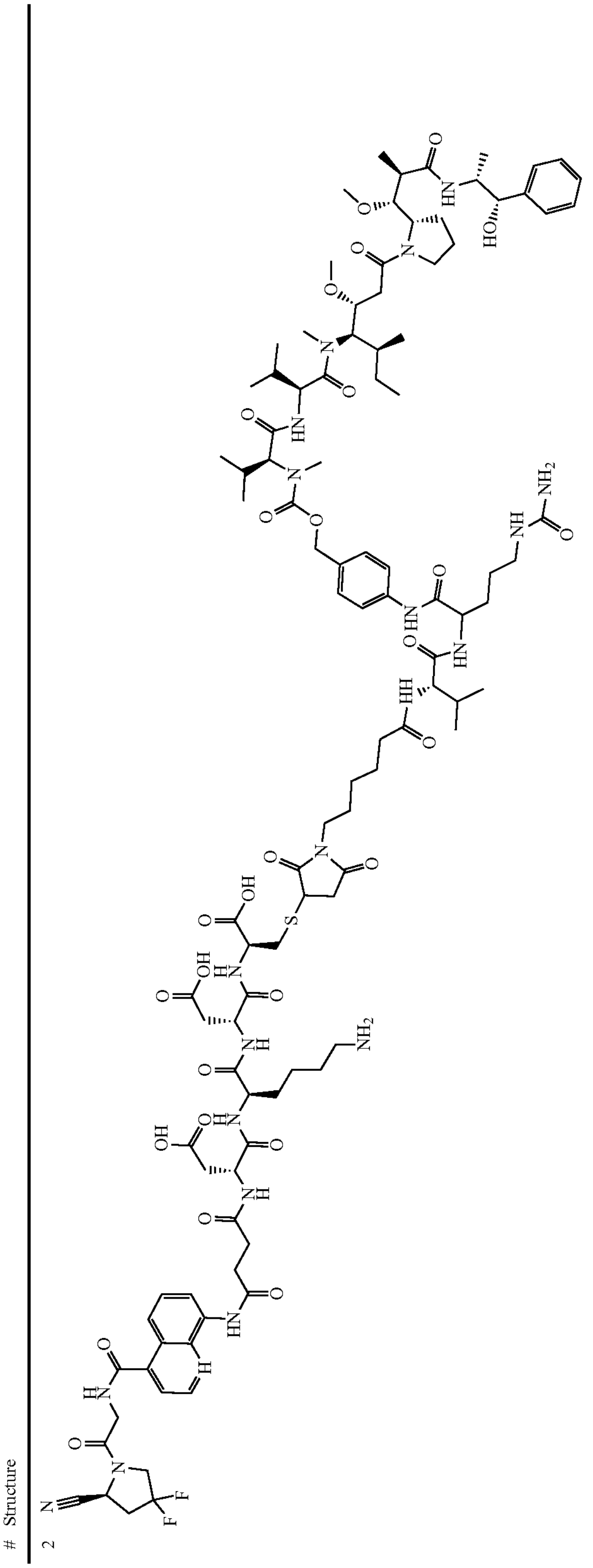 |

-continued
| # | Structure |
| --- | --- |
| 3 | 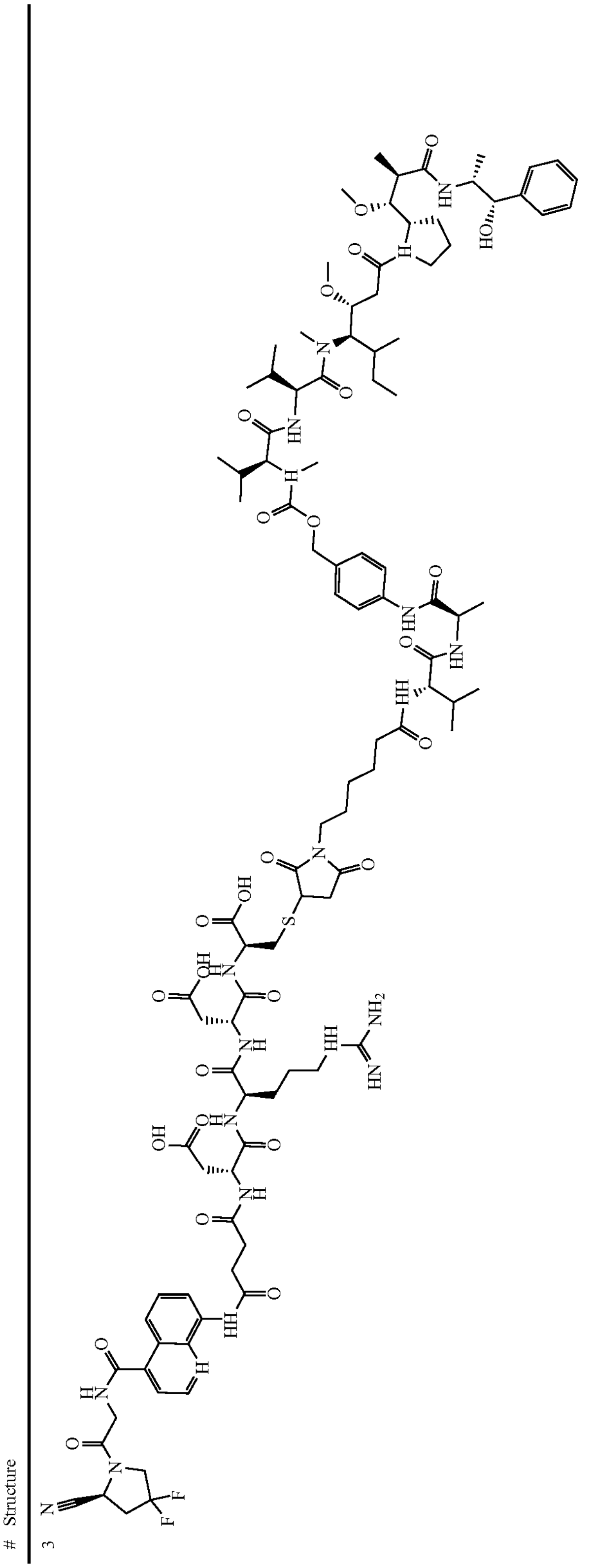 |
| 4 | 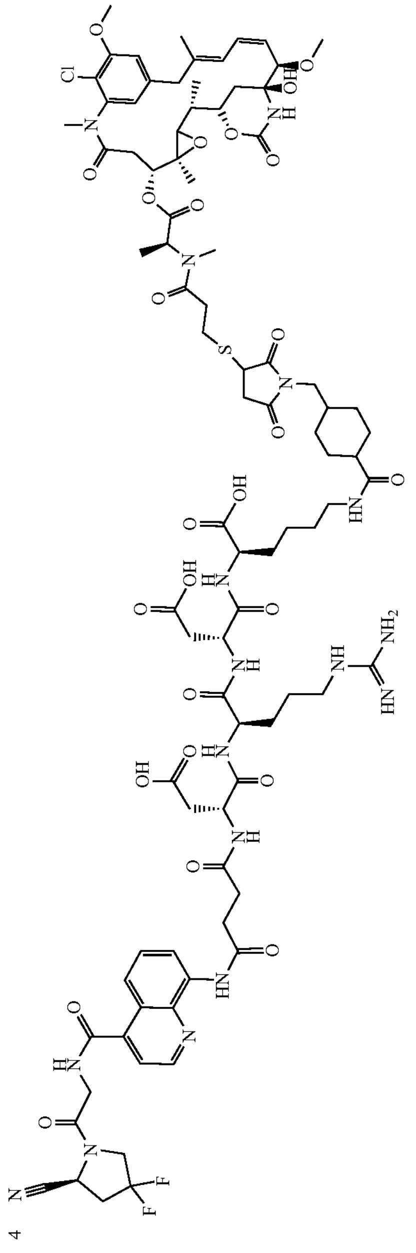 |

-continued
| # | Structure |
|---|---|
| 5 | 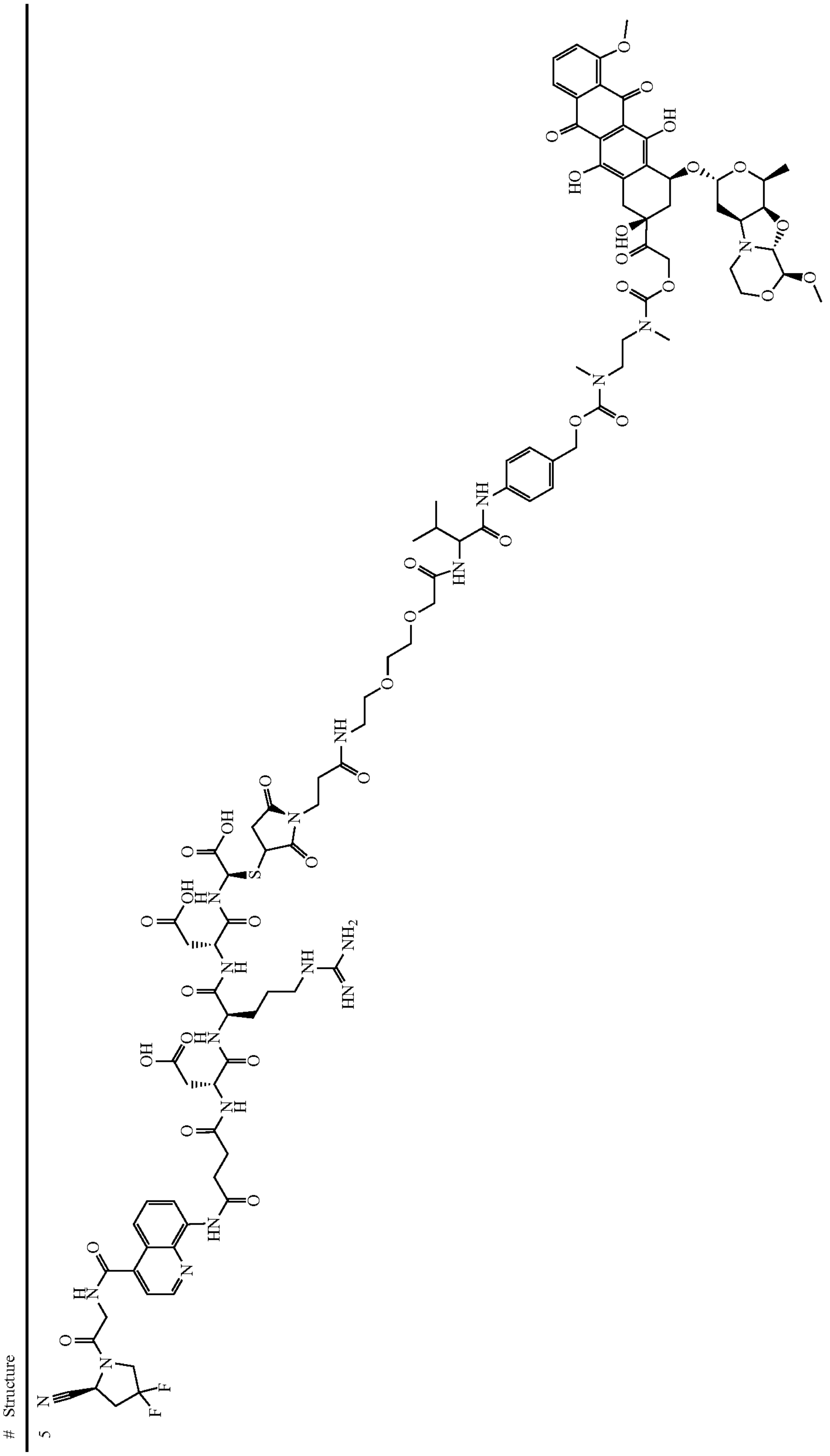 |

-continued
| # | Structure |
|---|---|
| 6 | 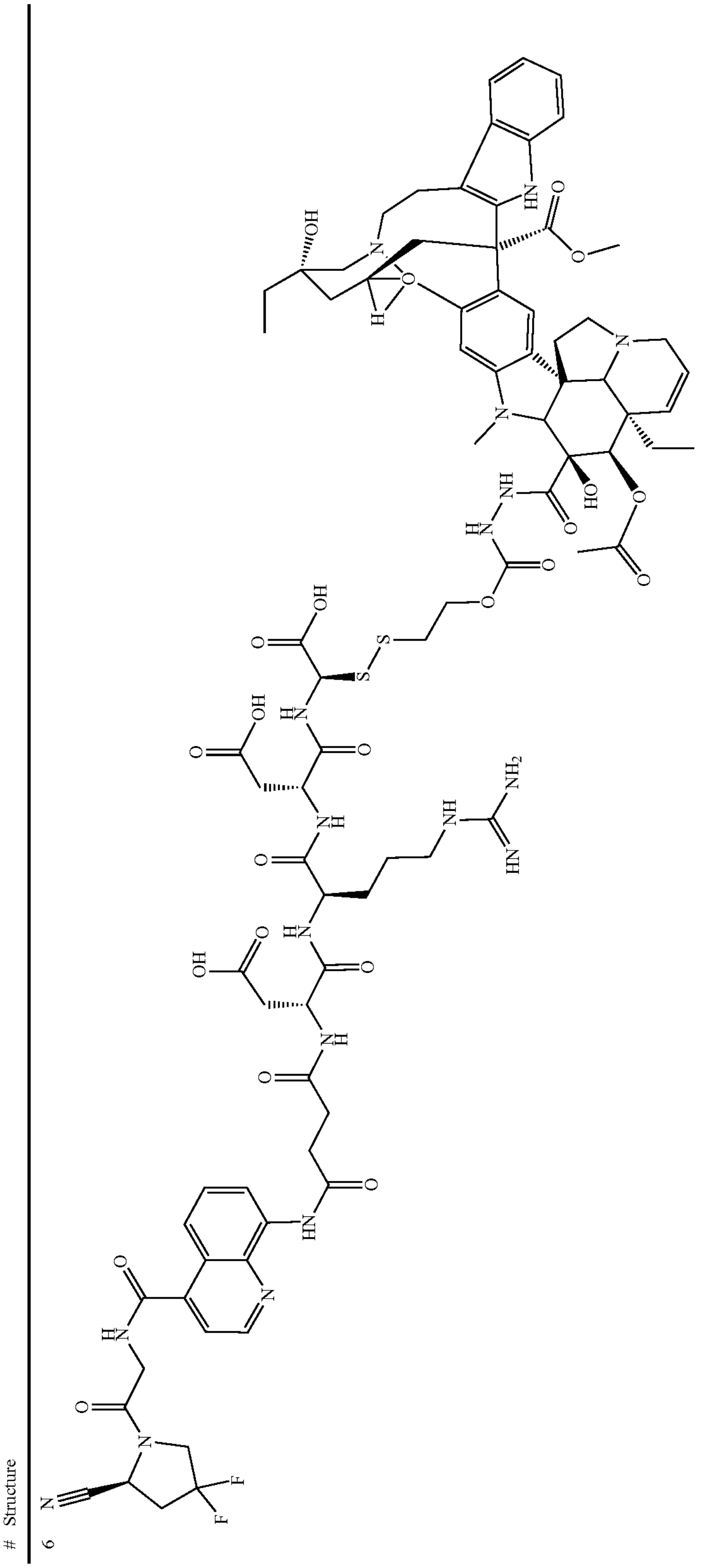 |

-continued
| # | Structure |
|---|---|
| 7 | 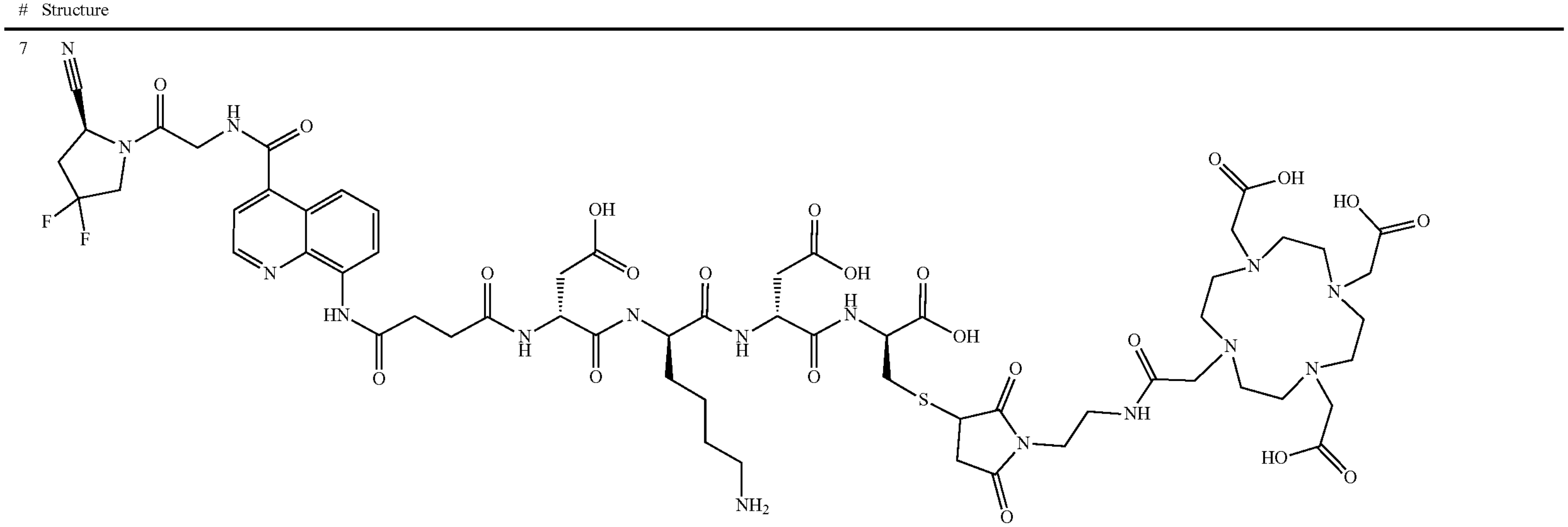 |
| 8 | 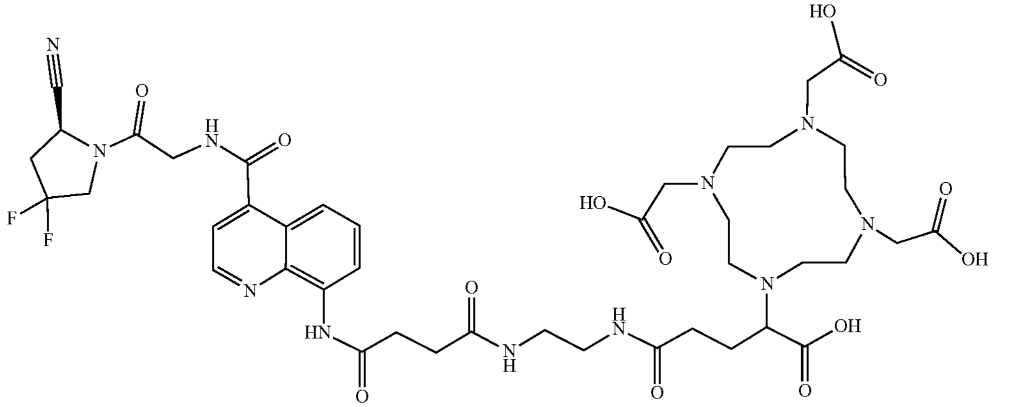 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CCN(CC(=O)O)CC3)cccc12] |

-continued
| # | Structure |
| --- | --- |
| 9 | 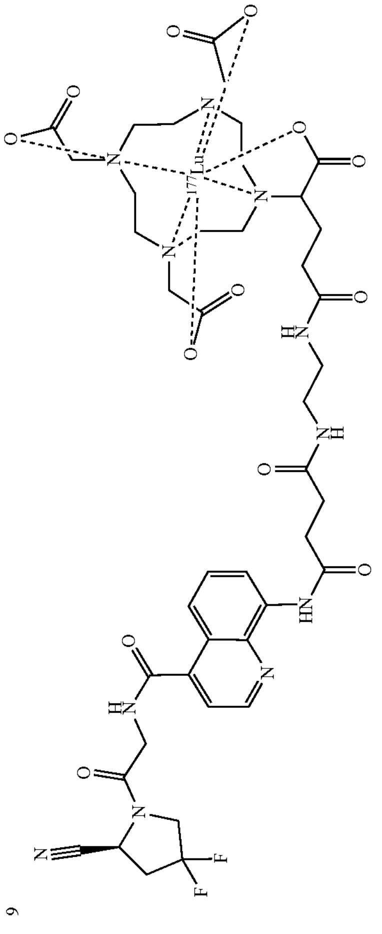 |
| 10 | 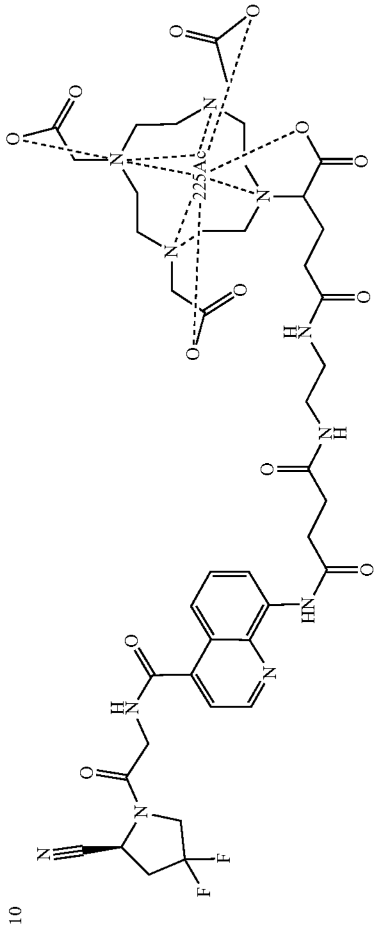 |

-continued
| # | Structure |
|---|---|
| 11 | 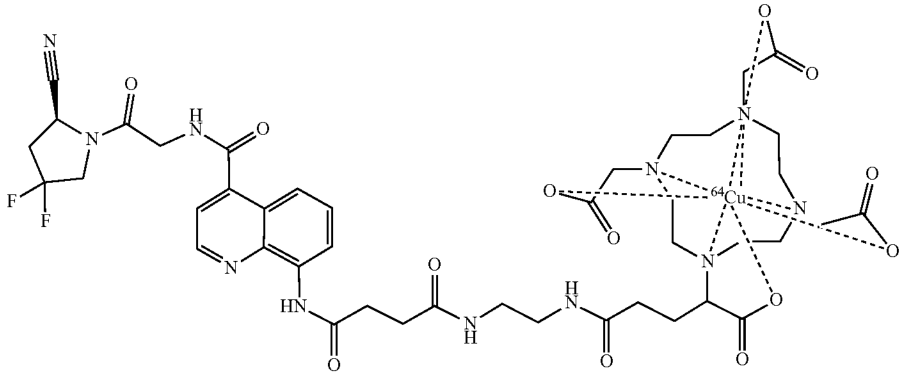 |
| 12 | 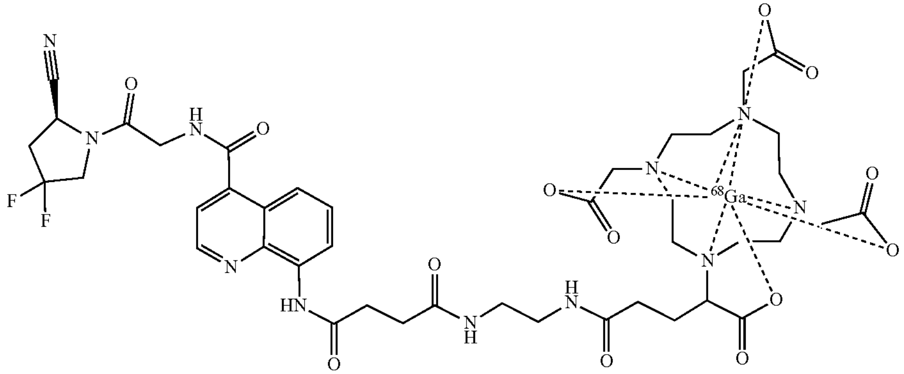 |

-continued
| # | Structure |
|---|---|
| 13 | 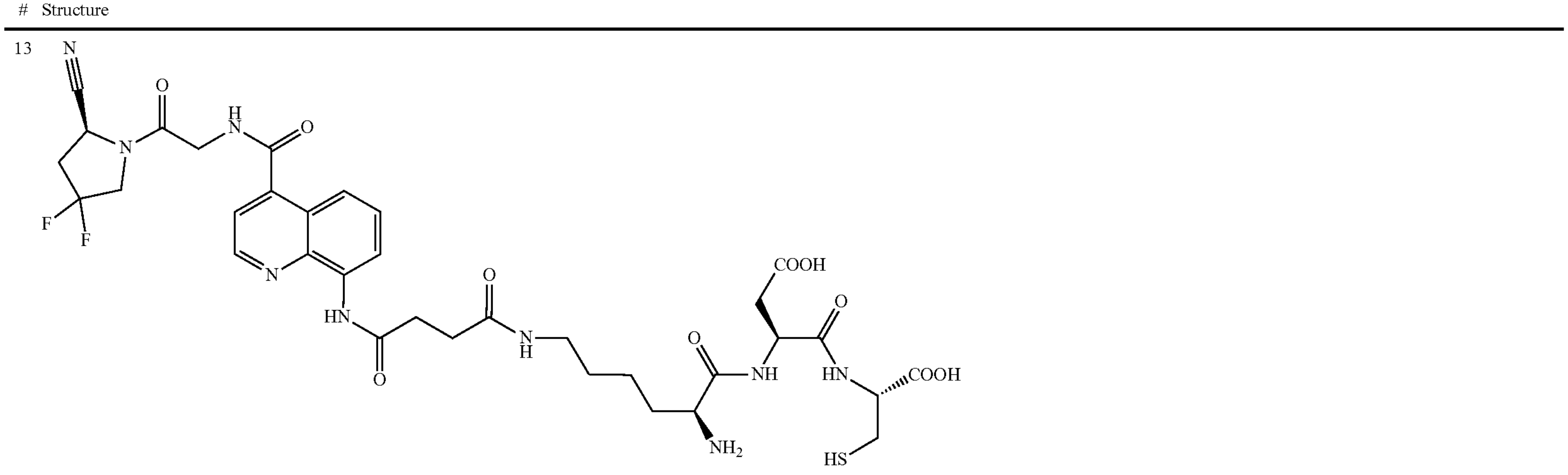 |
| 14 | 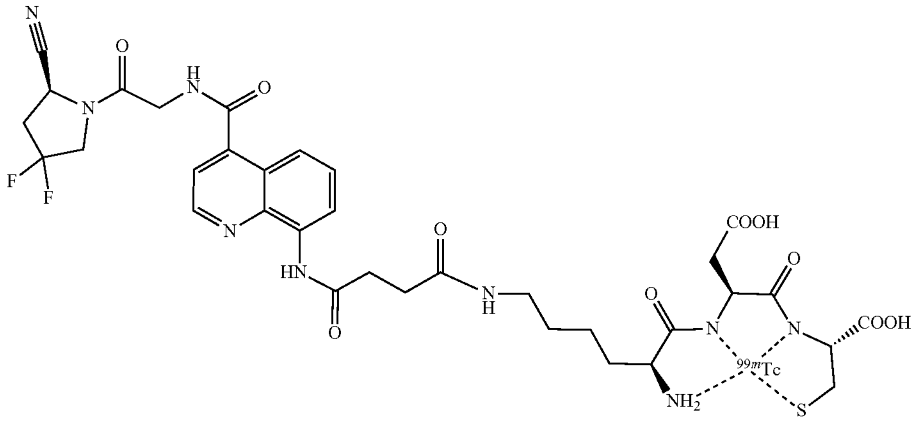 |

-continued
| # | Structure |
|---|---|
| 15 | 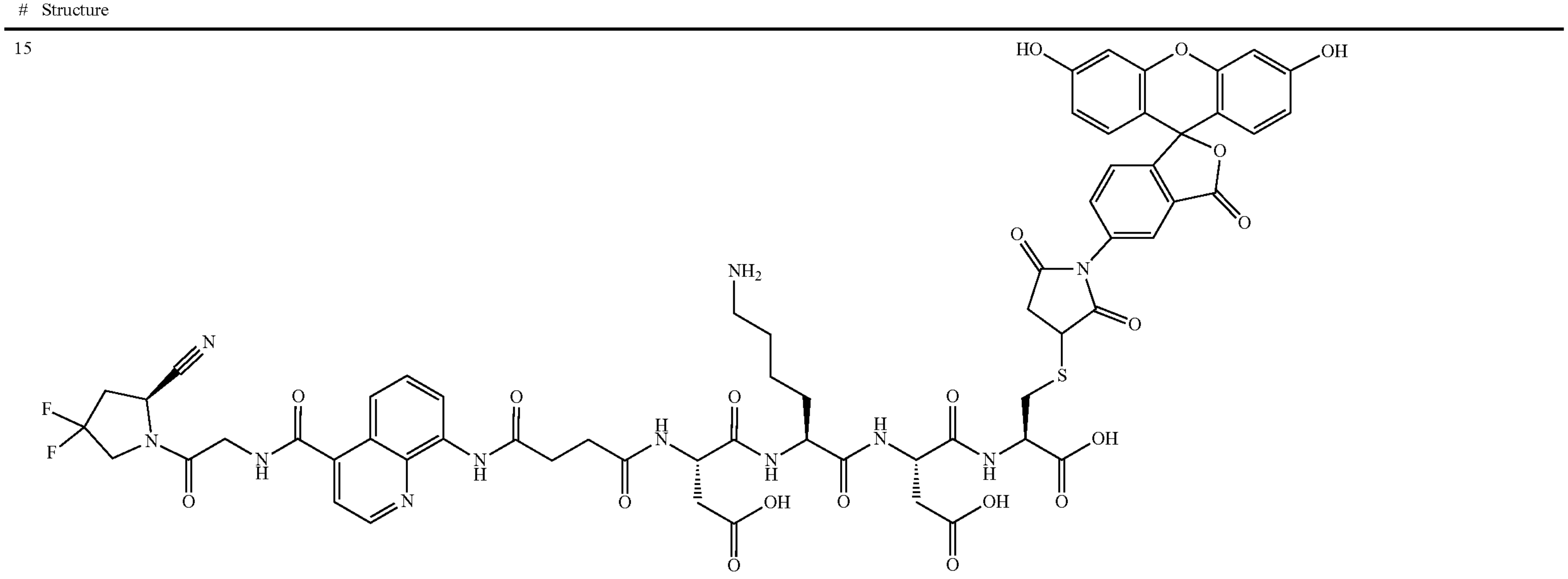 |

-continued
| # | Structure |
|---|---|
| 18 | 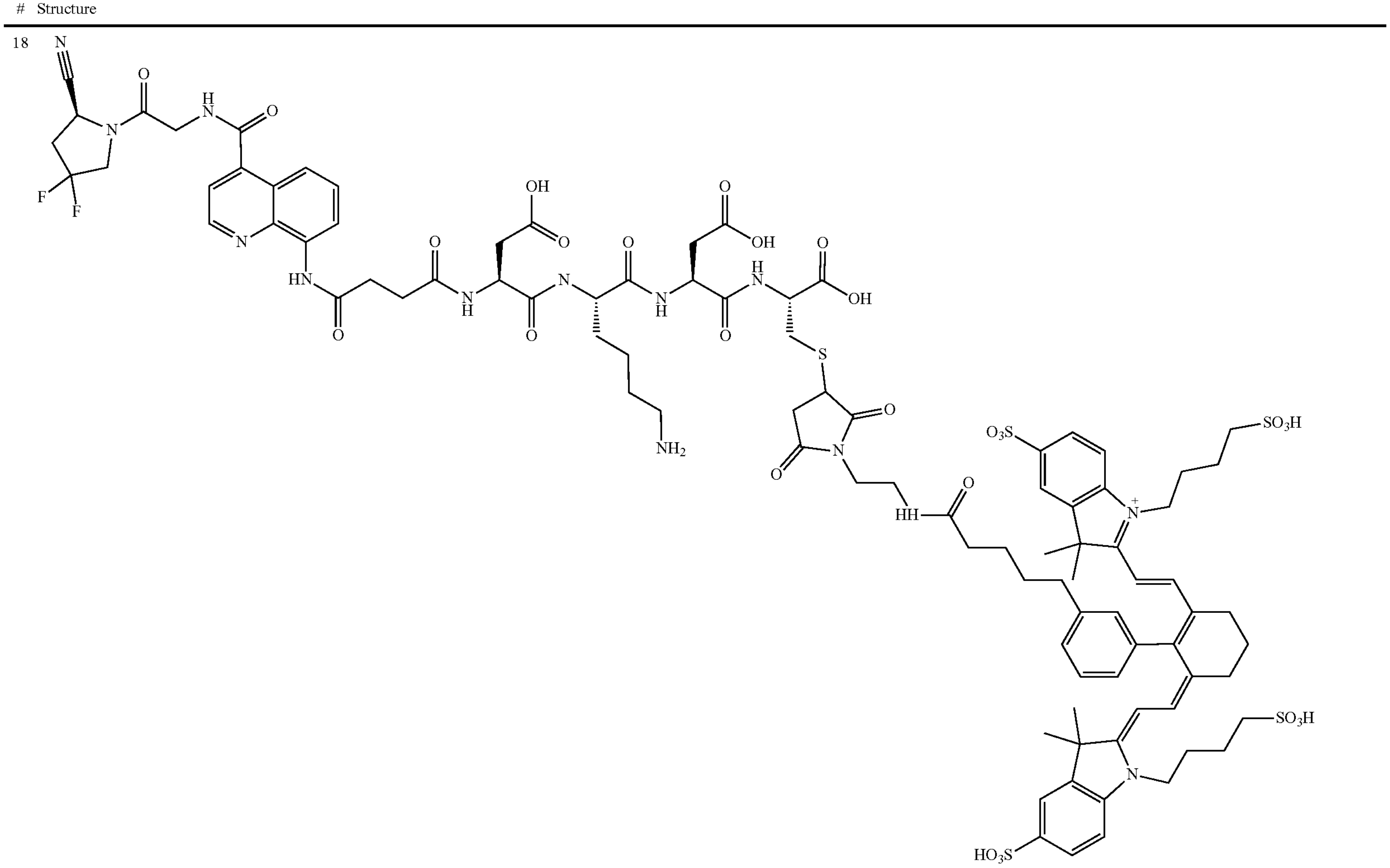 |

-continued
| # | Structure |
|---|---|
| 21 | 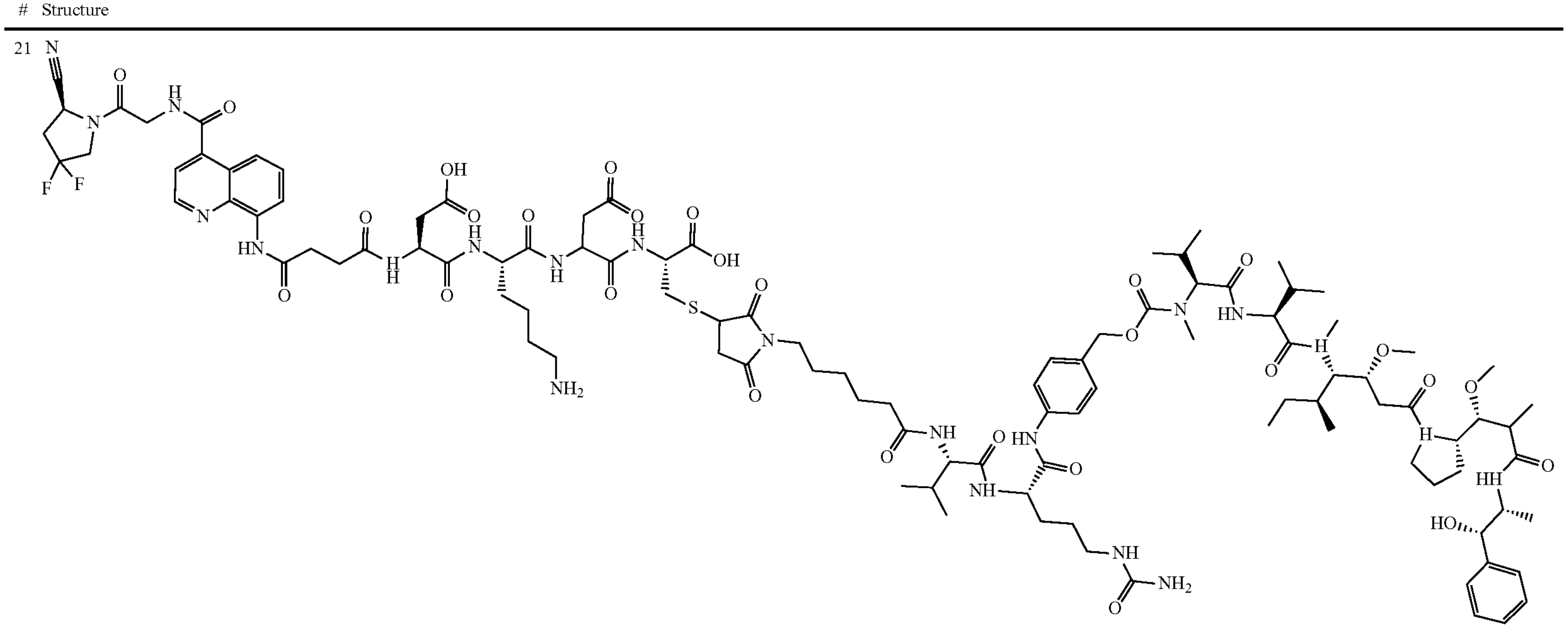 |

-continued
| # | Structure |
|---|---|
| 26 | 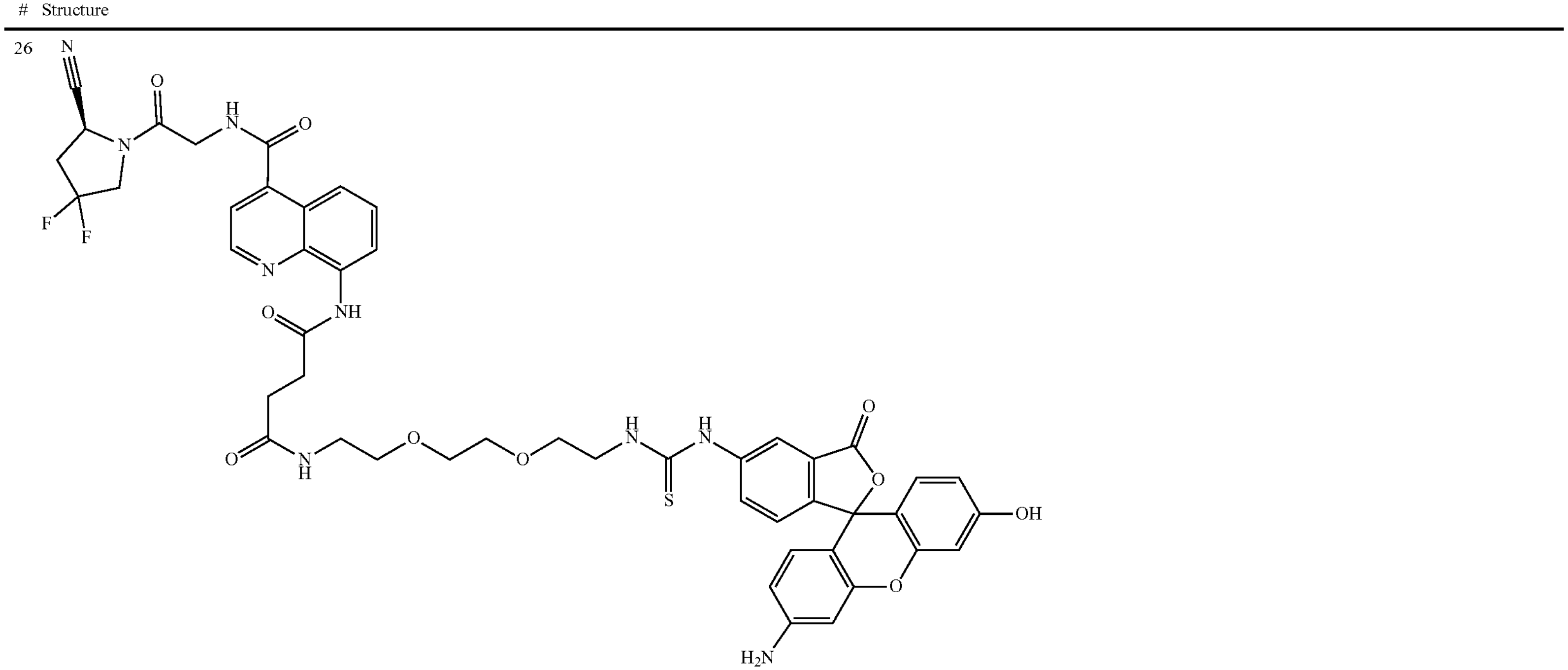 |

-continued
| # | Structure |
|---|---|
| 27 | 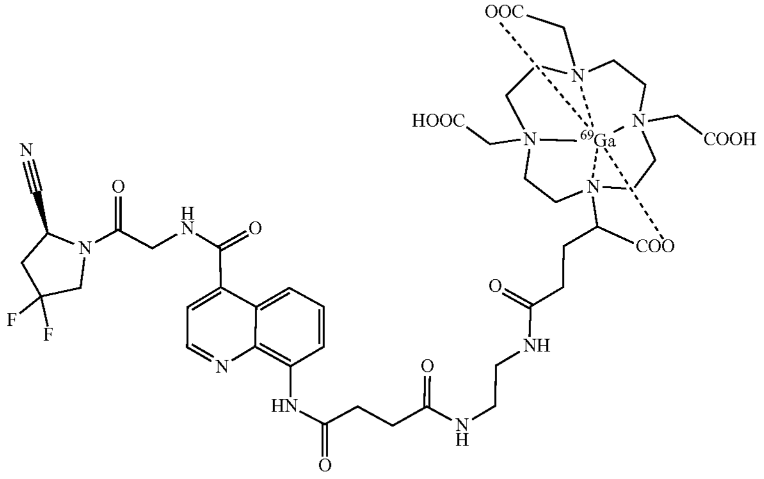 |
| 30 | 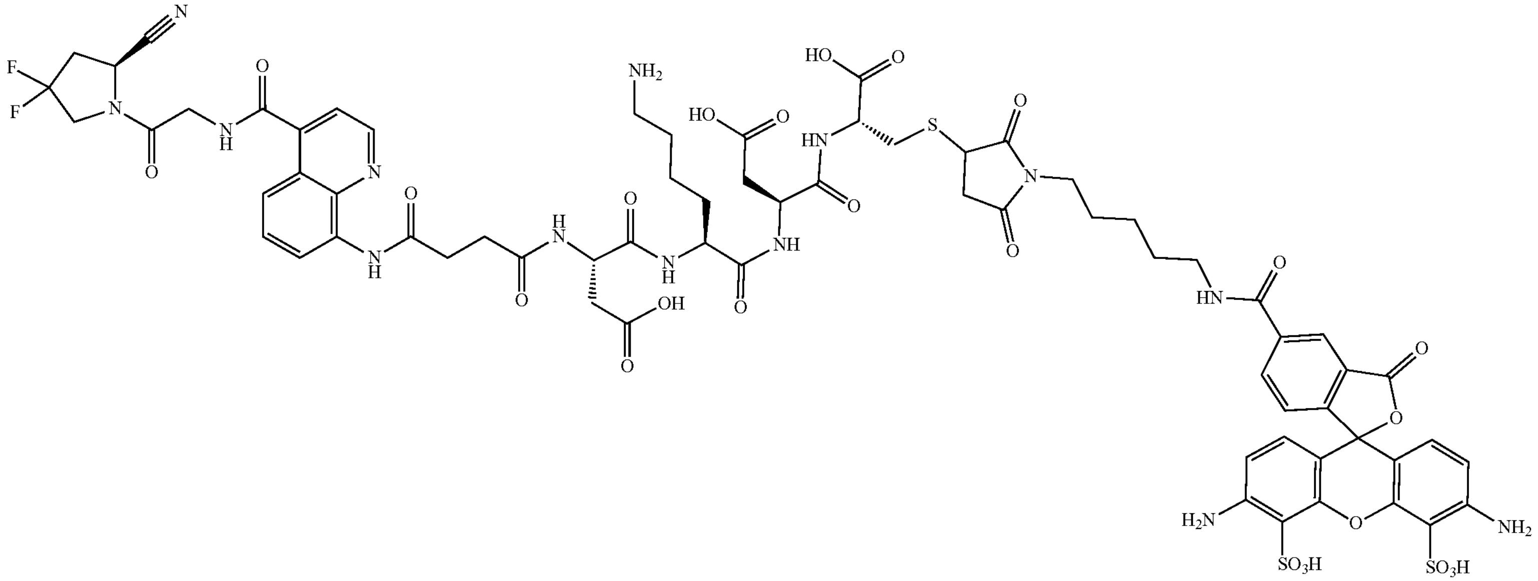 [SMILES: N#C[C@@H]1CC(F)(F)CN1C(=O)CNC(=O)c1ccnc2c(NC(=O)CCC(=O)N[C@@H](CC(=O)O)C(=O)N[C@@H](CCCCN)C(=O)N[C@@H](CC(=O)O)C(=O)N[C@@H](CSC3CC(=O)N(CCCCCNC(=O)c4ccc5c(c4)C(=O)OC54c5ccc(N)c(S(=O)(=O)O)c5Oc5c4ccc(N)c5S(=O)(=O)O)C3=O)C(=O)O)cccc12] |

-continued
| # | Structure |
|---|---|
| 31 | 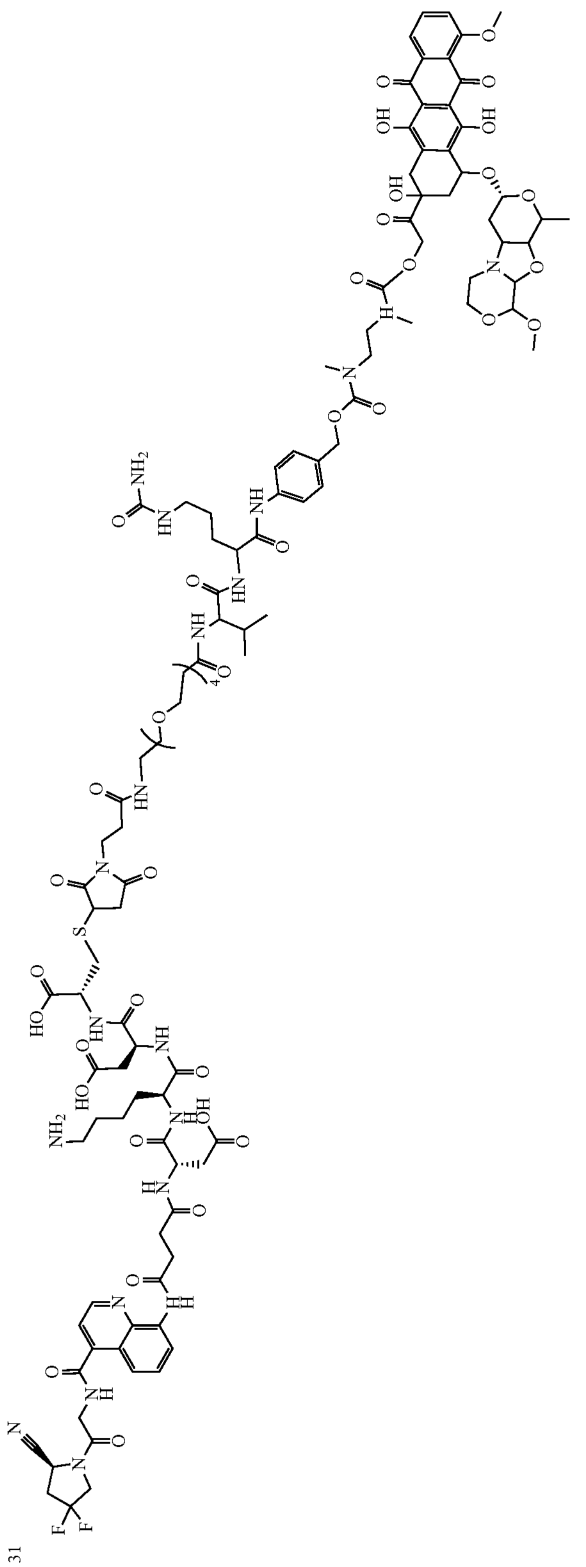 |

-continued
| # | Structure |
| --- | --- |
| 34 | 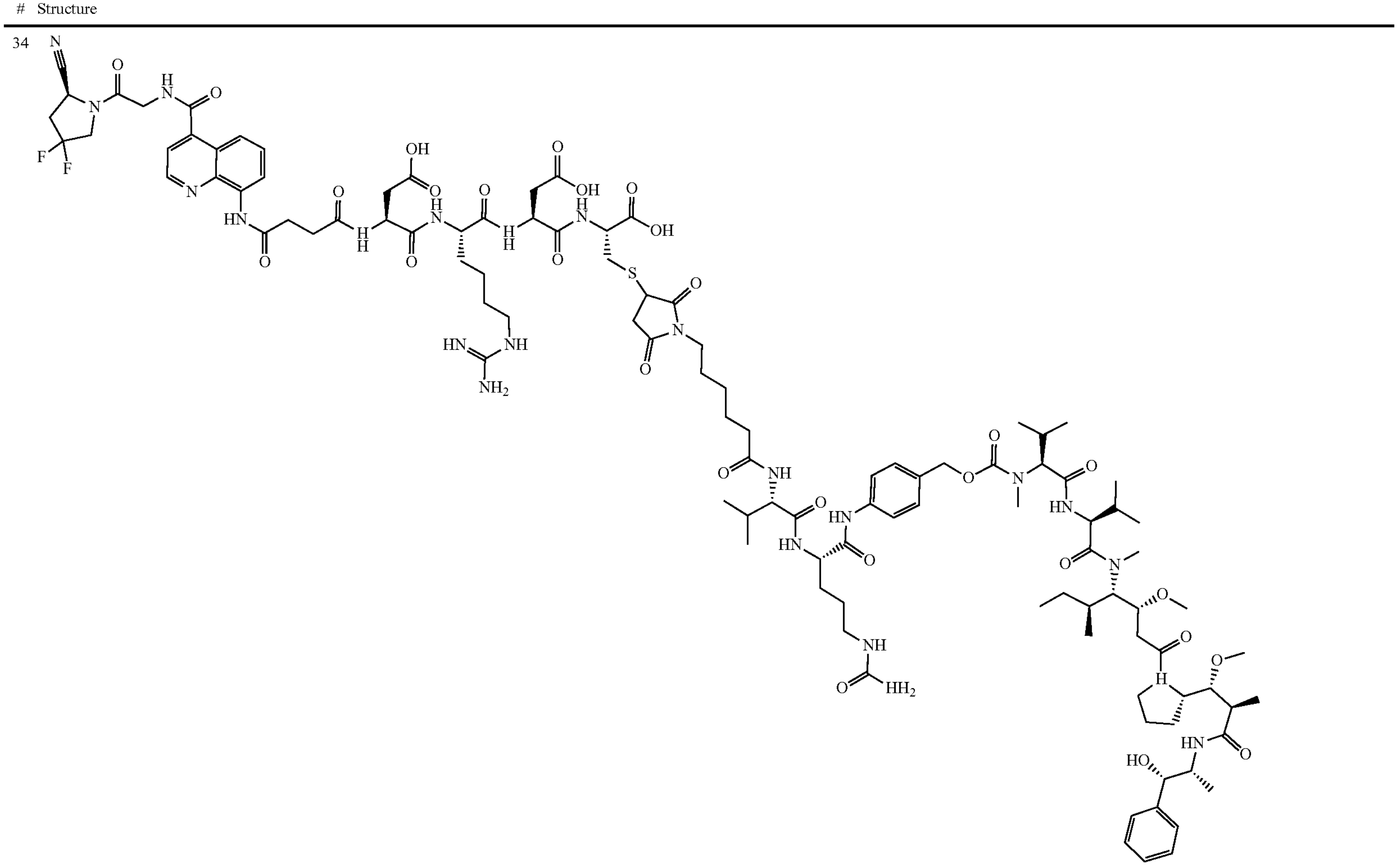 |

-continued
| # | Structure |
| --- | --- |
| 34a | 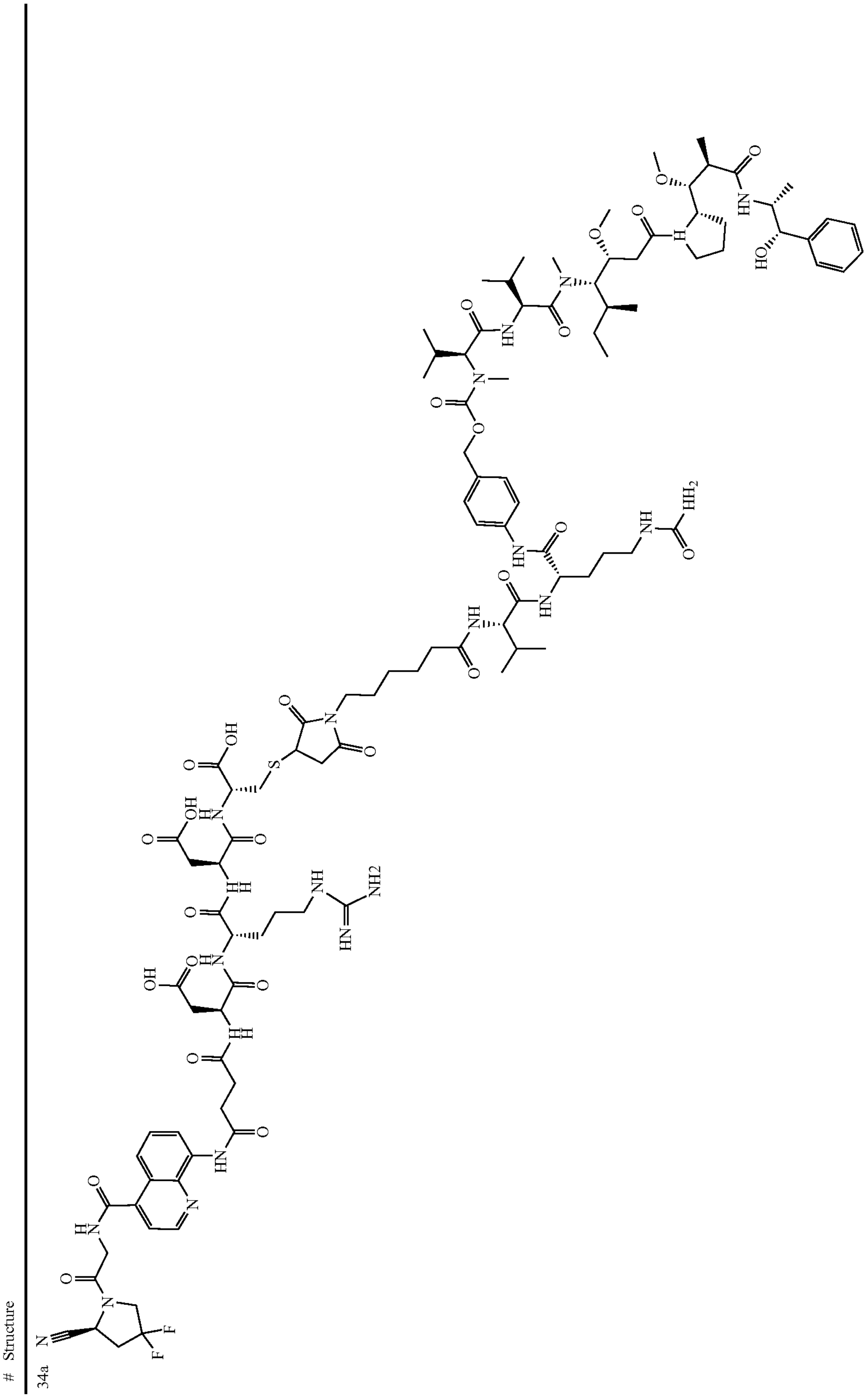 |

-continued
| # | Structure |
|---|---|
| 35 | 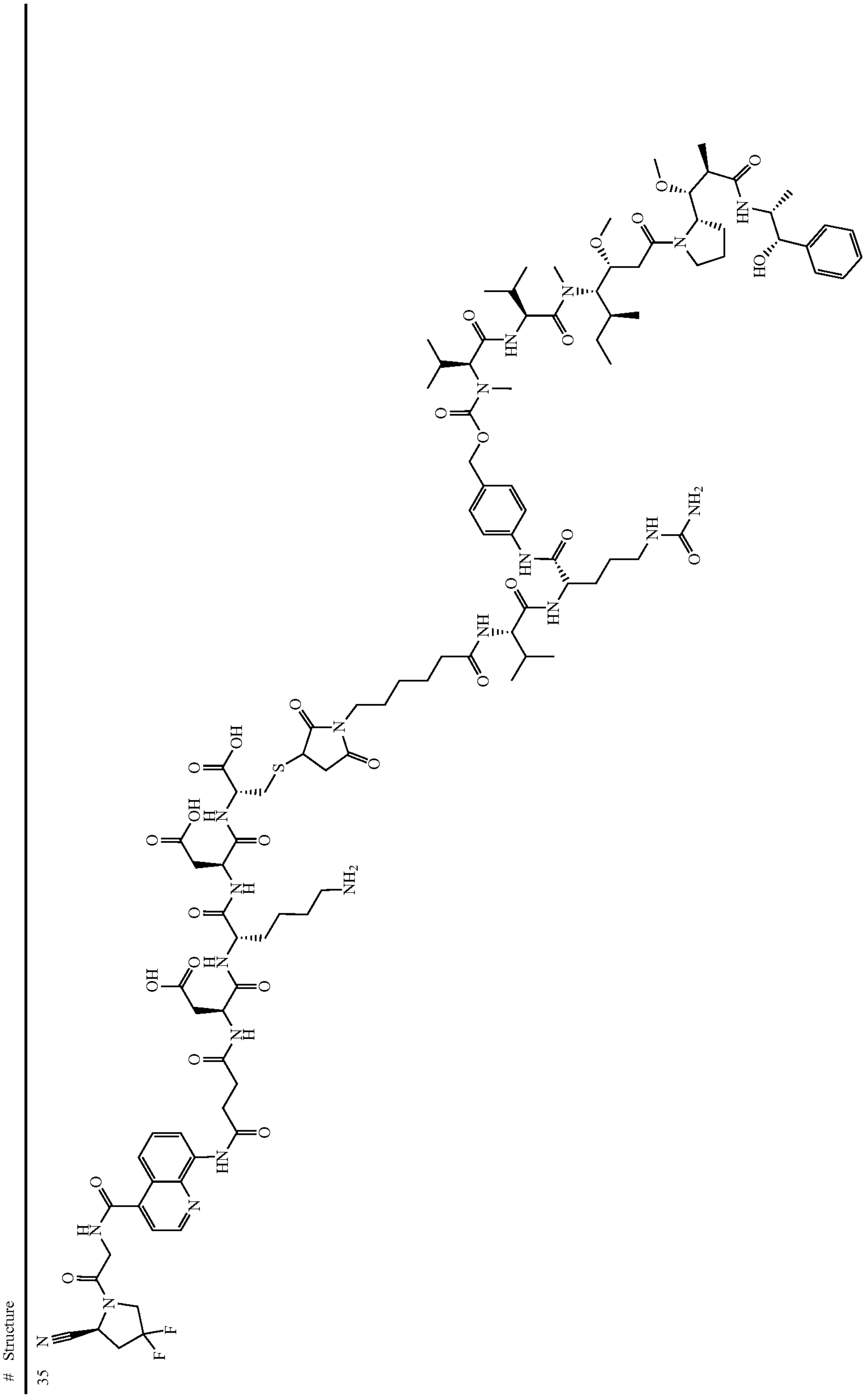 |

-continued
| # | Structure |
|---|---|
| 36 | 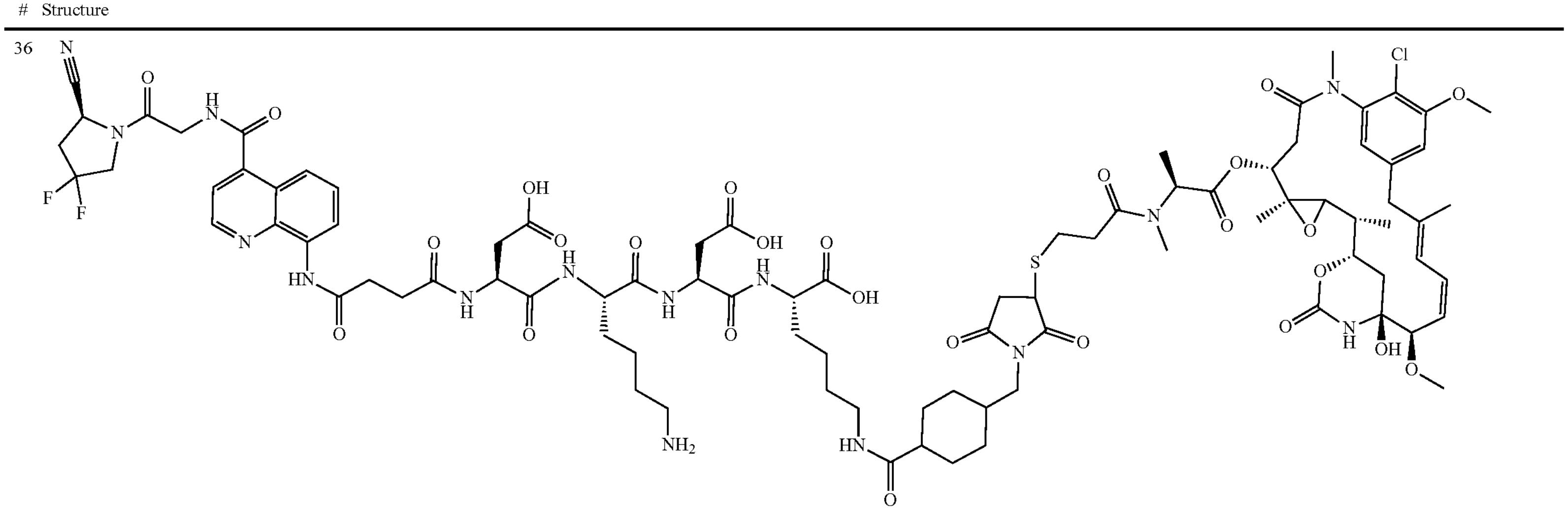 |

-continued
| # | Structure |
|---|---|
| 37 | 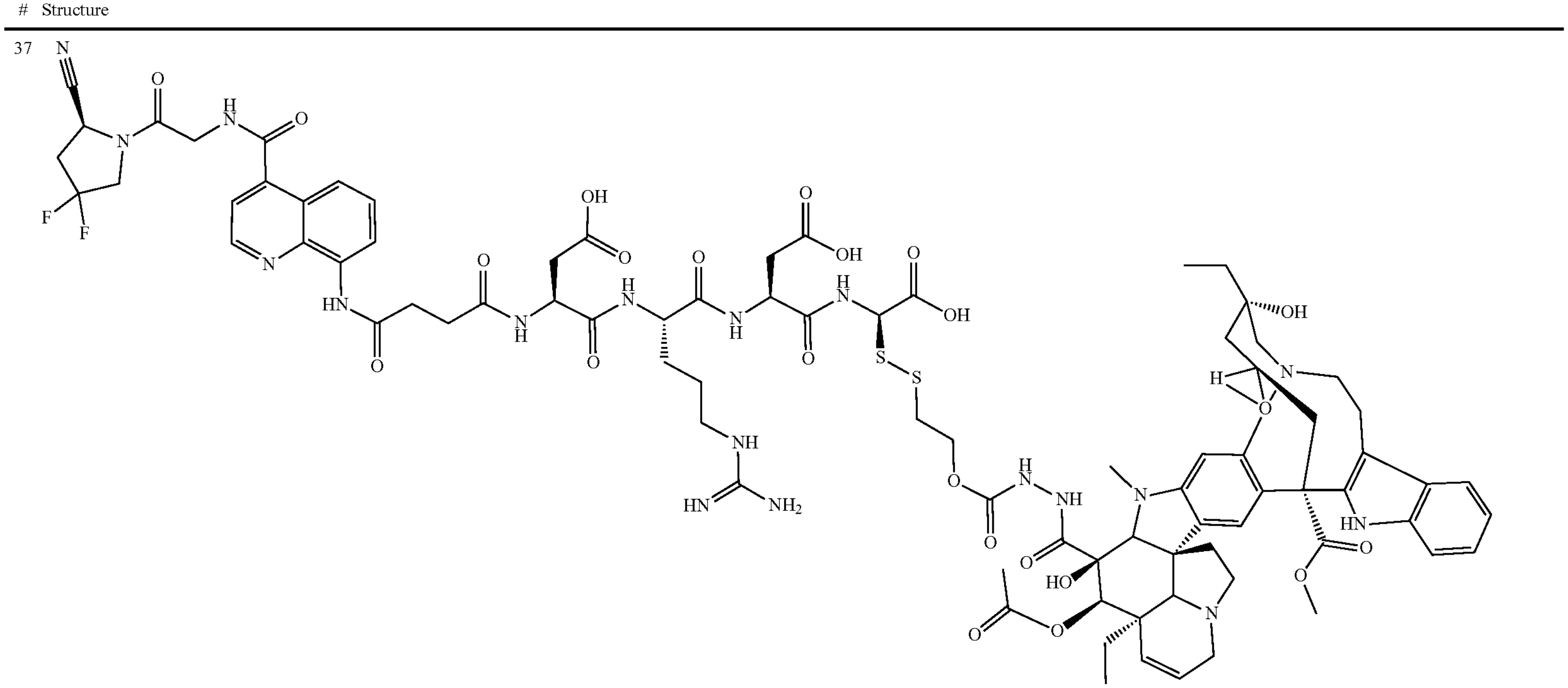 |

-continued
| # | Structure |
|---|---|
| 37a | 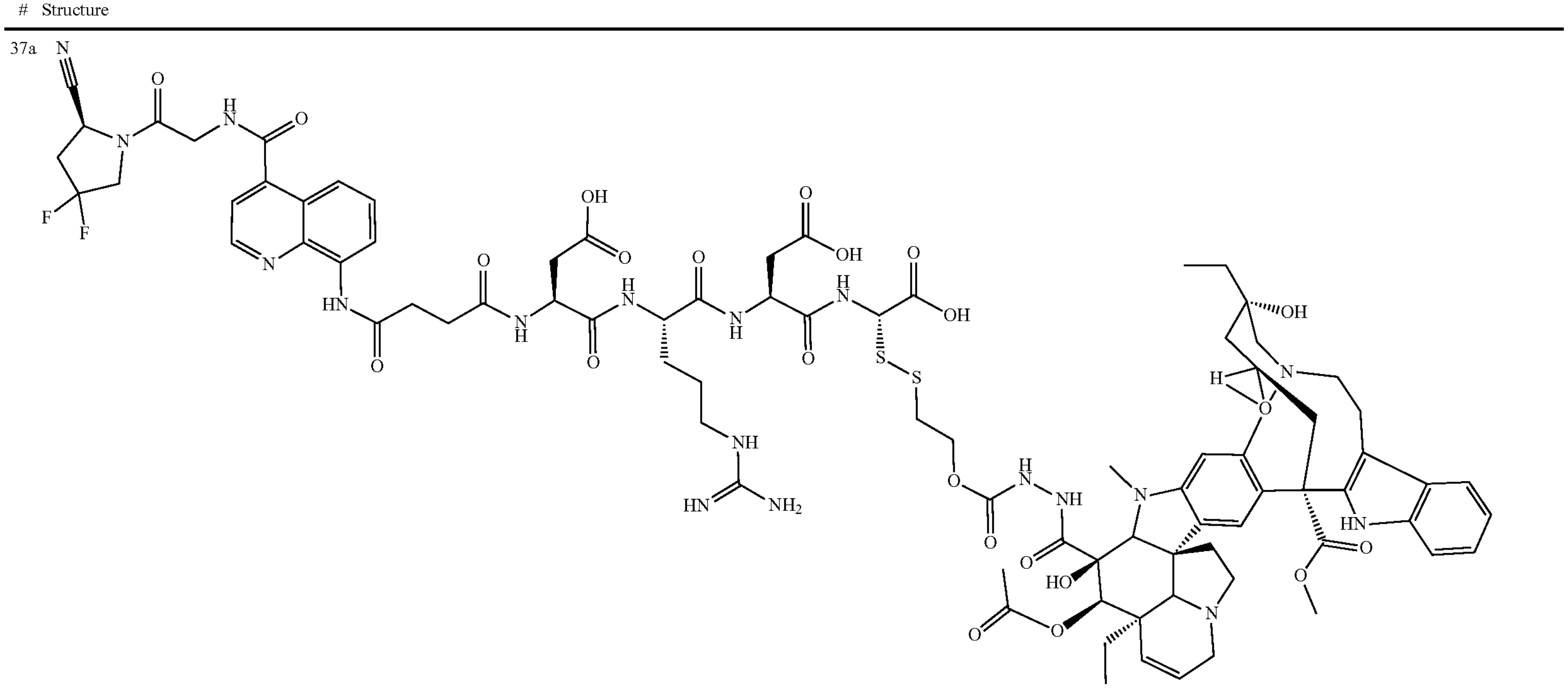 |

-continued
| # | Structure |
| --- | --- |
| 38 | 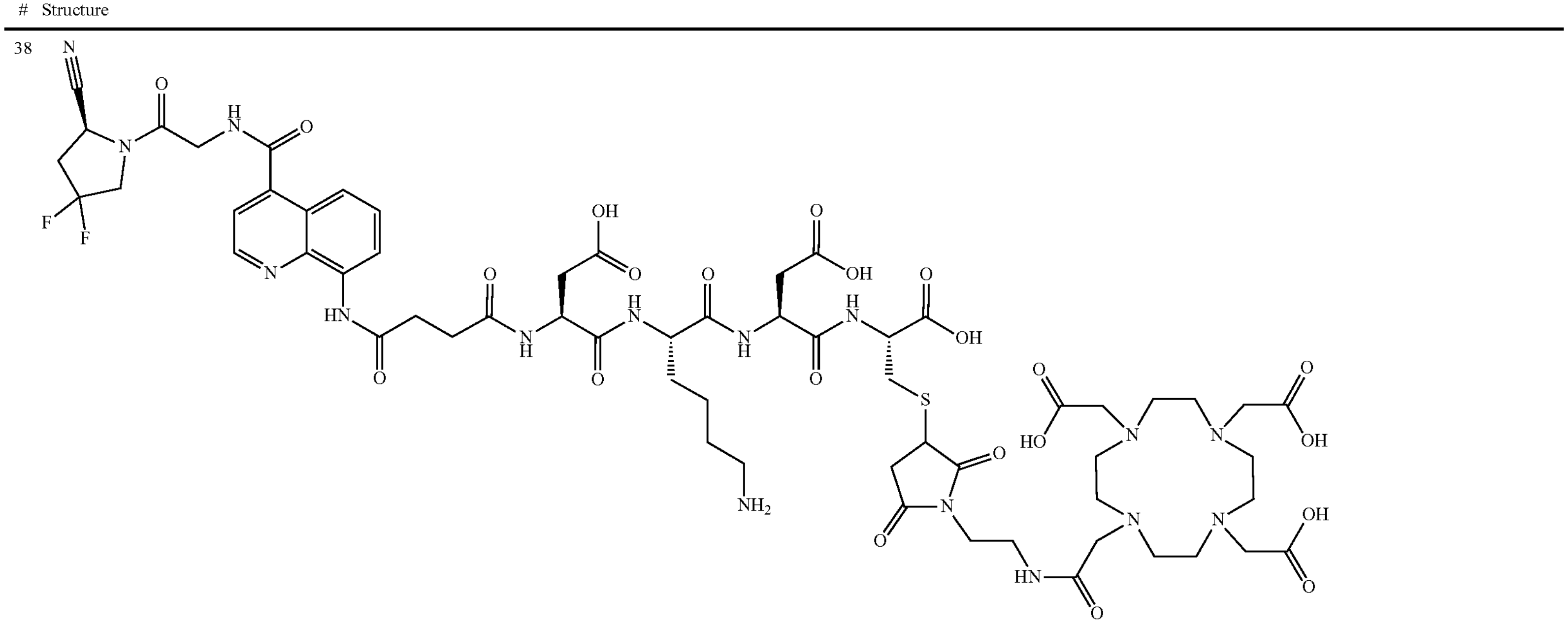 |

-continued
| # | Structure |
|---|---|
| 39 | 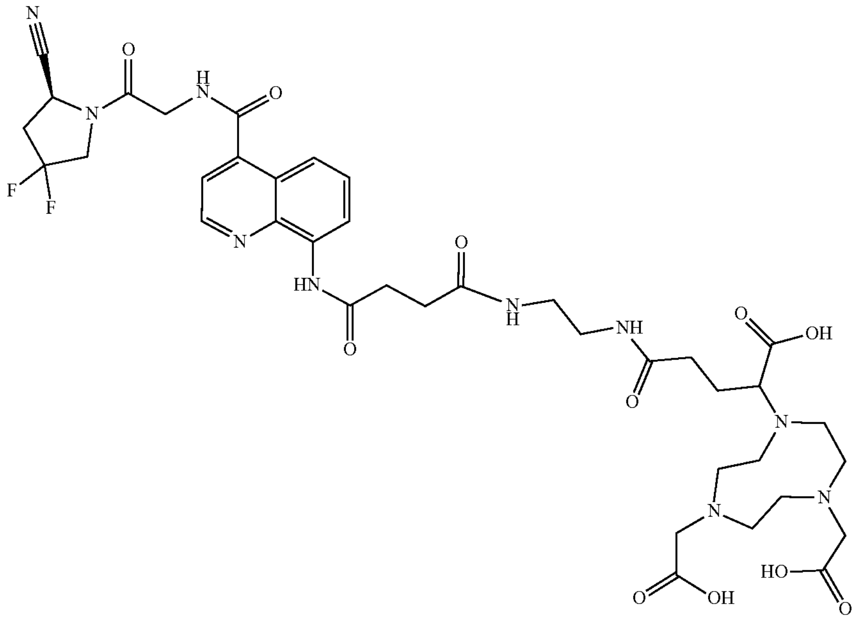 [SMILES: N#C[C@@H]1CC(F)(F)CN1C(=O)CNC(=O)c1ccnc2c(NC(=O)CCC(=O)NCCNC(=O)CCC(C(=O)O)N3CCN(CC(=O)O)CCN(CC(=O)O)CC3)cccc12] |

-continued
| # | Structure |
|---|---|
| 40 | 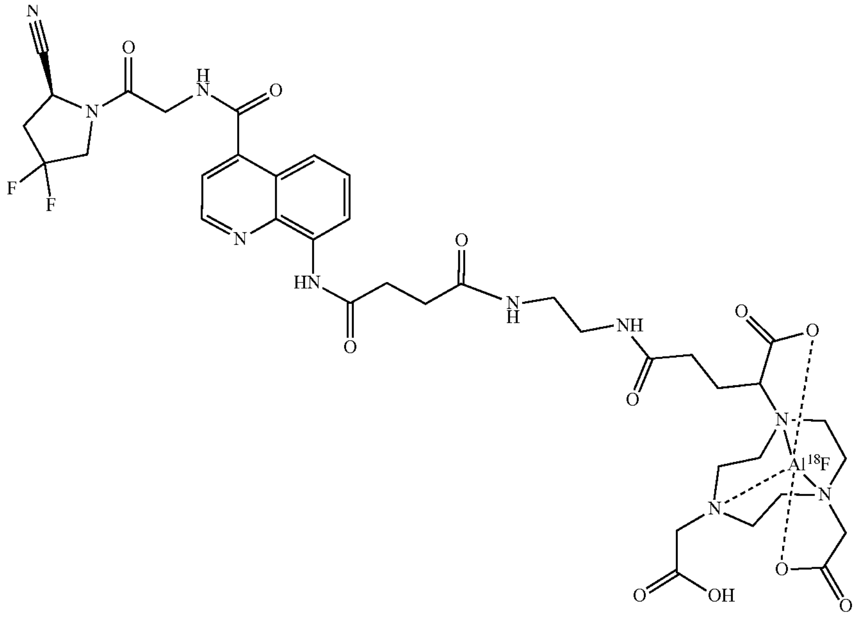 |

-continued
| # | Structure |
| --- | --- |
| 41 | 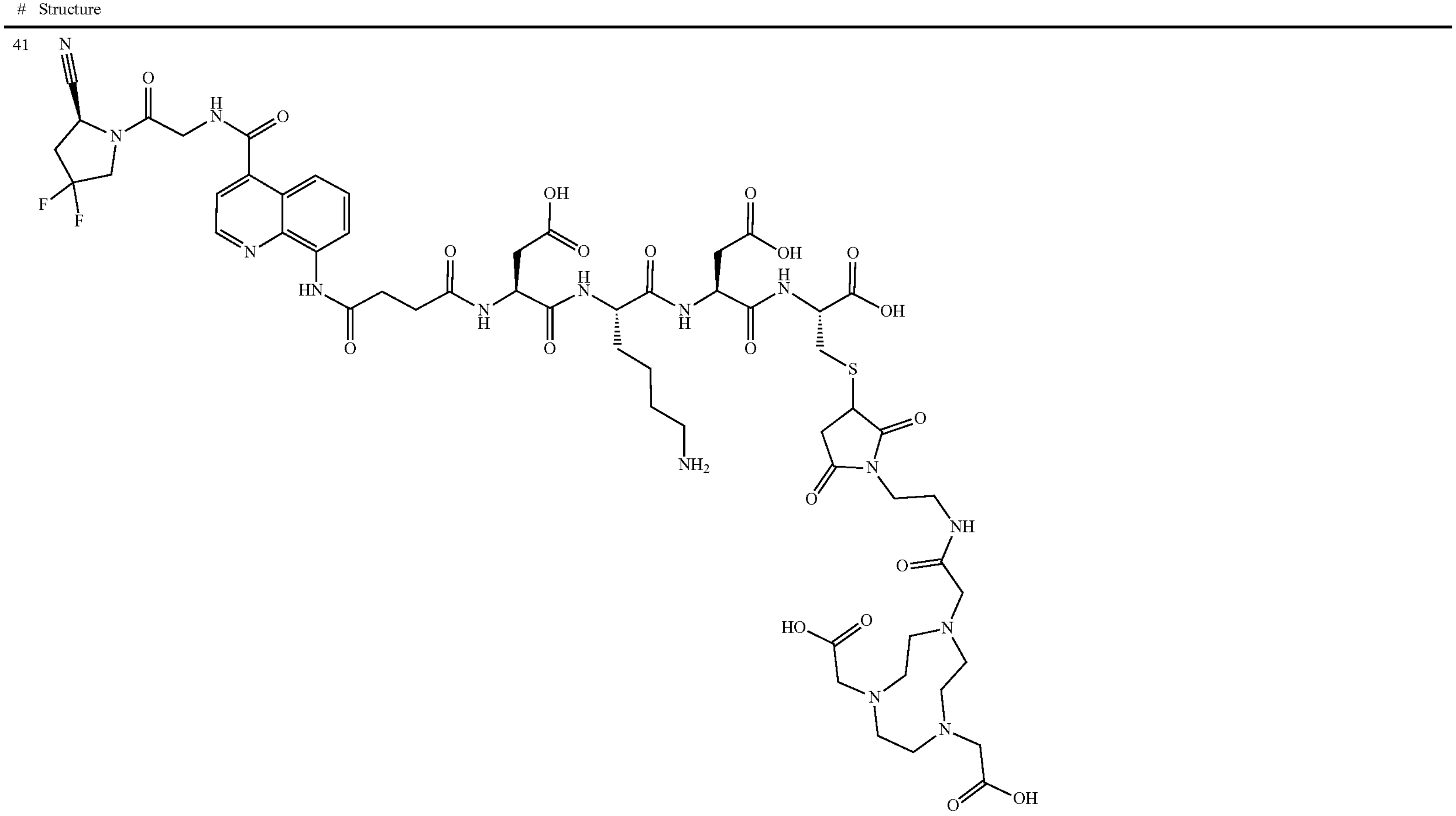 |

-continued
| # | Structure |
|---|---|
| 42 | 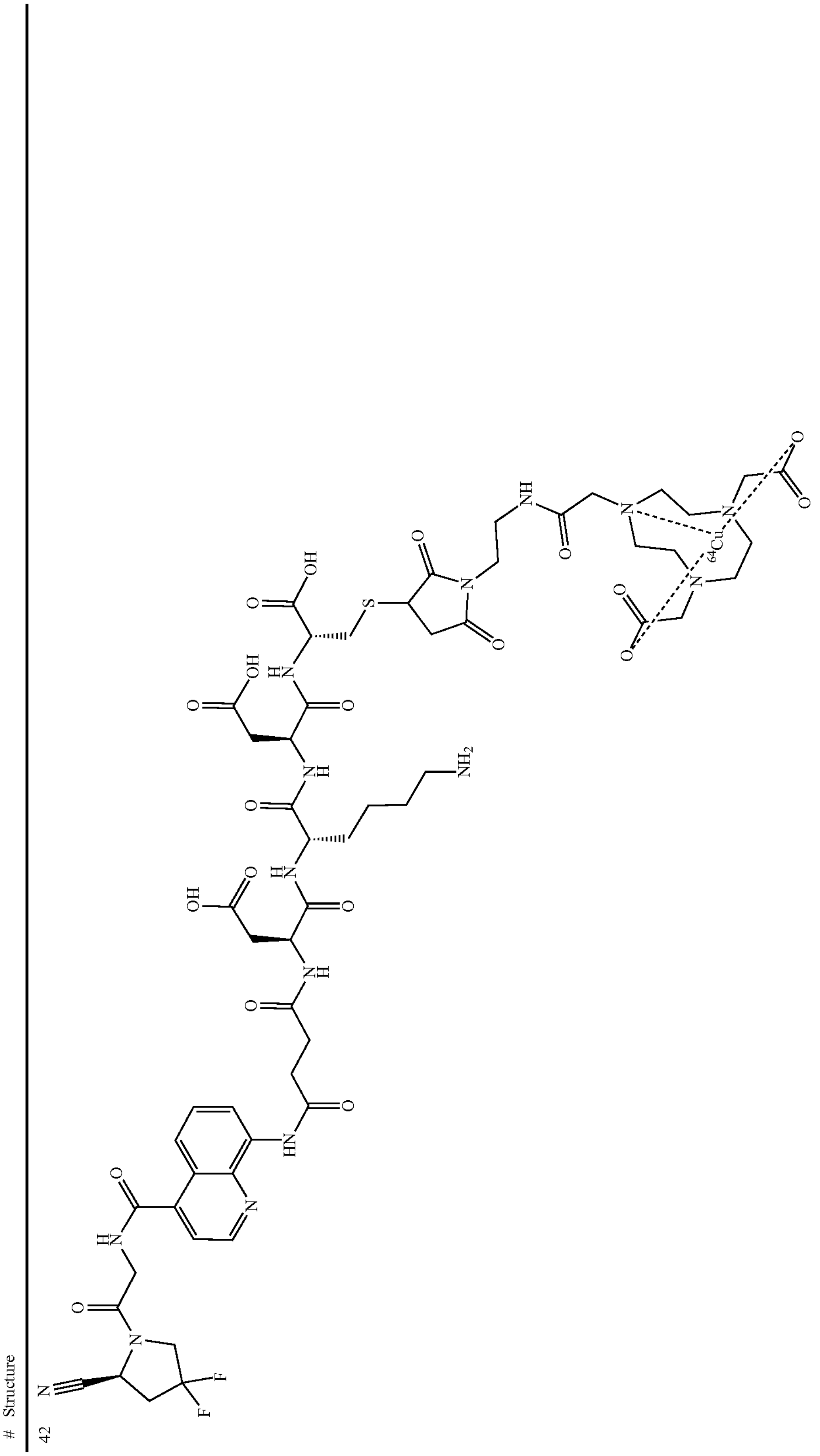 |

-continued
| # | Structure |
| --- | --- |
| 43 | 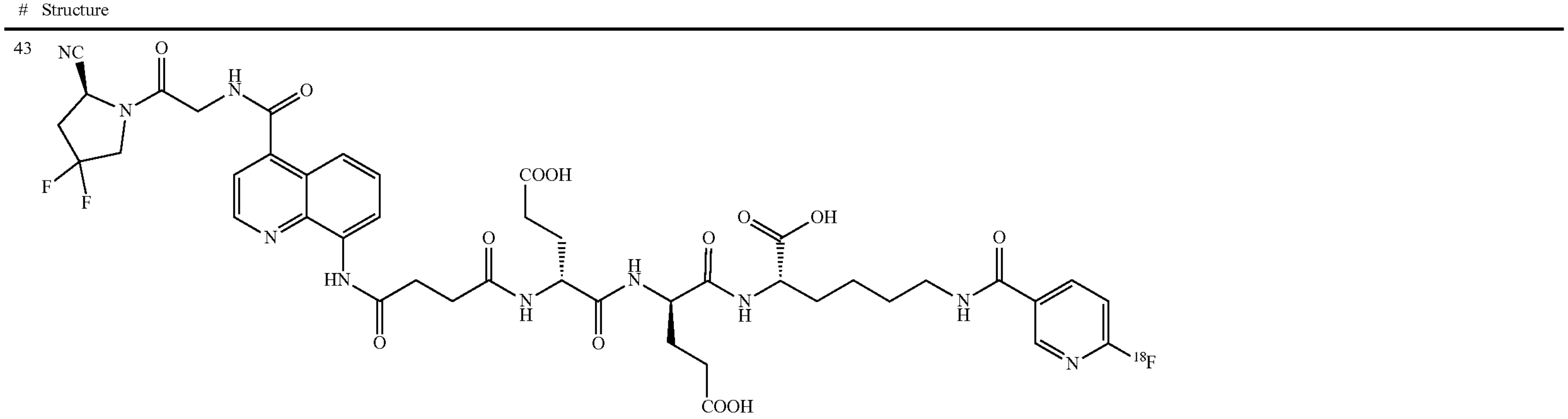 |
| 43a | 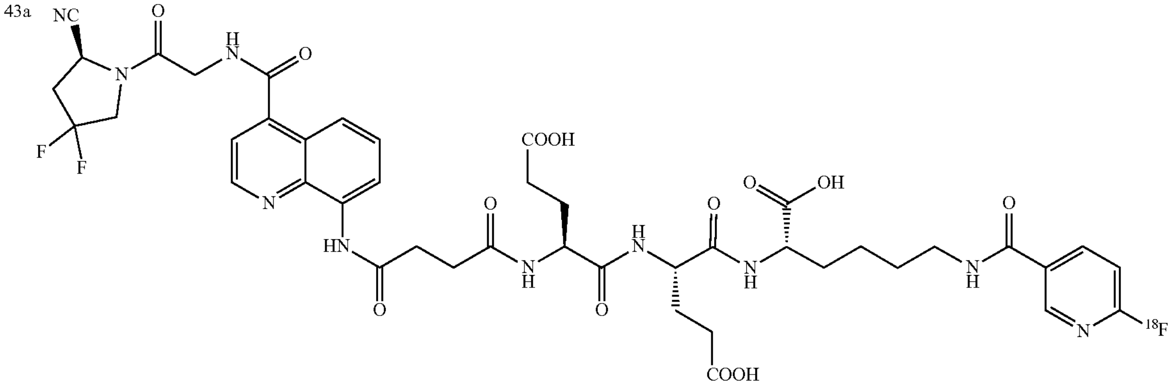 |

-continued
| # | Structure |
| --- | --- |
| 44 | 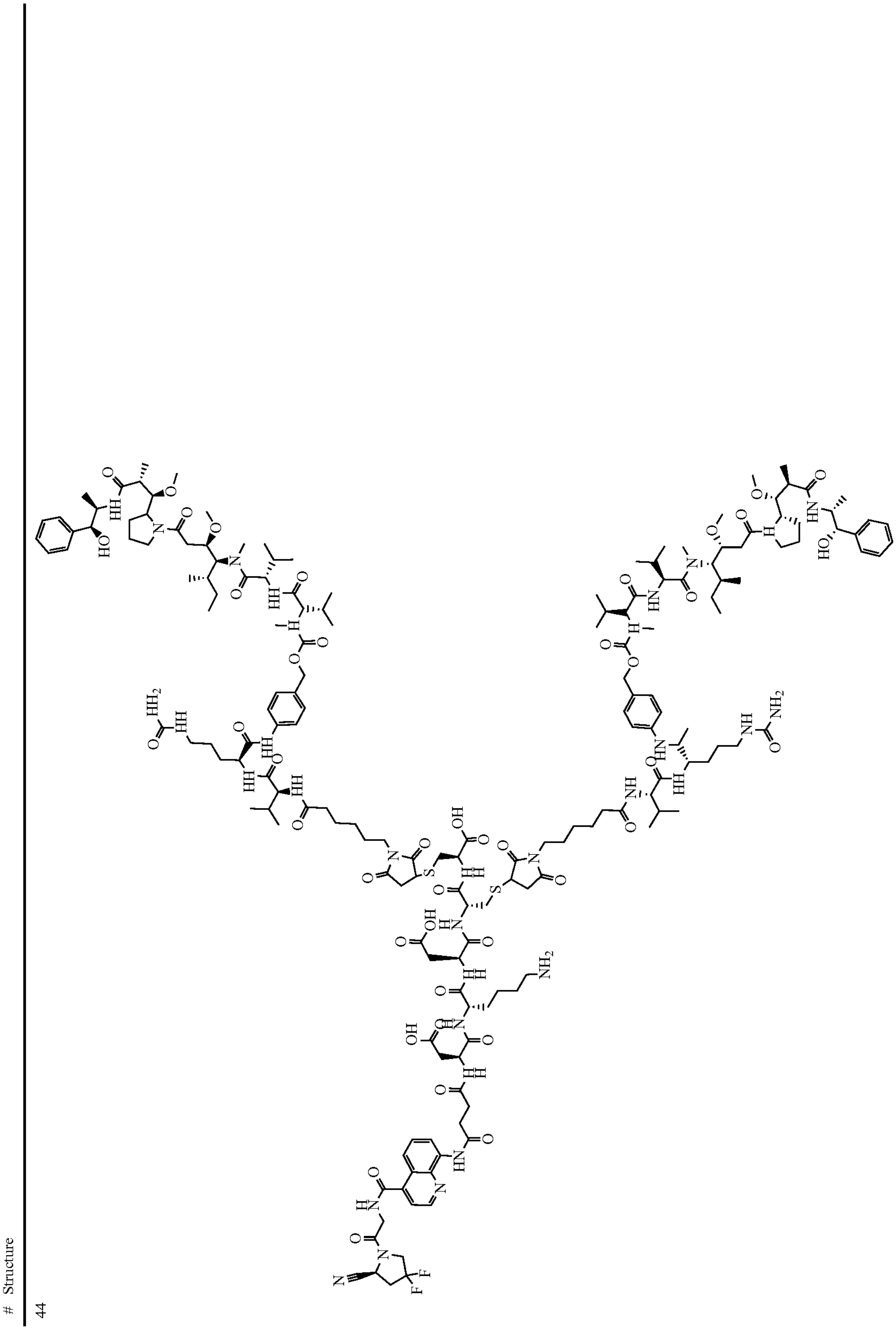 |

-continued
| # | Structure |
| --- | --- |
| 45 | 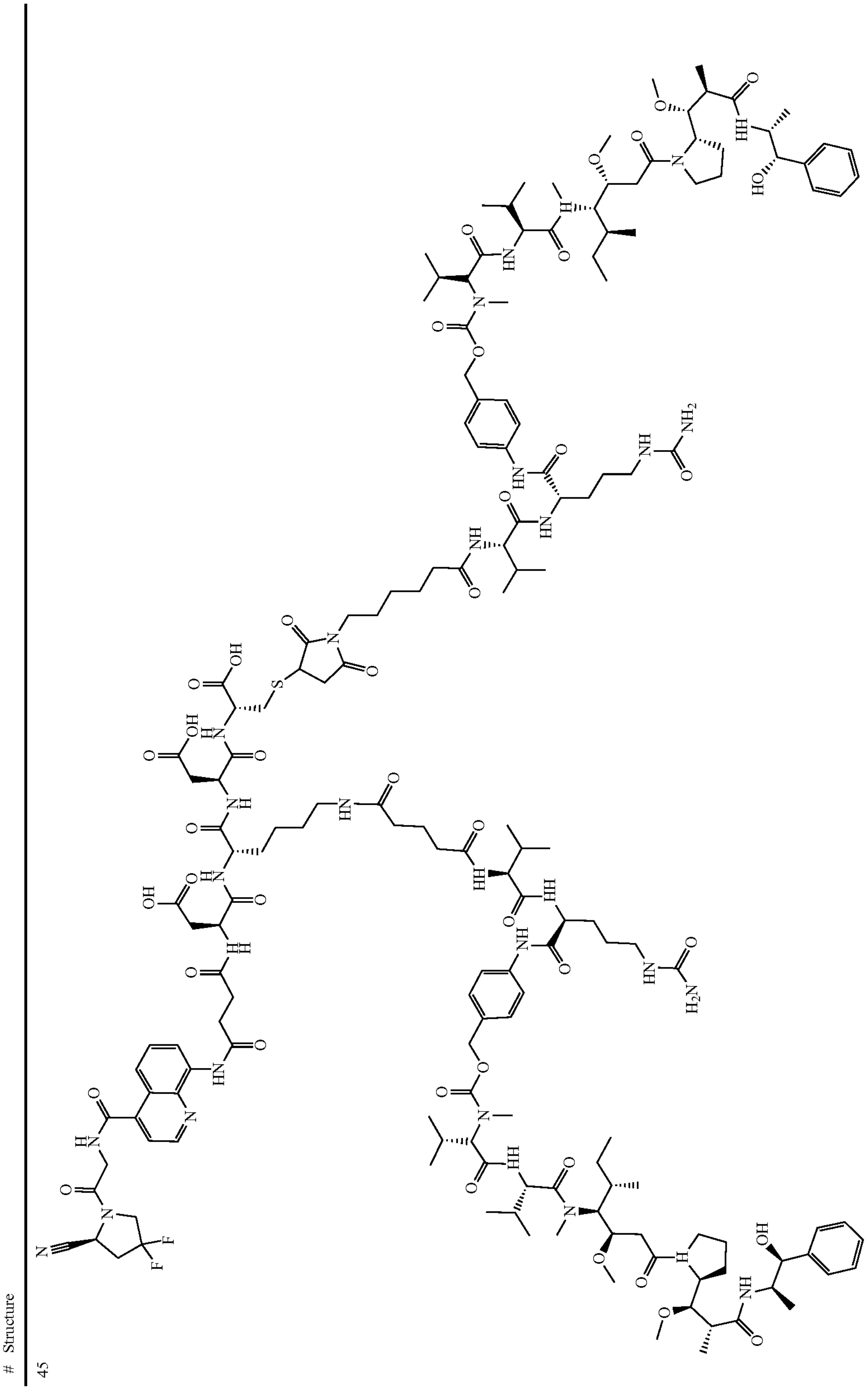 |

-continued
| # | Structure |
|---|---|
| 46 | 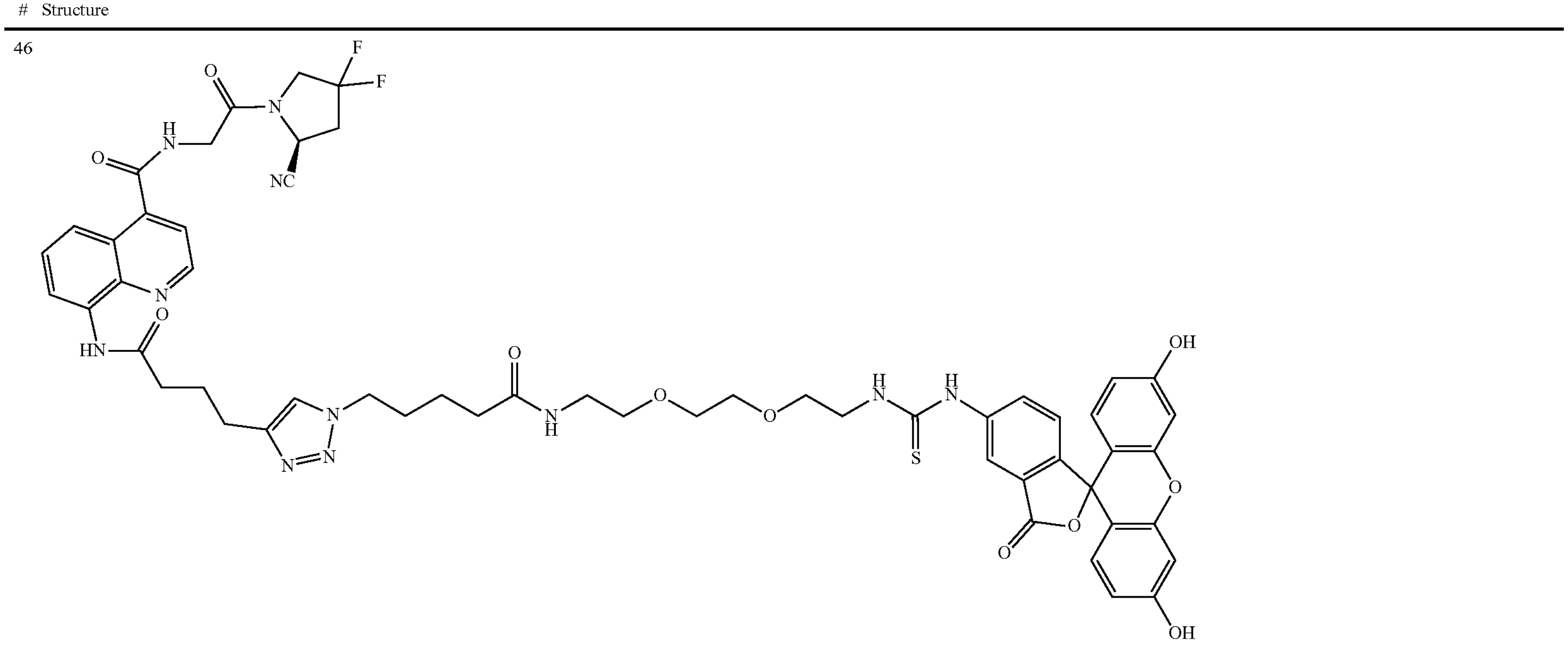 |

-continued
| # | Structure |
| --- | --- |
| 47 | 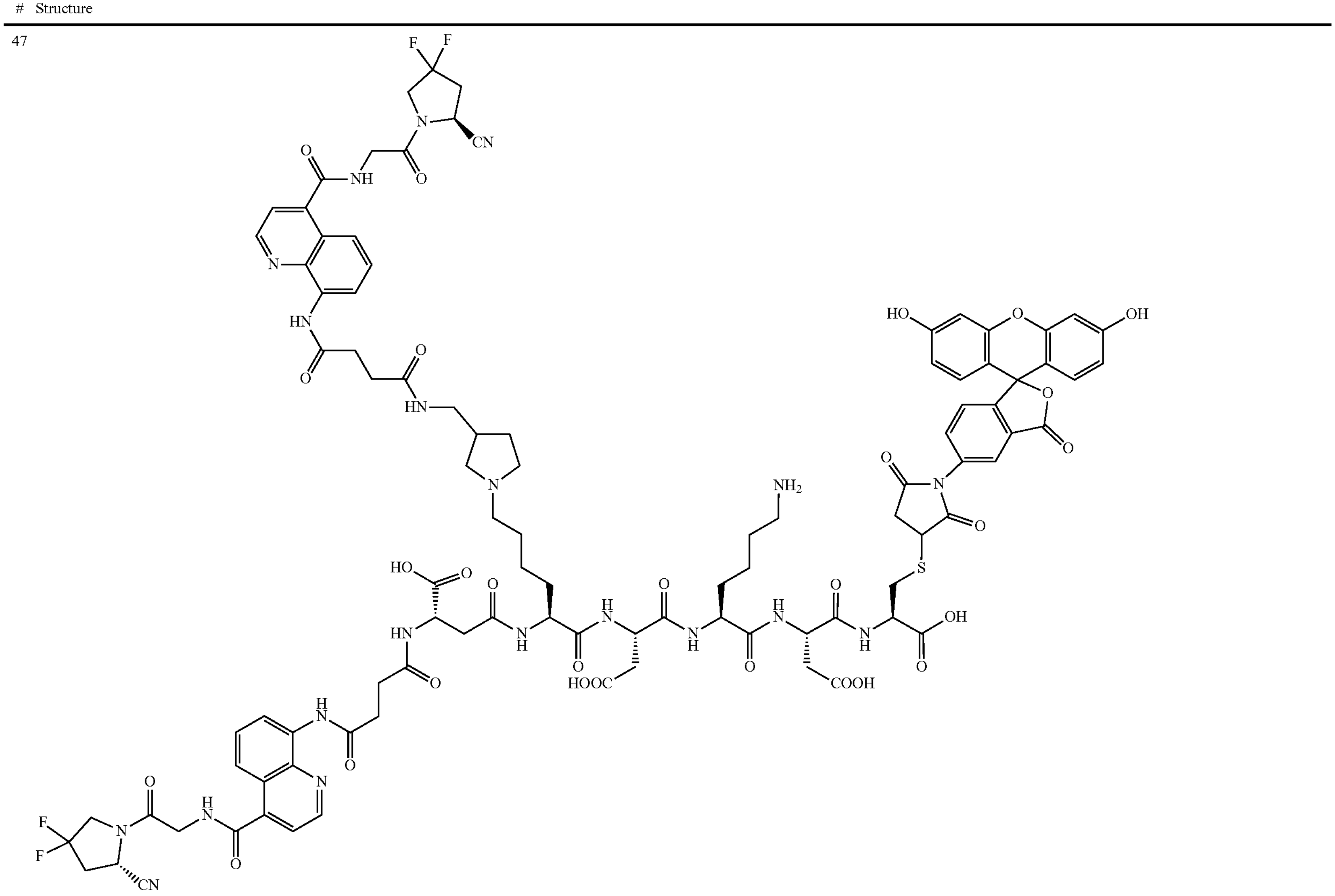 |

-continued
| # | Structure |
| --- | --- |
| 48 | 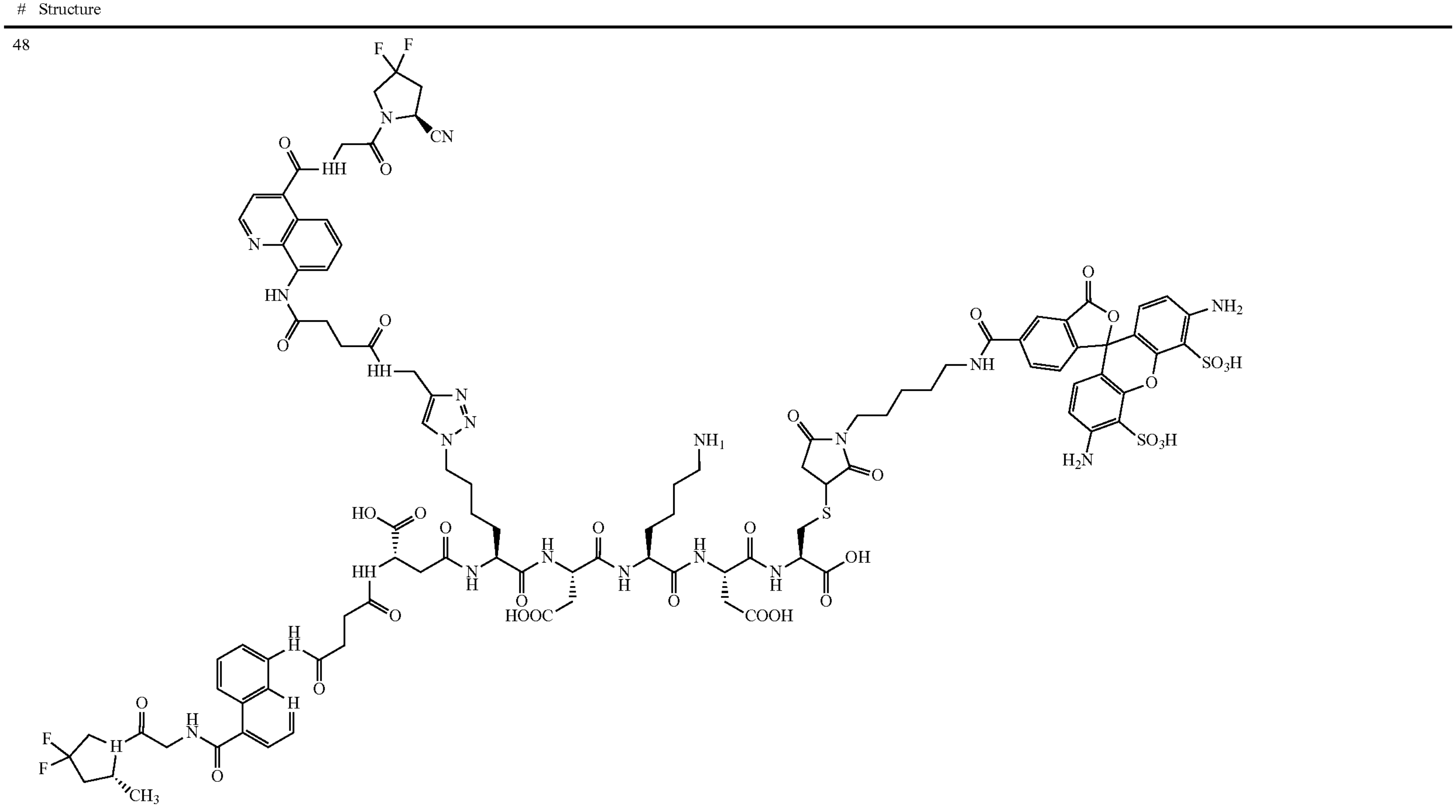 |

-continued
| # | Structure |
|---|---|
| 49 | 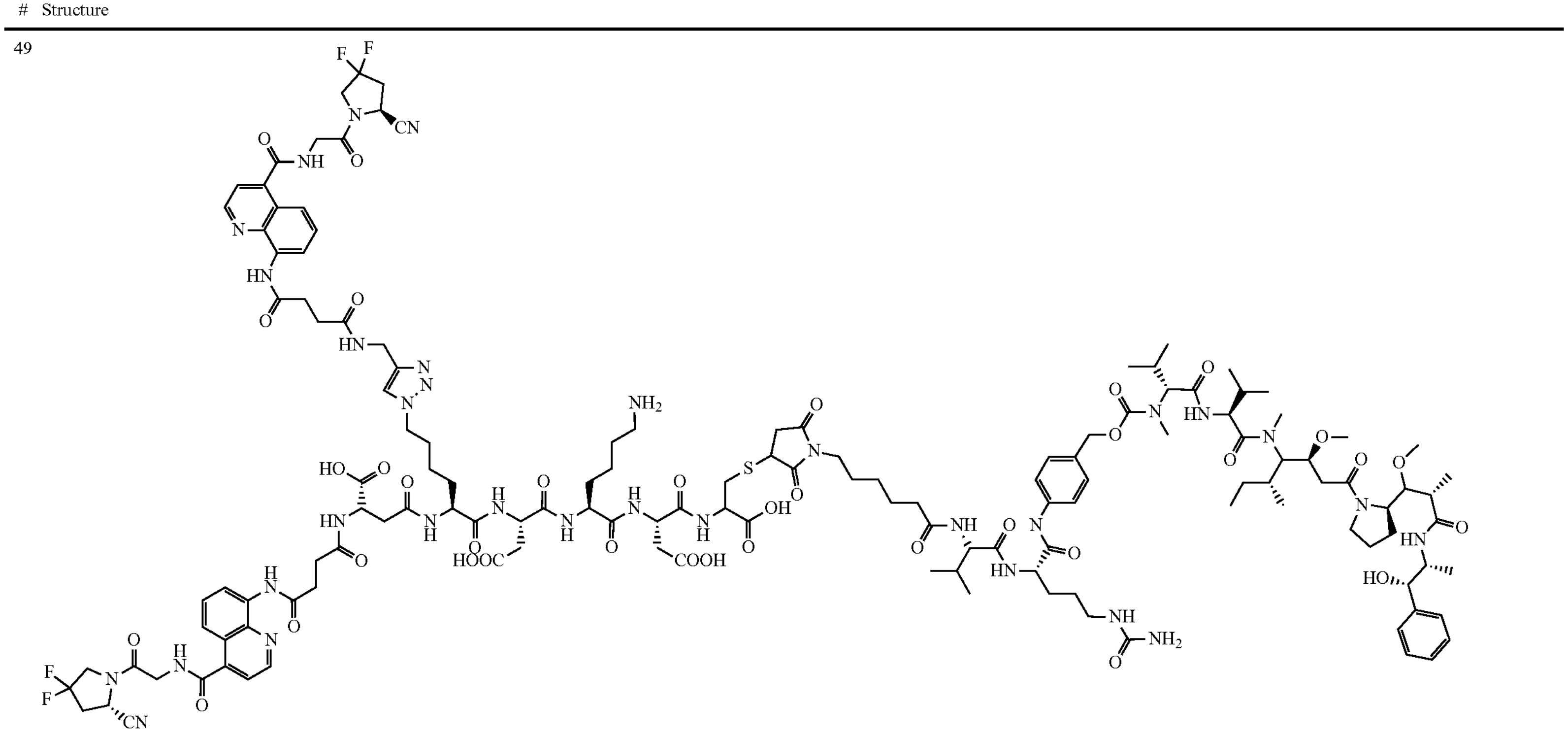 |

-continued
| # | Structure |
| --- | --- |
| 50 | 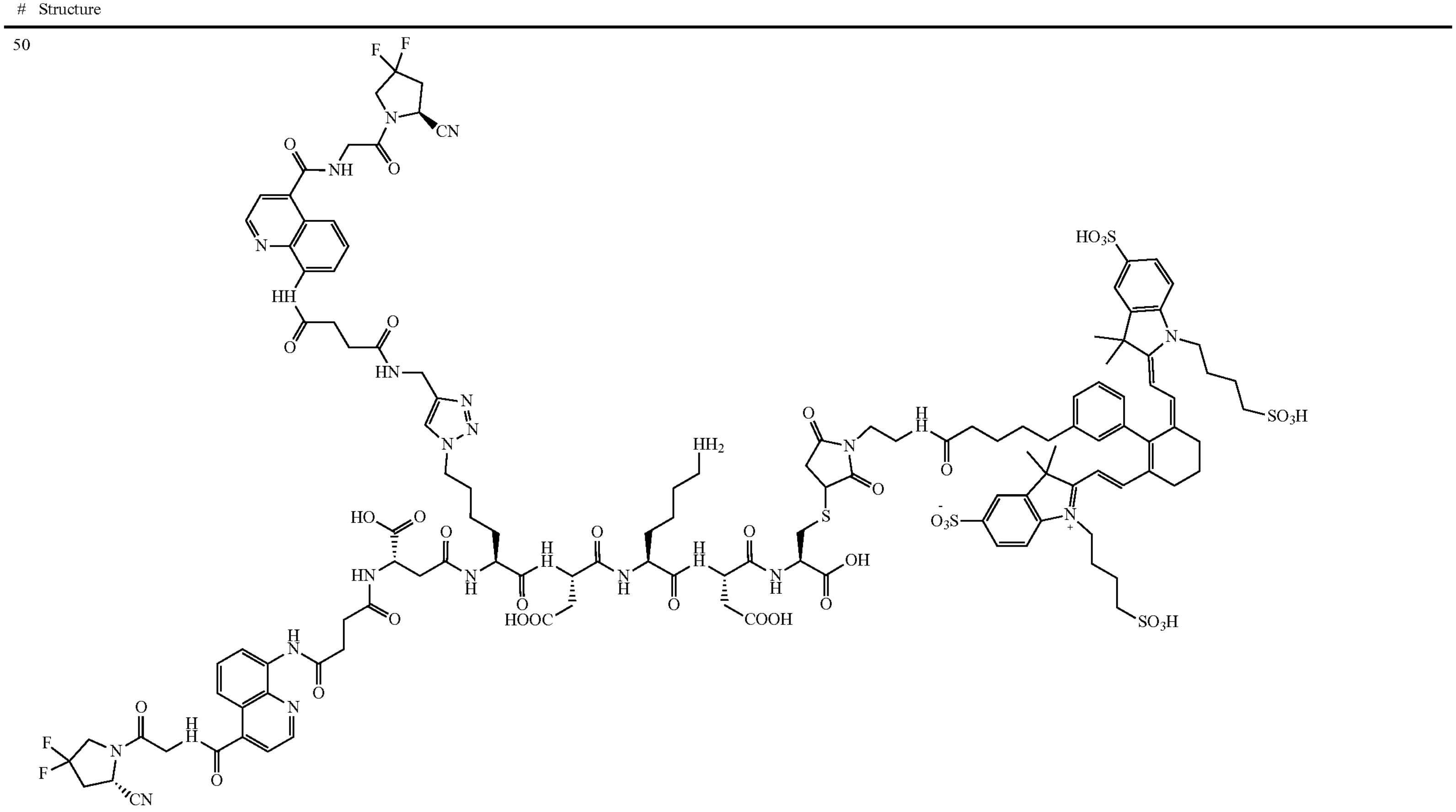 |

-continued
| # | Structure |
|---|---|
| 51 | 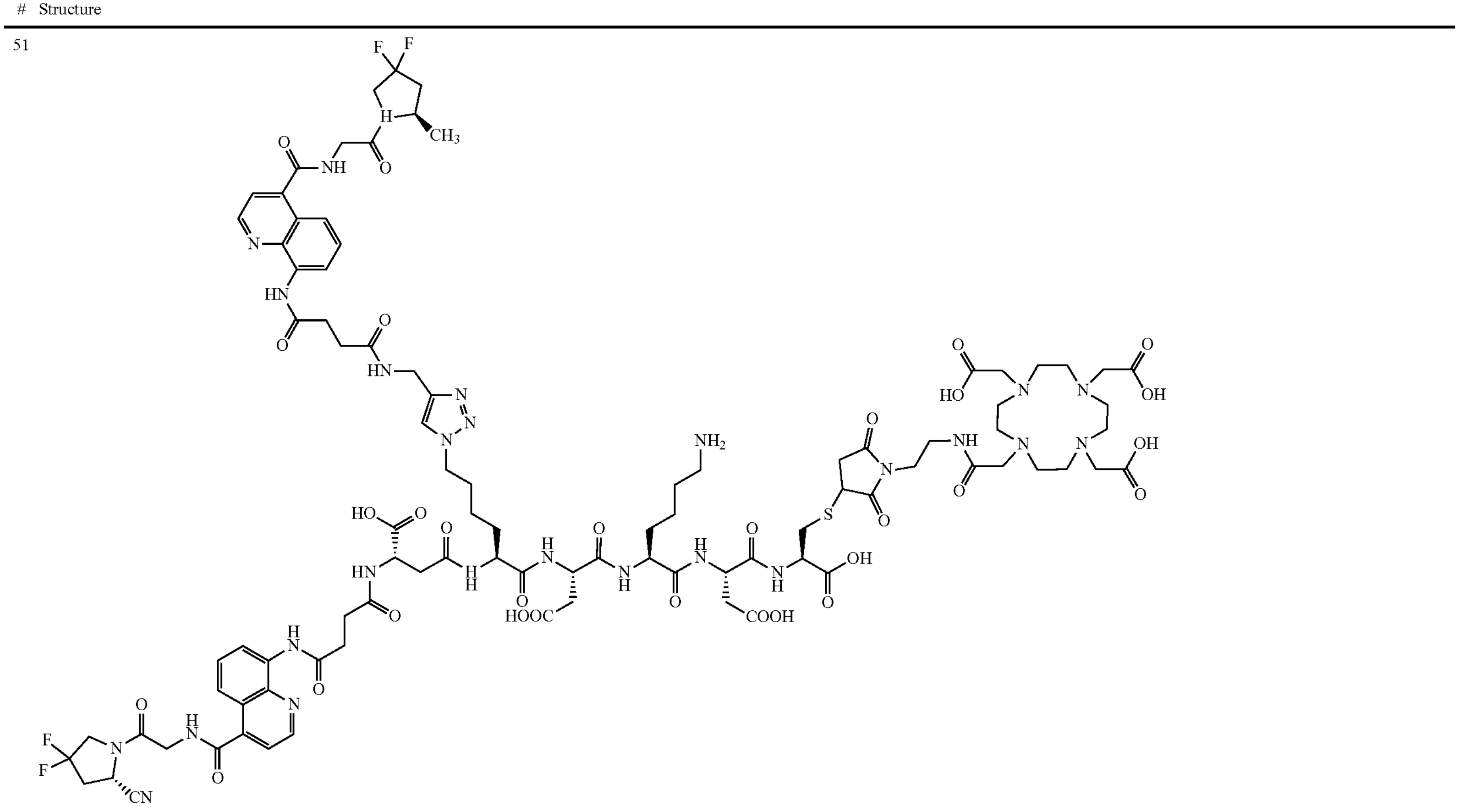 |

-continued
| # | Structure |
|---|---|
| 52 | 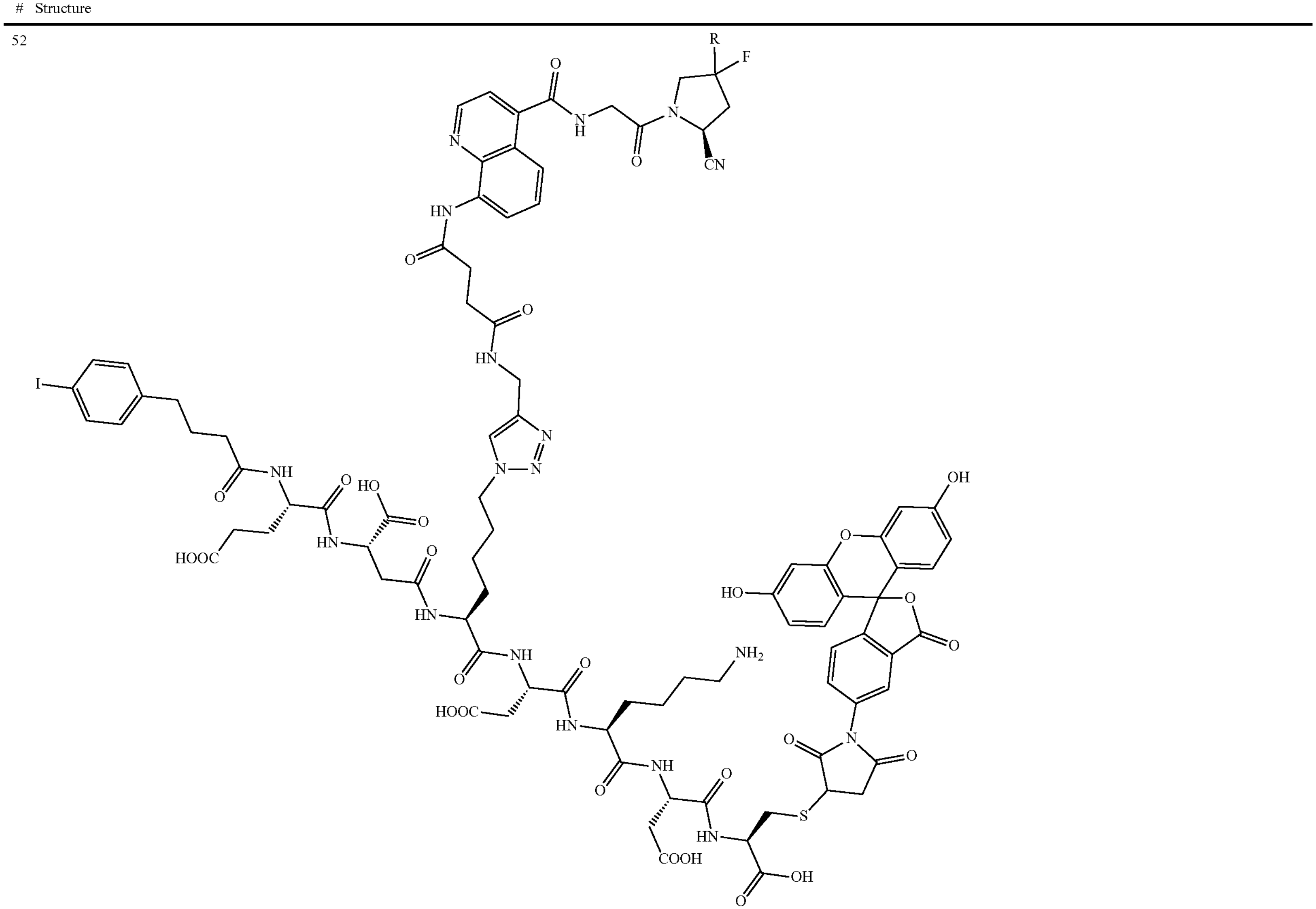 |

-continued
| # | Structure |
|---|---|
| 53 | 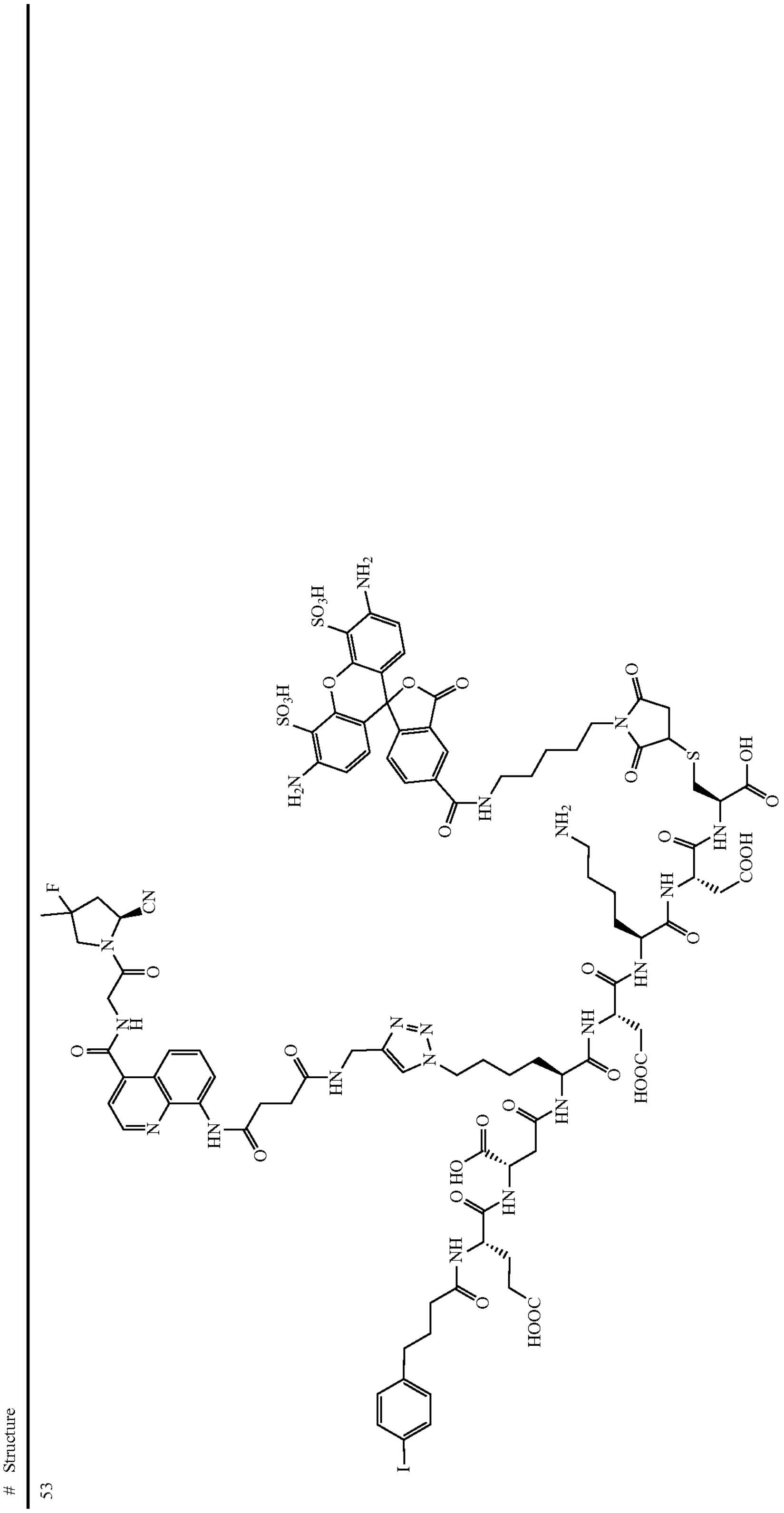 |

-continued
| # | Structure |
| --- | --- |
| 54 | 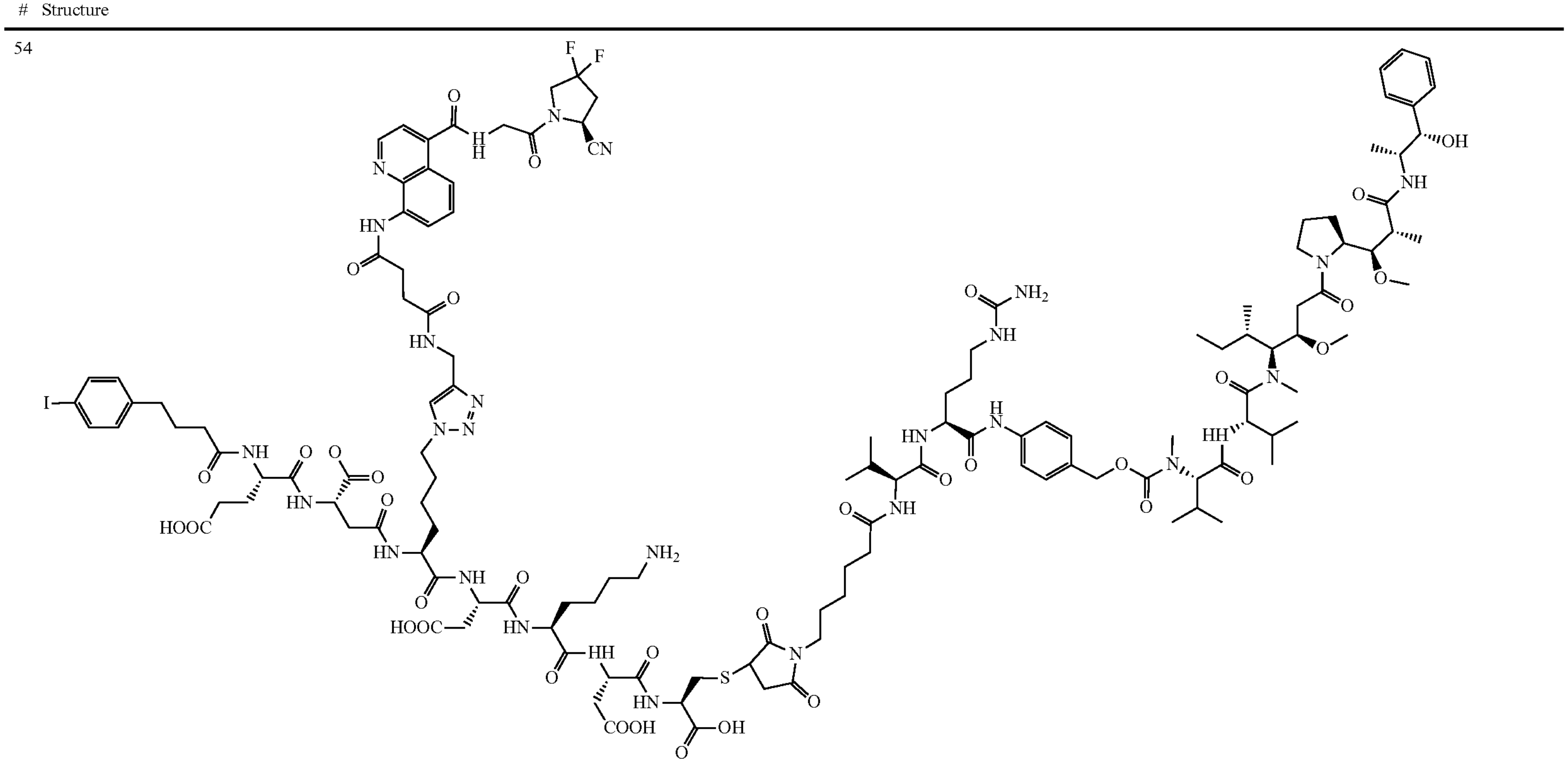 |

-continued
| # | Structure |
| --- | --- |
| 55 | 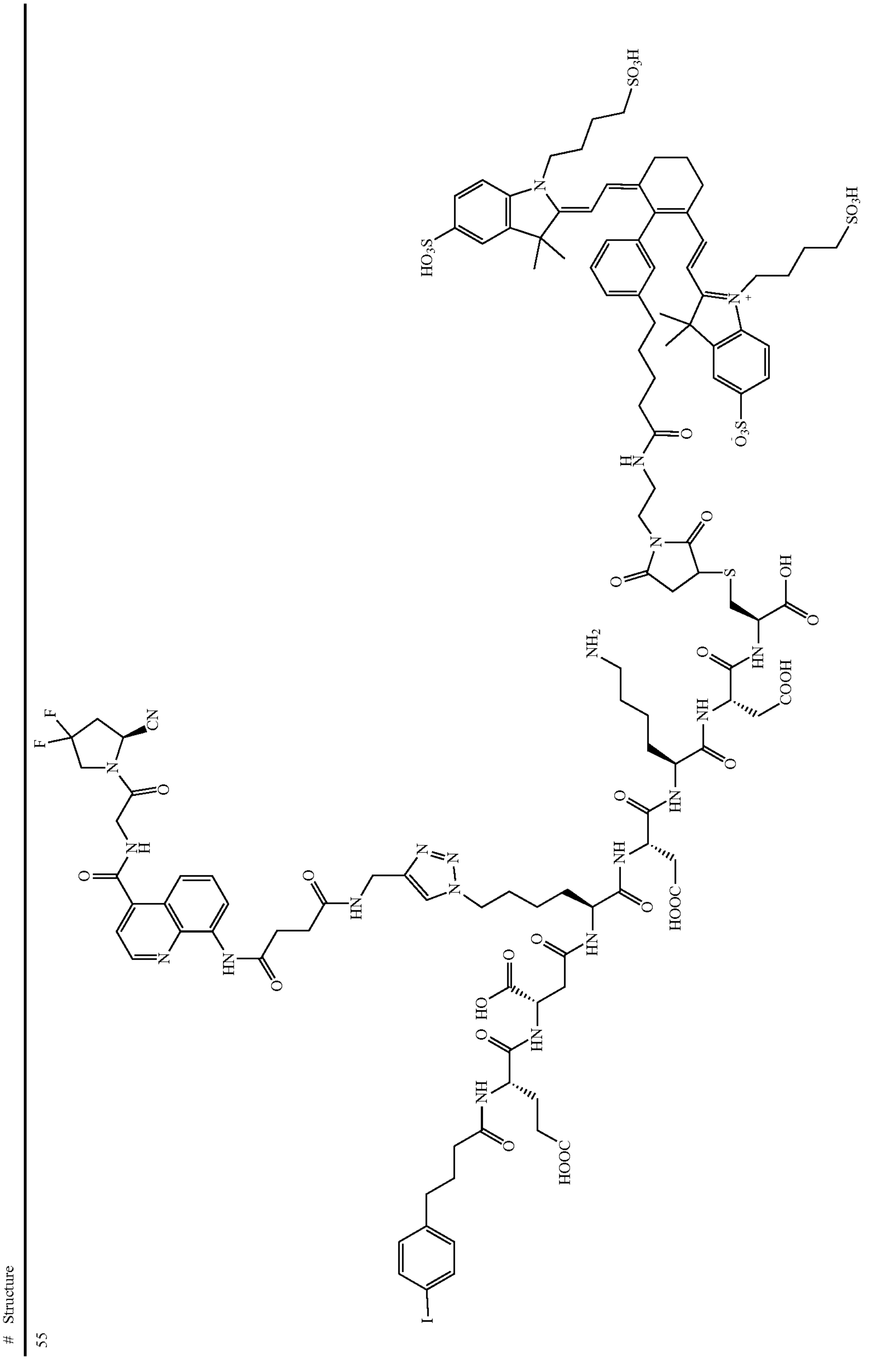 |

-continued
| # | Structure |
| --- | --- |
| 56 | 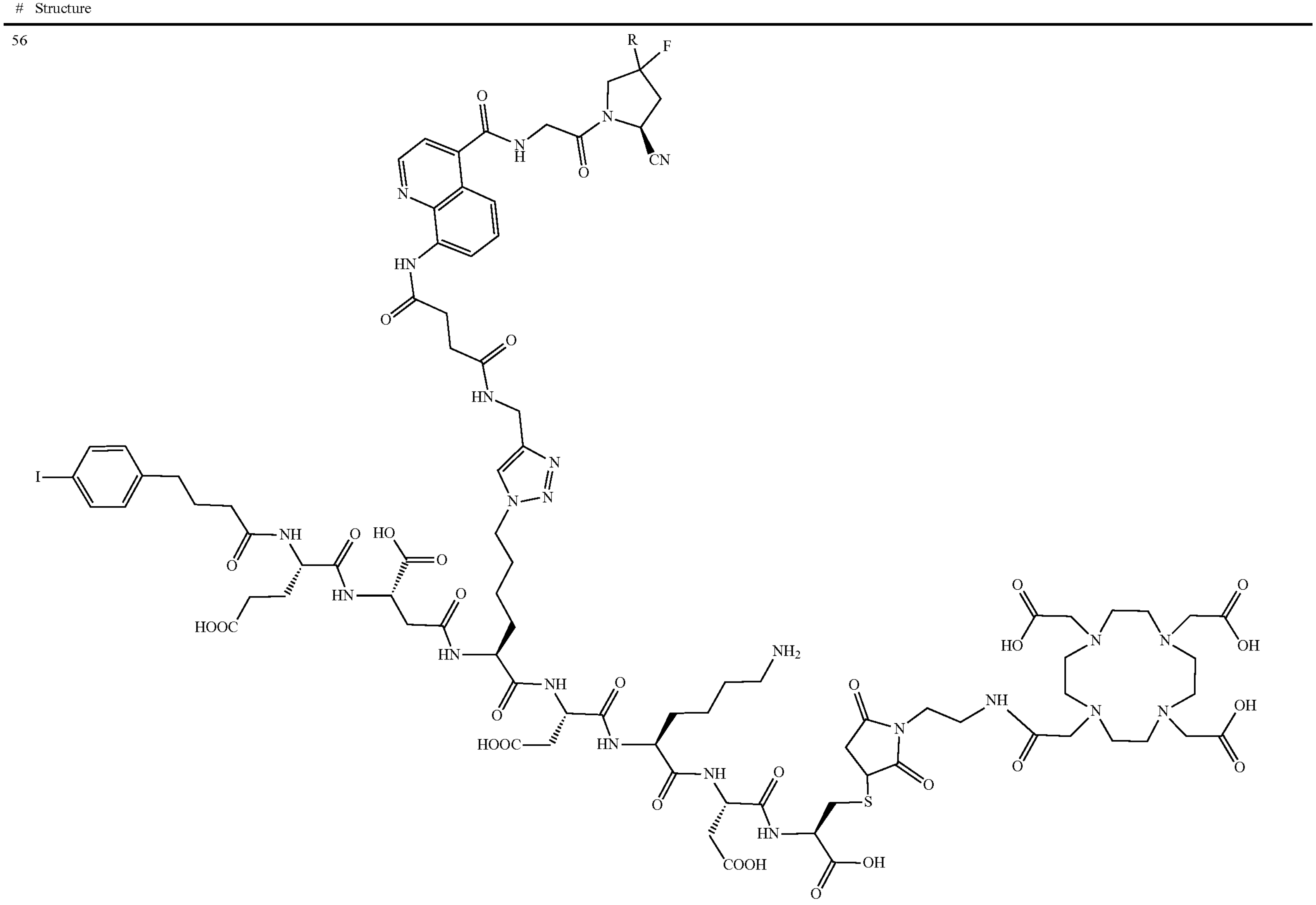 |

-continued
| # | Structure |
| --- | --- |
| 57 | 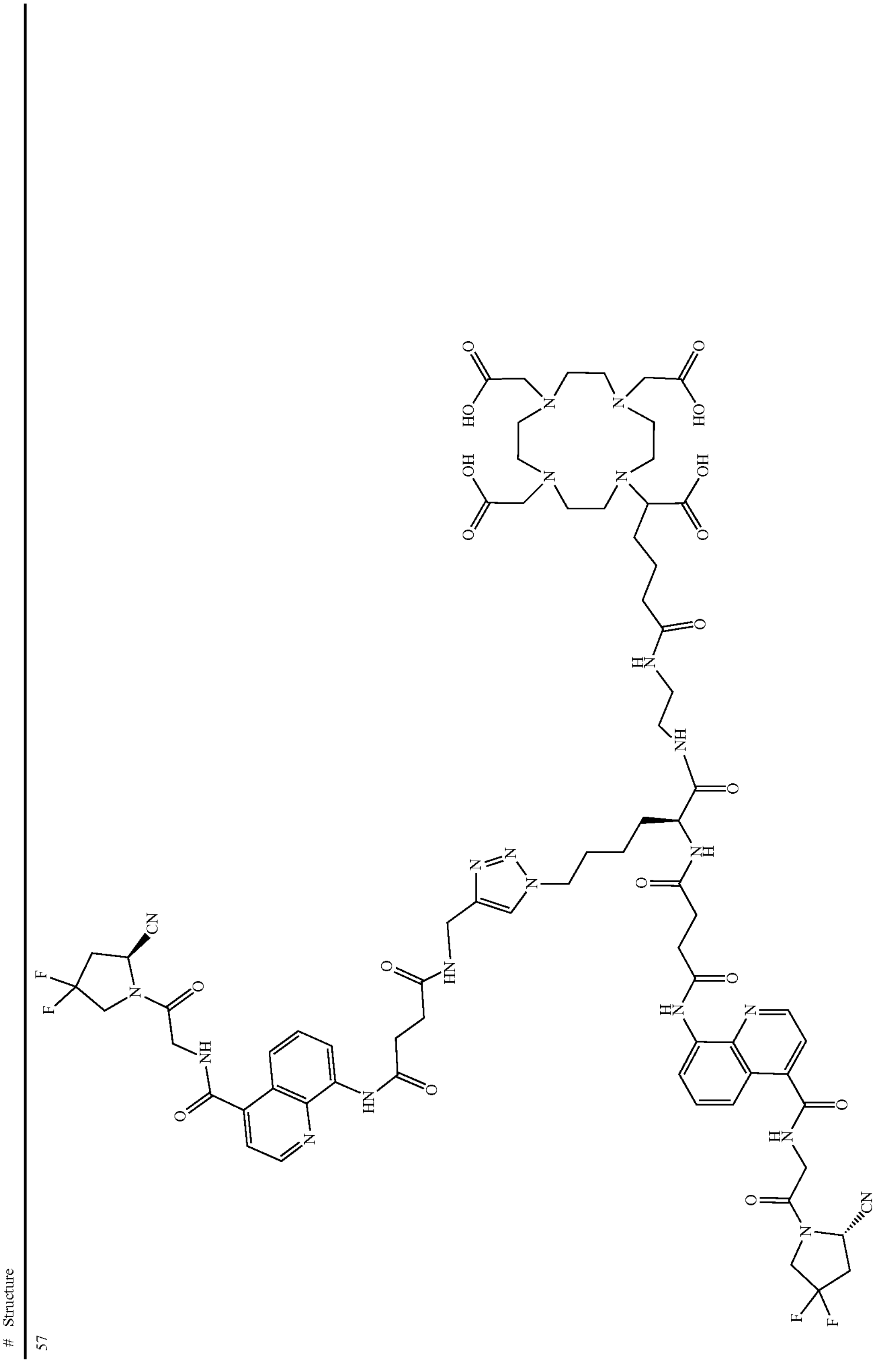 |

-continued
| # | Structure |
|---|---|
| 58<br>R derived from AA:<br>58a Glycine<br>58b Alanine<br>58c Valine<br>58d Isoleucine<br>58e Proline<br>58f Arginine | 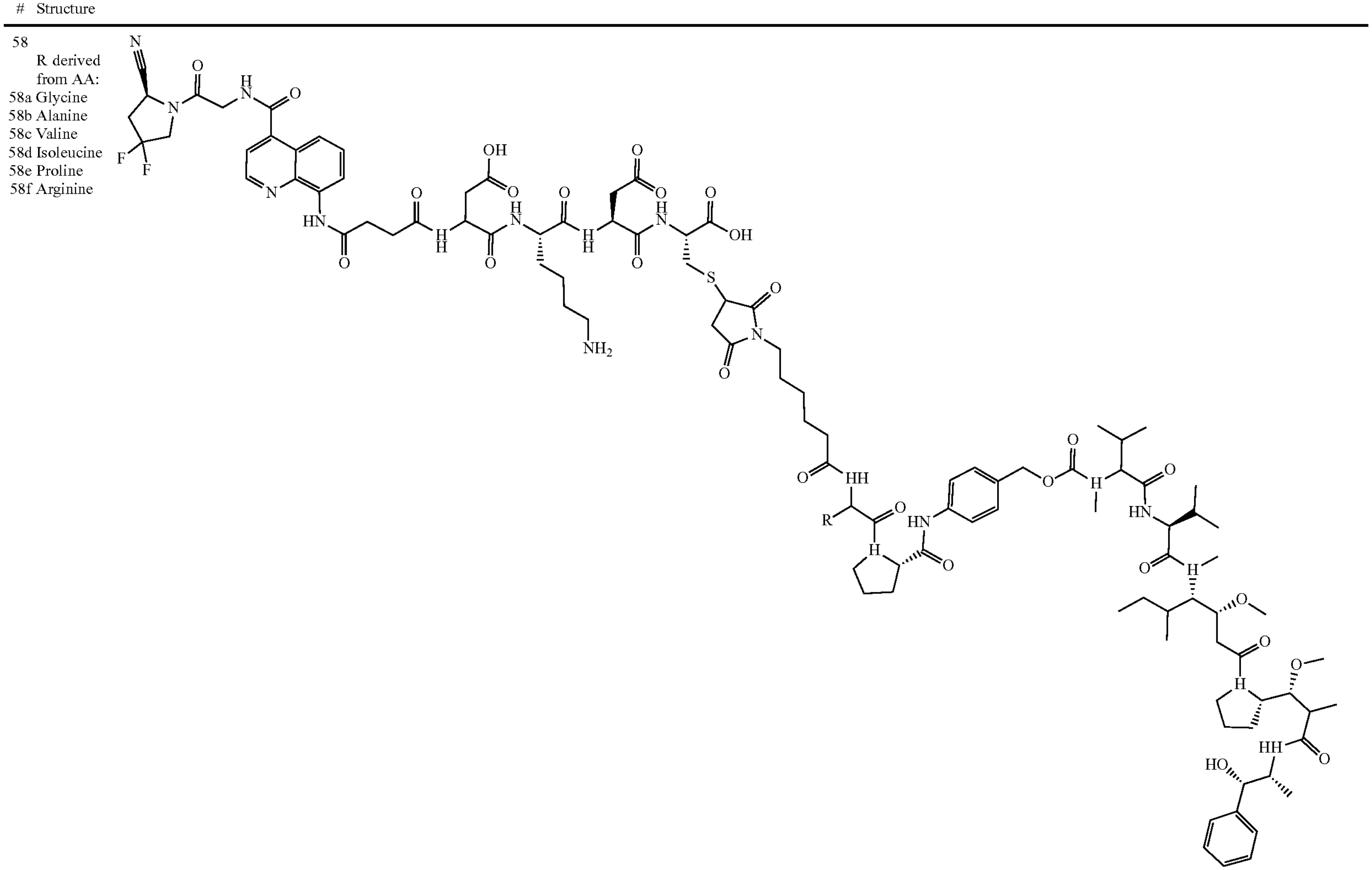 |

-continued
| # | Structure |
|---|---|
| 59<br>R R'<br>59a H H<br>59b $CH_3$ H<br>59c $CH_3$ $CH_3$ | 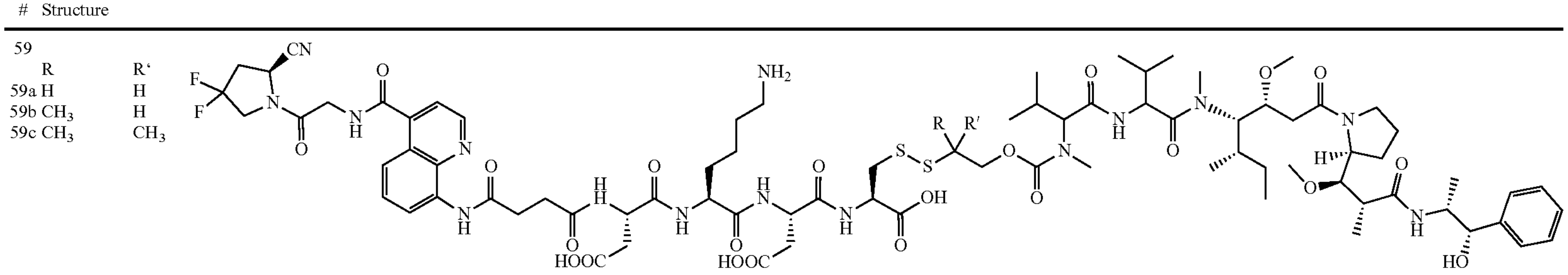 |
| 60<br>R R'<br>60a H H<br>60b $CH_3$ H<br>60c $CH_3$ $CH_3$ | 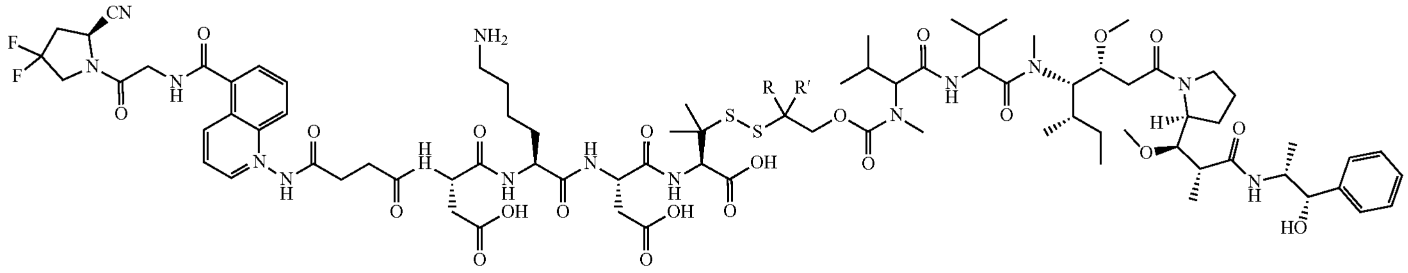 |

-continued
| # | Structure |
|---|---|
| 64 | 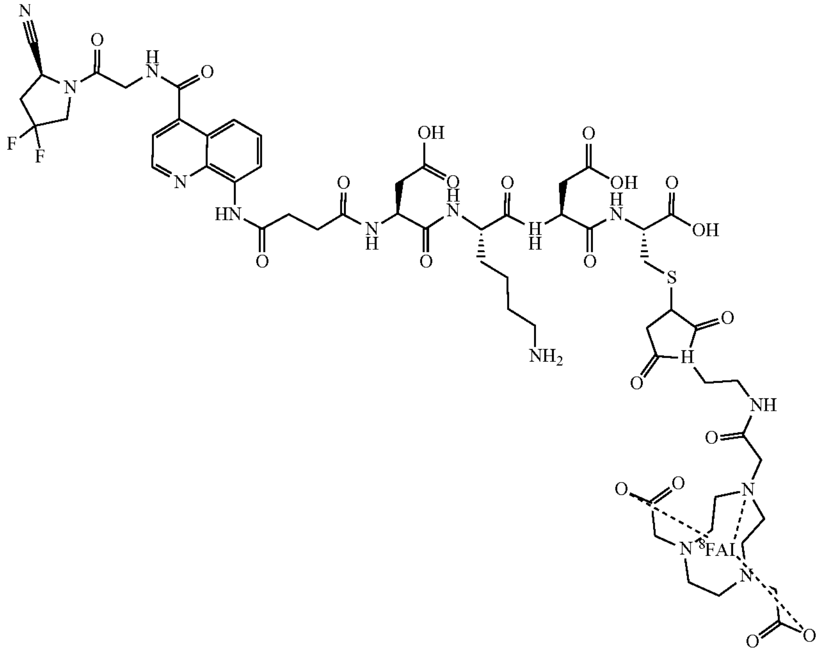 |

-continued
| # | Structure |
| --- | --- |
| 65 | 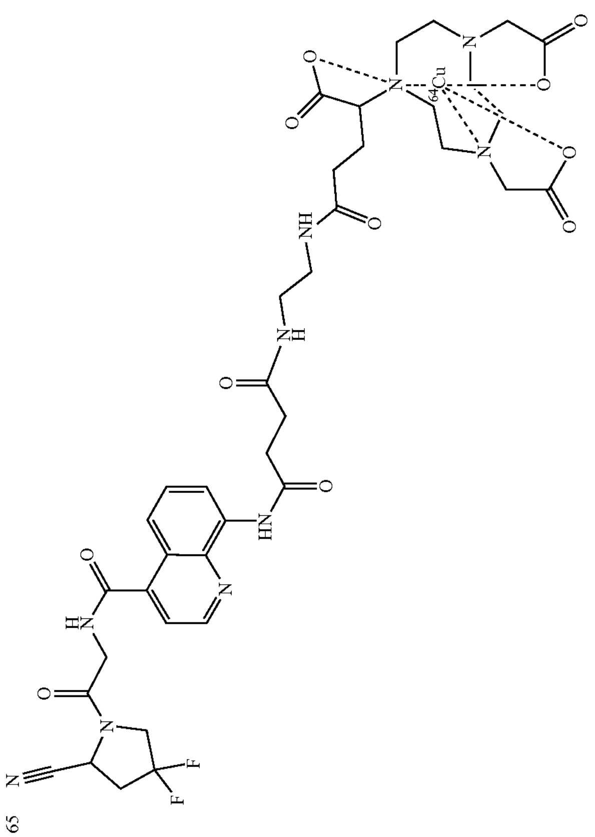 |

-continued
| # | Structure |
| --- | --- |
| 66 | 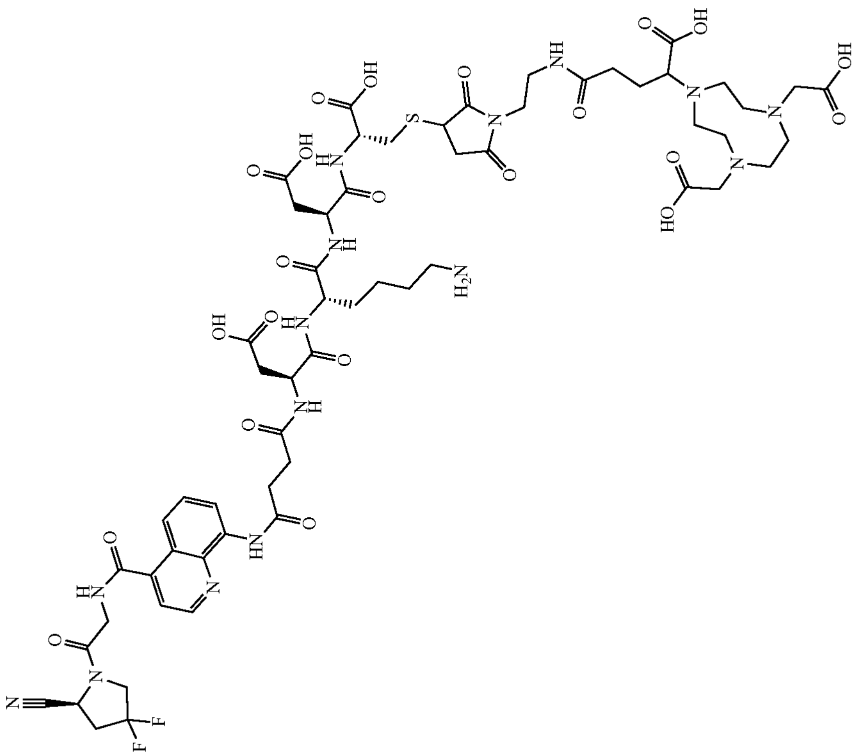 |

-continued
| # | Structure |
|---|---|
| 67 | 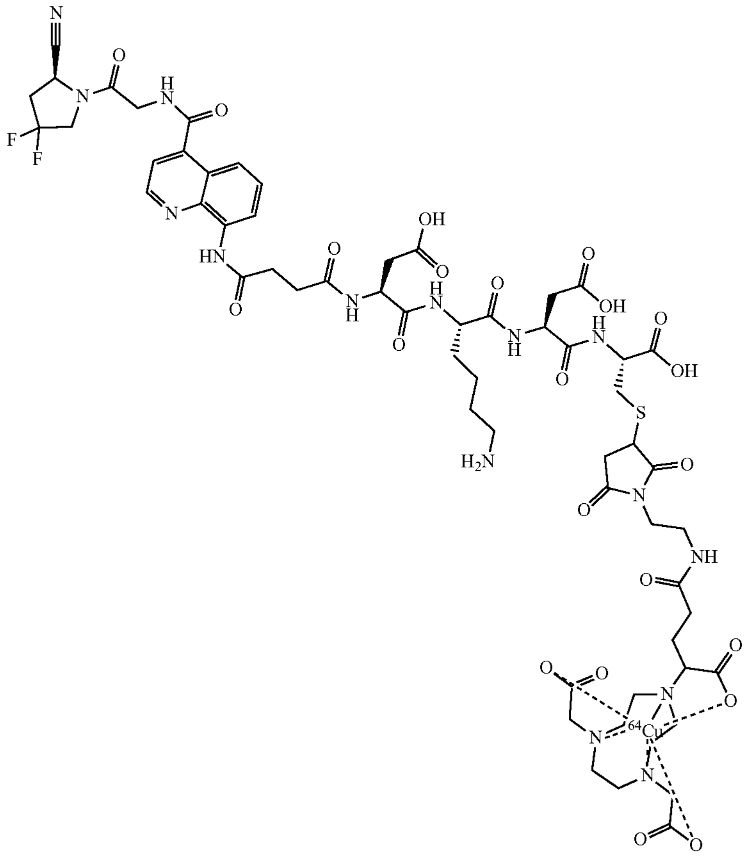 |

-continued
| # | Structure |
| --- | --- |
| 68 | 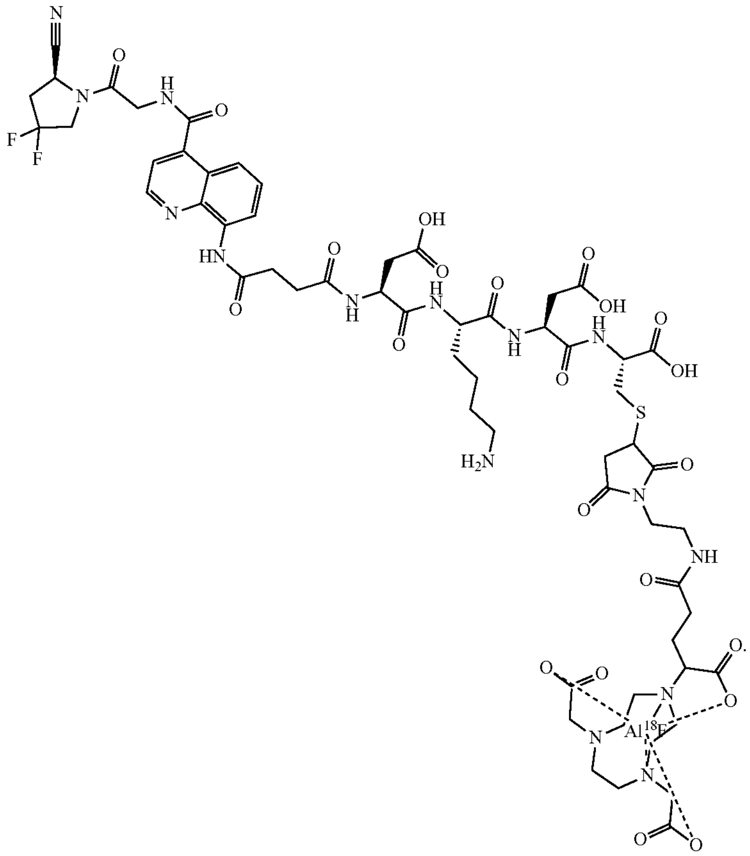 |

2. The compound according to claim 1, wherein the structure is selected from those with numbers 1, 2, 3, 4, 5, 6, 7, 8, 9, 10, 11, 12, 13, 14, 15, 18, 21, 26, 27, 30, 31, 34a, 35, 36, 37a, 38, 39, 40, 41, 42, 43, 43a, 44, 45, 47, 48, 49, 50, 51, 52, 53, 54, 55, 56, 57, 58a, 58b, 58c, 58d, 58e, 58f, 59a, 60a, 64, 65, 66, 67, and 68.

3. The compound according to claim 1, wherein the structure is selected from those with numbers 2, 7, 8, 9, 10, 11, 12, 13, 14, 15, 18, 21, 26, 27, 30, 31, 34a, 35, 36, 37a, 38, 39, 40, 41, 42, 43, 43a, 44, 45, 47, 48, 49, 50, 51, 52, 53, 54, 55, 56, 57, 58a, 58b, 58c, 58d, 58e, 58f, 59a, 60a, 64, 65, 66, 67, and 68.

4. The compound according to claim 1, wherein the structure is selected from those with numbers 8, 9, 10, 11, 12, 13, 14, 15, 18, 21, 26, 27, 30, 35, 38, 39, 40, 41, 42, 43a, 58a, 58b, 58c, 59a, 60a, 64, 65, 66, 67, and 68.

5. The compound according to claim 1, wherein the structure is selected from those with numbers 1, 2, 3, 4, 5, 6, 7, 8, 9, 10, 11, 12, 13, 14, 15, and 26.

6. The compound according to claim 1 having the structure 8.

* * * * *